(12) United States Patent
Brown et al.

(10) Patent No.: US 10,351,854 B2
(45) Date of Patent: Jul. 16, 2019

(54) THERAPEUTIC INHIBITION OF LACTATE DEHYDROGENASE AND AGENTS THEREFOR

(71) Applicant: Dicerna Pharmaceuticals, Inc., Cambridge, MA (US)

(72) Inventors: Bob D. Brown, Littleton, MA (US); Henryk T. Dudek, Wellesley, MA (US); Cheng Lai, Belmont, MA (US)

(73) Assignee: Dicerna Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/518,009

(22) PCT Filed: Oct. 9, 2015

(86) PCT No.: PCT/US2015/054959
§ 371 (c)(1),
(2) Date: Apr. 10, 2017

(87) PCT Pub. No.: WO2016/057932
PCT Pub. Date: Apr. 14, 2016

(65) Prior Publication Data
US 2017/0306332 A1    Oct. 26, 2017

Related U.S. Application Data

(60) Provisional application No. 62/062,424, filed on Oct. 10, 2014, provisional application No. 62/199,056, filed on Jul. 30, 2015.

(51) Int. Cl.
*C12N 15/113* (2010.01)

(52) U.S. Cl.
CPC .. *C12N 15/1137* (2013.01); *C12Y 101/01027* (2013.01); *C12N 2310/14* (2013.01); *C12N 2310/315* (2013.01); *C12N 2310/332* (2013.01); *C12N 2310/533* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 2010/0173973 A1 | 7/2010 | Brown | |
| 2011/0207799 A1* | 8/2011 | Rozema | A61K 9/08 514/44 A |
| 2011/0288147 A1* | 11/2011 | Brown | C12N 15/113 514/44 A |
| 2012/0121515 A1* | 5/2012 | Dang | C12Y 101/01042 424/9.3 |

FOREIGN PATENT DOCUMENTS

| | | |
|---|---|---|
| JP | 2014-518626 | 8/2014 |
| WO | WO 2005/089287 A2 | 9/2005 |
| WO | WO 2005/116204 A1 | 12/2005 |
| WO | WO 2006/006948 A2 | 1/2006 |
| WO | WO 2008/136902 A1 | 11/2008 |
| WO | WO 2012/156513 A1 | 11/2012 |

OTHER PUBLICATIONS

Ping Miao, et al., "Lactate dehydrogenase a in cancer: A promising target for diagnosis and therapy", IUBMB LIFE, vol. 65, No. 11, Nov. 1, 2013, pp. 904-910.
Shi L. Sheng et al., "Knockdown of lactate dehydrogenase A suppresses tumor growth and metastasis of human hepatocellular carcinoma", FEBS Journal, vol. 279, No. 20, Sep. 13, 2012, pp. 3898-3910.
Zhi-Yu Wang et al., "LDH-A silencing suppresses breast cancer tumorigenicity through induction of oxidative stress mediated mitochondrial pathway apoptosis", Breast Cancer Research and Treatment, Kluwer Academic Publishers, BO, vol. 131, No. 3, Mar. 31, 2011, pp. 791-800.
Langhammer S et al., "LDH-A gene suppression affects cell growth of colon carcinoma xenografts but not in culture conditions", European Journal of Cancer. Supplement, Pergamon, Oxford, GB, vol. 6, No. 9, Jul. 2, 2008, pp. 21-22.
Adeva M. et al., "Enzymes involved inl-lactate metabolism in humans", MITOCHONDRION, vol. 13, No. 6, 2013, pp. 615-629.
International Search Report issued in corresponding International Application Serial No. PCT/US2015/054959, dated Mar. 29, 2016, 6 pages.
Written Opinion of the International Searching Authority issued in corresponding International Application Ser. No. PCT/US2015/054959, dated Mar. 29, 2016, 11 pages.

* cited by examiner

*Primary Examiner* — J. E. Angell
(74) *Attorney, Agent, or Firm* — Wolf, Greenfield & Sacks, P.C.; Byron V. Olsen

(57) ABSTRACT

This invention relates to compounds, compositions, and methods useful for reducing lactate dehydrogenase target RNA and protein levels via use of dsRNAs, e.g., Dicer substrate siRNA (DsiRNA) agents.

34 Claims, 43 Drawing Sheets

Specification includes a Sequence Listing.

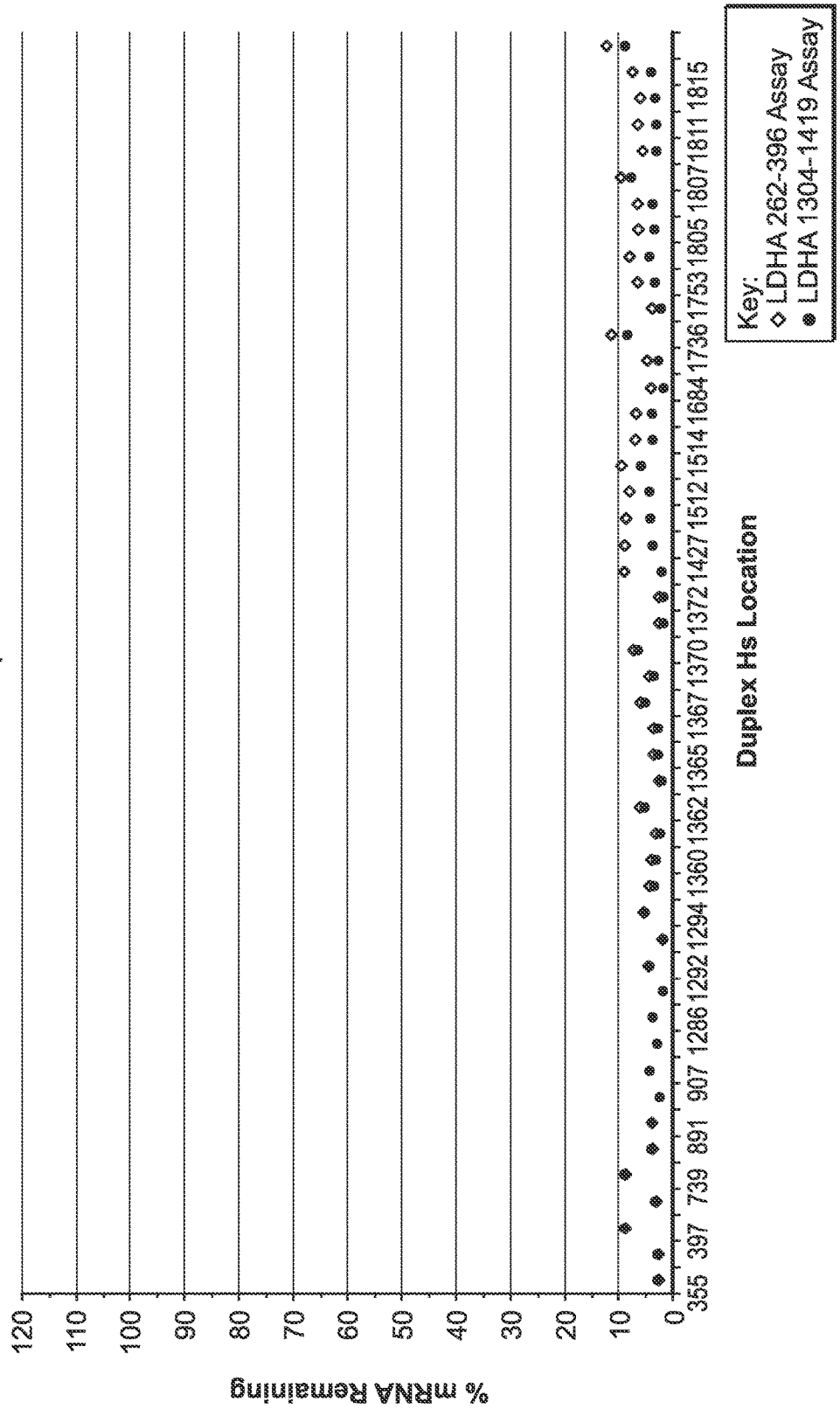

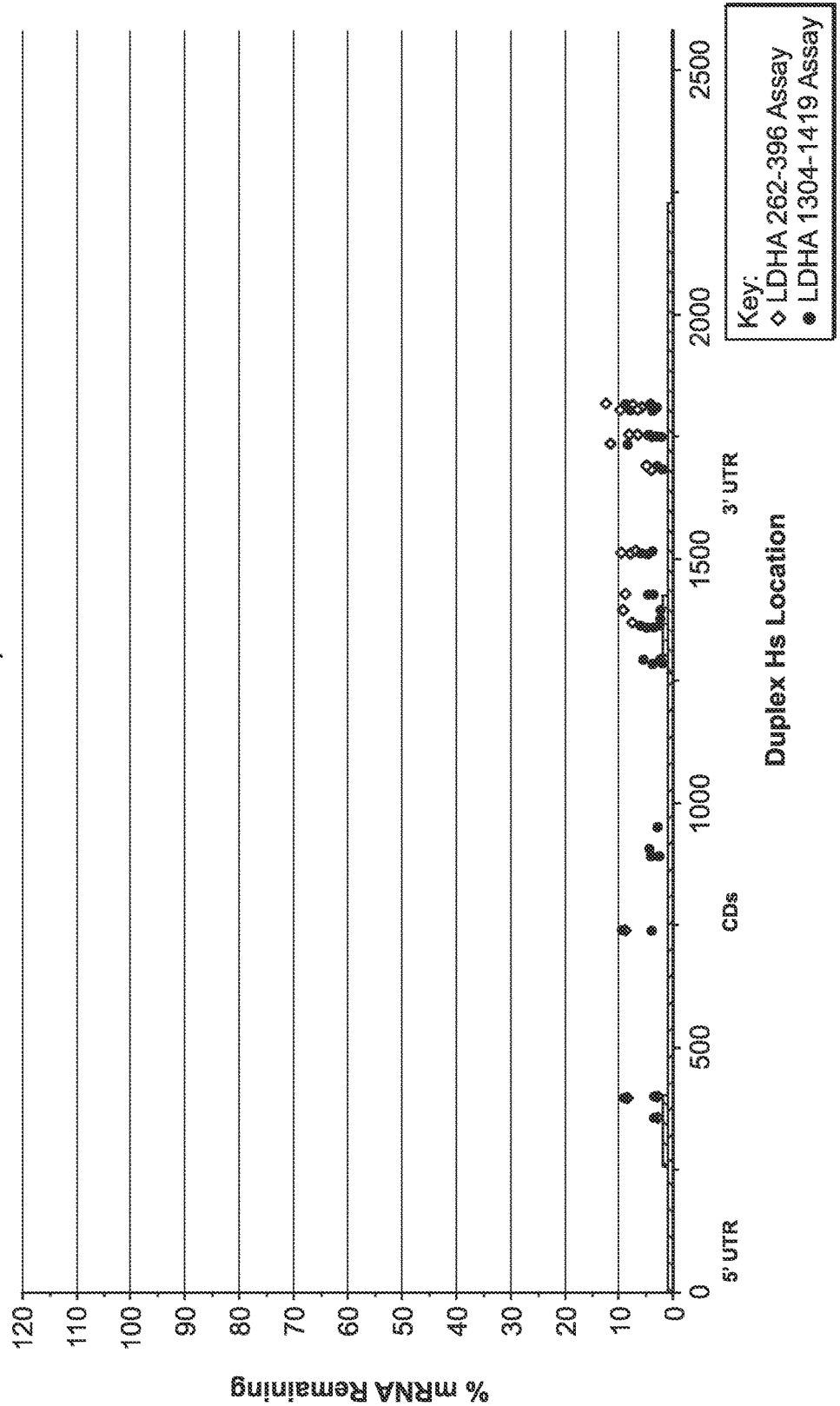

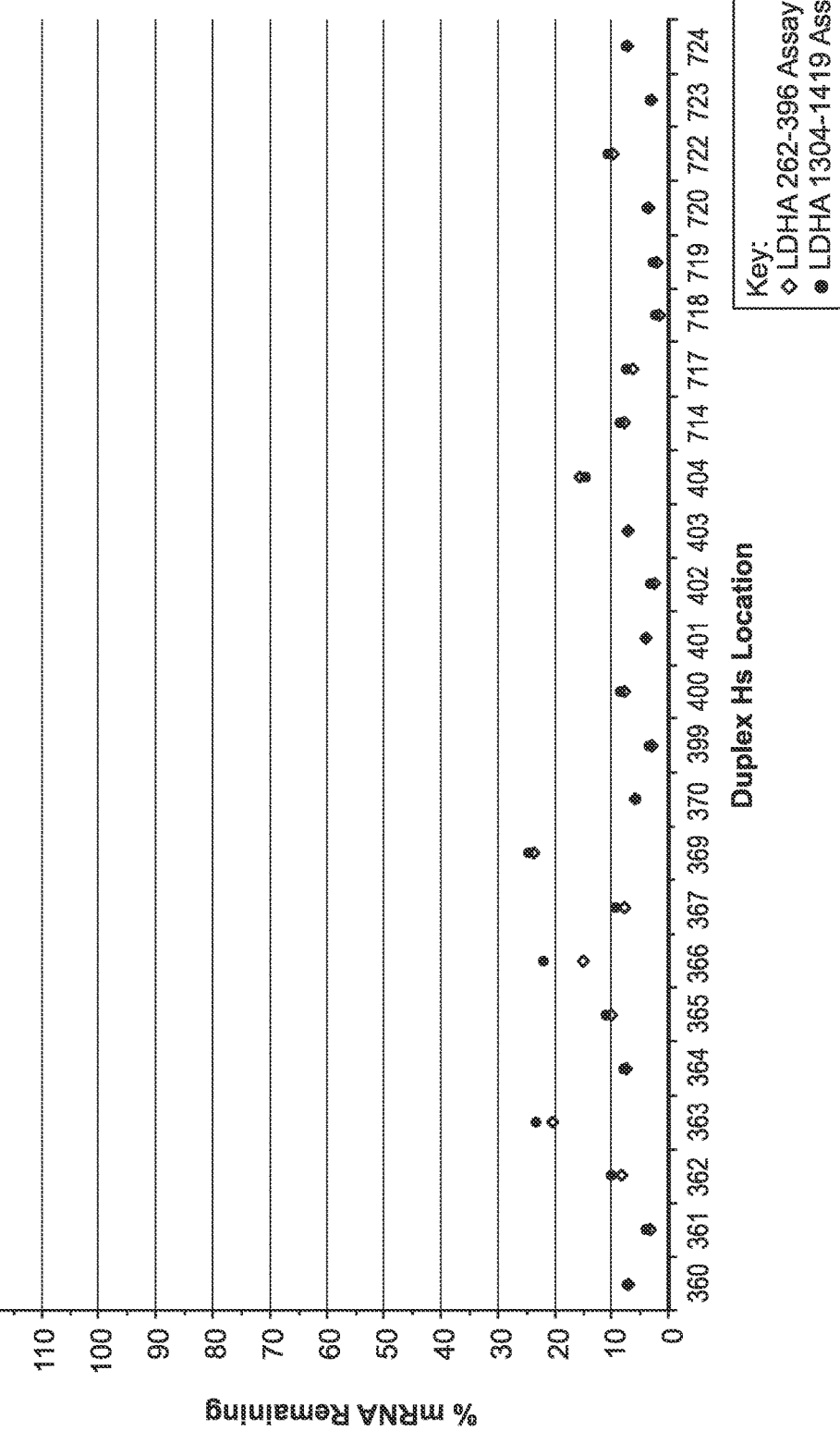

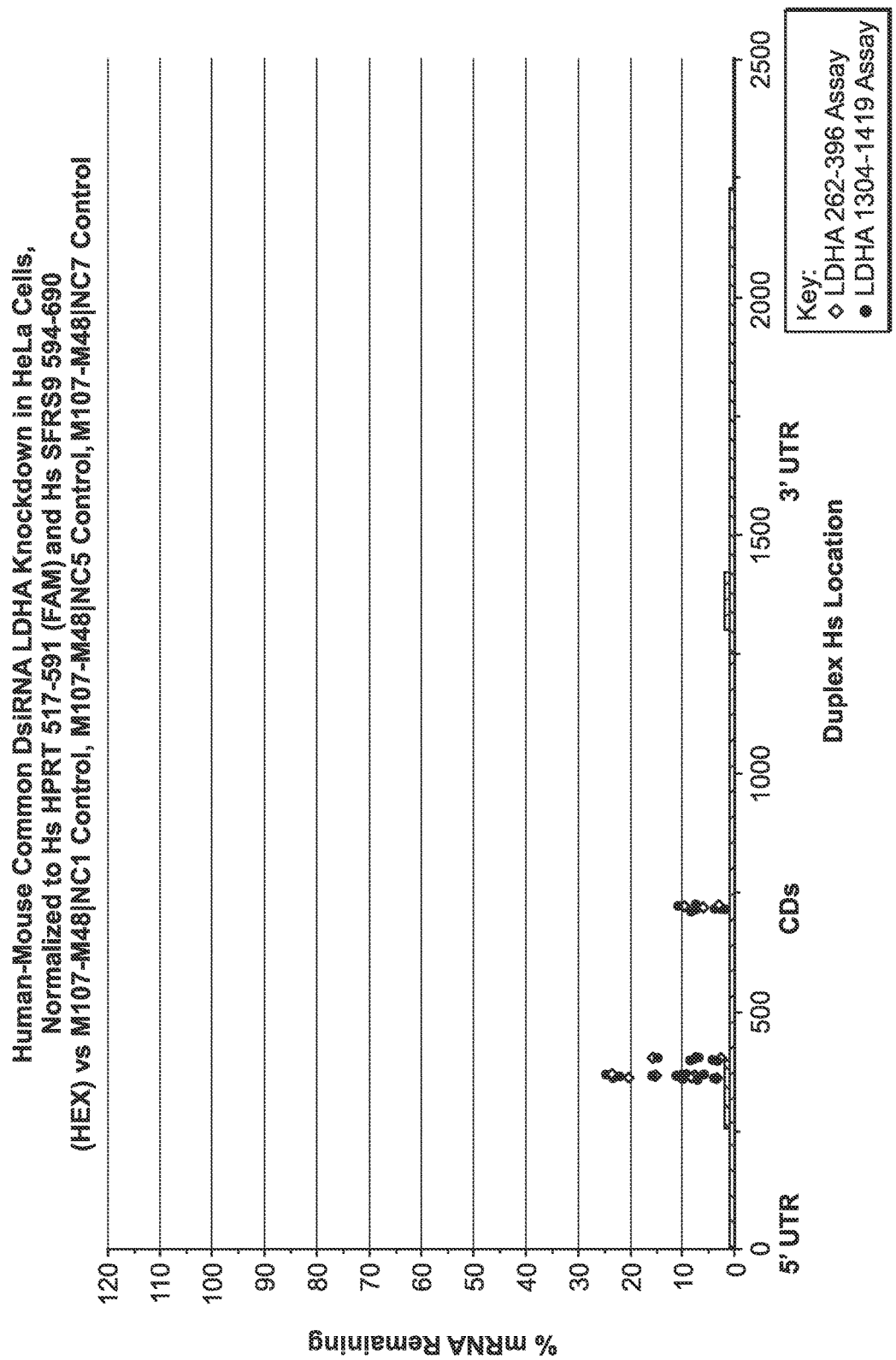

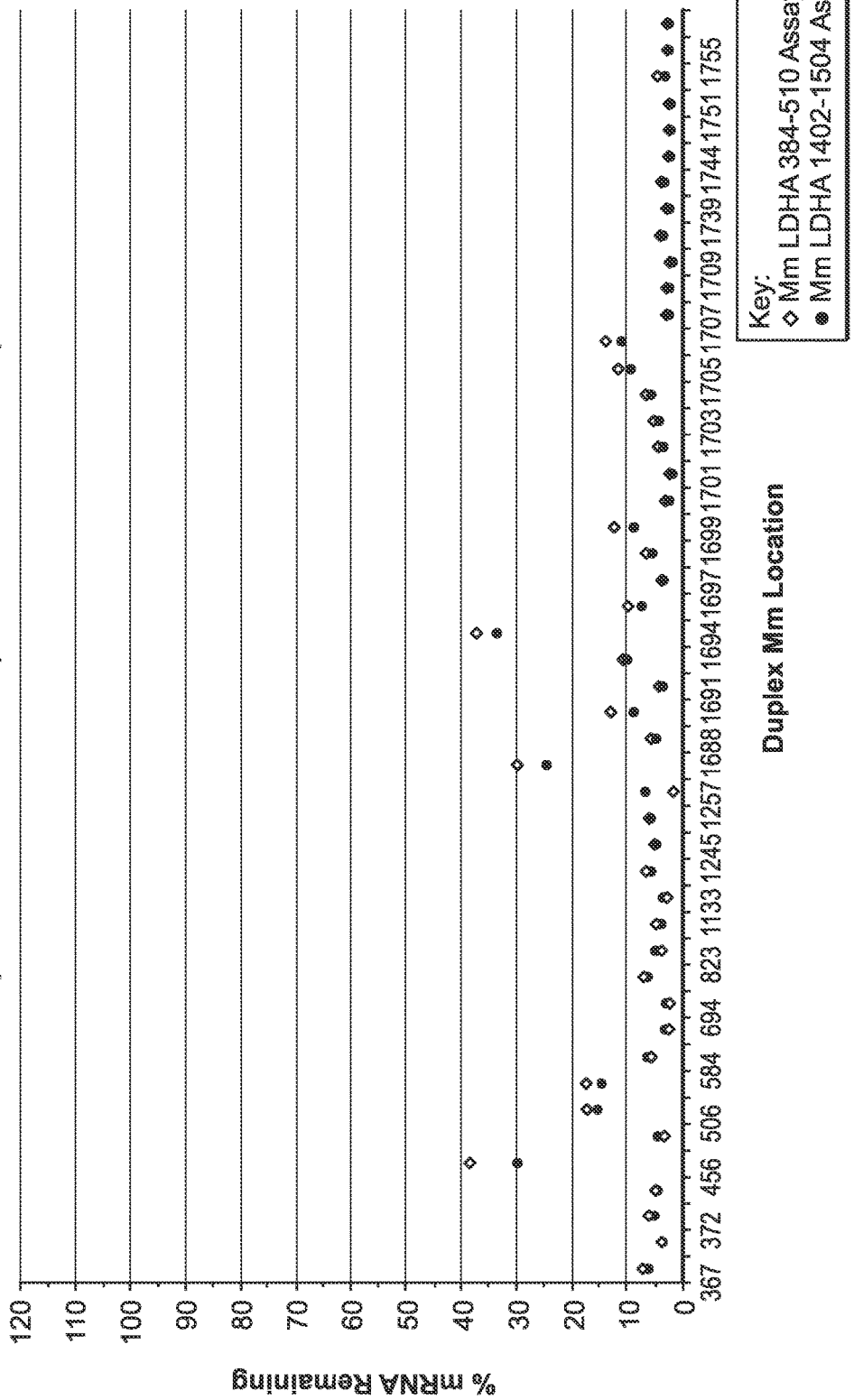

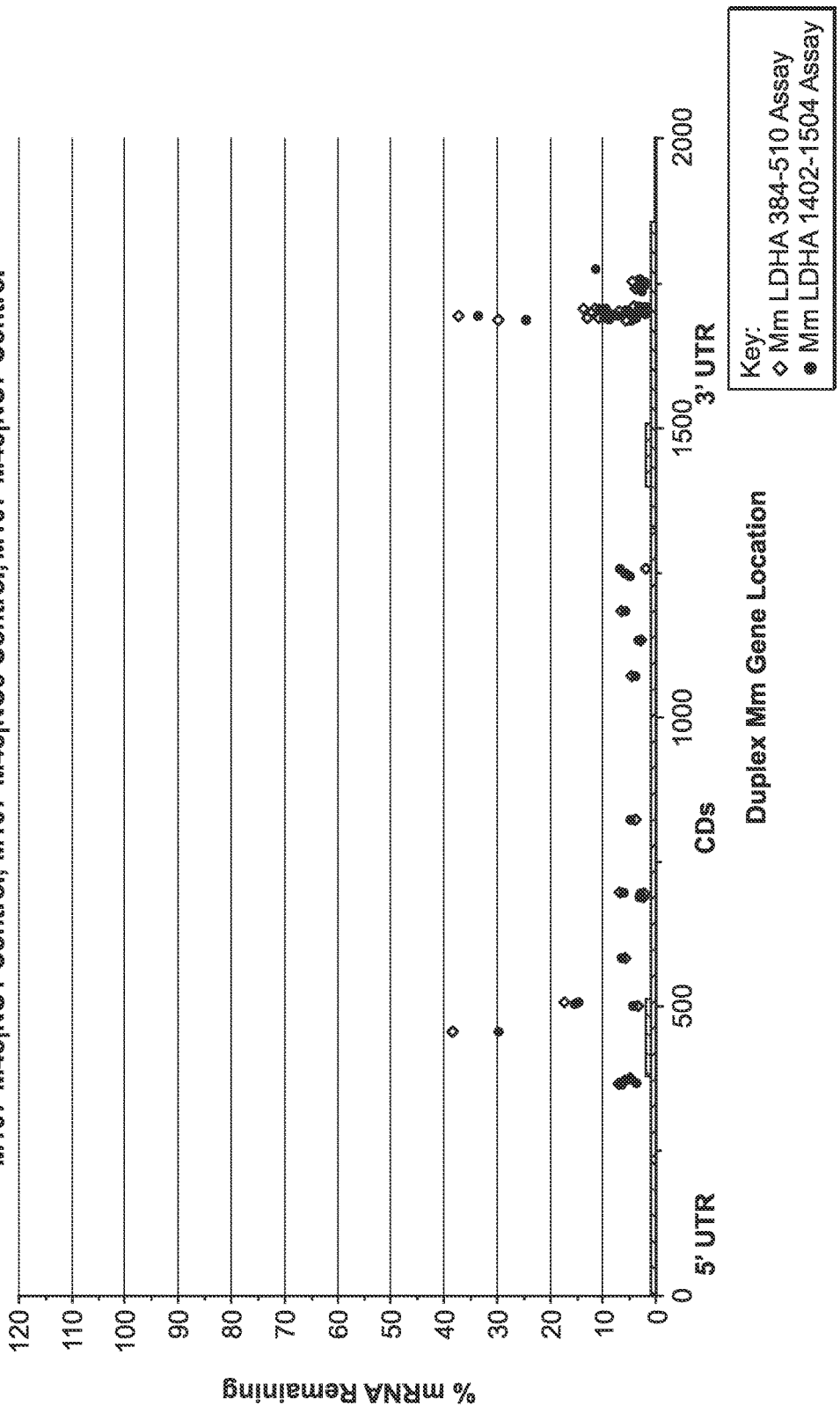

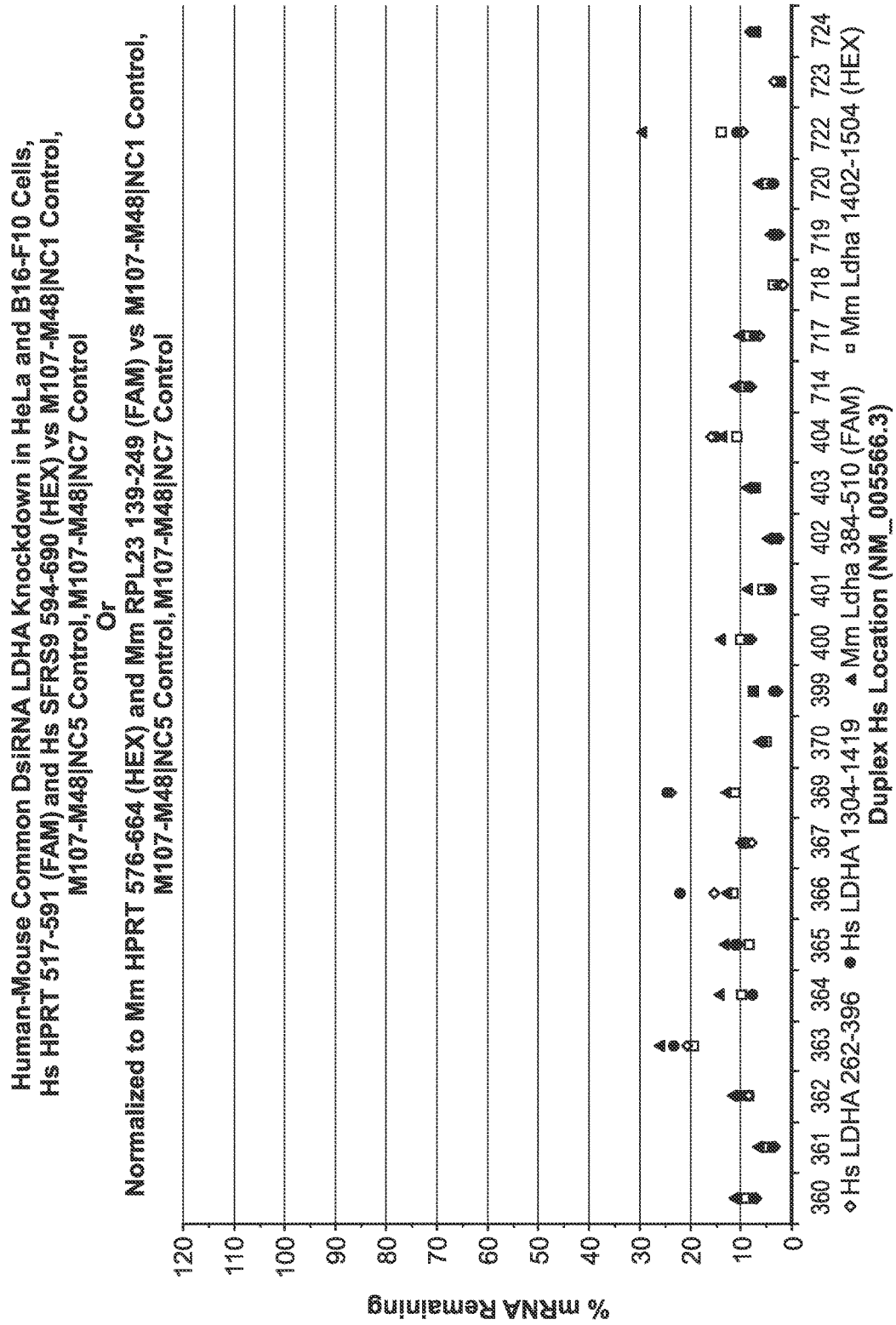

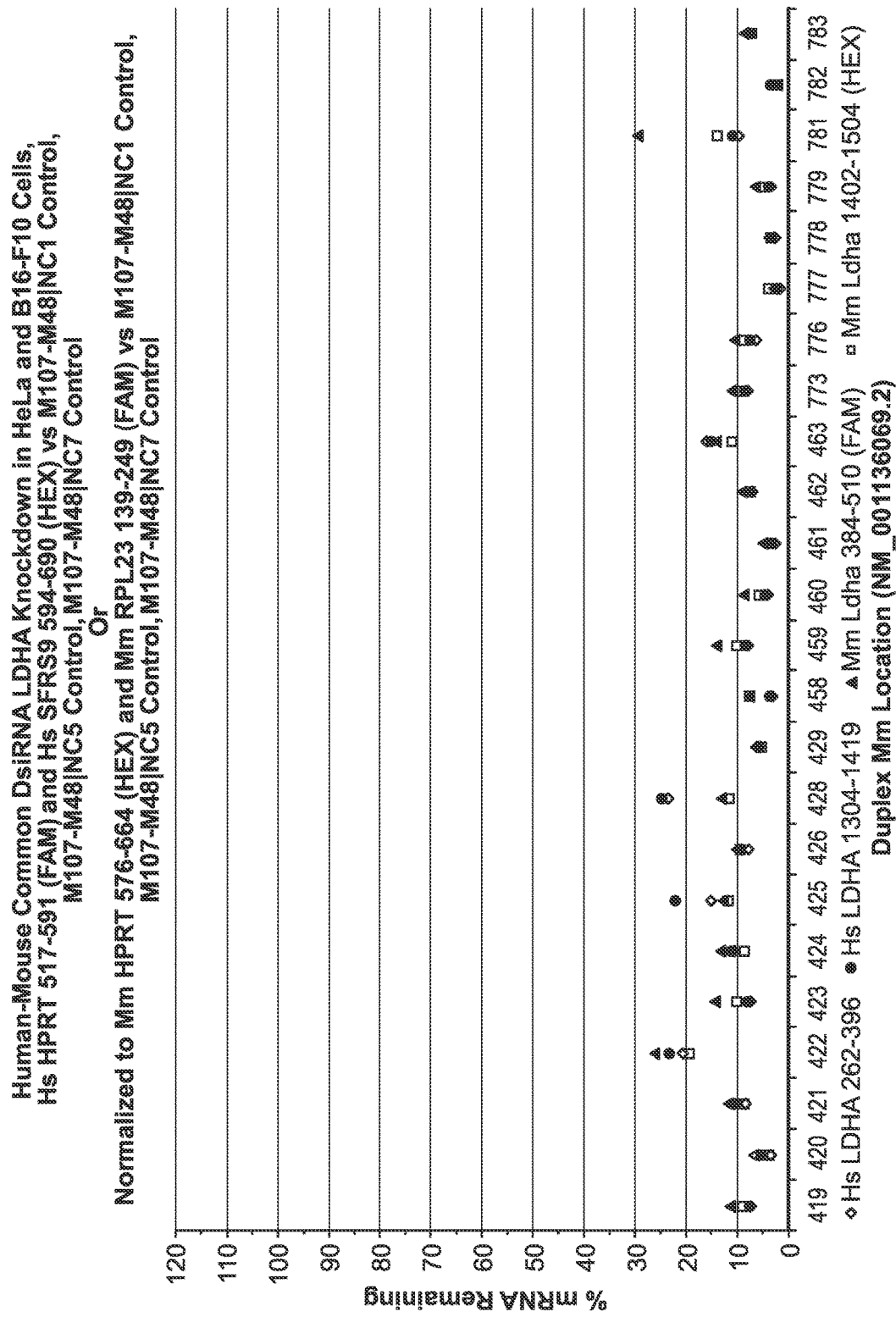

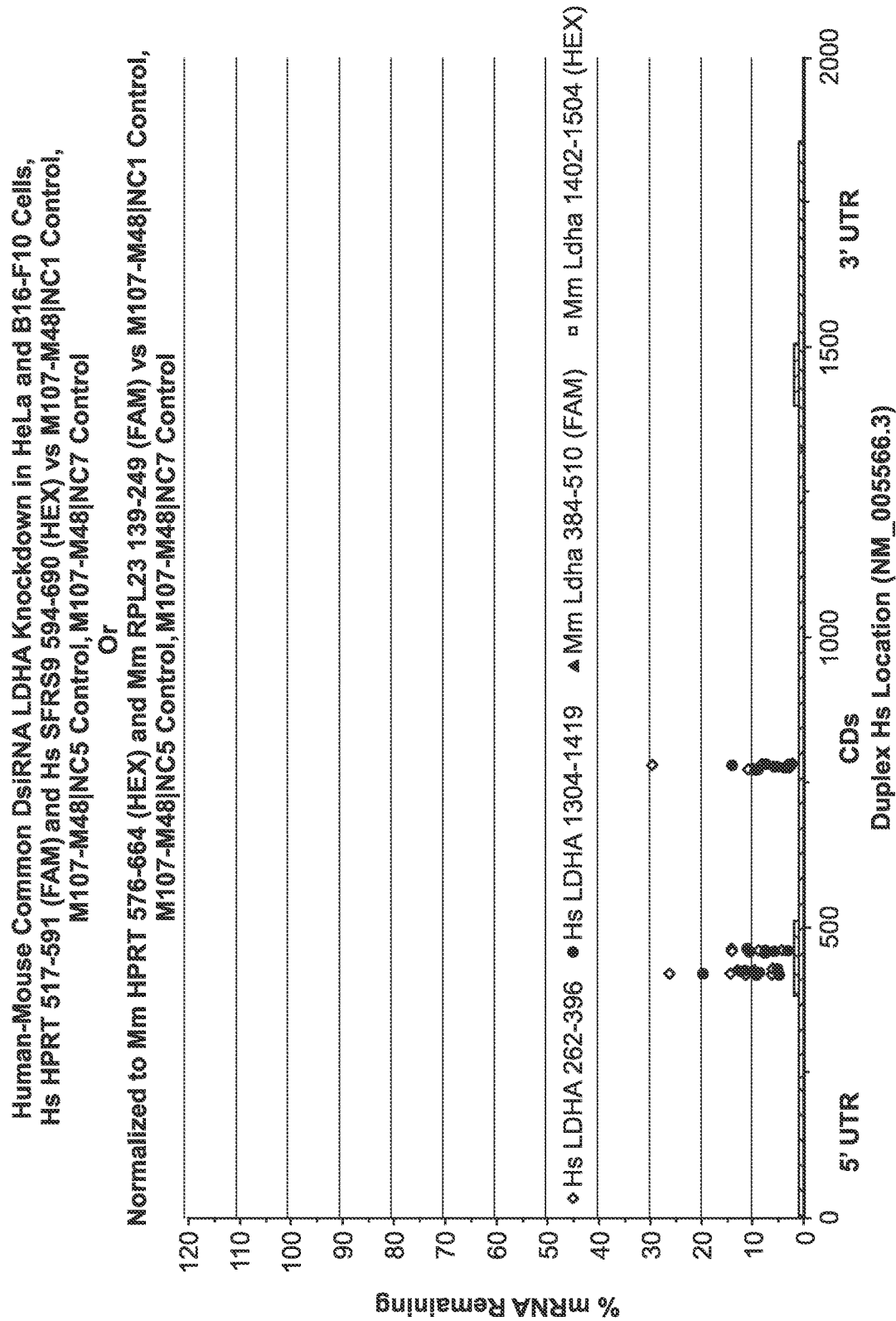

Significant knockdown of PRODH2, LDHA, GO, and AGXT mRNA and protein
Western analysis Reduced LDH activity in liver extracts

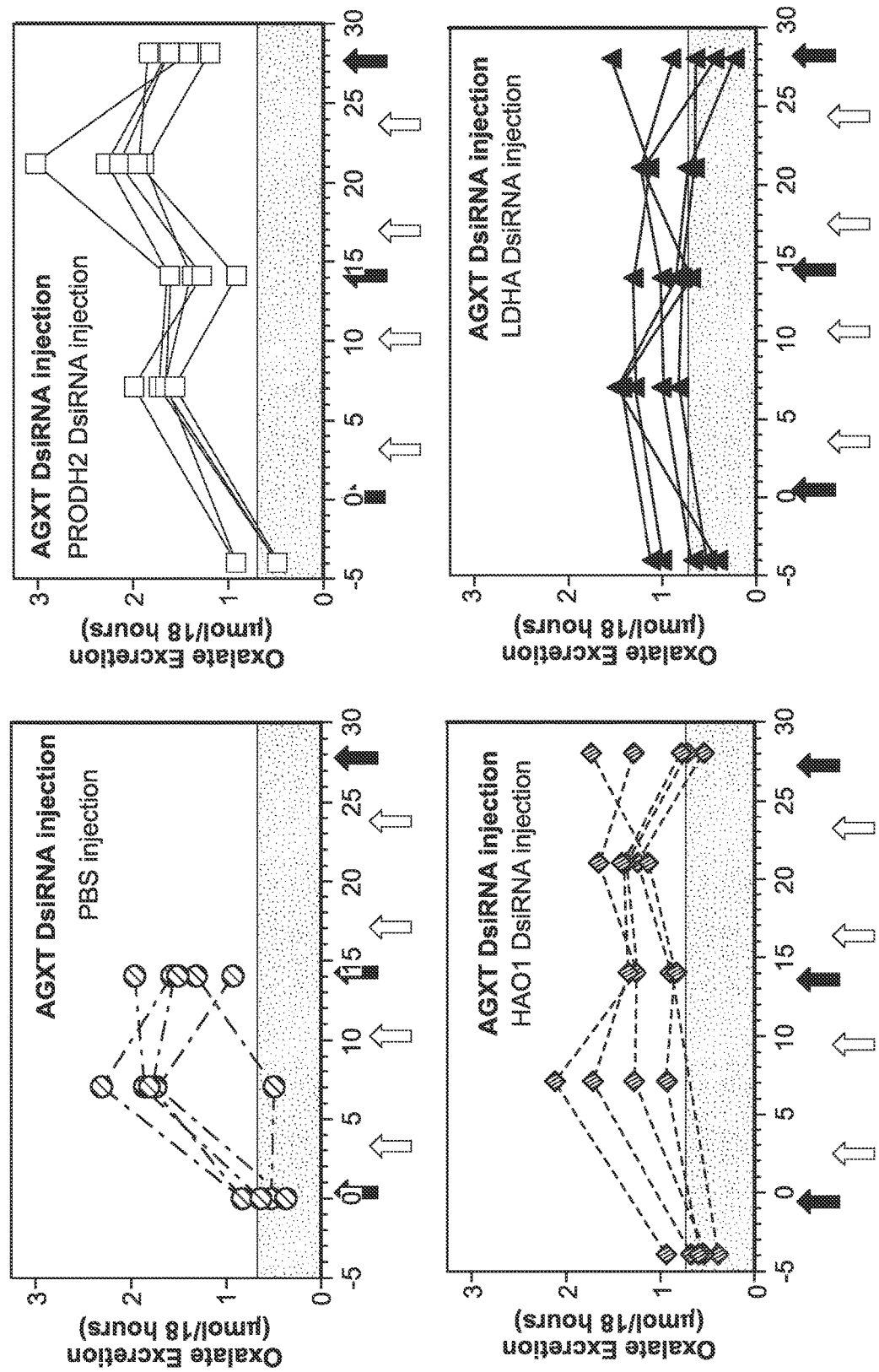

AGXT DsiRNA injection
HAO1, PRODH2 or LDHA DsiRNA injection

AGXT DsiRNA injection
HAO1, PRODH2 or LDHA DsiRNA injection

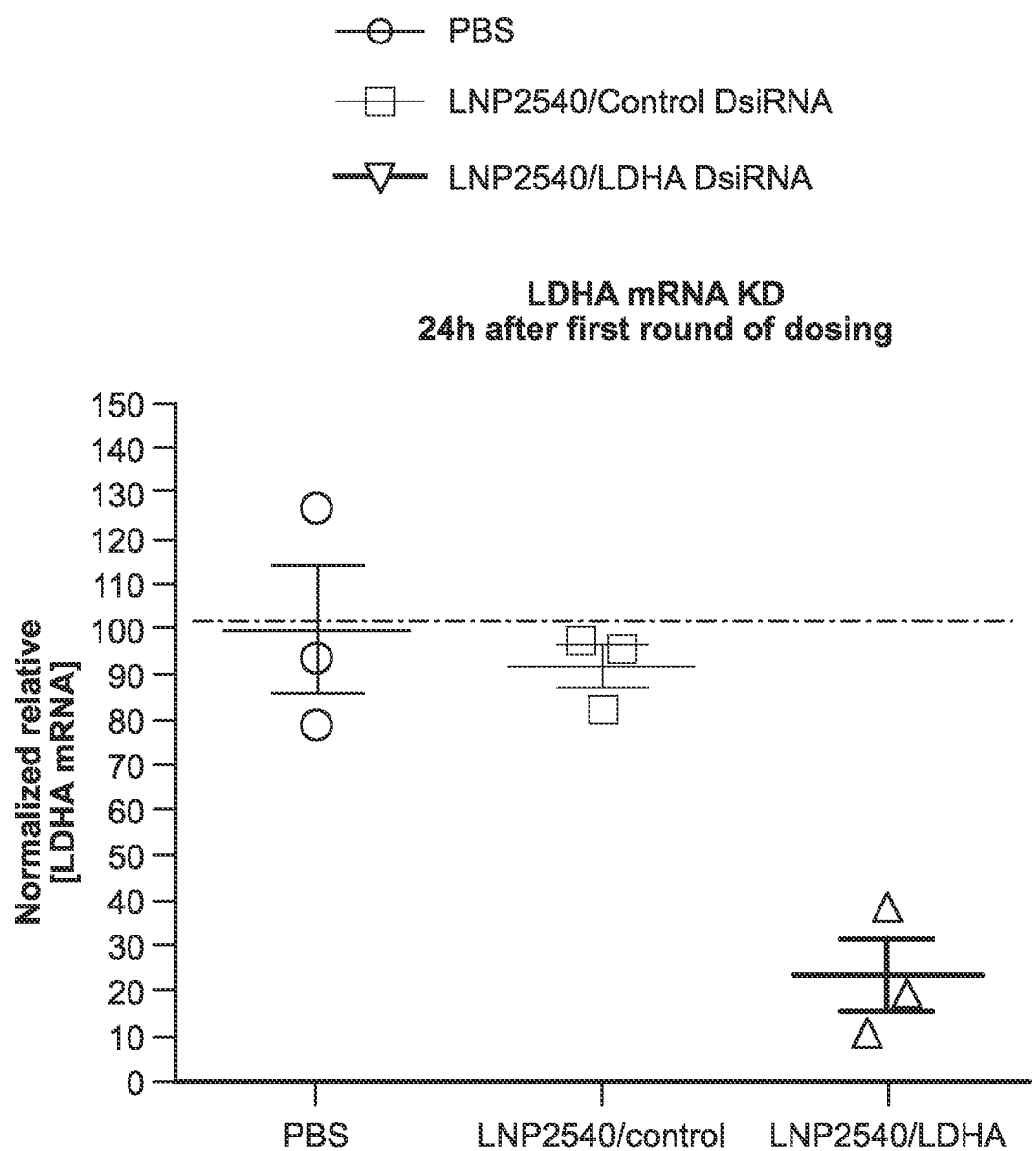

THERAPEUTIC INHIBITION OF LACTATE DEHYDROGENASE AND AGENTS THEREFOR

CROSS-REFERENCE TO RELATED APPLICATIONS

This application is the U.S. national stage pursuant to 35 U.S.C. § 371, of International Application Ser. No. PCT/US2015/054959, filed Oct. 9, 2015 and published in English on Apr. 14, 2016 as publication WO 2016/057932 A1, which is related to U.S. Provisional Patent Application Ser. No. 62/062,424, entitled "Methods and Compositions for the Specific Inhibition of Lactate Dehydrogenase by Double-Stranded RNA", which was filed Oct. 10, 2014, and to U.S. Provisional Patent Application Ser. No. 62/199,056, entitled "Therapeutic Inhibition of Lactate Dehydrogenase and Agents Therefor", which was filed Jul. 30, 2015. The entire contents of the preceding patent applications are hereby incorporated by reference herein.

FIELD OF THE INVENTION

The present invention relates to compounds, compositions, and methods for the study, diagnosis, and treatment of traits, diseases and conditions that respond to the modulation of lactate dehydrogenase gene expression and/or activity.

SEQUENCE SUBMISSION

The present application is being filed along with a Sequence Listing in electronic format. The Sequence Listing is entitled "48292_514001WO_Seq_Listing_9OCT2015", was created on Oct. 9, 2015, and is 1.4 MB in size. The information in the electronic format of the Sequence Listing is part of the present application and is incorporated herein by reference in its entirety.

BACKGROUND OF THE INVENTION

Primary hyperoxaluria Type 1 ("PH1") is a rare autosomal recessive inborn error of glyoxylate metabolism, caused by a deficiency of the liver-specific enzyme alanine:glyoxylate aminotransferase (also named serine-pyruvate aminotransferase). The disorder results in overproduction and excessive urinary excretion of oxalate, causing recurrent urolithiasis and nephrocalcinosis. As glomerular filtration rate declines due to progressive renal involvement, oxalate accumulates leading to systemic oxalosis. The diagnosis is based on clinical and sonographic findings, urine oxalate assessment, enzymology and/or DNA analysis. While early conservative treatment has aimed to maintain renal function, in chronic kidney disease Stages 4 and 5, the best outcomes to date have been achieved with combined liver-kidney transplantation (Cochat et al. *Nephrol Dial Transplant* 27: 1729-36).

PH1 is the most common form of primary hyperoxaluria and has an estimated prevalence of 1 to 3 cases per 1 million population and an incidence rate of approximately 1 case per 120,000 live births per year in Europe (Cochat et al. *Nephrol Dial Transplant* 10 (Suppl 8): 3-7; van Woerden et al. Nephrol Dial Transplant 18: 273-9). It accounts for 1 to 2% of cases of pediatric end-stage renal disease (ESRD), according to registries from Europe, the United States, and Japan (Harambat et al. *Clin J Am Soc Nephrol* 7: 458-65), but it appears to be more prevalent in countries in which consanguineous marriages are common (with a prevalence of 10% or higher in some North African and Middle Eastern nations; Kamoun and Lakhoua Pediatr Nephrol 10: 479-82; see Cochat and Rumsby *N Engl J Med* 369(7):649-58).

Lactate dehydrogenase (LDH) is the enzyme responsible for converting glyoxylate to oxalate in the mitochondrial/peroxisomal glycine metabolism pathway in the liver and pancreas. In the presence of LDH, increased production of glyoxylate (via, e.g., AGT1 mutation) drives oxalate accumulation (see FIG. 2), which ultimately results in the PH1 disease.

Double-stranded RNA (dsRNA) agents possessing strand lengths of 25 to 35 nucleotides have been described as effective inhibitors of target gene expression in mammalian cells (Rossi et al., U.S. Pat. No. 8,084,599 and U.S. Patent Application No. 2005/0277610). dsRNA agents of such length are believed to be processed by the Dicer enzyme of the RNA interference (RNAi) pathway, leading such agents to be termed "Dicer substrate siRNA" ("DsiRNA") agents. Additional modified structures of DsiRNA agents were previously described (Rossi et al., U.S. Patent Application No. 2007/0265220). Effective extended forms of Dicer substrates have also recently been described (see, e.g., Brown, U.S. Pat. Nos. 8,349,809 and 8,513,207).

Provided herein are improved nucleic acid agents that target lactate dehydrogenase. In particular, those targeting lactate dehydrogenase have been specifically exemplified.

BRIEF SUMMARY OF THE INVENTION

The present invention is based, at least in part, upon the identification of lactate dehydrogenase as an attractive target for RNA-based (particularly dsRNA-based) knockdown therapies. It was surprisingly identified herein that targeted knockdown of lactate dehydrogenase that appeared to exclude muscle tissue as a target organ for LDHA knockdown (e.g., primarily liver-targeted knockdown, e.g., using LNP-mediated delivery and/or GalNAc dsNA conjugates), such as can be achieved via use of dsRNAs as described herein in concert with delivery modalities (e.g., lipid nanoparticles, GalNAc conjugates, etc.) could provide therapeutic benefit to a subject having chronic kidney disease and/or pyruvate dehydrogenase complex deficiency. Identification of a therapeutic effect of such modalities when used against diseases or disorders such as chronic kidney disease, pyruvate dehydrogenase complex deficiency, or against PH1 (see, e.g., Example 4 and FIGS. 5A to 5G herein) and/or any other lactate dehydrogenase-associated disease or disorder, including, e.g., PH2 (see, e.g., Example 5 and FIG. 5H herein), PH3 and idiopathic hyperoxaluria, as well as oncology (when delivered in a manner that tends to target liver cells while being inefficient for muscle delivery, e.g., within a LNP—see, e.g., Example 7 and FIGS. 10A to 10B herein), was noted as remarkable, at least in part because of the critical role of lactate dehydrogenase in glycolysis. In particular, elevated lactose levels are known to be highly deleterious to cells and tissues, e.g., particularly in muscle and other tissues, and the robust levels of lactate dehydrogenase knockdown likely to be achieved using RNAi agents would therefore have been predicted to be harmful to a subject, in the absence of evidence to the contrary. However, the therapeutic potential of such approaches has now been identified herein, as the therapeutic modalities described herein have been established herein not only as effective but also well-tolerated (i.e., it has been discovered herein that robust knockdown of LDHA in liver does not produce a corresponding and potentially deleterious elevation of lactate levels in the circulation of mice—see, e.g., Example 8 and FIG. 11 herein).

The currently described LDHA-targeting therapies can be readily distinguished from small molecule-based approaches to performing LDHA inhibition (refer, e.g., to Shi and Pinto PLoS ONE 9(1): e86365 for certain small molecule inhibitors of LDHA). In particular, inhibition of LDHA using small molecule inhibitors cannot be readily targeted to specific organs without any impact upon other organs (e.g., without significant partitioning to muscle cells), due at least in part to the small sizes and partition coeffeicients of such small molecules.

Another disadvantage of small molecule-based approaches to inhibiting LDHA that is overcome by the oligonucleotide-based approaches of the current invention is the tendency of small molecule inhibitors of LDHA also to target other forms of LDH, for example, LDHB and/or LDHC. Such non-selective targeting of multiple forms of LDH can lead to more severe negative side effects in a treated individual than the truly LDHA-specific oligonucleotide-based therapies described herein.

Targeting of LDHA, especially using small molecule inhibitors that are not preferentially selective for LDHA relative to LDHB and/or LDHC, has been previously identified as an oncology therapy; however, use of LNP-mediated forms of oligonucleotide therapeutic delivery are identified herein as allowing for delivery of LDHA inhibitory activity to optimal target organs and/or tumors, while largely preventing anti-LDHA activity in tissues and/or organs where LDHA knockdown might be highly deleterious in certain individuals (e.g., in muscle cells of individuals having chronic kidney disease, pyruvate dehydrogenase complex deficiency, PH1 and/or any other lactate dehydrogenase-associated disease or disorder, including, e.g., PH2, PH3 and idiopathic hyperoxaluria, as well as certain types of cancer). Thus, LNP-mediated anti-LDHA RNAi agent delivery that tends not to deliver to muscle cells of a subject yet delivers to other target organs (including, e.g., tumor) is also identified herein as a highly attractive method for treating neoplasia in a subject.

In one aspect, the invention provides a method for treating a lactate dehydrogenase knockdown-treatable disease or disorder (e.g., chronic kidney disease, pyruvate dehydrogenase complex deficiency, PH1, PH2, PH3 and/or idiopathic hyperoxaluria) in a subject, involving administering to a subject having such a disease or disorder an agent that reduces expression of the LDHA gene in one or more tissues of the subject, thereby treating the disease or disorder in the subject.

In one embodiment, the subject has or is at elevated risk of chronic kidney disease or pyruvate dehydrogenase complex deficiency.

In another embodiment, the agent that reduces expression of the LDHA gene is an RNAi agent, optionally a double stranded nucleic acid ("dsNA"). Optionally, the agent is an RNAi agent having a hairpin or a tetraloop structure.

In certain embodiments, an agent of the invention is administered in a lipid nanoparticle. In related embodiments, administration of the agent largely targets the liver. Optionally, administration of the agent preferentially targets a neoplasia tissue. In certain embodiments, the agent is not delivered to muscle tissue (or is delivered to muscle tissue at very low levels as compared to, e.g., liver tissue).

In an additional embodiment, the one or more tissues of the subject include liver.

Another aspect of the invention provides a method for treating a neoplasia in a subject in need thereof, involving administering to a subject having a neoplasia an LNP-packaged agent that reduces expression of the LDHA gene in one or more tissues of the subject, thereby treating the neoplasia in the subject.

In one embodiment, the neoplasia is a hepatic tumor, e.g., hepatocellular carcinoma.

In another embodiment, administering of the agent does not reduce LDHA gene expression in muscle tissues of the subject.

Optionally, the agent preferentially reduces LDHA gene expression as compared to LDHB gene expression in the subject. In a related embodiment, LDHB gene expression is not reduced in the subject.

In certain embodiments, the agent that reduces expression of the LDHA gene is an RNAi molecule, optionally a double stranded nucleic acid ("dsNA").

In another embodiment, the agent that reduces expression of the LDHA gene is an RNAi molecule possessing a hairpin or a tetraloop structure.

In an additional embodiment, the agent that reduces expression of the LDHA gene is an RNAi molecule or a single-stranded antisense oligonucleotide.

In a related embodiment, the agent is a modified oligonucleotide. Optionally, the agent includes one or more of the following modifications: 2'-fluoro (2'-F), 2'-OMethyl (2'-OMe) and/or 2'-Methoxy ethoxy (2'-MOE) sugar modifications, inverted abasic caps, deoxynucleobases, and/or bicyclic nucleobase analogs such as locked nucleic acids (including LNA) and/or ENA In one embodiment, the agent includes an oligonucleotide of between 12 and 80 or more nucleotides in length.

In certain embodiments, the agent is an RNAi agent having one of the following structures:

a dsNA having a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand is 15-30 nucleotide residues in length, where starting from the 5' terminal nucleotide (position 1) positions 1 to 15 of the first strand include at least 8 ribonucleotides; the second strand is 36-80 nucleotide residues in length and, starting from the 3' terminal nucleotide, includes at least 8 ribonucleotides in the positions paired with positions 1-15 of the first strand to form a duplex; where at least the 3' terminal nucleotide of the second strand is unpaired with the first strand, and up to 6 consecutive 3' terminal nucleotides are unpaired with the first strand, thereby forming a 3' single stranded overhang of 1-6 nucleotides; where the 5' terminus of the second strand includes from 5-64 consecutive nucleotides which are unpaired with the first strand, thereby forming a 5-64 nucleotide single stranded 5' overhang; where at least the first strand 5' terminal and 3' terminal nucleotides are base paired with nucleotides of the second strand when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell;

a dsNA having a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the second strand is 19-30 nucleotide residues in length, where starting from the 5' terminal nucleotide (position 1) positions 1 to 19 of the second strand include at least 8 ribonucleotides; the first strand is 25-80 nucleotide residues in length and includes at least 8 ribonucleotides in positions paired with positions 1-19 of the second strand to form a duplex; where the 3' terminal nucleotide of the first strand is paired with the second strand, forming a blunt end, or up to 6 consecutive 3' terminal nucleotides are unpaired with the second strand, thereby forming a 3' single stranded overhang of 1-6 nucleotides; where the 5' terminus of the first strand includes from 5-61 consecutive nucleotides which are unpaired with the second strand, thereby forming a 5-61 nucleotide single stranded 5' overhang; where at least the second strand 5' terminal and 3' terminal nucleotides are base paired with nucleotides of the first strand when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell; or a dsNA having a first strand and a second strand, where the first strand and the second strand form a duplex region of 19-25 nucleotides in length, where the first strand has a 3' region that extends beyond the first strand-second strand duplex region and includes a nucleotide linker region, and the dsNA further includes a discontinuity between the 3' terminus of the first strand and the 5' terminus of the second strand, and the first or second strand is sufficiently complementary to a target lactate dehydrogenase mRNA sequence of SEQ ID NOs: 361-432 along at least 15 nucleotides of the second strand length to reduce lactate dehydrogenase target mRNA expression when the dsNA is introduced into a mammalian cell.

In certain embodiments, the nucleotide linker includes a tetraloop, optionally the nucleotide linker is a tetraloop.

In some embodiments, the agent includes one or more dynamic polyconjugate and/or GalNAc conjugate moieties.

In certain additional aspects, provided herein are nucleic acid compositions that reduce expression of lactate dehydrogenase. Such compositions contain nucleic acids such as double stranded RNA ("dsRNA"), and methods for preparing them. The nucleic acids of the invention are capable of reducing the expression of a target lactate dehydrogenase gene in a cell, either in vitro or in a mammalian subject.

In one aspect, the invention provides a nucleic acid having an oligonucleotide strand of 15-35 nucleotides in length that is sufficiently complementary to a target lactate dehydrogenase mRNA sequence of SEQ ID NOs: 361-432 along at least 15 nucleotides of the oligonucleotide strand length to reduce lactate dehydrogenase target mRNA expression when the nucleic acid is introduced into a mammalian cell. Optionally, the oligonucleotide strand is 19-35 nucleotides in length.

In another aspect, the invention provides a nucleic acid having an oligonucleotide strand of 19-35 nucleotides in length that is sufficiently complementary to a target lactate dehydrogenase mRNA sequence of SEQ ID NOs: 361-432 along at least 19 nucleotides of the oligonucleotide strand length to reduce lactate dehydrogenase target mRNA expression when the nucleic acid is introduced into a mammalian cell.

In a further aspect, the invention provides a double stranded nucleic acid (dsNA) having first and second nucleic acid strands that include RNA, where the first strand is 15-80 nucleotides in length and the second strand is 19-80 nucleotides in length and is sufficiently complementary to a target lactate dehydrogenase mRNA sequence of SEQ ID NOs: 361-432 along at least 15 nucleotides of the second oligonucleotide strand length to reduce lactate dehydrogenase target mRNA expression when the dsNA is introduced into a mammalian cell.

Optionally, the first strand is 15-53, 15-35, 19-53 or 19-35 nucleotides in length. In certain embodiments, the second strand is 19-53 or 19-35 nucleotides in length.

In an additional aspect, the invention provides a dsNA having first and second nucleic acid strands, where the first strand is 15-35 nucleotides in length and the second strand of the dsNA is 19-35 nucleotides in length and is sufficiently complementary to a target lactate dehydrogenase mRNA sequence of SEQ ID NOs: 361-432 along at least 19 nucleotides of the second oligonucleotide strand length to reduce lactate dehydrogenase target mRNA expression when the dsNA is introduced into a mammalian cell.

In another aspect, the invention provides a dsNA having first and second nucleic acid strands, where the first strand is 15-35 nucleotides in length and the second strand of the dsNA is 19-35 nucleotides in length and is sufficiently complementary to a target lactate dehydrogenase mRNA sequence of SEQ ID NOs: 361-432 along at least 19 nucleotides of the second oligonucleotide strand length to reduce lactate dehydrogenase target mRNA expression, and where, starting from the 5' end of the lactate dehydrogenase mRNA sequence of SEQ ID NOs: 361-432 (referred to as position 1), mammalian Ago2 cleaves the mRNA at a site between positions 9 and 10 of the sequence when the dsNA is introduced into a mammalian cell.

In a further aspect, the invention provides a dsNA molecule that consists of (a) a sense region and an antisense region, where the sense region and the antisense region together form a duplex region consisting of 25-35 base pairs and the antisense region comprises a sequence that is the complement of a sequence of any one (or more) of SEQ ID NOs: 361-432; and (b) from zero to two 3' overhang regions, where each overhang region is six or fewer nucleotides in length, and where, starting from the 5' end of the lactate dehydrogenase mRNA sequence of SEQ ID NOs: 361-432 (position 1), mammalian Ago2 cleaves the mRNA at a site between positions 9 and 10 of the sequence when the dsNA is introduced into a mammalian cell.

In an additional aspect, the invention provides a dsNA having first and second nucleic acid strands and a duplex region of at least 25 base pairs, where the first strand is 25-34 nucleotides in length and the second strand of the dsNA is 26-35 nucleotides in length and includes 1-5 single-stranded nucleotides at its 3' terminus, where the second oligonucleotide strand is sufficiently complementary to a target lactate dehydrogenase mRNA sequence of SEQ ID NOs: 361-432 along at least 19 nucleotides of the second oligonucleotide strand length to reduce lactate dehydrogenase target gene expression when the dsNA is introduced into a mammalian cell.

In another aspect, the invention provides a dsNA having first and second nucleic acid strands and a duplex region of at least 25 base pairs, where the first strand is 25-34 nucleotides in length and the second strand of the dsNA is 26-35 nucleotides in length and comprises 1-5 single-stranded nucleotides at its 3' terminus, where the 3' terminus of the first oligonucleotide strand and the 5' terminus of the second oligonucleotide strand form a blunt end, and second oligonucleotide strand is sufficiently complementary to a target lactate dehydrogenase sequence of SEQ ID NOs: 361-432 or 5109-7122 along at least 19 nucleotides of the second oligonucleotide strand length to reduce lactate dehydrogenase mRNA expression when the dsNA is introduced into a mammalian cell.

In an additional aspect, the invention provides a nucleic acid possessing an oligonucleotide strand of 15-35 nucleotides in length, where the oligonucleotide strand is hybridizable to a target lactate dehydrogenase mRNA sequence of SEQ ID NOs: 361-432 along at least 15 nucleotides of the oligonucleotide strand length.

Another aspect of the invention provides a dsNA having first and second nucleic acid strands that include RNA, where the first strand is 15-35 nucleotides in length and the second strand of the dsNA is 19-35 nucleotides in length, where the second oligonucleotide strand is hybridizable to a target lactate dehydrogenase mRNA sequence of SEQ ID NOs: 361-432 along at least 15 nucleotides of the second oligonucleotide strand length.

Other aspects of the invention provide a dsNA that is:

a dsNA comprising a first oligonucleotide strand having a 5' terminus and a 3' terminus and a second oligonucleotide strand having a 5' terminus and a 3' terminus, where the first strand is 25 to 53 nucleotide residues in length, where starting from the first nucleotide (position 1) at the 5' terminus of the first strand, positions 1 to 23 of the first strand are ribonucleotides or modified ribonucleotides; the second strand is 27 to 53 nucleotide residues in length and comprises 23 consecutive ribonucleotides or modified ribonucleotides that base pair with the ribonucleotides or ribonucleotides of positions 1 to 23 of the first strand to form a duplex; the 5' terminus of the first strand and the 3' terminus of the second strand form a blunt end, a 1-6 nucleotide 5' overhang or a 1-6 nucleotide 3' overhang; the 3' terminus of the first strand and the 5' terminus of the second strand form a blunt end, a 1-6 nucleotide 5' overhang or a 1-6 nucleotide 3' overhang; at least one of positions 24 to the 3' terminal nucleotide residue of the first strand is a deoxyribonucleotide or modified ribonucleotide that optionally base pairs with a deoxyribonucleotide of the second strand; and the second strand is sufficiently complementary to a target lactate dehydrogenase mRNA sequence selected from SEQ ID NOs: 361-432 along at least 15 nucleotides of the second oligonucleotide strand length to reduce lactate dehydrogenase target mRNA expression when the double stranded nucleic acid is introduced into a mammalian cell;

a dsNA comprising a first oligonucleotide strand having a 5' terminus and a 3' terminus and a second oligonucleotide strand having a 5' terminus and a 3' terminus, where the second strand is 27 to 53 nucleotide residues in length, where starting from the first nucleotide (position 1) at the 5' terminus of the second strand, positions 1 to 23 of the second strand are ribonucleotides or modified ribonucleotides; the first strand is 25 to 53 nucleotide residues in length and comprises 23 consecutive ribonucleotides or modified ribonucleotides that base pair sufficiently with the ribonucleotides of positions 1 to 23 of the second strand to form a duplex; at least one of positions 24 to the 3' terminal nucleotide residue of the second strand is a deoxyribonucleotide or modified ribonucleotide, optionally that base pairs with a deoxyribonucleotide or modified ribonucleotide of the first strand; and the second strand is sufficiently complementary to a target lactate dehydrogenase mRNA sequence selected from SEQ ID NOs: 361-432 along at least 15 nucleotides of the second oligonucleotide strand length to reduce lactate dehydrogenase target mRNA expression when the double stranded nucleic acid is introduced into a mammalian cell;

a dsNA comprising a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand (or the second strand) is 25-30 nucleotide residues in length, where starting from the 5' terminal nucleotide (position 1) positions 1 to 23 of the first strand (or the second strand) include at least 8 ribonucleotides; the second strand (or the first strand) is 36-80 nucleotide residues in length and, starting from the 3' terminal nucleotide, includes at least 8 ribonucleotides in the positions paired with positions 1-23 of the first strand to form a duplex; where at least the 3' terminal nucleotide of the second strand (or the first strand) is unpaired with the first strand (or the second strand), and up to 6 consecutive 3' terminal nucleotides are unpaired with the first strand (or the second strand), thereby forming a 3' single stranded overhang of 1-6 nucleotides; where the 5' terminus of the second strand (or the first strand) includes from 10-30 consecutive nucleotides which are unpaired with the first strand (or the second strand), thereby forming a 10-30 nucleotide single stranded 5' overhang; where at least the first strand (or the second strand) 5' terminal and 3' terminal nucleotides are base paired with nucleotides of the second strand (or first strand) when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell;

a dsNA comprising a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand is 25-35 nucleotide residues in length, where starting from the 5' terminal nucleotide (position 1) positions 1 to 25 of the second strand include at least 8 ribonucleotides; the second strand is 30-80 nucleotide residues in length and, starting from the 3' terminal nucleotide, comprises at least 8 ribonucleotides in the positions paired with positions 1-25 of the first strand to form a duplex; where the 5' terminus of the second strand comprises from 5-35 consecutive nucleotides which are unpaired with the first strand, thereby forming a 5-35 nucleotide single stranded 5' overhang; where at least the first strand 5' terminal and 3' terminal nucleotides are base paired with nucleotides of the second strand when the first and second strands are aligned for maximum complementarity, thereby forming a substantially duplexed region between the first and second strands; and the second strand is sufficiently complementary to a target lactate dehydrogenase mRNA sequence selected from SEQ ID NOs: 361-432 along at least 15 nucleotides of the second oligonucleotide strand length to reduce lactate dehydrogenase target mRNA expression when the double stranded nucleic acid is introduced into a mammalian cell;

a dsNA comprising a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the second strand is 19-30 nucleotide residues in length and optionally 25-30 nucleotide residues in length, where starting from the 5' terminal nucleotide (position 1) positions 1 to 17 (optionally positions 1 to 23) of the second strand include at least 8 ribonucleotides; the first strand is 24-80 nucleotide residues in length (optionally 30-80 nucleotide residues in length) and, starting from the 3' terminal nucleotide, comprises at least 8 ribonucleotides in the positions paired with positions 1 to 17 (optionally positions 1 to 23) of the second strand to form a duplex; where the 3' terminus of the first strand and the 5' terminus of the second strand form a blunt end, a 3' overhang or a 5' overhang, optionally where the overhang is 1-6 nucleotides in length; where the 5' terminus of the first strand comprises from 5-35 consecutive nucleotides which are unpaired with the second strand, thereby forming a 5-35 nucleotide single-stranded 5' overhang; where at least the second strand 5' terminal and 3' terminal nucleotides are base paired with nucleotides of the first strand when the first and second strands are aligned for maximum complementarity, thereby forming a substantially duplexed region between the first and second strands; and the second strand is sufficiently complementary to a target lactate dehydrogenase mRNA sequence selected from SEQ ID NOs: 361-432 along at least 15 nucleotides of the second oligonucleotide strand length to reduce lactate dehydrogenase target mRNA expression when the double stranded nucleic acid is introduced into a mammalian cell;

a dsNA comprising a first strand and a second strand, where the first strand and the second strand form a duplex region of 19-25 nucleotides in length, where the first strand comprises a 3' region that extends beyond the first strand-second strand duplex region and comprises a tetraloop, and the dsNA further comprises a discontinuity between the 3' terminus of the first strand and the 5' terminus of the second strand, and the first or second strand is sufficiently complementary to a target lactate dehydrogenase mRNA sequence selected from SEQ ID NOs: 361-432 along at least 15 nucleotides of the first or second strand length to reduce lactate dehydrogenase target mRNA expression when the dsNA is introduced into a mammalian cell; or a dsNA comprising a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first oligonucleotide strand is 25-53 nucleotides in length and the second is oligonucleotide strand is 25-53 nucleotides in length, and where the dsNA is sufficiently highly modified to substantially prevent dicer cleavage of the dsNA, optionally where the dsNA is cleaved by non-dicer nucleases to yield one or more 19-23 nucleotide strand length dsNAs capable of reducing LDH mRNA expression in a mammalian cell.

A further aspect of the invention provides an in vivo hybridization complex within a cell that includes an exogenous nucleic acid sequence and a target Lactate Dehydrogenase mRNA sequence of SEQ ID NOs: 361-432.

An additional aspect of the invention provides an in vitro hybridization complex within a cell that includes an exogenous nucleic acid sequence and a target Lactate Dehydrogenase mRNA sequence of SEQ ID NOs: 361-432.

In one embodiment, the dsNA has a duplex region that is 19-21 base pairs, 21-25 base pairs or at least 25 base pairs in length.

In another embodiment, the second oligonucleotide strand includes 1-5 single-stranded nucleotides at its 3' terminus.

In an additional embodiment, the first strand is 25-35 nucleotides in length. Optionally, the second strand is 25-35 nucleotides in length.

In another embodiment, the second oligonucleotide strand is complementary to target lactate dehydrogenase cDNA sequence GenBank Accession No. NM_005566.3 along at most 27 nucleotides of the second oligonucleotide strand length.

In one embodiment, the dsNA or hybridization complex comprises a modified nucleotide. Optionally, the modified nucleotide residue is of the group consisting of 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and 2'-O—(N-methylcarbamate).

In a further embodiment, starting from the first nucleotide (position 1) at the 3' terminus of the first oligonucleotide strand, position 1, 2 or 3 is substituted with a modified nucleotide. Optionally, the modified nucleotide residue of the 3' terminus of the first strand is a deoxyribonucleotide, an acyclonucleotide or a fluorescent molecule. In certain embodiments, position 1 of the 3' terminus of the first oligonucleotide strand is a deoxyribonucleotide.

In one embodiment, the first strand is 25 nucleotides in length and the second strand is 27 nucleotides in length. Optionally, the 3' terminus of the first strand and the 5' terminus of the second strand form a blunt end.

In another embodiment, starting from the 5' end of a lactate dehydrogenase mRNA sequence of SEQ ID NOs: 361-432 (position 1), mammalian Ago2 cleaves the mRNA at a site between positions 9 and 10 of the sequence, thereby reducing lactate dehydrogenase target mRNA expression when the dsNA is introduced into a mammalian cell. Optionally, the second strand includes a sequence of SEQ ID NOs: 73-144. In certain embodiments, the first strand includes a sequence of SEQ ID NOs: 1-72.

In one embodiment, the dsNA includes a pair of first strand/second strand sequences of Table 2.

In a further embodiment, each of the first and the second strands has a length which is at least 26 nucleotides.

In one embodiment, nucleotides of the 1-5 single-stranded nucleotides of the 3' terminus of the second strand include a modified nucleotide. Optionally, the modified nucleotide is a 2'-O-methyl ribonucleotide. In a related embodiment, all nucleotides of the 1-5 single-stranded nucleotides of the 3' terminus of the second strand are modified nucleotides. In certain embodiments, the 1-5 single-stranded nucleotides of the 3' terminus of the second strand are 1-4 nucleotides in length, are 1-3 nucleotides in length, or are 1-2 nucleotides in length. In a related embodiment, the 1-5 single-stranded nucleotides of the 3' terminus of the second strand is two nucleotides in length and includes a 2'-O-methyl modified ribonucleotide.

In one embodiment, the dsNA has a second strand possessing 5-35 nucleotides at its 3' terminus. Optionally, the single-stranded nucleotides include modified nucleotides. In certain embodiments, the modified nucleotide(s) are 2'-O-methyl, 2'-methoxyethoxy, 2'-fluoro, 2'-allyl, 2'-O-[2-(methylamino)-2-oxoethyl], 4'-thio, 4'-CH2-O-2'-bridge, 4'-(CH2)2-O-2'-bridge, 2'-LNA, 2'-amino and/or 2'-O—(N-methlycarbamate) modified nucleotides. In one embodiment, the single-stranded nucleotides include ribonucleotides. Optionally, the single-stranded nucleotides include deoxyribonucleotides.

In some embodiments, the agent, nucleic acid, dsNA or hybridization complex of the invention also reduces mRNA expression of LDHB and/or LDHC.

In another embodiment, the nucleic acid or dsNA of the invention reduces LDHA mRNA expression but does not reduce mRNA expression of LDHB or LDHC in the subject.

In certain embodiments, the second oligonucleotide strand includes a modification pattern of AS-M1 to AS-M84, AS-M88 to AS-M96, AS-M210, AS-M1* to AS-M84*, AS-M88* to AS-M96* or AS-M210*.

Optionally, the first oligonucleotide strand includes a modification pattern of SM1 to SM119 or SM250 to SM252.

In a further embodiment, each of the first and the second strands has a length which is at least 26 and at most 30 nucleotides.

Optionally, the dsNA is cleaved endogenously in the cell by Dicer.

In certain embodiments, a dsNA of the invention includes at least one unlocked nucleobase analog (UNA). Optionally, the at least one UNA is located in a 3'-overhang region, a 5'-overhang region, or both such regions of the dsNA, optionally on the guide strand of the dsNA.

In some embodiments, a dsNA of the invention is attached to a dynamic polyconjugate (DPC). In additional embodiments, a dsNA of the invention is administered with a DPC, where optionally the dsNA and DPC are not attached.

In some embodiments, a dsNA of the invention is attached to a GalNAc moiety (optionally, a tri-antennary or other multi-GalNAc moiety) and/or to cholesterol or a cholesterol targeting ligand.

In certain embodiments, the amount of the agent, nucleic acid, dsNA or hybridization complex of the invention sufficient to reduce expression of the target gene is 1 nanomolar or less, 200 picomolar or less, 100 picomolar or less, 50 picomolar or less, 20 picomolar or less, 10 picomolar or less, 5 picomolar or less, 2, picomolar or less or 1 picomolar or less in the environment of the cell.

In one embodiment, the agent, nucleic acid, dsNA or hybridization complex possesses greater potency than a 21mer siRNA directed to the identical at least 15 or 19 nucleotides of the target lactate dehydrogenase mRNA in reducing target lactate dehydrogenase mRNA expression when assayed in vitro in a mammalian cell at an effective concentration in the environment of a cell of 1 nanomolar or less. In certain embodiments, knockdown efficacy and/or potency is measured at a concentration of 1 nanomolar, 200 picomolar, 100 picomolar, 50 picomolar, 20 picomolar, 10 picomolar, 5 picomolar, 2, picomolar or 1 picomolar in the environment of a cell.

In another embodiment, the agent, nucleic acid, dsNA or hybridization complex is sufficiently complementary to the target lactate dehydrogenase mRNA sequence to reduce lactate dehydrogenase target mRNA expression by an amount (expressed by %) that is at least 10%, at least 50%, at least 80-90%, at least 95%, at least 98%, or at least 99% when the agent, nucleic acid, dsNA or hybridization complex is introduced into a mammalian cell.

In certain embodiments, the first and second strands are joined by a chemical linker. Optionally, the 3' terminus of the first strand and the 5' terminus of the second strand are joined by a chemical linker.

In one embodiment, a nucleotide of the second or first strand is substituted with a modified nucleotide that directs the orientation of Dicer cleavage.

Optionally, the agent, nucleic acid, dsNA or hybridization complex includes a deoxyribonucleotide, a dideoxyribonucleotide, an acyclonucleotide, a 3'-deoxyadenosine (cordycepin), a 3'-azido-3'-deoxythymidine (AZT), a 2',3'-dideoxyinosine (ddI), a 2',3'-dideoxy-3'-thiacytidine (3TC), a 2',3'-didehydro-2',3'-dideoxythymidine (d4T), a monophosphate nucleotide of 3'-azido-3'-deoxythymidine (AZT), a 2',3'-dideoxy-3'-thiacytidine (3TC) and a monophosphate nucleotide of 2',3'-didehydro-2',3'-dideoxythymidine (d4T), a 4-thiouracil, a 5-bromouracil, a 5-iodouracil, a 5-(3-aminoallyl)-uracil, a 2'-O-alkyl ribonucleotide, a 2'-O-methyl ribonucleotide, a 2'-amino ribonucleotide, a 2'-fluoro ribonucleotide, or a locked nucleic acid.

In certain embodiments, the agent, nucleic acid, dsNA or hybridization complex includes a phosphate backbone modification that is a phosphonate, a phosphorothioate or a phosphotriester.

In one embodiment, the agent, nucleic acid, dsNA or hybridization complex includes a morpholino nucleic acid or a peptide nucleic acid (PNA).

In another embodiment, the agent, nucleic acid, dsNA or hybridization complex comprises a sequence of 15 or 19 consecutive nucleotides that includes four or fewer mismatched nucleotide residues when the 15 or 19 consecutive nucleotides are aligned for maximum complementarity with the target lactate dehydrogenase mRNA sequence.

Optionally, the 15 or 19 consecutive nucleotides include three or fewer mismatched nucleotide residues when the 15 or 19 consecutive nucleotides are aligned for maximum complementarity with the target lactate dehydrogenase mRNA sequence. In certain embodiments, the 15 or 19 consecutive nucleotides include two or fewer mismatched nucleotide residues when the 15 or 19 consecutive nucleotides are aligned for maximum complementarity with the target lactate dehydrogenase mRNA sequence. In related embodiments, the 15 or 19 consecutive nucleotides include one mismatched nucleotide residue when the 15 or 19 consecutive nucleotides are aligned for maximum complementarity with the target lactate dehydrogenase mRNA sequence. In additional embodiments, the 15 or 19 consecutive nucleotides are perfectly complementary to the target lactate dehydrogenase mRNA sequence when the 15 or 19 consecutive nucleotides are aligned for maximum complementarity with the target lactate dehydrogenase mRNA sequence.

In one aspect, the invention provides a method for reducing expression of a target lactate dehydrogenase gene in a mammalian cell involving contacting a mammalian cell in vitro with an agent, nucleic acid, dsNA or hybridization complex of the invention in an amount sufficient to reduce expression of a target lactate dehydrogenase mRNA in the cell.

In one embodiment, target lactate dehydrogenase mRNA expression is reduced by at least 10%, at least 50% or at least 80-90%. Optionally, lactate dehydrogenase mRNA levels are reduced by at least 90% at least 8 days after the cell is contacted with the agent, nucleic acid, dsNA or hybridization complex. In certain embodiments, lactate dehydrogenase mRNA levels are reduced by at least 70% at least 10 days after the cell is contacted with the agent, nucleic acid, dsNA or hybridization complex.

In one aspect, the invention provides a method for reducing expression of a target lactate dehydrogenase mRNA in a mammal involving administering an agent, nucleic acid, dsNA or hybridization complex of the invention to a mammal in an amount sufficient to reduce expression of a target lactate dehydrogenase mRNA in the mammal.

In certain embodiments, the agent, nucleic acid, dsNA or hybridization complex is formulated in a lipid nanoparticle (LNP). In one embodiment, the agent, nucleic acid, dsNA or hybridization complex is administered at a dosage that is 1 microgram to 5 milligrams per kilogram of the mammal per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In certain embodiments, the agent, nucleic acid, dsNA or hybridization complex possesses greater potency than 21mer siRNAs directed to the identical at least 19 nucleotides of the target lactate dehydrogenase mRNA in reducing target lactate dehydrogenase mRNA expression when assayed in vitro in a mammalian cell at an effective concentration in the environment of a cell of 1 nanomolar or less. In certain embodiments, knockdown efficacy and/or potency is measured at a concentration of 1 nanomolar, 200 picomolar, 100 picomolar, 50 picomolar, 20 picomolar, 10 picomolar, 5 picomolar, 2, picomolar or 1 picomolar in the environment of a cell.

In another embodiment, lactate dehydrogenase mRNA levels are reduced in a tissue of the mammal by at least 70% at least 3 days after the agent, nucleic acid, dsNA or hybridization complex is administered to the mammal. Optionally, the tissue is liver tissue.

In certain embodiments, administering includes intravenous injection, intramuscular injection, intraperitoneal injection, infusion, subcutaneous injection, transdermal, aerosol, rectal, vaginal, topical, oral or inhaled delivery.

In another aspect, the invention provides a method for treating or preventing PH1 in a subject that involves administering an agent, nucleic acid, dsNA or hybridization complex of the invention to the subject in an amount sufficient to treat or prevent PH1 in the subject.

An additional aspect of the invention provides a method for treating or preventing primary hyperoxaluria type 2 (PH2) in a subject involving administering to the subject an amount of an agent, nucleic acid, dsNA or hybridization complex of the invention in an amount sufficient to treat or prevent PH2 in the subject.

Another aspect of the invention provides a method for treating or preventing primary hyperoxaluria type 3 (PH3) in a subject comprising administering to the subject an amount of an agent, nucleic acid, dsNA or hybridization complex of the invention in an amount sufficient to treat or prevent PH3 in the subject.

A further aspect of the invention provides a method for treating or preventing idiopathic hyperoxaluria in a subject comprising administering to the subject an amount of an agent, nucleic acid, dsNA or hybridization complex of the invention in an amount sufficient to treat or prevent idiopathic hyperoxaluria in the subject.

Another aspect of the invention provides a method for treating or preventing cancer in a subject comprising administering to the subject an amount of an agent, nucleic acid, dsNA or hybridization complex of the invention in an amount sufficient to treat or prevent cancer in the subject.

An additional aspect of the invention provides a method for treating or preventing chronic kidney disease or pyruvate dehydrogenase complex deficiency in a subject involving administering to the subject an amount of an agent, nucleic acid, dsNA or hybridization complex of the invention in an amount sufficient to treat or prevent chronic kidney disease or pyruvate dehydrogenase deficiency in the subject.

In one embodiment, the subject is human.

In certain embodiments, the method further involves administering an inhibitor of LDHB and/or LDHC. Optionally, the inhibitor of LDHB and/or LDHC is a dsNA (optionally a siRNA or a DsiRNA).

In a further aspect, the invention provides a formulation containing an agent, nucleic acid, dsNA or hybridization complex of the invention present in an amount effective to reduce target lactate dehydrogenase mRNA levels when the agent, nucleic acid, dsNA or hybridization complex is introduced into a mammalian cell in vitro by at least 10%, at least 50% or at least 80-90%.

In one embodiment, the effective amount is 1 nanomolar or less, 200 picomolar or less, 100 picomolar or less, 50 picomolar or less, 20 picomolar or less, 10 picomolar or less, 5 picomolar or less, 2, picomolar or less or 1 picomolar or less in the environment of the cell. In certain embodiments, knockdown efficacy is measured at a concentration of 1 nanomolar, 200 picomolar, 100 picomolar, 50 picomolar, 20 picomolar, 10 picomolar, 5 picomolar, 2, picomolar or 1 picomolar in the environment of a cell.

In another aspect, the invention provides a formulation including the agent, nucleic acid, dsNA or hybridization complex of the invention present in an amount effective to reduce target lactate dehydrogenase mRNA levels when the agent, nucleic acid, dsNA or hybridization complex is introduced into a cell of a mammalian subject by at least 10%, at least 50% or at least 80-90%. Optionally, the effective amount is a dosage of 1 microgram to 5 milligrams per kilogram of the subject per day, 100 micrograms to 0.5 milligrams per kilogram, 0.001 to 0.25 milligrams per kilogram, 0.01 to 20 micrograms per kilogram, 0.01 to 10 micrograms per kilogram, 0.10 to 5 micrograms per kilogram, or 0.1 to 2.5 micrograms per kilogram.

In certain embodiments, the formulation includes a lipid nanoparticle. Optionally, the formulation preferentially targets liver and/or neoplasia tissues. In another embodiment, the formulation preferentially targets muscle cells.

In an additional aspect, the invention provides a mammalian cell containing an agent, nucleic acid, dsNA or hybridization complex of the invention.

In a further aspect, the invention provides a pharmaceutical composition containing an agent, nucleic acid, dsNA or hybridization complex of the invention and a pharmaceutically acceptable carrier. In one embodiment, the pharmaceutical composition further includes an LDHB and/or LDHC inhibitor (e.g., a dsNA inhibitor of LDHB and/or LDHC).

In another aspect, the invention provides a kit that includes an agent, nucleic acid, dsNA or hybridization complex of the invention and instructions for its use.

In an additional aspect, the invention provides a composition possessing lactate dehydrogenase inhibitory activity that consists essentially of an agent, nucleic acid, dsNA or hybridization complex of the invention.

Another aspect of the invention provides a method of hybridizing an exogenous agent, nucleic acid, dsNA or hybridization complex to mRNA in a cell that involves introducing into the cell an exogenous agent, nucleic acid, dsNA or hybridization complex sequence and hybridizing the exogenous agent, nucleic acid, dsNA or hybridization complex to a target Lactate Dehydrogenase mRNA sequence that is a sequence of SEQ ID NOs: 361-432.

A further aspect of the invention provides a method of treating an individual with a liver or lung disease or disorder that involves introducing into cells of the individual an exogenous agent, nucleic acid, dsNA or hybridization complex and hybridizing the exogenous agent, nucleic acid, dsNA or hybridization complex to a target Lactate Dehydrogenase mRNA sequence of SEQ ID NOs: 361-432.

An additional aspect of the invention provides a method of forming an in vivo hybridization complex within a cell that involves introducing into the cell an exogenous agent, nucleic acid, dsNA or hybridization complex and hybridizing the exogenous agent, nucleic acid, dsNA or hybridization complex to a target Lactate Dehydrogenase mRNA sequence of SEQ ID NOs: 361-432.

A further aspect of the invention provides a method of inhibiting translation of a target mRNA into a protein within a cell that involves introducing into the cell an exogenous agent, nucleic acid, dsNA or hybridization complex and hybridizing the exogenous agent, nucleic acid, dsNA or hybridization complex to a target Lactate Dehydrogenase mRNA sequence of SEQ ID NOs: 361-432, complexing the exogenous agent, nucleic acid, dsNA or hybridization complex with RISC, and cleaving the mRNA.

In one embodiment, the exogenous agent, nucleic acid, dsNA or hybridization complex is complexed with RISC. In a related embodiment, the RISC cleaves the mRNA.

A further aspect of the invention provides a dsNA having a first strand and a second strand, where the first strand is between 32 and 80 nucleic acid residues in length and possesses a tetraloop, and a second strand of 19 to 30 nucleotides in length that anneals to the first strand to form a duplex, where the second oligonucleotide strand is sufficiently complementary to a target lactate dehydrogenase mRNA sequence of SEQ ID NOs: 361-432 along at least 15 nucleotides of the oligonucleotide strand length to reduce lactate dehydrogenase target mRNA expression when the dsNA is introduced into a mammalian cell.

In one embodiment, the pairs of first strand and second strand sequences are SEQ ID NOs: 7190 and 7191; SEQ ID NOs: 7192 and 7193; SEQ ID NOs: 7196 and 7197; SEQ ID NOs: 7198 and 7199; SEQ ID NOs: 7200 and 7201; SEQ ID NOs: 7202 and 7203; SEQ ID NOs: 7204 and 7205; SEQ ID NOs: 7206 and 7207; SEQ ID NOs: 7208 and 7209; SEQ ID NOs: 7210 and 7211; or SEQ ID NOs: 7212 and 7213.

Optionally, the dsNA is LNP-formulated and/or conjugated to GalNAc,

The invention also provides a method for treating a lactate dehydrogenase knockdown-treatable disease or disorder in a subject that involves administering to a subject having a lactate dehydrogenase knockdown-treatable disease or disorder a tetraloop-containing dsNA, where the administering reduces expression of the LDHA gene in one or more tissues of the subject, thereby treating the lactate dehydrogenase knockdown-treatable disease or disorder in the subject.

In one embodiment, the lactate dehydrogenase knockdown-treatable disease or disorder is a neoplasia, optionally a liver and/or pancreatic tumor(s).

BRIEF DESCRIPTION OF THE DRAWINGS

FIGS. 3A to 3J present primary screen data showing DsiRNA-mediated knockdown of human lactate dehydrogenase (FIGS. 3A to 3D), mouse lactate dehydrogenase (FIG. 3E to 3H), or a composite of both human and mouse lactate dehydrogenase knockdown data (FIGS. 3I and 3J), in human (HeLa) and mouse (B16-F10) cells, respectively. For each DsiRNA tested, two independent qPCR amplicons were assayed (in human cells, amplicons "262-396" and "1304-1419" were assayed, while in mouse cells, amplicons "384-510" and "1402-1504" were assayed).

FIG. 4B demonstrates the duration of the LDH knockdown effect observed for both mRNA and protein expression (using LDHA-718-M24/M527 (DP2685P:DP2692G) in 2185 LNP, 1 mg/kg, single dose, intravenous injection). FIG. 4C shows the specificity of knockdown effects for LDHA, PRODH2 and HAO1, in both mRNA expression levels and protein levels.

FIGS. 5A through 5D show that intravenous injection of LDHA-targeting DsiRNA also reduced oxalate excretion in PH1 model mice (mice pre-treated with AGXT DsiRNA to simulate PH1), as compared to PBS-injected control PH1 model mice, and even as compared to PH1 model mice administered DsiRNA targeting oxalate metabolism pathway components glycolate oxidase (HAO1) or PRODH2 (proline dehydrogenase (oxidase) 2; see FIG. 6). In FIGS. 5A through 5D, mice (n=5/group) were injected on day 0 and day 14 (and on additional days as indicated in the extended studies presented in FIGS. 5B and 5D) with AGXT-targeting DsiRNA (upper arrows of each series), then subjected to intravenous injection of PBS (upper left), anti-PRODH2 DsiRNA (upper right), anti-HAO1 DsiRNA (lower left) or anti-LDHA DsiRNA (lower right), respectively, at days 3, 10, 17 and 24 (and additional dates as shown for results presented in FIGS. 5B and 5D). Oxalate excretion was measured at days 0, 7 and 14 for PBS-treated PH1 model mice, while levels of oxalate excretion were assayed in DsiRNA-treated mice at days −4, 7, 14, 21 and 28 (and at indicated extended dates in FIGS. 5B and 5D). Both PBS- and PRODH2 DsiRNA-treated groups of mice were observed to exhibit dramatically elevated oxalate excretion levels when assayed at day 7 post-AGXT DsiRNA injection. PRODH2 DsiRNA-treated groups of mice were also observed to exhibit further elevated oxalate excretion levels when assayed at day 21 post-initial AGXT DsiRNA injection (while PBS-treated mice were only maintained until day 14). HAO1 DsiRNA-treated groups of mice were also observed to exhibit elevated oxalate excretion levels when assayed at day 7 or day 21 post-initial AGXT DsiRNA injection, though the levels of such elevations appeared to be reduced as compared to PBS-treated or PRODH2 DsiRNA-treated PH1 model mice, and ultimately appeared to converge with anti-LDHA-treated mice at extended timepoints. Remarkably, treatment of PH1 model mice with an LDHA-targeting DsiRNA under the same injection schedule revealed dramatic inhibitions of oxalate elevation at both day 7 and day 21 post-initial AGXT DsiRNA injection, as well as at extended timepoints, where assessed (e.g., FIGS. 5B and 5D). Thus, reduced levels of LDHA mRNA and protein (as demonstrated in FIGS. 4A to 4C above) also translated into phenotypic effects in inhibiting elevation of oxalate excretion in PH1 model mice. FIGS. 5C and 5D show that all DsiRNAs tested in PH1 model mice (PRODH2-, HAO1- and LDHA-targeting DsiRNAs) showed at least some inhibitory impact upon oxalate concentration (left pane of FIG. 5C); however, LDHA-targeting DsiRNA demonstrated the greatest reduction of oxalate excretion, even as compared to HAO1-targeting DsiRNA.

In FIG. 5E, LDHA-718-M24/M527 (DP2685P:DP2692G) in 2185 LNP in Male Agxt$^{-/-}$ mice challenged with ethylene glycol (a PH1 model) was observed to reduce urine oxalate levels, when urine samples were collected using metabolic cages except on day 27, which was collected manually, and kidneys were harvested at day 27 for calcium oxalate analysis. In FIG. 5F, administration of LDHA DsiRNA LDHA-718-M24/M527 (DP2685P:DP2692G) in 2185 LNP was observed to prevent ethylene glycol-induced kidney damage in Agxt$^{-/-}$ mice (0.7% EG was supplied with drinking water to all mice were treated with LDHA DsiRNA 1 (Early Treatment) or 3 weeks (Late Treatment) after EG fed). In FIG. 5G, administration of LDHA DsiRNA LDHA-718-M24/M527 (DP2685P:DP2692G) in 2185 LNP was also observed to prevent ethylene glycol-induced calcium oxalate crystals in Agxt$^{-/-}$ mice (0.7% EG was supplied with drinking water to all mice were treated with LDHA DsiRNA 1 (Early Treatment) or 3 weeks (Late Treatment) after EG fed), where half of each kidney was processed per animal, and 2 sections from each half were scored. All counting in FIG. 5G was performed manually, with crystals/staining visible at a 10× magnification counted.

In FIG. 7A, the M575/M492, M576/M491 and M582/M492 modification patterns present SEQ ID Nos: 7187 (tetraloop-possessing first strand sequence) and 7188 (second strand), with varying modification patterns across such sequences, as indicated. The M583/M494 structure in FIG. 7A presents SEQ ID Nos: 7187 (tetraloop-possessing first strand sequence) and 7189 (second strand, contains deoxynucleotides, where indicated). FIG. 7B shows histograms of % LDHA knockdown across various forms of modified tetraloop constructs, as indicated. FIG. 7C presents dose-response curves and IC$_{50}$ values for indicated modified forms of tetraloop-possessing constructs LDHA-723-M576/M491 (tetraloop-containing strand sequence is SEQ ID NO: 7190 and guide/antisense (lower) strand is SEQ ID NO: 7191), LDHA-1360-M576/M491 and LDHA-1360-M582/M492 (tetraloop-containing strand sequence for LDHA-1360 structures is SEQ ID NO: 7192 and guide/antisense (lower) strand is SEQ ID NO: 7193).

FIG. 8A shows the conversion of 25/27mer modification patterns into tetraloop-possessing agents that was performed. Sequences of 25/27mers are represented by SEQ ID NOs: 7194 and 7195, with the various modification patterns shown made to such sequences. Tetraloop-possessing sequences in FIGS. 8A to 8E correspond to SEQ ID NOs: 7187 and 7188. FIG. 8B to 8E show histograms of knockdown data obtained for all indicated tetraloop agents in vitro. Certain duplex sequences were selected for scale-up and additional testing.

In FIG. 9A, the oligonucleotides of LDHA-723-M576/M491 correspond to SEQ ID NOs: 7190 and 7191.

FIGS. 10A and 10B show that LNP-formulated LDHA-718-M571/M550 possessed high levels of anti-tumor efficacy (TGI of 78%; FIG. 10A) and also produced >75% knockdown of LDHA in Hep3B tumors of treated animals, on average (FIG. 10B), after a single round of dosing with the LNP/LDHA-718-M571/M550 DsiRNA.

DETAILED DESCRIPTION OF THE INVENTION

Figure 1:
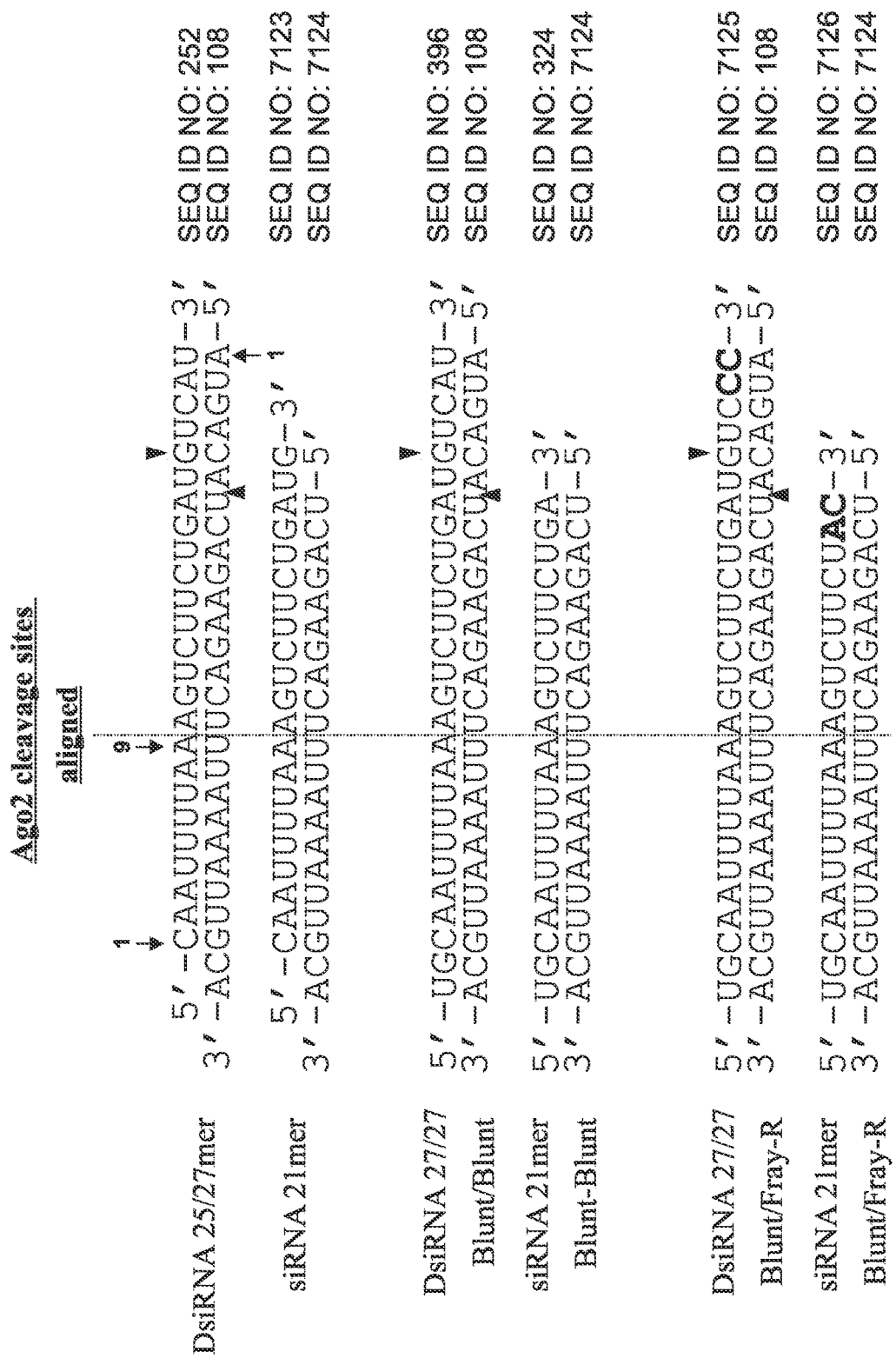
FIG. 1 shows the structures of exemplary DsiRNA agents of the invention targeting a site in the lactate dehydrogenase RNA referred to herein as the "lactate dehydrogenase-1287" or "LDHA-1287" target site. UPPER case=unmodified RNA, lower case=DNA, Bold=mismatch base pair nucleotides; arrowheads indicate projected Dicer enzyme cleavage sites; dashed line indicates sense strand (top strand) sequences corresponding to the projected Argonaute 2 (Ago2) cleavage site within the targeted lactate dehydrogenase sequence.

The present invention is directed to methods and agents that reduce and/or inhibit the expression and/or levels of LDHA in a cell, tissue and/or subject. Modes of delivery and/or LDHA inhibitory agents that are capable of being delivered in a manner that tends not to deliver to muscle and/or other tissue(s) in which LDHA inhibition might be deleterious in at least certain individuals are identified and described herein. Certain agents of the invention knock down expression of the LDHA transcript, in certain embodiments for therapeutic purpose. LDHA is identified herein as a therapeutic target for treatment of chronic kidney disease, pyruvate dehydrogenase complex deficiency, or for treatment of PH1 and/or any other lactate dehydrogenase-associated disease or disorder, including, e.g., PH2, PH3 and idiopathic hyperoxaluria, as well as oncology. In certain embodiments, the invention provides compositions that contain nucleic acids, for example double stranded NA ("dsNA"), and methods for preparing them, that are capable of reducing the level and/or expression of the lactate dehydrogenase gene in vivo or in vitro. In some embodiments, such dsNA molecules are substrates of the Dicer enzyme, having double-stranded duplex regions of approximately 25 or more nucleotides in length, optionally possessing extended single-stranded 5' overhang regions on either the guide or passenger strand of the Dicer substrate dsNA. In certain embodiments, a dsNA of the invention can have first and second strands of a duplex joined by a nucleotide linker—optionally, such a linker includes a tetraloop. In related embodiments, one of the strands of the dsRNA contains a region of nucleotide sequence that has a length that ranges from 19 to 35 nucleotides that can direct the destruction and/or translational inhibition of the targeted lactate dehydrogenase transcript. Optionally, a dsNA of the invention is modified, for example with 2'-O-methyl modifications and/or GalNAc moieties.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The present invention features one or more DsiRNA molecules that can modulate (e.g., inhibit) lactate dehydrogenase expression. The DsiRNAs of the invention optionally can be used in combination with modulators of other genes and/or gene products associated with the maintenance or development of diseases or disorders associated with lactate dehydrogenase misregulation (e.g., oxalate accumulation, PH1, chronic kidney disease, pyruvate dehydrogenase complex deficiency, etc.). The DsiRNA agents of the invention modulate lactate dehydrogenase RNAs such as those corresponding to the cDNA sequences referred to by GenBank Accession Nos. NM_005566.3 (human lactate dehydrogenase A) and NM_001136069.2 (mouse lactate dehydrogenase A), which are referred to herein generally as "lactate dehydrogenase."

The below description of the various aspects and embodiments of the invention is provided with reference to exemplary lactate dehydrogenase RNAs, generally referred to herein as lactate dehydrogenase, LDH or LDHA (for the "A" isoform most prominently targeted). However, such reference is meant to be exemplary only and the various aspects and embodiments of the invention are also directed to alternate lactate dehydrogenase RNAs, such as mutant lactate dehydrogenase RNAs or additional lactate dehydrogenase splice variants. Certain aspects and embodiments are also directed to other genes involved in lactate dehydrogenase pathways, including genes whose misregulation acts in association with that of lactate dehydrogenase (or is affected or affects lactate dehydrogenase regulation) to produce phenotypic effects that may be targeted for treatment (e.g., PH1, chronic kidney disease, pyruvate dehydrogenase complex deficiency, etc.). See, e.g., the enzymes of FIG. 2. Such additional genes, including those of pathways that act in coordination with lactate dehydrogenase, can be targeted using dsRNA and the methods described herein for use of lactate dehydrogenase-targeting dsRNAs. Thus, the inhibition and the effects of such inhibition of the other genes can be performed as described herein.

The term "lactate dehydrogenase" refers to nucleic acid sequences encoding a lactate dehydrogenase protein, peptide, or polypeptide (e.g., lactate dehydrogenase transcripts, such as the sequences of lactate dehydrogenase Genbank Accession Nos. NM_005566.3 and NM_001136069.2). In certain embodiments, the term "lactate dehydrogenase" is also meant to include other lactate dehydrogenase encoding sequence, such as other lactate dehydrogenase isoforms, mutant lactate dehydrogenase genes, splice variants of lactate dehydrogenase genes, and lactate dehydrogenase gene polymorphisms. The term "lactate dehydrogenase" is also used to refer to the polypeptide gene product of an lactate dehydrogenase gene/transcript, e.g., an lactate dehydrogenase protein, peptide, or polypeptide, such as those encoded by lactate dehydrogenase Genbank Accession Nos. NP_005557.1 and NP_001129541.2.

As used herein, a "lactate dehydrogenase knockdown-treatable disease or disorder" refers to a disease or disorder known in the art to be associated with altered lactate dehydrogenase expression, level and/or activity, or to a disease or disorder such as PH1 in which lactate dehydrogenase knockdown is known or predicted to be therapeutic or otherwise advantageous, or to PH2, PH3 or idiopathic hyperoxaluria, chronic kidney disease, pyruvate dehydrogenase complex deficiency or cancer. Notably, a "lactate dehydrogenase knockdown-treatable disease or disorder" includes PH1, PH2, PH3, idiopathic hyperoxaluria, chronic kidney disease, pyruvate dehydrogenase complex deficiency, cancer and other art recognized diseases or disorders associated with oxalate accumulation.

An anti-lactate dehydrogenase dsRNA of the invention is deemed to possess "lactate dehydrogenase inhibitory activity" if a statistically significant reduction in lactate dehydrogenase RNA (or when the lactate dehydrogenase protein is assessed, lactate dehydrogenase protein levels) is seen when an anti-lactate dehydrogenase dsRNA of the invention is administered to a system (e.g., cell-free in vitro system), cell, tissue or organism, as compared to a selected control. The distribution of experimental values and the number of replicate assays performed will tend to dictate the parameters of what levels of reduction in lactate dehydrogenase RNA (either as a % or in absolute terms) is deemed statistically significant (as assessed by standard methods of determining statistical significance known in the art). However, in certain embodiments, "lactate dehydrogenase inhibitory activity" is defined based upon a % or absolute level of reduction in the level of lactate dehydrogenase in a system, cell, tissue or organism. For example, in certain embodiments, a dsRNA of the invention is deemed to possess lactate dehydrogenase inhibitory activity if at least a 5% reduction or at least a 10% reduction in lactate dehydrogenase RNA is observed in the presence of a dsRNA of the invention relative to lactate dehydrogenase levels seen for a suitable control. (For example, in vivo lactate dehydrogenase levels in a tissue and/or subject can, in certain embodiments, be deemed to be inhibited by a dsRNA agent of the invention if, e.g., a 5% or 10% reduction in lactate dehydrogenase levels is observed relative to a control.) In certain other embodiments, a dsRNA of the invention is deemed to possess lactate dehydrogenase inhibitory activity if lactate dehydrogenase RNA levels are observed to be reduced by at least 15% relative to a selected control, by at least 20% relative to a selected control, by at least 25% relative to a selected control, by at least 30% relative to a selected control, by at least 35% relative to a selected control, by at least 40% relative to a selected control, by at least 45% relative to a selected control, by at least 50% relative to a selected control, by at least 55% relative to a selected control, by at least 60% relative to a selected control, by at least 65% relative to a selected control, by at least 70% relative to a selected control, by at least 75% relative to a selected control, by at least 80% relative to a selected control, by at least 85% relative to a selected control, by at least 90% relative to a selected control, by at least 95% relative to a selected control, by at least 96% relative to a selected control, by at least 97% relative to a selected control, by at least 98% relative to a selected control or by at least 99% relative to a selected control. In some embodiments, complete inhibition of lactate dehydrogenase is required for a dsRNA to be deemed to possess lactate dehydrogenase inhibitory activity. In certain models (e.g., cell culture), a dsRNA is deemed to possess lactate dehydrogenase inhibitory activity if at least a 50% reduction in lactate dehydrogenase levels is observed relative to a suitable control. In certain other embodiments, a dsRNA is deemed to possess lactate dehydrogenase inhibitory activity if at least an 80% reduction in lactate dehydrogenase levels is observed relative to a suitable control.

By way of specific example, in Example 2 below, a series of DsiRNAs targeting lactate dehydrogenase were tested for the ability to reduce lactate dehydrogenase mRNA levels in human HeLa or mouse B16-F10 cells in vitro, at 1 nM concentrations in the environment of such cells and in the presence of a transfection agent (Lipofectamine™ RNAiMAX, Invitrogen). Within Example 2 below, lactate dehydrogenase inhibitory activity was ascribed to those DsiRNAs that were observed to effect at least a 70% reduction of lactate dehydrogenase mRNA levels under the assayed conditions. It is contemplated that lactate dehydrogenase inhibitory activity could also be attributed to a dsRNA under either more or less stringent conditions than those employed for Example 2 below, even when the same or a similar assay and conditions are employed. For example, in certain embodiments, a tested dsRNA of the invention is deemed to possess lactate dehydrogenase inhibitory activity if at least a 10% reduction, at least a 20% reduction, at least a 30% reduction, at least a 40% reduction, at least a 50% reduction, at least a 60% reduction, at least a 75% reduction, at least an 80% reduction, at least an 85% reduction, at least a 90% reduction, or at least a 95% reduction in lactate dehydrogenase mRNA levels is observed in a mammalian cell line in vitro at 1 nM dsRNA concentration or lower in the environment of a cell, relative to a suitable control.

Use of other endpoints for determination of whether a double stranded RNA of the invention possesses lactate dehydrogenase inhibitory activity is also contemplated. Specifically, in one embodiment, in addition to or as an alternative to assessing lactate dehydrogenase mRNA levels, the ability of a tested dsRNA to reduce lactate dehydrogenase protein levels (e.g., at 48 hours after contacting a mammalian cell in vitro or in vivo) is assessed, and a tested dsRNA is deemed to possess lactate dehydrogenase inhibitory activity if at least a 10% reduction, at least a 20% reduction, at least a 30% reduction, at least a 40% reduction, at least a 50% reduction, at least a 60% reduction, at least a 70% reduction, at least a 75% reduction, at least an 80% reduction, at least an 85% reduction, at least a 90% reduction, or at least a 95% reduction in lactate dehydrogenase protein levels is observed in a mammalian cell contacted with the assayed double stranded RNA in vitro or in vivo, relative to a suitable control. Additional endpoints contemplated include, e.g., assessment of a phenotype associated with reduction of lactate dehydrogenase levels—e.g., reduction of oxalate accumulation and/or PH1 phenotypes and/or PH1-associated phenotypes (e.g., kidney diseases or disorders associated with oxalate accumulation), or diseases or disorders of other organs, e.g., muscle, associated with oxalate accumulation.

Lactate Dehydrogenase inhibitory activity can also be evaluated over time (duration) and over concentration ranges (potency), with assessment of what constitutes a dsRNA possessing lactate dehydrogenase inhibitory activity adjusted in accordance with concentrations administered and duration of time following administration. Thus, in certain embodiments, a dsRNA of the invention is deemed to possess lactate dehydrogenase inhibitory activity if at least a 50% reduction in lactate dehydrogenase activity is observed/persists at a duration of time of 2 hours, 5 hours, 10 hours, 1 day, 2 days, 3 days, 4 days, 5 days, 6 days, 7 days, 8 days, 9 days, 10 days or more after administration of the dsRNA to a cell or organism. In additional embodiments, a dsRNA of the invention is deemed to be a potent lactate dehydrogenase inhibitory agent if lactate dehydrogenase inhibitory activity (e.g., in certain embodiments, at least 50% inhibition of lactate dehydrogenase) is observed at a concentration of 1 nM or less, 500 pM or less, 200 pM or less, 100 pM or less, 50 pM or less, 20 pM or less, 10 pM or less, 5 pM or less, 2 pM or less or even 1 pM or less in the environment of a cell, for example, within an in vitro assay for lactate dehydrogenase inhibitory activity as described herein. In certain embodiments, a potent lactate dehydrogenase inhibitory dsRNA of the invention is defined as one that is capable of lactate dehydrogenase inhibitory activity (e.g., in certain embodiments, at least 20% reduction of lactate dehydrogenase levels) at a formulated concentration of 10 mg/kg or less when administered to a subject in an effective delivery vehicle (e.g., an effective lipid nanoparticle formulation). Preferably, a potent lactate dehydrogenase inhibitory dsRNA of the invention is defined as one that is capable of lactate dehydrogenase inhibitory activity (e.g., in certain embodiments, at least 50% reduction of lactate dehydrogenase levels) at a formulated concentration of 5 mg/kg or less when administered to a subject in an effective delivery vehicle. More preferably, a potent lactate dehydrogenase inhibitory dsRNA of the invention is defined as one that is capable of lactate dehydrogenase inhibitory activity (e.g., in certain embodiments, at least 50% reduction of lactate dehydrogenase levels) at a formulated concentration of 5 mg/kg or less when administered to a subject in an effective delivery vehicle. Optionally, a potent lactate dehydrogenase inhibitory dsRNA of the invention is defined as one that is capable of lactate dehydrogenase inhibitory activity (e.g., in certain embodiments, at least 50% reduction of lactate dehydrogenase levels) at a formulated concentration of 2 mg/kg or less, or even 1 mg/kg or less, when administered to a subject in an effective delivery vehicle. Exemplary discrete formulated concentrations of lactate dehydrogenase-targeting RNAi agents of the invention include about 5 mg/kg, about 2 mg/kg, about 1 mg/kg, about 500 µg/kg, about 250 µg/kg, about 100 µg/kg, about 50 µg/kg, about 25 µg/kg, about 10 µg/kg, about 5 µg/kg, about 2.5 µg/kg, about 1 µg/kg, about 500 ng/kg, about 250 ng/kg, about 100 ng/kg, about 50 ng/kg, about 25 ng/kg, about 10 ng/kg, about 5 ng/kg, about 2.5 ng/kg, about 1 ng/kg and about 500 µg/kg.

About: As used herein, the term "about" means+/−10% of the recited value. Use of "about" is contemplated in reference to all ranges and values recited herein.

In certain embodiments, the phrase "consists essentially of" is used in reference to the anti-lactate dehydrogenase dsRNAs of the invention. In some such embodiments, "consists essentially of" refers to a composition that comprises a dsRNA of the invention which possesses at least a certain level of lactate dehydrogenase inhibitory activity (e.g., at least 50% lactate dehydrogenase inhibitory activity) and that also comprises one or more additional components and/or modifications that do not significantly impact the lactate dehydrogenase inhibitory activity of the dsRNA. For example, in certain embodiments, a composition "consists essentially of" a dsRNA of the invention where modifications of the dsRNA of the invention and/or dsRNA-associated components of the composition do not alter the lactate dehydrogenase inhibitory activity (optionally including potency or duration of lactate dehydrogenase inhibitory activity) by greater than 3%, greater than 5%, greater than 10%, greater than 15%, greater than 20%, greater than 25%, greater than 30%, greater than 35%, greater than 40%, greater than 45%, or greater than 50% relative to the dsRNA of the invention in isolation. In certain embodiments, a composition is deemed to consist essentially of a dsRNA of the invention even if more dramatic reduction of lactate dehydrogenase inhibitory activity (e.g., 80% reduction, 90% reduction, etc. in efficacy, duration and/or potency) occurs in the presence of additional components or modifications, yet where lactate dehydrogenase inhibitory activity is not significantly elevated (e.g., observed levels of lactate dehydrogenase inhibitory activity are within 10% those observed for the dsRNA of the invention) in the presence of additional components and/or modifications.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and unlocked nucleic acids (UNAs or unlocked nucleobase analogs; see, e.g., Jensen et al. *Nucleic Acids Symposium Series* 52: 133-4), and derivatives thereof.

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, *Nucleic Acids Res.* 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge, 2'-LNA or other bicyclic or "bridged" nucleoside analog, and 2'-O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in Eckstein et al., U.S. Pat. No. 5,672,695 and Matulic-Adamic et al., U.S. Pat. No. 6,248,878. "Modified nucleotides" of the instant invention can also include nucleotide analogs as described above.

In reference to the nucleic acid molecules of the present disclosure, modifications may exist upon these agents in patterns on one or both strands of the double stranded ribonucleic acid (dsRNA). As used herein, "alternating positions" refers to a pattern where every other nucleotide is a modified nucleotide or there is an unmodified nucleotide (e.g., an unmodified ribonucleotide) between every modified nucleotide over a defined length of a strand of the dsRNA (e.g., 5'-MNMNMN-3'; 3'-MNMNMN-5'; where M is a modified nucleotide and N is an unmodified nucleotide). The modification pattern starts from the first nucleotide position at either the 5' or 3' terminus according to a position numbering convention, e.g., as described herein (in certain embodiments, position 1 is designated in reference to the terminal residue of a strand following a projected Dicer cleavage event of a DsiRNA agent of the invention; thus, position 1 does not always constitute a 3' terminal or 5' terminal residue of a pre-processed agent of the invention). The pattern of modified nucleotides at alternating positions may run the full length of the strand, but in certain embodiments includes at least 4, 6, 8, 10, 12, 14 nucleotides containing at least 2, 3, 4, 5, 6 or 7 modified nucleotides, respectively. As used herein, "alternating pairs of positions" refers to a pattern where two consecutive modified nucleotides are separated by two consecutive unmodified nucleotides over a defined length of a strand of the dsRNA (e.g., 5'-MMNNMMNNMMNN-3'; 3'-MMNNMMNNMMNN-5'; where M is a modified nucleotide and N is an unmodified nucleotide). The modification pattern starts from the first nucleotide position at either the 5' or 3' terminus according to a position numbering convention such as those described herein. The pattern of modified nucleotides at alternating positions may run the full length of the strand, but preferably includes at least 8, 12, 16, 20, 24, 28 nucleotides containing at least 4, 6, 8, 10, 12 or 14 modified nucleotides, respectively. It is emphasized that the above modification patterns are exemplary and are not intended as limitations on the scope of the invention.

As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In the dsRNAs of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the compounds and methods of the invention, e.g., those disclosed in U.S. Pat. Nos. 5,432,272 and 6,001,983 to Benner and US Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine) (K), 3-β-D-ribofuranosyl-(1-methyl-pyrazolo[4, 3-d]pyrimidine-5,7(4H,6H)-dione) (P), iso-cytosine (iso-C), iso-guanine (iso-G), 1-β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof (Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Preferably, the universal bases does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43).

As used herein, "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length. Examples of loops include the unpaired nucleotides present in such structures as hairpins, stem loops, or extended loops.

As used herein, "extended loop" in the context of a dsRNA refers to a single stranded loop and in addition 1, 2, 3, 4, 5, 6 or up to 20 base pairs or duplexes flanking the loop. In an extended loop, nucleotides that flank the loop on the 5' side form a duplex with nucleotides that flank the loop on the 3' side. An extended loop may form a hairpin or stem loop.

As used herein, "tetraloop" in the context of a dsRNA refers to a loop (a single stranded region) consisting of four nucleotides that forms a stable secondary structure that contributes to the stability of adjacent Watson-Crick hybridized nucleotides. Without being limited to theory, a tetraloop may stabilize an adjacent Watson-Crick base pair by stacking interactions. In addition, interactions among the four nucleotides in a tetraloop include but are not limited to non-Watson-Crick base pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM $NaHPO_4$ to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002; SHINJI et al. Nippon Kagakkai Koen Yokoshu VOL. 78th; NO. 2; PAGE. 731 (2000).)

As used herein, the term "siRNA" refers to a double stranded nucleic acid in which each strand comprises RNA, RNA analog(s) or RNA and DNA. The siRNA comprises between 19 and 23 nucleotides or comprises 21 nucleotides. The siRNA typically has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the lactate dehydrogenase gene/RNA.

Where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

The term "double-stranded RNA" or "dsRNA", as used herein, refers to a complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where separate RNA molecules, such dsRNA are often referred to as siRNA ("short interfering RNA") or DsiRNA ("Dicer substrate siRNAs"). Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop", "short hairpin RNA" or "shRNA". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. In addition, as used herein, "dsRNA" may include chemical modifications to ribonucleotides, internucleoside linkages, end-groups, caps, and conjugated moieties, including substantial modifications at multiple nucleotides and including all types of modifications disclosed herein or known in the art. Any such modifications, as used in a siRNA- or DsiRNA-type molecule, are encompassed by "dsRNA" for the purposes of this specification and claims.

The phrase "duplex region" refers to the region in two complementary or substantially complementary oligonucleotides that form base pairs with one another, either by Watson-Crick base pairing or other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As used herein "DsiRNAmm" refers to a DisRNA having a "mismatch tolerant region" containing one, two, three or four mismatched base pairs of the duplex formed by the sense and antisense strands of the DsiRNA, where such mismatches are positioned within the DsiRNA at a location(s) lying between (and thus not including) the two terminal base pairs of either end of the DsiRNA. The structure and mismatch positioning of exemplary forms of DsiRNAmm compositions are described in greater detail below.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, i.e., (the melting temperature; Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(° C.)=2(\# \text{ of A+T bases})+4(\# \text{ of G+C bases})$. For hybrids between 18 and 49 base pairs in length, $Tm(° C.)=81.5+16.6(\log_{10}[Na+])+0.41\ (\%\ G+C)-(600/N)$, where N is the number of bases in the hybrid, and [Na+] is the concentration of sodium ions in the hybridization buffer ([Na+] for 1×SSC=0.165 M). For example, a hybridization determination buffer is shown in Table 1.

TABLE 1

| | final conc. | Vender | Cat# | Lot# | m.w./Stock | To make 50 mL solution |
|---|---|---|---|---|---|---|
| NaCl | 100 mM | Sigma | S-5150 | 41K8934 | 5M | 1 mL |
| KCl | 80 mM | Sigma | P-9541 | 70K0002 | 74.55 | 0.298 g |
| $MgCl_2$ | 8 mM | Sigma | M-1028 | 120K8933 | 1M | 0.4 mL |
| sucrose | 2% w/v | Fisher | BP220-212 | 907105 | 342.3 | 1 g |
| Tris-HCl | 16 mM | Fisher | BP1757-500 | 12419 | 1M | 0.8 mL |
| $NaH_2PO_4$ | 1 mM | Sigma | S-3193 | 52H-029515 | 120.0 | 0.006 g |
| EDTA | 0.02 mM | Sigma | E-7889 | 110K89271 | 0.5M | 2 µL |
| $H_2O$ | | Sigma | W-4502 | 51K2359 adjust with HCl | | to 50 mL |
| pH = 7.0 at 20° C. | | | | | | |

Useful variations on hybridization conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York.

As used herein, "oligonucleotide strand" is a single stranded nucleic acid molecule. An oligonucleotide may comprise ribonucleotides, deoxyribonucleotides, modified nucleotides (e.g., nucleotides with 2' modifications, synthetic base analogs, etc.) or combinations thereof. Such modified oligonucleotides can be preferred over native forms because of properties such as, for example, enhanced cellular uptake and increased stability in the presence of nucleases.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide. As used herein, the term "ribonucleotide" specifically excludes a deoxyribonucleotide, which is a nucleotide possessing a single proton group at the 2' ribose ring position.

As used herein, the term "deoxyribonucleotide" encompasses natural and synthetic, unmodified and modified deoxyribonucleotides. Modifications include changes to the sugar moiety, to the base moiety and/or to the linkages between deoxyribonucleotide in the oligonucleotide. As used herein, the term "deoxyribonucleotide" also includes a modified ribonucleotide that does not permit Dicer cleavage of a dsRNA agent, e.g., a 2'-O-methyl ribonucleotide, a phosphorothioate-modified ribonucleotide residue, etc., that does not permit Dicer cleavage to occur at a bond of such a residue.

As used herein, the term "PS-NA" refers to a phosphorothioate-modified nucleotide residue. The term "PS-NA" therefore encompasses both phosphorothioate-modified ribonucleotides ("PS-RNAs") and phosphorothioate-modified deoxyribonucleotides ("PS-DNAs").

As used herein, "Dicer" refers to an endoribonuclease in the RNase III family that cleaves a dsRNA or dsRNA-containing molecule, e.g., double-stranded RNA (dsRNA) or pre-microRNA (miRNA), into double-stranded nucleic acid fragments 19-25 nucleotides long, usually with a two-base overhang on the 3' end. With respect to certain dsRNAs of the invention (e.g., "DsiRNAs"), the duplex formed by a dsRNA region of an agent of the invention is recognized by Dicer and is a Dicer substrate on at least one strand of the duplex. Dicer catalyzes the first step in the RNA interference pathway, which consequently results in the degradation of a target RNA. The protein sequence of human Dicer is provided at the NCBI database under accession number NP_085124, hereby incorporated by reference.

Dicer "cleavage" can be determined as follows (e.g., see Collingwood et al., Oligonucleotides 18:187-200 (2008)). In a Dicer cleavage assay, RNA duplexes (100 pmol) are incubated in 20 µL of 20 mM Tris pH 8.0, 200 mM NaCl, 2.5 mM MgCl2 with or without 1 unit of recombinant human Dicer (Stratagene, La Jolla, Calif.) at 37° C. for 18-24 hours. Samples are desalted using a Performa SR 96-well plate (Edge Biosystems, Gaithersburg, Md.). Electrospray-ionization liquid chromatography mass spectroscopy (ESI-LCMS) of duplex RNAs pre- and post-treatment with Dicer is done using an Oligo HTCS system (Novatia, Princeton, N.J.; Hail et al., 2004), which consists of a ThermoFinnigan TSQ7000, Xcalibur data system, ProMass data processing software and Paradigm MS4 HPLC (Michrom BioResources, Auburn, Calif.). In this assay, Dicer cleavage occurs where at least 5%, 10%, 20%, 30%, 40%, 50%, 60%, 70%, 80%, 90%, 95%, or even 100% of the Dicer substrate dsRNA, (i.e., 25-30 bp, dsRNA, preferably 26-30 bp dsRNA) is cleaved to a shorter dsRNA (e.g., 19-23 bp dsRNA, preferably, 21-23 bp dsRNA).

As used herein, "Dicer cleavage site" refers to the sites at which Dicer cleaves a dsRNA (e.g., the dsRNA region of a DsiRNA agent of the invention). Dicer contains two RNase III domains which typically cleave both the sense and antisense strands of a dsRNA. The average distance between the RNase III domains and the PAZ domain determines the length of the short double-stranded nucleic acid fragments it produces and this distance can vary (Macrae et al. (2006) Science 311: 195-8). As shown in FIG. 1, Dicer is projected to cleave certain double-stranded ribonucleic acids of the instant invention that possess an antisense strand having a 2 nucleotide 3' overhang at a site between the $21^{st}$ and $22^{nd}$ nucleotides removed from the 3' terminus of the antisense strand, and at a corresponding site between the $21^{st}$ and $22^{nd}$ nucleotides removed from the 5' terminus of the sense strand. The projected and/or prevalent Dicer cleavage site(s) for dsRNA molecules distinct from those depicted in FIG. 1 may be similarly identified via art-recognized methods, including those described in Macrae et al. While the Dicer cleavage events depicted in FIG. 1 generate 21 nucleotide siRNAs, it is noted that Dicer cleavage of a dsRNA (e.g., DsiRNA) can result in generation of Dicer-processed siRNA lengths of 19 to 23 nucleotides in length. Indeed, in certain embodiments, a double-stranded DNA region may be included within a dsRNA for purpose of directing prevalent Dicer excision of a typically non-preferred 19mer or 20mer siRNA, rather than a 21mer.

In certain embodiments, dsRNAs of the invention are Dicer substrate siRNAs ("DsiRNAs"). DsiRNAs can possess certain advantages as compared to inhibitory nucleic acids that are not dicer substrates ("non-DsiRNAs"). Such advantages include, but are not limited to, enhanced duration of effect of a DsiRNA relative to a non-DsiRNA, as well as enhanced inhibitory activity of a DsiRNA as compared to a non-DsiRNA (e.g., a 19-23mer siRNA) when each inhibitory nucleic acid is suitably formulated and assessed for inhibitory activity in a mammalian cell at the same concentration (in this latter scenario, the DsiRNA would be identified as more potent than the non-DsiRNA). Detection of the enhanced potency of a DsiRNA relative to a non-DsiRNA is often most readily achieved at a formulated concentration (e.g., transfection concentration of the dsRNA) that results in the DsiRNA eliciting approximately 30-70% knockdown activity upon a target RNA (e.g., a mRNA). For active DsiRNAs, such levels of knockdown activity are most often achieved at in vitro mammalian cell DsiRNA transfection concentrations of 1 nM or less of as suitably formulated, and in certain instances are observed at DsiRNA transfection concentrations of 200 pM or less, 100 pM or less, 50 pM or less, 20 pM or less, 10 pM or less, 5 pM or less, or even 1 pM or less. Indeed, due to the variability among DsiRNAs of the precise concentration at which 30-70% knockdown of a target RNA is observed, construction of an $IC_{50}$ curve via assessment of the inhibitory activity of DsiRNAs and non-DsiRNAs across a range of effective concentrations is a preferred method for detecting the enhanced potency of a DsiRNA relative to a non-DsiRNA inhibitory agent.

As used herein, "overhang" refers to unpaired nucleotides, in the context of a duplex having one or more free ends at the 5' terminus or 3' terminus of a dsRNA. In certain embodiments, the overhang is a 3' or 5' overhang on the antisense strand or sense strand. In some embodiments, the overhang is a 3' overhang having a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. "Blunt" or "blunt end" means that there are no unpaired nucleotides at that end of the dsRNA, i.e., no nucleotide overhang. For clarity, chemical caps or non-nucleotide chemical moieties conjugated to the 3' end or 5' end of an siRNA are not considered in determining whether an siRNA has an overhang or is blunt ended. In certain embodiments, the invention provides a dsRNA molecule for inhibiting the expression of the lactate dehydrogenase target gene in a cell or mammal, wherein the dsRNA comprises an antisense strand comprising a region of complementarity which is complementary to at least a part of an mRNA formed in the expression of the lactate dehydrogenase target gene, and wherein the region of complementarity is less than 35 nucleotides in length, optionally 19-24 nucleotides in length or 25-30 nucleotides in length, and wherein the dsRNA, upon contact with a cell expressing the lactate dehydrogenase target gene, inhibits the expression of the lactate dehydrogenase target gene by at least 10%, 25%, or 40%.

As used herein, the term "RNA processing" refers to processing activities performed by components of the siRNA, miRNA or RNase H pathways (e.g., Drosha, Dicer, Argonaute2 or other RISC endoribonucleases, and RNaseH), which are described in greater detail below (see "RNA Processing" section below). The term is explicitly distinguished from the post-transcriptional processes of 5' capping of RNA and degradation of RNA via non-RISC- or non-RNase H-mediated processes. Such "degradation" of an RNA can take several forms, e.g. deadenylation (removal of a 3' poly(A) tail), and/or nuclease digestion of part or all of the body of the RNA by one or more of several endo- or exo-nucleases (e.g., RNase III, RNase P, RNase T1, RNase A (1, 2, 3, 4/5), oligonucleotidase, etc.).

By "homologous sequence" is meant a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include conserved sequence regions shared by more than one polynucleotide sequence. Homology does not need to be perfect homology (e.g., 100%), as partially homologous sequences are also contemplated by the instant invention (e.g., 99%, 98%, 97%, 96%, 95%, 94%, 93%, 92%, 91%, 90%, 89%, 88%, 87%, 86%, 85%, 84%, 83%, 82%, 81%, 80% etc.). Indeed, design and use of the dsRNA agents of the instant invention contemplates the possibility of using such dsRNA agents not only against target RNAs of lactate dehydrogenase possessing perfect complementarity with the presently described dsRNA agents, but also against target lactate dehydrogenase RNAs possessing sequences that are, e.g., only 99%, 98%, 97%, 96%, 95%, 94%, 93%, 92%, 91%, 90%, 89%, 88%, 87%, 86%, 85%, 84%, 83%, 82%, 81%, 80% etc. complementary to said dsRNA agents. Similarly, it is contemplated that the presently described dsRNA agents of the instant invention might be readily altered by the skilled artisan to enhance the extent of complementarity between said dsRNA agents and a target lactate dehydrogenase RNA, e.g., of a specific allelic variant of lactate dehydrogenase (e.g., an allele of enhanced therapeutic interest). Indeed, dsRNA agent sequences with insertions, deletions, and single point mutations relative to the target lactate dehydrogenase sequence can also be effective for inhibition. Alternatively, dsRNA agent sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, a gapped alignment, the alignment is optimized by introducing appropriate gaps, and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, a global alignment the alignment is optimized by introducing appropriate gaps, and percent identity is determined over the entire length of the sequences aligned. (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the dsRNA antisense strand and the portion of the lactate dehydrogenase RNA sequence is preferred. Alternatively, the dsRNA may be defined functionally as a nucleotide sequence (or oligonucleotide sequence) that is capable of hybridizing with a portion of the lactate dehydrogenase RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4. The length of the identical nucleotide sequences may be at least 10, 12, 15, 17, 20, 22, 25, 27 or 30 bases.

By "conserved sequence region" is meant, a nucleotide sequence of one or more regions in a polynucleotide does not vary significantly between generations or from one biological system, subject, or organism to another biological system, subject, or organism. The polynucleotide can include both coding and non-coding DNA and RNA.

By "sense region" is meant a nucleotide sequence of a dsRNA molecule having complementarity to an antisense region of the dsRNA molecule. In addition, the sense region of a dsRNA molecule can comprise a nucleic acid sequence having homology with a target nucleic acid sequence.

In certain embodiments, an agent of the invention is an "antisense compound" or "antisense oligomeric compound", which refers to an oligomeric compound that is at least partially complementary to the region of a target nucleic acid molecule to which it hybridizes and which modulates (increases or decreases) its expression. This term includes oligonucleotides, oligonucleosides, oligonucleotide analogs, oligonucleotide mimetics, antisense compounds, antisense oligomeric compounds, and chimeric combinations of these, Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of antisense compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Antisense double-stranded compounds can be two strands hybridized to form double-stranded compounds or a single strand with sufficient self-complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, the antisense compound comprises a single stranded oligonucleotide. In some embodiments of the invention the antisense compound contains chemical modifications. In a certain embodiment, the antisense compound is a single stranded, chimeric oligonucleotide wherein the modifications of sugars, bases, and internucleoside linkages are independently selected.

Exemplary antisense compounds in accordance with this invention may comprise an antisense compound from about 12 to about 35 nucleobases or more (i.e. from about 12 to about 35 or more linked nucleosides). In other words, a single-stranded compound of the invention can comprise from about 12 to about 35 nucleobases, and a double-stranded antisense compound of the invention (such as a siRNA, for example, as described elsewhere herein) comprises two strands, each of which is independently from about 12 to about 35 or more nucleobases. This includes oligonucleotides 15 to 35 or more, e.g., 15 to 80 nucleobases in length and 16 to 35 or more nucleobases in length. Contained within the antisense compounds of the invention (whether single or double stranded and on at least one strand) are antisense portions. The "antisense portion" is that part of the antisense compound that is designed to work by one of the aforementioned antisense mechanisms. One of ordinary skill in the art will appreciate that about 12 to about 35 nucleobases includes 12, 13, 14, 15, 16, 17, 18, 19, 20, 21, 22, 23, 24, 25, 26, 27, 28, 29, 30, 31, 32, 33, 34, or 35 nucleobases.

Antisense compounds about 12 to 35 nucleobases in length, optionally about 15 to 35 nucleobases in length, comprising a stretch of at least eight (8), optionally at least 12, e.g., at least 15 consecutive nucleobases targeted to the active target regions, are considered to be suitable antisense compounds as well.

Modifications can be made to the agents, including, e.g., the antisense compounds of the instant invention, and may include conjugate groups attached to one of the termini, selected nucleobase positions, sugar positions or to one or more of the internucleoside linkages. Possible modifications include, but are not limited to, 2'-fluoro (2'-F), 2'-OMethyl (2'-OMe), 2'-Methoxy ethoxy (2'-MOE) sugar modifications, inverted abasic caps, deoxynucleobases, and bicyclic nucleobase analogs such as locked nucleic acids (including LNA) and ENA.

By "antisense region" is meant a nucleotide sequence of a dsRNA molecule having complementarity to a target nucleic acid sequence. In addition, the antisense region of a dsRNA molecule comprises a nucleic acid sequence having complementarity to a sense region of the dsRNA molecule.

As used herein, "antisense strand" refers to a single stranded nucleic acid molecule which has a sequence complementary to that of a target RNA. When the antisense strand contains modified nucleotides with base analogs, it is not necessarily complementary over its entire length, but must at least hybridize with a target RNA.

As used herein, "sense strand" refers to a single stranded nucleic acid molecule which has a sequence complementary to that of an antisense strand. When the antisense strand contains modified nucleotides with base analogs, the sense strand need not be complementary over the entire length of the antisense strand, but must at least duplex with the antisense strand.

As used herein, "guide strand" refers to a single stranded nucleic acid molecule of a dsRNA or dsRNA-containing molecule, which has a sequence sufficiently complementary to that of a target RNA to result in RNA interference. After cleavage of the dsRNA or dsRNA-containing molecule by Dicer, a fragment of the guide strand remains associated with RISC, binds a target RNA as a component of the RISC complex, and promotes cleavage of a target RNA by RISC. As used herein, the guide strand does not necessarily refer to a continuous single stranded nucleic acid and may comprise a discontinuity, preferably at a site that is cleaved by Dicer. A guide strand is an antisense strand.

As used herein, "passenger strand" refers to an oligonucleotide strand of a dsRNA or dsRNA-containing molecule, which has a sequence that is complementary to that of the guide strand. As used herein, the passenger strand does not necessarily refer to a continuous single stranded nucleic acid and may comprise a discontinuity, preferably at a site that is cleaved by Dicer. A passenger strand is a sense strand.

By "target nucleic acid" is meant a nucleic acid sequence whose expression, level or activity is to be modulated. The target nucleic acid can be DNA or RNA. For agents that target lactate dehydrogenase, in certain embodiments, the target nucleic acid is lactate dehydrogenase RNA, e.g., in certain embodiments, lactate dehydrogenase mRNA. lactate dehydrogenase RNA target sites can also interchangeably be referenced by corresponding cDNA sequences. Levels of lactate dehydrogenase may also be targeted via targeting of upstream effectors of lactate dehydrogenase, or the effects of modulated or misregulated lactate dehydrogenase may also be modulated by targeting of molecules downstream of lactate dehydrogenase in the lactate dehydrogenase signalling pathway.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence. In one embodiment, a dsRNA molecule of the invention comprises 19 to 30 (e.g., 19, 20, 21, 22, 23, 24, 25, 26, 27, 28, 29, or 30 or more) nucleotides that are complementary to one or more target nucleic acid molecules or a portion thereof.

As used herein, a dsNA, e.g., DsiRNA or siRNA, having a sequence "sufficiently complementary" to a target RNA or cDNA sequence (e.g., lactate dehydrogenase mRNA) means that the dsNA has a sequence sufficient to trigger the destruction of the target RNA (where a cDNA sequence is recited, the RNA sequence corresponding to the recited cDNA sequence) by the RNAi machinery (e.g., the RISC complex) or process. For example, a dsNA that is "sufficiently complementary" to a target RNA or cDNA sequence to trigger the destruction of the target RNA by the RNAi machinery or process can be identified as a dsNA that causes a detectable reduction in the level of the target RNA in an appropriate assay of dsNA activity (e.g., an in vitro assay as described in Example 2 below), or, in further examples, a dsNA that is sufficiently complementary to a target RNA or cDNA sequence to trigger the destruction of the target RNA by the RNAi machinery or process can be identified as a dsNA that produces at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least a 70%, at least a 75%, at least a 80%, at least a 85%, at least a 90%, at least a 95%, at least a 98% or at least a 99% reduction in the level of the target RNA in an appropriate assay of dsNA activity. In additional examples, a dsNA that is sufficiently complementary to a target RNA or cDNA sequence to trigger the destruction of the target RNA by the RNAi machinery or process can be identified based upon assessment of the duration of a certain level of inhibitory activity with respect to the target RNA or protein levels in a cell or organism. For example, a dsNA that is sufficiently complementary to a target RNA or cDNA sequence to trigger the destruction of the target RNA by the RNAi machinery or process can be identified as a dsNA capable of reducing target mRNA levels by at least 20% at least 48 hours post-administration of said dsNA to a cell or organism. Preferably, a dsNA that is sufficiently complementary to a target RNA or cDNA sequence to trigger the destruction of the target RNA by the RNAi machinery or process is identified as a dsNA capable of reducing target mRNA levels by at least 40% at least 72 hours post-administration of said dsNA to a cell or organism, by at least 40% at least four, five or seven days post-administration of said dsNA to a cell or organism, by at least 50% at least 48 hours post-administration of said dsNA to a cell or organism, by at least 50% at least 72 hours post-administration of said dsNA to a cell or organism, by at least 50% at least four, five or seven days post-administration of said dsNA to a cell or organism, by at least 80% at least 48 hours post-administration of said dsNA to a cell or organism, by at least 80% at least 72 hours post-administration of said dsNA to a cell or organism, or by at least 80% at least four, five or seven days post-administration of said dsNA to a cell or organism.

In certain embodiments, a nucleic acid of the invention (e.g., a DsiRNA or siRNA) possesses a sequence "sufficiently complementary to hybridize" to a target RNA or cDNA sequence, thereby achieving an inhibitory effect upon the target RNA. Hybridization, and conditions available for determining whether one nucleic acid is sufficiently complementary to another nucleic acid to allow the two sequences to hybridize, is described in greater detail below.

As will be clear to one of ordinary skill in the art, "sufficiently complementary" (contrasted with, e.g., "100% complementary") allows for one or more mismatches to exist between a dsNA of the invention and the target RNA or cDNA sequence (e.g., lactate dehydrogenase mRNA), provided that the dsNA possesses complementarity sufficient to trigger the destruction of the target RNA by the RNAi machinery (e.g., the RISC complex) or process. In certain embodiments, a "sufficiently complementary" dsNA of the invention can harbor one, two, three or even four or more mismatches between the dsNA sequence and the target RNA or cDNA sequence (e.g., in certain such embodiments, the antisense strand of the dsRNA harbors one, two, three, four, five or even six or more mismatches when aligned with the target RNA or cDNA sequence for maximum complementarity). Additional consideration of the preferred location of such mismatches within certain dsRNAs of the instant invention is considered in greater detail below.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell. Within certain aspects, the term "cell" refers specifically to mammalian cells, such as human cells, that contain one or more dsRNA molecules of the present disclosure. In particular aspects, a cell processes dsRNAs or dsRNA-containing molecules resulting in RNA interference of target nucleic acids, and contains proteins and protein complexes required for RNAi, e.g., Dicer and RISC.

By "RNA" is meant a molecule comprising at least one, and preferably at least 4, 8 and 12 ribonucleotide residues. The at least 4, 8 or 12 RNA residues may be contiguous. By "ribonucleotide" is meant a nucleotide with a hydroxyl group at the 2' position of a β-D-ribofuranose moiety. The terms include double-stranded RNA, single-stranded RNA, RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the dsRNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

In certain embodiments, an RNAi agent (e.g., dsRNA) of the invention can be an "isolated" RNAi agent, meaning that the RNAi agent is isolated from (removed and/or purified from) a natural environment.

In some embodiments, an RNAi agent (e.g., dsRNA) of the invention can be a "synthetic" RNAi agent. The term "synthetic" or "non-natural" refers to an RNAi agent (e.g., a dsRNA of the disclosure) that (i) is synthesized using a machine or (ii) that is not derived from a cell or organism that normally produces the RNAi agent.

By "subject" is meant an organism, which is a donor or recipient of explanted cells or the cells themselves. "Subject" also refers to an organism to which the dsRNA agents of the invention can be administered. A subject can be a mammal or mammalian cells, including a human or human cells.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA compositions may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent (e.g., a dsRNA agent or a vector or transgene encoding same) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

As used herein, "neoplasia" means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Hepatocellular carcinoma, colon cancer (e.g., colorectal cancer), lung cancer and ovarian cancer are examples (non-limiting) of a neoplastic condition.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to hepatic carcinoma, colon cancer, colorectal cancer, breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, esophageal cancer, gastrointestinal cancer, glioblastoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

Various methodologies of the instant invention include at least one step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent (e.g., DsiRNA) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Lactate Dehydrogenase as an RNAi Target

Primary Hyperoxaluria Type 1 (PH1)

Primary hyperoxaluria results in increased excretion of oxalate, with oxalate stones being common. The oxalalate in these common conditions is derived from dietary sources or is secondary to malabsorption. Primary hyperoxaluria, on the other hand, refers to a specific type of hyperoxaluria that is due to a metabolic defect resulting from a heritable genetic defect. PH1 refers to the form of primary hyperoxaluria associated with a metabolic defect of serine-pyruvate aminotransferase (an enzyme that in humans is encoded by the AGXT gene). Types of hyperoxaluria also include: type 2 primary (GRHPR-associated), type 3 primary (DHDPSL-associated), and idiopathic forms of hyperoxaluria.

The buildup of oxalate in the body causes increased excretion of oxalate, which in turn results in renal and bladder stones. Stones cause urinary obstruction (often with severe and acute pain), secondary infection of urine and eventually kidney damage.

Oxalate stones in primary hyperoxaluria tend to be severe, resulting in relatively early kidney damage (e.g., onset in teenage years to early adulthood), which impairs the excretion of oxalate, leading to a further acceleration in accumulation of oxalate in the body.

After the development of renal failure, patients may get deposits of oxalate in the bones, joints and bone marrow. Severe cases may develop haematological problems such as anaemia and thrombocytopaenia. The deposition of oxalate in the body is sometimes called "oxalosis" to be distinguished from "oxaluria" which refers to oxalate in the urine.

Renal failure is a serious complication requiring treatment in its own right. Dialysis can control renal failure but tends to be inadequate to dispose of excess oxalate. Renal transplant is more effective and this is the primary treatment of severe hyperoxaluria. Liver transplantation (often in addition to renal transplant) may be able to control the disease by correcting the metabolic defect.

In a proportion of patients with primary hyperoxaluria type 1, pyridoxine treatment (vitamin B6) may also decrease oxalate excretion and prevent kidney stone formation.

Figure 2:
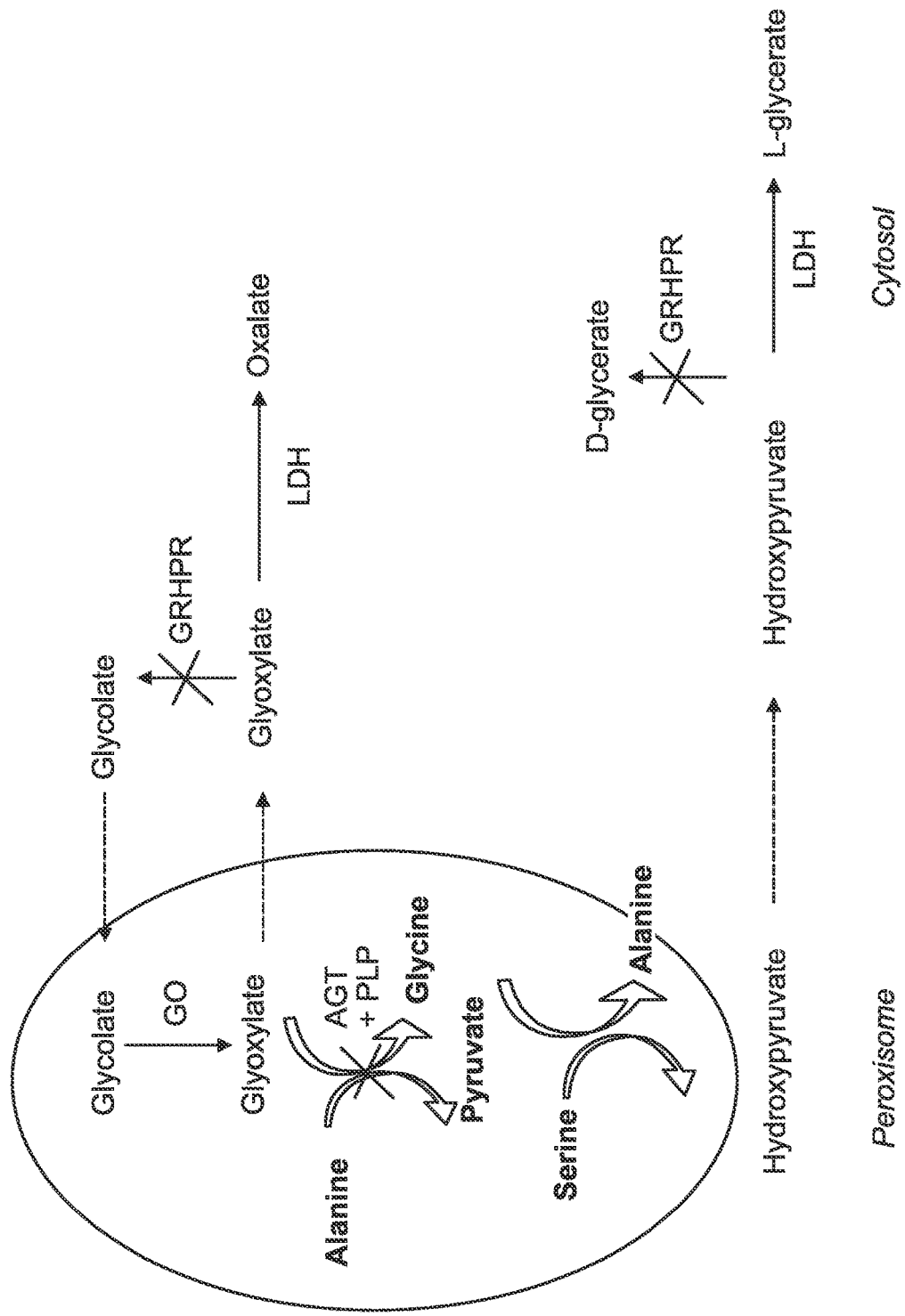
FIG. 2 depicts an image showing glyoxylate metabolism in human liver cells. Dashed and solid lines indicate diffusion across peroxisomal membrane and metabolism, respectively. The metabolic blocks in PH1 (AGT) and PH2 (GRHPR) are designated by the crosses. Oxalate overproduction characterizes both inborn errors of glyoxylate metabolism. However, in PH1, AGT deficiency causes accumulation of glyoxylate and glycolated with increased urinary glycolate execretion, while in PH2, GRHPR deficiency results in L-glycericaciduria. Abbreviations: AGT, alanine: glyoxylate aminotransferase; GRHPR, glyoxylate reductase/hydroxypyruvate reductase; GO, glycolate oxidase; LDH, lactate dehydrogenase; PLP, pyridoxal phosphate.
Figure 3J:
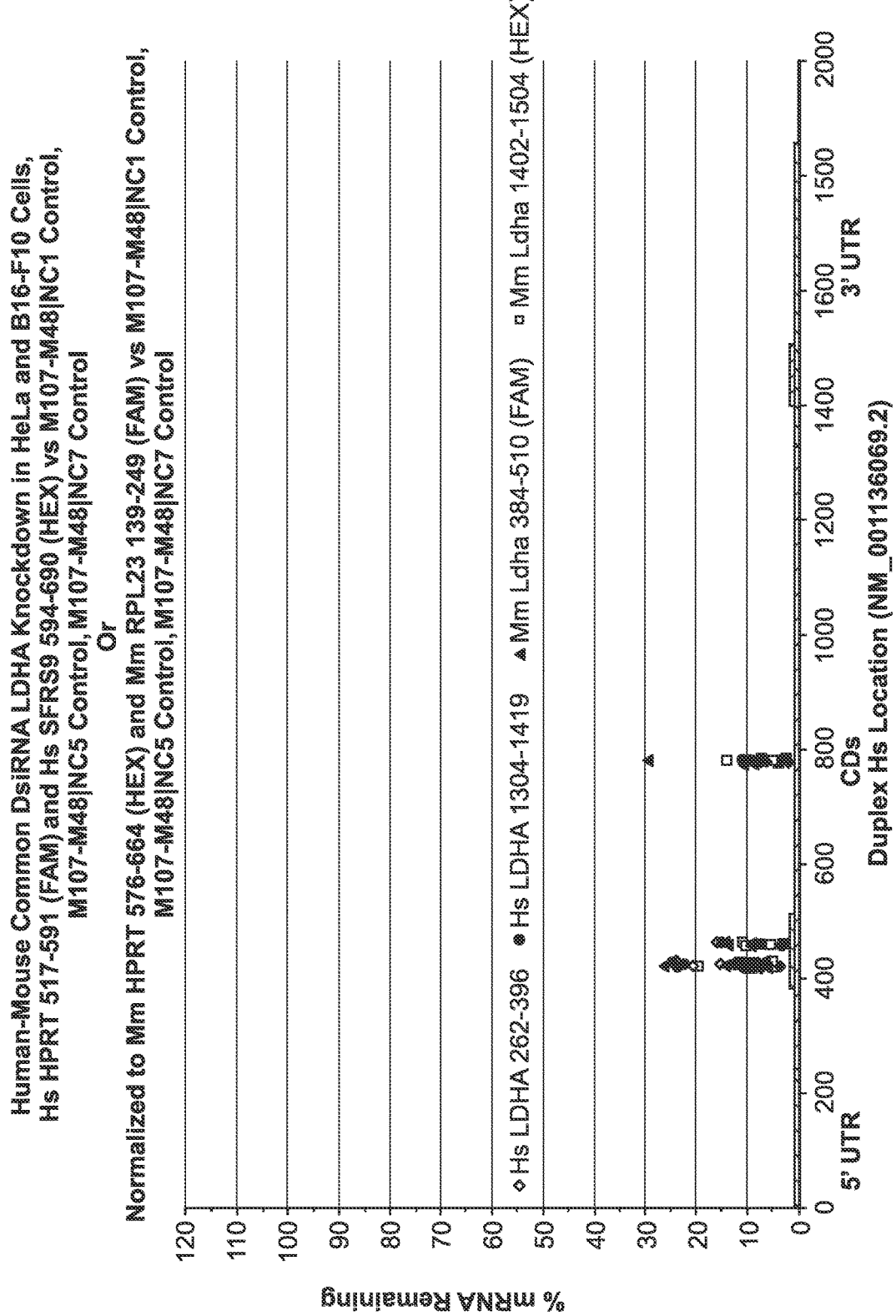

Lactate dehydrogenase is known to act as a dismutase converting glyoxylate to oxalate and glycolate (see FIG. 2). Without wishing to be bound by theory, because an accumulation of oxalate has been identified to cause PH1, inhibition of the enzymes that produce oxalate represents a therapeutic strategy for treatment of PH1. As the final enzyme acting within the oxalate synthesis pathway in the liver, LDH presents an attractive target—especially for liver-targeted dsRNAs, such as LNP-delivered DsiRNAs— for treatment or prevention of PH1.

Primary Types 2 and 3 (PH2 and PH3), and Idiopathic Hyperoxaluria

LHD is an attractive drug therapy target for metabolic disorders that result in oxalate accumulation. While not wishing to be bound by theory, PH1 and PH2 have been described as hereditary disorders of glyoxylate metabolism caused by deficiency of alanine:glyoxylate-aminotransferase (AGT) (Danpure and Jennings, *FEBS Lett* 1986; 201: 20-24) and glyoxylate reductase/hydroxypyruvate reductase (GRHPR) (*Nephrol. Dial. Transplant.* (1995) 10 (supp8): 58-60), respectively. When the activity of these enzymes is absent or reduced, LDH can convert glyoxylate into excess amounts of oxalate, which accumulates without degradation.

PH3, caused by mutations in HOGA1 (formerly DHDPSL), was recently identified (Belostotsky et al *Am J Hum Genet* 2010; 87:392-399). Patients with PH3 often experience calcium oxalate stone disease early in life, with 50% of them presenting with kidney stones before age 5. Data from the Rare Kidney Stone Consortium Primary Hyperoxaluria Registry has suggested that PH3 accounts for approximately 10% of patients with PH of known type. All forms of the PH disease share the common feature of over-production of oxalate from glyoxylate, a reaction catalyzed by LDH. LDH inhibitors such as the dsNAs described herein can thus provide relief to patients of all known forms of PH, as well as to patients having idiopathic forms of hyperoxaluria.

Oncology

LHDA is also an attractive target for cancer therapy because it is required for the initiation, maintenance and progression of tumors (Shi and Pinto, *PLOS ONE* January 2014, Volume 9, Issue 1, e86365; Le et al. *Proc Natl Acad Sci USA* 107: 2037-2042). Up-regulation of LDHA is a characteristic of many cancer types (Goldman R D et al., *Cancer Res* 24: 389-399; Koukourakis M I, et al., *Br J Cancer* 89: 877-885; Koukourakis M I, et al., *LJ Clin Oncol* 24: 4301-4308; Kolev Y, et al., *Ann Surg Oncol* 15: 2336-2344; Zhuang L, et al., *Mod Pathol* 23: 45-53), including, e.g., breast cancer, lymphoma, renal cancer (including renal cell cancer tumors), hereditary leiomyomatosis, pancreatic cancer, liver cancer (including hepatocellular carcinoma), and other forms of cancer.

Cancer cells preferentially undergo glycolysis followed by fermentation, even under aerobic conditions (Warburg O. London: Arnold Constable; 1930; Hanahan and Weinberg Cell 144: 646-674; Ward and Thompson, *CB Cancer Cell* 21: 297-308; Warburg O, *Science* 124: 269-270) and depend on LDHA for the conversion of pyruvate to lactate. It was shown that hereditary leiomyomatosis and renal cancer tumors overexpressed LDHA and that LDHA inhibition resulted in increased apoptosis in these cells (Xie H, et al., *Mol Cancer Ther* 2009; 8(3)). Inhibition of LDHA also impaired cell survival in carcinoma cells (Billiard et al., *Cancer & Metabolism* 2013, 1:19). LHDA inhibitors were also shown to induce lymphoma regression (Le et al. *Proc Natl Acad Sci USA* 107: 2037-2042).

LDHA is an attractive target for cancer therapy also because it is mainly expressed in skeletal muscle and is not present in red blood cells, in which glycolysis is an obligatory process. Individuals with LDHA deficiency only show myoglobinuria under intense exercise (Kanno T, et al., *Clin Chim Acta* 1988; 173:89-98; Kanno T, et al., *Clin Chim Acta* 1980; 108:267-76). Also individuals with complete lack of LDHA or LDHB subunits show no apparent increase in hemolysis (Kanno T, et al., *Curr Top Biol Med Res* 1983; 7:131-50; Miwa S, et al., *Rinsho Byori* 1971; 19 Suppl: 371). It is likely, therefore, that LDHA inhibitors even when delivered systemically will show only modest toxicity, with more targeted forms of delivery expected to mitigate any observed toxicity even further.

Pyruvate Dehydrogenase Deficiency

LHDA is an attractive drug therapy target for metabolic disorders that result in lactic acid accumulation. Pyruvate dehydrogenase (PDH) deficiency (also referred to herein as pyruvate dehydrogenase complex deficiency) is characterized by the buildup of lactic acid in the body and by a variety of neurological problems. The metabolic form presents as severe lactic acidosis with blood lactate concentrations often exceeding 10 mmol/l. Treatment is generally aimed at reversing or minimizing systemic lactic acid accumulation (Brown et al., *J Med Genet.* 31 (11): 875-879). LDHA catalyzes the conversion of pyruvate to lactate; therefore, reducing its activity—optionally in conjunction with other therapy or specialized diet—is likely to provide relief to PDH patients.

Chronic Kidney Disease

In certain aspects of the invention, it was surprisingly identified that targeting of LDHA with the agents of the invention (e.g., RNAi agents) could provide a therapeutic effect for subjects having chronic kidney disease. Without wishing to be bound by theory, it is likely that knockdown of LDHA in a liver-specific manner, which RNAi allows, can provide a therapeutic impact that is relatively free of deleterious effects of loss of LDH activity. In particular, still without wishing to be bound by theory, it is believed that residual LDH activity provided by, e.g., LDHB, allows for LDHA knockdown in the liver not to produce a deleterious effect, which would otherwise be expected if all LDH activity in even the liver was eliminated. Meanwhile, other tissues to which RNAi is currently unable to provide access are believed to benefit from not being subject to RNAi-mediated knockdown of LDHA.

Chronic kidney disease (CKD), also known as chronic renal disease, is a progressive loss in renal function over a period of months or years. The symptoms of worsening kidney function are not specific, and can include feeling generally unwell and experiencing a reduced appetite. Often, chronic kidney disease is diagnosed as a result of screening of people known to be at risk of kidney problems, such as those with high blood pressure or diabetes and those with a blood relative with CKD. This disease may also be identified when it leads to one of its recognized complications, such as cardiovascular disease, anemia, or pericarditis. It is differentiated from acute kidney disease in that the reduction in kidney function must be present for over 3 months.

Chronic kidney disease is identified by a blood test for creatinine, which is a breakdown product of muscle metabolism. Higher levels of creatinine indicate a lower glomerular filtration rate and as a result a decreased capability of the kidneys to excrete waste products. Creatinine levels may be normal in the early stages of CKD, and the condition is discovered if urinalysis (testing of a urine sample) shows the kidney is allowing the loss of protein or red blood cells into the urine. To fully investigate the underlying cause of kidney damage, various forms of medical imaging, blood tests, and sometimes a renal biopsy (removing a small sample of kidney tissue) are employed to find out if a reversible cause for the kidney malfunction is present.

Recent professional guidelines classify the severity of CKD in five stages, with stage 1 being the mildest and usually causing few symptoms and stage 5 being a severe illness with poor life expectancy if untreated. Stage 5 CKD is often called end stage kidney disease, end stage renal disease, or end-stage kidney failure, and is largely synonymous with the now outdated terms chronic renal failure or chronic kidney failure; and usually means the patient requires renal replacement therapy, which may involve a form of dialysis, but ideally constitutes a kidney transplant.

No specific treatment has been unequivocally shown to slow the worsening of CKD. If an underlying cause of CKD, such as vasculitis, or obstructive nephropathy (blockage to the drainage system of the kidneys) is found, it may be treated directly to slow the damage. In more advanced stages, treatments may be required for anemia and renal bone disease (also called renal osteodystrophy, secondary hyperparathyroidism or chronic kidney disease-mineral bone disorder (CKD-MBD)). Chronic kidney disease resulted in 956,000 deaths in 2013, up from 409,000 deaths in 1990.

CKD is initially without specific symptoms and is generally only detected as an increase in serum creatinine or protein in the urine. As the kidney function decreases:

Blood pressure is increased due to fluid overload and production of vasoactive hormones created by the kidney via the renin-angiotensin system, increasing one's risk of developing hypertension and/or suffering from congestive heart failure.

Urea accumulates, leading to azotemia and ultimately uremia (symptoms ranging from lethargy to pericarditis and encephalopathy). Due to its high systemic circulation, urea is excreted in eccrine sweat at high concentrations and crystallizes on skin as the sweat evaporates ("uremic frost").

Potassium accumulates in the blood (hyperkalemia with a range of symptoms including malaise and potentially fatal cardiac arrhythmias). Hyperkalemia usually does not develop until the glomerular filtration rate falls to less than 20-25 ml/min/1.73 m2, at which point the kidneys have decreased ability to excrete potassium. Hyperkalemia in CKD can be exacerbated by acidemia (which leads to extracellular shift of potassium) and from lack of insulin.

Erythropoietin synthesis is decreased causing anemia.

Fluid volume overload symptoms may range from mild edema to life-threatening pulmonary edema.

Hyperphosphatemia, due to reduced phosphate excretion, follows the decrease in glomerular filtration. Hyperphosphatemia is associated with increased cardiovascular risk, being a direct stimulus to vascular calcification.

Hypocalcemia, due to 1.25 dihydroxyvitamin D3 deficiency, is caused by stimulation of fibroblast growth factor-23. Osteocytes are responsible for the increased production of FGF23, which is a potent inhibitor of the enzyme 1-alpha-hydroxylase (responsible for the conversion of 25-hydroxycholecalciferol into 1.25 dihydroxyvitamin D3). Later, this progresses to secondary hyperparathyroidism, renal osteodystrophy, and vascular calcification that further impairs cardiac function.

Metabolic acidosis (due to accumulation of sulfates, phosphates, uric acid etc.) may cause altered enzyme activity by excess acid acting on enzymes; and also increased excitability of cardiac and neuronal membranes by the promotion of hyperkalemia due to excess acid (acidemia). Acidosis is also due to decreased capacity to generate enough ammonia from the cells of the proximal tubule.

Iron deficiency anemia, which increases in prevalence as kidney function decreases, is especially prevalent in those requiring haemodialysis. It is multifactoral in cause, but includes increased inflammation, reduction in erythropoietin, and hyperuricemia leading to bone marrow suppression.

People with CKD suffer from accelerated atherosclerosis and are more likely to develop cardiovascular disease than the general population. Patients afflicted with CKD and cardiovascular disease tend to have significantly worse prognoses than those suffering only from the latter.

Sexual dysfunction is very common in both men and women with CKD. A majority of men have a reduced sex drive, difficulty obtaining an erection, and reaching orgasm, and the problems get worse with age. A majority of women have trouble with sexual arousal, and painful menstruation and problems with performing and enjoying sex are common.

Diagnosis of CKD is largely based on the clinical picture combined with the measurement of the serum creatinine level (see above). In many CKD patients, previous renal disease or other underlying diseases are already known. A significant number present with CKD of unknown cause. In these patients, a cause is occasionally identified retrospectively.

It is important to differentiate CKD from acute kidney injury (AKI) because AKI can be reversible. Abdominal ultrasound, in which the size of the kidneys is measured, is commonly performed. Kidneys with CKD are usually smaller ($\leq 9$ cm) than normal kidneys, with notable exceptions such as in early diabetic nephropathy and polycystic kidney disease. Another diagnostic clue that helps differentiate CKD from AKI is a gradual rise in serum creatinine (over several months or years) as opposed to a sudden increase in the serum creatinine (several days to weeks). If these levels are unavailable (because the patient has been well and has had no blood tests), it is occasionally necessary to treat a patient briefly as having AKI until the renal impairment has been established to be irreversible.

Additional tests may include nuclear medicine MAG3 scan to confirm blood flow and establish the differential function between the two kidneys. Dimercaptosuccinic acid (DMSA) scans are also used in renal imaging; with both MAG3 and DMSA being used chelated with the radioactive element technetium-99.

In CKD numerous uremic toxins accumulate in the blood. Even when ESKD (largely synonymous with CKD5) is treated with dialysis, the toxin levels do not go back to normal as dialysis is not that efficient. Similarly, after a renal transplant, the levels may not go back to normal as the transplanted kidney may not work 100%. If it does, the creatinine level is often normal. The toxins show various cytotoxic activities in the serum and have different molecular weights, and some of them are bound to other proteins, primarily to albumin. Such toxic protein-bound substances are receiving the attention of scientists who are interested in improving the standard chronic dialysis procedures used today.

Screening those who have neither symptoms nor risk factors for CKD is not recommended. Those who should be screened include: those with hypertension or history of cardiovascular disease, those with diabetes or marked obesity, those aged >60 years, subjects with indigenous racial origin, those with a history of renal disease in the past, and subjects who have relatives who had kidney disease requiring dialysis. Screening should include calculation of estimated GFR from the serum creatinine level, and measurement of urine-to-albumin creatinine ratio (ACR) in a first-morning urine specimen (this reflects the amount of a protein called albumin in the urine), as well as a urine dipstick screen for hematuria. The GFR (glomerular filtration rate) is derived from the serum creatinine and is proportional to 1/creatinine, ie it is a reciprocal relationship (the higher the creatinine, the lower the GFR). It reflects one aspect of kidney function: how efficiently the glomeruli (filtering units) work. But as they make up <5% of the mass of the kidney, the GFR does not tell you about all aspects of kidney health and function. This can be done by combining the GFR level with the clinical assessment of the patient (especially fluid state) and measuring the levels of hemoglobin, potassium, phosphate and parathyroid hormone (PTH). Normal GFR is 90-120 mls/min. The units of creatinine vary from country to country.

Guidelines for referral to a nephrologist vary between countries. Though most would agree that nephrology referral is required by Stage 4 CKD (when eGFR/1.73m2 is less than 30 ml/min; or decreasing by more than 3 ml/min/year); and may be useful at an earlier stage (eg CKD3) when urine albumin-to-creatinine ratio is more than 30 mg/mmol, when blood pressure is difficult to control, or when hematuria or other findings suggest either a primarily glomerular disorder or secondary disease amenable to specific treatment. Other benefits of early nephrology referral include proper patient education regarding options for renal replacement therapy as well as pre-emptive transplantation, and timely workup and placement of an arteriovenous fistula in those patients opting for future hemodialysis All individuals with a glomerular filtration rate (GFR)<60 ml/min/1.73 m$^2$ for 3 months are classified as having chronic kidney disease, irrespective of the presence or absence of kidney damage. The rationale for including these individuals is that reduction in kidney function to this level or lower represents loss of half or more of the adult level of normal kidney function, which may be associated with a number of complications such as the development of cardiovascular disease.

The loss of protein in the urine is regarded as an independent marker for worsening of renal function and cardiovascular disease. Hence, British guidelines append the letter "P" to the stage of chronic kidney disease if protein loss is significant.

Stage 1

Slightly diminished function; kidney damage with normal or relatively high GFR (≥90 ml/min/1.73 m$^2$). Kidney damage is defined as pathological abnormalities or markers of damage, including abnormalities in blood or urine tests or imaging studies.

Stage 2

Mild reduction in GFR (60-89 ml/min/1.73 m2) with kidney damage. Kidney damage is defined as pathological abnormalities or markers of damage, including abnormalities in blood or urine tests or imaging studies.

Stage 3

Moderate reduction in GFR (30-59 ml/min/1.73 m2). British guidelines distinguish between stage 3A (GFR 45-59) and stage 3B (GFR 30-44) for purposes of screening and referral.

Stage 4

Severe reduction in GFR (15-29 ml/min/1.73 m2) Preparation for renal replacement therapy.

Stage 5

Established kidney failure (GFR <15 ml/min/1.73 m2), permanent renal replacement therapy, or end-stage kidney disease.

The term nondialysis dependent CKD (NDD-CKD) is a designation used to encompass the status of those persons with an established CKD who do not yet require the life-supporting treatments for renal failure known as renal replacement therapy (RRT, including maintenance dialysis or renal transplantation). The condition of individuals with CKD, who require either of the two types of renal replacement therapy (dialysis or transplant), is referred to as the end-stage renal disease (ESRD). Hence, the start of the ESRD is practically the irreversible conclusion of the NDD-CKD. Even though the NDD-CKD status refers to the status of persons with earlier stages of CKD (stages 1 to 4), patients with advanced stage of CKD (stage 5), who have not yet started renal replacement therapy, are also referred to as NDD-CKD.

The presence of CKD confers a markedly increased risk of cardiovascular disease, and people with CKD often have other risk factors for heart disease, such as high blood lipids. The most common cause of death in people with CKD is cardiovascular disease rather than renal failure. Aggressive treatment of hyperlipidemia is warranted.

Apart from controlling other risk factors, the goal of therapy is to slow down or halt the progression of CKD to stage 5. Control of blood pressure and treatment of the original disease, whenever feasible, are the broad principles of management. Generally, angiotensin converting enzyme inhibitors (ACEIs) or angiotensin II receptor antagonists (ARBs) are used, as they have been found to slow the progression of CKD in forms of the disease with increased levels of protein in the urine. Although the use of ACE inhibitors and ARBs represents the current standard of care for people with CKD, people progressively lose kidney function while on these medications, as seen in the IDNT and RENAL studies, which reported a decrease over time in estimated GFR (an accurate measure of CKD progression, as detailed in the K/DOQI guidelines) in people treated by these conventional methods.

Replacement of erythropoietin and calcitriol, two hormones processed by the kidney, is often necessary in people with advanced disease. Guidelines recommend treatment with parenteral iron prior to treatment with erythropoietin. A target hemoglobin level of 9-12 g/dl is recommended. The normalization of hemoglobin has not been found to be of benefit. It is unclear if androgens help with anemia. Phosphate binders are also used to control the serum phosphate levels, which are usually elevated in advanced chronic kidney disease. Although the evidence for them is limited, phosphodiesterase-5 inhibitors and zinc show potential for helping men with sexual dysfunction.

At stage 5 CKD, renal replacement therapy is usually required, in the form of either dialysis or a transplant.

The prognosis of patients with chronic kidney disease is guarded as epidemiological data have shown that all cause mortality (the overall death rate) increases as kidney function decreases. The leading cause of death in patients with chronic kidney disease is cardiovascular disease, regardless of whether there is progression to stage 5.

While renal replacement therapies can maintain patients indefinitely and prolong life, the quality of life is severely affected. Renal transplantation increases the survival of patients with stage 5 CKD significantly when compared to other therapeutic options; however, it is associated with an increased short-term mortality due to complications of the surgery. Transplantation aside, high-intensity home hemodialysis appears to be associated with improved survival and a greater quality of life, when compared to the conventional three-times-a-week hemodialysis and peritoneal dialysis.

Patients with ESKD are at increased overall risk for cancer. This risk is particularly high in younger patients and gradually diminishes with age. Medical specialty professional organizations recommend that physicians do not perform routine cancer screening in patients with limited life expectancies due to ESKD because evidence does not show that such tests lead to improved patient outcomes.

Chronic kidney disease resulted in 956,000 deaths in 2013 up from 409,000 deaths in 1990.

In Canada, 1.9 to 2.3 million people have CKD.[23] In the US, the Centers for Disease Control and Prevention found that CKD affected an estimated 16.8% of adults aged 20 years and older, during 1999 to 2004. UK estimates suggest that 8.8% of the population of Great Britain and Northern Ireland have symptomatic CKD.

CKD is a major concern in African Americans, mostly due to increased prevalence of hypertension. As an example, 37% of ESKD cases in African Americans can be attributed to high blood pressure, compared with 19% among Caucasians. Treatment efficacy also differs between racial groups. Administration of antihypertensive drugs generally halts disease progression in white populations, but has little effect in slowing renal disease among blacks, and additional treatment such as bicarbonate therapy is often required. While lower socioeconomic status contributes to prevalence of CKD, significant differences in CKD prevalence are still evident between African Americans and Whites when controlling for environmental factors. Studies have shown a true association between history of chronic kidney disease in first- or second-degree relatives, and risk of disease. In addition, African Americans may have higher serum levels of human leukocyte antigens (HLA). High HLA concentrations can contribute to increased systemic inflammation, which indirectly may lead to heightened susceptibility for developing kidney disease. Lack of nocturnal reduction in blood pressure among groups of African Americans is also offered as an explanation, which lends further credence to a genetic etiology of CKD racial disparities.

A high and so-far unexplained incidence of CKD, referred to as the Mesoamerican nephropathy, has been noted among male workers in Central America, mainly in sugar cane fields in the lowlands of El Salvador and Nicaragua. Heat stress from long hours of piece-rate work at high average temperatures (in the range of 96° F.) is suspected, as are agricultural chemicals and other factors. In Sri Lanka, another epidemic of CKD of unknown etiology has become a serious public health concern.

Currently, several compounds are in development for CKD. These include bardoxolone methyl, olmesartan medoxomil, sulodexide, and avosentan. It is contemplated that the agents set forth herein could be used alone or in combination with such therapies, e.g., to treat chronic kidney disease.

While the above-recited diseases and/or disorders are specifically identified herein as targets for LDHA knockdown, it is also contemplated that LDHA knockdown that is either systemic or that is selective for a tissue other than, e.g., liver and/or neoplasia tissue (even including, e.g., muscle tissue), could also exert therapeutic benefit within the correct patient population(s). Accordingly, delivery of the agents of the invention in a manner that is systemic or that preferentially targets tissues other than those most accessible to LNPs (such as liver, pancreatic, kidney, neoplasia and/or blood tissues) is also contemplated. Thus, the LDHA knockdown agents of the invention can optionally be targeted to lung, brain, lymphatic, muscle, etc. tissues.

Exemplary dsNA Structures

Certain aspects of the invention employ dsNA structures to knock down the LDHA target in cells and/or in a subject. Exemplary dsNA structures include the following:

In certain embodiments of the invention, tetraloop- and modified nucleotide-containing dsNAs are contemplated as described, e.g., in US 2011/0288147. In certain such embodiments, a dsNA of the invention possesses a first strand and a second strand, where the first strand and the second strand form a duplex region of 19-25 nucleotides in length, wherein the first strand comprises a 3' region that extends beyond the first strand-second strand duplex region and comprises a series of linking nucleotides, optionally a tetraloop, and the dsNA comprises a discontinuity between the 3' terminus of the first strand and the 5' terminus of the second strand. Optionally, the discontinuity is positioned at a projected dicer cleavage site of the tetraloop-containing dsNA.

In some embodiments, the DsiRNA of the instant invention further comprises a linking moiety or domain that joins the sense and antisense strands of a dsNA of the invention, e.g., a DNA:DNA-extended DsiRNA agent. Optionally, such a linking moiety domain joins the 3' end of the sense strand and the 5' end of the antisense strand. The linking moiety may be a chemical (non-nucleotide) linker, such as an oligomethylenediol linker, oligoethylene glycol linker, or other art-recognized linker moiety. Alternatively, the linker can be a nucleotide linker, optionally including an extended loop and/or tetraloop.

In one embodiment of the present invention, each oligonucleotide of a DsiRNA molecule of the invention is independently 19 to 80 nucleotides in length, in specific embodiments 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 or more nucleotides in length. For dsNAs possessing a strand that exceeds 30 nucleotides in length, available structures include those where only one strand exceeds 30 nucleotides in length (see, e.g., U.S. Pat. No. 8,349,809, where an exemplary double stranded nucleic acid possesses a first oligonucleotide strand having a 5' terminus and a 3' terminus and a second oligonucleotide strand having a 5' terminus and a 3' terminus, where each of the 5' termini has a 5' terminal nucleotide and each of the 3' termini has a 3' terminal nucleotide, where the first strand is 15-30 nucleotide residues in length, where starting from the 5' terminal nucleotide (position 1) positions 1 to 15 of the first strand include at least 8 ribonucleotides; the second strand is 36-80 nucleotide residues in length and, starting from the 3' terminal nucleotide, includes at least 8 ribonucleotides in the positions paired with positions 1-15 of the first strand to form a duplex; where at least the 3' terminal nucleotide of the second strand is unpaired with the first strand, and up to 6 consecutive 3' terminal nucleotides are unpaired with the first strand, thereby forming a 3' single stranded overhang of 1-6 nucleotides; where the 5' terminus of the second strand includes from 5-64 consecutive nucleotides which are unpaired with the first strand, thereby forming a 5-64 nucleotide single stranded 5' overhang; where at least the first strand 5' terminal and 3' terminal nucleotides are base paired with nucleotides of the second strand when the first and second strands are aligned for maximum complementarity, thereby forming a substantially duplexed region between the first and second strands; and the second strand is sufficiently complementary to a target RNA along at least 19 ribonucleotides of the second strand length to reduce target gene expression when the double stranded nucleic acid is introduced into a mammalian cell).

In another exemplary embodiment of dsNA structures of the invention, the first strand possesses a 5'-overhang region of 5-61 nucleotides in length, adjacent to the duplex region of sufficient complementarity between first and second strands to allow for duplex formation, where the 3'-terminus of the first strand and the 5'-terminus of the second strand form a blunt structure or form a second strand 5'-overhang of the first strand (e.g., of 1-6 nucleotides in length), where the second strand includes a sequence of at least 19 nucleotides sufficiently complementary to the target LDHA transcript to effect knockdown of LDHA when introduced to mammalian cells.

RNAi therapies are newly identified to provide an attractive, targeted means of treating PH1, PH2, PH3, idiopathic hyperoxaluria, pyruvate dehydrogenase deficiency, chronic kidney disease, cancer and other conditions, diseases or disorders for which reduction of LDH levels, particularly in the liver, can prove therapeutic or otherwise advantageous, at a molecular level. Notably, RNAi therapies, such as the dsRNAs that are specifically exemplified herein, have demonstrated particularly good ability to be delivered to the cells of the liver in vivo (via, e.g., lipid nanoparticles and/or conjugates such as dynamic polyconjugates or GalNAc conjugates—in certain exemplary embodiments, GalNAc can be conjugated to a 3'- and/or 5'-overhang region of a dsNA, optionally to an "extended" overhang region of a dsNA (e.g., to a 5 or more nucleotide, 8 or more nucleotide, etc. example of such an overhang); additionally and/or alternatively, GalNAc can be conjugated to ds extended regions of a dsNA, e.g., to the duplex region formed by the 5'-end region of the guide/antisense strand of a dsNA and the corresponding 3'-end region of the passenger/sense strand of a dsNA and/or to the duplex region formed by the 3'-end region of the guide/antisense strand of a dsNA and the corresponding 5'-end region of the passenger/sense strand of a dsNA). Thus, formulated RNAi therapies, such as those described herein, are attractive modalities for treating or preventing diseases or disorders that are present in, originate in or otherwise involve the liver (e.g., PH1, oxalate accumulation and/or other lactate dehydrogenase-associated diseases or disorders).

Even though a number of embodiments of the invention are directed to liver-targeted delivery of anti-lactate dehydrogenase dsRNAs, use of RNAi therapies to target lactate dehydrogenase at a molecular level in other tissues is also contemplated.

The dsRNA agents of the invention when formulated in delivery vehicles known in the art, e.g., lipid nanoparticles (LNPs) are known to target liver cells more readily than cells of other organs. This effect can be used to therapeutic advantage by avoiding induction of lactate dehydrogenase deficiency in non-liver cells during liver-specific targeting of LDH. Lactate dehydrogenase deficiency is a condition that affects how the body breaks down sugar to use as energy in cells, primarily muscle cells. There are two types of this condition: lactate dehydrogenase-A deficiency (sometimes called glycogen storage disease XI) and lactate dehydrogenase-B deficiency. People with lactate dehydrogenase-A deficiency experience fatigue, muscle pain, and cramps during exercise (exercise intolerance). In some people with lactate dehydrogenase-A deficiency, high-intensity exercise or other strenuous activity leads to the breakdown of muscle tissue (rhabdomyolysis). The destruction of muscle tissue releases a protein called myoglobin, which is processed by the kidneys and released in the urine (myoglobinuria). Myoglobin causes the urine to be red or brown. This protein can also damage the kidneys, in some cases leading to life-threatening kidney failure. Some people with lactate dehydrogenase-A deficiency develop skin rashes. The severity of the signs and symptoms among individuals with lactate dehydrogenase-A deficiency varies greatly. People with lactate dehydrogenase-B deficiency typically do not have any signs or symptoms of the condition. They do not have difficulty with physical activity or any specific physical features related to the condition. Affected individuals are usually discovered only when routine blood tests reveal reduced lactate dehydrogenase activity.

Lactate Dehydrogenase cDNA and Polypeptide Sequences

Known human and mouse lactate dehydrogenase (lactate dehydrogenase A or LDHA) cDNA and polypeptide sequences include the following: human lactate dehydrogenase NM_005566.3 and corresponding human lactate dehydrogenase polypeptide sequence GenBank Accession No. NP_005557.1; and mouse wild-type lactate dehydrogenase sequence GenBank Accession No. NM_001136069.2 (Mus musculus C57BL/6 Ldha, transcript variant 2) and corresponding mouse Ldha polypeptide sequence GenBank Accession No. NP_001129541.2. Other forms of mammalian lactate dehydrogenase include LDHB (NM_002300.6 and NM_008492.2; NP_002291.1 and NP_032518.1) and LDHC (NM_002301.4 and NM_013580.4; NP_002292.1 and NP_030698.1). It is contemplated that certain of the LDHA-targeting nucleic acids of the invention can also be used to target one or more of these additional forms of LDH, in certain instances for therapeutic benefit. Additionally and/or alternatively, combination therapies are contemplated that include both an LDHA-targeting nucleic acid of the invention and one or more inhibitors of LDHB and/or LDHC, in certain instances for added therapeutic benefit.

Assessment of Lactate Dehydrogenase Levels

In certain embodiments, dsRNA-mediated inhibition of a lactate dehydrogenase target sequence is assessed. In such embodiments, lactate dehydrogenase RNA levels can be assessed by art-recognized methods (e.g., RT-PCR, Northern blot, expression array, etc.), optionally via comparison of lactate dehydrogenase levels in the presence of an anti-lactate dehydrogenase dsRNA of the invention relative to the absence of such an anti-lactate dehydrogenase dsRNA. In certain embodiments, lactate dehydrogenase levels in the presence of an anti-lactate dehydrogenase dsRNA are compared to those observed in the presence of vehicle alone, in the presence of a dsRNA directed against an unrelated target RNA, or in the absence of any treatment.

It is also recognized that levels of lactate dehydrogenase protein can be assessed and that lactate dehydrogenase protein levels are, under different conditions, either directly or indirectly related to lactate dehydrogenase RNA levels and/or the extent to which a dsRNA inhibits lactate dehydrogenase expression, thus art-recognized methods of assessing lactate dehydrogenase protein levels (e.g., Western blot, immunoprecipitation, other antibody-based methods, etc.) can also be employed to examine the inhibitory effect of a dsRNA of the invention.

In certain embodiments, potency of a dsRNA of the invention is determined in reference to the number of copies of a dsRNA present in the cytoplasm of a target cell that are required to achieve a certain level of target gene knockdown. For example, in certain embodiments, a potent dsRNA is one capable of causing 50% or greater knockdown of a target mRNA when present in the cytoplasm of a target cell at a copy number of 1000 or fewer RISC-loaded antisense strands per cell. More preferably, a potent dsRNA is one capable of producing 50% or greater knockdown of a target mRNA when present in the cytoplasm of a target cell at a copy number of 500 or fewer RISC-loaded antisense strands per cell. Optionally, a potent dsRNA is one capable of producing 50% or greater knockdown of a target mRNA when present in the cytoplasm of a target cell at a copy number of 300 or fewer RISC-loaded antisense strands per cell.

In further embodiments, the potency of a DsiRNA of the invention can be defined in reference to a 19 to 23mer dsRNA directed to the same target sequence within the same target gene. For example, a DsiRNA of the invention that possesses enhanced potency relative to a corresponding 19 to 23mer dsRNA can be a DsiRNA that reduces a target gene by an additional 5% or more, an additional 10% or more, an additional 20% or more, an additional 30% or more, an additional 40% or more, or an additional 50% or more as compared to a corresponding 19 to 23mer dsRNA, when assayed in an in vitro assay as described herein at a sufficiently low concentration to allow for detection of a potency difference (e.g., transfection concentrations at or below 1 nM in the environment of a cell, at or below 100 pM in the environment of a cell, at or below 10 pM in the environment of a cell, at or below 1 nM in the environment of a cell, in an in vitro assay as described herein; notably, it is recognized that potency differences can be best detected via performance of such assays across a range of concentrations—e.g., 0.1 pM to 10 nM—for purpose of generating a dose-response curve and identifying an $IC_{50}$ value associated with a DsiRNA/dsRNA).

In certain embodiments, a nucleic acid of the invention is administered in an amount sufficient to reduce lactate dehydrogenase target mRNA expression when the nucleic acid is introduced into a mammalian cell. In exemplary embodiments, reduction of lactate dehydrogenase target mRNA expression is assessed to have occurred if lactate dehydrogenase target mRNA levels are decreased by at least 5% or more, 10% or more, 20% or more, 30% or more, 40% or more, 50% or more, 60% or more, 70% or more, 80% or more, or 90% or more, as compared to a corresponding mammalian cell administered an appropriate control that does not include the lactate dehydrogenase-targeting nucleic acid of the invention. In an exemplary embodiment, the mammalian cell used to determine whether reduction of lactate dehydrogenase target mRNA expression has occurred relative to an appropriate control is a HeLa cell, and the lactate dehydrogenase-targeting nucleic acid of the invention is optionally administered via transfection (e.g., using Lipofectamine™) at a concentration of at or below 1 nM in the environment of a cell, at or below 100 pM in the environment of a cell, at or below 10 pM in the environment of a cell, at or below 1 nM in the environment of a cell, in an in vitro assay as described herein.

Lactate dehydrogenase inhibitory levels and/or lactate dehydrogenase levels may also be assessed indirectly, e.g., measurement of a reduced level of PH1 and/or associated phenotypes, and/or other phenotypes associated with oxalate accumulation, can indicate lactate dehydrogenase inhibitory efficacy of a double-stranded nucleic acid of the instant invention.

Models Useful to Evaluate the Down-Regulation of Lactate Dehydrogenase mRNA Levels and Expression Therapeutic agents can be tested in selected animal model(s). For example, a dsRNA agent (or expression vector or transgene encoding same) as described herein can be used in an animal model to determine the efficacy, toxicity, or side effects of treatment with said agent. Alternatively, an agent (e.g., a therapeutic agent) can be used in an animal model to determine the mechanism of action of such an agent.

Cell Culture

The dsRNA agents of the invention can be tested for cleavage activity in vivo, for example, using the following procedure. The nucleotide sequences within the lactate dehydrogenase cDNA targeted by the dsRNA agents of the invention are shown in the above lactate dehydrogenase sequences.

The dsRNA reagents of the invention can be tested in cell culture using HeLa or other mammalian cells (e.g., human cell lines Hep3B, HepG2, DU145, Calu3, SW480, T84, PL45, Huh7 etc., and mouse cell lines B16-F10, AML12, Neuro2a, etc.) to determine the extent of lactate dehydrogenase RNA and lactate dehydrogenase protein inhibition. In certain embodiments, DsiRNA reagents (e.g., see FIG. 1, and exemplary structures recited elsewhere herein) are selected against the lactate dehydrogenase target as described herein. lactate dehydrogenase RNA inhibition is measured after delivery of these reagents by a suitable transfection agent to, for example, cultured HeLa cells or other transformed or non-transformed mammalian cells in culture. Relative amounts of target lactate dehydrogenase RNA are measured versus HPRT1, actin or other appropriate control using real-time PCR monitoring of amplification (e.g., ABI 7700 TAQMAN®). A comparison is made to the activity of oligonucleotide sequences made to unrelated targets or to a randomized DsiRNA control with the same overall length and chemistry, or simply to appropriate vehicle-treated or untreated controls. Primary and secondary lead reagents are chosen for the target and optimization performed.

TAQMAN® (Real-Time PCR Monitoring of Amplification) and Lightcycler Quantification of mRNA Total RNA is prepared from cells following DsiRNA delivery, for example, using Ambion Rnaqueous 4-PCR purification kit for large scale extractions, or Promega SV96 for 96-well assays. For Taqman analysis, dual-labeled probes are synthesized with, for example, the reporter dyes FAM or VIC covalently linked at the 5'-end and the quencher dye TAMRA conjugated to the 3'-end. PCR amplifications are performed on, for example, an ABI PRISM 7700 Sequence detector using 50 uL reactions consisting of 10 uL total RNA, 100 nM forward primer, 100 mM reverse primer, 100 nM probe, 1×TaqMan PCR reaction buffer (PE-Applied Biosystems), 5.5 mM MgCl2, 100 uM each dATP, dCTP, dGTP and dTTP, 0.2 U RNase Inhibitor (Promega), 0.025 U AmpliTaq Gold (PE-Applied Biosystems) and 0.2 U M-MLV Reverse Transcriptase (Promega). The thermal cycling conditions can consist of 30 minutes at 48° C., 10 minutes at 95° C., followed by 40 cycles of 15 seconds at 95° C. and 1 minute at 60° C. Quantitation of target lactate dehydrogenase mRNA level is determined relative to standards generated from serially diluted total cellular RNA (300, 100, 30, 10 ng/rxn) and normalizing to, for example, HPRT1 mRNA in either parallel or same tube TaqMan reactions.

Western Blotting

Cellular protein extracts can be prepared using a standard micro preparation technique (for example using RIPA buffer), or preferably, by extracting nuclear proteins by a method such as the NE-PER Nuclear and Cytoplasmic Extraction kit (Thermo-Fisher Scientific). Cellular protein extracts are run on Tris-Glycine polyacrylamide gel and transferred onto membranes. Non-specific binding can be blocked by incubation, for example, with 5% non-fat milk for 1 hour followed by primary antibody for 16 hours at 4° C. Following washes, the secondary antibody is applied, for example (1:10,000 dilution) for 1 hour at room temperature and the signal detected on a VersaDoc imaging system In several cell culture systems, cationic lipids have been shown to enhance the bioavailability of oligonucleotides to cells in culture (Bennet, et al., 1992, Mol. Pharmacology, 41, 1023-1033). In one embodiment, dsRNA molecules of the invention are complexed with cationic lipids for cell culture experiments. dsRNA and cationic lipid mixtures are prepared in serum-free OptimMEM (InVitrogen) immediately prior to addition to the cells. OptiMEM is warmed to room temperature (about 20-25° C.) and cationic lipid is added to the final desired concentration. dsRNA molecules are added to OptiMEM to the desired concentration and the solution is added to the diluted dsRNA and incubated for 15 minutes at room temperature. In dose response experiments, the RNA complex is serially diluted into OptiMEM prior to addition of the cationic lipid.

Animal Models

The efficacy of anti-lactate dehydrogenase dsRNA agents may be evaluated in an animal model. Animal models of PH1, and/or diseases, conditions, or disorders associated with oxalate accumulation or LDHA overexpression as are known in the art can be used for evaluation of the efficacy, potency, toxicity, etc. of anti-lactate dehydrogenase dsRNAs. Exemplary animal models of PH1 include, e.g., Agxt1 knockout mice. Animal models may be used as a source of cells or tissue for assays of the compositions of the invention. Such models can also be used or adapted for use for pre-clinical evaluation of the efficacy of dsRNA compositions of the invention in modulating lactate dehydrogenase gene expression toward therapeutic use.

Such models and/or wild-type mice can be used in evaluating the efficacy of dsRNA molecules of the invention to inhibit lactate dehydrogenase levels, expression, development of lactate dehydrogenase-associated phenotypes, diseases or disorders, etc. These models, wild-type mice and/or other models can similarly be used to evaluate the safety/toxicity and efficacy of dsRNA molecules of the invention in a pre-clinical setting.

Specific examples of animal model systems useful for evaluation of the lactate dehydrogenase-targeting dsRNAs of the invention include wild-type mice and Agxt1 knockout mice (see, e.g., Hernandez-Fernaud and Salido (*FEBS Journal* 277: 4766-74)). In an exemplary in vivo experiment, dsRNAs of the invention are tail vein injected into such mouse models at doses ranging from 1 to 10 mg/kg or, alternatively, repeated doses are administered at single-dose $IC_{50}$ levels, and organ samples (e.g., liver, but may also include prostate, kidney, lung, pancreas, colon, skin, spleen, bone marrow, lymph nodes, mammary fat pad, etc.) are harvested 24 hours after administration of the final dose. Such organs are then evaluated for mouse and/or human lactate dehydrogenase levels, depending upon the model used. Duration of action can also be examined at, e.g., 1, 4, 7, 14, 21 or more days after final dsRNA administration.

Lactate Dehydrogenase-Targeting dsRNAs

In certain embodiments, an anti-lactate dehydrogenase DsiRNA of the instant invention possesses strand lengths of at least 25 nucleotides. Accordingly, in certain embodiments, an anti-lactate dehydrogenase DsiRNA contains one oligonucleotide sequence, a first sequence, that is at least 25 nucleotides in length and no longer than 35 or up to 50 or more nucleotides. This sequence of RNA can be between 26 and 35, 26 and 34, 26 and 33, 26 and 32, 26 and 31, 26 and 30, and 26 and 29 nucleotides in length. This sequence can be 27 or 28 nucleotides in length or 27 nucleotides in length. The second sequence of the DsiRNA agent can be a sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotide sequence will have 21 or more complementary base pairs, or 25 or more complementary base pairs with the first oligonucleotide sequence. In one embodiment, the second sequence is the same length as the first sequence, and the DsiRNA agent is blunt ended. In another embodiment, the ends of the DsiRNA agent have one or more overhangs.

In certain embodiments, the first and second oligonucleotide sequences of the DsiRNA agent exist on separate oligonucleotide strands that can be and typically are chemically synthesized. In some embodiments, both strands are between 26 and 35 nucleotides in length. In other embodiments, both strands are between 25 and 30 or 26 and 30 nucleotides in length. In one embodiment, both strands are 27 nucleotides in length, are completely complementary and have blunt ends. In certain embodiments of the instant invention, the first and second sequences of an anti-lactate dehydrogenase DsiRNA exist on separate RNA oligonucleotides (strands). In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. In certain embodiments of the instant invention, the anti-lactate dehydrogenase DsiRNA agent is comprised of two oligonucleotide strands of differing lengths, with the anti-lactate dehydrogenase DsiRNA possessing a blunt end at the 3' terminus of a first strand (sense strand) and a 3' overhang at the 3' terminus of a second strand (antisense strand). The DsiRNA can also contain one or more deoxyribonucleic acid (DNA) base substitutions.

Suitable DsiRNA compositions that contain two separate oligonucleotides can be chemically linked outside their annealing region by chemical linking groups. Many suitable chemical linking groups are known in the art and can be used. Suitable groups will not block Dicer activity on the DsiRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the DsiRNA composition. The hairpin structure will not block Dicer activity on the DsiRNA and will not interfere with the directed destruction of the target RNA.

The dsRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand. In certain embodiments, substitutions and/or modifications are made at specific residues within a DsiRNA agent. Such substitutions and/or modifications can include, e.g., deoxy-modifications at one or more residues of positions 1, 2 and 3 when numbering from the 3' terminal position of the sense strand of a DsiRNA agent; and introduction of 2'-O-alkyl (e.g., 2'-O-methyl) modifications at the 3' terminal residue of the antisense strand of DsiRNA agents, with such modifications also being performed at overhang positions of the 3' portion of the antisense strand and at alternating residues of the antisense strand of the DsiRNA that are included within the region of a DsiRNA agent that is processed to form an active siRNA agent. The preceding modifications are offered as exemplary, and are not intended to be limiting in any manner. Further consideration of the structure of preferred DsiRNA agents, including further description of the modifications and substitutions that can be performed upon the anti-lactate dehydrogenase DsiRNA agents of the instant invention, can be found below.

A dsRNA of the invention comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the lactate dehydrogenase target gene, the other strand (the sense strand) comprises a region which is complementary to the antisense strand, such that the two strands hybridize and form a duplex structure when combined under suitable conditions. Generally, the duplex structure is between 15 and 35, optionally between 25 and 30, between 26 and 30, between 18 and 25, between 19 and 24, or between 19 and 21 base pairs in length. Similarly, the region of complementarity to the target sequence is between 15 and 35, optionally between 18 and 30, between 25 and 30, between 19 and 24, or between 19 and 21 nucleotides in length. The dsRNA of the invention may further comprise one or more single-stranded nucleotide overhang(s). It has been identified that dsRNAs comprising duplex structures of between 15 and 35 base pairs in length can be effective in inducing RNA interference, including DsiRNAs (generally of at least 25 base pairs in length) and siRNAs (in certain embodiments, duplex structures of siRNAs are between 20 and 23, and optionally, specifically 21 base pairs (Elbashir et al., *EMBO* 20: 6877-6888)). It has also been identified that dsRNAs possessing duplexes shorter than 20 base pairs can be effective as well (e.g., 15, 16, 17, 18 or 19 base pair duplexes). In certain embodiments, the dsRNAs of the invention can comprise at least one strand of a length of 19 nucleotides or more. In certain embodiments, it can be reasonably expected that shorter dsRNAs comprising a sequence complementary to one of the sequences of Tables 4, 6, 9 or 11, minus only a few nucleotides on one or both ends may be similarly effective as compared to the dsRNAs described above and in Tables 2-3, 7-8 and 12. Hence, dsRNAs comprising a partial sequence of at least 15, 16, 17, 18, 19, 20, or more contiguous nucleotides sufficiently complementary to one of the sequences of Tables 4, 6, 9 or 11, and differing in their ability to inhibit the expression of the lactate dehydrogenase target gene in an assay as described herein by not more than 5, 10, 15, 20, 25, or 30% inhibition from a dsRNA comprising the full sequence, are contemplated by the invention. In one embodiment, at least one end of the dsRNA has a single-stranded nucleotide overhang of 1 to 5, optionally 1 to 4, in certain embodiments, 1 or 2 nucleotides. Certain dsRNA structures having at least one nucleotide overhang possess superior inhibitory properties as compared to counterparts possessing base-paired blunt ends at both ends of the dsRNA molecule.

In one embodiment, dsRNA molecules of the invention that down regulate or reduce lactate dehydrogenase gene expression are used for treating, preventing or reducing lactate dehydrogenase-related diseases or disorders (e.g., PH1 or other disease or disorder associated with oxalate accumulation, and/or oncology or pyruvate dehydrogenase deficiency) in a subject or organism.

or those where both strands exceed 30 nucleotides in length (see, e.g., U.S. Pat. No. 8,513,207, where an exemplary double stranded nucleic acid (dsNA) possesses a first oligonucleotide strand having a 5' terminus and a 3' terminus and a second oligonucleotide strand having a 5' terminus and a 3' terminus, where the first strand is 31 to 49 nucleotide residues in length, where starting from the first nucleotide (position 1) at the 5' terminus of the first strand, positions 1 to 23 of the first strand are ribonucleotides; the second strand is 31 to 53 nucleotide residues in length and includes 23 consecutive ribonucleotides that base pair with the ribonucleotides of positions 1 to 23 of the first strand to form a duplex; the 5' terminus of the first strand and the 3' terminus of said second strand form a blunt end or a 1-4 nucleotide 3' overhang; the 3' terminus of the first strand and the 5' terminus of said second strand form a duplexed blunt end, a 5' overhang or a 3' overhang; optionally, at least one of positions 24 to the 3' terminal nucleotide residue of the first strand is a deoxyribonucleotide, optionally, that base pairs with a deoxyribonucleotide of said second strand; and the second strand is sufficiently complementary to a target RNA along at least 19 ribonucleotides of the second strand length to reduce target gene expression when the double stranded nucleic acid is introduced into a mammalian cell).

In certain embodiments, an active dsNA of the invention can possess a 5' overhang of the first strand (optionally, the passenger strand) with respect to the second strand (optionally, the guide strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 5' overhang "extended" region of the first strand is optionally modified at one or more residues (optionally, at alternating residues, all residues, or any other selection of residues).

In certain embodiments, an active dsNA of the invention can possess a 3' overhang of the first strand (optionally, the passenger strand) with respect to the second strand (optionally, the guide strand) of 2-50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50) or more in length. In related embodiments, the duplex region formed by the first and second strands of such a dsNA is 15, 16, 17, 18, 19, 20, 21, 22, 23, 24, 25 or more base pairs in length. The 3' overhang "extended" region of the first strand is optionally modified at one or more residues (optionally, at alternating residues, all residues, or any other selection of residues).

In another embodiment of the present invention, each sequence of a DsiRNA molecule of the invention is independently 25 to 35 nucleotides in length, in specific embodiments 25, 26, 27, 28, 29, 30, 31, 32, 33, 34 or 35 nucleotides in length. In another embodiment, the DsiRNA duplexes of the invention independently comprise 25 to 30 base pairs (e.g., 25, 26, 27, 28, 29, or 30). In another embodiment, one or more strands of the DsiRNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (lactate dehydrogenase) nucleic acid molecule. In certain embodiments, a DsiRNA molecule of the invention possesses a length of duplexed nucleotides between 25 and 34 nucleotides in length (e.g., 25, 26, 27, 28, 29, 30, 31, 32, 33 or 34 nucleotides in length; optionally, all such nucleotides base pair with cognate nucleotides of the opposite strand). (Exemplary DsiRNA molecules of the invention are shown in FIG. 1, and below.)

Stabilizing modifications (e.g., 2'-O-Methyl, phosphorothioate, deoxyribonucleotides, including dNTP base pairs, 2'-F, etc.) can be incorporated within any double stranded nucleic acid of the invention, and can be used in abundance, particularly within DsiRNAs possessing one or both strands exceeding 30 nucleotides in length.

In certain embodiments, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of a nucleic acid of the instant invention are modified residues. For a dsNA of the invention, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of the first strand are modified residues. Additionally and/or alternatively for a dsNA of the invention, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more of the nucleotide residues of the second strand are modified residues. For the dsNAs of the invention, modifications of both duplex (double-stranded) regions and overhang (single-stranded) regions are contemplated. Thus, in certain embodiments, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more (e.g., all) duplex nucleotide residues are modified residues. Additionally and/or alternatively, at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95% or more (e.g., all) overhang nucleotide residues of one or both strands are modified residues. Optionally, the modifications of the dsNAs of the invention do not include an inverted abasic (e.g., inverted deoxy abasic) or inverted dT end-protecting group. Alternatively, a dsNA of the invention includes a terminal cap moiety (e.g., an inverted deoxy abasic and/or inverted dT end-protecting group). Optionally, such a terminal cap moiety is located at the 5' end, at the 3' end, or at both the 5' end and the 3' end of the first strand, of the second strand, or of both first and second strands.

While the guide strand of a double stranded nucleic acid of the invention must possess a sequence of, e.g., 15, 16, 17, 18 or 19 nucleotides that are complementary to a target RNA (e.g., mRNA), additional sequence(s) of the guide strand need not be complementary to the target RNA. The end structures of double stranded nucleic acids possessing at least one strand length in excess of 30 nucleotides can also be varied while continuing to yield functional dsNAs—e.g. the 5' end of the guide strand and the 3' end of the passenger strand may form a 5'-overhang, a blunt end or a 3' overhang (for certain dsNAs, e.g., "single strand extended" dsNAs, the length of such a 5' or 3' overhang can be 1-4, 1-5, 1-6, 1-10, 1-15, 1-20 or even 1-25 or more); similarly, the 3' end of the guide strand and the 5' end of the passenger strand may form a 5'-overhang, a blunt end or a 3' overhang (for certain dsNAs, e.g., "single strand extended" dsNAs, the length of such a 5' or 3' overhang can be 1-4, 1-5, 1-6, 1-10, 1-15, 1-20 or even 1-25 or more). In certain embodiments, the length of the passenger strand is 31-49 nucleotides while the length of the guide strand is 31-53 nucleotides, optionally while the 5' end of the guide strand forms a blunt end (optionally, a base-paired blunt end) with the 3' end of the passenger strand, optionally, with the 3' end of the guide strand and the 5' end of the passenger strand forming a 3' overhang of 1-4 nucleotides in length. Exemplary "extended" Dicer substrate structures are set forth, e.g., in US 2010/0173974 and U.S. Pat. No. 8,349,809, both of which are incorporated herein by reference. In certain embodiments, one or more strands of the dsNA molecule of the invention independently comprises 19 to 35 nucleotides (e.g., 19, 20, 21, 22, 23, 24, 25, 26, 27, 28, 29, 30, 31, 32, 33, 34 or 35) that are complementary to a target (lactate dehydrogenase) nucleic acid molecule. In certain embodiments, a DsiRNA molecule of the invention possesses a length of duplexed nucleotides between 25 and 66 nucleotides, optionally between 25 and 49 nucleotides in length (e.g., 25, 26, 27, 28, 29, 30, 31, 32, 33, 34, 35, 36, 37, 38, 39, 40, 41, 42, 43, 44, 45, 46, 47, 48 or 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 nucleotides in length; optionally, all such nucleotides base pair with cognate nucleotides of the opposite strand). In related embodiments, a dsNA of the invention possesses strand lengths that are, independently, between 19 and 80 nucleotides in length, optionally between 25 and 53 nucleotides in length, e.g., 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 nucleotides in length. In certain embodiments, one strand length is 19-35 nucleotides in length, while the other strand length is 30-80 nucleotides in length and at least one strand has a 5' overhang of at least 5 nucleotides in length relative to the other strand. In certain related embodiments, the 3' end of the first strand and the 5' end of the second strand form a structure that is a blunt end or a 1-6 nucleotide 3' overhang, while the 5' end of the first strand forms a 5-60 nucleotide overhang with respect to the 3' end of the second strand.

Optionally, between one and all nucleotides of the 5-60 nucleotide overhang are modified nucleotides (optionally, deoxyribonucleotides and/or modified ribonucleotides).

In some embodiments, a dsNA of the invention has a first or second strand that has at least 8 contiguous ribonucleotides. In certain embodiments, a dsNA of the invention has 9, 10, 11, 12, 13, 14, 15, 16, 17, 18, 19, 20, 21, 22, 23 or more (e.g., 24, 25, 26, 27, 28, 29, 30, 31, 32, 33, 34, 35, 26, or more, up to the full length of the strand) ribonucleotides, optionally including modified ribonucleotides (2'-O-methyl ribonucleotides, phosphorothioate linkages, etc.). In certain embodiments, the ribonucleotides or modified ribonucleotides are contiguous.

In certain embodiments, a dsNA comprising a first strand and a second strand, each strand, independently, having a 5' terminus and a 3' terminus, and having, independently, respective strand lengths of 25-53 nucleotides in length, is sufficiently highly modified (e.g., at least 10% or more, at least 20% or more, at least 30% or more, at least 40% or more, at least 50% or more, at least 60% or more, at least 70% or more, at least 80% or more, at least 90% or more, at least 95% or more residues of one and/or both strands are modified such that dicer cleavage of the dsNA is prevented (optionally, modified residues occur at and/or flanking one or all predicted dicer cleavage sites of the dsNA). Such non-dicer-cleaved dsNAs retain LDH inhibition activity and are optionally cleaved by non-dicer nucleases to yield, e.g., 15-30, or in particular embodiments, 19-23 nucleotide strand length dsNAs capable of inhibiting LDH in a mammalian cell. In certain related embodiments, dsNAs possessing sufficiently extensive modification to block dicer cleavage of such dsNAs optionally possess regions of unmodified nucleotide residues (e.g., one or two or more consecutive nucleotides, forming a "gap" or "window" in a modification pattern) that allow for and/or promote cleavage of such dsNAs by non-Dicer nucleases. In other embodiments, Dicer-cleaved dsNAs of the invention can include extensive modification patterns that possess such "windows" or "gaps" in modification such that Dicer cleavage preferentially occurs at such sites (as compared to heavily modified regions within such dsNAs).

In certain embodiments, a DsiRNA (in a state as initially formed, prior to dicer cleavage) is more potent at reducing lactate dehydrogenase target gene expression in a mammalian cell than a 19, 20, 21, 22 or 23 base pair sequence that is contained within it. In certain such embodiments, a DsiRNA prior to dicer cleavage is more potent than a 19-21mer contained within it. Optionally, a DsiRNA prior to dicer cleavage is more potent than a 19 base pair duplex contained within it that is synthesized with symmetric dTdT overhangs (thereby forming a siRNA possessing 21 nucleotide strand lengths having dTdT overhangs). In certain embodiments, the DsiRNA is more potent than a 19-23mer siRNA (e.g., a 19 base pair duplex with dTdT overhangs) that targets at least 19 nucleotides of the 21 nucleotide target sequence that is recited for a DsiRNA of the invention (without wishing to be bound by theory, the identity of a such a target site for a DsiRNA is identified via identification of the Ago2 cleavage site for the DsiRNA; once the Ago2 cleavage site of a DsiRNA is determined for a DsiRNA, identification of the Ago2 cleavage site for any other inhibitory dsRNA can be performed and these Ago2 cleavage sites can be aligned, thereby determining the alignment of projected target nucleotide sequences for multiple dsRNAs). In certain related embodiments, the DsiRNA is more potent than a 19-23mer siRNA that targets at least 20 nucleotides of the 21 nucleotide target sequence that is recited for a DsiRNA of the invention. Optionally, the DsiRNA is more potent than a 19-23mer siRNA that targets the same 21 nucleotide target sequence that is recited for a DsiRNA of the invention. In certain embodiments, the DsiRNA is more potent than any 21mer siRNA that targets the same 21 nucleotide target sequence that is recited for a DsiRNA of the invention. Optionally, the DsiRNA is more potent than any 21 or 22mer siRNA that targets the same 21 nucleotide target sequence that is recited for a DsiRNA of the invention. In certain embodiments, the DsiRNA is more potent than any 21, 22 or 23mer siRNA that targets the same 21 nucleotide target sequence that is recited for a DsiRNA of the invention. As noted above, such potency assessments are most effectively performed upon dsRNAs that are suitably formulated (e.g., formulated with an appropriate transfection reagent) at a concentration of 1 nM or less. Optionally, an $IC_{50}$ assessment is performed to evaluate activity across a range of effective inhibitory concentrations, thereby allowing for robust comparison of the relative potencies of dsRNAs so assayed.

The dsRNA molecules of the invention are added directly, or can be complexed with lipids (e.g., cationic lipids), packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. In particular embodiments, the nucleic acid molecules of the invention comprise sequences shown in FIG. 1, and the below exemplary structures. Examples of such nucleic acid molecules consist essentially of sequences defined in these figures and exemplary structures. Furthermore, where such agents are modified in accordance with the below description of modification patterning of DsiRNA agents, chemically modified forms of constructs described in FIG. 1, and the below exemplary structures can be used in all uses described for the DsiRNA agents of FIG. 1, and the below exemplary structures.

In another aspect, the invention provides mammalian cells containing one or more dsRNA molecules of this invention. The one or more dsRNA molecules can independently be targeted to the same or different sites.

Modified Structures of Anti-Lactate Dehydrogenase DsiRNA Agents

In certain embodiments, the anti-lactate dehydrogenase DsiRNA agents of the invention can have the following structures:

In one such embodiment, the DsiRNA comprises:

5'-XXXXXXXXXXXXXXXXXXXXXXXXX-3'

3'-YXXXXXXXXXXXXXXXXXXXXXXXXX-5' wherein "X"=RNA and "Y" is an overhang domain comprised of 1-4 RNA monomers that are optionally 2'-O-methyl RNA monomers. In a related embodiment, the DsiRNA comprises:

5'-XXXXXXXXXXXXXXXXXXXXXXXDD-3'

3'-YXXXXXXXXXXXXXXXXXXXXXXXXX-5' wherein "X"=RNA, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand.

DsiRNAs of the invention can carry a broad range of modification patterns (e.g., 2'-O-methyl RNA patterns, e.g., within extended DsiRNA agents). Certain modification patterns of the second strand of DsiRNAs of the invention are presented below.

In one embodiment, the DsiRNA comprises:

5'-XXXXXXXXXXXXXXXXXXXXXXXXX-3'

3'-YX<u>XXXXXXXXX</u>XX<u>XXXXXXXXX</u>XXXXX-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

5'-XXXXXXXXXXXXXXXXXXXXXXXDD-3'

3'-YX<u>XXXXXXXXX</u>XX<u>XXXXXXXXX</u>XXXXX-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers, and "D"=DNA. The top strand is the sense strand, and the bottom strand is the antisense strand.

In another such embodiment, the DsiRNA comprises:

5'-XXXXXXXXXXXXXXXXXXXXXXXXX-3'

3'-YX<u>XXXXXXXXX</u>X<u>XXX</u>XXXXXXXXXX-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

5'-XXXXXXXXXXXXXXXXXXXXXXXDD-3'

3'-YX<u>XXXXXXXXX</u>X<u>XXX</u>XXXXXXXXXX-5' wherein "X"=RNA, "<u>X</u>"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In another such embodiment, the DsiRNA comprises:

5'-XXXXXXXXXXXXXXXXXXXXXXXXX-3'

3'-YX<u>XXXXXXXXX</u>XX<u>XXXXX</u>XXXXXXX-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

5'-XXXXXXXXXXXXXXXXXXXXXXXDD-3'

3'-YX<u>XXXXXXXXX</u>XX<u>XXXXX</u>XXXXXXX-5' wherein "X"=RNA, "<u>X</u>"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand.

In further embodiments, the DsiRNA comprises:

5'-XXXXXXXXXXXXXXXXXXXXXXXXX-3'

3'-YX<u>XXXXXXXXXX</u>X<u>XXXXXXXXX</u><u>XX</u>-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

5'-XXXXXXXXXXXXXXXXXXXXXXXDD-3'

3'-YX<u>XXXXXXXXXX</u>X<u>XXXXXXXXX</u><u>XX</u>-5' wherein "X"=RNA, "<u>X</u>"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

5'-XXXXXXXXXXXXXXXXXXXXXXXXX-3'

3'-<u>XXXXXXXXXXXXXXX</u>X<u>XXXXXXXXXX</u>-5' wherein "X"=RNA and "<u>X</u>"=2'-O-methyl RNA. In a further related embodiment, the DsiRNA comprises:

5'-XXXXXXXXXXXXXXXXXXXXXXXDD-3'

3'-<u>XXXXXXXXXXXXXXX</u>X<u>XXXXXXXXX</u><u>XX</u>-5' wherein "X"=RNA, "<u>X</u>"=2'-O-methyl RNA, and "D"=DNA. The top strand is the sense strand, and the bottom strand is the antisense strand. This modification pattern is also referred to herein as the "AS-M7" or "M7" modification pattern.

In additional embodiments, the DsiRNA comprises:

5'-XXXXXXXXXXXXXXXXXXXXXXXXX-3'

3'-YX<u>XXXXXXXXXXX</u>X<u>XXXXXXXXX</u><u>XX</u>-5' wherein "X"=RNA, "<u>X</u>"=2'-O-methyl RNA, "Y" is an overhang domain comprised of 1-4 RNA monomers that are optionally 2'-O-methyl RNA monomers and underlined residues are 2'-O-methyl RNA monomers. In a related embodiment, the DsiRNA comprises:

5'-XXXXXXXXXXXXXXXXXXXXXXXDD-3'

3'-YX<u>XXXXXXXXXXX</u>X<u>XXXXXXXXX</u><u>XX</u>-5' wherein "X"=RNA, "<u>X</u>"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. The top strand is the sense strand, and the bottom strand is the antisense strand. In another related embodiment, the DsiRNA comprises:

wherein "X"=RNA and "X"=2'-O-methyl RNA. The top strand is the sense strand, and the bottom strand is the antisense strand. In a further related embodiment, the DsiRNA comprises:

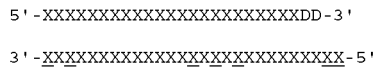

wherein "X"=RNA, "X"=2'-O-methyl RNA, and "D"=DNA. The top strand is the sense strand, and the bottom strand is the antisense strand. This modification pattern is also referred to herein as the "AS-M6" or "M6" modification pattern.

In other embodiments, the DsiRNA comprises:

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

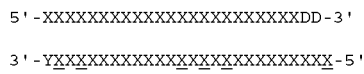

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

wherein "X"=RNA and "X"=2'-O-methyl RNA. The top strand is the sense strand, and the bottom strand is the antisense strand. In another related embodiment, the DsiRNA comprises:

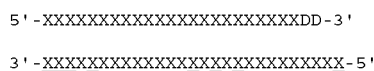

wherein "X"=RNA, "X"=2'-O-methyl RNA, and "D"=DNA. The top strand is the sense strand, and the bottom strand is the antisense strand. This modification pattern is also referred to herein as the "AS-M5" or "M5" modification pattern.

In further embodiments, the DsiRNA comprises:

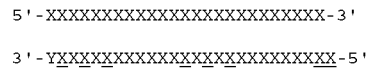

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

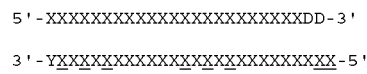

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In one related embodiment, the DsiRNA comprises:

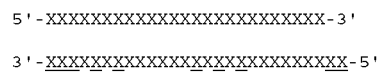

wherein "X"=RNA and "X"=2'-O-methyl RNA. The top strand is the sense strand, and the bottom strand is the antisense strand. In a further related embodiment, the DsiRNA comprises:

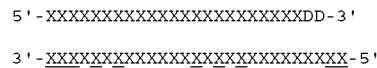

wherein "X"=RNA, "X"=2'-O-methyl RNA, and "D"=DNA. The top strand is the sense strand, and the bottom strand is the antisense strand. This modification pattern is also referred to herein as the "AS-M4" or "M4" modification pattern.

In additional embodiments, the DsiRNA comprises:

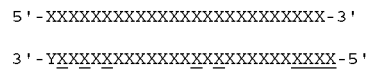

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

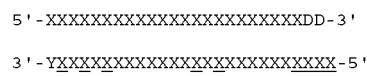

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M8" or "M8" modification pattern.

In other embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M3" or "M3" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M2" or "M2" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
```

```
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M1" or "M1" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M9" or "M9" modification pattern.

In other embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M10" or "M10" modification pattern.

In further embodiments, the DsiRNA comprises:

```
5'-XXXXXXXXXXXXXXXXXXXXXXXXX-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

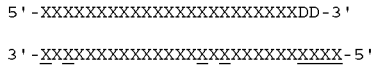

wherein "X"=RNA, "X"=2'-O-methyl RNA, and "D"=DNA. The top strand is the sense strand, and the bottom strand is the antisense strand. This modification pattern is also referred to herein as the "AS-M11" or "M11" modification pattern.

In additional embodiments, the DsiRNA comprises:

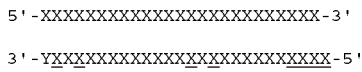

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

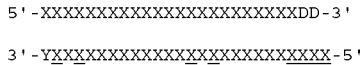

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

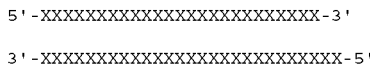

wherein "X"=RNA and "X"=2'-O-methyl RNA. The top strand is the sense strand, and the bottom strand is the antisense strand. In a further related embodiment, the DsiRNA comprises:

wherein "X"=RNA, "X"=2'-O-methyl RNA, and "D"=DNA. The top strand is the sense strand, and the bottom strand is the antisense strand. This modification pattern is also referred to herein as the "AS-M12" or "M12" modification pattern.

In further embodiments, the DsiRNA comprises:

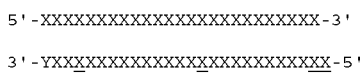

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

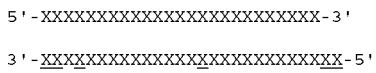

wherein "X"=RNA and "X"=2'-O-methyl RNA. The top strand is the sense strand, and the bottom strand is the antisense strand. In a further related embodiment, the DsiRNA comprises:

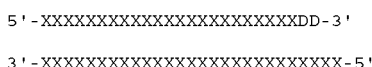

wherein "X"=RNA, "X"=2'-O-methyl RNA, and "D"=DNA. The top strand is the sense strand, and the bottom strand is the antisense strand. This modification pattern is also referred to herein as the "AS-M13" or "M13" modification pattern.

In other embodiments, the DsiRNA comprises:

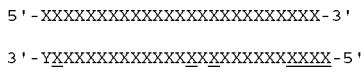

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In another related embodiment, the DsiRNA comprises:

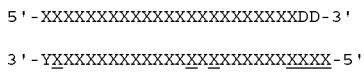

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

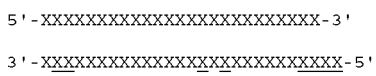

wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M21" or "M21" modification pattern.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M14" or "M14" modification pattern.

In additional embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M15" or "M15" modification pattern.

In further embodiments, the DsiRNA comprises:

```
5'-XXXXXXXXXXXXXXXXXXXXXXXXX-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In a related embodiment, the DsiRNA comprises:

```
5'-XXXXXXXXXXXXXXXXXXXXXXXDD-3'
3'-YXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
```

3'-XXXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M16" or "M16" modification pattern.

In additional embodiments, the DsiRNA comprises:

5'-XXXXXXXXXXXXXXXXXXXXXXXX-3'

3'-YXXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXDD-3'

3'-YXXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M17" or "M17" modification pattern.

In further embodiments, the DsiRNA comprises:

5'-XXXXXXXXXXXXXXXXXXXXXXXX-3'

3'-YXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXDD-3'

3'-YXXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M18" or "M18" modification pattern.

In additional embodiments, the DsiRNA comprises:

5'-XXXXXXXXXXXXXXXXXXXXXXXX-3'

3'-YXXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXDD-3'

3'-YXXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M19" or "M19" modification pattern.

In further embodiments, the DsiRNA comprises:

5'-XXXXXXXXXXXXXXXXXXXXXXX-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXX-3'

3'-XXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M20" or "M20" modification pattern.

In additional embodiments, the DsiRNA comprises:

5'-XXXXXXXXXXXXXXXXXXXXXXX-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXX-3'

3'-XXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M22" or "M22" modification pattern.

In further embodiments, the DsiRNA comprises:

5'-XXXXXXXXXXXXXXXXXXXXXXX-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXX-3'

3'-XXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

```
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M24" or "M24" modification pattern.

In additional embodiments, the DsiRNA comprises:

```
5'-XXXXXXXXXXXXXXXXXXXXXXX-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXX-3'

3'-XXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M25" or "M25" modification pattern.

In further embodiments, the DsiRNA comprises:

```
5'-XXXXXXXXXXXXXXXXXXXXXXX-3'

3'-YXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
``` wherein "X"=RNA, "X̲"=2'-O-methyl RNA, and "D"=DNA. The top strand is the sense strand, and the bottom strand is the antisense strand. This modification pattern is also referred to herein as the "AS-M26" or "M26" modification pattern.

In additional embodiments, the DsiRNA comprises:

```
5'-XXXXXXXXXXXXXXXXXXXXXXX-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXX-3'

3'-XXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
```

```
3'-XXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M27" or "M27" modification pattern.

In further embodiments, the DsiRNA comprises:

```
5'-XXXXXXXXXXXXXXXXXXXXXXXXX-3'

3'-YX̲X̲X̲X̲XXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YX̲X̲X̲X̲XXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-X̲X̲X̲X̲X̲XXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-X̲X̲X̲X̲X̲XXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M28" or "M28" modification pattern.

In further embodiments, the DsiRNA comprises:

```
5'-XXXXXXXXXXXXXXXXXXXXXXXXX-3'

3'-YX̲X̲X̲X̲XXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
```

```
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-X̲X̲X̲X̲XXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-X̲X̲X̲X̲XXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M29" or "M29" modification pattern.

In additional embodiments, the DsiRNA comprises:

```
5'-XXXXXXXXXXXXXXXXXXXXXXXXX-3'

3'-X̲X̲X̲X̲X̲XXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-X̲X̲X̲X̲X̲XXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M30" or "M30" modification pattern.

In further embodiments, the DsiRNA comprises:

```
5'-XXXXXXXXXXXXXXXXXXXXXXXXX-3'

3'-X̲X̲X̲X̲X̲XXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-X̲X̲X̲X̲X̲XXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M31" or "M31" modification pattern.

In additional embodiments, the DsiRNA comprises:

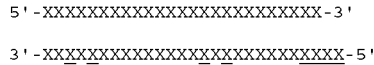

wherein "X"=RNA and "X"=2'-O-methyl RNA. The top strand is the sense strand, and the bottom strand is the antisense strand. In a further related embodiment, the DsiRNA comprises:

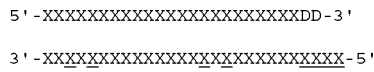

wherein "X"=RNA, "X"=2'-O-methyl RNA, and "D"=DNA. The top strand is the sense strand, and the bottom strand is the antisense strand. This modification pattern is also referred to herein as the "AS-M32" or "M32" modification pattern.

In further embodiments, the DsiRNA comprises:

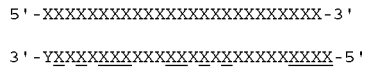

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

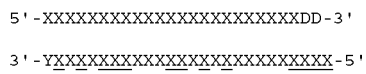

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

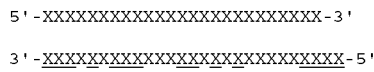

wherein "X"=RNA and "X"=2'-O-methyl RNA. The top strand is the sense strand, and the bottom strand is the antisense strand. In a further related embodiment, the DsiRNA comprises:

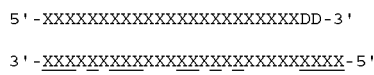

wherein "X"=RNA, "X"=2'-O-methyl RNA, and "D"=DNA. The top strand is the sense strand, and the bottom strand is the antisense strand. This modification pattern is also referred to herein as the "AS-M34" or "M34" modification pattern.

In additional embodiments, the DsiRNA comprises:

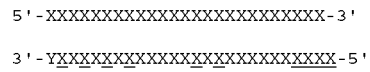

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

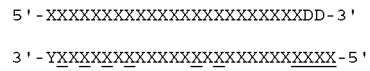

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

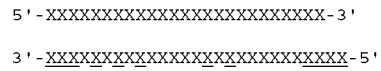

wherein "X"=RNA and "X"=2'-O-methyl RNA. The top strand is the sense strand, and the bottom strand is the antisense strand. In a further related embodiment, the DsiRNA comprises:

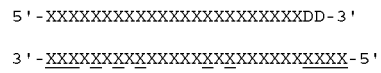

wherein "X"=RNA, "X"=2'-O-methyl RNA, and "D"=DNA. The top strand is the sense strand, and the bottom strand is the antisense strand. This modification pattern is also referred to herein as the "AS-M35" or "M35" modification pattern.

In further embodiments, the DsiRNA comprises:

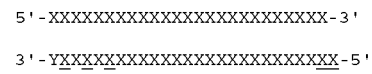

wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

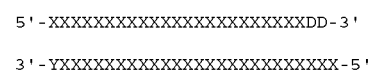

wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M37" or "M37" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M38" or "M38" modification pattern.

In further embodiments, the DsiRNA comprises:

```
5'-XXXXXXXXXXXXXXXXXXXXXXXXX-3'
```

```
3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M40" or "M40" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'

3'-YXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
```

-continued

```
3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M41" or "M41" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M36" or "M36" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M42" or "M42" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

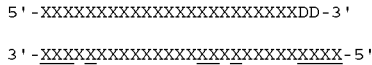

wherein "X"=RNA, "X̲"=2'-O-methyl RNA, and "D"=DNA. The top strand is the sense strand, and the bottom strand is the antisense strand. This modification pattern is also referred to herein as the "AS-M43" or "M43" modification pattern.

In additional embodiments, the DsiRNA comprises:

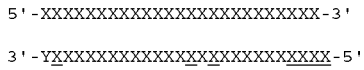

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

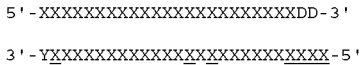

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

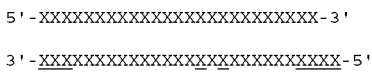

wherein "X"=RNA and "X̲"=2'-O-methyl RNA. The top strand is the sense strand, and the bottom strand is the antisense strand. In a further related embodiment, the DsiRNA comprises:

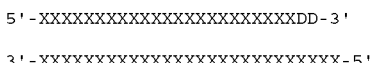

wherein "X"=RNA, "X̲"=2'-O-methyl RNA, and "D"=DNA. The top strand is the sense strand, and the bottom strand is the antisense strand. This modification pattern is also referred to herein as the "AS-M44" or "M44" modification pattern.

In further embodiments, the DsiRNA comprises:

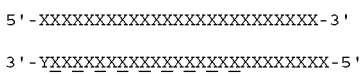

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

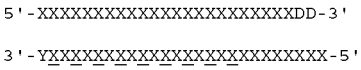

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

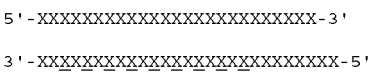

wherein "X"=RNA and "X̲"=2'-O-methyl RNA. The top strand is the sense strand, and the bottom strand is the antisense strand. In a further related embodiment, the DsiRNA comprises:

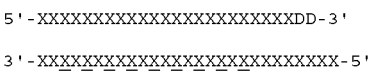

wherein "X"=RNA, "X̲"=2'-O-methyl RNA, and "D"=DNA. The top strand is the sense strand, and the bottom strand is the antisense strand. This modification pattern is also referred to herein as the "AS-M45" or "M45" modification pattern.

In additional embodiments, the DsiRNA comprises:

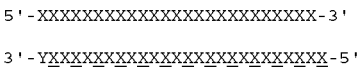

wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

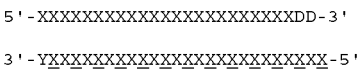

wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

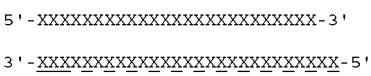

wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M46" or "M46" modification pattern.

In further embodiments, the DsiRNA comprises:

```
5'-XXXXXXXXXXXXXXXXXXXXXXXXX-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M47" or "M47" modification pattern.

In additional embodiments, the DsiRNA comprises:

```
5'-XXXXXXXXXXXXXXXXXXXXXXXXX-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M48" or "M48" modification pattern.

In further embodiments, the DsiRNA comprises:

```
5'-XXXXXXXXXXXXXXXXXXXXXXXXX-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXDD-3'
3'-YXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'
3'-XXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
```

3'-XXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M52" or "M52" modification pattern.

In further embodiments, the DsiRNA comprises:

5'-XXXXXXXXXXXXXXXXXXXXXXX-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-X̲XXX̲XXXXXXXXXXX̲XX̲XXXXXXX̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-X̲XXX̲XXXXXXXXXXX̲XX̲XXXXXXX̲X̲X̲X̲-5' wherein "X"=RNA, "X̲"=2'-O-methyl RNA, and "D"=DNA. The top strand is the sense strand, and the bottom strand is the antisense strand. This modification pattern is also referred to herein as the "AS-M54" or "M54" modification pattern.

In additional embodiments, the DsiRNA comprises:

5'-XXXXXXXXXXXXXXXXXXXXXXXXX-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. This modification pattern is also referred to herein as the "AS-M55" or "M55" modification pattern.

In further embodiments, the DsiRNA comprises:

5'-XXXXXXXXXXXXXXXXXXXXXXX-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXDD-3'

3'-YX̲XX̲XXXXXXXXXXX̲XX̲XXXXXXX̲X̲X̲X̲-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXX-3'

3'-X̲XXX̲XXXXXXXXXXX̲XX̲XXXXXXX̲X̲X̲X̲-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

```
3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M56" or "M56" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M57" or "M57" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
```

```
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M58" or "M58" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
```

```
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M59" or "M59" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M60" or "M60" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
```

```
3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M61" or "M61" modification pattern.

In further embodiments, the DsiRNA comprises:

```
5'-XXXXXXXXXXXXXXXXXXXXXXXXX-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
```

```
3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M62" or "M62" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M63" or "M63" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
```

```
3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M64" or "M64" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXXX-5'
``` wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
```

```
3'-XXXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M65" or "M65" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M66" or "M66" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
``` wherein "X"=RNA, "X̲"=2'-O-methyl RNA, and "D"=DNA. The top strand is the sense strand, and the bottom strand is the antisense strand. This modification pattern is also referred to herein as the "AS-M67" or "M67" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
```

```
3'-XXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M68" or "M68" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'

3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M69" or "M69" modification pattern.

In further embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXXDD-3'
```

```
3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'

3'-XXXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M70" or "M70" modification pattern.

In additional embodiments, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

```
5'-XXXXXXXXXXXXXXXXXXXXXXXXX-3'

3'-YXXXXXXXXXXXXXXXXXXXXXXXXXXXX-5'
``` wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXX-3'
```

3'-XXXXXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M71" or "M71" modification pattern.

In further embodiments, the DsiRNA comprises:

5'-XXXXXXXXXXXXXXXXXXXXXXXXX-3'

3'-YXXXXXXXXXXXXXXXXXXXXXXXXXXXXX-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXXDD-3'

3'-YXXXXXXXXXXXXXXXXXXXXXXXXXXXXX-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-XXXXXXXXXXXXXXXXXXXXXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXXDD-3'

3'-XXXXXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M72" or "M72" modification pattern.

In additional embodiments, the DsiRNA comprises:

5'-XXXXXXXXXXXXXXXXXXXXXXXXX-3'

3'-YXXXXXXXXXXXXXXXXXXXXXXXXXXXXX-5' wherein "X"=RNA, "X̲"=2'-O-methyl RNA, "Y" is an overhang domain comprised of 1-4 RNA monomers that are optionally 2'-O-methyl RNA monomers and underlined residues are 2'-O-methyl RNA monomers. The top strand is the sense strand, and the bottom strand is the antisense strand. In one related embodiment, the DsiRNA comprises:

5'-XXXXXXXXXXXXXXXXXXXXXXXXXDD-3'

3'-YXXXXXXXXXXXXXXXXXXXXXXXXXXXXX-5' wherein "X"=RNA, "X̲"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-XXXXXXXXXXXXXXXXXXXXXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXXDD-3'

3'-XXXXXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M73" or "M73" modification pattern.

In additional embodiments, the DsiRNA comprises:

5'-XXXXXXXXXXXXXXXXXXXXXXXXX-3'

3'-XXXXXXXXXXXXXXXXXXXXXXXXXXXXX-5' wherein "X"=RNA and "X̲"=2'-O-methyl RNA. In a further related embodiment, the DsiRNA comprises:

5'-XXXXXXXXXXXXXXXXXXXXXXXXXDD-3'

3'-XXXXXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M7*" or "M7*" modification pattern.

In further embodiments, the DsiRNA comprises:

5'-XXXXXXXXXXXXXXXXXXXXXXXXX-3'

3'-XXXXXXXXXXXXXXXXXXXXXXXXXXXXX-5' wherein "X"=RNA and "X̲"=2'-O-methyl RNA. The top strand is the sense strand, and the bottom strand is the antisense strand. In a further related embodiment, the DsiRNA comprises:

5'-XXXXXXXXXXXXXXXXXXXXXXXXXDD-3'

3'-XXXXXXXXXXXXXXXXXXXXXXXXXXXXX-5' wherein "X"=RNA, "X̲"=2'-O-methyl RNA, and "D"=DNA. The top strand is the sense strand, and the bottom strand is the antisense strand. This modification pattern is also referred to herein as the "AS-M6*" or "M6*" modification pattern.

In other embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In another related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M5*" or "M5*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M4*" or "M4*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M8*" or "M8*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M2*" or "M2*" modification pattern.

In other embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M10*" or "M10*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M11*" or "M11*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
```

-continued

```
3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M13*" or "M13*" modification pattern.

In further embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M14*" or "M14*" modification pattern.

In additional embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M15*" or "M15*" modification pattern.

In further embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M16*" or "M16*" modification pattern.

In additional embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M17*" or "M17*" modification pattern.

In further embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M18*" or "M18*" modification pattern.

In additional embodiments, the DsiRNA comprises:

```
5'-XXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M19*" or "M19*" modification pattern.

In further embodiments, the DsiRNA comprises:

```
5'-XXXXXXXXXXXXXXXXXXXXXDD-3'
```

3'-YXXXXXXXXXXXXXXXXXXXXXXXXX-5' wherein "X"=RNA, "X"=2'-O-methyl RNA, "Y" is an overhang domain comprised of 1-4 RNA monomers that are optionally 2'-O-methyl RNA monomers, underlined residues are 2'-O-methyl RNA monomers, and "D"=DNA. The top strand is the sense strand, and the bottom strand is the antisense strand. In another related embodiment, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M20*" or "M20*" modification pattern.

In additional embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M22*" or "M22*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M24*" or "M24*" modification pattern.

In additional embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M25*" or "M25*" modification pattern.

In further embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M26*" or "M26*" modification pattern.

In additional embodiments, the DsiRNA comprises:

5'-XXXXXXXXXXXXXXXXXXXXXXXXX-3'

3'-XXXXXXXXXXXXXXXXXXXXXXXXXX-5' wherein "X"=RNA and "X"=2'-O-methyl RNA. The top strand is the sense strand, and the bottom strand is the antisense strand. In a further related embodiment, the DsiRNA comprises:

5'-XXXXXXXXXXXXXXXXXXXXXXXDD-3'

3'-XXXXXXXXXXXXXXXXXXXXXXXXXX-5' wherein "X"=RNA, "X"=2'-O-methyl RNA, and "D"=DNA. The top strand is the sense strand, and the bottom strand is the antisense strand. This modification pattern is also referred to herein as the "AS-M27*" or "M27*" modification pattern.

In additional embodiments, the DsiRNA comprises:

5'-XXXXXXXXXXXXXXXXXXXXXXXXX-3'

```
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M28*" or "M28*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M29*" or "M29*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M34*" or "M34*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M35*" or "M35*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M37*" or "M37*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M38*" or "M38*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M40*" or "M40*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M41*" or "M41*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M36*" or "M36*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M42*" or "M42*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M43*" or "M43*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M44*" or "M44*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M46*" or "M46*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M47*" or "M47*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M48*" or "M48*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M52*" or "M52*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M54*" or "M54*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M55*" or "M55*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M56*" or "M56*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X̲"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X̲"=2'-O-methyl RNA, and "D"=DNA. The top strand is the sense strand, and the bottom strand is the antisense strand. This modification pattern is also referred to herein as the "AS-M57*" or "M57*" modification pattern.

In further embodiments, the DsiRNA comprises:

```
5'-XXXXXXXXXXXXXXXXXXXXXXXXX-3'
```

```
3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M58*" or "M58*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M59*" or "M59*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M60*" or "M60*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M61*" or "M61*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M62*" or "M62*" modification pattern.

In additional embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M63*" or "M63*" modification pattern.

In further embodiments, the DsiRNA comprises:

```
5'-XXXXXXXXXXXXXXXXXXXXXXXXX-3'

3'-XXXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'

3'-XXXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M64*" or "M64*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M65*" or "M65*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M66*" or "M66*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M67*" or "M67*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M68*" or "M68*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M69*" or "M69*" modification pattern.

In further embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M70*" or "M70*" modification pattern.

In additional embodiments, the DsiRNA comprises:

```
5'-XXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M71*" or "M71*" modification pattern.

In further embodiments, the DsiRNA comprises:

```
5'-XXXXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M72*" or "M72*" modification pattern.

In additional embodiments, the DsiRNA comprises:

```
5'-XXXXXXXXXXXXXXXXXXXXXXXXXXX-3'
3'-XXXXXXXXXXXXXXXXXXXXXXXXXXX-5'
``` wherein "X"=RNA and "X"=2'-O-methyl RNA. The top strand is the sense strand, and the bottom strand is the antisense strand. In a further related embodiment, the DsiRNA comprises:

```
5'-XXXXXXXXXXXXXXXXXXXXXXXXXDD-3'
3'-XXXXXXXXXXXXXXXXXXXXXXXXXXX-5'
``` wherein "X"=RNA, "X"=2'-O-methyl RNA, and "D"=DNA. The top strand is the sense strand, and the bottom strand is the antisense strand. This modification pattern is also referred to herein as the "AS-M73*" or "M73*" modification pattern.

Additional exemplary antisense strand modifications include the following:

```
3'-XXXXXXXXXXXXXXXXXXXXXXXXXXX-5'      "AS-M74"
3'-XXXXXXXXXXXXXXXXXXXXXXXXXXX-5'      "AS-M75"
3'-XXXXXXXXXXXXXXXXXXXXXXXXXXX-5'      "AS-M76"
3'-XXXXXXXXXXXXXXXXXXXXXXXXXXX-5'      "AS-M77"
3'-XXXXXXXXXXXXXXXXXXXXXXXXXXX-5'      "AS-M78"
3'-XXXXXXXXXXXXXXXXXXXXXXXXXXX-5'      "AS-M79"
3'-XXXXXXXXXXXXXXXXXXXXXXXXXXX-5'      "AS-M80"
3'-XXXXXXXXXXXXXXXXXXXXXXXXXXX-5'      "AS-M81"
```

-continued
```
3'-XpXXXXXXXXXXXXXXXXXXXXXXXXXX-5'     "AS-M82"
3'-XpXXXXXXXXXXXXXXXXXXXXXXXXXX-5'     "AS-M83"
3'-XXXXXXXXXXXXXXXXXXXXXXXXXXX-5'      "AS-M84"
3'-XXXXXXXXXXXXXXXXXXXXXXXXXXX-5'      "AS-M85"
3'-FFFXXXXXXXXXXXXXXXXXXXXFFFF-5'      "AS-M88"
3'-XXXXFXXFXFXXXXXXXXXXXXXXXX-5'       "AS-M89"
3'-FFFXFXFXFXFXFXFXXXXXXXFFFF-5'       "AS-M90"
3'-FFFXXXXXXXXXXXXXXXXXXXXXFF-5'       "AS-M91"
3'-XXXXXFXXXXXFXFXXXXXXXXXXXX-5'       "AS-M92"
3'-FFFXFXXXXXXXXXXFXXXXXXXX-5'         "AS-M93"
3'-FFFXFXFXXXXXFXFXFXXXXFFFF-5'        "AS-M94"
3'-FFFXFXFXFXFXFXFXXXXXXXFFFF-5'       "AS-M95"
3'-FFFXFXFXFXFXFXFXXXXXXXFFFpF-5'      "AS-M96"
3'-XXXXXXXXXXXXXXXXXXXXXXXXXXX-5'      "AS-M210"
3'-XXXXXXXXXXXXXXXXXXXXXXXXXXX-5'      "AS-M74*"
3'-XXXXXXXXXXXXXXXXXXXXXXXXXXX-5'      "AS-M75*"
3'-XXXXXXXXXXXXXXXXXXXXXXXXXXX-5'      "AS-M76*"
3'-XXXXXXXXXXXXXXXXXXXXXXXXXXX-5'      "AS-M77*"
3'-XXXXXXXXXXXXXXXXXXXXXXXXXXX-5'      "AS-M78*"
3'-XXXXXXXXXXXXXXXXXXXXXXXXXXX-5'      "AS-M79*"
3'-XXXXXXXXXXXXXXXXXXXXXXXXXXX-5'      "AS-M80*"
3'-XpXXXXXXXXXXXXXXXXXXXXXXXXXX-5'     "AS-M82*"
3'-XpXXXXXXXXXXXXXXXXXXXXXXXXXX-5'     "AS-M83*"
3'-XXXXXXXXXXXXXXXXXXXXXXXXXXX-5'      "AS-M84*"
3'-XFFXXXXXXXXXXXXXXXXXXXFFFF-5'       "AS-M88*"
3'-XXXXFXXXFXFXXXXXXXXXXXXXXX-5'       "AS-M89*"
3'-XFFXFXFXFXFXFXFXXXXXXXFFFF-5'       "AS-M90*"
3'-XFFXXXXXXXXXXXXXXXXXXXXXFF-5'       "AS-M91*"
3'-XXXXXFXXXXXFXFXXXXXXXXXXXX-5'       "AS-M92*"
3'-XFFXFXXXXXXXXXXFXXXXXXXX-5'         "AS-M93*"
3'-XFFXFXFXXXXXFXFXFXXXXFFFF-5'        "AS-M94*"
3'-XFFXFXFXFXFXFXFXXXXXXXFFFF-5'       "AS-M95*"
3'-XFFXFXFXFXFXFXFXXXXXXXFFFpF-5'      "AS-M96*"
3'-XXXXXXXXXXXXXXXXXXXXXXXXXXX-5'      "AS-M210*"
3'-XpXXXXXXXXXXXXXXXXXXXXXXXpX-5'      "AS-M101"
3'-XpXXXXXXXXXXXXXXXXXXXXXXXpX-5'      "AS-M104"
3'-XpXXXXXXXXXXXXXXXXXXXXXXXpX-5'      "AS-M104*"
3'-XpFpXFXFXFXFXFXFXFXFFXXXpX-5'       "AS-M105"
3'-XpFpXFXFXFXFXFXFXFXFFXXXpX-5'       "AS-M105*"
3'-XpXXXXXXXXXXXXXXXXXXXXXXXpX-5'      "AS-M106"
3'-XpXXXXXXXXXXXXXXXXXXXXXXXpX-5'      "AS-M106*"
```

-continued

| | |
|---|---|
| 3'-XXpXXXXXXXXXXXXXXXXXXXXXXXX-5' | "AS-M107" |
| 3'-XXpXXXXXXXXXXXXXXXXXXXXXXXX-5' | "AS-M107*" |
| 3'-ba-XXXXXXXXXXXXXXXXXXXXXXXXXXX-5'<br>(ba = inverted abasic for F7<br>stabilization at 3' end) | "AS-M108" |
| 3'-ba-XXXXXXXXXXXXXXXXXXXXXXXXXXX-5'<br>(ba = inverted abasic for F7<br>stabilization at 3' end) | "AS-M108*" |
| 3'-XDXXXXXXXXXXXXXXXXXXXXXXXXX-5' | "AS-M109" |
| 3'-XpXXFXFXFXXXXXXXXXXXXXXXXXpX-5' | "AS-M110" |
| 3'-XpXXFXFXFXXXXXXXXXXXXXXXXXpX-5' | "AS-M110*" |
| 3'-XpXXFXFXFXXXXFXFXFXXXXXXXpX-5' | "AS-M111" |
| 3'-XpXXFXFXFFXXXXXXXXXFXXXXXXpX-5' | "AS-M112" |
| 3'-XpXXFXFXFFXXFXXXXXXXFXXXXXXpX-5' | "AS-M113" |
| 3'-XpXXFXFXFFFFFXXXXXXXFXXXXXXpX-5' | "AS-M114" |
| 3'-XpXXFXFXFFFFFXXXXXXXFXXFXXXpX-5' | "AS-M115" |
| 3'-XpXXFXFXFFFFFXXXXXXXFFFXXXpX-5' | "AS-M116" |
| 3'-XpFXFXFXFXFXFXFXFXFXFXFXFpX-5' | "AS-M117" |
| 3'-XpXXFXFXFXXXXFXFXFXXXXXXXpX-5' | "AS-M111*" |
| 3'-XpXXFXFXFFXXXXXXXXXFXXXXXXpX-5' | "AS-M112*" |
| 3'-XpXXFXFXFFXFXXXXXXXFXXXXXpX-5' | "AS-M113*" |
| 3'-XpXXFXFXFFFFFXXXXXXXFXXXXXXpX-5' | "AS-M114*" |
| 3'-XpXXFXFXFFFFFXXXXXXXFXXFXXXpX-5' | "AS-M115*" |
| 3'-XpXXFXFXFFFFFXXXXXXXFFFXXXpX-5' | "AS-M116*" |
| 3'-XpFXFXFXFXFXFXFXFXFXFXFXFpX-5' | "AS-M117*" |
| 3'-XpXXXXXXXXXXXXXXXXXXXXXXXXpX-5' | "AS-M120" |
| 3'-XpXXXXXXXXXXXXXXXXXXXXXXXXpX-5' | "AS-M121" |
| 3'-XpXXXXXXXXXXXXXXXXXXXXXXXXpX-5' | "AS-M122" |
| 3'-XpXXXXXXXXXXXXXXXXXXXXXXXXpX-5' | "AS-M123" |
| 3'-XpXXXXXXXXXXXXXXXXXXXXXXXXpX-5' | "AS-M124" |
| 3'-XpXXXXXXXXXXXXXXXXXXXXXXXXpX-5' | "AS-M125" |
| 3'-XpFpXFXFXFXXXXXFXFXFXXXXFXpX-5' | "AS-M126" |
| 3'-XpFpXFXFXFXXXXXFXFXFXXXXFXpX-5' | "AS-M127" |
| 3'-XpFpXFXFXFXFXFXFXFXFXFFXXXpX-5' | "AS-M128" |
| 3'-XpFpXFXFXFXFXFXFXFXFXFXFFFFFpF-5' | "AS-M129" |
| 3'-XpFpXFXFXFXFXFXFXFXFXFXFXXXFXpX-5' | "AS-M130" |
| 3'-XpFpXFXFXFXFXFXFXFXFXFXFXFXFpX-5' | "AS-M131" |
| 3'-XpFpXFXFXFXFXFXFXFXFXFXFXXXpX-5' | "AS-M132" |
| 3'-XpFpXFXFXFXFXFXFXFXFXFXFXXXXpX-5' | "AS-M133" |
| 3'-XpFpXFXFXFXFXFXFXFXFXFXFFFpF-5' | "AS-M134" |
| 3'-XXXXXXXXXXXXXXXXXXXXXXXXXX-5' | "AS-M135" |
| 3'-XXXXXXXXXXXXXXXXXXXXXXXXXX-5' | "AS-M136" |
| 3'-XXXXXXXXXXXXXXXXXXXXXXXXXX-5' | "AS-M137" |
| 3'-XXXFXFXFXXXXXXFXFXFXXXXXXX-5' | "AS-M138" |
| 3'-XXXFXFXFFXXXXXXXXFXXXXXXX-5' | "AS-M139" |
| 3'-XpXXFXFXFXXXXXFXFXFFFXXXXXpX-5' | "AS-M140" |
| 3'-XpXXFXFXFFXXXFFXFXFFFXXXXpX-5' | "AS-M141" |
| 3'-XpXXFXFXFXFXFXFXFXFFFXXXXXpX-5' | "AS-M142" |
| 3'-XpXXFXFXFFFFFFFFXFXFFFXXXXpX-5' | "AS-M143" |
| 3'-XpXXFXFXFXFXFXFXFXFXFpXpFpXXXXXpX-5' | "AS-M144" |
| 3'-XXXXXXXXXXXXXXXXFXXXXXXXXX-5' | "AS-M145" |
| 3'-XXXXXXXXXXXXXXFXXXXXXXXXXX-5' | "AS-M146" |
| 3'-XXXXXXFXXXXXXXXXXXXXXXXXXX-5' | "AS-M147" |
| 3'-XXXXXXXXXXFXXXXXXXXXXXXXX-5' | "AS-M148" |
| 3'-XXXXXXXXXXXFXXXXXXXXXXXXXX-5' | "AS-M149" |
| 3'-XXXXXXXXXXXXFXXXXXXXXXXXXX-5' | "AS-M150" |
| 3'-XXXXXXXXXXXXFXXXFXXXXXXXXX-5' | "AS-M151" |
| 3'-XXXXXXXXXXXXFXXFXXXXXXXXXX-5' | "AS-M152" |
| 3'-XXXXXXXXFXXXXXXXXXXXXXXXXX-5' | "AS-M153" |
| 3'-XXXXXXXXFXXXXXXXXXXXXXXXXX-5' | "AS-M154" |
| 3'-XXXXXXFXXXXXXXXXXXXXXXXXXX-5' | "AS-M155" |
| 3'-XpXXXXXXXXXXXXXXXXXXXXXXXXXXpX-5' | "AS-M156" |
| 3'-XpXXXXXXXXXXXXXXXXXXXXXXXXXXpX-5' | "AS-M157" |
| 3'-XpXXFFFFXXXFXXFFXXXXXXXpX-5' | "AS-M158" |
| 3'-XpXXFFFFFFFFXXFXXFFXXXXXXpX-5' | "AS-M159" |
| 3'-XpXXFXXXFXXXXXFXXFFXXXXXXpX-5' | "AS-M160" |
| 3'-XpXXFXXXFXFXFXFXXFFXXXXXXpX-5' | "AS-M161" |
| 3'-XXXXXXXXXFXFXFXXXXXXXXXXX-5' | "AS-M162" |
| 3'-XXXXXXXXXXXXXXXXXXXXXXXXX-5' | "AS-M163" |
| 3'-XXXXXXXXDXXXXXXXXXXXXXXXXX-5' | "AS-M164" |
| 3'-XpXXXXXXXXXXXXXXXXXXXXXXXXpX-5' | "AS-M120*" |
| 3'-XpXXXXXXXXXXXXXXXXXXXXXXXXpX-5' | "AS-M121*" |
| 3'-XpXXXXXXXXXXXXXXXXXXXXXXXXpX-5' | "AS-M122*" |
| 3'-XpXXXXXXXXXXXXXXXXXXXXXXXXpX-5' | "AS-M123*" |
| 3'-XpXXXXXXXXXXXXXXXXXXXXXXXXpX-5' | "AS-M124*" |
| 3'-XpXXXXXXXXXXXXXXXXXXXXXXXXpX-5' | "AS-M125*" |
| 3'-XpFpXFXFXFXXXXXFXFXFXXXXFXpX-5' | "AS-M126*" |
| 3'-XpFpXFXFXFXXXXXFXFXFXXXXFXpX-5' | "AS-M127*" |
| 3'-XpFpXFXFXFXFXFXFXFXFXFFXXXpX-5' | "AS-M128*" |
| 3'-XpFpXFXFXFXFXFXFXFXFXFFFFFpF-5' | "AS-M129*" |
| 3'-XpFpXFXFXFXFXFXFXFXFXFXXXFXpX-5' | "AS-M130*" |
| 3'-XpFpXFXFXFXFXFXFXFXFXFXFXFpX-5' | "AS-M131*" |
| 3'-XpFpXFXFXFXFXFXFXFXFXFXXXXpX-5' | "AS-M132*" |

-continued

| | |
|---|---|
| 3'-XpFpXFXFXFXFXFXFXFXFXFXFXFXXXXpX-5' | "AS-M133*" |
| 3'-XpFpXFXFXFXFXFXFXFXFXFXFXFFFpF-5' | "AS-M134*" |
| 3'-XXXXXXXXXXXXXXXXXXXXXXXXXXXXXX-5' | "AS-M135*" |
| 3'-XXXXXXXXXXXXXXXXXXXXXXXXXXXXXX-5' | "AS-M136*" |
| 3'-XXXXXXXXXXXXXXXXXXXXXXXXXXXXXX-5' | "AS-M137*" |
| 3'-XXXFXFXFXXXXXFXFXFXFXXXXXXXX-5' | "AS-M138*" |
| 3'-XXXFXFXFFXXXXXXXFXXXXXXXX-5' | "AS-M139*" |
| 3'-XpXFXFXFXXXXXFXFFFXXXXXXpX-5' | "AS-M140*" |
| 3'-XpXXFXFXFFXXXFFXFXFFFXXXXXXpX-5' | "AS-M141*" |
| 3'-XpXXFXFXFXFXFXFXFFFXXXXXXpX-5' | "AS-M142*" |
| 3'-XpXXFXFXFFFFFFFXFXFFFXXXXXXpX-5' | "AS-M143*" |
| 3'-XpXXFXFXFXFXFXFXFXFpXpFpXXXXXXpX-5' | "AS-M144*" |
| 3'-XXXXXXXXXXXXXXFXXXXXXXXXXXX-5' | "AS-M145*" |
| 3'-XXXXXXXXXXXXXFXXXXXXXXXXXXX-5' | "AS-M146*" |
| 3'-XXXXXFXXXXXXXXXXXXXXXXXXXX-5' | "AS-M147*" |
| 3'-XXXXXXXXXFXXXXXXXXXXXXXXXX-5' | "AS-M148*" |
| 3'-XXXXXXXXXXFXXXXXXXXXXXXXXX-5' | "AS-M149*" |
| 3'-XXXXXXXXXXFXFXXXXXXXXXXXXX-5' | "AS-M150*" |
| 3'-XXXXXXXXXXXFXXFXXXXXXXXXXX-5' | "AS-M151*" |
| 3'-XXXXXXXXXXFXXXFXXXXXXXXXXX-5' | "AS-M152*" |
| 3'-XXXXXXXXFXXXXXXXXXXXXXXXXX-5' | "AS-M153*" |
| 3'-XXXXXXXXFXXXXXXXXXXXXXXXXX-5' | "AS-M154*" |
| 3'-XXXXXXFXXXXXXXXXXXXXXXXXXX-5' | "AS-M155*" |
| 3'-XpXXXXXXXXXXXXXXXXXXXXXXXXpX-5' | "AS-M156*" |
| 3'-XpXXXXXXXXXXXXXXXXXXXXXXXXXpX-5' | "AS-M157*" |
| 3'-XpXXFXFFFFXXXFXXFXFFXXXXXXpX-5' | "AS-M158*" |
| 3'-XpXXFXFFFFFFFFXXFXFXFFXXXXpX-5' | "AS-M159*" |
| 3'-XpXXFXXXFXXXXXFXFXXFFXXXXXXpX-5' | "AS-M160*" |
| 3'-XpXXFXXXFXFXFXFXXFFXXXXXXpX-5' | "AS-M161*" |
| 3'-XXXXXXXXFXFXFXXXXXXXXXXXXX-5' | "AS-M162*" |
| 3'-XXXXXXXXXXXXXXXXXXXXXXXXXXXX-5' | "AS-M163*" |
| 3'-XXXXXXXDXXXXXXXXXXXXXXXXXX-5' | "AS-M164*" |
| 3'-XXXXXXXXXXXXXXXXXXXXXXXXXXXX-5' | "AS-M211" |
| 3'-XXXXXXXXXXXXXXXXXXXXXXXXXXXX-5' | "AS-M212" |
| 3'-XXXXXXXXXXXXXXXXXXXXXXXXXXXX-5' | "AS-M215" |
| 3'-XXXXXXXXXXXXXXXXXXXXXXXXXXXX-5' | "AS-M216" |
| 3'-XXXXXXXXXXXXXXXXXXXXXXXXXXXX-5' | "AS-M217" |
| 3'-XXXXXXXXXXXXXXXXXXXXXXXXXXXX-5' | "AS-M218" |
| 3'-XXXXXXXXXXXXXXXXXXXXXXXXXXXX-5' | "AS-M219" |
| 3'-XXXXXXXXXXXXXXXXXXXXXXXXXXXX-5' | "AS-M220" |

-continued

| | |
|---|---|
| 3'-XXXXXXXXXXXXXXXXXXXXXXXXXXXX-5' | "AS-M221" |
| 3'-XXXXXXXXXXXXXXXXXXXXXXXXXXXX-5' | "AS-M222" |
| 3'-XXXXXXXXXXXXXXXXXXXXXXXXXXXX-5' | "AS-M223" |
| 3'-XXXXXXXXXXXXXXXXXXXXXXXXXXXX-5' | "AS-M224" |
| 3'-XXXXXXXXXXXXXXXXXXXXXXXXXXXX-5' | "AS-M225" |
| 3'-XXXXXXXXXXXXXXXXXXXXXXXXXXXX-5' | "AS-M226" |
| 3'-XXXXXXXXXXXXXXXXXXXXXXXXXXXX-5' | "AS-M230" |
| 3'-XXXXXXXXXXXXXXXXXXXXXXXXXXXX-5' | "AS-M231" |
| 3'-XXXXXXXXXXXXXXXXXXXXXXXXXXXX-5' | "AS-M232" |
| 3'-XXXXXXXXXXXXXXXXXXXXXXXXXXXX-5' | "AS-M233" |
| 3'-XXXXXXXXXXXXXXXXXXXXXXXXXXXX-5' | "AS-M234" |
| 3'-XXXXXXXXXXXXXXXXXXXXXXXXXXXX-5' | "AS-M235" |
| 3'-XXXXXXXXXXXXXXXXXXXXXXXXXXXX-5' | "AS-M236" |
| 3'-XXXXXXXXXXXXXXXXXXXXXXXXXXXX-5' | "AS-M237" |
| 3'-XXXXXXXXXXXXXXXXXXXXXXXXXXXX-5' | "AS-M238" |
| 3'-XXXXXXXXXXXXXXXXXXXXXXXXXXXX-5' | "AS-M239" |
| 3'-XXXXXXXXXXXXXXXXXXXXXXXXXXXX-5' | "AS-M240" |
| 3'-XXXXXXXXXXXXXXXXXXXXXXXXXXXX-5' | "AS-M241" |
| 3'-XXXXXXXXXXXXXXXXXXXXXXXXXXXX-5' | "AS-M242" |
| 3'-XpXXXXXXXXXXXXXXXXXXXXXXXXXpX-5' | "AS-M243" |
| 3'-XpXXXXXXXXXXXXXXXXXXXXXXXXXpX-5' | "AS-M244" |
| 3'-XpXXXXXXXXXXXXXXXXXXXXXXXXXpX-5' | "AS-M245" |
| 3'-XpXXXXXXXXXXXXXXXXXXXXXXXXXpX-5' | "AS-M246" |
| 3'-XpXXXXXXXXXXXXXXXXXXXXXXXXXpX-5' | "AS-M247" |
| 3'-XpXXXXXXXXXXXXXXXXXXXXXXXXXpX-5' | "AS-M248" |
| 3'-XpXXXXXXXXXXXXXXXXXXXXXXXXXpX-5' | "AS-M249" |
| 3'-XpXXXXXXXXXXXXXXXXXXXXXXXXXpX-5' | "AS-M250" |
| 3'-XpXXXXXXXXXXXXXXXXXXXXXXXXXpX-5' | "AS-M251" |
| 3'-XpXXXXXXXXXXXXXXXXXXXXXXXXXpX-5' | "AS-M252" |
| 3'-XpXXXXXXXXXXXXXXXXXXXXXXXXXpX-5' | "AS-M253" |
| 3'-XpXXXXXXXXXXXXXXXXXXXXXXXXXpX-5' | "AS-M254" |
| 3'-XpXXXXXXXXXXXXXXXXXXXXXXXXXpX-5' | "AS-M255" |
| 3'-XXXXXXXXXXXXXXXXXXXXXXXXXXXX-5' | "AS-M211*" |
| 3'-XXXXXXXXXXXXXXXXXXXXXXXXXXXX-5' | "AS-M212*" |
| 3'-XXXXXXXXXXXXXXXXXXXXXXXXXXXX-5' | "AS-M215*" |
| 3'-XXXXXXXXXXXXXXXXXXXXXXXXXXXX-5' | "AS-M216*" |
| 3'-XXXXXXXXXXXXXXXXXXXXXXXXXXXX-5' | "AS-M217*" |
| 3'-XXXXXXXXXXXXXXXXXXXXXXXXXXXX-5' | "AS-M218*" |
| 3'-XXXXXXXXXXXXXXXXXXXXXXXXXXXX-5' | "AS-M219*" |
| 3'-XXXXXXXXXXXXXXXXXXXXXXXXXXXX-5' | "AS-M220*" |
| 3'-XXXXXXXXXXXXXXXXXXXXXXXXXXXX-5' | "AS-M221*" |

-continued

```
3'-XXXXXXXXXXXXXXXXXXXXXXXXXXX-5'        "AS-M222*"
3'-XXXXXXXXXXXXXXXXXXXXXXXXXXX-5'        "AS-M223*"
3'-XXXXXXXXXXXXXXXXXXXXXXXXXXX-5'        "AS-M224*"
3'-XXXXXXXXXXXXXXXXXXXXXXXXXXX-5'        "AS-M225*"
3'-XXXXXXXXXXXXXXXXXXXXXXXXXXX-5'        "AS-M226*"
3'-XXXXXXXXXXXXXXXXXXXXXXXXXXX-5'        "AS-M230*"
3'-XXXXXXXXXXXXXXXXXXXXXXXXXXX-5'        "AS-M231*"
3'-XXXXXXXXXXXXXXXXXXXXXXXXXXX-5'        "AS-M232*"
3'-XXXXXXXXXXXXXXXXXXXXXXXXXXX-5'        "AS-M233*"
3'-XXXXXXXXXXXXXXXXXXXXXXXXXXX-5'        "AS-M234*"
3'-XXXXXXXXXXXXXXXXXXXXXXXXXXX-5'        "AS-M235*"
3'-XXXXXXXXXXXXXXXXXXXXXXXXXXX-5'        "AS-M236*"
3'-XXXXXXXXXXXXXXXXXXXXXXXXXXX-5'        "AS-M237*"
3'-XXXXXXXXXXXXXXXXXXXXXXXXXXX-5'        "AS-M238*"
3'-XXXXXXXXXXXXXXXXXXXXXXXXXXX-5'        "AS-M239*"
3'-XXXXXXXXXXXXXXXXXXXXXXXXXXX-5'        "AS-M240*"
3'-XXXXXXXXXXXXXXXXXXXXXXXXXXX-5'        "AS-M241*"
3'-XXXXXXXXXXXXXXXXXXXXXXXXXXX-5'        "AS-M242*"
3'-XpXXXXXXXXXXXXXXXXXXXXXXXXXpX-5'      "AS-M243*"
3'-XpXXXXXXXXXXXXXXXXXXXXXXXXXpX-5'      "AS-M244*"
3'-XpXXXXXXXXXXXXXXXXXXXXXXXXXpX-5'      "AS-M245*"
3'-XpXXXXXXXXXXXXXXXXXXXXXXXXXpX-5'      "AS-M246*"
3'-XpXXXXXXXXXXXXXXXXXXXXXXXXXpX-5'      "AS-M247*"
3'-XpXXXXXXXXXXXXXXXXXXXXXXXXXpX-5'      "AS-M248*"
3'-XpXXXXXXXXXXXXXXXXXXXXXXXXXpX-5'      "AS-M249*"
3'-XpXXXXXXXXXXXXXXXXXXXXXXXXXpX-5'      "AS-M250*"
3'-XpXXXXXXXXXXXXXXXXXXXXXXXXXpX-5'      "AS-M251*"
3'-XpXXXXXXXXXXXXXXXXXXXXXXXXXpX-5'      "AS-M252*"
3'-XpXXXXXXXXXXXXXXXXXXXXXXXXXpX-5'      "AS-M253*"
3'-XpXXXXXXXXXXXXXXXXXXXXXXXXXpX-5'      "AS-M254*"
3'-XpXXXXXXXXXXXXXXXXXXXXXXXXXpX-5'      "AS-M255*"
``` where "X"=RNA, "X"=2'-O-methyl RNA, "D"=DNA, "F"=2'-Fluoro NA and "p"=Phosphorothioate linkage.

In certain additional embodiments, the antisense strand of selected dsRNAs of the invention are extended, optionally at the 5' end, with an exemplary 5' extension of base "AS-M8", "AS-M17" and "AS-M48" modification patterns respectively represented as follows:

"AS-M8, extended"
(SEQ ID NO: 3493)
3'-XXXXXXXXXXXXXXXXXXXXXXXXXXXXUAGCUAUCGT-5'

"AS-M17, extended"
(SEQ ID NO: 3493)
3'-XXXXXXXXXXXXXXXXXXXXXXXXXXXXUAGCUAUCGT-5'

"AS-M48, extended"
(SEQ ID NO: 3493)
3'-XXXXXXXXXXXXXXXXXXXXXXXXXXXXUAGCUAUCGT-5' where "X"=RNA; "X"=2'-O-methyl RNA; "F"=2'-Fluoro NA and "A" in bold, italics indicates a 2'-Fluoro-adenine residue.

In certain embodiments, the sense strand of a DsiRNA of the invention is modified—specific exemplary forms of sense strand modifications are shown below, and it is contemplated that such modified sense strands can be substituted for the sense strand of any of the DsiRNAs shown above to generate a DsiRNA comprising a below-depicted sense strand that anneals with an above-depicted antisense strand. Exemplary sense strand modification patterns include:

```
5'-XXXXXXXXXXXXXXXXXXXXXXXXDD-3'        "SM1"
5'-XXXXXXXXXXXXXXXXXXXXXXXXDD-3'        "SM2"
5'-XXXXXXXXXXXXXXXXXXXXXXXXDD-3'        "SM3"
5'-XXXXXXXXXXXXXXXXXXXXXXXXDD-3'        "SM4"
5'-XXXXXXXXXXXXXXXXXXXXXXXXDD-3'        "SM5"
5'-XXXXXXXXXXXXXXXXXXXXXXXXDD-3'        "SM6"
5'-XXXXXXXXXXXXXXXXXXXXXXXXDD-3'        "SM7"
5'-XXXXXXXXXXXXXXXXXXXXXXXXDD-3'        "SM8"
5'-XXXXXXXXXXXXXXXXXXXXXXXXDD-3'        "SM9"
5'-XXXXXXXXXXXXXXXXXXXXXXXXDD-3'        "SM10"
5'-XXXXXXXXXXXXXXXXXXXXXXXXDD-3'        "SM11"
5'-XXXXXXXXXXXXXXXXXXXXXXXXDD-3'        "SM12"
5'-XXXXXXXXXXXXXXXXXXXXXXXXDD-3'        "SM13"
5'-XXXXXXXXXXXXXXXXXXXXXXXXDD-3'        "SM14"
5'-XXXXXXXXXXXXXXXXXXXXXXXXDD-3'        "SM15"
5'-XXXXXXXXXXXXXXXXXXXXXXXXDD-3'        "SM16"
5'-XXXXXXXXXXXXXXXXXXXXXXXXDD-3'        "SM17"
5'-XXXXXXXXXXXXXXXXXXXXXXXXDD-3'        "SM18"
5'-XXXXXXXXXXXXXXXXXXXXXXXXDD-3'        "SM19"
5'-XXXXXXXXXXXXXXXXXXXXXXXXDD-3'        "SM20"
5'-XXXXXXXXXXXXXXXXXXXXXXXXDD-3'        "SM21"
5'-XXXXXXXXXXXXXXXXXXXXXXXXDD-3'        "SM23"
5'-XXXXXXXXXXXXXXXXXXXXXXXXDD-3'        "SM24"
5'-XXXXXXXXXXXXXXXXXXXXXXXXDD-3'        "SM25"
5'-XXXXXXXXXXXXXXXXXXXXXXXXDD-3'        "SM30"
5'-XXXXXXXXXXXXXXXXXXXXXXXXDD-3'        "SM31"
5'-XXXXXXXXXXXXXXXXXXXXXXXXDD-3'        "SM32"
5'-XXXXXXXXXXXXXXXXXXXXXXXXDD-3'        "SM33"
5'-XXXXXXXXXXXXXXXXXXXXXXXXDD-3'        "SM34"
5'-XXXXXXXXXXXXXXXXXXXXXXXXDD-3'        "SM35"
```

| | | | |
|---|---|---|---|
| 5'-XXXXXXXXXXXXXXXXXXXXXXXXDD-3' | "SM36" | 5'-X pXpXXXXXXXXXXXXXXXXXXXXXDD-3' | "SM77" |
| 5'-XXXXXXXXXXXXXXXXXXXXXXXXDD-3' | "SM37" | 5'-X pXpXXXXXXXXXXXXXXXXXXXXXpDpD-3' | "SM78" |
| 5'-XXXXXXXXXXXXXXXXXXXXXXXXDD-3' | "SM38" | 5'-D pXpDXXXXXXXXXXXXXXXXXXXXDD-3' | "SM79" |
| 5'-XXXXXXXXXXXXXXXXXXXXXXXXDD-3' | "SM39" | 5'-X pXpDXXXXXXXXXDXXXXXXXXXXDD-3' | "SM80" |
| 5'-XXXXXXXXXXXXXXXXXXXXXXXXDD-3' | "SM40" | 5'-DXDXXXDXXXXXDXXXXXDXXXXDD-3' | "SM81" |
| 5'-XXXXXXXXXXXXXXXXXXXXXXXXDD-3' | "SM41" | 5'-DpXDXXXDXXXXXDXXXXXDXXXXpDpD-3' | "SM82" |
| 5'-XXXXXXXXXXXXXXXXXXXXXXXXDD-3' | "SM42" | 5' C3 spacer-XXXXXXXXXXXXXXXXXXXXXXXXDD-3' | "SM83" |
| 5'-XXXXXXXXXXXXXXXXXXXXXXXXDD-3' | "SM43" | 5' C3 spacer-XXDXXXXXXXXXDXXXXXXXXXXDD-3' | "SM84" |
| 5'-XXXXXXXXXXXXXXXXXXXXXXXXDD-3' | "SM44" | 5' C3 spacer-XXXXXXXXXXXXXXXXXXXXXXXXpDpD-3' | "SM85" |
| 5'-XXXXXXXXXXXXXXXXXXXXXXXXDD-3' | "SM45", "SM47" | 5'-XXXXXXXXXXXXXXXXXXXXXXXX pDpD-3' | "SM86" |
| 5'-XXXXXXXXXXXXXXXXXXXXXXXXDD-3' | "SM46" | 5'-XpXXXXXXXXXXXXXXXXXXXXXXXDD-3' | "SM87" |
| 5'-XXXXXXXXXXXXXXXXXXXXXXXXDD-3' | "SM48" | 5'-XpXXXXXXXXXXXXXXXXXXXXXXXpDpD-3' | "SM88" |
| 5'-XXXXXXXXXXXXXXXXXXXXXXXXDD-3' | "SM49" | 5'-DXXXXXXXXXXXXXXXXXXXXXXXXDD-3' | "SM89" |
| 5'-XXXXXXXXXXXXXXXXXXXXXXXXDD-3' | "SM50" | 5'-DpXXXXXXXXXXXXXXXXXXXXXXXpDpD-3' | "SM90" |
| 5'-XXXXXXXXXXXXXXXXXXXXXXXXDD-3' | "SM51" | 5'-DXDXXXXXXXXXXXXXXXXXXXXXDD-3' | "SM91" |
| 5'-XXXXXXXXXXXXXXXXXXXXXXXXDD-3' | "SM52" | 5'-DpXDXXXXXXXXXXXXXXXXXXXXXDD-3' | "SM92" |
| 5'-XXXXXXXXXXXXXXXXXXXXXXXXDD-3' | "SM53" | 5'-XXDXXXXXXXXXDXXXXXXXXXXDD-3' | "SM93" |
| 5'-XXXXXXXXXXXXXXXXXXXXXXXXDD-3' | "SM54" | 5'-XpXDXXXXXXXXXDXXXXXXXXXXDD-3' | "SM94" |
| 5'-XXXXXXXXXXXXXXXXXXXXXXXXDD-3' | "SM55" | 5'-DXDXXXXXXXXXDXXXXXDXXXXDD-3' | "SM95" |
| 5'-XXXXXXXXXXXXXXXXXXXXXXXXDD-3' | "SM56" | 5'-DpXDXXXXXXXXXDXXXXXDXXXXDD-3' | "SM96" |
| 5'-XXXXXXXXXXXXXXXXXXXXXXXXDD-3' | "SM57" | 5'-XpXpXXXXXXXXXXXXXXXXXXXXXDD-3' | "SM97" |
| 5'-XXXXXXXXXXXXXXXXXXXXXXXXDD-3' | "SM58" | 5'-XpXpXXXXXXXXXXXXXXXXXXXXXXpDpD-3' | "SM98" |
| 5'-XXXXXXXXXXXXXXXXXXXXXXXXDD-3' | "SM59" | 5'-DpXpDXXXXXXXXXXXXXXXXXXXXDD-3' | "SM99" |
| 5'-XXXXXXXXXXXXXXXXXXXXXXXXDD-3' | "SM60" | 5'-XpXpDXXXXXXXXXDXXXXXXXXXXDD-3' | "SM100" |
| 5'-XXXXXXXXXXXXXXXXXXXXXXXXDD-3' | "SM61" | 5'-DXDXXXXXXXXXDXDXXXDDXXDDD-3' | "SM101" |
| 5'-XXXXXXXXXXXXXXXXXXXXXXXXDD-3' | "SM62" | 5'-DpXDXXXDXXXXXDXXXXXDXXXXpDpD-3' | "SM102" |
| 5'-XXXXXXXXXXXXXXXXXXXXXXXXDD-3' | "SM63" | 5' C3 spacer-XXXXXXXXXXXXXXXXXXXXXXXXDD-3' | "SM103" |
| 5'-XXXXXXXXXXXXXXXXXXXXXXXXDD-3' | "SM64" | 5' C3 spacer-XXDXXXXXXXXXDXXXXXXXXXXDD-3' | "SM104" |
| 5'-XXXXXXXXXXXXXXXXXXXXXXXXDD-3' | "SM65" | 5' C3 spacer-XXXXXXXXXXXXXXXXXXXXXXXXpDpD-3' | "SM105" |
| 5'-XXXXXXXXXXXXXXXXXXXXXXXXXpDpD-3' | "SM66" | 5'-XXXXXXXXXXXXXXXXXXXXXXXXDD-3' | "SM106" |
| 5'-XpXXXXXXXXXXXXXXXXXXXXXXXDD-3' | "SM67" | 5'-XXXXXXXXXXXXXXXXXXXXXXXXDD-3' | "SM107" |
| 5'-XpXXXXXXXXXXXXXXXXXXXXXXXpDpD-3' | "SM68" | 5'-XXXXXXXXXXXXXXXXXXXXXXXXDD-3' | "SM108" |
| 5'-DXXXXXXXXXXXXXXXXXXXXXXXXDD-3' | "SM69" | 5'-XFXXXXXXXXXXXXXXXFXXXXXXDD-3' | "SM110" |
| 5'-DpXXXXXXXXXXXXXXXXXXXXXXXpDpD-3' | "SM70" | 5'-XXXFXFXXXXXXXXFXXXXXXXXDD-3' | "SM111" |
| 5'-DXDXXXXXXXXXXXXXXXXXXXXXDD-3' | "SM71" | 5'-XFXFXFXFXXXXFXFXFXFXXXXXDD-3' | "SM112" |
| 5'-DpXDXXXXXXXXXXXXXXXXXXXXXDD-3' | "SM72" | 5'-XpFXFXFXFXXXXFXFXFXFXXXXXpDpD-3' | "SM113" |
| 5'-XXDXXXXXXXXXDXXXXXXXXXXDD-3' | "SM73" | 5'-XFXXXXXXXXXXXXXXXXXXXXXXDD-3' | "SM114" |
| 5'-XpXDXXXXXXXXXDXXXXXXXXXXDD-3' | "SM74" | 5'-XXXXFFXFXXXFXFXXXXXXXXDD-3' | "SM115" |
| 5'-DXDXXXXXXXXXDXXXXXDXXXXDD-3' | "SM75" | | |
| 5'-DpXDXXXXXXXXXDXXXXXDXXXXDD-3' | "SM76" | | |

-continued

| | |
|---|---|
| 5'-XFXFXXXXXXXXXXXXFXXXXXXDD-3' | "SM116" |
| 5'-XFXFFFXFXXXFXFXFFFXXXXXDD-3' | "SM117" |
| 5'-XFXFXFXFXXXFXFXFXFXXXXXDD-3' | "SM118" |
| 5'-XpFXFXFXFXXXFXFXFXFXXXXXpDpD-3' | "SM119" |
| 5'-XXXXXXXXXXXXXXXXXXXXXXXDD-3' | "SM250" |
| 5'-XXXXXXXXXXXXXXXXXXXXXXXDD-3' | "SM251" |
| 5'-XXXXXXXXXXXXXXXXXXXXXXXDD-3' | "SM252" |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |
| 5'-XXXXXXXXXXXXXXXXXXXXXXXXX-3' | |

-continued

| | |
|---|---|
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | |
| 5'-XXXXXXXXXXXXXXXXXXXXXXXXXX-3' | "SM22" |
| 5'-XXXXXXXXXXXXXXXXXXXXXXXXXX-3 | |
| 5'-XXXXXXXXXXXXXXXXXXXXXXXXXX-3' | |
| 5'-XXXXXXXXXXXXXXXXXXXXXXXXXX-3' | |
| 5'-XpXXXXXXXXXXXXXXXXXXXXXXXDpD-3' | "SM120" |
| 5'-FpXFXFXFXFXFXFXFXFXFXFXXDpD-3' | "SM121" |
| 5'-XpXXXXXXXXXXXXXXXXXXXXXXXDpD-3' | "SM122" |
| 5'-XpXXXXXXXXXXXXXXXXXXXXXXXDpD-3' | "SM123" |
| 5'-FpXFXXXFXXXXXXXXXXXXXXXpDpD-3' | "SM124" |
| 5'-FpXFXXXFXXXXXFXFXXXXXXXXpDpD-3' | "SM125" |
| 5'-FpXFXXXFXFFFXFXFXXXXXXXXpDpD-3' | "SM126" |
| 5'-FpXFXXXFXFFFXFXFXXXFXXXXpDpD-3' | "SM127" |
| 5'-FpXFXXXFXFFFXFXFXXXFFXXpDpD-3' | "SM128" |
| 5'-FpXFXXXFXFFFXFXFXXXFFFFpDpD-3' | "SM129" |
| 5'-FpXFXFXFXFXFXFXFXFXFXFpDpD-3' | "SM130" |
| 5'-XpXXXXXXXXXXXXXXXXXXXXXXXpX-3' | |
| 5'-FpXFXFXFXFXFXFXFXFXFXFXXXpX-3' | |
| 5'-XpXXXXXXXXXXXXXXXXXXXXXXXpX-3' | |
| 5'-XpXXXXXXXXXXXXXXXXXXXXXXXpX-3' | |
| 5'-FpXFXXXFXXXXXXXXXXXXXXXpXpX-3' | |
| 5'-FpXFXXXFXXXXXFXFXXXXXXXXpXpX-3' | |
| 5'-FpXFXXXFXFFFXFXFXXXXXXXXpXpX-3' | |
| 5'-FpXFXXXFXFFFXFXFXXXFXXXXpXpX-3' | |
| 5'-FpXFXXXFXFFFXFXFXXXFFXXpXpX-3' | |
| 5'-FpXFXXXFXFFFXFXFXXXFFFFpXpX-3' | |
| 5'-FpXFXFXFXFXFXFXFXFXFXFpXpX-3' | |
| 5'-XpXXXXXXXXXXXXXXXXXXXXXXXpDpD-3' | "SM133" |
| 5'-XpXXXXXXXXXXXXXXXXXXXXXXXpDpD-3' | "SM134" |

```
5'-XpXXXXXXXXXXXXXXXXXXXXXpDpD-3'                "SM135"
5'-XpXXXXXXXXXXXXXXXXXXXXXpDpD-3'                "SM136"
5'-XpXXXXXXXXXXXXXXXXXXXXXpDpD-3'                "SM137"
5'-XpXXXXXXXXXXXXXXXXXXXXXpDpD-3'                "SM138"
5'-XpXXXXXXXXXXXXXXXXXXXXXXpXpX-3'
5'-XpXXXXXXXXXXXXXXXXXXXXXXpXpX-3'
5'-XpXXXXXXXXXXXXXXXXXXXXXXpXpX-3'
5'-XpXXXXXXXXXXXXXXXXXXXXXXpXpX-3'
5'-XpXXXXXXXXXXXXXXXXXXXXXXpXpX-3'
5'-XpXXXXXXXXXXXXXXXXXXXXXXpXpX-3'
5'-XpXXXXXXXXXXXXXXXXXXXXXDpD-3'                 "SM140"
5'-XpXXXXXXXXXXXXXXXXXXXXXDpD-3'                 "SM141"
5'-XpXXXXXXXXXXXXXXXXXXXXXDpD-3'                 "SM142"
5'-FpXFXFXFXFXFXFXFXFXXXFDpD-3'                  "SM143"
5'-FpXFXFXFXFXFXFXFXFFFFFDpD-3'                  "SM144"
5'-FpXFXFXFXFXFXFXFXFXXXXDpD-3'                  "SM145"
5'-FpXFXFXFXFXFXFXFXFXFXFDpD-3'                  "SM146"
5'-FXFXXXFXFFFXFXFXXXXXXXXDD-3'                  "SM147"
5'-FXFXXXFXFFFXFXFXXXFFXXXDD-3'                  "SM148"
5'-FXFXXXFXFFFXFXFXXXFFXXFDD-3'                  "SM149"
5'-FXFXXXFXFFFXFXFXXXFFFFFDD-3'                  "SM150"
5'-FpXFXFXFXFFFXFXFXFFXXFDpD-3'                  "SM151"
5'-FpXFXFXFXFFFXXXFXFXFXXXXDpD-3'                "SM152"
5'-FpXFXFXXXFFFFFXXXFXFXXXFXXDpD-3'              "SM153"
5'-ab-XXFXXFFFXXFFXXXFFFFXpXXXDD-3'              "SM154"
(ab = abasic for F7 stabilization at 5' end)
5'-XpXXXXXXXXXXXXXXXXXXXXXXpX-3'                 "SM155"
5'-XpXXXXXXXXXXXXXXXXXXXXXXpX-3'                 "SM156"
5'-FpXFXXXFFFFFFFXXXFXXFXXFXpX-3'                "SM157"
5'-XpXFXFXXFFFFXFXFXFXFXXXXpX-3'                 "SM158"
5'-FpXFXXXFXFFXFXXXFXXXFXXXXpX-3'                "SM159"
5'-FpXFXFXFXFFFXFXFXFXFXXXXXX-3'                 "SM160"
5'-XpXXXXXXXXXXXXXXXXXXXXXXpX-3'
5'-XpXXXXXXXXXXXXXXXXXXXXXXpX-3'
5'-XpXXXXXXXXXXXXXXXXXXXXXXpX-3'
5'-FpXFXFXFXFXFXFXFXFXXXFXpX-3'
5'-FpXFXFXFXFXFXFXFXFFFFFXpX-3'
5'-FpXFXFXFXFXFXFXFXFXXXXXpX-3'
5'-FpXFXFXFXFXFXFXFXFXFXFXpX-3'
5'-FXFXXXFXFFFXFXFXXXXXXXXXX-3'
5'-FXFXXXFXFFFXFXFXXXFFXXXXX-3'
5'-FXFXXXFXFFFXFXFXXXFFXXFXX-3'
5'-FXFXXXFXFFFXFXFXXXFFFFFXX-3'
5'-FpXFXFXFXFFFXFXFXFXFXXFXpX-3'
5'-FpXFXFXFXFFFXXXFXFXFXXXXpX-3'
5'-FpXFXFXXXFFFFFXXXFXFXXXXXpX-3'
5'-ab-XXFXXFFFXXFFXXXFFFFXpXXXXX-3'
(ab = abasic for F7 stabilization at 5' end)
5'-XpXXXXXXXXXXXXXXXXXXXXXXpX-3'
5'-XpXXXXXXXXXXXXXXXXXXXXXXpX-3'
5'-FpXFXXXFFFFFFFXXXFXXFXXFXpX-3'
5'-XpXFXFXXFFFFXFXFXFXFXXXXpX-3'
5'-FpXFXXXFXFFXFXXXFXXXFXXXXpX-3'
5'-FpXFXFXFXFFFXFXFXFXFXXXXXX-3'
5'-XXXXXXXXXXXXXXXXXXXXXXXDD-3'                  "SM253"
5'-XXXXXXXXXXXXXXXXXXXXXXXDD-3'                  "SM255"
5'-XXXXXXXXXXXXXXXXXXXXXXXDD-3'                  "SM256"
5'-XXXXXXXXXXXXXXXXXXXXXXXDD-3'                  "SM257"
5'-XXXXXXXXXXXXXXXXXXXXXXXDD-3'                  "SM258"
5'-XXXXXXXXXXXXXXXXXXXXXXXDD-3'                  "SM259"
5'-XXXXXXXXXXXXXXXXXXXXXXXDD-3'                  "SM260"
5'-XXXXXXXXXXXXXXXXXXXXXXXDD-3'                  "SM261"
5'-XXXXXXXXXXXXXXXXXXXXXXXDD-3'                  "SM262"
5'-XXXXXXXXXXXXXXXXXXXXXXXDD-3'                  "SM263"
5'-XXXXXXXXXXXXXXXXXXXXXXXDD-3'                  "SM264"
5'-XXXXXXXXXXXXXXXXXXXXXXXDD-3'                  "SM265"
5'-XXXXXXXXXXXXXXXXXXXXXXXDD-3'                  "SM266"
5'-XXXXXXXXXXXXXXXXXXXXXXXDD-3'                  "SM267"
5'-XXXXXXXXXXXXXXXXXXXXXXXDD-3'                  "SM268"
5'-XXXXXXXXXXXXXXXXXXXXXXXDD-3'                  "SM269"
5'-XXXXXXXXXXXXXXXXXXXXXXXDD-3'                  "SM270"
5'-XXXXXXXXXXXXXXXXXXXXXXXDD-3'                  "SM271"
5'-XXXXXXXXXXXXXXXXXXXXXXXDD-3'                  "SM275"
5'-XXXXXXXXXXXXXXXXXXXXXXXDD-3'                  "SM276"
5'-XXXXXXXXXXXXXXXXXXXXXXXDD-3'                  "SM277"
5'-XXXXXXXXXXXXXXXXXXXXXXXDD-3'                  "SM278"
5'-XXXXXXXXXXXXXXXXXXXXXXXDD-3'                  "SM279"
5'-XXXXXXXXXXXXXXXXXXXXXXXDD-3'                  "SM280"
5'-XXXXXXXXXXXXXXXXXXXXXXXDD-3'                  "SM281"
5'-XXXXXXXXXXXXXXXXXXXXXXXDD-3'                  "SM282"
5'-XXXXXXXXXXXXXXXXXXXXXXXDD-3'                  "SM283"
```

```
5'-XXXXXXXXXXXXXXXXXXXXXXXXXDD-3'          "SM284"
5'-XXXXXXXXXXXXXXXXXXXXXXXXXDD-3'          "SM285"
5'-XXXXXXXXXXXXXXXXXXXXXXXXXDD-3'          "SM286"
5'-XXXXXXXXXXXXXXXXXXXXXXXXXDD-3'          "SM287"
5'-XXXXXXXXXXXXXXXXXXXXXXXXXDD-3'          "SM288"
5'-XXXXXXXXXXXXXXXXXXXXXXXXXDD-3'          "SM289"
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXXX-3'
5'-XXXXXXXXXXXXXXXXXXXXXXXXXDD-3'          "SM300"
5'-XpXXXXXXXXXXXXXXXXXXXXXXXXXDpD-3'       "SM301"
5'-XpXXXXXXXXXXXXXXXXXXXXXXXXXDpD-3'       "SM302"
5'-XpXXXXXXXXXXXXXXXXXXXXXXXXXDpD-3'       "SM303"
5'-XpXXXXXXXXXXXXXXXXXXXXXXXXXDpD-3'       "SM304"
5'-XpXXXXXXXXXXXXXXXXXXXXXXXXXDpD-3'       "SM305"
5'-XpXXXXXXXXXXXXXXXXXXXXXXXXXDpD-3'       "SM306"
5'-XpXXXXXXXXXXXXXXXXXXXXXXXXXDpD-3'       "SM307"
5'-XpXXXXXXXXXXXXXXXXXXXXXXXXXDpD-3'       "SM308"
5'-XpXXXXXXXXXXXXXXXXXXXXXXXXXDpD-3'       "SM309"
5'-XpXXXXXXXXXXXXXXXXXXXXXXXXXDpD-3'       "SM310"
5'-XXXXXXXXXXXXXXXXXXXXXXXXXXX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
5'-XpXXXXXXXXXXXXXXXXXXXXXXXXXpX-3'
``` where "X"=RNA, "$\underline{X}$"=2'-O-methyl RNA, "D"=DNA, "F"=2'-Fluoro NA and "p"=Phosphorothioate linkage.

The above modification patterns can also be incorporated into, e.g., the extended DsiRNA structures and mismatch and/or frayed DsiRNA structures described below.

In another embodiment, the DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary 27mer DsiRNA agent with two terminal mismatched residues is shown:

```
5'-XXXXXXXXXXXXXXXXXXXXXXXXXX$X^M$ $M$-3'
3'-XXXXXXXXXXXXXXXXXXXXXXXXXX$X_M$ $M$-5'
``` wherein "X"=RNA, "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand is the sense strand, and the bottom strand is the antisense strand. Alternatively, the bottom strand is the sense strand and the top strand is the antisense strand.

In certain additional embodiments, the present invention provides compositions for RNA interference (RNAi) that possess one or more base paired deoxyribonucleotides within a region of a double stranded ribonucleic acid (dsRNA) that is positioned 3' of a projected sense strand Dicer cleavage site and correspondingly 5' of a projected antisense strand Dicer cleavage site. The compositions of the invention comprise a dsRNA which is a precursor molecule, i.e., the dsRNA of the present invention is processed in vivo to produce an active small interfering nucleic acid (siRNA). The dsRNA is processed by Dicer to an active siRNA which is incorporated into RISC.

In certain embodiments, the DsiRNA agents of the invention can have the following exemplary structures (noting that any of the following exemplary structures can be combined, e.g., with the bottom strand modification patterns of the above-described structures—in one specific example, the bottom strand modification pattern shown in any of the above structures is applied to the 27 most 3' residues of the bottom strand of any of the following structures; in another specific example, the bottom strand modification pattern shown in any of the above structures upon the 23 most 3' residues of the bottom strand is applied to the 23 most 3' residues of the bottom strand of any of the following structures):

In one such embodiment, the DsiRNA comprises the following (an exemplary "right-extended", "DNA extended" DsiRNA):

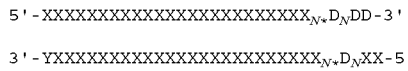

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

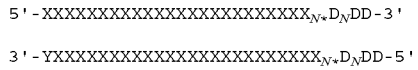

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

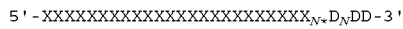

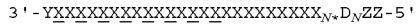

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

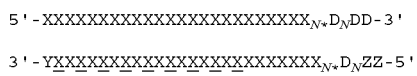

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

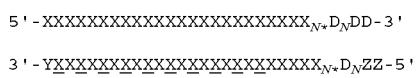

wherein "X"=RNA, "X"=2'-O-methyl RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

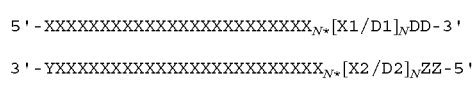

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In the structures depicted herein, the 5' end of either the sense strand or antisense strand can optionally comprise a phosphate group.

In another embodiment, a DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

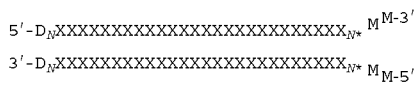

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-15 or, optionally, 1-8. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In one embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. An exemplary structure for such a molecule is shown:

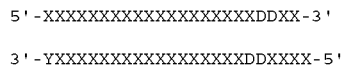

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. In one embodiment, the top strand is the sense strand, and the bottom strand is the antisense strand. Alternatively, the bottom strand is the sense strand and the top strand is the antisense strand. The above structure is modeled to force Dicer to cleave a minimum of a 21mer duplex as its primary post-processing form. In embodiments where the bottom strand of the above structure is the antisense strand, the positioning of two deoxyribonucleotide residues at the ultimate and penultimate residues of the 5' end of the antisense strand will help reduce off-target effects (as prior studies have shown a 2'-O-methyl modification of at least the penultimate position from the 5' terminus of the antisense strand to reduce off-target effects; see, e.g., US 2007/0223427).

In one embodiment, the DsiRNA comprises the following (an exemplary "left-extended", "DNA extended" DsiRNA):

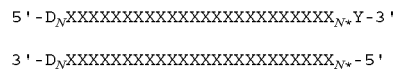

wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, "D"=DNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In a related embodiment, the DsiRNA comprises:

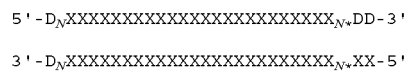

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In an additional embodiment, the DsiRNA comprises:

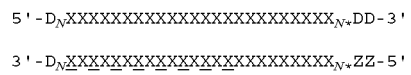

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

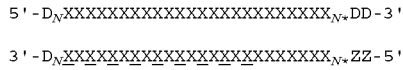

wherein "X"=RNA, optionally a 2'-O-methyl RNA monomers "D"=DNA, "N"=1 to 50 or more, but is optionally 1-8 or 1-10. "N*"=0 to 15 or more, but is optionally 0, 1, 2, 3, 4, 5 or 6. "Z"=DNA or RNA. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

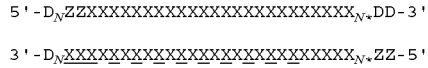

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another such embodiment, the DsiRNA comprises:

wherein "X"=RNA, "$\underline{X}$"=2'-O-methyl RNA, "D"=DNA, "Z"=DNA or RNA, and "N"=1 to 50 or more, but is optionally 1-8 or 1-10. "N*"=0 to 15 or more, but is optionally 0, 1, 2, 3, 4, 5 or 6. "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DsiRNA comprises:

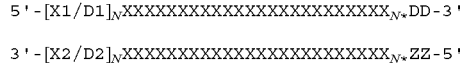

wherein "X"=RNA, "D"=DNA, "Z"=DNA or RNA, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In a related embodiment, the DsiRNA comprises:

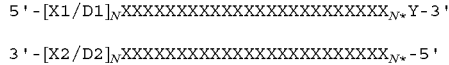

wherein "X"=RNA, "D"=DNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "N"=1 to 50 or more, but is optionally 1-8 or 1-10, where at least one $D1_N$ is present in the top strand and is base paired with a corresponding $D2_N$ in the bottom strand. Optionally, $D1_N$ and $D1_{N+1}$ are base paired with corresponding $D2_N$ and $D2_{N+1}$; $D1_N$, $D1_{N+1}$ and $D1_{N+2}$ are base paired with corresponding $D2_N$, $D1_{N+1}$ and $D1_{N+2}$, etc. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand, with 2'-O-methyl RNA monomers located at alternating residues along the top strand, rather than the bottom strand presently depicted in the above schematic.

In another embodiment, the DNA:DNA-extended DsiRNA comprises strands having equal lengths possessing 1-3 mismatched residues that serve to orient Dicer cleavage (specifically, one or more of positions 1, 2 or 3 on the first strand of the DsiRNA, when numbering from the 3'-terminal residue, are mismatched with corresponding residues of the 5'-terminal region on the second strand when first and second strands are annealed to one another). An exemplary DNA:DNA-extended DsiRNA agent with two terminal mismatched residues is shown:

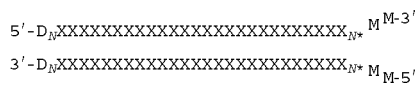

wherein "X"=RNA, "M"=Nucleic acid residues (RNA, DNA or non-natural or modified nucleic acids) that do not base pair (hydrogen bond) with corresponding "M" residues of otherwise complementary strand when strands are annealed, "D"=DNA and "N"=1 to 50 or more, but is optionally 1-8 or 1-10. "N*"=0 to 15 or more, but is optionally 0, 1, 2, 3, 4, 5 or 6. Any of the residues of such agents can optionally be 2'-O-methyl RNA monomers—alternating positioning of 2'-O-methyl RNA monomers that commences from the 3'-terminal residue of the bottom (second) strand, as shown for above asymmetric agents, can also be used in the above "blunt/fray" DsiRNA agent. In one embodiment, the top strand (first strand) is the sense strand, and the bottom strand (second strand) is the antisense strand. Alternatively, the bottom strand is the sense strand and the top strand is the antisense strand. Modification and DNA:DNA extension patterns paralleling those shown above for asymmetric/overhang agents can also be incorporated into such "blunt/frayed" agents.

In another embodiment, a length-extended DsiRNA agent is provided that comprises deoxyribonucleotides positioned at sites modeled to function via specific direction of Dicer cleavage, yet which does not require the presence of a base-paired deoxyribonucleotide in the dsRNA structure. Exemplary structures for such a molecule are shown:

```
5'-XXDDXXXXXXXXXXXXXXXXXXXX_{N*}Y-3'

3'-DDXXXXXXXXXXXXXXXXXXXXXX_{N*}-5'
or

5'-XDXDXXXXXXXXXXXXXXXXXXXX_{N*}Y-3'

3'-DXDXXXXXXXXXXXXXXXXXXXXX_{N*}-5'
``` wherein "X"=RNA, "Y" is an optional overhang domain comprised of 0-10 RNA monomers that are optionally 2'-O-methyl RNA monomers—in certain embodiments, "Y" is an overhang domain comprised of 1-4 RNA monomers that are optionally 2'-O-methyl RNA monomers, and "D"=DNA. "N*"=0 to 15 or more, but is optionally 0, 1, 2, 3, 4, 5 or 6. In one embodiment, the top strand is the sense strand, and the bottom strand is the antisense strand. Alternatively, the bottom strand is the sense strand and the top strand is the antisense strand.

In any of the above embodiments where the bottom strand of the above structure is the antisense strand, the positioning of two deoxyribonucleotide residues at the ultimate and penultimate residues of the 5' end of the antisense strand will help reduce off-target effects (as prior studies have shown a 2'-O-methyl modification of at least the penultimate position from the 5' terminus of the antisense strand to reduce off-target effects; see, e.g., US 2007/0223427).

In certain embodiments, the "D" residues of the above structures include at least one PS-DNA or PS-RNA. Optionally, the "D" residues of the above structures include at least one modified nucleotide that inhibits Dicer cleavage.

While the above-described "DNA-extended" DsiRNA agents can be categorized as either "left extended" or "right extended", DsiRNA agents comprising both left- and right-extended DNA-containing sequences within a single agent (e.g., both flanks surrounding a core dsRNA structure are dsDNA extensions) can also be generated and used in similar manner to those described herein for "right-extended" and "left-extended" agents.

In some embodiments, the DsiRNA of the instant invention further comprises a linking moiety or domain that joins the sense and antisense strands of a dsNA of the invention, e.g., a DNA:DNA-extended DsiRNA agent. Optionally, such a linking moiety domain joins the 3' end of the sense strand and the 5' end of the antisense strand. The linking moiety may be a chemical (non-nucleotide) linker, such as an oligomethylenediol linker, oligoethylene glycol linker, or other art-recognized linker moiety. Alternatively, the linker can be a nucleotide linker, optionally including an extended loop and/or tetraloop.

In one embodiment, the DsiRNA agent has an asymmetric structure, with the sense strand having a 25-base pair length, and the antisense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxynucleotides at the 3' end of the sense strand.

In another embodiment, the DsiRNA agent has an asymmetric structure, with the antisense strand having a 25-base pair length, and the sense strand having a 27-base pair length with a 1-4 base 3'-overhang (e.g., a one base 3'-overhang, a two base 3'-overhang, a three base 3'-overhang or a four base 3'-overhang). In another embodiment, this DsiRNA agent has an asymmetric structure further containing 2 deoxyribonucleotides at the 3' end of the antisense strand.

Exemplary Lactate Dehydrogenase targeting DsiRNA agents of the invention, and their associated lactate dehydrogenase target sequences, include the following, presented in the below series of tables:
Table Number:
(2) Selected Human Anti-Lactate Dehydrogenase DsiRNA Agents (Asymmetrics);
(3) Selected Human Anti-Lactate Dehydrogenase DsiRNAs, Unmodified Duplexes (Asymmetrics);
(4) DsiRNA Target Sequences (21mers) in Human Lactate Dehydrogenase mRNA;
(5) Selected Human Anti-Lactate Dehydrogenase "Blunt/Blunt" DsiRNAs;
(6) DsiRNA Component 19 Nucleotide Target Sequences in Human Lactate Dehydrogenase mRNA;
(7) Selected Mouse Anti-Lactate Dehydrogenase DsiRNA Agents (Asymmetrics);
(8) Selected Mouse Anti-Lactate Dehydrogenase DsiRNAs, Unmodified Duplexes (Asymmetrics);
(9) DsiRNA Target Sequences (21mers) in Mouse Lactate Dehydrogenase mRNA;
(10) Selected Mouse Anti-Lactate Dehydrogenase "Blunt/Blunt" DsiRNAs;
(11) DsiRNA Component 19 Nucleotide Target Sequences in Mouse Lactate Dehydrogenase mRNA; and
(12) Additional Selected Human Anti-Lactate Dehydrogenase DsiRNA Agents (Asymmetrics)

TABLE 2

Selected Human Anti-Lactate Dehydrogenase DsiRNA Agents (Asymmetries)

| | | |
|---|---|---|
| | 5'-AG<u>AA</u>UAAGAUUAC<u>A</u>G<u>UU</u>GUUGGGgt-3' | (SEQ ID NO: 1) |
| | 3'-<u>GGUCUU</u>AUUCUAAUG<u>UC</u>AACAAC<u>CCCA</u>-5' | (SEQ ID NO: 73) |
| LDHA-355 Target: | 5'-CCAGAATAAGATTACAGTTGTTGGGGT-3' | (SEQ ID NO: 145) |
| | 5'-G<u>AA</u>UAAGAUUAC<u>A</u>G<u>UU</u>GUUGGGGtt-3' | (SEQ ID NO: 2) |
| | 3'-<u>GUCUU</u>AUUCUAAUG<u>UC</u><u>AA</u>CAACC<u>CCAA</u>-5' | (SEQ ID NO: 74) |
| LDHA-356 Target: | 5'-CAGAATAAGATTACAGTTGTTGGGGTT-3' | (SEQ ID NO: 146) |
| | 5'-A<u>AG</u>AUUACAGUUG<u>UU</u>GGGGUUGGtg-3' | (SEQ ID NO: 3) |
| | 3'-<u>UAUU</u>CUAAUGUCAAC<u>AA</u>CCCCAA<u>CC</u>AC-5' | (SEQ ID NO: 75) |
| LDHA-360 Target: | 5'-ATAAGATTACAGTTGTTGGGGTTGGTG-3' | (SEQ ID NO: 147) |
| | 5'-AG<u>A</u>UUACAGUUGU<u>U</u>GGGGUUGGUgc-3' | (SEQ ID NO: 4) |
| | 3'-<u>AUUCU</u>AAUGUCAAC<u>AA</u>CCCCAAC<u>CACG</u>-5' | (SEQ ID NO: 76) |
| LDHA-361 Target: | 5'-TAAGATTACAGTTGTTGGGGTTGGTGC-3' | (SEQ ID NO: 148) |

TABLE 2-continued

Selected Human Anti-Lactate Dehydrogenase DsiRNA Agents (Asymmetries)

|  |  |  |
|---|---|---|
| LDHA-362 Target: | 5'-GAUUACAGUUGUUGGGGUUGGUGct-3'<br>3'-UUCUAAUGUCAACAACCCCAACCACGA-5'<br>5'-AAGATTACAGTTGTTGGGGTTGGTGCT-3' | (SEQ ID NO: 5)<br>(SEQ ID NO: 77)<br>(SEQ ID NO: 149) |
| LDHA-363 Target: | 5'-AUUACAGUUGUUGGGGUUGGUGCtg-3'<br>3'-UCUAAUGUCAACAACCCCAACCACGAC-5'<br>5'-AGATTACAGTTGTTGGGGTTGGTGCTG-3' | (SEQ ID NO: 6)<br>(SEQ ID NO: 78)<br>(SEQ ID NO: 150) |
| LDHA-364 Target: | 5'-UUACAGUUGUUGGGGUUGGUGCUgt-3'<br>3'-CUAAUGUCAACAACCCCAACCACGACA-5'<br>5'-GATTACAGTTGTTGGGGTTGGTGCTGT-3' | (SEQ ID NO: 7)<br>(SEQ ID NO: 79)<br>(SEQ ID NO: 151) |
| LDHA-365 Target: | 5'-UACAGUUGUUGGGGUUGGUGCUGtt-3'<br>3'-UAAUGUCAACAACCCCAACCACGACAA-5'<br>5'-ATTACAGTTGTTGGGGTTGGTGCTGTT-3' | (SEQ ID NO: 8)<br>(SEQ ID NO: 80)<br>(SEQ ID NO: 152) |
| LDHA-366 Target: | 5'-ACAGUUGUUGGGGUUGGUGCUGUtg-3'<br>3'-AAUGUCAACAACCCCAACCACGACAAC-5'<br>5'-TTACAGTTGTTGGGGTTGGTGCTGTTG-3' | (SEQ ID NO: 9)<br>(SEQ ID NO: 81)<br>(SEQ ID NO: 153) |
| LDHA-367 Target: | 5'-CAGUUGUUGGGGUUGGUGCUGUUgg-3'<br>3'-AUGUCAACAACCCCAACCACGACAACC-5'<br>5'-TACAGTTGTTGGGGTTGGTGCTGTTGG-3' | (SEQ ID NO: 10)<br>(SEQ ID NO: 82)<br>(SEQ ID NO: 154) |
| LDHA-369 Target: | 5'-GUUGUUGGGGUUGGUGCUGUUGGca-3'<br>3'-GUCAACAACCCCAACCACGACAACCGU-5'<br>5'-CAGTTGTTGGGGTTGGTGCTGTTGGCA-3' | (SEQ ID NO: 11)<br>(SEQ ID NO: 83)<br>(SEQ ID NO: 155) |
| LDHA-370 Target: | 5'-UUGUUGGGGUUGGUGCUGUUGGCat-3'<br>3'-UCAACAACCCCAACCACGACAACCGUA-5'<br>5'-AGTTGTTGGGGTTGGTGCTGTTGGCAT-3' | (SEQ ID NO: 12)<br>(SEQ ID NO: 84)<br>(SEQ ID NO: 156) |
| LDHA-397 Target: | 5'-CCUGUGCCAUCAGUAUCUUAAUGaa-3'<br>3'-CCGGACACGGUAGUCAUAGAAUUACUU-5'<br>5'-GGCCTGTGCCATCAGTATCTTAATGAA-3' | (SEQ ID NO: 13)<br>(SEQ ID NO: 85)<br>(SEQ ID NO: 157) |
| LDHA-398 Target: | 5'-CUGUGCCAUCAGUAUCUUAAUGAag-3'<br>3'-CGGACACGGUAGUCAUAGAAUUACUUC-5'<br>5'-GCCTGTGCCATCAGTATCTTAATGAAG-3' | (SEQ ID NO: 14)<br>(SEQ ID NO: 86)<br>(SEQ ID NO: 158) |
| LDHA-399 Target: | 5'-UGUGCCAUCAGUAUCUUAAUGAAgg-3'<br>3'-GGACACGGUAGUCAUAGAAUUACUUCC-5'<br>5'-CCTGTGCCATCAGTATCTTAATGAAGG-3' | (SEQ ID NO: 15)<br>(SEQ ID NO: 87)<br>(SEQ ID NO: 159) |
| LDHA-400 Target: | 5'-GUGCCAUCAGUAUCUUAAUGAAGga-3'<br>3'-GACACGGUAGUCAUAGAAUUACUUCCU-5'<br>5'-CTGTGCCATCAGTATCTTAATGAAGGA-3' | (SEQ ID NO: 16)<br>(SEQ ID NO: 88)<br>(SEQ ID NO: 160) |
| LDHA-401 Target: | 5'-UGCCAUCAGUAUCUUAAUGAAGGac-3'<br>3'-ACACGGUAGUCAUAGAAUUACUUCCUG-5'<br>5'-TGTGCCATCAGTATCTTAATGAAGGAC-3' | (SEQ ID NO: 17)<br>(SEQ ID NO: 89)<br>(SEQ ID NO: 161) |
| LDHA-402 Target: | 5'-GCCAUCAGUAUCUUAAUGAAGGAct-3'<br>3'-CACGGUAGUCAUAGAAUUACUUCCUGA-5'<br>5'-GTGCCATCAGTATCTTAATGAAGGACT-3' | (SEQ ID NO: 18)<br>(SEQ ID NO: 90)<br>(SEQ ID NO: 162) |
| LDHA-403 Target: | 5'-CCAUCAGUAUCUUAAUGAAGGACtt-3'<br>3'-ACGGUAGUCAUAGAAUUACUUCCUGAA-5'<br>5'-TGCCATCAGTATCTTAATGAAGGACTT-3' | (SEQ ID NO: 19)<br>(SEQ ID NO: 91)<br>(SEQ ID NO: 163) |
| LDHA-404 Target: | 5'-CAUCAGUAUCUUAAUGAAGGACUtg-3'<br>3'-CGGUAGUCAUAGAAUUACUUCCUGAAC-5'<br>5'-GCCATCAGTATCTTAATGAAGGACTTG-3' | (SEQ ID NO: 20)<br>(SEQ ID NO: 92)<br>(SEQ ID NO: 164) |
| LDHA-714 Target: | 5'-GUGGAUAUCUUGACCUACGUGGCtt-3'<br>3'-GUCACCUAUAGAACUGGAUGCACCGAA-5'<br>5'-CAGTGGATATCTTGACCTACGTGGCTT-3' | (SEQ ID NO: 21)<br>(SEQ ID NO: 93)<br>(SEQ ID NO: 165) |
| LDHA-717 Target: | 5'-GAUAUCUUGACCUACGUGGCUUGga-3'<br>3'-ACCUAUAGAACUGGAUGCACCGAACCU-5'<br>5'-TGGATATCTTGACCTACGTGGCTTGGA-3' | (SEQ ID NO: 22)<br>(SEQ ID NO: 94)<br>(SEQ ID NO: 166) |
| LDHA-718 Target: | 5'-AUAUCUUGACCUACGUGGCUUGGaa-3'<br>3'-CCUAUAGAACUGGAUGCACCGAACCUU-5'<br>5'-GGATATCTTGACCTACGTGGCTTGGAA-3' | (SEQ ID NO: 23)<br>(SEQ ID NO: 95)<br>(SEQ ID NO: 167) |

TABLE 2-continued

Selected Human Anti-Lactate Dehydrogenase DsiRNA Agents (Asymmetries)

|  |  |  |
|---|---|---|
| LDHA-719 Target: | 5'-UAUCUUGACCUACGUGGCUUGGAag-3'<br>3'-CUAUAGAACUGGAUGCACCGAACCUUC-5'<br>5'-GATATCTTGACCTACGTGGCTTGGAAG-3' | (SEQ ID NO: 24)<br>(SEQ ID NO: 96)<br>(SEQ ID NO: 168) |
| LDHA-720 Target: | 5'-AUCUUGACCUACGUGGCUUGGAAga-3'<br>3'-UAUAGAACUGGAUGCACCGAACCUUCU-5'<br>5'-ATATCTTGACCTACGTGGCTTGGAAGA-3' | (SEQ ID NO: 25)<br>(SEQ ID NO: 97)<br>(SEQ ID NO: 169) |
| LDHA-722 Target: | 5'-CUUGACCUACGUGGCUUGGAAGAta-3'<br>3'-UAGAACUGGAUGCACCGAACCUUCUAU-5'<br>5'-ATCTTGACCTACGTGGCTTGGAAGATA-3' | (SEQ ID NO: 26)<br>(SEQ ID NO: 98)<br>(SEQ ID NO: 170) |
| LDHA-723 Target: | 5'-UUGACCUACGUGGCUUGGAAGAUaa-3'<br>3'-AGAACUGGAUGCACCGAACCUUCUAUU-5'<br>5'-TCTTGACCTACGTGGCTTGGAAGATAA-3' | (SEQ ID NO: 27)<br>(SEQ ID NO: 99)<br>(SEQ ID NO: 171) |
| LDHA-724 Target: | 5'-UGACCUACGUGGCUUGGAAGAUAag-3'<br>3'-GAACUGGAUGCACCGAACCUUCUAUUC-5'<br>5'-CTTGACCTACGTGGCTTGGAAGATAAG-3' | (SEQ ID NO: 28)<br>(SEQ ID NO: 100)<br>(SEQ ID NO: 172) |
| LDHA-739 Target: | 5'-GGAAGAUAAGUGGUUUUCCCAAAaa-3'<br>3'-AACCUUCUAUUCACCAAAAGGGUUUUU-5'<br>5'-TTGGAAGATAAGTGGTTTTCCCAAAAA-3' | (SEQ ID NO: 29)<br>(SEQ ID NO: 101)<br>(SEQ ID NO: 173) |
| LDHA-740 Target: | 5'-GAAGAUAAGUGGUUUUCCCAAAAac-3'<br>3'-ACCUUCUAUUCACCAAAAGGGUUUUUG-5'<br>5'-TGGAAGATAAGTGGTTTTCCCAAAAAC-3' | (SEQ ID NO: 30)<br>(SEQ ID NO: 102)<br>(SEQ ID NO: 174) |
| LDHA-891 Target: | 5'-CCUGUAUGGAGUGGAAUGAAUGUtg-3'<br>3'-ACGGACAUACCUCACCUUACUUACAAC-5'<br>5'-TGCCTGTATGGAGTGGAATGAATGTTG-3' | (SEQ ID NO: 31)<br>(SEQ ID NO: 103)<br>(SEQ ID NO: 175) |
| LDHA-892 Target: | 5'-CUGUAUGGAGUGGAAUGAAUGUUgc-3'<br>3'-CGGACAUACCUCACCUUACUUACAACG-5'<br>5'-GCCTGTATGGAGTGGAATGAATGTTGC-3' | (SEQ ID NO: 32)<br>(SEQ ID NO: 104)<br>(SEQ ID NO: 176) |
| LDHA-907 Target: | 5'-UGAAUGUUGCUGGUGUCUCUCUGaa-3'<br>3'-UUACUUACAACGACCACAGAGAGACUU-5'<br>5'-AATGAATGTTGCTGGTGTCTCTCTGAA-3' | (SEQ ID NO: 33)<br>(SEQ ID NO: 105)<br>(SEQ ID NO: 177) |
| LDHA-952 Target: | 5'-GGACUGAUAAAGAUAAGGAACAGtg-3'<br>3'-UCCCUGACUAUUUCUAUUCCUUGUCAC-5'<br>5'-AGGGACTGATAAAGATAAGGAACAGTG-3' | (SEQ ID NO: 34)<br>(SEQ ID NO: 106)<br>(SEQ ID NO: 178) |
| LDHA-1286 Target: | 5'-GCAAUUUUAAAGUCUUCUGAUGUca-3'<br>3'-GACGUUAAAAUUUCAGAAGACUACAGU-5'<br>5'-CTGCAATTTTAAAGTCTTCTGATGTCA-3' | (SEQ ID NO: 35)<br>(SEQ ID NO: 107)<br>(SEQ ID NO: 179) |
| LDHA-1287 Target: | 5'-CAAUUUUAAAGUCUUCUGAUGUCat-3'<br>3'-ACGUUAAAAUUUCAGAAGACUACAGUA-5'<br>5'-TGCAATTTTAAAGTCTTCTGATGTCAT-3' | (SEQ ID NO: 36)<br>(SEQ ID NO: 108)<br>(SEQ ID NO: 180) |
| LDHA-1292 Target: | 5'-UUAAAGUCUUCUGAUGUCAUAUCat-3'<br>3'-AAAAUUUCAGAAGACUACAGUAUAGUA-5'<br>5'-TTTTAAAGTCTTCTGATGTCATATCAT-3' | (SEQ ID NO: 37)<br>(SEQ ID NO: 109)<br>(SEQ ID NO: 181) |
| LDHA-1293 Target: | 5'-UAAAGUCUUCUGAUGUCAUAUCAtt-3'<br>3'-AAAUUUCAGAAGACUACAGUAUAGUAA-5'<br>5'-TTTAAAGTCTTCTGATGTCATATCATT-3' | (SEQ ID NO: 38)<br>(SEQ ID NO: 110)<br>(SEQ ID NO: 182) |
| LDHA-1294 Target: | 5'-AAAGUCUUCUGAUGUCAUAUCAUtt-3'<br>3'-AAUUUCAGAAGACUACAGUAUAGUAAA-5'<br>5'-TTAAAGTCTTCTGATGTCATATCATTT-3' | (SEQ ID NO: 39)<br>(SEQ ID NO: 111)<br>(SEQ ID NO: 183) |
| LDHA-1359 Target: | 5'-CAUGUUGUCCUUUUUAUCUGAUCtg-3'<br>3'-ACGUACAACAGGAAAAAUAGACUAGAC-5'<br>5'-TGCATGTTGTCCTTTTTATCTGATCTG-3' | (SEQ ID NO: 40)<br>(SEQ ID NO: 112)<br>(SEQ ID NO: 184) |
| LDHA-1360 Target: | 5'-AUGUUGUCCUUUUUAUCUGAUCgt-3'<br>3'-CGUACAACAGGAAAAAUAGACUAGACA-5'<br>5'-GCATGTTGTCCTTTTTATCTGATCTGT-3' | (SEQ ID NO: 41)<br>(SEQ ID NO: 113)<br>(SEQ ID NO: 185) |
| LDHA-1361 Target: | 5'-UGUUGUCCUUUUUAUCUGAUCUGtg-3'<br>3'-GUACAACAGGAAAAAUAGACUAGACAC-5'<br>5'-CATGTTGTCCTTTTTATCTGATCTGTG-3' | (SEQ ID NO: 42)<br>(SEQ ID NO: 114)<br>(SEQ ID NO: 186) |

TABLE 2-continued

Selected Human Anti-Lactate Dehydrogenase DsiRNA Agents (Asymmetries)

|  |  |  |  |
|---|---|---|---|
| LDHA-1362 | Target: | 5'-GUUGUCCUUUUUAUCUGAUCUGUga-3'<br>3'-UACAACAGGAAAAAUAGACUAGACACU-5'<br>5'-ATGTTGTCCTTTTTATCTGATCTGTGA-3' | (SEQ ID NO: 43)<br>(SEQ ID NO: 115)<br>(SEQ ID NO: 187) |
| LDHA-1363 | Target: | 5'-UUGUCCUUUUUAUCUGAUCUGUGat-3'<br>3'-ACAACAGGAAAAAUAGACUAGACACUA-5'<br>5'-TGTTGTCCTTTTTATCTGATCTGTGAT-3' | (SEQ ID NO: 44)<br>(SEQ ID NO: 116)<br>(SEQ ID NO: 188) |
| LDHA-1365 | Target: | 5'-GUCCUUUUUAUCUGAUCUGUGAUta-3'<br>3'-AACAGGAAAAAUAGACUAGACACUAAU-5'<br>5'-TTGTCCTTTTTATCTGATCTGTGATTA-3' | (SEQ ID NO: 45)<br>(SEQ ID NO: 117)<br>(SEQ ID NO: 189) |
| LDHA-1366 | Target: | 5'-UCCUUUUUAUCUGAUCUGUGAUUaa-3'<br>3'-ACAGGAAAAAUAGACUAGACACUAAUU-5'<br>5'-TGTCCTTTTTATCTGATCTGTGATTAA-3' | (SEQ ID NO: 46)<br>(SEQ ID NO: 118)<br>(SEQ ID NO: 190) |
| LDHA-1367 | Target: | 5'-CCUUUUUAUCUGAUCUGUGAUUAaa-3'<br>3'-CAGGAAAAAUAGACUAGACACUAAUUU-5'<br>5'-GTCCTTTTTATCTGATCTGTGATTAAA-3' | (SEQ ID NO: 47)<br>(SEQ ID NO: 119)<br>(SEQ ID NO: 191) |
| LDHA-1368 | Target: | 5'-CUUUUUAUCUGAUCUGUGAUUAAag-3'<br>3'-AGGAAAAAUAGACUAGACACUAAUUUC-5'<br>5'-TCCTTTTTATCTGATCTGTGATTAAAG-3' | (SEQ ID NO: 48)<br>(SEQ ID NO: 120)<br>(SEQ ID NO: 192) |
| LDHA-1370 | Target: | 5'-UUUUAUCUGAUCUGUGAUUAAAGca-3'<br>3'-GAAAAAUAGACUAGACACUAAUUUCGU-5'<br>5'-CTTTTTATCTGATCTGTGATTAAAGCA-3' | (SEQ ID NO: 49)<br>(SEQ ID NO: 121)<br>(SEQ ID NO: 193) |
| LDHA-1371 | Target: | 5'-UUUAUCUGAUCUGUGAUUAAAGCag-3'<br>3'-AAAAAUAGACUAGACACUAAUUUCGUC-5'<br>5'-TTTTTATCTGATCTGTGATTAAAGCAG-3' | (SEQ ID NO: 50)<br>(SEQ ID NO: 122)<br>(SEQ ID NO: 194) |
| LDHA-1372 | Target: | 5'-UUAUCUGAUCUGUGAUUAAAGCAgt-3'<br>3'-AAAAUAGACUAGACACUAAUUUCGUCA-5'<br>5'-TTTTATCTGATCTGTGATTAAAGCAGT-3' | (SEQ ID NO: 51)<br>(SEQ ID NO: 123)<br>(SEQ ID NO: 195) |
| LDHA-1393 | Target: | 5'-CAGUAAUAUUUUAAGAUGGACUGgg-3'<br>3'-UCGUCAUUAUAAAAUUCUACCUGACCC-5'<br>5'-AGCAGTAATATTTTAAGATGGACTGGG-3' | (SEQ ID NO: 52)<br>(SEQ ID NO: 124)<br>(SEQ ID NO: 196) |
| LDHA-1427 | Target: | 5'-AACUCCUGAAGUUAGAAAUAAGAat-3'<br>3'-AGUUGAGGACUUCAAUCUUUAUUCUUA-5'<br>5'-TCAACTCCTGAAGTTAGAAATAAGAAT-3' | (SEQ ID NO: 53)<br>(SEQ ID NO: 125)<br>(SEQ ID NO: 197) |
| LDHA-1428 | Target: | 5'-ACUCCUGAAGUUAGAAAUAAGAAtg-3'<br>3'-GUUGAGGACUUCAAUCUUUAUUCUUAC-5'<br>5'-CAACTCCTGAAGTTAGAAATAAGAATG-3' | (SEQ ID NO: 54)<br>(SEQ ID NO: 126)<br>(SEQ ID NO: 198) |
| LDHA-1512 | Target: | 5'-AACUGGUUAGUGUGAAAUAGUUCtg-3'<br>3'-AGUUGACCAAUCACACUUUAUCAAGAC-5'<br>5'-TCAACTGGTTAGTGTGAAATAGTTCTG-3' | (SEQ ID NO: 55)<br>(SEQ ID NO: 127)<br>(SEQ ID NO: 199) |
| LDHA-1513 | Target: | 5'-ACUGGUUAGUGUGAAAUAGUUCUgc-3'<br>3'-GUUGACCAAUCACACUUUAUCAAGACG-5'<br>5'-CAACTGGTTAGTGTGAAATAGTTCTGC-3' | (SEQ ID NO: 56)<br>(SEQ ID NO: 128)<br>(SEQ ID NO: 200) |
| LDHA-1514 | Target: | 5'-CUGGUUAGUGUGAAAUAGUUCUGcc-3'<br>3'-UUGACCAAUCACACUUUAUCAAGACGG-5'<br>5'-AACTGGTTAGTGTGAAATAGTTCTGCC-3' | (SEQ ID NO: 57)<br>(SEQ ID NO: 129)<br>(SEQ ID NO: 201) |
| LDHA-1516 | Target: | 5'-GGUUAGUGUGAAAUAGUUCUGCCac-3'<br>3'-GACCAAUCACACUUUAUCAAGACGGUG-5'<br>5'-CTGGTTAGTGTGAAATAGTTCTGCCAC-3' | (SEQ ID NO: 58)<br>(SEQ ID NO: 130)<br>(SEQ ID NO: 202) |
| LDHA-1684 | Target: | 5'-AUCCAGUGUAUAAAUCCAAUAUCat-3'<br>3'-CCUAGGUCACAUAUUUAGGUUAUAGUA-5'<br>5'-GGATCCAGTGTATAAATCCAATATCAT-3' | (SEQ ID NO: 59)<br>(SEQ ID NO: 131)<br>(SEQ ID NO: 203) |
| LDHA-1688 | Target: | 5'-AGUGUAUAAAUCCAAUAUCAUGUct-3'<br>3'-GGUCACAUAUUUAGGUUAUAGUACAGA-5'<br>5'-CCAGTGTATAAATCCAATATCATGTCT-3' | (SEQ ID NO: 60)<br>(SEQ ID NO: 132)<br>(SEQ ID NO: 204) |
| LDHA-1736 | Target: | 5'-CUUAUUUUGUGAACUAUAUCAGUag-3'<br>3'-UAGAAUAAAACACUUGAUAUAGUCAUC-5'<br>5'-ATCTTATTTTGTGAACTATATCAGTAG-3' | (SEQ ID NO: 61)<br>(SEQ ID NO: 133)<br>(SEQ ID NO: 205) |

TABLE 2-continued

Selected Human Anti-Lactate Dehydrogenase DsiRNA Agents (Asymmetries)

|  |  |  |
|---|---|---|
| LDHA-1750 Target: | 5'-UAUAUCAGUAGUGUACAUUACCAta-3'<br>3'-UGAUAUAGUCAUCACAUGUAAUGGUAU-5'<br>5'-ACTATATCAGTAGTGTACATTACCATA-3' | (SEQ ID NO: 62)<br>(SEQ ID NO: 134)<br>(SEQ ID NO: 206) |
| LDHA-1753 Target: | 5'-AUCAGUAGUGUACAUUACCAUAUaa-3'<br>3'-UAUAGUCAUCACAUGUAAUGGUAUAUU-5'<br>5'-ATATCAGTAGTGTACATTACCATATAA-3' | (SEQ ID NO: 63)<br>(SEQ ID NO: 135)<br>(SEQ ID NO: 207) |
| LDHA-1754 Target: | 5'-UCAGUAGUGUACAUUACCAUAUAat-3'<br>3'-AUAGUCAUCACAUGUAAUGGUAUAUUA-5'<br>5'-TATCAGTAGTGTACATTACCATATAAT-3' | (SEQ ID NO: 64)<br>(SEQ ID NO: 136)<br>(SEQ ID NO: 208) |
| LDHA-1805 Target: | 5'-CAACCAACUAUCCAAGUGUUAUAcc-3'<br>3'-ACGUUGGUUGAUAGGUUCACAAUAUGG-5'<br>5'-TGCAACCAACTATCCAAGTGTTATACC-3' | (SEQ ID NO: 65)<br>(SEQ ID NO: 137)<br>(SEQ ID NO: 209) |
| LDHA-1806 Target: | 5'-AACCAACUAUCCAAGUGUUAUACca-3'<br>3'-CGUUGGUUGAUAGGUUCACAAUAUGGU-5'<br>5'-GCAACCAACTATCCAAGTGTTATACCA-3' | (SEQ ID NO: 66)<br>(SEQ ID NO: 138)<br>(SEQ ID NO: 210) |
| LDHA-1807 Target: | 5'-ACCAACUAUCCAAGUGUUAUACCaa-3'<br>3'-GUUGGUUGAUAGGUUCACAAUAUGGUU-5'<br>5'-CAACCAACTATCCAAGTGTTATACCAA-3' | (SEQ ID NO: 67)<br>(SEQ ID NO: 139)<br>(SEQ ID NO: 211) |
| LDHA-1808 Target: | 5'-CCAACUAUCCAAGUGUUAUACCAac-3'<br>3'-UUGGUUGAUAGGUUCACAAUAUGGUUG-5'<br>5'-AACCAACTATCCAAGTGTTATACCAAC-3' | (SEQ ID NO: 68)<br>(SEQ ID NO: 140)<br>(SEQ ID NO: 212) |
| LDHA-1811 Target: | 5'-ACUAUCCAAGUGUUAUACCAACUaa-3'<br>3'-GUUGAUAGGUUCACAAUAUGGUUGAUU-5'<br>5'-CAACTATCCAAGTGTTATACCAACTAA-3' | (SEQ ID NO: 69)<br>(SEQ ID NO: 141)<br>(SEQ ID NO: 213) |
| LDHA-1812 Target: | 5'-CUAUCCAAGUGUUAUACCAACUAaa-3'<br>3'-UUGAUAGGUUCACAAUAUGGUUGAUUU-5'<br>5'-AACTATCCAAGTGTTATACCAACTAAA-3' | (SEQ ID NO: 70)<br>(SEQ ID NO: 142)<br>(SEQ ID NO: 214) |
| LDHA-1815 Target: | 5'-UCCAAGUGUUAUACCAACUAAAAcc-3'<br>3'-AUAGGUUCACAAUAUGGUUGAUUUUGG-5'<br>5'-TATCCAAGTGTTATACCAACTAAAACC-3' | (SEQ ID NO: 71)<br>(SEQ ID NO: 143)<br>(SEQ ID NO: 215) |
| LDHA-1816 Target: | 5'-CCAAGUGUUAUACCAACUAAAACcc-3'<br>3'-UAGGUUCACAAUAUGGUUGAUUUUGGG-5'<br>5'-ATCCAAGTGTTATACCAACTAAAACCC-3' | (SEQ ID NO: 72)<br>(SEQ ID NO: 144)<br>(SEQ ID NO: 216) |

TABLE 3

Selected Human Anti-Lactate Dehydrogenase DsiRNAs, Unmodified Duplexes (Asymmetrics)

|  |  |  |
|---|---|---|
| LDHA-355 Target: | 5'-AGAAUAAGAUUACAGUUGUUGGGGU-3'<br>3'-GGUCUUAUUCUAAUGUCAACAACCCCA-5'<br>5'-CCAGAATAAGATTACAGTTGTTGGGGT-3' | (SEQ ID NO: 217)<br>(SEQ ID NO: 73)<br>(SEQ ID NO: 145) |
| LDHA-356 Target: | 5'-GAAUAAGAUUACAGUUGUUGGGGUU-3'<br>3'-GUCUUAUUCUAAUGUCAACAACCCCAA-5'<br>5'-CAGAATAAGATTACAGTTGTTGGGGTT-3' | (SEQ ID NO: 218)<br>(SEQ ID NO: 74)<br>(SEQ ID NO: 146) |
| LDHA-360 Target: | 5'-AAGAUUACAGUUGUUGGGGUUGGUG-3'<br>3'-UAUUCUAAUGUCAACAACCCCAACCAC-5'<br>5'-ATAAGATTACAGTTGTTGGGGTTGGTG-3' | (SEQ ID NO: 219)<br>(SEQ ID NO: 75)<br>(SEQ ID NO: 147) |
| LDHA-361 Target: | 5'-AGAUUACAGUUGUUGGGGUUGGUGC-3'<br>3'-AUUCUAAUGUCAACAACCCCAACCACG-5'<br>5'-TAAGATTACAGTTGTTGGGGTTGGTGC-3' | (SEQ ID NO: 220)<br>(SEQ ID NO: 76)<br>(SEQ ID NO: 148) |
| LDHA-362 Target: | 5'-GAUUACAGUUGUUGGGGUUGGUGCU-3'<br>3'-UUCUAAUGUCAACAACCCCAACCACGA-5'<br>5'-AAGATTACAGTTGTTGGGGTTGGTGCT-3' | (SEQ ID NO: 221)<br>(SEQ ID NO: 77)<br>(SEQ ID NO: 149) |
| LDHA-363 Target: | 5'-AUUACAGUUGUUGGGGUUGGUGCUG-3'<br>3'-UCUAAUGUCAACAACCCCAACCACGAC-5'<br>5'-AGATTACAGTTGTTGGGGTTGGTGCTG-3' | (SEQ ID NO: 222)<br>(SEQ ID NO: 78)<br>(SEQ ID NO: 150) |

TABLE 3-continued

Selected Human Anti-Lactate Dehydrogenase DsiRNAs, Unmodified Duplexes (Asymmetrics)

|  |  |  |
|---|---|---|
| LDHA-364 Target: | 5'-UUACAGUUGUUGGGGUUGGUGCUGU-3'<br>3'-CUAAUGUCAACAACCCCAACCACGACA-5'<br>5'-GATTACAGTTGTTGGGGTTGGTGCTGT-3' | (SEQ ID NO: 223)<br>(SEQ ID NO: 79)<br>(SEQ ID NO: 151) |
| LDHA-365 Target: | 5'-UACAGUUGUUGGGGUUGGUGCUGUU-3'<br>3'-UAAUGUCAACAACCCCAACCACGACAA-5'<br>5'-ATTACAGTTGTTGGGGTTGGTGCTGTT-3' | (SEQ ID NO: 224)<br>(SEQ ID NO: 80)<br>(SEQ ID NO: 152) |
| LDHA-366 Target: | 5'-ACAGUUGUUGGGGUUGGUGCUGUUG-3'<br>3'-AAUGUCAACAACCCCAACCACGACAAC-5'<br>5'-TTACAGTTGTTGGGGTTGGTGCTGTTG-3' | (SEQ ID NO: 225)<br>(SEQ ID NO: 81)<br>(SEQ ID NO: 153) |
| LDHA-367 Target: | 5'-CAGUUGUUGGGGUUGGUGCUGUUGG-3'<br>3'-AUGUCAACAACCCCAACCACGACAACC-5'<br>5'-TACAGTTGTTGGGGTTGGTGCTGTTGG-3' | (SEQ ID NO: 226)<br>(SEQ ID NO: 82)<br>(SEQ ID NO: 154) |
| LDHA-369 Target: | 5'-GUUGUUGGGGUUGGUGCUGUUGGCA-3'<br>3'-GUCAACAACCCCAACCACGACAACCGU-5'<br>5'-CAGTTGTTGGGGTTGGTGCTGTTGGCA-3' | (SEQ ID NO: 227)<br>(SEQ ID NO: 83)<br>(SEQ ID NO: 155) |
| LDHA-370 Target: | 5'-UUGUUGGGGUUGGUGCUGUUGGCAU-3'<br>3'-UCAACAACCCCAACCACGACAACCGUA-5'<br>5'-AGTTGTTGGGGTTGGTGCTGTTGGCAT-3' | (SEQ ID NO: 228)<br>(SEQ ID NO: 84)<br>(SEQ ID NO: 156) |
| LDHA-397 Target: | 5'-CCUGUGCCAUCAGUAUCUUAAUGAA-3'<br>3'-CCGGACACGGUAGUCAUAGAAUUACUU-5'<br>5'-GGCCTGTGCCATCAGTATCTTAATGAA-3' | (SEQ ID NO: 229)<br>(SEQ ID NO: 85)<br>(SEQ ID NO: 157) |
| LDHA-398 Target: | 5'-CUGUGCCAUCAGUAUCUUAAUGAAG-3'<br>3'-CGGACACGGUAGUCAUAGAAUUACUUC-5'<br>5'-GCCTGTGCCATCAGTATCTTAATGAAG-3' | (SEQ ID NO: 230)<br>(SEQ ID NO: 86)<br>(SEQ ID NO: 158) |
| LDHA-399 Target: | 5'-UGUGCCAUCAGUAUCUUAAUGAAGG-3'<br>3'-GGACACGGUAGUCAUAGAAUUACUUCC-5'<br>5'-CCTGTGCCATCAGTATCTTAATGAAGG-3' | (SEQ ID NO: 231)<br>(SEQ ID NO: 87)<br>(SEQ ID NO: 159) |
| LDHA-400 Target: | 5'-GUGCCAUCAGUAUCUUAAUGAAGGA-3'<br>3'-GACACGGUAGUCAUAGAAUUACUUCCU-5'<br>5'-CTGTGCCATCAGTATCTTAATGAAGGA-3' | (SEQ ID NO: 232)<br>(SEQ ID NO: 88)<br>(SEQ ID NO: 160) |
| LDHA-401 Target: | 5'-UGCCAUCAGUAUCUUAAUGAAGGAC-3'<br>3'-ACACGGUAGUCAUAGAAUUACUUCCUG-5'<br>5'-TGTGCCATCAGTATCTTAATGAAGGAC-3' | (SEQ ID NO: 233)<br>(SEQ ID NO: 89)<br>(SEQ ID NO: 161) |
| LDHA-402 Target: | 5'-GCCAUCAGUAUCUUAAUGAAGGACU-3'<br>3'-CACGGUAGUCAUAGAAUUACUUCCUGA-5'<br>5'-GTGCCATCAGTATCTTAATGAAGGACT-3' | (SEQ ID NO: 234)<br>(SEQ ID NO: 90)<br>(SEQ ID NO: 162) |
| LDHA-403 Target: | 5'-CCAUCAGUAUCUUAAUGAAGGACUU-3'<br>3'-ACGGUAGUCAUAGAAUUACUUCCUGAA-5'<br>5'-TGCCATCAGTATCTTAATGAAGGACTT-3' | (SEQ ID NO: 235)<br>(SEQ ID NO: 91)<br>(SEQ ID NO: 163) |
| LDHA-404 Target: | 5'-CAUCAGUAUCUUAAUGAAGGACUUG-3'<br>3'-CGGUAGUCAUAGAAUUACUUCCUGAAC-5'<br>5'-GCCATCAGTATCTTAATGAAGGACTTG-3' | (SEQ ID NO: 236)<br>(SEQ ID NO: 92)<br>(SEQ ID NO: 164) |
| LDHA-714 Target: | 5'-GUGGAUAUCUUGACCUACGUGGCUU-3'<br>3'-GUCACCUAUAGAACUGGAUGCACCGAA-5'<br>5'-CAGTGGATATCTTGACCTACGTGGCTT-3' | (SEQ ID NO: 237)<br>(SEQ ID NO: 93)<br>(SEQ ID NO: 165) |
| LDHA-717 Target: | 5'-GAUAUCUUGACCUACGUGGCUUGGA-3'<br>3'-ACCUAUAGAACUGGAUGCACCGAACCU-5'<br>5'-TGGATATCTTGACCTACGTGGCTTGGA-3' | (SEQ ID NO: 238)<br>(SEQ ID NO: 94)<br>(SEQ ID NO: 166) |
| LDHA-718 Target: | 5'-AUAUCUUGACCUACGUGGCUUGGAA-3'<br>3'-CCUAUAGAACUGGAUGCACCGAACCUU-5'<br>5'-GGATATCTTGACCTACGTGGCTTGGAA-3' | (SEQ ID NO: 239)<br>(SEQ ID NO: 95)<br>(SEQ ID NO: 167) |
| LDHA-719 Target: | 5'-UAUCUUGACCUACGUGGCUUGGAAG-3'<br>3'-CUAUAGAACUGGAUGCACCGAACCUUC-5'<br>5'-GATATCTTGACCTACGTGGCTTGGAAG-3' | (SEQ ID NO: 240)<br>(SEQ ID NO: 96)<br>(SEQ ID NO: 168) |
| LDHA-720 Target: | 5'-AUCUUGACCUACGUGGCUUGGAAGA-3'<br>3'-UAUAGAACUGGAUGCACCGAACCUUCU-5'<br>5'-ATATCTTGACCTACGTGGCTTGGAAGA-3' | (SEQ ID NO: 241)<br>(SEQ ID NO: 97)<br>(SEQ ID NO: 169) |

TABLE 3-continued

Selected Human Anti-Lactate Dehydrogenase DsiRNAs, Unmodified Duplexes
(Asymmetrics)

| Name | Sequence | SEQ ID NO |
|---|---|---|
| | 5'-CUUGACCUACGUGGCUUGGAAGAUA-3' | (SEQ ID NO: 242) |
| | 3'-UAGAACUGGAUGCACCGAACCUUCUAU-5' | (SEQ ID NO: 98) |
| LDHA-722 Target: | 5'-ATCTTGACCTACGTGGCTTGGAAGATA-3' | (SEQ ID NO: 170) |
| | 5'-UUGACCUACGUGGCUUGGAAGAUAA-3' | (SEQ ID NO: 243) |
| | 3'-AGAACUGGAUGCACCGAACCUUCUAUU-5' | (SEQ ID NO: 99) |
| LDHA-723 Target: | 5'-TCTTGACCTACGTGGCTTGGAAGATAA-3' | (SEQ ID NO: 171) |
| | 5'-UGACCUACGUGGCUUGGAAGAUAAG-3' | (SEQ ID NO: 244) |
| | 3'-GAACUGGAUGCACCGAACCUUCUAUUC-5' | (SEQ ID NO: 100) |
| LDHA-724 Target: | 5'-CTTGACCTACGTGGCTTGGAAGATAAG-3' | (SEQ ID NO: 172) |
| | 5'-GGAAGAUAAGUGGUUUUCCCAAAAA-3' | (SEQ ID NO: 245) |
| | 3'-AACCUUCUAUUCACCAAAAGGGUUUUU-5' | (SEQ ID NO: 101) |
| LDHA-739 Target: | 5'-TTGGAAGATAAGTGGTTTTCCCAAAAA-3' | (SEQ ID NO: 173) |
| | 5'-GAAGAUAAGUGGUUUUCCCAAAAAC-3' | (SEQ ID NO: 246) |
| | 3'-ACCUUCUAUUCACCAAAAGGGUUUUUG-5' | (SEQ ID NO: 102) |
| LDHA-740 Target: | 5'-TGGAAGATAAGTGGTTTTCCCAAAAAC-3' | (SEQ ID NO: 174) |
| | 5'-CCUGUAUGGAGUGGAAUGAAUGUUG-3' | (SEQ ID NO: 247) |
| | 3'-ACGGACAUACCUCACCUUACUUACAAC-5' | (SEQ ID NO: 103) |
| LDHA-891 Target: | 5'-TGCCTGTATGGAGTGGAATGAATGTTG-3' | (SEQ ID NO: 175) |
| | 5'-CUGUAUGGAGUGGAAUGAAUGUUGC-3' | (SEQ ID NO: 248) |
| | 3'-CGGACAUACCUCACCUUACUUACAACG-5' | (SEQ ID NO: 104) |
| LDHA-892 Target: | 5'-GCCTGTATGGAGTGGAATGAATGTTGC-3' | (SEQ ID NO: 176) |
| | 5'-UGAAUGUUGCUGGUGUCUCUCUGAA-3' | (SEQ ID NO: 249) |
| | 3'-UUACUUACAACGACCACAGAGAGACUU-5' | (SEQ ID NO: 105) |
| LDHA-907 Target: | 5'-AATGAATGTTGCTGGTGTCTCTCTGAA-3' | (SEQ ID NO: 177) |
| | 5'-GGACUGAUAAAGAUAAGGAACAGUG-3' | (SEQ ID NO: 250) |
| | 3'-UCCCUGACUAUUUCUAUUCCUUGUCAC-5' | (SEQ ID NO: 106) |
| LDHA-952 Target: | 5'-AGGGACTGATAAAGATAAGGAACAGTG-3' | (SEQ ID NO: 178) |
| | 5'-GCAAUUUUAAAGUCUUCUGAUGUCA-3' | (SEQ ID NO: 251) |
| | 3'-GACGUUAAAAUUUCAGAAGACUACAGU-5' | (SEQ ID NO: 107) |
| LDHA-1286 Target: | 5'-CTGCAATTTTAAAGTCTTCTGATGTCA-3' | (SEQ ID NO: 179) |
| | 5'-CAAUUUUAAAGUCUUCUGAUGUCAU-3' | (SEQ ID NO: 252) |
| | 3'-ACGUUAAAAUUUCAGAAGACUACAGUA-5' | (SEQ ID NO: 108) |
| LDHA-1287 Target: | 5'-TGCAATTTTAAAGTCTTCTGATGTCAT-3' | (SEQ ID NO: 180) |
| | 5'-UUAAAGUCUUCUGAUGUCAUAUCAU-3' | (SEQ ID NO: 253) |
| | 3'-AAAAUUUCAGAAGACUACAGUAUAGUA-5' | (SEQ ID NO: 109) |
| LDHA-1292 Target: | 5'-TTTTAAAGTCTTCTGATGTCATATCAT-3' | (SEQ ID NO: 181) |
| | 5'-UAAAGUCUUCUGAUGUCAUAUCAUU-3' | (SEQ ID NO: 254) |
| | 3'-AAAUUUCAGAAGACUACAGUAUAGUAA-5' | (SEQ ID NO: 110) |
| LDHA-1293 Target: | 5'-TTTAAAGTCTTCTGATGTCATATCATT-3' | (SEQ ID NO: 182) |
| | 5'-AAAGUCUUCUGAUGUCAUAUCAUUU-3' | (SEQ ID NO: 255) |
| | 3'-AAUUUCAGAAGACUACAGUAUAGUAAA-5' | (SEQ ID NO: 111) |
| LDHA-1294 Target: | 5'-TTAAAGTCTTCTGATGTCATATCATTT-3' | (SEQ ID NO: 183) |
| | 5'-CAUGUUGUCCUUUUUAUCUGAUCUG-3' | (SEQ ID NO: 256) |
| | 3'-ACGUACAACAGGAAAAAUAGACUAGAC-5' | (SEQ ID NO: 112) |
| LDHA-1359 Target: | 5'-TGCATGTTGTCCTTTTTATCTGATCTG-3' | (SEQ ID NO: 184) |
| | 5'-AUGUUGUCCUUUUUAUCUGAUCUGU-3' | (SEQ ID NO: 257) |
| | 3'-CGUACAACAGGAAAAAUAGACUAGACA-5' | (SEQ ID NO: 113) |
| LDHA-1360 Target: | 5'-GCATGTTGTCCTTTTTATCTGATCTGT-3' | (SEQ ID NO: 185) |
| | 5'-UGUUGUCCUUUUUAUCUGAUCUGUG-3' | (SEQ ID NO: 258) |
| | 3'-GUACAACAGGAAAAAUAGACUAGACAC-5' | (SEQ ID NO: 114) |
| LDHA-1361 Target: | 5'-CATGTTGTCCTTTTTATCTGATCTGTG-3' | (SEQ ID NO: 186) |
| | 5'-GUUGUCCUUUUUAUCUGAUCUGUGA-3' | (SEQ ID NO: 259) |
| | 3'-UACAACAGGAAAAAUAGACUAGACACU-5' | (SEQ ID NO: 115) |
| LDHA-1362 Target: | 5'-ATGTTGTCCTTTTTATCTGATCTGTGA-3' | (SEQ ID NO: 187) |
| | 5'-UUGUCCUUUUUAUCUGAUCUGUGAU-3' | (SEQ ID NO: 260) |
| | 3'-ACAACAGGAAAAAUAGACUAGACACUA-5' | (SEQ ID NO: 116) |
| LDHA-1363 Target: | 5'-TGTTGTCCTTTTTATCTGATCTGTGAT-3' | (SEQ ID NO: 188) |

TABLE 3-continued

Selected Human Anti-Lactate Dehydrogenase DsiRNAs, Unmodified Duplexes (Asymmetrics)

| | | |
|---|---|---|
| | 5'-GUCCUUUUAUCUGAUCUGUGAUUA-3' | (SEQ ID NO: 261) |
| | 3'-AACAGGAAAAAUAGACUAGACACUAAU-5' | (SEQ ID NO: 117) |
| LDHA-1365 Target: | 5'-TTGTCCTTTTTATCTGATCTGTGATTA-3' | (SEQ ID NO: 189) |
| | 5'-UCCUUUUUAUCUGAUCUGUGAUUAA-3' | (SEQ ID NO: 262) |
| | 3'-ACAGGAAAAAUAGACUAGACACUAAUU-5' | (SEQ ID NO: 118) |
| LDHA-1366 Target: | 5'-TGTCCTTTTTATCTGATCTGTGATTAA-3' | (SEQ ID NO: 190) |
| | 5'-CCUUUUUAUCUGAUCUGUGAUUAAA-3' | (SEQ ID NO: 263) |
| | 3'-CAGGAAAAAUAGACUAGACACUAAUUU-5' | (SEQ ID NO: 119) |
| LDHA-1367 Target: | 5'-GTCCTTTTTATCTGATCTGTGATTAAA-3' | (SEQ ID NO: 191) |
| | 5'-CUUUUUAUCUGAUCUGUGAUUAAAG-3' | (SEQ ID NO: 264) |
| | 3'-AGGAAAAAUAGACUAGACACUAAUUUC-5' | (SEQ ID NO: 120) |
| LDHA-1368 Target: | 5'-TCCTTTTTATCTGATCTGTGATTAAAG-3' | (SEQ ID NO: 192) |
| | 5'-UUUUAUCUGAUCUGUGAUUAAAGCA-3' | (SEQ ID NO: 265) |
| | 3'-GAAAAAUAGACUAGACACUAAUUUCGU-5' | (SEQ ID NO: 121) |
| LDHA-1370 Target: | 5'-CTTTTTATCTGATCTGTGATTAAAGCA-3' | (SEQ ID NO: 193) |
| | 5'-UUUAUCUGAUCUGUGAUUAAAGCAG-3' | (SEQ ID NO: 266) |
| | 3'-AAAAAUAGACUAGACACUAAUUUCGUC-5' | (SEQ ID NO: 122) |
| LDHA-1371 Target: | 5'-TTTTTATCTGATCTGTGATTAAAGCAG-3' | (SEQ ID NO: 194) |
| | 5'-UUAUCUGAUCUGUGAUUAAAGCAGU-3' | (SEQ ID NO: 267) |
| | 3'-AAAAUAGACUAGACACUAAUUUCGUCA-5' | (SEQ ID NO: 123) |
| LDHA-1372 Target: | 5'-TTTTATCTGATCTGTGATTAAAGCAGT-3' | (SEQ ID NO: 195) |
| | 5'-CAGUAAUAUUUUAAGAUGGACUGGG-3' | (SEQ ID NO: 268) |
| | 3'-UCGUCAUUAUAAAAUUCUACCUGACCC-5' | (SEQ ID NO: 124) |
| LDHA-1393 Target: | 5'-AGCAGTAATATTTTAAGATGGACTGGG-3' | (SEQ ID NO: 196) |
| | 5'-AACUCCUGAAGUUAGAAAUAAGAAU-3' | (SEQ ID NO: 269) |
| | 3'-AGUUGAGGACUUCAAUCUUUAUUCUUA-5' | (SEQ ID NO: 125) |
| LDHA-1427 Target: | 5'-TCAACTCCTGAAGTTAGAAATAAGAAT-3' | (SEQ ID NO: 197) |
| | 5'-ACUCCUGAAGUUAGAAAUAAGAAUG-3' | (SEQ ID NO: 270) |
| | 3'-GUUGAGGACUUCAAUCUUUAUUCUUAC-5' | (SEQ ID NO: 126) |
| LDHA-1428 Target: | 5'-CAACTCCTGAAGTTAGAAATAAGAATG-3' | (SEQ ID NO: 198) |
| | 5'-AACUGGUUAGUGUGAAAUAGUUCUG-3' | (SEQ ID NO: 271) |
| | 3'-AGUUGACCAAUCACACUUUAUCAAGAC-5' | (SEQ ID NO: 127) |
| LDHA-1512 Target: | 5'-TCAACTGGTTAGTGTGAAATAGTTCTG-3' | (SEQ ID NO: 199) |
| | 5'-ACUGGUUAGUGUGAAAUAGUUCUGC-3' | (SEQ ID NO: 272) |
| | 3'-GUUGACCAAUCACACUUUAUCAAGACG-5' | (SEQ ID NO: 128) |
| LDHA-1513 Target: | 5'-CAACTGGTTAGTGTGAAATAGTTCTGC-3' | (SEQ ID NO: 200) |
| | 5'-CUGGUUAGUGUGAAAUAGUUCUGCC-3' | (SEQ ID NO: 273) |
| | 3'-UUGACCAAUCACACUUUAUCAAGACGG-5' | (SEQ ID NO: 129) |
| LDHA-1514 Target: | 5'-AACTGGTTAGTGTGAAATAGTTCTGCC-3' | (SEQ ID NO: 201) |
| | 5'-GGUUAGUGUGAAAUAGUUCUGCCAC-3' | (SEQ ID NO: 274) |
| | 3'-GACCAAUCACACUUUAUCAAGACGGUG-5' | (SEQ ID NO: 130) |
| LDHA-1516 Target: | 5'-CTGGTTAGTGTGAAATAGTTCTGCCAC-3' | (SEQ ID NO: 202) |
| | 5'-AUCCAGUGUAUAAAUCCAAUAUCAU-3' | (SEQ ID NO: 275) |
| | 3'-CCUAGGUCACAUAUUUAGGUUAUAGUA-5' | (SEQ ID NO: 131) |
| LDHA-1684 Target: | 5'-GGATCCAGTGTATAAATCCAATATCAT-3' | (SEQ ID NO: 203) |
| | 5'-AGUGUAUAAAUCCAAUAUCAUGUCU-3' | (SEQ ID NO: 276) |
| | 3'-GGUCACAUAUUUAGGUUAUAGUACAGA-5' | (SEQ ID NO: 132) |
| LDHA-1688 Target: | 5'-CCAGTGTATAAATCCAATATCATGTCT-3' | (SEQ ID NO: 204) |
| | 5'-CUUAUUUUGUGAACUAUAUCAGUAG-3' | (SEQ ID NO: 277) |
| | 3'-UAGAAUAAAACACUUGAUAUAGUCAUC-5' | (SEQ ID NO: 133) |
| LDHA-1736 Target: | 5'-ATCTTATTTTGTGAACTATATCAGTAG-3' | (SEQ ID NO: 205) |
| | 5'-UAUAUCAGUAGUGUACAUUACCAUA-3' | (SEQ ID NO: 278) |
| | 3'-UGAUAUAGUCAUCACAUGUAAUGGUAU-5' | (SEQ ID NO: 134) |
| LDHA-1750 Target: | 5'-ACTATATCAGTAGTGTACATTACCATA-3' | (SEQ ID NO: 206) |
| | 5'-AUCAGUAGUGUACAUUACCAUAUAA-3' | (SEQ ID NO: 279) |
| | 3'-UAUAGUCAUCACAUGUAAUGGUAUAUU-5' | (SEQ ID NO: 135) |
| LDHA-1753 Target: | 5'-ATATCAGTAGTGTACATTACCATATAA-3' | (SEQ ID NO: 207) |

TABLE 3-continued

Selected Human Anti-Lactate Dehydrogenase DsiRNAs, Unmodified Duplexes (Asymmetrics)

|  |  |  |
|---|---|---|
| LDHA-1754 Target: | 5'-UCAGUAGUGUACAUUACCAUAUAAU-3'<br>3'-AUAGUCAUCACAUGUAAUGGUAUAUUA-5'<br>5'-TATCAGTAGTGTACATTACCATATAAT-3' | (SEQ ID NO: 280)<br>(SEQ ID NO: 136)<br>(SEQ ID NO: 208) |
| LDHA-1805 Target: | 5'-CAACCAACUAUCCAAGUGUUAUACC-3'<br>3'-ACGUUGGUUGAUAGGUUCACAAUAUGG-5'<br>5'-TGCAACCAACTATCCAAGTGTTATACC-3' | (SEQ ID NO: 281)<br>(SEQ ID NO: 137)<br>(SEQ ID NO: 209) |
| LDHA-1806 Target: | 5'-AACCAACUAUCCAAGUGUUAUACCA-3'<br>3'-CGUUGGUUGAUAGGUUCACAAUAUGGU-5'<br>5'-GCAACCAACTATCCAAGTGTTATACCA-3' | (SEQ ID NO: 282)<br>(SEQ ID NO: 138)<br>(SEQ ID NO: 210) |
| LDHA-1807 Target: | 5'-ACCAACUAUCCAAGUGUUAUACCAA-3'<br>3'-GUUGGUUGAUAGGUUCACAAUAUGGUU-5'<br>5'-CAACCAACTATCCAAGTGTTATACCAA-3' | (SEQ ID NO: 283)<br>(SEQ ID NO: 139)<br>(SEQ ID NO: 211) |
| LDHA-1808 Target: | 5'-CCAACUAUCCAAGUGUUAUACCAAC-3'<br>3'-UUGGUUGAUAGGUUCACAAUAUGGUUG-5'<br>5'-AACCAACTATCCAAGTGTTATACCAAC-3' | (SEQ ID NO: 284)<br>(SEQ ID NO: 140)<br>(SEQ ID NO: 212) |
| LDHA-1811 Target: | 5'-ACUAUCCAAGUGUUAUACCAACUAA-3'<br>3'-GUUGAUAGGUUCACAAUAUGGUUGAUU-5'<br>5'-CAACTATCCAAGTGTTATACCAACTAA-3' | (SEQ ID NO: 285)<br>(SEQ ID NO: 141)<br>(SEQ ID NO: 213) |
| LDHA-1812 Target: | 5'-CUAUCCAAGUGUUAUACCAACUAAA-3'<br>3'-UUGAUAGGUUCACAAUAUGGUUGAUUU-5'<br>5'-AACTATCCAAGTGTTATACCAACTAAA-3' | (SEQ ID NO: 286)<br>(SEQ ID NO: 142)<br>(SEQ ID NO: 214) |
| LDHA-1815 Target: | 5'-UCCAAGUGUUAUACCAACUAAAACC-3'<br>3'-AUAGGUUCACAAUAUGGUUGAUUUUGG-5'<br>5'-TATCCAAGTGTTATACCAACTAAAACC-3' | (SEQ ID NO: 287)<br>(SEQ ID NO: 143)<br>(SEQ ID NO: 215) |
| LDHA-1816 Target: | 5'-CCAAGUGUUAUACCAACUAAAACCC-3'<br>3'-UAGGUUCACAAUAUGGUUGAUUUUGGG-5'<br>5'-ATCCAAGTGTTATACCAACTAAAACCC-3' | (SEQ ID NO: 288)<br>(SEQ ID NO: 144)<br>(SEQ ID NO: 216) |

TABLE 4

DsiRNA Target Sequences (21mers) in Human Lactate Dehydrogenase mRNA

| | | |
|---|---|---|
| LDHA-355 21 nt Target: | 5'-CCAGAAUAAGAUUACAGUUGU-3' | (SEQ ID NO: 289) |
| LDHA-356 21 nt Target: | 5'-CAGAAUAAGAUUACAGUUGUU-3' | (SEQ ID NO: 290) |
| LDHA-360 21 nt Target: | 5'-AUAAGAUUACAGUUGUUGGGG-3' | (SEQ ID NO: 291) |
| LDHA-361 21 nt Target: | 5'-UAAGAUUACAGUUGUUGGGGU-3' | (SEQ ID NO: 292) |
| LDHA-362 21 nt Target: | 5'-AAGAUUACAGUUGUUGGGGUU-3' | (SEQ ID NO: 293) |
| LDHA-363 21 nt Target: | 5'-AGAUUACAGUUGUUGGGGUUG-3' | (SEQ ID NO: 294) |
| LDHA-364 21 nt Target: | 5'-GAUUACAGUUGUUGGGGUUGG-3' | (SEQ ID NO: 295) |
| LDHA-365 21 nt Target: | 5'-AUUACAGUUGUUGGGGUUGGU-3' | (SEQ ID NO: 296) |
| LDHA-366 21 nt Target: | 5'-UUACAGUUGUUGGGGUUGGUG-3' | (SEQ ID NO: 297) |
| LDHA-367 21 nt Target: | 5'-UACAGUUGUUGGGGUUGGUGC-3' | (SEQ ID NO: 298) |
| LDHA-369 21 nt Target: | 5'-CAGUUGUUGGGGUUGGUGCUG-3' | (SEQ ID NO: 299) |
| LDHA-370 21 nt Target: | 5'-AGUUGUUGGGGUUGGUGCUGU-3' | (SEQ ID NO: 300) |
| LDHA-397 21 nt Target: | 5'-GGCCUGUGCCAUCAGUAUCUU-3' | (SEQ ID NO: 301) |
| LDHA-398 21 nt Target: | 5'-GCCUGUGCCAUCAGUAUCUUA-3' | (SEQ ID NO: 302) |
| LDHA-399 21 nt Target: | 5'-CCUGUGCCAUCAGUAUCUUAA-3' | (SEQ ID NO: 303) |
| LDHA-400 21 nt Target: | 5'-CUGUGCCAUCAGUAUCUUAAU-3' | (SEQ ID NO: 304) |
| LDHA-401 21 nt Target: | 5'-UGUGCCAUCAGUAUCUUAAUG-3' | (SEQ ID NO: 305) |

TABLE 4-continued

DsiRNA Target Sequences (21mers) in Human Lactate Dehydrogenase mRNA

| | | |
|---|---|---|
| LDHA-402 21 nt Target: | 5'-GUGCCAUCAGUAUCUUAAUGA-3' | (SEQ ID NO: 306) |
| LDHA-403 21 nt Target: | 5'-UGCCAUCAGUAUCUUAAUGAA-3' | (SEQ ID NO: 307) |
| LDHA-404 21 nt Target: | 5'-GCCAUCAGUAUCUUAAUGAAG-3' | (SEQ ID NO: 308) |
| LDHA-714 21 nt Target: | 5'-CAGUGGAUAUCUUGACCUACG-3' | (SEQ ID NO: 309) |
| LDHA-717 21 nt Target: | 5'-UGGAUAUCUUGACCUACGUGG-3' | (SEQ ID NO: 310) |
| LDHA-718 21 nt Target: | 5'-GGAUAUCUUGACCUACGUGGC-3' | (SEQ ID NO: 311) |
| LDHA-719 21 nt Target: | 5'-GAUAUCUUGACCUACGUGGCU-3' | (SEQ ID NO: 312) |
| LDHA-720 21 nt Target: | 5'-AUAUCUUGACCUACGUGGCUU-3' | (SEQ ID NO: 313) |
| LDHA-722 21 nt Target: | 5'-AUCUUGACCUACGUGGCUUGG-3' | (SEQ ID NO: 314) |
| LDHA-723 21 nt Target: | 5'-UCUUGACCUACGUGGCUUGGA-3' | (SEQ ID NO: 315) |
| LDHA-724 21 nt Target: | 5'-CUUGACCUACGUGGCUUGGAA-3' | (SEQ ID NO: 316) |
| LDHA-739 21 nt Target: | 5'-UUGGAAGAUAAGUGGUUUUCC-3' | (SEQ ID NO: 317) |
| LDHA-740 21 nt Target: | 5'-UGGAAGAUAAGUGGUUUUCCC-3' | (SEQ ID NO: 318) |
| LDHA-891 21 nt Target: | 5'-UGCCUGUAUGGAGUGGAAUGA-3' | (SEQ ID NO: 319) |
| LDHA-892 21 nt Target: | 5'-GCCUGUAUGGAGUGGAAUGAA-3' | (SEQ ID NO: 320) |
| LDHA-907 21 nt Target: | 5'-AAUGAAUGUUGCUGGUGUCUC-3' | (SEQ ID NO: 321) |
| LDHA-952 21 nt Target: | 5'-AGGGACUGAUAAAGAUAAGGA-3' | (SEQ ID NO: 322) |
| LDHA-1286 21 nt Target: | 5'-CUGCAAUUUUAAAGUCUUCUG-3' | (SEQ ID NO: 323) |
| LDHA-1287 21 nt Target: | 5'-UGCAAUUUUAAAGUCUUCUGA-3' | (SEQ ID NO: 324) |
| LDHA-1292 21 nt Target: | 5'-UUUUAAAGUCUUCUGAUGUCA-3' | (SEQ ID NO: 325) |
| LDHA-1293 21 nt Target: | 5'-UUUAAAGUCUUCUGAUGUCAU-3' | (SEQ ID NO: 326) |
| LDHA-1294 21 nt Target: | 5'-UUAAAGUCUUCUGAUGUCAUA-3' | (SEQ ID NO: 327) |
| LDHA-1359 21 nt Target: | 5'-UGCAUGUUGUCCUUUUUAUCU-3' | (SEQ ID NO: 328) |
| LDHA-1360 21 nt Target: | 5'-GCAUGUUGUCCUUUUUAUCUG-3' | (SEQ ID NO: 329) |
| LDHA-1361 21 nt Target: | 5'-CAUGUUGUCCUUUUUAUCUGA-3' | (SEQ ID NO: 330) |
| LDHA-1362 21 nt Target: | 5'-AUGUUGUCCUUUUUAUCUGAU-3' | (SEQ ID NO: 331) |
| LDHA-1363 21 nt Target: | 5'-UGUUGUCCUUUUUAUCUGAUC-3' | (SEQ ID NO: 332) |
| LDHA-1365 21 nt Target: | 5'-UUGUCCUUUUUAUCUGAUCUG-3' | (SEQ ID NO: 333) |
| LDHA-1366 21 nt Target: | 5'-UGUCCUUUUUAUCUGAUCUGU-3' | (SEQ ID NO: 334) |
| LDHA-1367 21 nt Target: | 5'-GUCCUUUUUAUCUGAUCUGUG-3' | (SEQ ID NO: 335) |
| LDHA-1368 21 nt Target: | 5'-UCCUUUUUAUCUGAUCUGUGA-3' | (SEQ ID NO: 336) |
| LDHA-1370 21 nt Target: | 5'-CUUUUUAUCUGAUCUGUGAUU-3' | (SEQ ID NO: 337) |
| LDHA-1371 21 nt Target: | 5'-UUUUUAUCUGAUCUGUGAUUA-3' | (SEQ ID NO: 338) |
| LDHA-1372 21 nt Target: | 5'-UUUUAUCUGAUCUGUGAUUAA-3' | (SEQ ID NO: 339) |
| LDHA-1393 21 nt Target: | 5'-AGCAGUAAUAUUUUAAGAUGG-3' | (SEQ ID NO: 340) |
| LDHA-1427 21 nt Target: | 5'-UCAACUCCUGAAGUUAGAAAU-3' | (SEQ ID NO: 341) |
| LDHA-1428 21 nt Target: | 5'-CAACUCCUGAAGUUAGAAAUA-3' | (SEQ ID NO: 342) |
| LDHA-1512 21 nt Target: | 5'-UCAACUGGUUAGUGUGAAAUA-3' | (SEQ ID NO: 343) |
| LDHA-1513 21 nt Target: | 5'-CAACUGGUUAGUGUGAAAUAG-3' | (SEQ ID NO: 344) |

TABLE 4-continued

| DsiRNA Target Sequences (21mers) in Human Lactate Dehydrogenase mRNA | | |
|---|---|---|
| LDHA-1514 21 nt Target: | 5'-AACUGGUUAGUGUGAAAUAGU-3' | (SEQ ID NO: 345) |
| LDHA-1516 21 nt Target: | 5'-CUGGUUAGUGUGAAAUAGUUC-3' | (SEQ ID NO: 346) |
| LDHA-1684 21 nt Target: | 5'-GGAUCCAGUGUAUAAAUCCAA-3' | (SEQ ID NO: 347) |
| LDHA-1688 21 nt Target: | 5'-CCAGUGUAUAAAUCCAAUAUC-3' | (SEQ ID NO: 348) |
| LDHA-1736 21 nt Target: | 5'-AUCUUAUUUGUGAACUAUAU-3' | (SEQ ID NO: 349) |
| LDHA-1750 21 nt Target: | 5'-ACUAUAUCAGUAGUGUACAUU-3' | (SEQ ID NO: 350) |
| LDHA-1753 21 nt Target: | 5'-AUAUCAGUAGUGUACAUUACC-3' | (SEQ ID NO: 351) |
| LDHA-1754 21 nt Target: | 5'-UAUCAGUAGUGUACAUUACCA-3' | (SEQ ID NO: 352) |
| LDHA-1805 21 nt Target: | 5'-UGCAACCAACUAUCCAAGUGU-3' | (SEQ ID NO: 353) |
| LDHA-1806 21 nt Target: | 5'-GCAACCAACUAUCCAAGUGUU-3' | (SEQ ID NO: 354) |
| LDHA-1807 21 nt Target: | 5'-CAACCAACUAUCCAAGUGUUA-3' | (SEQ ID NO: 355) |
| LDHA-1808 21 nt Target: | 5'-AACCAACUAUCCAAGUGUUAU-3' | (SEQ ID NO: 356) |
| LDHA-1811 21 nt Target: | 5'-CAACUAUCCAAGUGUUAUACC-3' | (SEQ ID NO: 357) |
| LDHA-1812 21 nt Target: | 5'-AACUAUCCAAGUGUUAUACCA-3' | (SEQ ID NO: 358) |
| LDHA-1815 21 nt Target: | 5'-UAUCCAAGUGUUAUACCAACU-3' | (SEQ ID NO: 359) |
| LDHA-1816 21 nt Target: | 5'-AUCCAAGUGUUAUACCAACUA-3' | (SEQ ID NO: 360) |

TABLE 5

| Selected Human Anti-Lactate Dehydrogenase "Blunt/Blunt" DsiRNAs | | |
|---|---|---|
| | 5'-CCAGAAUAAGAUUACAGUUGUUGGGGU-3' | (SEQ ID NO: 361) |
| | 3'-GGUCUUAUUCUAAUGUCAACAACCCCA-5' | (SEQ ID NO: 73) |
| LDHA-355 Target: | 5'-CCAGAATAAGATTACAGTTGTTGGGGT-3' | (SEQ ID NO: 145) |
| | 5'-CAGAAUAAGAUUACAGUUGUUGGGGUU-3' | (SEQ ID NO: 362) |
| | 3'-GUCUUAUUCUAAUGUCAACAACCCCAA-5' | (SEQ ID NO: 74) |
| LDHA-356 Target: | 5'-CAGAATAAGATTACAGTTGTTGGGGTT-3' | (SEQ ID NO: 146) |
| | 5'-AUAAGAUUACAGUUGUUGGGGUUGGUG-3' | (SEQ ID NO: 363) |
| | 3'-UAUUCUAAUGUCAACAACCCCAACCAC-5' | (SEQ ID NO: 75) |
| LDHA-360 Target: | 5'-ATAAGATTACAGTTGTTGGGGTTGGTG-3' | (SEQ ID NO: 147) |
| | 5'-UAAGAUUACAGUUGUUGGGGUUGGUGC-3' | (SEQ ID NO: 364) |
| | 3'-AUUCUAAUGUCAACAACCCCAACCACG-5' | (SEQ ID NO: 76) |
| LDHA-361 Target: | 5'-TAAGATTACAGTTGTTGGGGTTGGTGC-3' | (SEQ ID NO: 148) |
| | 5'-AAGAUUACAGUUGUUGGGGUUGGUGCU-3' | (SEQ ID NO: 365) |
| | 3'-UUCUAAUGUCAACAACCCCAACCACGA-5' | (SEQ ID NO: 77) |
| LDHA-362 Target: | 5'-AAGATTACAGTTGTTGGGGTTGGTGCT-3' | (SEQ ID NO: 149) |
| | 5'-AGAUUACAGUUGUUGGGGUUGGUGCUG-3' | (SEQ ID NO: 366) |
| | 3'-UCUAAUGUCAACAACCCCAACCACGAC-5' | (SEQ ID NO: 78) |
| LDHA-363 Target: | 5'-AGATTACAGTTGTTGGGGTTGGTGCTG-3' | (SEQ ID NO: 150) |
| | 5'-GAUUACAGUUGUUGGGGUUGGUGCUGU-3' | (SEQ ID NO: 367) |
| | 3'-CUAAUGUCAACAACCCCAACCACGACA-5' | (SEQ ID NO: 79) |
| LDHA-364 Target: | 5'-GATTACAGTTGTTGGGGTTGGTGCTGT-3' | (SEQ ID NO: 151) |
| | 5'-AUUACAGUUGUUGGGGUUGGUGCUGUU-3' | (SEQ ID NO: 368) |
| | 3'-UAAUGUCAACAACCCCAACCACGACAA-5' | (SEQ ID NO: 80) |
| LDHA-365 Target: | 5'-ATTACAGTTGTTGGGGTTGGTGCTGTT-3' | (SEQ ID NO: 152) |
| | 5'-UUACAGUUGUUGGGGUUGGUGCUGUUG-3' | (SEQ ID NO: 369) |
| | 3'-AAUGUCAACAACCCCAACCACGACAAC-5' | (SEQ ID NO: 81) |
| LDHA-366 Target: | 5'-TTACAGTTGTTGGGGTTGGTGCTGTTG-3' | (SEQ ID NO: 153) |
| | 5'-UACAGUUGUUGGGGUUGGUGCUGUUGG-3' | (SEQ ID NO: 370) |
| | 3'-AUGUCAACAACCCCAACCACGACAACC-5' | (SEQ ID NO: 82) |
| LDHA-367 Target: | 5'-TACAGTTGTTGGGGTTGGTGCTGTTGG-3' | (SEQ ID NO: 154) |

TABLE 5-continued

Selected Human Anti-Lactate Dehydrogenase "Blunt/Blunt" DsiRNAs

|  | | |
|---|---|---|
| | 5'-CAGUUGUUGGGGUUGGUGCUGUUGGCA-3' | (SEQ ID NO: 371) |
| | 3'-GUCAACAACCCCAACCACGACAACCGU-5' | (SEQ ID NO: 83) |
| LDHA-369 Target: | 5'-CAGTTGTTGGGGTTGGTGCTGTTGGCA-3' | (SEQ ID NO: 155) |
| | 5'-AGUUGUUGGGGUUGGUGCUGUUGGCAU-3' | (SEQ ID NO: 372) |
| | 3'-UCAACAACCCCAACCACGACAACCGUA-5' | (SEQ ID NO: 84) |
| LDHA-370 Target: | 5'-AGTTGTTGGGGTTGGTGCTGTTGGCAT-3' | (SEQ ID NO: 156) |
| | 5'-GGCCUGUGCCAUCAGUAUCUUAAUGAA-3' | (SEQ ID NO: 373) |
| | 3'-CCGGACACGGUAGUCAUAGAAUUACUU-5' | (SEQ ID NO: 85) |
| LDHA-397 Target: | 5'-GGCCTGTGCCATCAGTATCTTAATGAA-3' | (SEQ ID NO: 157) |
| | 5'-GCCUGUGCCAUCAGUAUCUUAAUGAAG-3' | (SEQ ID NO: 374) |
| | 3'-CGGACACGGUAGUCAUAGAAUUACUUC-5' | (SEQ ID NO: 86) |
| LDHA-398 Target: | 5'-GCCTGTGCCATCAGTATCTTAATGAAG-3' | (SEQ ID NO: 158) |
| | 5'-CCUGUGCCAUCAGUAUCUUAAUGAAGG-3' | (SEQ ID NO: 375) |
| | 3'-GGACACGGUAGUCAUAGAAUUACUUCC-5' | (SEQ ID NO: 87) |
| LDHA-399 Target: | 5'-CCTGTGCCATCAGTATCTTAATGAAGG-3' | (SEQ ID NO: 159) |
| | 5'-CUGUGCCAUCAGUAUCUUAAUGAAGGA-3' | (SEQ ID NO: 376) |
| | 3'-GACACGGUAGUCAUAGAAUUACUUCCU-5' | (SEQ ID NO: 88) |
| LDHA-400 Target: | 5'-CTGTGCCATCAGTATCTTAATGAAGGA-3' | (SEQ ID NO: 160) |
| | 5'-UGUGCCAUCAGUAUCUUAAUGAAGGAC-3' | (SEQ ID NO: 377) |
| | 3'-ACACGGUAGUCAUAGAAUUACUUCCUG-5' | (SEQ ID NO: 89) |
| LDHA-401 Target: | 5'-TGTGCCATCAGTATCTTAATGAAGGAC-3' | (SEQ ID NO: 161) |
| | 5'-GUGCCAUCAGUAUCUUAAUGAAGGACU-3' | (SEQ ID NO: 378) |
| | 3'-CACGGUAGUCAUAGAAUUACUUCCUGA-5' | (SEQ ID NO: 90) |
| LDHA-402 Target: | 5'-GTGCCATCAGTATCTTAATGAAGGACT-3' | (SEQ ID NO: 162) |
| | 5'-UGCCAUCAGUAUCUUAAUGAAGGACUU-3' | (SEQ ID NO: 379) |
| | 3'-ACGGUAGUCAUAGAAUUACUUCCUGAA-5' | (SEQ ID NO: 91) |
| LDHA-403 Target: | 5'-TGCCATCAGTATCTTAATGAAGGACTT-3' | (SEQ ID NO: 163) |
| | 5'-GCCAUCAGUAUCUUAAUGAAGGACUUG-3' | (SEQ ID NO: 380) |
| | 3'-CGGUAGUCAUAGAAUUACUUCCUGAAC-5' | (SEQ ID NO: 92) |
| LDHA-404 Target: | 5'-GCCATCAGTATCTTAATGAAGGACTTG-3' | (SEQ ID NO: 164) |
| | 5'-CAGUGGAUAUCUUGACCUACGUGGCUU-3' | (SEQ ID NO: 381) |
| | 3'-GUCACCUAUAGAACUGGAUGCACCGAA-5' | (SEQ ID NO: 93) |
| LDHA-714 Target: | 5'-CAGTGGATATCTTGACCTACGTGGCTT-3' | (SEQ ID NO: 165) |
| | 5'-UGGAUAUCUUGACCUACGUGGCUUGGA-3' | (SEQ ID NO: 382) |
| | 3'-ACCUAUAGAACUGGAUGCACCGAACCU-5' | (SEQ ID NO: 94) |
| LDHA-717 Target: | 5'-TGGATATCTTGACCTACGTGGCTTGGA-3' | (SEQ ID NO: 166) |
| | 5'-GGAUAUCUUGACCUACGUGGCUUGGAA-3' | (SEQ ID NO: 383) |
| | 3'-CCUAUAGAACUGGAUGCACCGAACCUU-5' | (SEQ ID NO: 95) |
| LDHA-718 Target: | 5'-GGATATCTTGACCTACGTGGCTTGGAA-3' | (SEQ ID NO: 167) |
| | 5'-GAUAUCUUGACCUACGUGGCUUGGAAG-3' | (SEQ ID NO: 384) |
| | 3'-CUAUAGAACUGGAUGCACCGAACCUUC-5' | (SEQ ID NO: 96) |
| LDHA-719 Target: | 5'-GATATCTTGACCTACGTGGCTTGGAAG-3' | (SEQ ID NO: 168) |
| | 5'-AUAUCUUGACCUACGUGGCUUGGAAGA-3' | (SEQ ID NO: 385) |
| | 3'-UAUAGAACUGGAUGCACCGAACCUUCU-5' | (SEQ ID NO: 97) |
| LDHA-720 Target: | 5'-ATATCTTGACCTACGTGGCTTGGAAGA-3' | (SEQ ID NO: 169) |
| | 5'-AUCUUGACCUACGUGGCUUGGAAGAUA-3' | (SEQ ID NO: 386) |
| | 3'-UAGAACUGGAUGCACCGAACCUUCUAU-5' | (SEQ ID NO: 98) |
| LDHA-722 Target: | 5'-ATCTTGACCTACGTGGCTTGGAAGATA-3' | (SEQ ID NO: 170) |
| | 5'-UCUUGACCUACGUGGCUUGGAAGAUAA-3' | (SEQ ID NO: 387) |
| | 3'-AGAACUGGAUGCACCGAACCUUCUAUU-5' | (SEQ ID NO: 99) |
| LDHA-723 Target: | 5'-TCTTGACCTACGTGGCTTGGAAGATAA-3' | (SEQ ID NO: 171) |
| | 5'-CUUGACCUACGUGGCUUGGAAGAUAAG-3' | (SEQ ID NO: 388) |
| | 3'-GAACUGGAUGCACCGAACCUUCUAUUC-5' | (SEQ ID NO: 100) |
| LDHA-724 Target: | 5'-CTTGACCTACGTGGCTTGGAAGATAAG-3' | (SEQ ID NO: 172) |
| | 5'-UUGGAAGAUAAGUGGUUUUCCCAAAAA-3' | (SEQ ID NO: 389) |
| | 3'-AACCUUCUAUUCACCAAAAGGGUUUUU-5' | (SEQ ID NO: 101) |
| LDHA-739 Target: | 5'-TTGGAAGATAAGTGGTTTTCCCAAAAA-3' | (SEQ ID NO: 173) |

TABLE 5-continued

Selected Human Anti-Lactate Dehydrogenase "Blunt/Blunt" DsiRNAs

|  |  |  |
|---|---|---|
| LDHA-740 Target: | 5'-UGGAAGAUAAGUGGUUUUCCCAAAAAC-3'<br>3'-ACCUUCUAUUCACCAAAAGGGUUUUUG-5'<br>5'-TGGAAGATAAGTGGTTTTCCCAAAAAC-3' | (SEQ ID NO: 390)<br>(SEQ ID NO: 102)<br>(SEQ ID NO: 174) |
| LDHA-891 Target: | 5'-UGCCUGUAUGGAGUGGAAUGAAUGUUG-3'<br>3'-ACGGACAUACCUCACCUUACUUACAAC-5'<br>5'-TGCCTGTATGGAGTGGAATGAATGTTG-3' | (SEQ ID NO: 391)<br>(SEQ ID NO: 103)<br>(SEQ ID NO: 175) |
| LDHA-892 Target: | 5'-GCCUGUAUGGAGUGGAAUGAAUGUUGC-3'<br>3'-CGGACAUACCUCACCUUACUUACAACG-5'<br>5'-GCCTGTATGGAGTGGAATGAATGTTGC-3' | (SEQ ID NO: 392)<br>(SEQ ID NO: 104)<br>(SEQ ID NO: 176) |
| LDHA-907 Target: | 5'-AAUGAAUGUUGCUGGUGUCUCUCUGAA-3'<br>3'-UUACUUACAACGACCACAGAGAGACUU-5'<br>5'-AATGAATGTTGCTGGTGTCTCTCTGAA-3' | (SEQ ID NO: 393)<br>(SEQ ID NO: 105)<br>(SEQ ID NO: 177) |
| LDHA-952 Target: | 5'-AGGGACUGAUAAAGAUAAGGAACAGUG-3'<br>3'-UCCCUGACUAUUUCUAUUCCUUGUCAC-5'<br>5'-AGGGACTGATAAAGATAAGGAACAGTG-3' | (SEQ ID NO: 394)<br>(SEQ ID NO: 106)<br>(SEQ ID NO: 178) |
| LDHA-1286 Target: | 5'-CUGCAAUUUUAAAGUCUUCUGAUGUCA-3'<br>3'-GACGUUAAAAUUUCAGAAGACUACAGU-5'<br>5'-CTGCAATTTTAAAGTCTTCTGATGTCA-3' | (SEQ ID NO: 395)<br>(SEQ ID NO: 107)<br>(SEQ ID NO: 179) |
| LDHA-1287 Target: | 5'-UGCAAUUUUAAAGUCUUCUGAUGUCAU-3'<br>3'-ACGUUAAAAUUUCAGAAGACUACAGUA-5'<br>5'-TGCAATTTTAAAGTCTTCTGATGTCAT-3' | (SEQ ID NO: 396)<br>(SEQ ID NO: 108)<br>(SEQ ID NO: 180) |
| LDHA-1292 Target: | 5'-UUUUAAAGUCUUCUGAUGUCAUAUCAU-3'<br>3'-AAAAUUUCAGAAGACUACAGUAUAGUA-5'<br>5'-TTTTAAAGTCTTCTGATGTCATATCAT-3' | (SEQ ID NO: 397)<br>(SEQ ID NO: 109)<br>(SEQ ID NO: 181) |
| LDHA-1293 Target: | 5'-UUUAAAGUCUUCUGAUGUCAUAUCAUU-3'<br>3'-AAAUUUCAGAAGACUACAGUAUAGUAA-5'<br>5'-TTTAAAGTCTTCTGATGTCATATCATT-3' | (SEQ ID NO: 398)<br>(SEQ ID NO: 110)<br>(SEQ ID NO: 182) |
| LDHA-1294 Target: | 5'-UUAAAGUCUUCUGAUGUCAUAUCAUUU-3'<br>3'-AAUUUCAGAAGACUACAGUAUAGUAAA-5'<br>5'-TTAAAGTCTTCTGATGTCATATCATTT-3' | (SEQ ID NO: 399)<br>(SEQ ID NO: 111)<br>(SEQ ID NO: 183) |
| LDHA-1359 Target: | 5'-UGCAUGUUGUCCUUUUUAUCUGAUCUG-3'<br>3'-ACGUACAACAGGAAAAAUAGACUAGAC-5'<br>5'-TGCATGTTGTCCTTTTTATCTGATCTG-3' | (SEQ ID NO: 400)<br>(SEQ ID NO: 112)<br>(SEQ ID NO: 184) |
| LDHA-1360 Target: | 5'-GCAUGUUGUCCUUUUUAUCUGAUCUGU-3'<br>3'-CGUACAACAGGAAAAAUAGACUAGACA-5'<br>5'-GCATGTTGTCCTTTTTATCTGATCTGT-3' | (SEQ ID NO: 401)<br>(SEQ ID NO: 113)<br>(SEQ ID NO: 185) |
| LDHA-1361 Target: | 5'-CAUGUUGUCCUUUUUAUCUGAUCUGUG-3'<br>3'-GUACAACAGGAAAAAUAGACUAGACAC-5'<br>5'-CATGTTGTCCTTTTTATCTGATCTGTG-3' | (SEQ ID NO: 402)<br>(SEQ ID NO: 114)<br>(SEQ ID NO: 186) |
| LDHA-1362 Target: | 5'-AUGUUGUCCUUUUUAUCUGAUCUGUGA-3'<br>3'-UACAACAGGAAAAAUAGACUAGACACU-5'<br>5'-ATGTTGTCCTTTTTATCTGATCTGTGA-3' | (SEQ ID NO: 403)<br>(SEQ ID NO: 115)<br>(SEQ ID NO: 187) |
| LDHA-1363 Target: | 5'-UGUUGUCCUUUUUAUCUGAUCUGUGAU-3'<br>3'-ACAACAGGAAAAAUAGACUAGACACUA-5'<br>5'-TGTTGTCCTTTTTATCTGATCTGTGAT-3' | (SEQ ID NO: 404)<br>(SEQ ID NO: 116)<br>(SEQ ID NO: 188) |
| LDHA-1365 Target: | 5'-UUGUCCUUUUUAUCUGAUCUGUGAUUA-3'<br>3'-AACAGGAAAAAUAGACUAGACACUAAU-5'<br>5'-TTGTCCTTTTTATCTGATCTGTGATTA-3' | (SEQ ID NO: 405)<br>(SEQ ID NO: 117)<br>(SEQ ID NO: 189) |
| LDHA-1366 Target: | 5'-UGUCCUUUUUAUCUGAUCUGUGAUUAA-3'<br>3'-ACAGGAAAAAUAGACUAGACACUAAUU-5'<br>5'-TGTCCTTTTTATCTGATCTGTGATTAA-3' | (SEQ ID NO: 406)<br>(SEQ ID NO: 118)<br>(SEQ ID NO: 190) |
| LDHA-1367 Target: | 5'-GUCCUUUUUAUCUGAUCUGUGAUUAAA-3'<br>3'-CAGGAAAAAUAGACUAGACACUAAUUU-5'<br>5'-GTCCTTTTTATCTGATCTGTGATTAAA-3' | (SEQ ID NO: 407)<br>(SEQ ID NO: 119)<br>(SEQ ID NO: 191) |
| LDHA-1368 Target: | 5'-UCCUUUUUAUCUGAUCUGUGAUUAAAG-3'<br>3'-AGGAAAAAUAGACUAGACACUAAUUUC-5'<br>5'-TCCTTTTTATCTGATCTGTGATTAAAG-3' | (SEQ ID NO: 408)<br>(SEQ ID NO: 120)<br>(SEQ ID NO: 192) |

TABLE 5-continued

Selected Human Anti-Lactate Dehydrogenase "Blunt/Blunt" DsiRNAs

```
                 5'-CUUUUUAUCUGAUCUGUGAUUAAAGCA-3'    (SEQ ID NO: 409)
                 3'-GAAAAAUAGACUAGACACUAAUUUCGU-5'    (SEQ ID NO: 121)
LDHA-1370 Target: 5'-CTTTTTATCTGATCTGTGATTAAAGCA-3'   (SEQ ID NO: 193)

5'-UUUUUAUCUGAUCUGUGAUUAAAGCAG-3'    (SEQ ID NO: 410)
                 3'-AAAAAUAGACUAGACACUAAUUUCGUC-5'    (SEQ ID NO: 122)
LDHA-1371 Target: 5'-TTTTTATCTGATCTGTGATTAAAGCAG-3'   (SEQ ID NO: 194)

5'-UUUUAUCUGAUCUGUGAUUAAAGCAGU-3'    (SEQ ID NO: 411)
                 3'-AAAAUAGACUAGACACUAAUUUCGUCA-5'    (SEQ ID NO: 123)
LDHA-1372 Target: 5'-TTTTATCTGATCTGTGATTAAAGCAGT-3'   (SEQ ID NO: 195)

5'-AGCAGUAAUAUUUUAAGAUGGACUGGG-3'    (SEQ ID NO: 412)
                 3'-UCGUCAUUAUAAAAUUCUACCUGACCC-5'    (SEQ ID NO: 124)
LDHA-1393 Target: 5'-AGCAGTAATATTTTAAGATGGACTGGG-3'   (SEQ ID NO: 196)

5'-UCAACUCCUGAAGUUAGAAAUAAGAAU-3'    (SEQ ID NO: 413)
                 3'-AGUUGAGGACUUCAAUCUUUAUUCUUA-5'    (SEQ ID NO: 125)
LDHA-1427 Target: 5'-TCAACTCCTGAAGTTAGAAATAAGAAT-3'   (SEQ ID NO: 197)

5'-CAACUCCUGAAGUUAGAAAUAAGAAUG-3'    (SEQ ID NO: 414)
                 3'-GUUGAGGACUUCAAUCUUUAUUCUUAC-5'    (SEQ ID NO: 126)
LDHA-1428 Target: 5'-CAACTCCTGAAGTTAGAAATAAGAATG-3'   (SEQ ID NO: 198)

5'-UCAACUGGUUAGUGUGAAAUAGUUCUG-3'    (SEQ ID NO: 415)
                 3'-AGUUGACCAAUCACACUUUAUCAAGAC-5'    (SEQ ID NO: 127)
LDHA-1512 Target: 5'-TCAACTGGTTAGTGTGAAATAGTTCTG-3'   (SEQ ID NO: 199)

5'-CAACUGGUUAGUGUGAAAUAGUUCUGC-3'    (SEQ ID NO: 416)
                 3'-GUUGACCAAUCACACUUUAUCAAGACG-5'    (SEQ ID NO: 128)
LDHA-1513 Target: 5'-CAACTGGTTAGTGTGAAATAGTTCTGC-3'   (SEQ ID NO: 200)

5'-AACUGGUUAGUGUGAAAUAGUUCUGCC-3'    (SEQ ID NO: 417)
                 3'-UUGACCAAUCACACUUUAUCAAGACGG-5'    (SEQ ID NO: 129)
LDHA-1514 Target: 5'-AACTGGTTAGTGTGAAATAGTTCTGCC-3'   (SEQ ID NO: 201)

5'-CUGGUUAGUGUGAAAUAGUUCUGCCAC-3'    (SEQ ID NO: 418)
                 3'-GACCAAUCACACUUUAUCAAGACGGUG-5'    (SEQ ID NO: 130)
LDHA-1516 Target: 5'-CTGGTTAGTGTGAAATAGTTCTGCCAC-3'   (SEQ ID NO: 202)

5'-GGAUCCAGUGUAUAAAUCCAAUAUCAU-3'    (SEQ ID NO: 419)
                 3'-CCUAGGUCACAUAUUUAGGUUAUAGUA-5'    (SEQ ID NO: 131)
LDHA-1684 Target: 5'-GGATCCAGTGTATAAATCCAATATCAT-3'   (SEQ ID NO: 203)

5'-CCAGUGUAUAAAUCCAAUAUCAUGUCU-3'    (SEQ ID NO: 420)
                 3'-GGUCACAUAUUUAGGUUAUAGUACAGA-5'    (SEQ ID NO: 132)
LDHA-1688 Target: 5'-CCAGTGTATAAATCCAATATCATGTCT-3'   (SEQ ID NO: 204)

5'-AUCUUAUUUUGUGAACUAUAUCAGUAG-3'    (SEQ ID NO: 421)
                 3'-UAGAAUAAAACACUUGAUAUAGUCAUC-5'    (SEQ ID NO: 133)
LDHA-1736 Target: 5'-ATCTTATTTTGTGAACTATATCAGTAG-3'   (SEQ ID NO: 205)

5'-ACUAUAUCAGUAGUGUACAUUACCAUA-3'    (SEQ ID NO: 422)
                 3'-UGAUAUAGUCAUCACAUGUAAUGGUAU-5'    (SEQ ID NO: 134)
LDHA-1750 Target: 5'-ACTATATCAGTAGTGTACATTACCATA-3'   (SEQ ID NO: 206)

5'-AUAUCAGUAGUGUACAUUACCAUAUAA-3'    (SEQ ID NO: 423)
                 3'-UAUAGUCAUCACAUGUAAUGGUAUAUU-5'    (SEQ ID NO: 135)
LDHA-1753 Target: 5'-ATATCAGTAGTGTACATTACCATATAA-3'   (SEQ ID NO: 207)

5'-UAUCAGUAGUGUACAUUACCAUAUAAU-3'    (SEQ ID NO: 424)
                 3'-AUAGUCAUCACAUGUAAUGGUAUAUUA-5'    (SEQ ID NO: 136)
LDHA-1754 Target: 5'-TATCAGTAGTGTACATTACCATATAAT-3'   (SEQ ID NO: 208)

5'-UGCAACCAACUAUCCAAGUGUUAUACC-3'    (SEQ ID NO: 425)
                 3'-ACGUUGGUUGAUAGGUUCACAAUAUGG-5'    (SEQ ID NO: 137)
LDHA-1805 Target: 5'-TGCAACCAACTATCCAAGTGTTATACC-3'   (SEQ ID NO: 209)

5'-GCAACCAACUAUCCAAGUGUUAUACCA-3'    (SEQ ID NO: 426)
                 3'-CGUUGGUUGAUAGGUUCACAAUAUGGU-5'    (SEQ ID NO: 138)
LDHA-1806 Target: 5'-GCAACCAACTATCCAAGTGTTATACCA-3'   (SEQ ID NO: 210)

5'-CAACCAACUAUCCAAGUGUUAUACCAA-3'    (SEQ ID NO: 427)
                 3'-GUUGGUUGAUAGGUUCACAAUAUGGUU-5'    (SEQ ID NO: 139)
LDHA-1807 Target: 5'-CAACCAACTATCCAAGTGTTATACCAA-3'   (SEQ ID NO: 211)
```

TABLE 5-continued

Selected Human Anti-Lactate Dehydrogenase "Blunt/Blunt" DsiRNAs

```
                  5'-AACCAACUAUCCAAGUGUUAUACCAAC-3'      (SEQ ID NO: 428)
                  3'-UUGGUUGAUAGGUUCACAAUAUGGUUG-5'      (SEQ ID NO: 140)
LDHA-1808 Target: 5'-AACCAACTATCCAAGTGTTATACCAAC-3'      (SEQ ID NO: 212)

5'-CAACUAUCCAAGUGUUAUACCAACUAA-3'      (SEQ ID NO: 429)
                  3'-GUUGAUAGGUUCACAAUAUGGUUGAUU-5'      (SEQ ID NO: 141)
LDHA-1811 Target: 5'-CAACTATCCAAGTGTTATACCAACTAA-3'      (SEQ ID NO: 213)

5'-AACUAUCCAAGUGUUAUACCAACUAAA-3'      (SEQ ID NO: 430)
                  3'-UUGAUAGGUUCACAAUAUGGUUGAUUU-5'      (SEQ ID NO: 142)
LDHA-1812 Target: 5'-AACTATCCAAGTGTTATACCAACTAAA-3'      (SEQ ID NO: 214)

5'-UAUCCAAGUGUUAUACCAACUAAAACC-3'      (SEQ ID NO: 431)
                  3'-AUAGGUUCACAAUAUGGUUGAUUUUGG-5'      (SEQ ID NO: 143)
LDHA-1815 Target: 5'-TATCCAAGTGTTATACCAACTAAAACC-3'      (SEQ ID NO: 215)

5'-AUCCAAGUGUUAUACCAACUAAAACCC-3'      (SEQ ID NO: 432)
                  3'-UAGGUUCACAAUAUGGUUGAUUUUGGG-5'      (SEQ ID NO: 144)
LDHA-1816 Target: 5'-ATCCAAGTGTTATACCAACTAAAACCC-3'      (SEQ ID NO: 216)
```

TABLE 6

DsiRNA Component 19 Nucleotide Target Sequences in Human Lactate Dehydrogenase mRNA

```
LDHA-355 19 nt Target #1:   5'-AGAAUAAGAUUACAGUUGU-3'   (SEQ ID NO: 433)

LDHA-355 19 nt Target #2:   5'-CAGAAUAAGAUUACAGUUG-3'   (SEQ ID NO: 505)

LDHA-355 19 nt Target #3:   5'-CCAGAAUAAGAUUACAGUU-3'   (SEQ ID NO: 577)

LDHA-356 19 nt Target #1:   5'-GAAUAAGAUUACAGUUGUU-3'   (SEQ ID NO: 434)

LDHA-356 19 nt Target #2:   5'-AGAAUAAGAUUACAGUUGU-3'   (SEQ ID NO: 506)

LDHA-356 19 nt Target #3:   5'-CAGAAUAAGAUUACAGUUG-3'   (SEQ ID NO: 578)

LDHA-360 19 nt Target #1:   5'-AAGAUUACAGUUGUUGGGG-3'   (SEQ ID NO: 435)

LDHA-360 19 nt Target #2:   5'-UAAGAUUACAGUUGUUGGG-3'   (SEQ ID NO: 507)

LDHA-360 19 nt Target #3:   5'-AUAAGAUUACAGUUGUUGG-3'   (SEQ ID NO: 579)

LDHA-361 19 nt Target #1:   5'-AGAUUACAGUUGUUGGGGU-3'   (SEQ ID NO: 436)

LDHA-361 19 nt Target #2:   5'-AAGAUUACAGUUGUUGGGG-3'   (SEQ ID NO: 508)

LDHA-361 19 nt Target #3:   5'-UAAGAUUACAGUUGUUGGG-3'   (SEQ ID NO: 580)

LDHA-362 19 nt Target #1:   5'-GAUUACAGUUGUUGGGGUU-3'   (SEQ ID NO: 437)

LDHA-362 19 nt Target #2:   5'-AGAUUACAGUUGUUGGGGU-3'   (SEQ ID NO: 509)

LDHA-362 19 nt Target #3:   5'-AAGAUUACAGUUGUUGGGG-3'   (SEQ ID NO: 581)

LDHA-363 19 nt Target #1:   5'-AUUACAGUUGUUGGGGUUG-3'   (SEQ ID NO: 438)

LDHA-363 19 nt Target #2:   5'-GAUUACAGUUGUUGGGGUU-3'   (SEQ ID NO: 510)

LDHA-363 19 nt Target #3:   5'-AGAUUACAGUUGUUGGGGU-3'   (SEQ ID NO: 582)

LDHA-364 19 nt Target #1:   5'-UUACAGUUGUUGGGGUUGG-3'   (SEQ ID NO: 439)

LDHA-364 19 nt Target #2:   5'-AUUACAGUUGUUGGGGUUG-3'   (SEQ ID NO: 511)

LDHA-364 19 nt Target #3:   5'-GAUUACAGUUGUUGGGGUU-3'   (SEQ ID NO: 583)

LDHA-365 19 nt Target #1:   5'-UACAGUUGUUGGGGUUGGU-3'   (SEQ ID NO: 440)

LDHA-365 19 nt Target #2:   5'-UUACAGUUGUUGGGGUUGG-3'   (SEQ ID NO: 512)

LDHA-365 19 nt Target #3:   5'-AUUACAGUUGUUGGGGUUG-3'   (SEQ ID NO: 584)

LDHA-366 19 nt Target #1:   5'-ACAGUUGUUGGGGUUGGUG-3'   (SEQ ID NO: 441)
```

TABLE 6-continued

DsiRNA Component 19 Nucleotide Target Sequences in Human Lactate Dehydrogenase mRNA

| | | |
|---|---|---|
| LDHA-366 19 nt Target #2: | 5'-UACAGUUGUUGGGGUUGGU-3' | (SEQ ID NO: 513) |
| LDHA-366 19 nt Target #3: | 5'-UUACAGUUGUUGGGGUUGG-3' | (SEQ ID NO: 585) |
| LDHA-367 19 nt Target #1: | 5'-CAGUUGUUGGGGUUGGUGC-3' | (SEQ ID NO: 442) |
| LDHA-367 19 nt Target #2: | 5'-ACAGUUGUUGGGGUUGGUG-3' | (SEQ ID NO: 514) |
| LDHA-367 19 nt Target #3: | 5'-UACAGUUGUUGGGGUUGGU-3' | (SEQ ID NO: 586) |
| LDHA-369 19 nt Target #1: | 5'-GUUGUUGGGGUUGGUGCUG-3' | (SEQ ID NO: 443) |
| LDHA-369 19 nt Target #2: | 5'-AGUUGUUGGGGUUGGUGCU-3' | (SEQ ID NO: 515) |
| LDHA-369 19 nt Target #3: | 5'-CAGUUGUUGGGGUUGGUGC-3' | (SEQ ID NO: 587) |
| LDHA-370 19 nt Target #1: | 5'-UUGUUGGGGUUGGUGCUGU-3' | (SEQ ID NO: 444) |
| LDHA-370 19 nt Target #2: | 5'-GUUGUUGGGGUUGGUGCUG-3' | (SEQ ID NO: 516) |
| LDHA-370 19 nt Target #3: | 5'-AGUUGUUGGGGUUGGUGCU-3' | (SEQ ID NO: 588) |
| LDHA-397 19 nt Target #1: | 5'-CCUGUGCCAUCAGUAUCUU-3' | (SEQ ID NO: 445) |
| LDHA-397 19 nt Target #2: | 5'-GCCUGUGCCAUCAGUAUCU-3' | (SEQ ID NO: 517) |
| LDHA-397 19 nt Target #3: | 5'-GGCCUGUGCCAUCAGUAUC-3' | (SEQ ID NO: 589) |
| LDHA-398 19 nt Target #1: | 5'-CUGUGCCAUCAGUAUCUUA-3' | (SEQ ID NO: 446) |
| LDHA-398 19 nt Target #2: | 5'-CCUGUGCCAUCAGUAUCUU-3' | (SEQ ID NO: 518) |
| LDHA-398 19 nt Target #3: | 5'-GCCUGUGCCAUCAGUAUCU-3' | (SEQ ID NO: 590) |
| LDHA-399 19 nt Target #1: | 5'-UGUGCCAUCAGUAUCUUAA-3' | (SEQ ID NO: 447) |
| LDHA-399 19 nt Target #2: | 5'-CUGUGCCAUCAGUAUCUUA-3' | (SEQ ID NO: 519) |
| LDHA-399 19 nt Target #3: | 5'-CCUGUGCCAUCAGUAUCUU-3' | (SEQ ID NO: 591) |
| LDHA-400 19 nt Target #1: | 5'-GUGCCAUCAGUAUCUUAAU-3' | (SEQ ID NO: 448) |
| LDHA-400 19 nt Target #2: | 5'-UGUGCCAUCAGUAUCUUAA-3' | (SEQ ID NO: 520) |
| LDHA-400 19 nt Target #3: | 5'-CUGUGCCAUCAGUAUCUUA-3' | (SEQ ID NO: 592) |
| LDHA-401 19 nt Target #1: | 5'-UGCCAUCAGUAUCUUAAUG-3' | (SEQ ID NO: 449) |
| LDHA-401 19 nt Target #2: | 5'-GUGCCAUCAGUAUCUUAAU-3' | (SEQ ID NO: 521) |
| LDHA-401 19 nt Target #3: | 5'-UGUGCCAUCAGUAUCUUAA-3' | (SEQ ID NO: 593) |
| LDHA-402 19 nt Target #1: | 5'-GCCAUCAGUAUCUUAAUGA-3' | (SEQ ID NO: 450) |
| LDHA-402 19 nt Target #2: | 5'-UGCCAUCAGUAUCUUAAUG-3' | (SEQ ID NO: 522) |
| LDHA-402 19 nt Target #3: | 5'-GUGCCAUCAGUAUCUUAAU-3' | (SEQ ID NO: 594) |
| LDHA-403 19 nt Target #1: | 5'-CCAUCAGUAUCUUAAUGAA-3' | (SEQ ID NO: 451) |
| LDHA-403 19 nt Target #2: | 5'-GCCAUCAGUAUCUUAAUGA-3' | (SEQ ID NO: 523) |
| LDHA-403 19 nt Target #3: | 5'-UGCCAUCAGUAUCUUAAUG-3' | (SEQ ID NO: 595) |
| LDHA-404 19 nt Target #1: | 5'-CAUCAGUAUCUUAAUGAAG-3' | (SEQ ID NO: 452) |
| LDHA-404 19 nt Target #2: | 5'-CCAUCAGUAUCUUAAUGAA-3' | (SEQ ID NO: 524) |
| LDHA-404 19 nt Target #3: | 5'-GCCAUCAGUAUCUUAAUGA-3' | (SEQ ID NO: 596) |
| LDHA-714 19 nt Target #1: | 5'-GUGGAUAUCUUGACCUACG-3' | (SEQ ID NO: 453) |
| LDHA-714 19 nt Target #2: | 5'-AGUGGAUAUCUUGACCUAC-3' | (SEQ ID NO: 525) |
| LDHA-714 19 nt Target #3: | 5'-CAGUGGAUAUCUUGACCUA-3' | (SEQ ID NO: 597) |

TABLE 6-continued

DsiRNA Component 19 Nucleotide Target Sequences in Human Lactate Dehydrogenase mRNA

| | | |
|---|---|---|
| LDHA-717 19 nt Target #1: | 5'-GAUAUCUUGACCUACGUGG-3' | (SEQ ID NO: 454) |
| LDHA-717 19 nt Target #2: | 5'-GGAUAUCUUGACCUACGUG-3' | (SEQ ID NO: 526) |
| LDHA-717 19 nt Target #3: | 5'-UGGAUAUCUUGACCUACGU-3' | (SEQ ID NO: 598) |
| LDHA-718 19 nt Target #1: | 5'-AUAUCUUGACCUACGUGGC-3' | (SEQ ID NO: 455) |
| LDHA-718 19 nt Target #2: | 5'-GAUAUCUUGACCUACGUGG-3' | (SEQ ID NO: 527) |
| LDHA-718 19 nt Target #3: | 5'-GGAUAUCUUGACCUACGUG-3' | (SEQ ID NO: 599) |
| LDHA-719 19 nt Target #1: | 5'-UAUCUUGACCUACGUGGCU-3' | (SEQ ID NO: 456) |
| LDHA-719 19 nt Target #2: | 5'-AUAUCUUGACCUACGUGGC-3' | (SEQ ID NO: 528) |
| LDHA-719 19 nt Target #3: | 5'-GAUAUCUUGACCUACGUGG-3' | (SEQ ID NO: 600) |
| LDHA-720 19 nt Target #1: | 5'-AUCUUGACCUACGUGGCUU-3' | (SEQ ID NO: 457) |
| LDHA-720 19 nt Target #2: | 5'-UAUCUUGACCUACGUGGCU-3' | (SEQ ID NO: 529) |
| LDHA-720 19 nt Target #3: | 5'-AUAUCUUGACCUACGUGGC-3' | (SEQ ID NO: 601) |
| LDHA-722 19 nt Target #1: | 5'-CUUGACCUACGUGGCUUGG-3' | (SEQ ID NO: 458) |
| LDHA-722 19 nt Target #2: | 5'-UCUUGACCUACGUGGCUUG-3' | (SEQ ID NO: 530) |
| LDHA-722 19 nt Target #3: | 5'-AUCUUGACCUACGUGGCUU-3' | (SEQ ID NO: 602) |
| LDHA-723 19 nt Target #1: | 5'-UUGACCUACGUGGCUUGGA-3' | (SEQ ID NO: 459) |
| LDHA-723 19 nt Target #2: | 5'-CUUGACCUACGUGGCUUGG-3' | (SEQ ID NO: 531) |
| LDHA-723 19 nt Target #3: | 5'-UCUUGACCUACGUGGCUUG-3' | (SEQ ID NO: 603) |
| LDHA-724 19 nt Target #1: | 5'-UGACCUACGUGGCUUGGAA-3' | (SEQ ID NO: 460) |
| LDHA-724 19 nt Target #2: | 5'-UUGACCUACGUGGCUUGGA-3' | (SEQ ID NO: 532) |
| LDHA-724 19 nt Target #3: | 5'-CUUGACCUACGUGGCUUGG-3' | (SEQ ID NO: 604) |
| LDHA-739 19 nt Target #1: | 5'-GGAAGAUAAGUGGUUUUCC-3' | (SEQ ID NO: 461) |
| LDHA-739 19 nt Target #2: | 5'-UGGAAGAUAAGUGGUUUUC-3' | (SEQ ID NO: 533) |
| LDHA-739 19 nt Target #3: | 5'-UUGGAAGAUAAGUGGUUUU-3' | (SEQ ID NO: 605) |
| LDHA-740 19 nt Target #1: | 5'-GAAGAUAAGUGGUUUUCCC-3' | (SEQ ID NO: 462) |
| LDHA-740 19 nt Target #2: | 5'-GGAAGAUAAGUGGUUUUCC-3' | (SEQ ID NO: 534) |
| LDHA-740 19 nt Target #3: | 5'-UGGAAGAUAAGUGGUUUUC-3' | (SEQ ID NO: 606) |
| LDHA-891 19 nt Target #1: | 5'-CCUGUAUGGAGUGGAAUGA-3' | (SEQ ID NO: 463) |
| LDHA-891 19 nt Target #2: | 5'-GCCUGUAUGGAGUGGAAUG-3' | (SEQ ID NO: 535) |
| LDHA-891 19 nt Target #3: | 5'-UGCCUGUAUGGAGUGGAAU-3' | (SEQ ID NO: 607) |
| LDHA-892 19 nt Target #1: | 5'-CUGUAUGGAGUGGAAUGAA-3' | (SEQ ID NO: 464) |
| LDHA-892 19 nt Target #2: | 5'-CCUGUAUGGAGUGGAAUGA-3' | (SEQ ID NO: 536) |
| LDHA-892 19 nt Target #3: | 5'-GCCUGUAUGGAGUGGAAUG-3' | (SEQ ID NO: 608) |
| LDHA-907 19 nt Target #1: | 5'-UGAAUGUUGCUGGUGUCUC-3' | (SEQ ID NO: 465) |
| LDHA-907 19 nt Target #2: | 5'-AUGAAUGUUGCUGGUGUCU-3' | (SEQ ID NO: 537) |
| LDHA-907 19 nt Target #3: | 5'-AAUGAAUGUUGCUGGUGUC-3' | (SEQ ID NO: 609) |
| LDHA-952 19 nt Target #1: | 5'-GGACUGAUAAAGAUAAGGA-3' | (SEQ ID NO: 466) |
| LDHA-952 19 nt Target #2: | 5'-GGGACUGAUAAAGAUAAGG-3' | (SEQ ID NO: 538) |
| LDHA-952 19 nt Target #3: | 5'-AGGGACUGAUAAAGAUAAG-3' | (SEQ ID NO: 610) |

TABLE 6-continued

DsiRNA Component 19 Nucleotide Target Sequences in Human Lactate Dehydrogenase mRNA LDHA-1286 19 nt Target #1: 5'-GCAAUUUUAAAGUCUUCUG-3'  (SEQ ID NO: 467)

LDHA-1286 19 nt Target #2: 5'-UGCAAUUUUAAAGUCUUCU-3'  (SEQ ID NO: 539)

LDHA-1286 19 nt Target #3: 5'-CUGCAAUUUUAAAGUCUUC-3'  (SEQ ID NO: 611)

LDHA-1287 19 nt Target #1: 5'-CAAUUUUAAAGUCUUCUGA-3'  (SEQ ID NO: 468)

LDHA-1287 19 nt Target #2: 5'-GCAAUUUUAAAGUCUUCUG-3'  (SEQ ID NO: 540)

LDHA-1287 19 nt Target #3: 5'-UGCAAUUUUAAAGUCUUCU-3'  (SEQ ID NO: 612)

LDHA-1292 19 nt Target #1: 5'-UUAAAGUCUUCUGAUGUCA-3'  (SEQ ID NO: 469)

LDHA-1292 19 nt Target #2: 5'-UUUAAAGUCUUCUGAUGUC-3'  (SEQ ID NO: 541)

LDHA-1292 19 nt Target #3: 5'-UUUUAAAGUCUUCUGAUGU-3'  (SEQ ID NO: 613)

LDHA-1293 19 nt Target #1: 5'-UAAAGUCUUCUGAUGUCAU-3'  (SEQ ID NO: 470)

LDHA-1293 19 nt Target #2: 5'-UUAAAGUCUUCUGAUGUCA-3'  (SEQ ID NO: 542)

LDHA-1293 19 nt Target #3: 5'-UUUAAAGUCUUCUGAUGUC-3'  (SEQ ID NO: 614)

LDHA-1294 19 nt Target #1: 5'-AAAGUCUUCUGAUGUCAUA-3'  (SEQ ID NO: 471)

LDHA-1294 19 nt Target #2: 5'-UAAAGUCUUCUGAUGUCAU-3'  (SEQ ID NO: 543)

LDHA-1294 19 nt Target #3: 5'-UUAAAGUCUUCUGAUGUCA-3'  (SEQ ID NO: 615)

LDHA-1359 19 nt Target #1: 5'-CAUGUUGUCCUUUUUAUCU-3'  (SEQ ID NO: 472)

LDHA-1359 19 nt Target #2: 5'-GCAUGUUGUCCUUUUUAUC-3'  (SEQ ID NO: 544)

LDHA-1359 19 nt Target #3: 5'-UGCAUGUUGUCCUUUUUAU-3'  (SEQ ID NO: 616)

LDHA-1360 19 nt Target #1: 5'-AUGUUGUCCUUUUUAUCUG-3'  (SEQ ID NO: 473)

LDHA-1360 19 nt Target #2: 5'-CAUGUUGUCCUUUUUAUCU-3'  (SEQ ID NO: 545)

LDHA-1360 19 nt Target #3: 5'-GCAUGUUGUCCUUUUUAUC-3'  (SEQ ID NO: 617)

LDHA-1361 19 nt Target #1: 5'-UGUUGUCCUUUUUAUCUGA-3'  (SEQ ID NO: 474)

LDHA-1361 19 nt Target #2: 5'-AUGUUGUCCUUUUUAUCUG-3'  (SEQ ID NO: 546)

LDHA-1361 19 nt Target #3: 5'-CAUGUUGUCCUUUUUAUCU-3'  (SEQ ID NO: 618)

LDHA-1362 19 nt Target #1: 5'-GUUGUCCUUUUUAUCUGAU-3'  (SEQ ID NO: 475)

LDHA-1362 19 nt Target #2: 5'-UGUUGUCCUUUUUAUCUGA-3'  (SEQ ID NO: 547)

LDHA-1362 19 nt Target #3: 5'-AUGUUGUCCUUUUUAUCUG-3'  (SEQ ID NO: 619)

LDHA-1363 19 nt Target #1: 5'-UUGUCCUUUUUAUCUGAUC-3'  (SEQ ID NO: 476)

LDHA-1363 19 nt Target #2: 5'-GUUGUCCUUUUUAUCUGAU-3'  (SEQ ID NO: 548)

LDHA-1363 19 nt Target #3: 5'-UGUUGUCCUUUUUAUCUGA-3'  (SEQ ID NO: 620)

LDHA-1365 19 nt Target #1: 5'-GUCCUUUUUAUCUGAUCUG-3'  (SEQ ID NO: 477)

LDHA-1365 19 nt Target #2: 5'-UGUCCUUUUUAUCUGAUCU-3'  (SEQ ID NO: 549)

LDHA-1365 19 nt Target #3: 5'-UUGUCCUUUUUAUCUGAUC-3'  (SEQ ID NO: 621)

LDHA-1366 19 nt Target #1: 5'-UCCUUUUUAUCUGAUCUGU-3'  (SEQ ID NO: 478)

LDHA-1366 19 nt Target #2: 5'-GUCCUUUUUAUCUGAUCUG-3'  (SEQ ID NO: 550)

LDHA-1366 19 nt Target #3: 5'-UGUCCUUUUUAUCUGAUCU-3'  (SEQ ID NO: 622)

LDHA-1367 19 nt Target #1: 5'-CCUUUUUAUCUGAUCUGUG-3'  (SEQ ID NO: 479)

LDHA-1367 19 nt Target #2: 5'-UCCUUUUUAUCUGAUCUGU-3'  (SEQ ID NO: 551)

TABLE 6-continued

DsiRNA Component 19 Nucleotide Target Sequences in Human Lactate Dehydrogenase mRNA

| | | |
|---|---|---|
| LDHA-1367 19 nt Target #3: | 5'-GUCCUUUUUAUCUGAUCUG-3' | (SEQ ID NO: 623) |
| LDHA-1368 19 nt Target #1: | 5'-CUUUUUAUCUGAUCUGUGA-3' | (SEQ ID NO: 480) |
| LDHA-1368 19 nt Target #2: | 5'-CCUUUUUAUCUGAUCUGUG-3' | (SEQ ID NO: 552) |
| LDHA-1368 19 nt Target #3: | 5'-UCCUUUUUAUCUGAUCUGU-3' | (SEQ ID NO: 624) |
| LDHA-1370 19 nt Target #1: | 5'-UUUUAUCUGAUCUGUGAUU-3' | (SEQ ID NO: 481) |
| LDHA-1370 19 nt Target #2: | 5'-UUUUUAUCUGAUCUGUGAU-3' | (SEQ ID NO: 553) |
| LDHA-1370 19 nt Target #3: | 5'-CUUUUUAUCUGAUCUGUGA-3' | (SEQ ID NO: 625) |
| LDHA-1371 19 nt Target #1: | 5'-UUUAUCUGAUCUGUGAUUA-3' | (SEQ ID NO: 482) |
| LDHA-1371 19 nt Target #2: | 5'-UUUUAUCUGAUCUGUGAUU-3' | (SEQ ID NO: 554) |
| LDHA-1371 19 nt Target #3: | 5'-UUUUUAUCUGAUCUGUGAU-3' | (SEQ ID NO: 626) |
| LDHA-1372 19 nt Target #1: | 5'-UUAUCUGAUCUGUGAUUAA-3' | (SEQ ID NO: 483) |
| LDHA-1372 19 nt Target #2: | 5'-UUUAUCUGAUCUGUGAUUA-3' | (SEQ ID NO: 555) |
| LDHA-1372 19 nt Target #3: | 5'-UUUUAUCUGAUCUGUGAUU-3' | (SEQ ID NO: 627) |
| LDHA-1393 19 nt Target #1: | 5'-CAGUAAUAUUUUAAGAUGG-3' | (SEQ ID NO: 484) |
| LDHA-1393 19 nt Target #2: | 5'-GCAGUAAUAUUUUAAGAUG-3' | (SEQ ID NO: 556) |
| LDHA-1393 19 nt Target #3: | 5'-AGCAGUAAUAUUUUAAGAU-3' | (SEQ ID NO: 628) |
| LDHA-1427 19 nt Target #1: | 5'-AACUCCUGAAGUUAGAAAU-3' | (SEQ ID NO: 485) |
| LDHA-1427 19 nt Target #2: | 5'-CAACUCCUGAAGUUAGAAA-3' | (SEQ ID NO: 557) |
| LDHA-1427 19 nt Target #3: | 5'-UCAACUCCUGAAGUUAGAA-3' | (SEQ ID NO: 629) |
| LDHA-1428 19 nt Target #1: | 5'-ACUCCUGAAGUUAGAAAUA-3' | (SEQ ID NO: 486) |
| LDHA-1428 19 nt Target #2: | 5'-AACUCCUGAAGUUAGAAAU-3' | (SEQ ID NO: 558) |
| LDHA-1428 19 nt Target #3: | 5'-CAACUCCUGAAGUUAGAAA-3' | (SEQ ID NO: 630) |
| LDHA-1512 19 nt Target #1: | 5'-AACUGGUUAGUGUGAAAUA-3' | (SEQ ID NO: 487) |
| LDHA-1512 19 nt Target #2: | 5'-CAACUGGUUAGUGUGAAAU-3' | (SEQ ID NO: 559) |
| LDHA-1512 19 nt Target #3: | 5'-UCAACUGGUUAGUGUGAAA-3' | (SEQ ID NO: 631) |
| LDHA-1513 19 nt Target #1: | 5'-ACUGGUUAGUGUGAAAUAG-3' | (SEQ ID NO: 488) |
| LDHA-1513 19 nt Target #2: | 5'-AACUGGUUAGUGUGAAAUA-3' | (SEQ ID NO: 560) |
| LDHA-1513 19 nt Target #3: | 5'-CAACUGGUUAGUGUGAAAU-3' | (SEQ ID NO: 632) |
| LDHA-1514 19 nt Target #1: | 5'-CUGGUUAGUGUGAAAUAGU-3' | (SEQ ID NO: 489) |
| LDHA-1514 19 nt Target #2: | 5'-ACUGGUUAGUGUGAAAUAG-3' | (SEQ ID NO: 561) |
| LDHA-1514 19 nt Target #3: | 5'-AACUGGUUAGUGUGAAAUA-3' | (SEQ ID NO: 633) |
| LDHA-1516 19 nt Target #1: | 5'-GGUUAGUGUGAAAUAGUUC-3' | (SEQ ID NO: 490) |
| LDHA-1516 19 nt Target #2: | 5'-UGGUUAGUGUGAAAUAGUU-3' | (SEQ ID NO: 562) |
| LDHA-1516 19 nt Target #3: | 5'-CUGGUUAGUGUGAAAUAGU-3' | (SEQ ID NO: 634) |
| LDHA-1684 19 nt Target #1: | 5'-AUCCAGUGUAUAAAUCCAA-3' | (SEQ ID NO: 491) |
| LDHA-1684 19 nt Target #2: | 5'-GAUCCAGUGUAUAAAUCCA-3' | (SEQ ID NO: 563) |
| LDHA-1684 19 nt Target #3: | 5'-GGAUCCAGUGUAUAAAUCC-3' | (SEQ ID NO: 635) |
| LDHA-1688 19 nt Target #1: | 5'-AGUGUAUAAAUCCAAUAUC-3' | (SEQ ID NO: 492) |
| LDHA-1688 19 nt Target #2: | 5'-CAGUGUAUAAAUCCAAUAU-3' | (SEQ ID NO: 564) |

TABLE 6-continued

DsiRNA Component 19 Nucleotide Target Sequences in Human Lactate Dehydrogenase mRNA

```
LDHA-1688 19 nt Target #3: 5'-CCAGUGUAUAAAUCCAAUA-3'  (SEQ ID NO: 636)

LDHA-1736 19 nt Target #1: 5'-CUUAUUUUGUGAACUAUAU-3'  (SEQ ID NO: 493)

LDHA-1736 19 nt Target #2: 5'-UCUUAUUUUGUGAACUAUA-3'  (SEQ ID NO: 565)

LDHA-1736 19 nt Target #3: 5'-AUCUUAUUUUGUGAACUAU-3'  (SEQ ID NO: 637)

LDHA-1750 19 nt Target #1: 5'-UAUAUCAGUAGUGUACAUU-3'  (SEQ ID NO: 494)

LDHA-1750 19 nt Target #2: 5'-CUAUAUCAGUAGUGUACAU-3'  (SEQ ID NO: 566)

LDHA-1750 19 nt Target #3: 5'-ACUAUAUCAGUAGUGUACA-3'  (SEQ ID NO: 638)

LDHA-1753 19 nt Target #1: 5'-AUCAGUAGUGUACAUUACC-3'  (SEQ ID NO: 495)

LDHA-1753 19 nt Target #2: 5'-UAUCAGUAGUGUACAUUAC-3'  (SEQ ID NO: 567)

LDHA-1753 19 nt Target #3: 5'-AUAUCAGUAGUGUACAUUA-3'  (SEQ ID NO: 639)

LDHA-1754 19 nt Target #1: 5'-UCAGUAGUGUACAUUACCA-3'  (SEQ ID NO: 496)

LDHA-1754 19 nt Target #2: 5'-AUCAGUAGUGUACAUUACC-3'  (SEQ ID NO: 568)

LDHA-1754 19 nt Target #3: 5'-UAUCAGUAGUGUACAUUAC-3'  (SEQ ID NO: 640)

LDHA-1805 19 nt Target #1: 5'-CAACCAACUAUCCAAGUGU-3'  (SEQ ID NO: 497)

LDHA-1805 19 nt Target #2: 5'-GCAACCAACUAUCCAAGUG-3'  (SEQ ID NO: 569)

LDHA-1805 19 nt Target #3: 5'-UGCAACCAACUAUCCAAGU-3'  (SEQ ID NO: 641)

LDHA-1806 19 nt Target #1: 5'-AACCAACUAUCCAAGUGUU-3'  (SEQ ID NO: 498)

LDHA-1806 19 nt Target #2: 5'-CAACCAACUAUCCAAGUGU-3'  (SEQ ID NO: 570)

LDHA-1806 19 nt Target #3: 5'-GCAACCAACUAUCCAAGUG-3'  (SEQ ID NO: 642)

LDHA-1807 19 nt Target #1: 5'-ACCAACUAUCCAAGUGUUA-3'  (SEQ ID NO: 499)

LDHA-1807 19 nt Target #2: 5'-AACCAACUAUCCAAGUGUU-3'  (SEQ ID NO: 571)

LDHA-1807 19 nt Target #3: 5'-CAACCAACUAUCCAAGUGU-3'  (SEQ ID NO: 643)

LDHA-1808 19 nt Target #1: 5'-CCAACUAUCCAAGUGUUAU-3'  (SEQ ID NO: 500)

LDHA-1808 19 nt Target #2: 5'-ACCAACUAUCCAAGUGUUA-3'  (SEQ ID NO: 572)

LDHA-1808 19 nt Target #3: 5'-AACCAACUAUCCAAGUGUU-3'  (SEQ ID NO: 644)

LDHA-1811 19 nt Target #1: 5'-ACUAUCCAAGUGUUAUACC-3'  (SEQ ID NO: 501)

LDHA-1811 19 nt Target #2: 5'-AACUAUCCAAGUGUUAUAC-3'  (SEQ ID NO: 573)

LDHA-1811 19 nt Target #3: 5'-CAACUAUCCAAGUGUUAUA-3'  (SEQ ID NO: 645)

LDHA-1812 19 nt Target #1: 5'-CUAUCCAAGUGUUAUACCA-3'  (SEQ ID NO: 502)

LDHA-1812 19 nt Target #2: 5'-ACUAUCCAAGUGUUAUACC-3'  (SEQ ID NO: 574)

LDHA-1812 19 nt Target #3: 5'-AACUAUCCAAGUGUUAUAC-3'  (SEQ ID NO: 646)

LDHA-1815 19 nt Target #1: 5'-UCCAAGUGUUAUACCAACU-3'  (SEQ ID NO: 503)

LDHA-1815 19 nt Target #2: 5'-AUCCAAGUGUUAUACCAAC-3'  (SEQ ID NO: 575)

LDHA-1815 19 nt Target #3: 5'-UAUCCAAGUGUUAUACCAA-3'  (SEQ ID NO: 647)

LDHA-1816 19 nt Target #1: 5'-CCAAGUGUUAUACCAACUA-3'  (SEQ ID NO: 504)

LDHA-1816 19 nt Target #2: 5'-UCCAAGUGUUAUACCAACU-3'  (SEQ ID NO: 576)

LDHA-1816 19 nt Target #3: 5'-AUCCAAGUGUUAUACCAAC-3'  (SEQ ID NO: 648)
```

TABLE 7

Selected Mouse Anti-Lactate Dehydrogenase DsiRNA Agents (Asymmetrics)

| | | |
|---|---|---|
| LDHA-m367 | 5'-CAAGGACCAGCUGAUUGUGAAUCtt-3'<br>3'-GAGUUCCUGGUCGACUAACACUUAGAA-5'<br>Target: 5'-CTCAAGGACCAGCTGATTGTGAATCTT-3' | (SEQ ID NO: 649)<br>(SEQ ID NO: 697)<br>(SEQ ID NO: 745) |
| LDHA-m368 | 5'-AAGGACCAGCUGAUUGUGAAUCUtc-3'<br>3'-AGUUCCUGGUCGACUAACACUUAGAAG-5'<br>Target: 5'-TCAAGGACCAGCTGATTGTGAATCTTC-3' | (SEQ ID NO: 650)<br>(SEQ ID NO: 698)<br>(SEQ ID NO: 746) |
| LDHA-m372 | 5'-ACCAGCUGAUUGUGAAUCUUCUUaa-3'<br>3'-CCUGGUCGACUAACACUUAGAAGAAUU-5'<br>Target: 5'-GGACCAGCTGATTGTGAATCTTCTTAA-3' | (SEQ ID NO: 651)<br>(SEQ ID NO: 699)<br>(SEQ ID NO: 747) |
| LDHA-m376 | 5'-GCUGAUUGUGAAUCUUCUUAAGGaa-3'<br>3'-GUCGACUAACACUUAGAAGAAUUCCUU-5'<br>Target: 5'-CAGCTGATTGTGAATCTTCTTAAGGAA-3' | (SEQ ID NO: 652)<br>(SEQ ID NO: 700)<br>(SEQ ID NO: 748) |
| LDHA-m456 | 5'-CUUGUGCCAUCAGUAUCUUAAUGaa-3'<br>3'-CCGAACACGGUAGUCAUAGAAUUACUU-5'<br>Target: 5'-GGCTTGTGCCATCAGTATCTTAATGAA-3' | (SEQ ID NO: 653)<br>(SEQ ID NO: 701)<br>(SEQ ID NO: 749) |
| LDHA-m501 | 5'-CCCUUGUUGACGUCAUGGAAGACaa-3'<br>3'-ACGGGAACAACUGCAGUACCUUCUGUU-5'<br>Target: 5'-TGCCCTTGTTGACGTCATGGAAGACAA-3' | (SEQ ID NO: 654)<br>(SEQ ID NO: 702)<br>(SEQ ID NO: 750) |
| LDHA-m506 | 5'-GUUGACGUCAUGGAAGACAAACUca-3'<br>3'-AACAACUGCAGUACCUUCUGUUUGAGU-5'<br>Target: 5'-TTGTTGACGTCATGGAAGACAAACTCA-3' | (SEQ ID NO: 655)<br>(SEQ ID NO: 703)<br>(SEQ ID NO: 751) |
| LDHA-m507 | 5'-UUGACGUCAUGGAAGACAAACUCaa-3'<br>3'-ACAACUGCAGUACCUUCUGUUUGAGUU-5'<br>Target: 5'-TGTTGACGTCATGGAAGACAAACTCAA-3' | (SEQ ID NO: 656)<br>(SEQ ID NO: 704)<br>(SEQ ID NO: 752) |
| LDHA-m584 | 5'-AUUGUCUCCAGCAAAGACUACUGtg-3'<br>3'-UUUAACAGAGGUCGUUUCUGAUGACAC-5'<br>Target: 5'-AAATTGTCTCCAGCAAAGACTACTGTG-3' | (SEQ ID NO: 657)<br>(SEQ ID NO: 705)<br>(SEQ ID NO: 753) |
| LDHA-m689 | 5'-CGAAACGUGAACAUCUUCAAGUUca-3'<br>3'-UCGCUUUGCACUUGUAGAAGUUCAAGU-5'<br>Target: 5'-AGCGAAACGTGAACATCTTCAAGTTCA-3' | (SEQ ID NO: 658)<br>(SEQ ID NO: 706)<br>(SEQ ID NO: 754) |
| LDHA-m694 | 5'-CGUGAACAUCUUCAAGUUCAUCAtt-3'<br>3'-UUGCACUUGUAGAAGUUCAAGUAGUAA-5'<br>Target: 5'-AACGTGAACATCTTCAAGTTCATCATT-3' | (SEQ ID NO: 659)<br>(SEQ ID NO: 707)<br>(SEQ ID NO: 755) |
| LDHA-m695 | 5'-GUGAACAUCUUCAAGUUCAUCAUtc-3'<br>3'-UGCACUUGUAGAAGUUCAAGUAGUAAG-5'<br>Target: 5'-ACGTGAACATCTTCAAGTTCATCATTC-3' | (SEQ ID NO: 660)<br>(SEQ ID NO: 708)<br>(SEQ ID NO: 756) |
| LDHA-m823 | 5'-CCGAGUAAUUGGAAGUGGUUGCAat-3'<br>3'-UUGGCUCAUUAACCUUCACCAACGUUA-5'<br>Target: 5'-AACCGAGTAATTGGAAGTGGTTGCAAT-3' | (SEQ ID NO: 661)<br>(SEQ ID NO: 709)<br>(SEQ ID NO: 757) |
| LDHA-m1071 | 5'-ACGAGGUGAUCAAGCUGAAAGGUta-3'<br>3'-GAUGCUCCACUAGUUCGACUUUCCAAU-5'<br>Target: 5'-CTACGAGGTGATCAAGCTGAAAGGTTA-3' | (SEQ ID NO: 662)<br>(SEQ ID NO: 710)<br>(SEQ ID NO: 758) |
| LDHA-m1133 | 5'-GCUGAGAGCAUAAUGAAGAACCUta-3'<br>3'-ACCGACUCUCGUAUUACUUCUUGGAAU-5'<br>Target: 5'-TGGCTGAGAGCATAATGAAGAACCTTA-3' | (SEQ ID NO: 663)<br>(SEQ ID NO: 711)<br>(SEQ ID NO: 759) |
| LDHA-m1183 | 5'-GAUUAAGGGUCUCUAUGGAAUCAat-3'<br>3'-UACUAAUUCCCAGAGAUACCUUAGUUA-5'<br>Target: 5'-ATGATTAAGGGTCTCTATGGAATCAAT-3' | (SEQ ID NO: 664)<br>(SEQ ID NO: 712)<br>(SEQ ID NO: 760) |
| LDHA-m1245 | 5'-AAAAUGGAAUCUCGGAUGUUGUGaa-3'<br>3'-UGUUUUACCUUAGAGCCUACAACACUU-5'<br>Target: 5'-ACAAAATGGAATCTCGGATGTTGTGAA-3' | (SEQ ID NO: 665)<br>(SEQ ID NO: 713)<br>(SEQ ID NO: 761) |
| LDHA-m1250 | 5'-GGAAUCUCGGAUGUUGUGAAGGUga-3'<br>3'-UACCUUAGAGCCUACAACACUUCCACU-5'<br>Target: 5'-ATGGAATCTCGGATGTTGTGAAGGTGA-3' | (SEQ ID NO: 666)<br>(SEQ ID NO: 714)<br>(SEQ ID NO: 762) |
| LDHA-m1257 | 5'-CGGAUGUUGUGAAGGUGACACUGac-3'<br>3'-GAGCCUACAACACUUCCACUGUGACUG-5'<br>Target: 5'-CTCGGATGTTGTGAAGGTGACACTGAC-3' | (SEQ ID NO: 667)<br>(SEQ ID NO: 715)<br>(SEQ ID NO: 763) |

TABLE 7-continued

Selected Mouse Anti-Lactate Dehydrogenase DsiRNA Agents (Asymmetrics)

| | | |
|---|---|---|
| | 5'-GAUGCAUAUCUUGUGCAUAAAUGtt-3' | (SEQ ID NO: 668) |
| | 3'-UACUACGUAUAGAACACGUAUUUACAA-5' | (SEQ ID NO: 716) |
| LDHA-m1687 Target: | 5'-ATGATGCATATCTTGTGCATAAATGTT-3' | (SEQ ID NO: 764) |
| | 5'-AUGCAUAUCUUGUGCAUAAAUGUtg-3' | (SEQ ID NO: 669) |
| | 3'-ACUACGUAUAGAACACGUAUUUACAAC-5' | (SEQ ID NO: 717) |
| LDHA-m1688 Target: | 5'-TGATGCATATCTTGTGCATAAATGTTG-3' | (SEQ ID NO: 765) |
| | 5'-GCAUAUCUUGUGCAUAAAUGUUGta-3' | (SEQ ID NO: 670) |
| | 3'-UACGUAUAGAACACGUAUUUACAACAU-5' | (SEQ ID NO: 718) |
| LDHA-m1690 Target: | 5'-ATGCATATCTTGTGCATAAATGTTGTA-3' | (SEQ ID NO: 766) |
| | 5'-CAUAUCUUGUGCAUAAAUGUUGUac-3' | (SEQ ID NO: 671) |
| | 3'-ACGUAUAGAACACGUAUUUACAACAUG-5' | (SEQ ID NO: 719) |
| LDHA-m1691 Target: | 5'-TGCATATCTTGTGCATAAATGTTGTAC-3' | (SEQ ID NO: 767) |
| | 5'-AUAUCUUGUGCAUAAAUGUUGUAca-3' | (SEQ ID NO: 672) |
| | 3'-CGUAUAGAACACGUAUUUACAACAUGU-5' | (SEQ ID NO: 720) |
| LDHA-m1692 Target: | 5'-GCATATCTTGTGCATAAATGTTGTACA-3' | (SEQ ID NO: 768) |
| | 5'-AUCUUGUGCAUAAAUGUUGUACAgg-3' | (SEQ ID NO: 673) |
| | 3'-UAUAGAACACGUAUUUACAACAUGUCC-5' | (SEQ ID NO: 721) |
| LDHA-m1694 Target: | 5'-ATATCTTGTGCATAAATGTTGTACAGG-3' | (SEQ ID NO: 769) |
| | 5'-UCUUGUGCAUAAAUGUUGUACAGga-3' | (SEQ ID NO: 674) |
| | 3'-AUAGAACACGUAUUUACAACAUGUCCU-5' | (SEQ ID NO: 722) |
| LDHA-m1695 Target: | 5'-TATCTTGTGCATAAATGTTGTACAGGA-3' | (SEQ ID NO: 770) |
| | 5'-UUGUGCAUAAAUGUUGUACAGGAta-3' | (SEQ ID NO: 675) |
| | 3'-AGAACACGUAUUUACAACAUGUCCUAU-5' | (SEQ ID NO: 723) |
| LDHA-m1697 Target: | 5'-TCTTGTGCATAAATGTTGTACAGGATA-3' | (SEQ ID NO: 771) |
| | 5'-UGUGCAUAAAUGUUGUACAGGAUat-3' | (SEQ ID NO: 676) |
| | 3'-GAACACGUAUUUACAACAUGUCCUAUA-5' | (SEQ ID NO: 724) |
| LDHA-m1698 Target: | 5'-CTTGTGCATAAATGTTGTACAGGATAT-3' | (SEQ ID NO: 772) |
| | 5'-GUGCAUAAAUGUUGUACAGGAUAtt-3' | (SEQ ID NO: 677) |
| | 3'-AACACGUAUUUACAACAUGUCCUAUAA-5' | (SEQ ID NO: 725) |
| LDHA-m1699 Target: | 5'-TTGTGCATAAATGTTGTACAGGATATT-3' | (SEQ ID NO: 773) |
| | 5'-UGCAUAAAUGUUGUACAGGAUAUtt-3' | (SEQ ID NO: 678) |
| | 3'-ACACGUAUUUACAACAUGUCCUAUAAA-5' | (SEQ ID NO: 726) |
| LDHA-m1700 Target: | 5'-TGTGCATAAATGTTGTACAGGATATTT-3' | (SEQ ID NO: 774) |
| | 5'-GCAUAAAUGUUGUACAGGAUAUUtt-3' | (SEQ ID NO: 679) |
| | 3'-CACGUAUUUACAACAUGUCCUAUAAAA-5' | (SEQ ID NO: 727) |
| LDHA-m1701 Target: | 5'-GTGCATAAATGTTGTACAGGATATTTT-3' | (SEQ ID NO: 775) |
| | 5'-CAUAAAUGUUGUACAGGAUAUUUta-3' | (SEQ ID NO: 680) |
| | 3'-ACGUAUUUACAACAUGUCCUAUAAAAU-5' | (SEQ ID NO: 728) |
| LDHA-m1702 Target: | 5'-TGCATAAATGTTGTACAGGATATTTTA-3' | (SEQ ID NO: 776) |
| | 5'-AUAAAUGUUGUACAGGAUAUUUUat-3' | (SEQ ID NO: 681) |
| | 3'-CGUAUUUACAACAUGUCCUAUAAAAUA-5' | (SEQ ID NO: 729) |
| LDHA-m1703 Target: | 5'-GCATAAATGTTGTACAGGATATTTTAT-3' | (SEQ ID NO: 777) |
| | 5'-UAAAUGUUGUACAGGAUAUUUUAta-3' | (SEQ ID NO: 682) |
| | 3'-GUAUUUACAACAUGUCCUAUAAAAUAU-5' | (SEQ ID NO: 730) |
| LDHA-m1704 Target: | 5'-CATAAATGTTGTACAGGATATTTTATA-3' | (SEQ ID NO: 778) |
| | 5'-AAAUGUUGUACAGGAUAUUUUAUat-3' | (SEQ ID NO: 683) |
| | 3'-UAUUUACAACAUGUCCUAUAAAAUAUA-5' | (SEQ ID NO: 731) |
| LDHA-m1705 Target: | 5'-ATAAATGTTGTACAGGATATTTTATAT-3' | (SEQ ID NO: 779) |
| | 5'-AAUGUUGUACAGGAUAUUUUAUAta-3' | (SEQ ID NO: 684) |
| | 3'-AUUUACAACAUGUCCUAUAAAAUAUAU-5' | (SEQ ID NO: 732) |
| LDHA-m1706 Target: | 5'-TAAATGTTGTACAGGATATTTTATATA-3' | (SEQ ID NO: 780) |
| | 5'-AUGUUGUACAGGAUAUUUUAUAUat-3' | (SEQ ID NO: 685) |
| | 3'-UUUACAACAUGUCCUAUAAAAUAUAUA-5' | (SEQ ID NO: 733) |
| LDHA-m1707 Target: | 5'-AAATGTTGTACAGGATATTTTATATAT-3' | (SEQ ID NO: 781) |
| | 5'-UGUUGUACAGGAUAUUUUAUAUAtt-3' | (SEQ ID NO: 686) |
| | 3'-UUACAACAUGUCCUAUAAAAUAUAUAA-5' | (SEQ ID NO: 734) |
| LDHA-m1708 Target: | 5'-AATGTTGTACAGGATATTTTATATATT-3' | (SEQ ID NO: 782) |

TABLE 7-continued

Selected Mouse Anti-Lactate Dehydrogenase DsiRNA Agents (Asymmetrics)

```
                5'-GUUGUACAGGAUAUUUAUAUAUta-3'      (SEQ ID NO: 687)
                3'-UACAACAUGUCCUAUAAAAUAUAUAAU-5'   (SEQ ID NO: 735)
LDHA-m1709 Target: 5'-ATGTTGTACAGGATATTTTATATATTA-3' (SEQ ID NO: 783)

5'-UUGUACAGGAUAUUUAUAUAUUat-3'      (SEQ ID NO: 688)
                3'-ACAACAUGUCCUAUAAAAUAUAUAAUA-5'   (SEQ ID NO: 736)
LDHA-m1710 Target: 5'-TGTTGTACAGGATATTTTATATATTAT-3' (SEQ ID NO: 784)

5'-GUCUGUAGUGUGCAUUGCAAUAUta-3'     (SEQ ID NO: 689)
                3'-CACAGACAUCACACGUAACGUUAUAAU-5'   (SEQ ID NO: 737)
LDHA-m1739 Target: 5'-GTGTCTGTAGTGTGCATTGCAATATTA-3' (SEQ ID NO: 785)

5'-GUAGUGUGCAUUGCAAUAUUAUGtg-3'     (SEQ ID NO: 690)
                3'-GACAUCACACGUAACGUUAUAAUACAC-5'   (SEQ ID NO: 738)
LDHA-m1743 Target: 5'-CTGTAGTGTGCATTGCAATATTATGTG-3' (SEQ ID NO: 786)

5'-UAGUGUGCAUUGCAAUAUUAUGUga-3'     (SEQ ID NO: 691)
                3'-ACAUCACACGUAACGUUAUAAUACACU-5'   (SEQ ID NO: 739)
LDHA-m1744 Target: 5'-TGTAGTGTGCATTGCAATATTATGTGA-3' (SEQ ID NO: 787)

5'-GUGUGCAUUGCAAUAUUAUGUGAga-3'     (SEQ ID NO: 692)
                3'-AUCACACGUAACGUUAUAAUACACUCU-5'   (SEQ ID NO: 740)
LDHA-m1746 Target: 5'-TAGTGTGCATTGCAATATTATGTGAGA-3' (SEQ ID NO: 788)

5'-CAUUGCAAUAUUAUGUGAGAUGUaa-3'     (SEQ ID NO: 693)
                3'-ACGUAACGUUAUAAUACACUCUACAUU-5'   (SEQ ID NO: 741)
LDHA-m1751 Target: 5'-TGCATTGCAATATTATGTGAGATGTAA-3' (SEQ ID NO: 789)

5'-AUUGCAAUAUUAUGUGAGAUGUAag-3'     (SEQ ID NO: 694)
                3'-CGUAACGUUAUAAUACACUCUACAUUC-5'   (SEQ ID NO: 742)
LDHA-m1752 Target: 5'-GCATTGCAATATTATGTGAGATGTAAG-3' (SEQ ID NO: 790)

5'-GCAAUAUUAUGUGAGAUGUAAGAtc-3'     (SEQ ID NO: 695)
                3'-AACGUUAUAAUACACUCUACAUUCUAG-5'   (SEQ ID NO: 743)
LDHA-m1755 Target: 5'-TTGCAATATTATGTGAGATGTAAGATC-3' (SEQ ID NO: 791)

5'-CAAUAUUAUGUGAGAUGUAAGAUct-3'     (SEQ ID NO: 696)
                3'-ACGUUAUAAUACACUCUACAUUCUAGA-5'   (SEQ ID NO: 744)
LDHA-m1756 Target: 5'-TGCAATATTATGTGAGATGTAAGATCT-3' (SEQ ID NO: 792)
```

TABLE 8

Selected Mouse Anti-Lactate Dehydrogenase DsiRNAs, Unmodified Duplexes (Asymmetrics)

```
                5'-CAAGGACCAGCUGAUUGUGAAUCUU-3'    (SEQ ID NO: 793)
                3'-GAGUUCCUGGUCGACUAACACUUAGAA-5'  (SEQ ID NO: 697)
LDHA-m367 Target: 5'-CTCAAGGACCAGCTGATTGTGAATCTT-3' (SEQ ID NO: 745)

5'-AAGGACCAGCUGAUUGUGAAUCUUC-3'    (SEQ ID NO: 794)
                3'-AGUUCCUGGUCGACUAACACUUAGAAG-5'  (SEQ ID NO: 698)
LDHA-m368 Target: 5'-TCAAGGACCAGCTGATTGTGAATCTTC-3' (SEQ ID NO: 746)

5'-ACCAGCUGAUUGUGAAUCUUCUUAA-3'    (SEQ ID NO: 795)
                3'-CCUGGUCGACUAACACUUAGAAGAAUU-5'  (SEQ ID NO: 699)
LDHA-m372 Target: 5'-GGACCAGCTGATTGTGAATCTTCTTAA-3' (SEQ ID NO: 747)

5'-GCUGAUUGUGAAUCUUCUUAAGGAA-3'    (SEQ ID NO: 796)
                3'-GUCGACUAACACUUAGAAGAAUUCCUU-5'  (SEQ ID NO: 700)
LDHA-m376 Target: 5'-CAGCTGATTGTGAATCTTCTTAAGGAA-3' (SEQ ID NO: 748)

5'-CUUGUGCCAUCAGUAUCUUAAUGAA-3'    (SEQ ID NO: 797)
                3'-CCGAACACGGUAGUCAUAGAAUUACUU-5'  (SEQ ID NO: 701)
LDHA-m456 Target: 5'-GGCTTGTGCCATCAGTATCTTAATGAA-3' (SEQ ID NO: 749)

5'-CCCUUGUUGACGUCAUGGAAGACAA-3'    (SEQ ID NO: 798)
                3'-ACGGGAACAACUGCAGUACCUUCUGUU-5'  (SEQ ID NO: 702)
LDHA-m501 Target: 5'-TGCCCTTGTTGACGTCATGGAAGACAA-3' (SEQ ID NO: 750)

5'-GUUGACGUCAUGGAAGACAAACUCA-3'    (SEQ ID NO: 799)
                3'-AACAACUGCAGUACCUUCUGUUUGAGU-5'  (SEQ ID NO: 703)
LDHA-m506 Target: 5'-TTGTTGACGTCATGGAAGACAAACTCA-3' (SEQ ID NO: 751)
```

TABLE 8-continued

Selected Mouse Anti-Lactate Dehydrogenase DsiRNAs, Unmodified
Duplexes (Asymmetrics)

|  |  |  |
| --- | --- | --- |
|  | 5'-UUGACGUCAUGGAAGACAAACUCAA-3' | (SEQ ID NO: 800) |
|  | 3'-ACAACUGCAGUACCUUCUGUUUGAGUU-5' | (SEQ ID NO: 704) |
| LDHA-m507 Target: | 5'-TGTTGACGTCATGGAAGACAAACTCAA-3' | (SEQ ID NO: 752) |
|  | 5'-AUUGUCUCCAGCAAAGACUACUGUG-3' | (SEQ ID NO: 801) |
|  | 3'-UUUAACAGAGGUCGUUUCUGAUGACAC-5' | (SEQ ID NO: 705) |
| LDHA-m584 Target: | 5'-AAATTGTCTCCAGCAAAGACTACTGTG-3' | (SEQ ID NO: 753) |
|  | 5'-CGAAACGUGAACAUCUUCAAGUUCA-3' | (SEQ ID NO: 802) |
|  | 3'-UCGCUUUGCACUUGUAGAAGUUCAAGU-5' | (SEQ ID NO: 706) |
| LDHA-m689 Target: | 5'-AGCGAAACGTGAACATCTTCAAGTTCA-3' | (SEQ ID NO: 754) |
|  | 5'-CGUGAACAUCUUCAAGUUCAUCAUU-3' | (SEQ ID NO: 803) |
|  | 3'-UUGCACUUGUAGAAGUUCAAGUAGUAA-5' | (SEQ ID NO: 707) |
| LDHA-m694 Target: | 5'-AACGTGAACATCTTCAAGTTCATCATT-3' | (SEQ ID NO: 755) |
|  | 5'-GUGAACAUCUUCAAGUUCAUCAUUC-3' | (SEQ ID NO: 804) |
|  | 3'-UGCACUUGUAGAAGUUCAAGUAGUAAG-5' | (SEQ ID NO: 708) |
| LDHA-m695 Target: | 5'-ACGTGAACATCTTCAAGTTCATCATTC-3' | (SEQ ID NO: 756) |
|  | 5'-CCGAGUAAUUGGAAGUGGUUGCAAU-3' | (SEQ ID NO: 805) |
|  | 3'-UUGGCUCAUUAACCUUCACCAACGUUA-5' | (SEQ ID NO: 709) |
| LDHA-m823 Target: | 5'-AACCGAGTAATTGGAAGTGGTTGCAAT-3' | (SEQ ID NO: 757) |
|  | 5'-ACGAGGUGAUCAAGCUGAAAGGUUA-3' | (SEQ ID NO: 806) |
|  | 3'-GAUGCUCCACUAGUUCGACUUUCCAAU-5' | (SEQ ID NO: 710) |
| LDHA-m1071 Target: | 5'-CTACGAGGTGATCAAGCTGAAAGGTTA-3' | (SEQ ID NO: 758) |
|  | 5'-GCUGAGAGCAUAAUGAAGAACCUUA-3' | (SEQ ID NO: 807) |
|  | 3'-ACCGACUCUCGUAUUACUUCUUGGAAU-5' | (SEQ ID NO: 711) |
| LDHA-m1133 Target: | 5'-TGGCTGAGAGCATAATGAAGAACCTTA-3' | (SEQ ID NO: 759) |
|  | 5'-GAUUAAGGGUCUCUAUGGAAUCAAU-3' | (SEQ ID NO: 808) |
|  | 3'-UACUAAUUCCCAGAGAUACCUUAGUUA-5' | (SEQ ID NO: 712) |
| LDHA-m1183 Target: | 5'-ATGATTAAGGGTCTCTATGGAATCAAT-3' | (SEQ ID NO: 760) |
|  | 5'-AAAAUGGAAUCUCGGAUGUUGUGAA-3' | (SEQ ID NO: 809) |
|  | 3'-UGUUUUACCUUAGAGCCUACAACACUU-5' | (SEQ ID NO: 713) |
| LDHA-m1245 Target: | 5'-ACAAAATGGAATCTCGGATGTTGTGAA-3' | (SEQ ID NO: 761) |
|  | 5'-GGAAUCUCGGAUGUUGUGAAGGUGA-3' | (SEQ ID NO: 810) |
|  | 3'-UACCUUAGAGCCUACAACACUUCCACU-5' | (SEQ ID NO: 714) |
| LDHA-m1250 Target: | 5'-ATGGAATCTCGGATGTTGTGAAGGTGA-3' | (SEQ ID NO: 762) |
|  | 5'-CGGAUGUUGUGAAGGUGACACUGAC-3' | (SEQ ID NO: 811) |
|  | 3'-GAGCCUACAACACUUCCACUGUGACUG-5' | (SEQ ID NO: 715) |
| LDHA-m1257 Target: | 5'-CTCGGATGTTGTGAAGGTGACACTGAC-3' | (SEQ ID NO: 763) |
|  | 5'-GAUGCAUAUCUUGUGCAUAAAUGUU-3' | (SEQ ID NO: 812) |
|  | 3'-UACUACGUAUAGAACACGUAUUUACAA-5' | (SEQ ID NO: 716) |
| LDHA-m1687 Target: | 5'-ATGATGCATATCTTGTGCATAAATGTT-3' | (SEQ ID NO: 764) |
|  | 5'-AUGCAUAUCUUGUGCAUAAAUGUUG-3' | (SEQ ID NO: 813) |
|  | 3'-ACUACGUAUAGAACACGUAUUUACAAC-5' | (SEQ ID NO: 717) |
| LDHA-m1688 Target: | 5'-TGATGCATATCTTGTGCATAAATGTTG-3' | (SEQ ID NO: 765) |
|  | 5'-GCAUAUCUUGUGCAUAAAUGUUGUA-3' | (SEQ ID NO: 814) |
|  | 3'-UACGUAUAGAACACGUAUUUACAACAU-5' | (SEQ ID NO: 718) |
| LDHA-m1690 Target: | 5'-ATGCATATCTTGTGCATAAATGTTGTA-3' | (SEQ ID NO: 766) |
|  | 5'-CAUAUCUUGUGCAUAAAUGUUGUAC-3' | (SEQ ID NO: 815) |
|  | 3'-ACGUAUAGAACACGUAUUUACAACAUG-5' | (SEQ ID NO: 719) |
| LDHA-m1691 Target: | 5'-TGCATATCTTGTGCATAAATGTTGTAC-3' | (SEQ ID NO: 767) |
|  | 5'-AUAUCUUGUGCAUAAAUGUUGUACA-3' | (SEQ ID NO: 816) |
|  | 3'-CGUAUAGAACACGUAUUUACAACAUGU-5' | (SEQ ID NO: 720) |
| LDHA-m1692 Target: | 5'-GCATATCTTGTGCATAAATGTTGTACA-3' | (SEQ ID NO: 768) |
|  | 5'-AUCUUGUGCAUAAAUGUUGUACAGG-3' | (SEQ ID NO: 817) |
|  | 3'-UAUAGAACACGUAUUUACAACAUGUCC-5' | (SEQ ID NO: 721) |
| LDHA-m1694 Target: | 5'-ATATCTTGTGCATAAATGTTGTACAGG-3' | (SEQ ID NO: 769) |
|  | 5'-UCUUGUGCAUAAAUGUUGUACAGGA-3' | (SEQ ID NO: 818) |
|  | 3'-AUAGAACACGUAUUUACAACAUGUCCU-5' | (SEQ ID NO: 722) |
| LDHA-m1695 Target: | 5'-TATCTTGTGCATAAATGTTGTACAGGA-3' | (SEQ ID NO: 770) |

TABLE 8-continued

Selected Mouse Anti-Lactate Dehydrogenase DsiRNAs, Unmodified Duplexes (Asymmetrics)

|  |  |  |
|---|---|---|
|  | 5'-UUGUGCAUAAAUGUUGUACAGGAUA-3' | (SEQ ID NO: 819) |
|  | 3'-AGAACACGUAUUUACAACAUGUCCUAU-5' | (SEQ ID NO: 723) |
| LDHA-m1697 Target: | 5'-TCTTGTGCATAAATGTTGTACAGGATA-3' | (SEQ ID NO: 771) |
|  | 5'-UGUGCAUAAAUGUUGUACAGGAUAU-3' | (SEQ ID NO: 820) |
|  | 3'-GAACACGUAUUUACAACAUGUCCUAUA-5' | (SEQ ID NO: 724) |
| LDHA-m1698 Target: | 5'-CTTGTGCATAAATGTTGTACAGGATAT-3' | (SEQ ID NO: 772) |
|  | 5'-GUGCAUAAAUGUUGUACAGGAUAUU-3' | (SEQ ID NO: 821) |
|  | 3'-AACACGUAUUUACAACAUGUCCUAUAA-5' | (SEQ ID NO: 725) |
| LDHA-m1699 Target: | 5'-TTGTGCATAAATGTTGTACAGGATATT-3' | (SEQ ID NO: 773) |
|  | 5'-UGCAUAAAUGUUGUACAGGAUAUUU-3' | (SEQ ID NO: 822) |
|  | 3'-ACACGUAUUUACAACAUGUCCUAUAAA-5' | (SEQ ID NO: 726) |
| LDHA-m1700 Target: | 5'-TGTGCATAAATGTTGTACAGGATATTT-3' | (SEQ ID NO: 774) |
|  | 5'-GCAUAAAUGUUGUACAGGAUAUUUU-3' | (SEQ ID NO: 823) |
|  | 3'-CACGUAUUUACAACAUGUCCUAUAAAA-5' | (SEQ ID NO: 727) |
| LDHA-m1701 Target: | 5'-GTGCATAAATGTTGTACAGGATATTTT-3' | (SEQ ID NO: 775) |
|  | 5'-CAUAAAUGUUGUACAGGAUAUUUUA-3' | (SEQ ID NO: 824) |
|  | 3'-ACGUAUUUACAACAUGUCCUAUAAAAU-5' | (SEQ ID NO: 728) |
| LDHA-m1702 Target: | 5'-TGCATAAATGTTGTACAGGATATTTTA-3' | (SEQ ID NO: 776) |
|  | 5'-AUAAAUGUUGUACAGGAUAUUUUAU-3' | (SEQ ID NO: 825) |
|  | 3'-CGUAUUUACAACAUGUCCUAUAAAAUA-5' | (SEQ ID NO: 729) |
| LDHA-m1703 Target: | 5'-GCATAAATGTTGTACAGGATATTTTAT-3' | (SEQ ID NO: 777) |
|  | 5'-UAAAUGUUGUACAGGAUAUUUUAUA-3' | (SEQ ID NO: 826) |
|  | 3'-GUAUUUACAACAUGUCCUAUAAAAUAU-5' | (SEQ ID NO: 730) |
| LDHA-m1704 Target: | 5'-CATAAATGTTGTACAGGATATTTTATA-3' | (SEQ ID NO: 778) |
|  | 5'-AAAUGUUGUACAGGAUAUUUUAUAU-3' | (SEQ ID NO: 827) |
|  | 3'-UAUUUACAACAUGUCCUAUAAAAUAUA-5' | (SEQ ID NO: 731) |
| LDHA-m1705 Target: | 5'-ATAAATGTTGTACAGGATATTTTATAT-3' | (SEQ ID NO: 779) |
|  | 5'-AAUGUUGUACAGGAUAUUUUAUAUA-3' | (SEQ ID NO: 828) |
|  | 3'-AUUUACAACAUGUCCUAUAAAAUAUAU-5' | (SEQ ID NO: 732) |
| LDHA-m1706 Target: | 5'-TAAATGTTGTACAGGATATTTTATATA-3' | (SEQ ID NO: 780) |
|  | 5'-AUGUUGUACAGGAUAUUUUAUAUAU-3' | (SEQ ID NO: 829) |
|  | 3'-UUUACAACAUGUCCUAUAAAAUAUAUA-5' | (SEQ ID NO: 733) |
| LDHA-m1707 Target: | 5'-AAATGTTGTACAGGATATTTTATATAT-3' | (SEQ ID NO: 781) |
|  | 5'-UGUUGUACAGGAUAUUUUAUAUAUU-3' | (SEQ ID NO: 830) |
|  | 3'-UUACAACAUGUCCUAUAAAAUAUAUAA-5' | (SEQ ID NO: 734) |
| LDHA-m1708 Target: | 5'-AATGTTGTACAGGATATTTTATATATT-3' | (SEQ ID NO: 782) |
|  | 5'-GUUGUACAGGAUAUUUUAUAUAUUA-3' | (SEQ ID NO: 831) |
|  | 3'-UACAACAUGUCCUAUAAAAUAUAUAAU-5' | (SEQ ID NO: 735) |
| LDHA-m1709 Target: | 5'-ATGTTGTACAGGATATTTTATATATTA-3' | (SEQ ID NO: 783) |
|  | 5'-UUGUACAGGAUAUUUUAUAUAUUAU-3' | (SEQ ID NO: 832) |
|  | 3'-ACAACAUGUCCUAUAAAAUAUAUAAUA-5' | (SEQ ID NO: 736) |
| LDHA-m1710 Target: | 5'-TGTTGTACAGGATATTTTATATATTAT-3' | (SEQ ID NO: 784) |
|  | 5'-GUCUGUAGUGUGCAUUGCAAUAUUA-3' | (SEQ ID NO: 833) |
|  | 3'-CACAGACAUCACACGUAACGUUAUAAU-5' | (SEQ ID NO: 737) |
| LDHA-m1739 Target: | 5'-GTGTCTGTAGTGTGCATTGCAATATTA-3' | (SEQ ID NO: 785) |
|  | 5'-GUAGUGUGCAUUGCAAUAUUAUGUG-3' | (SEQ ID NO: 834) |
|  | 3'-GACAUCACACGUAACGUUAUAAUACAC-5' | (SEQ ID NO: 738) |
| LDHA-m1743 Target: | 5'-CTGTAGTGTGCATTGCAATATTATGTG-3' | (SEQ ID NO: 786) |
|  | 5'-UAGUGUGCAUUGCAAUAUUAUGUGA-3' | (SEQ ID NO: 835) |
|  | 3'-ACAUCACACGUAACGUUAUAAUACACU-5' | (SEQ ID NO: 739) |
| LDHA-m1744 Target: | 5'-TGTAGTGTGCATTGCAATATTATGTGA-3' | (SEQ ID NO: 787) |
|  | 5'-GUGUGCAUUGCAAUAUUAUGUGAGA-3' | (SEQ ID NO: 836) |
|  | 3'-AUCACACGUAACGUUAUAAUACACUCU-5' | (SEQ ID NO: 740) |
| LDHA-m1746 Target: | 5'-TAGTGTGCATTGCAATATTATGTGAGA-3' | (SEQ ID NO: 788) |
|  | 5'-CAUUGCAAUAUUAUGUGAGAUGUAA-3' | (SEQ ID NO: 837) |
|  | 3'-ACGUAACGUUAUAAUACACUCUACAUU-5' | (SEQ ID NO: 741) |
| LDHA-m1751 Target: | 5'-TGCATTGCAATATTATGTGAGATGTAA-3' | (SEQ ID NO: 789) |

TABLE 8-continued

Selected Mouse Anti-Lactate Dehydrogenase DsiRNAs, Unmodified Duplexes (Asymmetrics)

```
                  5'-AUUGCAAUAUUAUGUGAGAUGUAAG-3'     (SEQ ID NO: 838)
                  3'-CGUAACGUUAUAAUACACUCUACAUUC-5'   (SEQ ID NO: 742)
LDHA-m1752 Target:5'-GCATTGCAATATTATGTGAGATGTAAG-3'   (SEQ ID NO: 790)

5'-GCAAUAUUAUGUGAGAUGUAAGAUC-3'     (SEQ ID NO: 839)
                  3'-AACGUUAUAAUACACUCUACAUUCUAG-5'   (SEQ ID NO: 743)
LDHA-m1755 Target:5'-TTGCAATATTATGTGAGATGTAAGATC-3'   (SEQ ID NO: 791)

5'-CAAUAUUAUGUGAGAUGUAAGAUCU-3'     (SEQ ID NO: 840)
                  3'-ACGUUAUAAUACACUCUACAUUCUAGA-5'   (SEQ ID NO: 744)
LDHA-m1756 Target:5'-TGCAATATTATGTGAGATGTAAGATCT-3'   (SEQ ID NO: 792)
```

TABLE 9

DsiRNA Target Sequences (21mers) in Mouse Lactate Dehydrogenase mRNA

```
LDHA-m367  21 nt Target:  5'-CUCAAGGACCAGCUGAUUGUG-3'  (SEQ ID NO: 841)
LDHA-m368  21 nt Target:  5'-UCAAGGACCAGCUGAUUGUGA-3'  (SEQ ID NO: 842)
LDHA-m372  21 nt Target:  5'-GGACCAGCUGAUUGUGAAUCU-3'  (SEQ ID NO: 843)
LDHA-m376  21 nt Target:  5'-CAGCUGAUUGUGAAUCUUCUU-3'  (SEQ ID NO: 844)
LDHA-m456  21 nt Target:  5'-GGCUUGUGCCAUCAGUAUCUU-3'  (SEQ ID NO: 845)
LDHA-m501  21 nt Target:  5'-UGCCCUUGUUGACGUCAUGGA-3'  (SEQ ID NO: 846)
LDHA-m506  21 nt Target:  5'-UUGUUGACGUCAUGGAAGACA-3'  (SEQ ID NO: 847)
LDHA-m507  21 nt Target:  5'-UGUUGACGUCAUGGAAGACAA-3'  (SEQ ID NO: 848)
LDHA-m584  21 nt Target:  5'-AAAUUGUCUCCAGCAAAGACU-3'  (SEQ ID NO: 849)
LDHA-m689  21 nt Target:  5'-AGCGAAACGUGAACAUCUUCA-3'  (SEQ ID NO: 850)
LDHA-m694  21 nt Target:  5'-AACGUGAACAUCUUCAAGUUC-3'  (SEQ ID NO: 851)
LDHA-m695  21 nt Target:  5'-ACGUGAACAUCUUCAAGUUCA-3'  (SEQ ID NO: 852)
LDHA-m823  21 nt Target:  5'-AACCGAGUAAUUGGAAGUGGU-3'  (SEQ ID NO: 853)
LDHA-m1071 21 nt Target:  5'-CUACGAGGUGAUCAAGCUGAA-3'  (SEQ ID NO: 854)
LDHA-m1133 21 nt Target:  5'-UGGCUGAGAGCAUAAUGAAGA-3'  (SEQ ID NO: 855)
LDHA-m1183 21 nt Target:  5'-AUGAUUAAGGGUCUCUAUGGA-3'  (SEQ ID NO: 856)
LDHA-m1245 21 nt Target:  5'-ACAAAAUGGAAUCUCGGAUGU-3'  (SEQ ID NO: 857)
LDHA-m1250 21 nt Target:  5'-AUGGAAUCUCGGAUGUUGUGA-3'  (SEQ ID NO: 858)
LDHA-m1257 21 nt Target:  5'-CUCGGAUGUUGUGAAGGUGAC-3'  (SEQ ID NO: 859)
LDHA-m1687 21 nt Target:  5'-AUGAUGCAUAUCUUGUGCAUA-3'  (SEQ ID NO: 860)
LDHA-m1688 21 nt Target:  5'-UGAUGCAUAUCUUGUGCAUAA-3'  (SEQ ID NO: 861)
LDHA-m1690 21 nt Target:  5'-AUGCAUAUCUUGUGCAUAAAU-3'  (SEQ ID NO: 862)
LDHA-m1691 21 nt Target:  5'-UGCAUAUCUUGUGCAUAAAUG-3'  (SEQ ID NO: 863)
LDHA-m1692 21 nt Target:  5'-GCAUAUCUUGUGCAUAAAUGU-3'  (SEQ ID NO: 864)
LDHA-m1694 21 nt Target:  5'-AUAUCUUGUGCAUAAAUGUUG-3'  (SEQ ID NO: 865)
LDHA-m1695 21 nt Target:  5'-UAUCUUGUGCAUAAAUGUUGU-3'  (SEQ ID NO: 866)
LDHA-m1697 21 nt Target:  5'-UCUUGUGCAUAAAUGUUGUAC-3'  (SEQ ID NO: 867)
LDHA-m1698 21 nt Target:  5'-CUUGUGCAUAAAUGUUGUACA-3'  (SEQ ID NO: 868)
LDHA-m1699 21 nt Target:  5'-UUGUGCAUAAAUGUUGUACAG-3'  (SEQ ID NO: 869)
```

TABLE 9-continued

DsiRNA Target Sequences (21mers) in Mouse Lactate Dehydrogenase mRNA

LDHA-m1700 21 nt Target: 5'-UGUGCAUAAAUGUUGUACAGG-3' (SEQ ID NO: 870)

LDHA-m1701 21 nt Target: 5'-GUGCAUAAAUGUUGUACAGGA-3' (SEQ ID NO: 871)

LDHA-m1702 21 nt Target: 5'-UGCAUAAAUGUUGUACAGGAU-3' (SEQ ID NO: 872)

LDHA-m1703 21 nt Target: 5'-GCAUAAAUGUUGUACAGGAUA-3' (SEQ ID NO: 873)

LDHA-m1704 21 nt Target: 5'-CAUAAAUGUUGUACAGGAUAU-3' (SEQ ID NO: 874)

LDHA-m1705 21 nt Target: 5'-AUAAAUGUUGUACAGGAUAUU-3' (SEQ ID NO: 875)

LDHA-m1706 21 nt Target: 5'-UAAAUGUUGUACAGGAUAUUU-3' (SEQ ID NO: 876)

LDHA-m1707 21 nt Target: 5'-AAAUGUUGUACAGGAUAUUUU-3' (SEQ ID NO: 877)

LDHA-m1708 21 nt Target: 5'-AAUGUUGUACAGGAUAUUUUA-3' (SEQ ID NO: 878)

LDHA-m1709 21 nt Target: 5'-AUGUUGUACAGGAUAUUUUAU-3' (SEQ ID NO: 879)

LDHA-m1710 21 nt Target: 5'-UGUUGUACAGGAUAUUUUAUA-3' (SEQ ID NO: 880)

LDHA-m1739 21 nt Target: 5'-GUGUCUGUAGUGUGCAUUGCA-3' (SEQ ID NO: 881)

LDHA-m1743 21 nt Target: 5'-CUGUAGUGUGCAUUGCAAUAU-3' (SEQ ID NO: 882)

LDHA-m1744 21 nt Target: 5'-UGUAGUGUGCAUUGCAAUAUU-3' (SEQ ID NO: 883)

LDHA-m1746 21 nt Target: 5'-UAGUGUGCAUUGCAAUAUUAU-3' (SEQ ID NO: 884)

LDHA-m1751 21 nt Target: 5'-UGCAUUGCAAUAUUAUGUGAG-3' (SEQ ID NO: 885)

LDHA-m1752 21 nt Target: 5'-GCAUUGCAAUAUUAUGUGAGA-3' (SEQ ID NO: 886)

LDHA-m1755 21 nt Target: 5'-UUGCAAUAUUAUGUGAGAUGU-3' (SEQ ID NO: 887)

LDHA-m1756 21 nt Target: 5'-UGCAAUAUUAUGUGAGAUGUA-3' (SEQ ID NO: 888)

TABLE 10

Selected Mouse Anti-Lactate Dehydrogenase "Blunt/Blunt" DsiRNAs

```
               5'-CUCAAGGACCAGCUGAUUGUGAAUCUU-3'  (SEQ ID NO: 889)
               3'-GAGUUCCUGGUCGACUAACACUUAGAA-5'  (SEQ ID NO: 697)
LDHA-m367 Target: 5'-CTCAAGGACCAGCTGATTGTGAATCTT-3'  (SEQ ID NO: 745)

5'-UCAAGGACCAGCUGAUUGUGAAUCUUC-3'  (SEQ ID NO: 890)
               3'-AGUUCCUGGUCGACUAACACUUAGAAG-5'  (SEQ ID NO: 698)
LDHA-m368 Target: 5'-TCAAGGACCAGCTGATTGTGAATCTTC-3'  (SEQ ID NO: 746)

5'-GGACCAGCUGAUUGUGAAUCUUCUUAA-3'  (SEQ ID NO: 891)
               3'-CCUGGUCGACUAACACUUAGAAGAAUU-5'  (SEQ ID NO: 699)
LDHA-m372 Target: 5'-GGACCAGCTGATTGTGAATCTTCTTAA-3'  (SEQ ID NO: 747)

5'-CAGCUGAUUGUGAAUCUUCUUAAGGAA-3'  (SEQ ID NO: 892)
               3'-GUCGACUAACACUUAGAAGAAUUCCUU-5'  (SEQ ID NO: 700)
LDHA-m376 Target: 5'-CAGCTGATTGTGAATCTTCTTAAGGAA-3'  (SEQ ID NO: 748)

5'-GGCUUGUGCCAUCAGUAUCUUAAUGAA-3'  (SEQ ID NO: 893)
               3'-CCGAACACGGUAGUCAUAGAAUUACUU-5'  (SEQ ID NO: 701)
LDHA-m456 Target: 5'-GGCTTGTGCCATCAGTATCTTAATGAA-3'  (SEQ ID NO: 749)

5'-UGCCCUUGUUGACGUCAUGGAAGACAA-3'  (SEQ ID NO: 894)
               3'-ACGGGAACAACUGCAGUACCUUCUGUU-5'  (SEQ ID NO: 702)
LDHA-m501 Target: 5'-TGCCCTTGTTGACGTCATGGAAGACAA-3'  (SEQ ID NO: 750)

5'-UUGUUGACGUCAUGGAAGACAAACUCA-3'  (SEQ ID NO: 895)
               3'-AACAACUGCAGUACCUUCUGUUUGAGU-5'  (SEQ ID NO: 703)
LDHA-m506 Target: 5'-TTGTTGACGTCATGGAAGACAAACTCA-3'  (SEQ ID NO: 751)

5'-UGUUGACGUCAUGGAAGACAAACUCAA-3'  (SEQ ID NO: 896)
               3'-ACAACUGCAGUACCUUCUGUUUGAGUU-5'  (SEQ ID NO: 704)
LDHA-m507 Target: 5'-TGTTGACGTCATGGAAGACAAACTCAA-3'  (SEQ ID NO: 752)
```

TABLE 10-continued

Selected Mouse Anti-Lactate Dehydrogenase "Blunt/Blunt" DsiRNAs

|  |  |  |
|---|---|---|
|  | 5'-AAAUUGUCUCCAGCAAAGACUACUGUG-3' | (SEQ ID NO: 897) |
|  | 3'-UUUAACAGAGGUCGUUUCUGAUGACAC-5' | (SEQ ID NO: 705) |
| LDHA-m584 Target: | 5'-AAATTGTCTCCAGCAAAGACTACTGTG-3' | (SEQ ID NO: 753) |
|  | 5'-AGCGAAACGUGAACAUCUUCAAGUUCA-3' | (SEQ ID NO: 898) |
|  | 3'-UCGCUUUGCACUUGUAGAAGUUCAAGU-5' | (SEQ ID NO: 706) |
| LDHA-m689 Target: | 5'-AGCGAAACGTGAACATCTTCAAGTTCA-3' | (SEQ ID NO: 754) |
|  | 5'-AACGUGAACAUCUUCAAGUUCAUCAUU-3' | (SEQ ID NO: 899) |
|  | 3'-UUGCACUUGUAGAAGUUCAAGUAGUAA-5' | (SEQ ID NO: 707) |
| LDHA-m694 Target: | 5'-AACGTGAACATCTTCAAGTTCATCATT-3' | (SEQ ID NO: 755) |
|  | 5'-ACGUGAACAUCUUCAAGUUCAUCAUUC-3' | (SEQ ID NO: 900) |
|  | 3'-UGCACUUGUAGAAGUUCAAGUAGUAAG-5' | (SEQ ID NO: 708) |
| LDHA-m695 Target: | 5'-ACGTGAACATCTTCAAGTTCATCATTC-3' | (SEQ ID NO: 756) |
|  | 5'-AACCGAGUAAUUGGAAGUGGUUGCAAU-3' | (SEQ ID NO: 901) |
|  | 3'-UUGGCUCAUUAACCUUCACCAACGUUA-5' | (SEQ ID NO: 709) |
| LDHA-m823 Target: | 5'-AACCGAGTAATTGGAAGTGGTTGCAAT-3' | (SEQ ID NO: 757) |
|  | 5'-CUACGAGGUGAUCAAGCUGAAAGGUUA-3' | (SEQ ID NO: 902) |
|  | 3'-GAUGCUCCACUAGUUCGACUUUCCAAU-5' | (SEQ ID NO: 710) |
| LDHA-m1071 Target: | 5'-CTACGAGGTGATCAAGCTGAAAGGTTA-3' | (SEQ ID NO: 758) |
|  | 5'-UGGCUGAGAGCAUAAUGAAGAACCUUA-3' | (SEQ ID NO: 903) |
|  | 3'-ACCGACUCUCGUAUUACUUCUUGGAAU-5' | (SEQ ID NO: 711) |
| LDHA-m1133 Target: | 5'-TGGCTGAGAGCATAATGAAGAACCTTA-3' | (SEQ ID NO: 759) |
|  | 5'-AUGAUUAAGGGUCUCUAUGGAAUCAAU-3' | (SEQ ID NO: 904) |
|  | 3'-UACUAAUUCCCAGAGAUACCUUAGUUA-5' | (SEQ ID NO: 712) |
| LDHA-m1183 Target: | 5'-ATGATTAAGGGTCTCTATGGAATCAAT-3' | (SEQ ID NO: 760) |
|  | 5'-ACAAAAUGGAAUCUCGGAUGUUGUGAA-3' | (SEQ ID NO: 905) |
|  | 3'-UGUUUUACCUUAGAGCCUACAACACUU-5' | (SEQ ID NO: 713) |
| LDHA-m1245 Target: | 5'-ACAAAATGGAATCTCGGATGTTGTGAA-3' | (SEQ ID NO: 761) |
|  | 5'-AUGGAAUCUCGGAUGUUGUGAAGGUGA-3' | (SEQ ID NO: 906) |
|  | 3'-UACCUUAGAGCCUACAACACUUCCACU-5' | (SEQ ID NO: 714) |
| LDHA-m1250 Target: | 5'-ATGGAATCTCGGATGTTGTGAAGGTGA-3' | (SEQ ID NO: 762) |
|  | 5'-CUCGGAUGUUGUGAAGGUGACACUGAC-3' | (SEQ ID NO: 907) |
|  | 3'-GAGCCUACAACACUUCCACUGUGACUG-5' | (SEQ ID NO: 715) |
| LDHA-m1257 Target: | 5'-CTCGGATGTTGTGAAGGTGACACTGAC-3' | (SEQ ID NO: 763) |
|  | 5'-AUGAUGCAUAUCUUGUGCAUAAAUGUU-3' | (SEQ ID NO: 908) |
|  | 3'-UACUACGUAUAGAACACGUAUUUACAA-5' | (SEQ ID NO: 716) |
| LDHA-m1687 Target: | 5'-ATGATGCATATCTTGTGCATAAATGTT-3' | (SEQ ID NO: 764) |
|  | 5'-UGAUGCAUAUCUUGUGCAUAAAUGUUG-3' | (SEQ ID NO: 909) |
|  | 3'-ACUACGUAUAGAACACGUAUUUACAAC-5' | (SEQ ID NO: 717) |
| LDHA-m1688 Target: | 5'-TGATGCATATCTTGTGCATAAATGTTG-3' | (SEQ ID NO: 765) |
|  | 5'-AUGCAUAUCUUGUGCAUAAAUGUUGUA-3' | (SEQ ID NO: 910) |
|  | 3'-UACGUAUAGAACACGUAUUUACAACAU-5' | (SEQ ID NO: 718) |
| LDHA-m1690 Target: | 5'-ATGCATATCTTGTGCATAAATGTTGTA-3' | (SEQ ID NO: 766) |
|  | 5'-UGCAUAUCUUGUGCAUAAAUGUUGUAC-3' | (SEQ ID NO: 911) |
|  | 3'-ACGUAUAGAACACGUAUUUACAACAUG-5' | (SEQ ID NO: 719) |
| LDHA-m1691 Target: | 5'-TGCATATCTTGTGCATAAATGTTGTAC-3' | (SEQ ID NO: 767) |
|  | 5'-GCAUAUCUUGUGCAUAAAUGUUGUACA-3' | (SEQ ID NO: 912) |
|  | 3'-CGUAUAGAACACGUAUUUACAACAUGU-5' | (SEQ ID NO: 720) |
| LDHA-m1692 Target: | 5'-GCATATCTTGTGCATAAATGTTGTACA-3' | (SEQ ID NO: 768) |
|  | 5'-AUAUCUUGUGCAUAAAUGUUGUACAGG-3' | (SEQ ID NO: 913) |
|  | 3'-UAUAGAACACGUAUUUACAACAUGUCC-5' | (SEQ ID NO: 721) |
| LDHA-m1694 Target: | 5'-ATATCTTGTGCATAAATGTTGTACAGG-3' | (SEQ ID NO: 769) |
|  | 5'-UAUCUUGUGCAUAAAUGUUGUACAGGA-3' | (SEQ ID NO: 914) |
|  | 3'-AUAGAACACGUAUUUACAACAUGUCCU-5' | (SEQ ID NO: 722) |
| LDHA-m1695 Target: | 5'-TATCTTGTGCATAAATGTTGTACAGGA-3' | (SEQ ID NO: 770) |
|  | 5'-UCUUGUGCAUAAAUGUUGUACAGGAUA-3' | (SEQ ID NO: 915) |
|  | 3'-AGAACACGUAUUUACAACAUGUCCUAU-5' | (SEQ ID NO: 723) |
| LDHA-m1697 Target: | 5'-TCTTGTGCATAAATGTTGTACAGGATA-3' | (SEQ ID NO: 771) |

TABLE 10-continued

Selected Mouse Anti-Lactate Dehydrogenase "Blunt/Blunt" DsiRNAs

```
                     5'-CUUGUGCAUAAAUGUUGUACAGGAUAU-3'    (SEQ ID NO: 916)
                     3'-GAACACGUAUUUACAACAUGUCCUAUA-5'    (SEQ ID NO: 724)
LDHA-m1698 Target: 5'-CTTGTGCATAAATGTTGTACAGGATAT-3'      (SEQ ID NO: 772)

5'-UUGUGCAUAAAUGUUGUACAGGAUAUU-3'    (SEQ ID NO: 917)
                     3'-AACACGUAUUUACAACAUGUCCUAUAA-5'    (SEQ ID NO: 725)
LDHA-m1699 Target: 5'-TTGTGCATAAATGTTGTACAGGATATT-3'      (SEQ ID NO: 773)

5'-UGUGCAUAAAUGUUGUACAGGAUAUUU-3'    (SEQ ID NO: 918)
                     3'-ACACGUAUUUACAACAUGUCCUAUAAA-5'    (SEQ ID NO: 726)
LDHA-m1700 Target: 5'-TGTGCATAAATGTTGTACAGGATATTT-3'      (SEQ ID NO: 774)

5'-GUGCAUAAAUGUUGUACAGGAUAUUUU-3'    (SEQ ID NO: 919)
                     3'-CACGUAUUUACAACAUGUCCUAUAAAA-5'    (SEQ ID NO: 727)
LDHA-m1701 Target: 5'-GTGCATAAATGTTGTACAGGATATTTT-3'      (SEQ ID NO: 775)

5'-UGCAUAAAUGUUGUACAGGAUAUUUUA-3'    (SEQ ID NO: 920)
                     3'-ACGUAUUUACAACAUGUCCUAUAAAAU-5'    (SEQ ID NO: 728)
LDHA-m1702 Target: 5'-TGCATAAATGTTGTACAGGATATTTTA-3'      (SEQ ID NO: 776)

5'-GCAUAAAUGUUGUACAGGAUAUUUUAU-3'    (SEQ ID NO: 921)
                     3'-CGUAUUUACAACAUGUCCUAUAAAAUA-5'    (SEQ ID NO: 729)
LDHA-m1703 Target: 5'-GCATAAATGTTGTACAGGATATTTTAT-3'      (SEQ ID NO: 777)

5'-CAUAAAUGUUGUACAGGAUAUUUUAUA-3'    (SEQ ID NO: 922)
                     3'-GUAUUUACAACAUGUCCUAUAAAAUAU-5'    (SEQ ID NO: 730)
LDHA-m1704 Target: 5'-CATAAATGTTGTACAGGATATTTTATA-3'      (SEQ ID NO: 778)

5'-AUAAAUGUUGUACAGGAUAUUUUAUAU-3'    (SEQ ID NO: 923)
                     3'-UAUUUACAACAUGUCCUAUAAAAUAUA-5'    (SEQ ID NO: 731)
LDHA-m1705 Target: 5'-ATAAATGTTGTACAGGATATTTTATAT-3'      (SEQ ID NO: 779)

5'-UAAAUGUUGUACAGGAUAUUUUAUAUA-3'    (SEQ ID NO: 924)
                     3'-AUUUACAACAUGUCCUAUAAAAUAUAU-5'    (SEQ ID NO: 732)
LDHA-m1706 Target: 5'-TAAATGTTGTACAGGATATTTTATATA-3'      (SEQ ID NO: 780)

5'-AAAUGUUGUACAGGAUAUUUUAUAUAU-3'    (SEQ ID NO: 925)
                     3'-UUUACAACAUGUCCUAUAAAAUAUAUA-5'    (SEQ ID NO: 733)
LDHA-m1707 Target: 5'-AAATGTTGTACAGGATATTTTATATAT-3'      (SEQ ID NO: 781)

5'-AAUGUUGUACAGGAUAUUUUAUAUAUU-3'    (SEQ ID NO: 926)
                     3'-UUACAACAUGUCCUAUAAAAUAUAUAA-5'    (SEQ ID NO: 734)
LDHA-m1708 Target: 5'-AATGTTGTACAGGATATTTTATATATT-3'      (SEQ ID NO: 782)

5'-AUGUUGUACAGGAUAUUUUAUAUAUUA-3'    (SEQ ID NO: 927)
                     3'-UACAACAUGUCCUAUAAAAUAUAUAAU-5'    (SEQ ID NO: 735)
LDHA-m1709 Target: 5'-ATGTTGTACAGGATATTTTATATATTA-3'      (SEQ ID NO: 783)

5'-UGUUGUACAGGAUAUUUUAUAUAUUAU-3'    (SEQ ID NO: 928)
                     3'-ACAACAUGUCCUAUAAAAUAUAUAAUA-5'    (SEQ ID NO: 736)
LDHA-m1710 Target: 5'-TGTTGTACAGGATATTTTATATATTAT-3'      (SEQ ID NO: 784)

5'-GUGUCUGUAGUGUGCAUUGCAAUAUUA-3'    (SEQ ID NO: 929)
                     3'-CACAGACAUCACACGUAACGUUAUAAU-5'    (SEQ ID NO: 737)
LDHA-m1739 Target: 5'-GTGTCTGTAGTGTGCATTGCAATATTA-3'      (SEQ ID NO: 785)

5'-CUGUAGUGUGCAUUGCAAUAUUAUGUG-3'    (SEQ ID NO: 930)
                     3'-GACAUCACACGUAACGUUAUAAUACAC-5'    (SEQ ID NO: 738)
LDHA-m1743 Target: 5'-CTGTAGTGTGCATTGCAATATTATGTG-3'      (SEQ ID NO: 786)

5'-UGUAGUGUGCAUUGCAAUAUUAUGUGA-3'    (SEQ ID NO: 931)
                     3'-ACAUCACACGUAACGUUAUAAUACACU-5'    (SEQ ID NO: 739)
LDHA-m1744 Target: 5'-TGTAGTGTGCATTGCAATATTATGTGA-3'      (SEQ ID NO: 787)

5'-UAGUGUGCAUUGCAAUAUUAUGUGAGA-3'    (SEQ ID NO: 932)
                     3'-AUCACACGUAACGUUAUAAUACACUCU-5'    (SEQ ID NO: 740)
LDHA-m1746 Target: 5'-TAGTGTGCATTGCAATATTATGTGAGA-3'      (SEQ ID NO: 788)

5'-UGCAUUGCAAUAUUAUGUGAGAUGUAA-3'    (SEQ ID NO: 933)
                     3'-ACGUAACGUUAUAAUACACUCUACAUU-5'    (SEQ ID NO: 741)
LDHA-m1751 Target: 5'-TGCATTGCAATATTATGTGAGATGTAA-3'      (SEQ ID NO: 789)

5'-GCAUUGCAAUAUUAUGUGAGAUGUAAG-3'    (SEQ ID NO: 934)
                     3'-CGUAACGUUAUAAUACACUCUACAUUC-5'    (SEQ ID NO: 742)
LDHA-m1752 Target: 5'-GCATTGCAATATTATGTGAGATGTAAG-3'      (SEQ ID NO: 790)
```

TABLE 10-continued

Selected Mouse Anti-Lactate Dehydrogenase "Blunt/Blunt" DsiRNAs

```
                 5'-UUGCAAUAUUAUGUGAGAUGUAAGAUC-3'  (SEQ ID NO: 935)
                 3'-AACGUUAUAAUACACUCUACAUUCUAG-5'  (SEQ ID NO: 743)
LDHA-m1755 Target:5'-TTGCAATATTATGTGAGATGTAAGATC-3' (SEQ ID NO: 791)

5'-UGCAAUAUUAUGUGAGAUGUAAGAUCU-3'  (SEQ ID NO: 936)
                 3'-ACGUUAUAAUACACUCUACAUUCUAGA-5'  (SEQ ID NO: 744)
LDHA-m1756 Target:5'-TGCAATATTATGTGAGATGTAAGATCT-3' (SEQ ID NO: 792)
```

TABLE 11

DsiRNA Component 19 Nucleotide Target Sequences in Mouse Lactate Dehydrogenase mRNA

| | | |
|---|---|---|
| LDHA-m367 19 nt Target #1: | 5'-CAAGGACCAGCUGAUUGUG-3' | (SEQ ID NO: 937) |
| LDHA-m367 19 nt Target #2: | 5'-UCAAGGACCAGCUGAUUGU-3' | (SEQ ID NO: 985) |
| LDHA-m367 19 nt Target #3: | 5'-CUCAAGGACCAGCUGAUUG-3' | (SEQ ID NO: 1033) |
| LDHA-m368 19 nt Target #1: | 5'-AAGGACCAGCUGAUUGUGA-3' | (SEQ ID NO: 938) |
| LDHA-m368 19 nt Target #2: | 5'-CAAGGACCAGCUGAUUGUG-3' | (SEQ ID NO: 986) |
| LDHA-m368 19 nt Target #3: | 5'-UCAAGGACCAGCUGAUUGU-3' | (SEQ ID NO: 1034) |
| LDHA-m372 19 nt Target #1: | 5'-ACCAGCUGAUUGUGAAUCU-3' | (SEQ ID NO: 939) |
| LDHA-m372 19 nt Target #2: | 5'-GACCAGCUGAUUGUGAAUC-3' | (SEQ ID NO: 987) |
| LDHA-m372 19 nt Target #3: | 5'-GGACCAGCUGAUUGUGAAU-3' | (SEQ ID NO: 1035) |
| LDHA-m376 19 nt Target #1: | 5'-GCUGAUUGUGAAUCUUCUU-3' | (SEQ ID NO: 940) |
| LDHA-m376 19 nt Target #2: | 5'-AGCUGAUUGUGAAUCUUCU-3' | (SEQ ID NO: 988) |
| LDHA-m376 19 nt Target #3: | 5'-CAGCUGAUUGUGAAUCUUC-3' | (SEQ ID NO: 1036) |
| LDHA-m456 19 nt Target #1: | 5'-CUUGUGCCAUCAGUAUCUU-3' | (SEQ ID NO: 941) |
| LDHA-m456 19 nt Target #2: | 5'-GCUUGUGCCAUCAGUAUCU-3' | (SEQ ID NO: 989) |
| LDHA-m456 19 nt Target #3: | 5'-GGCUUGUGCCAUCAGUAUC-3' | (SEQ ID NO: 1037) |
| LDHA-m501 19 nt Target #1: | 5'-CCCUUGUUGACGUCAUGGA-3' | (SEQ ID NO: 942) |
| LDHA-m501 19 nt Target #2: | 5'-GCCCUUGUUGACGUCAUGG-3' | (SEQ ID NO: 990) |
| LDHA-m501 19 nt Target #3: | 5'-UGCCCUUGUUGACGUCAUG-3' | (SEQ ID NO: 1038) |
| LDHA-m506 19 nt Target #1: | 5'-GUUGACGUCAUGGAAGACA-3' | (SEQ ID NO: 943) |
| LDHA-m506 19 nt Target #2: | 5'-UGUUGACGUCAUGGAAGAC-3' | (SEQ ID NO: 991) |
| LDHA-m506 19 nt Target #3: | 5'-UUGUUGACGUCAUGGAAGA-3' | (SEQ ID NO: 1039) |
| LDHA-m507 19 nt Target #1: | 5'-UUGACGUCAUGGAAGACAA-3' | (SEQ ID NO: 944) |
| LDHA-m507 19 nt Target #2: | 5'-GUUGACGUCAUGGAAGACA-3' | (SEQ ID NO: 992) |
| LDHA-m507 19 nt Target #3: | 5'-UGUUGACGUCAUGGAAGAC-3' | (SEQ ID NO: 1040) |
| LDHA-m584 19 nt Target #1: | 5'-AUUGUCUCCAGCAAAGACU-3' | (SEQ ID NO: 945) |
| LDHA-m584 19 nt Target #2: | 5'-AAUUGUCUCCAGCAAAGAC-3' | (SEQ ID NO: 993) |
| LDHA-m584 19 nt Target #3: | 5'-AAAUUGUCUCCAGCAAAGA-3' | (SEQ ID NO: 1041) |
| LDHA-m689 19 nt Target #1: | 5'-CGAAACGUGAACAUCUUCA-3' | (SEQ ID NO: 946) |
| LDHA-m689 19 nt Target #2: | 5'-GCGAAACGUGAACAUCUUC-3' | (SEQ ID NO: 994) |
| LDHA-m689 19 nt Target #3: | 5'-AGCGAAACGUGAACAUCUU-3' | (SEQ ID NO: 1042) |
| LDHA-m694 19 nt Target #1: | 5'-CGUGAACAUCUUCAAGUUC-3' | (SEQ ID NO: 947) |

TABLE 11-continued

DsiRNA Component 19 Nucleotide Target Sequences in Mouse Lactate Dehydrogenase mRNA

| | | | |
|---|---|---|---|
| LDHA-m694 19 nt Target #2: | 5'-ACGUGAACAUCUUCAAGUU-3' | (SEQ ID NO: 995) |
| LDHA-m694 19 nt Target #3: | 5'-AACGUGAACAUCUUCAAGU-3' | (SEQ ID NO: 1043) |
| LDHA-m695 19 nt Target #1: | 5'-GUGAACAUCUUCAAGUUCA-3' | (SEQ ID NO: 948) |
| LDHA-m695 19 nt Target #2: | 5'-CGUGAACAUCUUCAAGUUC-3' | (SEQ ID NO: 996) |
| LDHA-m695 19 nt Target #3: | 5'-ACGUGAACAUCUUCAAGUU-3' | (SEQ ID NO: 1044) |
| LDHA-m823 19 nt Target #1: | 5'-CCGAGUAAUUGGAAGUGGU-3' | (SEQ ID NO: 949) |
| LDHA-m823 19 nt Target #2: | 5'-ACCGAGUAAUUGGAAGUGG-3' | (SEQ ID NO: 997) |
| LDHA-m823 19 nt Target #3: | 5'-AACCGAGUAAUUGGAAGUG-3' | (SEQ ID NO: 1045) |
| LDHA-m1071 19 nt Target #1: | 5'-ACGAGGUGAUCAAGCUGAA-3' | (SEQ ID NO: 950) |
| LDHA-m1071 19 nt Target #2: | 5'-UACGAGGUGAUCAAGCUGA-3' | (SEQ ID NO: 998) |
| LDHA-m1071 19 nt Target #3: | 5'-CUACGAGGUGAUCAAGCUG-3' | (SEQ ID NO: 1046) |
| LDHA-m1133 19 nt Target #1: | 5'-GCUGAGAGCAUAAUGAAGA-3' | (SEQ ID NO: 951) |
| LDHA-m1133 19 nt Target #2: | 5'-GGCUGAGAGCAUAAUGAAG-3' | (SEQ ID NO: 999) |
| LDHA-m1133 19 nt Target #3: | 5'-UGGCUGAGAGCAUAAUGAA-3' | (SEQ ID NO: 1047) |
| LDHA-m1183 19 nt Target #1: | 5'-GAUUAAGGGUCUCUAUGGA-3' | (SEQ ID NO: 952) |
| LDHA-m1183 19 nt Target #2: | 5'-UGAUUAAGGGUCUCUAUGG-3' | (SEQ ID NO: 1000) |
| LDHA-m1183 19 nt Target #3: | 5'-AUGAUUAAGGGUCUCUAUG-3' | (SEQ ID NO: 1048) |
| LDHA-m1245 19 nt Target #1: | 5'-AAAAUGGAAUCUCGGAUGU-3' | (SEQ ID NO: 953) |
| LDHA-m1245 19 nt Target #2: | 5'-CAAAAUGGAAUCUCGGAUG-3' | (SEQ ID NO: 1001) |
| LDHA-m1245 19 nt Target #3: | 5'-ACAAAAUGGAAUCUCGGAU-3' | (SEQ ID NO: 1049) |
| LDHA-m1250 19 nt Target #1: | 5'-GGAAUCUCGGAUGUUGUGA-3' | (SEQ ID NO: 954) |
| LDHA-m1250 19 nt Target #2: | 5'-UGGAAUCUCGGAUGUUGUG-3' | (SEQ ID NO: 1002) |
| LDHA-m1250 19 nt Target #3: | 5'-AUGGAAUCUCGGAUGUUGU-3' | (SEQ ID NO: 1050) |
| LDHA-m1257 19 nt Target #1: | 5'-CGGAUGUUGUGAAGGUGAC-3' | (SEQ ID NO: 955) |
| LDHA-m1257 19 nt Target #2: | 5'-UCGGAUGUUGUGAAGGUGA-3' | (SEQ ID NO: 1003) |
| LDHA-m1257 19 nt Target #3: | 5'-CUCGGAUGUUGUGAAGGUG-3' | (SEQ ID NO: 1051) |
| LDHA-m1687 19 nt Target #1: | 5'-GAUGCAUAUCUUGUGCAUA-3' | (SEQ ID NO: 956) |
| LDHA-m1687 19 nt Target #2: | 5'-UGAUGCAUAUCUUGUGCAU-3' | (SEQ ID NO: 1004) |
| LDHA-m1687 19 nt Target #3: | 5'-AUGAUGCAUAUCUUGUGCA-3' | (SEQ ID NO: 1052) |
| LDHA-m1688 19 nt Target #1: | 5'-AUGCAUAUCUUGUGCAUAA-3' | (SEQ ID NO: 957) |
| LDHA-m1688 19 nt Target #2: | 5'-GAUGCAUAUCUUGUGCAUA-3' | (SEQ ID NO: 1005) |
| LDHA-m1688 19 nt Target #3: | 5'-UGAUGCAUAUCUUGUGCAU-3' | (SEQ ID NO: 1053) |
| LDHA-m1690 19 nt Target #1: | 5'-GCAUAUCUUGUGCAUAAAU-3' | (SEQ ID NO: 958) |
| LDHA-m1690 19 nt Target #2: | 5'-UGCAUAUCUUGUGCAUAAA-3' | (SEQ ID NO: 1006) |
| LDHA-m1690 19 nt Target #3: | 5'-AUGCAUAUCUUGUGCAUAA-3' | (SEQ ID NO: 1054) |
| LDHA-m1691 19 nt Target #1: | 5'-CAUAUCUUGUGCAUAAAUG-3' | (SEQ ID NO: 959) |
| LDHA-m1691 19 nt Target #2: | 5'-GCAUAUCUUGUGCAUAAAU-3' | (SEQ ID NO: 1007) |
| LDHA-m1691 19 nt Target #3: | 5'-UGCAUAUCUUGUGCAUAAA-3' | (SEQ ID NO: 1055) |

TABLE 11-continued

DsiRNA Component 19 Nucleotide Target Sequences in Mouse Lactate
Dehydrogenase mRNA

| | | |
|---|---|---|
| LDHA-m1692 19 nt Target #1: | 5'-AUAUCUUGUGCAUAAAUGU-3' | (SEQ ID NO: 960) |
| LDHA-m1692 19 nt Target #2: | 5'-CAUAUCUUGUGCAUAAAUG-3' | (SEQ ID NO: 1008) |
| LDHA-m1692 19 nt Target #3: | 5'-GCAUAUCUUGUGCAUAAAU-3' | (SEQ ID NO: 1056) |
| LDHA-m1694 19 nt Target #1: | 5'-AUCUUGUGCAUAAAUGUUG-3' | (SEQ ID NO: 961) |
| LDHA-m1694 19 nt Target #2: | 5'-UAUCUUGUGCAUAAAUGUU-3' | (SEQ ID NO: 1009) |
| LDHA-m1694 19 nt Target #3: | 5'-AUAUCUUGUGCAUAAAUGU-3' | (SEQ ID NO: 1057) |
| LDHA-m1695 19 nt Target #1: | 5'-UCUUGUGCAUAAAUGUUGU-3' | (SEQ ID NO: 962) |
| LDHA-m1695 19 nt Target #2: | 5'-AUCUUGUGCAUAAAUGUUG-3' | (SEQ ID NO: 1010) |
| LDHA-m1695 19 nt Target #3: | 5'-UAUCUUGUGCAUAAAUGUU-3' | (SEQ ID NO: 1058) |
| LDHA-m1697 19 nt Target #1: | 5'-UUGUGCAUAAAUGUUGUAC-3' | (SEQ ID NO: 963) |
| LDHA-m1697 19 nt Target #2: | 5'-CUUGUGCAUAAAUGUUGUA-3' | (SEQ ID NO: 1011) |
| LDHA-m1697 19 nt Target #3: | 5'-UCUUGUGCAUAAAUGUUGU-3' | (SEQ ID NO: 1059) |
| LDHA-m1698 19 nt Target #1: | 5'-UGUGCAUAAAUGUUGUACA-3' | (SEQ ID NO: 964) |
| LDHA-m1698 19 nt Target #2: | 5'-UUGUGCAUAAAUGUUGUAC-3' | (SEQ ID NO: 1012) |
| LDHA-m1698 19 nt Target #3: | 5'-CUUGUGCAUAAAUGUUGUA-3' | (SEQ ID NO: 1060) |
| LDHA-m1699 19 nt Target #1: | 5'-GUGCAUAAAUGUUGUACAG-3' | (SEQ ID NO: 965) |
| LDHA-m1699 19 nt Target #2: | 5'-UGUGCAUAAAUGUUGUACA-3' | (SEQ ID NO: 1013) |
| LDHA-m1699 19 nt Target #3: | 5'-UUGUGCAUAAAUGUUGUAC-3' | (SEQ ID NO: 1061) |
| LDHA-m1700 19 nt Target #1: | 5'-UGCAUAAAUGUUGUACAGG-3' | (SEQ ID NO: 966) |
| LDHA-m1700 19 nt Target #2: | 5'-GUGCAUAAAUGUUGUACAG-3' | (SEQ ID NO: 1014) |
| LDHA-m1700 19 nt Target #3: | 5'-UGUGCAUAAAUGUUGUACA-3' | (SEQ ID NO: 1062) |
| LDHA-m1701 19 nt Target #1: | 5'-GCAUAAAUGUUGUACAGGA-3' | (SEQ ID NO: 967) |
| LDHA-m1701 19 nt Target #2: | 5'-UGCAUAAAUGUUGUACAGG-3' | (SEQ ID NO: 1015) |
| LDHA-m1701 19 nt Target #3: | 5'-GUGCAUAAAUGUUGUACAG-3' | (SEQ ID NO: 1063) |
| LDHA-m1702 19 nt Target #1: | 5'-CAUAAAUGUUGUACAGGAU-3' | (SEQ ID NO: 968) |
| LDHA-m1702 19 nt Target #2: | 5'-GCAUAAAUGUUGUACAGGA-3' | (SEQ ID NO: 1016) |
| LDHA-m1702 19 nt Target #3: | 5'-UGCAUAAAUGUUGUACAGG-3' | (SEQ ID NO: 1064) |
| LDHA-m1703 19 nt Target #1: | 5'-AUAAAUGUUGUACAGGAUA-3' | (SEQ ID NO: 969) |
| LDHA-m1703 19 nt Target #2: | 5'-CAUAAAUGUUGUACAGGAU-3' | (SEQ ID NO: 1017) |
| LDHA-m1703 19 nt Target #3: | 5'-GCAUAAAUGUUGUACAGGA-3' | (SEQ ID NO: 1065) |
| LDHA-m1704 19 nt Target #1: | 5'-UAAAUGUUGUACAGGAUAU-3' | (SEQ ID NO: 970) |
| LDHA-m1704 19 nt Target #2: | 5'-AUAAAUGUUGUACAGGAUA-3' | (SEQ ID NO: 1018) |
| LDHA-m1704 19 nt Target #3: | 5'-CAUAAAUGUUGUACAGGAU-3' | (SEQ ID NO: 1066) |
| LDHA-m1705 19 nt Target #1: | 5'-AAAUGUUGUACAGGAUAUU-3' | (SEQ ID NO: 971) |
| LDHA-m1705 19 nt Target #2: | 5'-UAAAUGUUGUACAGGAUAU-3' | (SEQ ID NO: 1019) |
| LDHA-m1705 19 nt Target #3: | 5'-AUAAAUGUUGUACAGGAUA-3' | (SEQ ID NO: 1067) |
| LDHA-m1706 19 nt Target #1: | 5'-AAUGUUGUACAGGAUAUUU-3' | (SEQ ID NO: 972) |
| LDHA-m1706 19 nt Target #2: | 5'-AAAUGUUGUACAGGAUAUU-3' | (SEQ ID NO: 1020) |
| LDHA-m1706 19 nt Target #3: | 5'-UAAAUGUUGUACAGGAUAU-3' | (SEQ ID NO: 1068) |

TABLE 11-continued

DsiRNA Component 19 Nucleotide Target Sequences in Mouse Lactate Dehydrogenase mRNA

```
LDHA-m1707 19 nt Target #1:  5'-AUGUUGUACAGGAUAUUUU-3'  (SEQ ID NO: 973)

LDHA-m1707 19 nt Target #2:  5'-AAUGUUGUACAGGAUAUUU-3'  (SEQ ID NO: 1021)

LDHA-m1707 19 nt Target #3:  5'-AAAUGUUGUACAGGAUAUU-3'  (SEQ ID NO: 1069)

LDHA-m1708 19 nt Target #1:  5'-UGUUGUACAGGAUAUUUUA-3'  (SEQ ID NO: 974)

LDHA-m1708 19 nt Target #2:  5'-AUGUUGUACAGGAUAUUUU-3'  (SEQ ID NO: 1022)

LDHA-m1708 19 nt Target #3:  5'-AAUGUUGUACAGGAUAUUU-3'  (SEQ ID NO: 1070)

LDHA-m1709 19 nt Target #1:  5'-GUUGUACAGGAUAUUUUAU-3'  (SEQ ID NO: 975)

LDHA-m1709 19 nt Target #2:  5'-UGUUGUACAGGAUAUUUUA-3'  (SEQ ID NO: 1023)

LDHA-m1709 19 nt Target #3:  5'-AUGUUGUACAGGAUAUUUU-3'  (SEQ ID NO: 1071)

LDHA-m1710 19 nt Target #1:  5'-UUGUACAGGAUAUUUUAUA-3'  (SEQ ID NO: 976)

LDHA-m1710 19 nt Target #2:  5'-GUUGUACAGGAUAUUUUAU-3'  (SEQ ID NO: 1024)

LDHA-m1710 19 nt Target #3:  5'-UGUUGUACAGGAUAUUUUA-3'  (SEQ ID NO: 1072)

LDHA-m1739 19 nt Target #1:  5'-GUCUGUAGUGUGCAUUGCA-3'  (SEQ ID NO: 977)

LDHA-m1739 19 nt Target #2:  5'-UGUCUGUAGUGUGCAUUGC-3'  (SEQ ID NO: 1025)

LDHA-m1739 19 nt Target #3:  5'-GUGUCUGUAGUGUGCAUUG-3'  (SEQ ID NO: 1073)

LDHA-m1743 19 nt Target #1:  5'-GUAGUGUGCAUUGCAAUAU-3'  (SEQ ID NO: 978)

LDHA-m1743 19 nt Target #2:  5'-UGUAGUGUGCAUUGCAAUA-3'  (SEQ ID NO: 1026)

LDHA-m1743 19 nt Target #3:  5'-CUGUAGUGUGCAUUGCAAU-3'  (SEQ ID NO: 1074)

LDHA-m1744 19 nt Target #1:  5'-UAGUGUGCAUUGCAAUAUU-3'  (SEQ ID NO: 979)

LDHA-m1744 19 nt Target #2:  5'-GUAGUGUGCAUUGCAAUAU-3'  (SEQ ID NO: 1027)

LDHA-m1744 19 nt Target #3:  5'-UGUAGUGUGCAUUGCAAUA-3'  (SEQ ID NO: 1075)

LDHA-m1746 19 nt Target #1:  5'-GUGUGCAUUGCAAUAUUAU-3'  (SEQ ID NO: 980)

LDHA-m1746 19 nt Target #2:  5'-AGUGUGCAUUGCAAUAUUA-3'  (SEQ ID NO: 1028)

LDHA-m1746 19 nt Target #3:  5'-UAGUGUGCAUUGCAAUAUU-3'  (SEQ ID NO: 1076)

LDHA-m1751 19 nt Target #1:  5'-CAUUGCAAUAUUAUGUGAG-3'  (SEQ ID NO: 981)

LDHA-m1751 19 nt Target #2:  5'-GCAUUGCAAUAUUAUGUGA-3'  (SEQ ID NO: 1029)

LDHA-m1751 19 nt Target #3:  5'-UGCAUUGCAAUAUUAUGUG-3'  (SEQ ID NO: 1077)

LDHA-m1752 19 nt Target #1:  5'-AUUGCAAUAUUAUGUGAGA-3'  (SEQ ID NO: 982)

LDHA-m1752 19 nt Target #2:  5'-CAUUGCAAUAUUAUGUGAG-3'  (SEQ ID NO: 1030)

LDHA-m1752 19 nt Target #3:  5'-GCAUUGCAAUAUUAUGUGA-3'  (SEQ ID NO: 1078)

LDHA-m1755 19 nt Target #1:  5'-GCAAUAUUAUGUGAGAUGU-3'  (SEQ ID NO: 983)

LDHA-m1755 19 nt Target #2:  5'-UGCAAUAUUAUGUGAGAUG-3'  (SEQ ID NO: 1031)

LDHA-m1755 19 nt Target #3:  5'-UUGCAAUAUUAUGUGAGAU-3'  (SEQ ID NO: 1079)

LDHA-m1756 19 nt Target #1:  5'-CAAUAUUAUGUGAGAUGUA-3'  (SEQ ID NO: 984)

LDHA-m1756 19 nt Target #2:  5'-GCAAUAUUAUGUGAGAUGU-3'  (SEQ ID NO: 1032)

LDHA-m1756 19 nt Target #3:  5'-UGCAAUAUUAUGUGAGAUG-3'  (SEQ ID NO: 1080)
```

TABLE 12

Additional Selected Human Anti-Lactate Dehydrogenase DsiRNA Agents (Asymmetrics)

| | | |
|---|---|---|
| LDHA-27 Target: | 5'-CUGCCGGUCGGUUGUCUGGCUGCgc-3'<br>3'-CAGACGGCCAGCCAACAGACCGACGCG-5'<br>5'-GTCTGCCGGTCGGTTGTCTGGCTGCGC-3' | (SEQ ID NO: 1081)<br>(SEQ ID NO: 3095)<br>(SEQ ID NO: 5109) |
| LDHA-28 Target: | 5'-UGCCGGUCGGUUGUCUGGCUGCcg-3'<br>3'-AGACGGCCAGCCAACAGACCGACGCGC-5'<br>5'-TCTGCCGGTCGGTTGTCTGGCTGCGCG-3' | (SEQ ID NO: 1082)<br>(SEQ ID NO: 3096)<br>(SEQ ID NO: 5110) |
| LDHA-29 Target: | 5'-GCCGGUCGGUUGUCUGGCUGCGCgc-3'<br>3'-GACGGCCAGCCAACAGACCGACGCGCG-5'<br>5'-CTGCCGGTCGGTTGTCTGGCTGCGCGC-3' | (SEQ ID NO: 1083)<br>(SEQ ID NO: 3097)<br>(SEQ ID NO: 5111) |
| LDHA-33 Target: | 5'-GUCGGUUGUCUGGCUGCGCGCGCca-3'<br>3'-GCCAGCCAACAGACCGACGCGCGCGGU-5'<br>5'-CGGTCGGTTGTCTGGCTGCGCGCGCCA-3' | (SEQ ID NO: 1084)<br>(SEQ ID NO: 3098)<br>(SEQ ID NO: 5112) |
| LDHA-72 Target: | 5'-GUGCCCCGCCUGGCUCGGCAUCCac-3'<br>3'-GUCACGGGGCGGACCGAGCCGUAGGUG-5'<br>5'-CAGTGCCCCGCCTGGCTCGGCATCCAC-3' | (SEQ ID NO: 1085)<br>(SEQ ID NO: 3099)<br>(SEQ ID NO: 5113) |
| LDHA-77 Target: | 5'-CCGCCUGGCUCGGCAUCCACCCCca-3'<br>3'-GGGGCGGACCGAGCCGUAGGUGGGGGU-5'<br>5'-CCCCGCCTGGCTCGGCATCCACCCCCA-3' | (SEQ ID NO: 1086)<br>(SEQ ID NO: 3100)<br>(SEQ ID NO: 5114) |
| LDHA-78 Target: | 5'-CGCCUGGCUCGGCAUCCACCCCCag-3'<br>3'-GGGCGGACCGAGCCGUAGGUGGGGGUC-5'<br>5'-CCCGCCTGGCTCGGCATCCACCCCCAG-3' | (SEQ ID NO: 1087)<br>(SEQ ID NO: 3101)<br>(SEQ ID NO: 5115) |
| LDHA-80 Target: | 5'-CCUGGCUCGGCAUCCACCCCCAGcc-3'<br>3'-GCGGACCGAGCCGUAGGUGGGGGUCGG-5'<br>5'-CGCCTGGCTCGGCATCCACCCCCAGCC-3' | (SEQ ID NO: 1088)<br>(SEQ ID NO: 3102)<br>(SEQ ID NO: 5116) |
| LDHA-82 Target: | 5'-UGGCUCGGCAUCCACCCCCAGCCcg-3'<br>3'-GGACCGAGCCGUAGGUGGGGGUCGGGC-5'<br>5'-CCTGGCTCGGCATCCACCCCCAGCCCG-3' | (SEQ ID NO: 1089)<br>(SEQ ID NO: 3103)<br>(SEQ ID NO: 5117) |
| LDHA-83 Target: | 5'-GGCUCGGCAUCCACCCCCAGCCCga-3'<br>3'-GACCGAGCCGUAGGUGGGGGUCGGGCU-5'<br>5'-CTGGCTCGGCATCCACCCCCAGCCCGA-3' | (SEQ ID NO: 1090)<br>(SEQ ID NO: 3104)<br>(SEQ ID NO: 5118) |
| LDHA-84 Target: | 5'-GCUCGGCAUCCACCCCCAGCCCGac-3'<br>3'-ACCGAGCCGUAGGUGGGGGUCGGGCUG-5'<br>5'-TGGCTCGGCATCCACCCCCAGCCCGAC-3' | (SEQ ID NO: 1091)<br>(SEQ ID NO: 3105)<br>(SEQ ID NO: 5119) |
| LDHA-85 Target: | 5'-CUCGGCAUCCACCCCCAGCCCGAct-3'<br>3'-CCGAGCCGUAGGUGGGGGUCGGGCUGA-5'<br>5'-GGCTCGGCATCCACCCCCAGCCCGACT-3' | (SEQ ID NO: 1092)<br>(SEQ ID NO: 3106)<br>(SEQ ID NO: 5120) |
| LDHA-86 Target: | 5'-UCGGCAUCCACCCCCAGCCCGACtc-3'<br>3'-CGAGCCGUAGGUGGGGGUCGGGCUGAG-5'<br>5'-GCTCGGCATCCACCCCCAGCCCGACTC-3' | (SEQ ID NO: 1093)<br>(SEQ ID NO: 3107)<br>(SEQ ID NO: 5121) |
| LDHA-87 Target: | 5'-CGGCAUCCACCCCCAGCCCGACUca-3'<br>3'-GAGCCGUAGGUGGGGGUCGGGCUGAGU-5'<br>5'-CTCGGCATCCACCCCCAGCCCGACTCA-3' | (SEQ ID NO: 1094)<br>(SEQ ID NO: 3108)<br>(SEQ ID NO: 5122) |
| LDHA-88 Target: | 5'-GGCAUCCACCCCCAGCCCGACUCac-3'<br>3'-AGCCGUAGGUGGGGGUCGGGCUGAGUG-5'<br>5'-TCGGCATCCACCCCCAGCCCGACTCAC-3' | (SEQ ID NO: 1095)<br>(SEQ ID NO: 3109)<br>(SEQ ID NO: 5123) |
| LDHA-89 Target: | 5'-GCAUCCACCCCCAGCCCGACUCAca-3'<br>3'-GCCGUAGGUGGGGGUCGGGCUGAGUGU-5'<br>5'-CGGCATCCACCCCCAGCCCGACTCACA-3' | (SEQ ID NO: 1096)<br>(SEQ ID NO: 3110)<br>(SEQ ID NO: 5124) |
| LDHA-90 Target: | 5'-CAUCCACCCCCAGCCCGACUCACac-3'<br>3'-CCGUAGGUGGGGGUCGGGCUGAGUGUG-5'<br>5'-GGCATCCACCCCCAGCCCGACTCACAC-3' | (SEQ ID NO: 1097)<br>(SEQ ID NO: 3111)<br>(SEQ ID NO: 5125) |
| LDHA-91 Target: | 5'-AUCCACCCCCAGCCCGACUCACAcg-3'<br>3'-CGUAGGUGGGGGUCGGGCUGAGUGUGC-5'<br>5'-GCATCCACCCCCAGCCCGACTCACACG-3' | (SEQ ID NO: 1098)<br>(SEQ ID NO: 3112)<br>(SEQ ID NO: 5126) |
| LDHA-92 Target: | 5'-UCCACCCCCAGCCCGACUCACACgt-3'<br>3'-GUAGGUGGGGGUCGGGCUGAGUGUGCA-5'<br>5'-CATCCACCCCCAGCCCGACTCACACGT-3' | (SEQ ID NO: 1099)<br>(SEQ ID NO: 3113)<br>(SEQ ID NO: 5127) |

TABLE 12-continued

Additional Selected Human Anti-Lactate Dehydrogenase DsiRNA Agents (Asymmetrics)

| | | |
|---|---|---|
| LDHA-93 Target: | 5'-CCACCCCCAGCCCGACUCACACGtg-3'<br>3'-UAGGUGGGGGUCGGGCUGAGUGUGCAC-5'<br>5'-ATCCACCCCAGCCCGACTCACACGTG-3' | (SEQ ID NO: 1100)<br>(SEQ ID NO: 3114)<br>(SEQ ID NO: 5128) |
| LDHA-94 Target: | 5'-CACCCCCAGCCCGACUCACACGUgg-3'<br>3'-AGGUGGGGGUCGGGCUGAGUGUGCACC-5'<br>5'-TCCACCCCCAGCCCGACTCACACGTGG-3' | (SEQ ID NO: 1101)<br>(SEQ ID NO: 3115)<br>(SEQ ID NO: 5129) |
| LDHA-95 Target: | 5'-ACCCCCAGCCCGACUCACACGUGgg-3'<br>3'-GGUGGGGGUCGGGCUGAGUGUGCACCC-5'<br>5'-CCACCCCCAGCCCGACTCACACGTGGG-3' | (SEQ ID NO: 1102)<br>(SEQ ID NO: 3116)<br>(SEQ ID NO: 5130) |
| LDHA-96 Target: | 5'-CCCCCAGCCCGACUCACACGUGGgt-3'<br>3'-GUGGGGGUCGGGCUGAGUGUGCACCCA-5'<br>5'-CACCCCCAGCCCGACTCACACGTGGGT-3' | (SEQ ID NO: 1103)<br>(SEQ ID NO: 3117)<br>(SEQ ID NO: 5131) |
| LDHA-97 Target: | 5'-CCCCAGCCCGACUCACACGUGGGtt-3'<br>3'-UGGGGGUCGGGCUGAGUGUGCACCCAA-5'<br>5'-ACCCCCAGCCCGACTCACACGTGGGTT-3' | (SEQ ID NO: 1104)<br>(SEQ ID NO: 3118)<br>(SEQ ID NO: 5132) |
| LDHA-98 Target: | 5'-CCCAGCCCGACUCACACGUGGGUtc-3'<br>3'-GGGGGUCGGGCUGAGUGUGCACCCAAG-5'<br>5'-CCCCCAGCCCGACTCACACGTGGGTTC-3' | (SEQ ID NO: 1105)<br>(SEQ ID NO: 3119)<br>(SEQ ID NO: 5133) |
| LDHA-99 Target: | 5'-CCAGCCCGACUCACACGUGGGUUcc-3'<br>3'-GGGGUCGGGCUGAGUGUGCACCCAAGG-5'<br>5'-CCCCAGCCCGACTCACACGTGGGTTCC-3' | (SEQ ID NO: 1106)<br>(SEQ ID NO: 3120)<br>(SEQ ID NO: 5134) |
| LDHA-100 Target: | 5'-CAGCCCGACUCACACGUGGGUUCcc-3'<br>3'-GGGUCGGGCUGAGUGUGCACCCAAGGG-5'<br>5'-CCCAGCCCGACTCACACGTGGGTTCCC-3' | (SEQ ID NO: 1107)<br>(SEQ ID NO: 3121)<br>(SEQ ID NO: 5135) |
| LDHA-101 Target: | 5'-AGCCCGACUCACACGUGGGUUCCcg-3'<br>3'-GGUCGGGCUGAGUGUGCACCCAAGGGC-5'<br>5'-CCAGCCCGACTCACACGTGGGTTCCCG-3' | (SEQ ID NO: 1108)<br>(SEQ ID NO: 3122)<br>(SEQ ID NO: 5136) |
| LDHA-102 Target: | 5'-GCCCGACUCACACGUGGGUUCCCgc-3'<br>3'-GUCGGGCUGAGUGUGCACCCAAGGGCG-5'<br>5'-CAGCCCGACTCACACGTGGGTTCCCGC-3' | (SEQ ID NO: 1109)<br>(SEQ ID NO: 3123)<br>(SEQ ID NO: 5137) |
| LDHA-103 Target: | 5'-CCCGACUCACACGUGGGUUCCCGca-3'<br>3'-UCGGGCUGAGUGUGCACCCAAGGGCGU-5'<br>5'-AGCCCGACTCACACGTGGGTTCCCGCA-3' | (SEQ ID NO: 1110)<br>(SEQ ID NO: 3124)<br>(SEQ ID NO: 5138) |
| LDHA-104 Target: | 5'-CCGACUCACACGUGGGUUCCCGCac-3'<br>3'-CGGGCUGAGUGUGCACCCAAGGGCGUG-5'<br>5'-GCCCGACTCACACGTGGGTTCCCGCAC-3' | (SEQ ID NO: 1111)<br>(SEQ ID NO: 3125)<br>(SEQ ID NO: 5139) |
| LDHA-105 Target: | 5'-CGACUCACACGUGGGUUCCCGCAcg-3'<br>3'-GGGCUGAGUGUGCACCCAAGGGCGUGC-5'<br>5'-CCCGACTCACACGTGGGTTCCCGCACG-3' | (SEQ ID NO: 1112)<br>(SEQ ID NO: 3126)<br>(SEQ ID NO: 5140) |
| LDHA-106 Target: | 5'-GACUCACACGUGGGUUCCCGCACgt-3'<br>3'-GGCUGAGUGUGCACCCAAGGGCGUGCA-5'<br>5'-CCGACTCACACGTGGGTTCCCGCACGT-3' | (SEQ ID NO: 1113)<br>(SEQ ID NO: 3127)<br>(SEQ ID NO: 5141) |
| LDHA-107 Target: | 5'-ACUCACACGUGGGUUCCCGCACGtc-3'<br>3'-GCUGAGUGUGCACCCAAGGGCGUGCAG-5'<br>5'-CGACTCACACGTGGGTTCCCGCACGTC-3' | (SEQ ID NO: 1114)<br>(SEQ ID NO: 3128)<br>(SEQ ID NO: 5142) |
| LDHA-108 Target: | 5'-CUCACACGUGGGUUCCCGCACGUcc-3'<br>3'-CUGAGUGUGCACCCAAGGGCGUGCAGG-5'<br>5'-GACTCACACGTGGGTTCCCGCACGTCC-3' | (SEQ ID NO: 1115)<br>(SEQ ID NO: 3129)<br>(SEQ ID NO: 5143) |
| LDHA-109 Target: | 5'-UCACACGUGGGUUCCCGCACGUCcg-3'<br>3'-UGAGUGUGCACCCAAGGGCGUGCAGGC-5'<br>5'-ACTCACACGTGGGTTCCCGCACGTCCG-3' | (SEQ ID NO: 1116)<br>(SEQ ID NO: 3130)<br>(SEQ ID NO: 5144) |
| LDHA-110 Target: | 5'-CACACGUGGGUUCCCGCACGUCCgc-3'<br>3'-GAGUGUGCACCCAAGGGCGUGCAGGCG-5'<br>5'-CTCACACGTGGGTTCCCGCACGTCCGC-3' | (SEQ ID NO: 1117)<br>(SEQ ID NO: 3131)<br>(SEQ ID NO: 5145) |
| LDHA-111 Target: | 5'-ACACGUGGGUUCCCGCACGUCCgcc-3'<br>3'-AGUGUGCACCCAAGGGCGUGCAGGCGG-5'<br>5'-TCACACGTGGGTTCCCGCACGTCCGCC-3' | (SEQ ID NO: 1118)<br>(SEQ ID NO: 3132)<br>(SEQ ID NO: 5146) |

TABLE 12-continued

Additional Selected Human Anti-Lactate Dehydrogenase DsiRNA Agents (Asymmetrics)

| | | |
|---|---|---|
| LDHA-112 Target: | 5'-CACGUGGGUUCCCGCACGUCCGCcg-3'<br>3'-GUGUGCACCCAAGGGCGUGCAGGCGGC-5'<br>5'-CACACGTGGGTTCCCGCACGTCCGCCG-3' | (SEQ ID NO: 1119)<br>(SEQ ID NO: 3133)<br>(SEQ ID NO: 5147) |
| LDHA-135 Target: | 5'-CGGCCCCCCCCGCUGACGUCAGCat-3'<br>3'-CGGCCGGGGGGGGCGACUGCAGUCGUA-5'<br>5'-GCCGGCCCCCCCCGCTGACGTCAGCAT-3' | (SEQ ID NO: 1120)<br>(SEQ ID NO: 3134)<br>(SEQ ID NO: 5148) |
| LDHA-136 Target: | 5'-GGCCCCCCCCGCUGACGUCAGCAta-3'<br>3'-GGCCGGGGGGGGCGACUGCAGUCGUAU-5'<br>5'-CCGGCCCCCCCCGCTGACGTCAGCATA-3' | (SEQ ID NO: 1121)<br>(SEQ ID NO: 3135)<br>(SEQ ID NO: 5149) |
| LDHA-137 Target: | 5'-GCCCCCCCCGCUGACGUCAGCAUag-3'<br>3'-GCCGGGGGGGGCGACUGCAGUCGUAUC-5'<br>5'-CGGCCCCCCCCGCTGACGTCAGCATAG-3' | (SEQ ID NO: 1122)<br>(SEQ ID NO: 3136)<br>(SEQ ID NO: 5150) |
| LDHA-138 Target: | 5'-CCCCCCCCGCUGACGUCAGCAUAgc-3'<br>3'-CCGGGGGGGGCGACUGCAGUCGUAUCG-5'<br>5'-GGCCCCCCCCGCTGACGTCAGCATAGC-3' | (SEQ ID NO: 1123)<br>(SEQ ID NO: 3137)<br>(SEQ ID NO: 5151) |
| LDHA-139 Target: | 5'-CCCCCCCGCUGACGUCAGCAUAGct-3'<br>3'-CGGGGGGGGCGACUGCAGUCGUAUCGA-5'<br>5'-GCCCCCCCCGCTGACGTCAGCATAGCT-3' | (SEQ ID NO: 1124)<br>(SEQ ID NO: 3138)<br>(SEQ ID NO: 5152) |
| LDHA-140 Target: | 5'-CCCCCCGCUGACGUCAGCAUAGCtg-3'<br>3'-GGGGGGGGCGACUGCAGUCGUAUCGAC-5'<br>5'-CCCCCCCCGCTGACGTCAGCATAGCTG-3' | (SEQ ID NO: 1125)<br>(SEQ ID NO: 3139)<br>(SEQ ID NO: 5153) |
| LDHA-141 Target: | 5'-CCCCCGCUGACGUCAGCAUAGCUgt-3'<br>3'-GGGGGGGCGACUGCAGUCGUAUCGACA-5'<br>5'-CCCCCCCGCTGACGTCAGCATAGCTGT-3' | (SEQ ID NO: 1126)<br>(SEQ ID NO: 3140)<br>(SEQ ID NO: 5154) |
| LDHA-142 Target: | 5'-CCCCGCUGACGUCAGCAUAGCUGtt-3'<br>3'-GGGGGGCGACUGCAGUCGUAUCGACAA-5'<br>5'-CCCCCCGCTGACGTCAGCATAGCTGTT-3' | (SEQ ID NO: 1127)<br>(SEQ ID NO: 3141)<br>(SEQ ID NO: 5155) |
| LDHA-143 Target: | 5'-CCCGCUGACGUCAGCAUAGCUGUtc-3'<br>3'-GGGGGCGACUGCAGUCGUAUCGACAAG-5'<br>5'-CCCCCGCTGACGTCAGCATAGCTGTTC-3' | (SEQ ID NO: 1128)<br>(SEQ ID NO: 3142)<br>(SEQ ID NO: 5156) |
| LDHA-144 Target: | 5'-CCGCUGACGUCAGCAUAGCUGUUcc-3'<br>3'-GGGGCGACUGCAGUCGUAUCGACAAGG-5'<br>5'-CCCCGCTGACGTCAGCATAGCTGTTCC-3' | (SEQ ID NO: 1129)<br>(SEQ ID NO: 3143)<br>(SEQ ID NO: 5157) |
| LDHA-145 Target: | 5'-CGCUGACGUCAGCAUAGCUGUUCca-3'<br>3'-GGGCGACUGCAGUCGUAUCGACAAGGU-5'<br>5'-CCCGCTGACGTCAGCATAGCTGTTCCA-3' | (SEQ ID NO: 1130)<br>(SEQ ID NO: 3144)<br>(SEQ ID NO: 5158) |
| LDHA-146 Target: | 5'-GCUGACGUCAGCAUAGCUGUUCCac-3'<br>3'-GGCGACUGCAGUCGUAUCGACAAGGUG-5'<br>5'-CCGCTGACGTCAGCATAGCTGTTCCAC-3' | (SEQ ID NO: 1131)<br>(SEQ ID NO: 3145)<br>(SEQ ID NO: 5159) |
| LDHA-147 Target: | 5'-CUGACGUCAGCAUAGCUGUUCCAct-3'<br>3'-GCGACUGCAGUCGUAUCGACAAGGUGA-5'<br>5'-CGCTGACGTCAGCATAGCTGTTCCACT-3' | (SEQ ID NO: 1132)<br>(SEQ ID NO: 3146)<br>(SEQ ID NO: 5160) |
| LDHA-148 Target: | 5'-UGACGUCAGCAUAGCUGUUCCACtt-3'<br>3'-CGACUGCAGUCGUAUCGACAAGGUGAA-5'<br>5'-GCTGACGTCAGCATAGCTGTTCCACTT-3' | (SEQ ID NO: 1133)<br>(SEQ ID NO: 3147)<br>(SEQ ID NO: 5161) |
| LDHA-149 Target: | 5'-GACGUCAGCAUAGCUGUUCCACUta-3'<br>3'-GACUGCAGUCGUAUCGACAAGGUGAAU-5'<br>5'-CTGACGTCAGCATAGCTGTTCCACTTA-3' | (SEQ ID NO: 1134)<br>(SEQ ID NO: 3148)<br>(SEQ ID NO: 5162) |
| LDHA-150 Target: | 5'-ACGUCAGCAUAGCUGUUCCACUUaa-3'<br>3'-ACUGCAGUCGUAUCGACAAGGUGAAUU-5'<br>5'-TGACGTCAGCATAGCTGTTCCACTTAA-3' | (SEQ ID NO: 1135)<br>(SEQ ID NO: 3149)<br>(SEQ ID NO: 5163) |
| LDHA-151 Target: | 5'-CGUCAGCAUAGCUGUUCCACUUAag-3'<br>3'-CUGCAGUCGUAUCGACAAGGUGAAUUC-5'<br>5'-GACGTCAGCATAGCTGTTCCACTTAAG-3' | (SEQ ID NO: 1136)<br>(SEQ ID NO: 3150)<br>(SEQ ID NO: 5164) |
| LDHA-152 Target: | 5'-GUCAGCAUAGCUGUUCCACUUAAgg-3'<br>3'-UGCAGUCGUAUCGACAAGGUGAAUUCC-5'<br>5'-ACGTCAGCATAGCTGTTCCACTTAAGG-3' | (SEQ ID NO: 1137)<br>(SEQ ID NO: 3151)<br>(SEQ ID NO: 5165) |

TABLE 12-continued

Additional Selected Human Anti-Lactate Dehydrogenase DsiRNA Agents (Asymmetrics)

| | | |
|---|---|---|
| LDHA-153 Target: | 5'-UCAGCAUAGCUGUUCCACUUAAGgc-3'<br>3'-GCAGUCGUAUCGACAAGGUGAAUUCCG-5'<br>5'-CGTCAGCATAGCTGTTCCACTTAAGGC-3' | (SEQ ID NO: 1138)<br>(SEQ ID NO: 3152)<br>(SEQ ID NO: 5166) |
| LDHA-154 Target: | 5'-CAGCAUAGCUGUUCCACUUAAGGcc-3'<br>3'-CAGUCGUAUCGACAAGGUGAAUUCCGG-5'<br>5'-GTCAGCATAGCTGTTCCACTTAAGGCC-3' | (SEQ ID NO: 1139)<br>(SEQ ID NO: 3153)<br>(SEQ ID NO: 5167) |
| LDHA-155 Target: | 5'-AGCAUAGCUGUUCCACUUAAGGCcc-3'<br>3'-AGUCGUAUCGACAAGGUGAAUUCCGGG-5'<br>5'-TCAGCATAGCTGTTCCACTTAAGGCCC-3' | (SEQ ID NO: 1140)<br>(SEQ ID NO: 3154)<br>(SEQ ID NO: 5168) |
| LDHA-156 Target: | 5'-GCAUAGCUGUUCCACUUAAGGCCcc-3'<br>3'-GUCGUAUCGACAAGGUGAAUUCCGGGG-5'<br>5'-CAGCATAGCTGTTCCACTTAAGGCCCC-3' | (SEQ ID NO: 1141)<br>(SEQ ID NO: 3155)<br>(SEQ ID NO: 5169) |
| LDHA-157 Target: | 5'-CAUAGCUGUUCCACUUAAGGCCCct-3'<br>3'-UCGUAUCGACAAGGUGAAUUCCGGGGA-5'<br>5'-AGCATAGCTGTTCCACTTAAGGCCCCT-3' | (SEQ ID NO: 1142)<br>(SEQ ID NO: 3156)<br>(SEQ ID NO: 5170) |
| LDHA-158 Target: | 5'-AUAGCUGUUCCACUUAAGGCCCCtc-3'<br>3'-CGUAUCGACAAGGUGAAUUCCGGGGAG-5'<br>5'-GCATAGCTGTTCCACTTAAGGCCCCTC-3' | (SEQ ID NO: 1143)<br>(SEQ ID NO: 3157)<br>(SEQ ID NO: 5171) |
| LDHA-159 Target: | 5'-UAGCUGUUCCACUUAAGGCCCCUcc-3'<br>3'-GUAUCGACAAGGUGAAUUCCGGGGAGG-5'<br>5'-CATAGCTGTTCCACTTAAGGCCCCTCC-3' | (SEQ ID NO: 1144)<br>(SEQ ID NO: 3158)<br>(SEQ ID NO: 5172) |
| LDHA-160 Target: | 5'-AGCUGUUCCACUUAAGGCCCCUCcc-3'<br>3'-UAUCGACAAGGUGAAUUCCGGGGAGGG-5'<br>5'-ATAGCTGTTCCACTTAAGGCCCCTCCC-3' | (SEQ ID NO: 1145)<br>(SEQ ID NO: 3159)<br>(SEQ ID NO: 5173) |
| LDHA-161 Target: | 5'-GCUGUUCCACUUAAGGCCCCUCCcg-3'<br>3'-AUCGACAAGGUGAAUUCCGGGGAGGGC-5'<br>5'-TAGCTGTTCCACTTAAGGCCCCTCCCG-3' | (SEQ ID NO: 1146)<br>(SEQ ID NO: 3160)<br>(SEQ ID NO: 5174) |
| LDHA-162 Target: | 5'-CUGUUCCACUUAAGGCCCCUCCCgc-3'<br>3'-UCGACAAGGUGAAUUCCGGGGAGGGCG-5'<br>5'-AGCTGTTCCACTTAAGGCCCCTCCCGC-3' | (SEQ ID NO: 1147)<br>(SEQ ID NO: 3161)<br>(SEQ ID NO: 5175) |
| LDHA-179 Target: | 5'-CCUCCCGCGCCCAGCUCAGAGUGct-3'<br>3'-GGGGAGGGCGCGGGUCGAGUCUCACGA-5'<br>5'-CCCCTCCCGCGCCCAGCTCAGAGTGCT-3' | (SEQ ID NO: 1148)<br>(SEQ ID NO: 3162)<br>(SEQ ID NO: 5176) |
| LDHA-182 Target: | 5'-CCCGCGCCCAGCUCAGAGUGCUGca-3'<br>3'-GAGGGCGCGGGUCGAGUCUCACGACGU-5'<br>5'-CTCCCGCGCCCAGCTCAGAGTGCTGCA-3' | (SEQ ID NO: 1149)<br>(SEQ ID NO: 3163)<br>(SEQ ID NO: 5177) |
| LDHA-183 Target: | 5'-CCGCGCCCAGCUCAGAGUGCUGCag-3'<br>3'-AGGGCGCGGGUCGAGUCUCACGACGUC-5'<br>5'-TCCCGCGCCCAGCTCAGAGTGCTGCAG-3' | (SEQ ID NO: 1150)<br>(SEQ ID NO: 3164)<br>(SEQ ID NO: 5178) |
| LDHA-184 Target: | 5'-CGCGCCCAGCUCAGAGUGCUGCAgc-3'<br>3'-GGGCGCGGGUCGAGUCUCACGACGUCG-5'<br>5'-CCCGCGCCCAGCTCAGAGTGCTGCAGC-3' | (SEQ ID NO: 1151)<br>(SEQ ID NO: 3165)<br>(SEQ ID NO: 5179) |
| LDHA-185 Target: | 5'-GCGCCCAGCUCAGAGUGCUGCAGcc-3'<br>3'-GGCGCGGGUCGAGUCUCACGACGUCGG-5'<br>5'-CCGCGCCCAGCTCAGAGTGCTGCAGCC-3' | (SEQ ID NO: 1152)<br>(SEQ ID NO: 3166)<br>(SEQ ID NO: 5180) |
| LDHA-187 Target: | 5'-GCCCAGCUCAGAGUGCUGCAGCCgc-3'<br>3'-CGCGGGUCGAGUCUCACGACGUCGGCG-5'<br>5'-GCGCCCAGCTCAGAGTGCTGCAGCCGC-3' | (SEQ ID NO: 1153)<br>(SEQ ID NO: 3167)<br>(SEQ ID NO: 5181) |
| LDHA-188 Target: | 5'-CCCAGCUCAGAGUGCUGCAGCCGct-3'<br>3'-GCGGGUCGAGUCUCACGACGUCGGCGA-5'<br>5'-CGCCCAGCTCAGAGTGCTGCAGCCGCT-3' | (SEQ ID NO: 1154)<br>(SEQ ID NO: 3168)<br>(SEQ ID NO: 5182) |
| LDHA-190 Target: | 5'-CAGCUCAGAGUGCUGCAGCCGCUgc-3'<br>3'-GGGUCGAGUCUCACGACGUCGGCGACG-5'<br>5'-CCCAGCTCAGAGTGCTGCAGCCGCTGC-3' | (SEQ ID NO: 1155)<br>(SEQ ID NO: 3169)<br>(SEQ ID NO: 5183) |
| LDHA-191 Target: | 5'-AGCUCAGAGUGCUGCAGCCGCUGcc-3'<br>3'-GGUCGAGUCUCACGACGUCGGCGACGG-5'<br>5'-CCAGCTCAGAGTGCTGCAGCCGCTGCC-3' | (SEQ ID NO: 1156)<br>(SEQ ID NO: 3170)<br>(SEQ ID NO: 5184) |

TABLE 12-continued

Additional Selected Human Anti-Lactate Dehydrogenase DsiRNA Agents (Asymmetrics)

| | | |
|---|---|---|
| LDHA-192 Target: | 5'-GCUCAGAGUGCUGCAGCCGCUGCcg-3'<br>3'-GUCGAGUCUCACGACGUCGGCGACGGC-5'<br>5'-CAGCTCAGAGTGCTGCAGCCGCTGCCG-3' | (SEQ ID NO: 1157)<br>(SEQ ID NO: 3171)<br>(SEQ ID NO: 5185) |
| LDHA-193 Target: | 5'-CUCAGAGUGCUGCAGCCGCUGCCgc-3'<br>3'-UCGAGUCUCACGACGUCGGCGACGGCG-5'<br>5'-AGCTCAGAGTGCTGCAGCCGCTGCCGC-3' | (SEQ ID NO: 1158)<br>(SEQ ID NO: 3172)<br>(SEQ ID NO: 5186) |
| LDHA-208 Target: | 5'-CCGCUGCCGCCGAUUCCGGAUCUca-3'<br>3'-UCGGCGACGGCGGCUAAGGCCUAGAGU-5'<br>5'-AGCCGCTGCCGCCGATTCCGGATCTCA-3' | (SEQ ID NO: 1159)<br>(SEQ ID NO: 3173)<br>(SEQ ID NO: 5187) |
| LDHA-209 Target: | 5'-CGCUGCCGCCGAUUCCGGAUCUCat-3'<br>3'-CGGCGACGGCGGCUAAGGCCUAGAGUA-5'<br>5'-GCCGCTGCCGCCGATTCCGGATCTCAT-3' | (SEQ ID NO: 1160)<br>(SEQ ID NO: 3174)<br>(SEQ ID NO: 5188) |
| LDHA-210 Target: | 5'-GCUGCCGCCGAUUCCGGAUCUCAtt-3'<br>3'-GGCGACGGCGGCUAAGGCCUAGAGUAA-5'<br>5'-CCGCTGCCGCCGATTCCGGATCTCATT-3' | (SEQ ID NO: 1161)<br>(SEQ ID NO: 3175)<br>(SEQ ID NO: 5189) |
| LDHA-211 Target: | 5'-CUGCCGCCGAUUCCGGAUCUCAUtg-3'<br>3'-GCGACGGCGGCUAAGGCCUAGAGUAAC-5'<br>5'-CGCTGCCGCCGATTCCGGATCTCATTG-3' | (SEQ ID NO: 1162)<br>(SEQ ID NO: 3176)<br>(SEQ ID NO: 5190) |
| LDHA-212 Target: | 5'-UGCCGCCGAUUCCGGAUCUCAUUgc-3'<br>3'-CGACGGCGGCUAAGGCCUAGAGUAACG-5'<br>5'-GCTGCCGCCGATTCCGGATCTCATTGC-3' | (SEQ ID NO: 1163)<br>(SEQ ID NO: 3177)<br>(SEQ ID NO: 5191) |
| LDHA-213 Target: | 5'-GCCGCCGAUUCCGGAUCUCAUUGcc-3'<br>3'-GACGGCGGCUAAGGCCUAGAGUAACGG-5'<br>5'-CTGCCGCCGATTCCGGATCTCATTGCC-3' | (SEQ ID NO: 1164)<br>(SEQ ID NO: 3178)<br>(SEQ ID NO: 5192) |
| LDHA-214 Target: | 5'-CCGCCGAUUCCGGAUCUCAUUGCca-3'<br>3'-ACGGCGGCUAAGGCCUAGAGUAACGGU-5'<br>5'-TGCCGCCGATTCCGGATCTCATTGCCA-3' | (SEQ ID NO: 1165)<br>(SEQ ID NO: 3179)<br>(SEQ ID NO: 5193) |
| LDHA-215 Target: | 5'-CGCCGAUUCCGGAUCUCAUUGCCac-3'<br>3'-CGGCGGCUAAGGCCUAGAGUAACGGUG-5'<br>5'-GCCGCCGATTCCGGATCTCATTGCCAC-3' | (SEQ ID NO: 1166)<br>(SEQ ID NO: 3180)<br>(SEQ ID NO: 5194) |
| LDHA-216 Target: | 5'-GCCGAUUCCGGAUCUCAUUGCCAcg-3'<br>3'-GGCGGCUAAGGCCUAGAGUAACGGUGC-5'<br>5'-CCGCCGATTCCGGATCTCATTGCCACG-3' | (SEQ ID NO: 1167)<br>(SEQ ID NO: 3181)<br>(SEQ ID NO: 5195) |
| LDHA-217 Target: | 5'-CCGAUUCCGGAUCUCAUUGCCACgc-3'<br>3'-GCGGCUAAGGCCUAGAGUAACGGUGCG-5'<br>5'-CGCCGATTCCGGATCTCATTGCCACGC-3' | (SEQ ID NO: 1168)<br>(SEQ ID NO: 3182)<br>(SEQ ID NO: 5196) |
| LDHA-218 Target: | 5'-CGAUUCCGGAUCUCAUUGCCACGcg-3'<br>3'-CGGCUAAGGCCUAGAGUAACGGUGCGC-5'<br>5'-GCCGATTCCGGATCTCATTGCCACGCG-3' | (SEQ ID NO: 1169)<br>(SEQ ID NO: 3183)<br>(SEQ ID NO: 5197) |
| LDHA-219 Target: | 5'-GAUUCCGGAUCUCAUUGCCACGCgc-3'<br>3'-GGCUAAGGCCUAGAGUAACGGUGCGCG-5'<br>5'-CCGATTCCGGATCTCATTGCCACGCGC-3' | (SEQ ID NO: 1170)<br>(SEQ ID NO: 3184)<br>(SEQ ID NO: 5198) |
| LDHA-220 Target: | 5'-AUUCCGGAUCUCAUUGCCACGCGcc-3'<br>3'-GCUAAGGCCUAGAGUAACGGUGCGCGG-5'<br>5'-CGATTCCGGATCTCATTGCCACGCGCC-3' | (SEQ ID NO: 1171)<br>(SEQ ID NO: 3185)<br>(SEQ ID NO: 5199) |
| LDHA-221 Target: | 5'-UUCCGGAUCUCAUUGCCACGCGCcc-3'<br>3'-CUAAGGCCUAGAGUAACGGUGCGCGGG-5'<br>5'-GATTCCGGATCTCATTGCCACGCGCCC-3' | (SEQ ID NO: 1172)<br>(SEQ ID NO: 3186)<br>(SEQ ID NO: 5200) |
| LDHA-222 Target: | 5'-UCCGGAUCUCAUUGCCACGCGCCcc-3'<br>3'-UAAGGCCUAGAGUAACGGUGCGCGGGG-5'<br>5'-ATTCCGGATCTCATTGCCACGCGCCCC-3' | (SEQ ID NO: 1173)<br>(SEQ ID NO: 3187)<br>(SEQ ID NO: 5201) |
| LDHA-223 Target: | 5'-CCGGAUCUCAUUGCCACGCGCCCcc-3'<br>3'-AAGGCCUAGAGUAACGGUGCGCGGGGG-5'<br>5'-TTCCGGATCTCATTGCCACGCGCCCCC-3' | (SEQ ID NO: 1174)<br>(SEQ ID NO: 3188)<br>(SEQ ID NO: 5202) |
| LDHA-224 Target: | 5'-CGGAUCUCAUUGCCACGCGCCCCcg-3'<br>3'-AGGCCUAGAGUAACGGUGCGCGGGGGC-5'<br>5'-TCCGGATCTCATTGCCACGCGCCCCCG-3' | (SEQ ID NO: 1175)<br>(SEQ ID NO: 3189)<br>(SEQ ID NO: 5203) |

TABLE 12-continued

Additional Selected Human Anti-Lactate Dehydrogenase DsiRNA Agents (Asymmetrics)

| | | |
|---|---|---|
| LDHA-225 | 5'-GGAUCUCAUUGCCACGCGCCCCCga-3'<br>3'-GGCCUAGAGUAACGGUGCGCGGGGGCU-5'<br>Target: 5'-CCGGATCTCATTGCCACGCGCCCCCGA-3' | (SEQ ID NO: 1176)<br>(SEQ ID NO: 3190)<br>(SEQ ID NO: 5204) |
| LDHA-226 | 5'-GAUCUCAUUGCCACGCGCCCCCGac-3'<br>3'-GCCUAGAGUAACGGUGCGCGGGGGCUG-5'<br>Target: 5'-CGGATCTCATTGCCACGCGCCCCCGAC-3' | (SEQ ID NO: 1177)<br>(SEQ ID NO: 3191)<br>(SEQ ID NO: 5205) |
| LDHA-227 | 5'-AUCUCAUUGCCACGCGCCCCCGAcg-3'<br>3'-CCUAGAGUAACGGUGCGCGGGGGCUGC-5'<br>Target: 5'-GGATCTCATTGCCACGCGCCCCCGACG-3' | (SEQ ID NO: 1178)<br>(SEQ ID NO: 3192)<br>(SEQ ID NO: 5206) |
| LDHA-228 | 5'-UCUCAUUGCCACGCGCCCCCGACga-3'<br>3'-CUAGAGUAACGGUGCGCGGGGGCUGCU-5'<br>Target: 5'-GATCTCATTGCCACGCGCCCCCGACGA-3' | (SEQ ID NO: 1179)<br>(SEQ ID NO: 3193)<br>(SEQ ID NO: 5207) |
| LDHA-229 | 5'-CUCAUUGCCACGCGCCCCCGACGac-3'<br>3'-UAGAGUAACGGUGCGCGGGGGCUGCUG-5'<br>Target: 5'-ATCTCATTGCCACGCGCCCCCGACGAC-3' | (SEQ ID NO: 1180)<br>(SEQ ID NO: 3194)<br>(SEQ ID NO: 5208) |
| LDHA-230 | 5'-UCAUUGCCACGCGCCCCCGACGAcc-3'<br>3'-AGAGUAACGGUGCGCGGGGGCUGCUGG-5'<br>Target: 5'-TCTCATTGCCACGCGCCCCCGACGACC-3' | (SEQ ID NO: 1181)<br>(SEQ ID NO: 3195)<br>(SEQ ID NO: 5209) |
| LDHA-231 | 5'-CAUUGCCACGCGCCCCCGACGACcg-3'<br>3'-GAGUAACGGUGCGCGGGGGCUGCUGGC-5'<br>Target: 5'-CTCATTGCCACGCGCCCCCGACGACCG-3' | (SEQ ID NO: 1182)<br>(SEQ ID NO: 3196)<br>(SEQ ID NO: 5210) |
| LDHA-232 | 5'-AUUGCCACGCGCCCCCGACGACCgc-3'<br>3'-AGUAACGGUGCGCGGGGGCUGCUGGCG-5'<br>Target: 5'-TCATTGCCACGCGCCCCCGACGACCGC-3' | (SEQ ID NO: 1183)<br>(SEQ ID NO: 3197)<br>(SEQ ID NO: 5211) |
| LDHA-244 | 5'-CCCCGACGACCGCCCGACGUGCAtt-3'<br>3'-CGGGGCUGCUGGCGGGCUGCACGUAA-5'<br>Target: 5'-GCCCCGACGACCGCCCGACGTGCATT-3' | (SEQ ID NO: 1184)<br>(SEQ ID NO: 3198)<br>(SEQ ID NO: 5212) |
| LDHA-245 | 5'-CCCGACGACCGCCCGACGUGCAUtc-3'<br>3'-GGGGGCUGCUGGCGGGCUGCACGUAAG-5'<br>Target: 5'-CCCCCGACGACCGCCCGACGTGCATTC-3' | (SEQ ID NO: 1185)<br>(SEQ ID NO: 3199)<br>(SEQ ID NO: 5213) |
| LDHA-246 | 5'-CCGACGACCGCCCGACGUGCAUUcc-3'<br>3'-GGGGCUGCUGGCGGGCUGCACGUAAGG-5'<br>Target: 5'-CCCCGACGACCGCCCGACGTGCATTCC-3' | (SEQ ID NO: 1186)<br>(SEQ ID NO: 3200)<br>(SEQ ID NO: 5214) |
| LDHA-247 | 5'-CGACGACCGCCCGACGUGCAUUCcc-3'<br>3'-GGGCUGCUGGCGGGCUGCACGUAAGGG-5'<br>Target: 5'-CCCGACGACCGCCCGACGTGCATTCCC-3' | (SEQ ID NO: 1187)<br>(SEQ ID NO: 3201)<br>(SEQ ID NO: 5215) |
| LDHA-248 | 5'-GACGACCGCCCGACGUGCAUUCCcg-3'<br>3'-GGCUGCUGGCGGGCUGCACGUAAGGGC-5'<br>Target: 5'-CCGACGACCGCCCGACGTGCATTCCCG-3' | (SEQ ID NO: 1188)<br>(SEQ ID NO: 3202)<br>(SEQ ID NO: 5216) |
| LDHA-249 | 5'-ACGACCGCCCGACGUGCAUUCCCga-3'<br>3'-GCUGCUGGCGGGCUGCACGUAAGGGCU-5'<br>Target: 5'-CGACGACCGCCCGACGTGCATTCCCGA-3' | (SEQ ID NO: 1189)<br>(SEQ ID NO: 3203)<br>(SEQ ID NO: 5217) |
| LDHA-250 | 5'-CGACCGCCCGACGUGCAUUCCCGat-3'<br>3'-CUGCUGGCGGGCUGCACGUAAGGGCUA-5'<br>Target: 5'-GACGACCGCCCGACGTGCATTCCCGAT-3' | (SEQ ID NO: 1190)<br>(SEQ ID NO: 3204)<br>(SEQ ID NO: 5218) |
| LDHA-251 | 5'-GACCGCCCGACGUGCAUUCCCGAtt-3'<br>3'-UGCUGGCGGGCUGCACGUAAGGGCUAA-5'<br>Target: 5'-ACGACCGCCCGACGTGCATTCCCGATT-3' | (SEQ ID NO: 1191)<br>(SEQ ID NO: 3205)<br>(SEQ ID NO: 5219) |
| LDHA-252 | 5'-ACCGCCCGACGUGCAUUCCCGAUtc-3'<br>3'-GCUGGCGGGCUGCACGUAAGGGCUAAG-5'<br>Target: 5'-CGACCGCCCGACGTGCATTCCCGATTC-3' | (SEQ ID NO: 1192)<br>(SEQ ID NO: 3206)<br>(SEQ ID NO: 5220) |
| LDHA-253 | 5'-CCGCCCGACGUGCAUUCCCGAUUcc-3'<br>3'-CUGGCGGGCUGCACGUAAGGGCUAAGG-5'<br>Target: 5'-GACCGCCCGACGTGCATTCCCGATTCC-3' | (SEQ ID NO: 1193)<br>(SEQ ID NO: 3207)<br>(SEQ ID NO: 5221) |
| LDHA-254 | 5'-CGCCCGACGUGCAUUCCCGAUUCct-3'<br>3'-UGGCGGGCUGCACGUAAGGGCUAAGGA-5'<br>Target: 5'-ACCGCCCGACGTGCATTCCCGATTCCT-3' | (SEQ ID NO: 1194)<br>(SEQ ID NO: 3208)<br>(SEQ ID NO: 5222) |

TABLE 12-continued

Additional Selected Human Anti-Lactate Dehydrogenase DsiRNA Agents (Asymmetrics)

| | | |
|---|---|---|
| LDHA-255 Target: | 5'-GCCCGACGUGCAUUCCCGAUUCCtt-3'<br>3'-GGCGGGCUGCACGUAAGGGCUAAGGAA-5'<br>5'-CCGCCCGACGTGCATTCCCGATTCCTT-3' | (SEQ ID NO: 1195)<br>(SEQ ID NO: 3209)<br>(SEQ ID NO: 5223) |
| LDHA-256 Target: | 5'-CCCGACGUGCAUUCCCGAUUCCUtt-3'<br>3'-GCGGGCUGCACGUAAGGGCUAAGGAAA-5'<br>5'-CGCCCGACGTGCATTCCCGATTCCTTT-3' | (SEQ ID NO: 1196)<br>(SEQ ID NO: 3210)<br>(SEQ ID NO: 5224) |
| LDHA-257 Target: | 5'-CCGACGUGCAUUCCCGAUUCCUUtt-3'<br>3'-CGGGCUGCACGUAAGGGCUAAGGAAAA-5'<br>5'-GCCCGACGTGCATTCCCGATTCCTTTT-3' | (SEQ ID NO: 1197)<br>(SEQ ID NO: 3211)<br>(SEQ ID NO: 5225) |
| LDHA-258 Target: | 5'-CGACGUGCAUUCCCGAUUCCUUUtg-3'<br>3'-GGGCUGCACGUAAGGGCUAAGGAAAAC-5'<br>5'-CCCGACGTGCATTCCCGATTCCTTTTG-3' | (SEQ ID NO: 1198)<br>(SEQ ID NO: 3212)<br>(SEQ ID NO: 5226) |
| LDHA-259 Target: | 5'-GACGUGCAUUCCCGAUUCCUUUUgg-3'<br>3'-GGCUGCACGUAAGGGCUAAGGAAAACC-5'<br>5'-CCGACGTGCATTCCCGATTCCTTTTGG-3' | (SEQ ID NO: 1199)<br>(SEQ ID NO: 3213)<br>(SEQ ID NO: 5227) |
| LDHA-260 Target: | 5'-ACGUGCAUUCCCGAUUCCUUUUGgt-3'<br>3'-GCUGCACGUAAGGGCUAAGGAAAACCA-5'<br>5'-CGACGTGCATTCCCGATTCCTTTTGGT-3' | (SEQ ID NO: 1200)<br>(SEQ ID NO: 3214)<br>(SEQ ID NO: 5228) |
| LDHA-261 Target: | 5'-CGUGCAUUCCCGAUUCCUUUUGGtt-3'<br>3'-CUGCACGUAAGGGCUAAGGAAAACCAA-5'<br>5'-GACGTGCATTCCCGATTCCTTTTGGTT-3' | (SEQ ID NO: 1201)<br>(SEQ ID NO: 3215)<br>(SEQ ID NO: 5229) |
| LDHA-262 Target: | 5'-GUGCAUUCCCGAUUCCUUUUGGUtc-3'<br>3'-UGCACGUAAGGGCUAAGGAAAACCAAG-5'<br>5'-ACGTGCATTCCCGATTCCTTTTGGTTC-3' | (SEQ ID NO: 1202)<br>(SEQ ID NO: 3216)<br>(SEQ ID NO: 5230) |
| LDHA-263 Target: | 5'-UGCAUUCCCGAUUCCUUUUGGUUcc-3'<br>3'-GCACGUAAGGGCUAAGGAAAACCAAGG-5'<br>5'-CGTGCATTCCCGATTCCTTTTGGTTCC-3' | (SEQ ID NO: 1203)<br>(SEQ ID NO: 3217)<br>(SEQ ID NO: 5231) |
| LDHA-264 Target: | 5'-GCAUUCCCGAUUCCUUUUGGUUCca-3'<br>3'-CACGUAAGGGCUAAGGAAAACCAAGGU-5'<br>5'-GTGCATTCCCGATTCCTTTTGGTTCCA-3' | (SEQ ID NO: 1204)<br>(SEQ ID NO: 3218)<br>(SEQ ID NO: 5232) |
| LDHA-265 Target: | 5'-CAUUCCCGAUUCCUUUUGGUUCCaa-3'<br>3'-ACGUAAGGGCUAAGGAAAACCAAGGUU-5'<br>5'-TGCATTCCCGATTCCTTTTGGTTCCAA-3' | (SEQ ID NO: 1205)<br>(SEQ ID NO: 3219)<br>(SEQ ID NO: 5233) |
| LDHA-266 Target: | 5'-AUUCCCGAUUCCUUUUGGUUCCAag-3'<br>3'-CGUAAGGGCUAAGGAAAACCAAGGUUC-5'<br>5'-GCATTCCCGATTCCTTTTGGTTCCAAG-3' | (SEQ ID NO: 1206)<br>(SEQ ID NO: 3220)<br>(SEQ ID NO: 5234) |
| LDHA-267 Target: | 5'-UUCCCGAUUCCUUUUGGUUCCAAgt-3'<br>3'-GUAAGGGCUAAGGAAAACCAAGGUUCA-5'<br>5'-CATTCCCGATTCCTTTTGGTTCCAAGT-3' | (SEQ ID NO: 1207)<br>(SEQ ID NO: 3221)<br>(SEQ ID NO: 5235) |
| LDHA-268 Target: | 5'-UCCCGAUUCCUUUUGGUUCCAAGtc-3'<br>3'-UAAGGGCUAAGGAAAACCAAGGUUCAG-5'<br>5'-ATTCCCGATTCCTTTTGGTTCCAAGTC-3' | (SEQ ID NO: 1208)<br>(SEQ ID NO: 3222)<br>(SEQ ID NO: 5236) |
| LDHA-269 Target: | 5'-CCCGAUUCCUUUUGGUUCCAAGUcc-3'<br>3'-AAGGGCUAAGGAAAACCAAGGUUCAGG-5'<br>5'-TTCCCGATTCCTTTTGGTTCCAAGTCC-3' | (SEQ ID NO: 1209)<br>(SEQ ID NO: 3223)<br>(SEQ ID NO: 5237) |
| LDHA-270 Target: | 5'-CCGAUUCCUUUUGGUUCCAAGUCca-3'<br>3'-AGGGCUAAGGAAAACCAAGGUUCAGGU-5'<br>5'-TCCCGATTCCTTTTGGTTCCAAGTCCA-3' | (SEQ ID NO: 1210)<br>(SEQ ID NO: 3224)<br>(SEQ ID NO: 5238) |
| LDHA-271 Target: | 5'-CGAUUCCUUUUGGUUCCAAGUCCaa-3'<br>3'-GGGCUAAGGAAAACCAAGGUUCAGGUU-5'<br>5'-CCCGATTCCTTTTGGTTCCAAGTCCAA-3' | (SEQ ID NO: 1211)<br>(SEQ ID NO: 3225)<br>(SEQ ID NO: 5239) |
| LDHA-272 Target: | 5'-GAUUCCUUUUGGUUCCAAGUCCAat-3'<br>3'-GGCUAAGGAAAACCAAGGUUCAGGUUA-5'<br>5'-CCGATTCCTTTTGGTTCCAAGTCCAAT-3' | (SEQ ID NO: 1212)<br>(SEQ ID NO: 3226)<br>(SEQ ID NO: 5240) |
| LDHA-273 Target: | 5'-AUUCCUUUUGGUUCCAAGUCCAAta-3'<br>3'-GCUAAGGAAAACCAAGGUUCAGGUUAU-5'<br>5'-CGATTCCTTTTGGTTCCAAGTCCAATA-3' | (SEQ ID NO: 1213)<br>(SEQ ID NO: 3227)<br>(SEQ ID NO: 5241) |

TABLE 12-continued

Additional Selected Human Anti-Lactate Dehydrogenase DsiRNA Agents (Asymmetrics)

| | | |
|---|---|---|
| LDHA-274 Target: | 5'-UUCCUUUUGGUUCCAAGUCCAAUat-3'<br>3'-CUAAGGAAAACCAAGGUUCAGGUUAUA-5'<br>5'-GATTCCTTTTGGTTCCAAGTCCAATAT-3' | (SEQ ID NO: 1214)<br>(SEQ ID NO: 3228)<br>(SEQ ID NO: 5242) |
| LDHA-275 Target: | 5'-UCCUUUUGGUUCCAAGUCCAAUAtg-3'<br>3'-UAAGGAAAACCAAGGUUCAGGUUAUAC-5'<br>5'-ATTCCTTTTGGTTCCAAGTCCAATATG-3' | (SEQ ID NO: 1215)<br>(SEQ ID NO: 3229)<br>(SEQ ID NO: 5243) |
| LDHA-276 Target: | 5'-CCUUUUGGUUCCAAGUCCAAUAUGg-3'<br>3'-AAGGAAAACCAAGGUUCAGGUUAUACC-5'<br>5'-TTCCTTTTGGTTCCAAGTCCAATATGG-3' | (SEQ ID NO: 1216)<br>(SEQ ID NO: 3230)<br>(SEQ ID NO: 5244) |
| LDHA-277 Target: | 5'-CUUUUGGUUCCAAGUCCAAUAUGgc-3'<br>3'-AGGAAAACCAAGGUUCAGGUUAUACCG-5'<br>5'-TCCTTTTGGTTCCAAGTCCAATATGGC-3' | (SEQ ID NO: 1217)<br>(SEQ ID NO: 3231)<br>(SEQ ID NO: 5245) |
| LDHA-278 Target: | 5'-UUUUGGUUCCAAGUCCAAUAUGGca-3'<br>3'-GGAAAACCAAGGUUCAGGUUAUACCGU-5'<br>5'-CCTTTTGGTTCCAAGTCCAATATGGCA-3' | (SEQ ID NO: 1218)<br>(SEQ ID NO: 3232)<br>(SEQ ID NO: 5246) |
| LDHA-279 Target: | 5'-UUUGGUUCCAAGUCCAAUAUGGCaa-3'<br>3'-GAAAACCAAGGUUCAGGUUAUACCGUU-5'<br>5'-CTTTTGGTTCCAAGTCCAATATGGCAA-3' | (SEQ ID NO: 1219)<br>(SEQ ID NO: 3233)<br>(SEQ ID NO: 5247) |
| LDHA-280 Target: | 5'-UUGGUUCCAAGUCCAAUAUGGCAac-3'<br>3'-AAAACCAAGGUUCAGGUUAUACCGUUG-5'<br>5'-TTTTGGTTCCAAGTCCAATATGGCAAC-3' | (SEQ ID NO: 1220)<br>(SEQ ID NO: 3234)<br>(SEQ ID NO: 5248) |
| LDHA-281 Target: | 5'-UGGUUCCAAGUCCAAUAUGGCAAct-3'<br>3'-AAACCAAGGUUCAGGUUAUACCGUUGA-5'<br>5'-TTTGGTTCCAAGTCCAATATGGCAACT-3' | (SEQ ID NO: 1221)<br>(SEQ ID NO: 3235)<br>(SEQ ID NO: 5249) |
| LDHA-282 Target: | 5'-GGUUCCAAGUCCAAUAUGGCAACtc-3'<br>3'-AACCAAGGUUCAGGUUAUACCGUUGAG-5'<br>5'-TTGGTTCCAAGTCCAATATGGCAACTC-3' | (SEQ ID NO: 1222)<br>(SEQ ID NO: 3236)<br>(SEQ ID NO: 5250) |
| LDHA-283 Target: | 5'-GUUCCAAGUCCAAUAUGGCAACUct-3'<br>3'-ACCAAGGUUCAGGUUAUACCGUUGAGA-5'<br>5'-TGGTTCCAAGTCCAATATGGCAACTCT-3' | (SEQ ID NO: 1223)<br>(SEQ ID NO: 3237)<br>(SEQ ID NO: 5251) |
| LDHA-284 Target: | 5'-UUCCAAGUCCAAUAUGGCAACUCta-3'<br>3'-CCAAGGUUCAGGUUAUACCGUUGAGAU-5'<br>5'-GGTTCCAAGTCCAATATGGCAACTCTA-3' | (SEQ ID NO: 1224)<br>(SEQ ID NO: 3238)<br>(SEQ ID NO: 5252) |
| LDHA-285 Target: | 5'-UCCAAGUCCAAUAUGGCAACUCUaa-3'<br>3'-CAAGGUUCAGGUUAUACCGUUGAGAUU-5'<br>5'-GTTCCAAGTCCAATATGGCAACTCTAA-3' | (SEQ ID NO: 1225)<br>(SEQ ID NO: 3239)<br>(SEQ ID NO: 5253) |
| LDHA-286 Target: | 5'-CCAAGUCCAAUAUGGCAACUCUAaa-3'<br>3'-AAGGUUCAGGUUAUACCGUUGAGAUUU-5'<br>5'-TTCCAAGTCCAATATGGCAACTCTAAA-3' | (SEQ ID NO: 1226)<br>(SEQ ID NO: 3240)<br>(SEQ ID NO: 5254) |
| LDHA-287 Target: | 5'-CAAGUCCAAUAUGGCAACUCUAAag-3'<br>3'-AGGUUCAGGUUAUACCGUUGAGAUUUC-5'<br>5'-TCCAAGTCCAATATGGCAACTCTAAAG-3' | (SEQ ID NO: 1227)<br>(SEQ ID NO: 3241)<br>(SEQ ID NO: 5255) |
| LDHA-288 Target: | 5'-AAGUCCAAUAUGGCAACUCUAAAgg-3'<br>3'-GGUUCAGGUUAUACCGUUGAGAUUUCC-5'<br>5'-CCAAGTCCAATATGGCAACTCTAAAGG-3' | (SEQ ID NO: 1228)<br>(SEQ ID NO: 3242)<br>(SEQ ID NO: 5256) |
| LDHA-289 Target: | 5'-AGUCCAAUAUGGCAACUCUAAAGga-3'<br>3'-GUUCAGGUUAUACCGUUGAGAUUUCCU-5'<br>5'-CAAGTCCAATATGGCAACTCTAAAGGA-3' | (SEQ ID NO: 1229)<br>(SEQ ID NO: 3243)<br>(SEQ ID NO: 5257) |
| LDHA-290 Target: | 5'-GUCCAAUAUGGCAACUCUAAAGGat-3'<br>3'-UUCAGGUUAUACCGUUGAGAUUUCCUA-5'<br>5'-AAGTCCAATATGGCAACTCTAAAGGAT-3' | (SEQ ID NO: 1230)<br>(SEQ ID NO: 3244)<br>(SEQ ID NO: 5258) |
| LDHA-291 Target: | 5'-UCCAAUAUGGCAACUCUAAAGGAtc-3'<br>3'-UCAGGUUAUACCGUUGAGAUUUCCUAG-5'<br>5'-AGTCCAATATGGCAACTCTAAAGGATC-3' | (SEQ ID NO: 1231)<br>(SEQ ID NO: 3245)<br>(SEQ ID NO: 5259) |
| LDHA-292 Target: | 5'-CCAAUAUGGCAACUCUAAAGGAUca-3'<br>3'-CAGGUUAUACCGUUGAGAUUUCCUAGU-5'<br>5'-GTCCAATATGGCAACTCTAAAGGATCA-3' | (SEQ ID NO: 1232)<br>(SEQ ID NO: 3246)<br>(SEQ ID NO: 5260) |

TABLE 12-continued

Additional Selected Human Anti-Lactate Dehydrogenase DsiRNA Agents (Asymmetrics)

|  |  |  |
|---|---|---|
| LDHA-293 Target: | 5'-CAAUAUGGCAACUCUAAAGGAUCag-3'<br>3'-AGGUUAUACCGUUGAGAUUUCCUAGUC-5'<br>5'-TCCAATATGGCAACTCTAAAGGATCAG-3' | (SEQ ID NO: 1233)<br>(SEQ ID NO: 3247)<br>(SEQ ID NO: 5261) |
| LDHA-294 Target: | 5'-AAUAUGGCAACUCUAAAGGAUCAgc-3'<br>3'-GGUUAUACCGUUGAGAUUUCCUAGUCG-5'<br>5'-CCAATATGGCAACTCTAAAGGATCAGC-3' | (SEQ ID NO: 1234)<br>(SEQ ID NO: 3248)<br>(SEQ ID NO: 5262) |
| LDHA-295 Target: | 5'-AUAUGGCAACUCUAAAGGAUCAGct-3'<br>3'-GUUAUACCGUUGAGAUUUCCUAGUCGA-5'<br>5'-CAATATGGCAACTCTAAAGGATCAGCT-3' | (SEQ ID NO: 1235)<br>(SEQ ID NO: 3249)<br>(SEQ ID NO: 5263) |
| LDHA-296 Target: | 5'-UAUGGCAACUCUAAAGGAUCAGCtg-3'<br>3'-UUAUACCGUUGAGAUUUCCUAGUCGAC-5'<br>5'-AATATGGCAACTCTAAAGGATCAGCTG-3' | (SEQ ID NO: 1236)<br>(SEQ ID NO: 3250)<br>(SEQ ID NO: 5264) |
| LDHA-297 Target: | 5'-AUGGCAACUCUAAAGGAUCAGCUga-3'<br>3'-UAUACCGUUGAGAUUUCCUAGUCGACU-5'<br>5'-ATATGGCAACTCTAAAGGATCAGCTGA-3' | (SEQ ID NO: 1237)<br>(SEQ ID NO: 3251)<br>(SEQ ID NO: 5265) |
| LDHA-298 Target: | 5'-UGGCAACUCUAAAGGAUCAGCUGat-3'<br>3'-AUACCGUUGAGAUUUCCUAGUCGACUA-5'<br>5'-TATGGCAACTCTAAAGGATCAGCTGAT-3' | (SEQ ID NO: 1238)<br>(SEQ ID NO: 3252)<br>(SEQ ID NO: 5266) |
| LDHA-299 Target: | 5'-GGCAACUCUAAAGGAUCAGCUGAtt-3'<br>3'-UACCGUUGAGAUUUCCUAGUCGACUAA-5'<br>5'-ATGGCAACTCTAAAGGATCAGCTGATT-3' | (SEQ ID NO: 1239)<br>(SEQ ID NO: 3253)<br>(SEQ ID NO: 5267) |
| LDHA-300 Target: | 5'-GCAACUCUAAAGGAUCAGCUGAUtt-3'<br>3'-ACCGUUGAGAUUUCCUAGUCGACUAAA-5'<br>5'-TGGCAACTCTAAAGGATCAGCTGATTT-3' | (SEQ ID NO: 1240)<br>(SEQ ID NO: 3254)<br>(SEQ ID NO: 5268) |
| LDHA-301 Target: | 5'-CAACUCUAAAGGAUCAGCUGAUUta-3'<br>3'-CCGUUGAGAUUUCCUAGUCGACUAAAU-5'<br>5'-GGCAACTCTAAAGGATCAGCTGATTTA-3' | (SEQ ID NO: 1241)<br>(SEQ ID NO: 3255)<br>(SEQ ID NO: 5269) |
| LDHA-302 Target: | 5'-AACUCUAAAGGAUCAGCUGAUUUat-3'<br>3'-CGUUGAGAUUUCCUAGUCGACUAAAUA-5'<br>5'-GCAACTCTAAAGGATCAGCTGATTTAT-3' | (SEQ ID NO: 1242)<br>(SEQ ID NO: 3256)<br>(SEQ ID NO: 5270) |
| LDHA-303 Target: | 5'-ACUCUAAAGGAUCAGCUGAUUUAta-3'<br>3'-GUUGAGAUUUCCUAGUCGACUAAAUAU-5'<br>5'-CAACTCTAAAGGATCAGCTGATTTATA-3' | (SEQ ID NO: 1243)<br>(SEQ ID NO: 3257)<br>(SEQ ID NO: 5271) |
| LDHA-304 Target: | 5'-CUCUAAAGGAUCAGCUGAUUUAUaa-3'<br>3'-UUGAGAUUUCCUAGUCGACUAAAUAUU-5'<br>5'-AACTCTAAAGGATCAGCTGATTTATAA-3' | (SEQ ID NO: 1244)<br>(SEQ ID NO: 3258)<br>(SEQ ID NO: 5272) |
| LDHA-305 Target: | 5'-UCUAAAGGAUCAGCUGAUUUAUAat-3'<br>3'-UGAGAUUUCCUAGUCGACUAAAUAUUA-5'<br>5'-ACTCTAAAGGATCAGCTGATTTATAAT-3' | (SEQ ID NO: 1245)<br>(SEQ ID NO: 3259)<br>(SEQ ID NO: 5273) |
| LDHA-306 Target: | 5'-CUAAAGGAUCAGCUGAUUUAUAAtc-3'<br>3'-GAGAUUUCCUAGUCGACUAAAUAUUAG-5'<br>5'-CTCTAAAGGATCAGCTGATTTATAATC-3' | (SEQ ID NO: 1246)<br>(SEQ ID NO: 3260)<br>(SEQ ID NO: 5274) |
| LDHA-307 Target: | 5'-UAAAGGAUCAGCUGAUUUAUAAUct-3'<br>3'-AGAUUUCCUAGUCGACUAAAUAUUAGA-5'<br>5'-TCTAAAGGATCAGCTGATTTATAATCT-3' | (SEQ ID NO: 1247)<br>(SEQ ID NO: 3261)<br>(SEQ ID NO: 5275) |
| LDHA-308 Target: | 5'-AAAGGAUCAGCUGAUUUAUAAUCtt-3'<br>3'-GAUUUCCUAGUCGACUAAAUAUUAGAA-5'<br>5'-CTAAAGGATCAGCTGATTTATAATCTT-3' | (SEQ ID NO: 1248)<br>(SEQ ID NO: 3262)<br>(SEQ ID NO: 5276) |
| LDHA-309 Target: | 5'-AAGGAUCAGCUGAUUUAUAAUCUtc-3'<br>3'-AUUUCCUAGUCGACUAAAUAUUAGAAG-5'<br>5'-TAAAGGATCAGCTGATTTATAATCTTC-3' | (SEQ ID NO: 1249)<br>(SEQ ID NO: 3263)<br>(SEQ ID NO: 5277) |
| LDHA-310 Target: | 5'-AGGAUCAGCUGAUUUAUAAUCUUct-3'<br>3'-UUUCCUAGUCGACUAAAUAUUAGAAGA-5'<br>5'-AAAGGATCAGCTGATTTATAATCTTCT-3' | (SEQ ID NO: 1250)<br>(SEQ ID NO: 3264)<br>(SEQ ID NO: 5278) |
| LDHA-311 Target: | 5'-GGAUCAGCUGAUUUAUAAUCUUCta-3'<br>3'-UUCCUAGUCGACUAAAUAUUAGAAGAU-5'<br>5'-AAGGATCAGCTGATTTATAATCTTCTA-3' | (SEQ ID NO: 1251)<br>(SEQ ID NO: 3265)<br>(SEQ ID NO: 5279) |

TABLE 12-continued

Additional Selected Human Anti-Lactate Dehydrogenase DsiRNA Agents (Asymmetrics)

| | | | |
|---|---|---|---|
| | 5'-GA<u>C</u>AGCUGAUUUA<u>U</u>A<u>U</u>AUCUUCUaa-3' | (SEQ ID NO: 1252) | |
| | 3'-<u>UCCU</u>AGUCGACUAAA<u>U</u>AUUAGAAGA<u>U</u>UU-5' | (SEQ ID NO: 3266) | |
| LDHA-312 Target: | 5'-AGGATCAGCTGATTTATAATCTTCTAA-3' | (SEQ ID NO: 5280) | |
| | 5'-A<u>U</u>CAGCUGAUUUA<u>U</u>A<u>A</u>UCUUCUAaa-3' | (SEQ ID NO: 1253) | |
| | 3'-<u>CCU</u>AGUCGACUAAA<u>U</u>A<u>U</u>UAGAAGA<u>U</u>UU-5' | (SEQ ID NO: 3267) | |
| LDHA-313 Target: | 5'-GGATCAGCTGATTTATAATCTTCTAAA-3' | (SEQ ID NO: 5281) | |
| | 5'-U<u>C</u>AGCUGAUUUAU<u>A</u>A<u>U</u>CUUCUAAag-3' | (SEQ ID NO: 1254) | |
| | 3'-<u>CUAG</u>UCGACUAAAU<u>A</u>U<u>U</u>AGAAGA<u>UUUC</u>-5' | (SEQ ID NO: 3268) | |
| LDHA-314 Target: | 5'-GATCAGCTGATTTATAATCTTCTAAAG-3' | (SEQ ID NO: 5282) | |
| | 5'-C<u>A</u>GCUGAUUUAUA<u>A</u>U<u>C</u>UUCUAAAgg-3' | (SEQ ID NO: 1255) | |
| | 3'-<u>U</u>AG<u>U</u>CGACUAAAU<u>A</u>UUAGAAGAU<u>UUCC</u>-5' | (SEQ ID NO: 3269) | |
| LDHA-315 Target: | 5'-ATCAGCTGATTTATAATCTTCTAAAGG-3' | (SEQ ID NO: 5283) | |
| | 5'-A<u>G</u>CUGAUUUAUAA<u>U</u>C<u>U</u>UCUAAAGga-3' | (SEQ ID NO: 1256) | |
| | 3'-<u>A</u>GU<u>C</u>GACUAAAU<u>A</u>UUAGAAGAUUU<u>CCU</u>-5' | (SEQ ID NO: 3270) | |
| LDHA-316 Target: | 5'-TCAGCTGATTTATAATCTTCTAAAGGA-3' | (SEQ ID NO: 5284) | |
| | 5'-GC<u>U</u>GAUUUAUAAUC<u>U</u>UCUAAAGGaa-3' | (SEQ ID NO: 1257) | |
| | 3'-<u>GU</u>C<u>G</u>ACUAAAUAU<u>U</u>AGAAGAUUU<u>CCUU</u>-5' | (SEQ ID NO: 3271) | |
| LDHA-317 Target: | 5'-CAGCTGATTTATAATCTTCTAAAGGAA-3' | (SEQ ID NO: 5285) | |
| | 5'-C<u>U</u>GAUUUAUAAUC<u>UU</u>CUAAAGGAag-3' | (SEQ ID NO: 1258) | |
| | 3'-<u>UCGA</u>CUAAAUAUUAGAAGAUUU<u>CCUUC</u>-5' | (SEQ ID NO: 3272) | |
| LDHA-318 Target: | 5'-AGCTGATTTATAATCTTCTAAAGGAAG-3' | (SEQ ID NO: 5286) | |
| | 5'-UGA<u>U</u>UUAUAAUC<u>U</u>UCUAAAGGAAga-3' | (SEQ ID NO: 1259) | |
| | 3'-<u>CGA</u>CUAAAUAUUAGA<u>A</u>GAUUUCC<u>UUCU</u>-5' | (SEQ ID NO: 3273) | |
| LDHA-319 Target: | 5'-GCTGATTTATAATCTTCTAAAGGAAGA-3' | (SEQ ID NO: 5287) | |
| | 5'-GA<u>U</u>UUAUAAUC<u>U</u>CUAAAGGAAGaa-3' | (SEQ ID NO: 1260) | |
| | 3'-<u>GACU</u>AAAUAUUAGA<u>A</u>GAUUUCC<u>UUCUU</u>-5' | (SEQ ID NO: 3274) | |
| LDHA-320 Target: | 5'-CTGATTTATAATCTTCTAAAGGAAGAA-3' | (SEQ ID NO: 5288) | |
| | 5'-A<u>U</u>UUAUAAUCUUC<u>U</u>AAAGGAAGAac-3' | (SEQ ID NO: 1261) | |
| | 3'-<u>AC</u>UAAAUAUUAGAA<u>G</u>AUUUCCUU<u>CUUG</u>-5' | (SEQ ID NO: 3275) | |
| LDHA-321 Target: | 5'-TGATTTATAATCTTCTAAAGGAAGAAC-3' | (SEQ ID NO: 5289) | |
| | 5'-U<u>U</u>UAUAAUCUUCU<u>AA</u>AGGAAGAAca-3' | (SEQ ID NO: 1262) | |
| | 3'-<u>CU</u>AAAUAUUAGAAG<u>A</u>UUUCCUUC<u>UUGU</u>-5' | (SEQ ID NO: 3276) | |
| LDHA-322 Target: | 5'-GATTTATAATCTTCTAAAGGAAGAACA-3' | (SEQ ID NO: 5290) | |
| | 5'-UU<u>U</u>AUAAUCUUCUA<u>A</u>AGGAAGAACag-3' | (SEQ ID NO: 1263) | |
| | 3'-<u>U</u>AA<u>A</u>UAUUAGAAGA<u>U</u>UUCCUUC<u>UUGUC</u>-5' | (SEQ ID NO: 3277) | |
| LDHA-323 Target: | 5'-ATTTATAATCTTCTAAAGGAAGAACAG-3' | (SEQ ID NO: 5291) | |
| | 5'-U<u>A</u>U<u>A</u>AUCUUCUAA<u>A</u>GGAAGAACAga-3' | (SEQ ID NO: 1264) | |
| | 3'-<u>AAA</u>UAUUAGAAGAUUUCCUUC<u>UUGUCU</u>-5' | (SEQ ID NO: 3278) | |
| LDHA-324 Target: | 5'-TTTATAATCTTCTAAAGGAAGAACAGA-3' | (SEQ ID NO: 5292) | |
| | 5'-A<u>U</u>A<u>A</u>UCUUCUAAA<u>GG</u>AAGAACAGac-3' | (SEQ ID NO: 1265) | |
| | 3'-<u>AA</u>UAUUAGAAGAUUU<u>CC</u>UUCUUGU<u>CUG</u>-5' | (SEQ ID NO: 3279) | |
| LDHA-325 Target: | 5'-TTATAATCTTCTAAAGGAAGAACAGAC-3' | (SEQ ID NO: 5293) | |
| | 5'-U<u>AA</u>UCUUCUAAAGG<u>A</u>AGAACAGAcc-3' | (SEQ ID NO: 1266) | |
| | 3'-<u>A</u>UAUUAGAAGAUUU<u>CC</u>UUCUUGU<u>CUGG</u>-5' | (SEQ ID NO: 3280) | |
| LDHA-326 Target: | 5'-TATAATCTTCTAAAGGAAGAACAGACC-3' | (SEQ ID NO: 5294) | |
| | 5'-AA<u>U</u>CUUCUAAAGG<u>A</u>AGAACAGACcc-3' | (SEQ ID NO: 1267) | |
| | 3'-<u>U</u>AUUAGAAGAUUU<u>CC</u>UUCUUGU<u>CUGGG</u>-5' | (SEQ ID NO: 3281) | |
| LDHA-327 Target: | 5'-ATAATCTTCTAAAGGAAGAACAGACCC-3' | (SEQ ID NO: 5295) | |
| | 5'-A<u>U</u>CUUCUAAAGGA<u>A</u>GAACAGACCcc-3' | (SEQ ID NO: 1268) | |
| | 3'-<u>A</u>UUAGAAGAUUUCC<u>UU</u>CUUGUCU<u>GGGG</u>-5' | (SEQ ID NO: 3282) | |
| LDHA-328 Target: | 5'-TAATCTTCTAAAGGAAGAACAGACCCC-3' | (SEQ ID NO: 5296) | |
| | 5'-U<u>C</u>UUCUAAAGGAAG<u>AA</u>CAGACCCcc-3' | (SEQ ID NO: 1269) | |
| | 3'-<u>UU</u>AGAAGAUUUCCUU<u>C</u>UUGUCU<u>GGGGG</u>-5' | (SEQ ID NO: 3283) | |
| LDHA-329 Target: | 5'-AATCTTCTAAAGGAAGAACAGACCCCC-3' | (SEQ ID NO: 5297) | |
| | 5'-C<u>UU</u>CUAAAGGAAG<u>AA</u>CAGACCCCcc-3' | (SEQ ID NO: 1270) | |
| | 3'-<u>UAGAA</u>GAUUUCC<u>UU</u>C<u>U</u>UGUCU<u>GGGGG</u>-5' | (SEQ ID NO: 3284) | |
| LDHA-330 Target: | 5'-ATCTTCTAAAGGAAGAACAGACCCCCC-3' | (SEQ ID NO: 5298) | |

TABLE 12-continued

Additional Selected Human Anti-Lactate Dehydrogenase DsiRNA Agents (Asymmetrics)

| | | |
|---|---|---|
| LDHA-331 Target: | 5'-UUCUAAAGGAAGAACAGACCCCCca-3'<br>3'-AGAAGAUUUCCUUCUUGUCUGGGGGGU-5'<br>5'-TCTTCTAAAGGAAGAACAGACCCCCCA-3' | (SEQ ID NO: 1271)<br>(SEQ ID NO: 3285)<br>(SEQ ID NO: 5299) |
| LDHA-332 Target: | 5'-UCUAAAGGAAGAACAGACCCCCCag-3'<br>3'-GAAGAUUUCCUUCUUGUCUGGGGGGUC-5'<br>5'-CTTCTAAAGGAAGAACAGACCCCCCAG-3' | (SEQ ID NO: 1272)<br>(SEQ ID NO: 3286)<br>(SEQ ID NO: 5300) |
| LDHA-333 Target: | 5'-CUAAAGGAAGAACAGACCCCCCAga-3'<br>3'-AAGAUUUCCUUCUUGUCUGGGGGGUCU-5'<br>5'-TTCTAAAGGAAGAACAGACCCCCCAGA-3' | (SEQ ID NO: 1273)<br>(SEQ ID NO: 3287)<br>(SEQ ID NO: 5301) |
| LDHA-334 Target: | 5'-UAAAGGAAGAACAGACCCCCCAGaa-3'<br>3'-AGAUUUCCUUCUUGUCUGGGGGGUCUU-5'<br>5'-TCTAAAGGAAGAACAGACCCCCCAGAA-3' | (SEQ ID NO: 1274)<br>(SEQ ID NO: 3288)<br>(SEQ ID NO: 5302) |
| LDHA-335 Target: | 5'-AAAGGAAGAACAGACCCCCCAGAat-3'<br>3'-GAUUUCCUUCUUGUCUGGGGGGUCUUA-5'<br>5'-CTAAAGGAAGAACAGACCCCCCAGAAT-3' | (SEQ ID NO: 1275)<br>(SEQ ID NO: 3289)<br>(SEQ ID NO: 5303) |
| LDHA-336 Target: | 5'-AAGGAAGAACAGACCCCCCAGAAta-3'<br>3'-AUUUCCUUCUUGUCUGGGGGGUCUUAU-5'<br>5'-TAAAGGAAGAACAGACCCCCCAGAATA-3' | (SEQ ID NO: 1276)<br>(SEQ ID NO: 3290)<br>(SEQ ID NO: 5304) |
| LDHA-337 Target: | 5'-AGGAAGAACAGACCCCCCAGAAUaa-3'<br>3'-UUUCCUUCUUGUCUGGGGGGUCUUAUU-5'<br>5'-AAAGGAAGAACAGACCCCCCAGAATAA-3' | (SEQ ID NO: 1277)<br>(SEQ ID NO: 3291)<br>(SEQ ID NO: 5305) |
| LDHA-338 Target: | 5'-GGAAGAACAGACCCCCCAGAAUAag-3'<br>3'-UUCCUUCUUGUCUGGGGGGUCUUAUUC-5'<br>5'-AAGGAAGAACAGACCCCCCAGAATAAG-3' | (SEQ ID NO: 1278)<br>(SEQ ID NO: 3292)<br>(SEQ ID NO: 5306) |
| LDHA-339 Target: | 5'-GAAGAACAGACCCCCCAGAAUAAga-3'<br>3'-UCCUUCUUGUCUGGGGGGUCUUAUUCU-5'<br>5'-AGGAAGAACAGACCCCCCAGAATAAGA-3' | (SEQ ID NO: 1279)<br>(SEQ ID NO: 3293)<br>(SEQ ID NO: 5307) |
| LDHA-340 Target: | 5'-AAGAACAGACCCCCCAGAAUAAGat-3'<br>3'-CCUUCUUGUCUGGGGGGUCUUAUUCUA-5'<br>5'-GGAAGAACAGACCCCCCAGAATAAGAT-3' | (SEQ ID NO: 1280)<br>(SEQ ID NO: 3294)<br>(SEQ ID NO: 5308) |
| LDHA-341 Target: | 5'-AGAACAGACCCCCCAGAAUAAGAtt-3'<br>3'-CUUCUUGUCUGGGGGGUCUUAUUCUAA-5'<br>5'-GAAGAACAGACCCCCCAGAATAAGATT-3' | (SEQ ID NO: 1281)<br>(SEQ ID NO: 3295)<br>(SEQ ID NO: 5309) |
| LDHA-342 Target: | 5'-GAACAGACCCCCCAGAAUAAGAUta-3'<br>3'-UUCUUGUCUGGGGGGUCUUAUUCUAAU-5'<br>5'-AAGAACAGACCCCCCAGAATAAGATTA-3' | (SEQ ID NO: 1282)<br>(SEQ ID NO: 3296)<br>(SEQ ID NO: 5310) |
| LDHA-343 Target: | 5'-AACAGACCCCCCAGAAUAAGAUUac-3'<br>3'-UCUUGUCUGGGGGGUCUUAUUCUAAUG-5'<br>5'-AGAACAGACCCCCCAGAATAAGATTAC-3' | (SEQ ID NO: 1283)<br>(SEQ ID NO: 3297)<br>(SEQ ID NO: 5311) |
| LDHA-344 Target: | 5'-ACAGACCCCCCAGAAUAAGAUUAca-3'<br>3'-CUUGUCUGGGGGGUCUUAUUCUAAUGU-5'<br>5'-GAACAGACCCCCCAGAATAAGATTACA-3' | (SEQ ID NO: 1284)<br>(SEQ ID NO: 3298)<br>(SEQ ID NO: 5312) |
| LDHA-345 Target: | 5'-CAGACCCCCCAGAAUAAGAUUACag-3'<br>3'-UUGUCUGGGGGGUCUUAUUCUAAUGUC-5'<br>5'-AACAGACCCCCCAGAATAAGATTACAG-3' | (SEQ ID NO: 1285)<br>(SEQ ID NO: 3299)<br>(SEQ ID NO: 5313) |
| LDHA-346 Target: | 5'-AGACCCCCCAGAAUAAGAUUACAgt-3'<br>3'-UGUCUGGGGGGUCUUAUUCUAAUGUCA-5'<br>5'-ACAGACCCCCCAGAATAAGATTACAGT-3' | (SEQ ID NO: 1286)<br>(SEQ ID NO: 3300)<br>(SEQ ID NO: 5314) |
| LDHA-347 Target: | 5'-GACCCCCCAGAAUAAGAUUACAGtt-3'<br>3'-GUCUGGGGGGUCUUAUUCUAAUGUCAA-5'<br>5'-CAGACCCCCCAGAATAAGATTACAGTT-3' | (SEQ ID NO: 1287)<br>(SEQ ID NO: 3301)<br>(SEQ ID NO: 5315) |
| LDHA-348 Target: | 5'-ACCCCCCAGAAUAAGAUUACAGUtg-3'<br>3'-UCUGGGGGGUCUUAUUCUAAUGUCAAC-5'<br>5'-AGACCCCCCAGAATAAGATTACAGTTG-3' | (SEQ ID NO: 1288)<br>(SEQ ID NO: 3302)<br>(SEQ ID NO: 5316) |
| LDHA-349 Target: | 5'-CCCCCCAGAAUAAGAUUACAGUUgt-3'<br>3'-CUGGGGGGUCUUAUUCUAAUGUCAACA-5'<br>5'-GACCCCCCAGAATAAGATTACAGTTGT-3' | (SEQ ID NO: 1289)<br>(SEQ ID NO: 3303)<br>(SEQ ID NO: 5317) |

TABLE 12-continued

Additional Selected Human Anti-Lactate Dehydrogenase DsiRNA Agents (Asymmetrics)

| | | |
|---|---|---|
| LDHA-350 Target: | 5'-CCCCCAGAAUAAGAUUACAGUUGtt-3'<br>3'-UGGGGGGUCUUAUUCUAAUGUCAACAA-5'<br>5'-ACCCCCCAGAATAAGATTACAGTTGTT-3' | (SEQ ID NO: 1290)<br>(SEQ ID NO: 3304)<br>(SEQ ID NO: 5318) |
| LDHA-351 Target: | 5'-CCCCAGAAUAAGAUUACAGUUGtg-3'<br>3'-GGGGGGUCUUAUUCUAAUGUCAACAAC-5'<br>5'-CCCCCCAGAATAAGATTACAGTTGTTG-3' | (SEQ ID NO: 1291)<br>(SEQ ID NO: 3305)<br>(SEQ ID NO: 5319) |
| LDHA-352 Target: | 5'-CCCAGAAUAAGAUUACAGUUGUUgg-3'<br>3'-GGGGGUCUUAUUCUAAUGUCAACAACC-5'<br>5'-CCCCCAGAATAAGATTACAGTTGTTGG-3' | (SEQ ID NO: 1292)<br>(SEQ ID NO: 3306)<br>(SEQ ID NO: 5320) |
| LDHA-353 Target: | 5'-CCAGAAUAAGAUUACAGUUGUUGgg-3'<br>3'-GGGGUCUUAUUCUAAUGUCAACAACCC-5'<br>5'-CCCCAGAATAAGATTACAGTTGTTGGG-3' | (SEQ ID NO: 1293)<br>(SEQ ID NO: 3307)<br>(SEQ ID NO: 5321) |
| LDHA-354 Target: | 5'-CAGAAUAAGAUUACAGUUGUUGGgg-3'<br>3'-GGGUCUUAUUCUAAUGUCAACAACCCC-5'<br>5'-CCCAGAATAAGATTACAGTTGTTGGGG-3' | (SEQ ID NO: 1294)<br>(SEQ ID NO: 3308)<br>(SEQ ID NO: 5322) |
| LDHA-357 Target: | 5'-AAUAAGAUUACAGUUGUUGGGGGUtg-3'<br>3'-UCUUAUUCUAAUGUCAACAACCCCCAAC-5'<br>5'-AGAATAAGATTACAGTTGTTGGGGTTG-3' | (SEQ ID NO: 1295)<br>(SEQ ID NO: 3309)<br>(SEQ ID NO: 5323) |
| LDHA-358 Target: | 5'-AUAAGAUUACAGUUGUUGGGGUUgg-3'<br>3'-CUUAUUCUAAUGUCAACAACCCCAACC-5'<br>5'-GAATAAGATTACAGTTGTTGGGGTTGG-3' | (SEQ ID NO: 1296)<br>(SEQ ID NO: 3310)<br>(SEQ ID NO: 5324) |
| LDHA-359 Target: | 5'-UAAGAUUACAGUUGUUGGGGUUGgt-3'<br>3'-UUAUUCUAAUGUCAACAACCCCAACCA-5'<br>5'-AATAAGATTACAGTTGTTGGGGTTGGT-3' | (SEQ ID NO: 1297)<br>(SEQ ID NO: 3311)<br>(SEQ ID NO: 5325) |
| LDHA-368 Target: | 5'-AGUUGUUGGGGUUGGUGCUGUUGgc-3'<br>3'-UGUCAACAACCCCAACCACGACAACCG-5'<br>5'-ACAGTTGTTGGGGTTGGTGCTGTTGGC-3' | (SEQ ID NO: 1298)<br>(SEQ ID NO: 3312)<br>(SEQ ID NO: 5326) |
| LDHA-371 Target: | 5'-UGUUGGGGUUGGUGCUGUUGGCAtg-3'<br>3'-CAACAACCCCAACCACGACAACCGUAC-5'<br>5'-GTTGTTGGGGTTGGTGCTGTTGGCATG-3' | (SEQ ID NO: 1299)<br>(SEQ ID NO: 3313)<br>(SEQ ID NO: 5327) |
| LDHA-372 Target: | 5'-GUUGGGGUUGGUGCUGUUGGCAUgg-3'<br>3'-AACAACCCCAACCACGACAACCGUACC-5'<br>5'-TTGTTGGGGTTGGTGCTGTTGGCATGG-3' | (SEQ ID NO: 1300)<br>(SEQ ID NO: 3314)<br>(SEQ ID NO: 5328) |
| LDHA-373 Target: | 5'-UUGGGGUUGGUGCUGUUGGCAUGgc-3'<br>3'-ACAACCCCAACCACGACAACCGUACCG-5'<br>5'-TGTTGGGGTTGGTGCTGTTGGCATGGC-3' | (SEQ ID NO: 1301)<br>(SEQ ID NO: 3315)<br>(SEQ ID NO: 5329) |
| LDHA-374 Target: | 5'-UGGGGUUGGUGCUGUUGGCAUGGcc-3'<br>3'-CAACCCCAACCACGACAACCGUACCGG-5'<br>5'-GTTGGGGTTGGTGCTGTTGGCATGGCC-3' | (SEQ ID NO: 1302)<br>(SEQ ID NO: 3316)<br>(SEQ ID NO: 5330) |
| LDHA-375 Target: | 5'-GGGGUUGGUGCUGUUGGCAUGGCct-3'<br>3'-AACCCCAACCACGACAACCGUACCGGA-5'<br>5'-TTGGGGTTGGTGCTGTTGGCATGGCCT-3' | (SEQ ID NO: 1303)<br>(SEQ ID NO: 3317)<br>(SEQ ID NO: 5331) |
| LDHA-376 Target: | 5'-GGGUUGGUGCUGUUGGCAUGGCCtg-3'<br>3'-ACCCCAACCACGACAACCGUACCGGAC-5'<br>5'-TGGGGTTGGTGCTGTTGGCATGGCCTG-3' | (SEQ ID NO: 1304)<br>(SEQ ID NO: 3318)<br>(SEQ ID NO: 5332) |
| LDHA-377 Target: | 5'-GGUUGGUGCUGUUGGCAUGGCCUgt-3'<br>3'-CCCCAACCACGACAACCGUACCGGACA-5'<br>5'-GGGGTTGGTGCTGTTGGCATGGCCTGT-3' | (SEQ ID NO: 1305)<br>(SEQ ID NO: 3319)<br>(SEQ ID NO: 5333) |
| LDHA-378 Target: | 5'-GUUGGUGCUGUUGGCAUGGCCUGtg-3'<br>3'-CCCAACCACGACAACCGUACCGGACAC-5'<br>5'-GGGTTGGTGCTGTTGGCATGGCCTGTG-3' | (SEQ ID NO: 1306)<br>(SEQ ID NO: 3320)<br>(SEQ ID NO: 5334) |
| LDHA-379 Target: | 5'-UUGGUGCUGUUGGCAUGGCCUGUgc-3'<br>3'-CCAACCACGACAACCGUACCGGACACG-5'<br>5'-GGTTGGTGCTGTTGGCATGGCCTGTGC-3' | (SEQ ID NO: 1307)<br>(SEQ ID NO: 3321)<br>(SEQ ID NO: 5335) |
| LDHA-380 Target: | 5'-UGGUGCUGUUGGCAUGGCCUGUGcc-3'<br>3'-CAACCACGACAACCGUACCGGACACGG-5'<br>5'-GTTGGTGCTGTTGGCATGGCCTGTGCC-3' | (SEQ ID NO: 1308)<br>(SEQ ID NO: 3322)<br>(SEQ ID NO: 5336) |

TABLE 12-continued

Additional Selected Human Anti-Lactate Dehydrogenase DsiRNA Agents (Asymmetrics)

|  |  |  |
|---|---|---|
| LDHA-381 Target: | 5'-GGUGCUGUUGGCAUGGCCUGUGCca-3'<br>3'-AACCACGACAACCGUACCGGACACGGU-5'<br>5'-TTGGTGCTGTTGGCATGGCCTGTGCCA-3' | (SEQ ID NO: 1309)<br>(SEQ ID NO: 3323)<br>(SEQ ID NO: 5337) |
| LDHA-382 Target: | 5'-GUGCUGUUGGCAUGGCCUGUGCCat-3'<br>3'-ACCACGACAACCGUACCGGACACGGUA-5'<br>5'-TGGTGCTGTTGGCATGGCCTGTGCCAT-3' | (SEQ ID NO: 1310)<br>(SEQ ID NO: 3324)<br>(SEQ ID NO: 5338) |
| LDHA-383 Target: | 5'-UGCUGUUGGCAUGGCCUGUGCCAtc-3'<br>3'-CCACGACAACCGUACCGGACACGGUAG-5'<br>5'-GGTGCTGTTGGCATGGCCTGTGCCATC-3' | (SEQ ID NO: 1311)<br>(SEQ ID NO: 3325)<br>(SEQ ID NO: 5339) |
| LDHA-384 Target: | 5'-GCUGUUGGCAUGGCCUGUGCCAUca-3'<br>3'-CACGACAACCGUACCGGACACGGUAGU-5'<br>5'-GTGCTGTTGGCATGGCCTGTGCCATCA-3' | (SEQ ID NO: 1312)<br>(SEQ ID NO: 3326)<br>(SEQ ID NO: 5340) |
| LDHA-385 Target: | 5'-CUGUUGGCAUGGCCUGUGCCAUCag-3'<br>3'-ACGACAACCGUACCGGACACGGUAGUC-5'<br>5'-TGCTGTTGGCATGGCCTGTGCCATCAG-3' | (SEQ ID NO: 1313)<br>(SEQ ID NO: 3327)<br>(SEQ ID NO: 5341) |
| LDHA-386 Target: | 5'-UGUUGGCAUGGCCUGUGCCAUCAgt-3'<br>3'-CGACAACCGUACCGGACACGGUAGUCA-5'<br>5'-GCTGTTGGCATGGCCTGTGCCATCAGT-3' | (SEQ ID NO: 1314)<br>(SEQ ID NO: 3328)<br>(SEQ ID NO: 5342) |
| LDHA-387 Target: | 5'-GUUGGCAUGGCCUGUGCCAUCAGta-3'<br>3'-GACAACCGUACCGGACACGGUAGUCAU-5'<br>5'-CTGTTGGCATGGCCTGTGCCATCAGTA-3' | (SEQ ID NO: 1315)<br>(SEQ ID NO: 3329)<br>(SEQ ID NO: 5343) |
| LDHA-388 Target: | 5'-UUGGCAUGGCCUGUGCCAUCAGUat-3'<br>3'-ACAACCGUACCGGACACGGUAGUCAUA-5'<br>5'-TGTTGGCATGGCCTGTGCCATCAGTAT-3' | (SEQ ID NO: 1316)<br>(SEQ ID NO: 3330)<br>(SEQ ID NO: 5344) |
| LDHA-389 Target: | 5'-UGGCAUGGCCUGUGCCAUCAGUAtc-3'<br>3'-CAACCGUACCGGACACGGUAGUCAUAG-5'<br>5'-GTTGGCATGGCCTGTGCCATCAGTATC-3' | (SEQ ID NO: 1317)<br>(SEQ ID NO: 3331)<br>(SEQ ID NO: 5345) |
| LDHA-390 Target: | 5'-GGCAUGGCCUGUGCCAUCAGUAUct-3'<br>3'-AACCGUACCGGACACGGUAGUCAUAGA-5'<br>5'-TTGGCATGGCCTGTGCCATCAGTATCT-3' | (SEQ ID NO: 1318)<br>(SEQ ID NO: 3332)<br>(SEQ ID NO: 5346) |
| LDHA-391 Target: | 5'-GCAUGGCCUGUGCCAUCAGUAUCtt-3'<br>3'-ACCGUACCGGACACGGUAGUCAUAGAA-5'<br>5'-TGGCATGGCCTGTGCCATCAGTATCTT-3' | (SEQ ID NO: 1319)<br>(SEQ ID NO: 3333)<br>(SEQ ID NO: 5347) |
| LDHA-392 Target: | 5'-CAUGGCCUGUGCCAUCAGUAUCUta-3'<br>3'-CCGUACCGGACACGGUAGUCAUAGAAU-5'<br>5'-GGCATGGCCTGTGCCATCAGTATCTTA-3' | (SEQ ID NO: 1320)<br>(SEQ ID NO: 3334)<br>(SEQ ID NO: 5348) |
| LDHA-393 Target: | 5'-AUGGCCUGUGCCAUCAGUAUCUUaa-3'<br>3'-CGUACCGGACACGGUAGUCAUAGAAUU-5'<br>5'-GCATGGCCTGTGCCATCAGTATCTTAA-3' | (SEQ ID NO: 1321)<br>(SEQ ID NO: 3335)<br>(SEQ ID NO: 5349) |
| LDHA-394 Target: | 5'-UGGCCUGUGCCAUCAGUAUCUUAat-3'<br>3'-GUACCGGACACGGUAGUCAUAGAAUUA-5'<br>5'-CATGGCCTGTGCCATCAGTATCTTAAT-3' | (SEQ ID NO: 1322)<br>(SEQ ID NO: 3336)<br>(SEQ ID NO: 5350) |
| LDHA-395 Target: | 5'-GGCCUGUGCCAUCAGUAUCUUAAtg-3'<br>3'-UACCGGACACGGUAGUCAUAGAAUUAC-5'<br>5'-ATGGCCTGTGCCATCAGTATCTTAATG-3' | (SEQ ID NO: 1323)<br>(SEQ ID NO: 3337)<br>(SEQ ID NO: 5351) |
| LDHA-396 Target: | 5'-GCCUGUGCCAUCAGUAUCUUAAUga-3'<br>3'-ACCGGACACGGUAGUCAUAGAAUUACU-5'<br>5'-TGGCCTGTGCCATCAGTATCTTAATGA-3' | (SEQ ID NO: 1324)<br>(SEQ ID NO: 3338)<br>(SEQ ID NO: 5352) |
| LDHA-405 Target: | 5'-AUCAGUAUCUUAAUGAAGGACUUgg-3'<br>3'-GGUAGUCAUAGAAUUACUUCCUGAACC-5'<br>5'-CCATCAGTATCTTAATGAAGGACTTGG-3' | (SEQ ID NO: 1325)<br>(SEQ ID NO: 3339)<br>(SEQ ID NO: 5353) |
| LDHA-406 Target: | 5'-UCAGUAUCUUAAUGAAGGACUUGgc-3'<br>3'-GUAGUCAUAGAAUUACUUCCUGAACCG-5'<br>5'-CATCAGTATCTTAATGAAGGACTTGGC-3' | (SEQ ID NO: 1326)<br>(SEQ ID NO: 3340)<br>(SEQ ID NO: 5354) |
| LDHA-407 Target: | 5'-CAGUAUCUUAAUGAAGGACUUGGca-3'<br>3'-UAGUCAUAGAAUUACUUCCUGAACCGU-5'<br>5'-ATCAGTATCTTAATGAAGGACTTGGCA-3' | (SEQ ID NO: 1327)<br>(SEQ ID NO: 3341)<br>(SEQ ID NO: 5355) |

TABLE 12-continued

Additional Selected Human Anti-Lactate Dehydrogenase DsiRNA Agents (Asymmetrics)

| | | |
|---|---|---|
| LDHA-408 Target: | 5'-AGUAUCUUAAUGAAGGACUUGGCag-3'<br>3'-AGUCAUAGAAUUACUUCCUGAACCGUC-5'<br>5'-TCAGTATCTTAATGAAGGACTTGGCAG-3' | (SEQ ID NO: 1328)<br>(SEQ ID NO: 3342)<br>(SEQ ID NO: 5356) |
| LDHA-409 Target: | 5'-GUAUCUUAAUGAAGGACUUGGCAga-3'<br>3'-GUCAUAGAAUUACUUCCUGAACCGUCU-5'<br>5'-CAGTATCTTAATGAAGGACTTGGCAGA-3' | (SEQ ID NO: 1329)<br>(SEQ ID NO: 3343)<br>(SEQ ID NO: 5357) |
| LDHA-410 Target: | 5'-UAUCUUAAUGAAGGACUUGGCAGat-3'<br>3'-UCAUAGAAUUACUUCCUGAACCGUCUA-5'<br>5'-AGTATCTTAATGAAGGACTTGGCAGAT-3' | (SEQ ID NO: 1330)<br>(SEQ ID NO: 3344)<br>(SEQ ID NO: 5358) |
| LDHA-411 Target: | 5'-AUCUUAAUGAAGGACUUGGCAGAtg-3'<br>3'-CAUAGAAUUACUUCCUGAACCGUCUAC-5'<br>5'-GTATCTTAATGAAGGACTTGGCAGATG-3' | (SEQ ID NO: 1331)<br>(SEQ ID NO: 3345)<br>(SEQ ID NO: 5359) |
| LDHA-412 Target: | 5'-UCUUAAUGAAGGACUUGGCAGAUga-3'<br>3'-AUAGAAUUACUUCCUGAACCGUCUACU-5'<br>5'-TATCTTAATGAAGGACTTGGCAGATGA-3' | (SEQ ID NO: 1332)<br>(SEQ ID NO: 3346)<br>(SEQ ID NO: 5360) |
| LDHA-413 Target: | 5'-CUUAAUGAAGGACUUGGCAGAUGaa-3'<br>3'-UAGAAUUACUUCCUGAACCGUCUACUU-5'<br>5'-ATCTTAATGAAGGACTTGGCAGATGAA-3' | (SEQ ID NO: 1333)<br>(SEQ ID NO: 3347)<br>(SEQ ID NO: 5361) |
| LDHA-414 Target: | 5'-UUAAUGAAGGACUUGGCAGAUGAac-3'<br>3'-AGAAUUACUUCCUGAACCGUCUACUUG-5'<br>5'-TCTTAATGAAGGACTTGGCAGATGAAC-3' | (SEQ ID NO: 1334)<br>(SEQ ID NO: 3348)<br>(SEQ ID NO: 5362) |
| LDHA-415 Target: | 5'-UAAUGAAGGACUUGGCAGAUGAAct-3'<br>3'-GAAUUACUUCCUGAACCGUCUACUUGA-5'<br>5'-CTTAATGAAGGACTTGGCAGATGAACT-3' | (SEQ ID NO: 1335)<br>(SEQ ID NO: 3349)<br>(SEQ ID NO: 5363) |
| LDHA-416 Target: | 5'-AAUGAAGGACUUGGCAGAUGAACtt-3'<br>3'-AAUUACUUCCUGAACCGUCUACUUGAA-5'<br>5'-TTAATGAAGGACTTGGCAGATGAACTT-3' | (SEQ ID NO: 1336)<br>(SEQ ID NO: 3350)<br>(SEQ ID NO: 5364) |
| LDHA-417 Target: | 5'-AUGAAGGACUUGGCAGAUGAACUtg-3'<br>3'-AUUACUUCCUGAACCGUCUACUUGAAC-5'<br>5'-TAATGAAGGACTTGGCAGATGAACTTG-3' | (SEQ ID NO: 1337)<br>(SEQ ID NO: 3351)<br>(SEQ ID NO: 5365) |
| LDHA-418 Target: | 5'-UGAAGGACUUGGCAGAUGAACUUgc-3'<br>3'-UUACUUCCUGAACCGUCUACUUGAACG-5'<br>5'-AATGAAGGACTTGGCAGATGAACTTGC-3' | (SEQ ID NO: 1338)<br>(SEQ ID NO: 3352)<br>(SEQ ID NO: 5366) |
| LDHA-419 Target: | 5'-GAAGGACUUGGCAGAUGAACUUGct-3'<br>3'-UACUUCCUGAACCGUCUACUUGAACGA-5'<br>5'-ATGAAGGACTTGGCAGATGAACTTGCT-3' | (SEQ ID NO: 1339)<br>(SEQ ID NO: 3353)<br>(SEQ ID NO: 5367) |
| LDHA-420 Target: | 5'-AAGGACUUGGCAGAUGAACUUGCtc-3'<br>3'-ACUUCCUGAACCGUCUACUUGAACGAG-5'<br>5'-TGAAGGACTTGGCAGATGAACTTGCTC-3' | (SEQ ID NO: 1340)<br>(SEQ ID NO: 3354)<br>(SEQ ID NO: 5368) |
| LDHA-421 Target: | 5'-AGGACUUGGCAGAUGAACUUGCUct-3'<br>3'-CUUCCUGAACCGUCUACUUGAACGAGA-5'<br>5'-GAAGGACTTGGCAGATGAACTTGCTCT-3' | (SEQ ID NO: 1341)<br>(SEQ ID NO: 3355)<br>(SEQ ID NO: 5369) |
| LDHA-422 Target: | 5'-GGACUUGGCAGAUGAACUUGCUCtt-3'<br>3'-UUCCUGAACCGUCUACUUGAACGAGAA-5'<br>5'-AAGGACTTGGCAGATGAACTTGCTCTT-3' | (SEQ ID NO: 1342)<br>(SEQ ID NO: 3356)<br>(SEQ ID NO: 5370) |
| LDHA-423 Target: | 5'-GACUUGGCAGAUGAACUUGCUCUtg-3'<br>3'-UCCUGAACCGUCUACUUGAACGAGAAC-5'<br>5'-AGGACTTGGCAGATGAACTTGCTCTTG-3' | (SEQ ID NO: 1343)<br>(SEQ ID NO: 3357)<br>(SEQ ID NO: 5371) |
| LDHA-424 Target: | 5'-ACUUGGCAGAUGAACUUGCUCUUgt-3'<br>3'-CCUGAACCGUCUACUUGAACGAGAACA-5'<br>5'-GGACTTGGCAGATGAACTTGCTCTTGT-3' | (SEQ ID NO: 1344)<br>(SEQ ID NO: 3358)<br>(SEQ ID NO: 5372) |
| LDHA-425 Target: | 5'-CUUGGCAGAUGAACUUGCUCUUGtt-3'<br>3'-CUGAACCGUCUACUUGAACGAGAACAA-5'<br>5'-GACTTGGCAGATGAACTTGCTCTTGTT-3' | (SEQ ID NO: 1345)<br>(SEQ ID NO: 3359)<br>(SEQ ID NO: 5373) |
| LDHA-426 Target: | 5'-UUGGCAGAUGAACUUGCUCUUGUtg-3'<br>3'-UGAACCGUCUACUUGAACGAGAACAAC-5'<br>5'-ACTTGGCAGATGAACTTGCTCTTGTTG-3' | (SEQ ID NO: 1346)<br>(SEQ ID NO: 3360)<br>(SEQ ID NO: 5374) |

TABLE 12-continued

Additional Selected Human Anti-Lactate Dehydrogenase DsiRNA Agents (Asymmetrics)

|  |  |  |
|---|---|---|
| LDHA-427 Target: | 5'-UGGCAGAUGAACUUGCUCUUGUUGa-3'<br>3'-GAACCGUCUACUUGAACGAGAACAACU-5'<br>5'-CTTGGCAGATGAACTTGCTCTTGTTGA-3' | (SEQ ID NO: 1347)<br>(SEQ ID NO: 3361)<br>(SEQ ID NO: 5375) |
| LDHA-428 Target: | 5'-GGCAGAUGAACUUGCUCUUGUUGat-3'<br>3'-AACCGUCUACUUGAACGAGAACAACUA-5'<br>5'-TTGGCAGATGAACTTGCTCTTGTTGAT-3' | (SEQ ID NO: 1348)<br>(SEQ ID NO: 3362)<br>(SEQ ID NO: 5376) |
| LDHA-429 Target: | 5'-GCAGAUGAACUUGCUCUUGUUGAtg-3'<br>3'-ACCGUCUACUUGAACGAGAACAACUAC-5'<br>5'-TGGCAGATGAACTTGCTCTTGTTGATG-3' | (SEQ ID NO: 1349)<br>(SEQ ID NO: 3363)<br>(SEQ ID NO: 5377) |
| LDHA-430 Target: | 5'-CAGAUGAACUUGCUCUUGUUGAUgt-3'<br>3'-CCGUCUACUUGAACGAGAACAACUACA-5'<br>5'-GGCAGATGAACTTGCTCTTGTTGATGT-3' | (SEQ ID NO: 1350)<br>(SEQ ID NO: 3364)<br>(SEQ ID NO: 5378) |
| LDHA-431 Target: | 5'-AGAUGAACUGCUCUUGUUGAUGtc-3'<br>3'-CGUCUACUUGAACGAGAACAACUACAG-5'<br>5'-GCAGATGAACTTGCTCTTGTTGATGTC-3' | (SEQ ID NO: 1351)<br>(SEQ ID NO: 3365)<br>(SEQ ID NO: 5379) |
| LDHA-432 Target: | 5'-GAUGAACUUGCUCUUGUUGAUGUca-3'<br>3'-GUCUACUUGAACGAGAACAACUACAGU-5'<br>5'-CAGATGAACTTGCTCTTGTTGATGTCA-3' | (SEQ ID NO: 1352)<br>(SEQ ID NO: 3366)<br>(SEQ ID NO: 5380) |
| LDHA-433 Target: | 5'-AUGAACUUGCUCUUGUUGAUGUCat-3'<br>3'-UCUACUUGAACGAGAACAACUACAGUA-5'<br>5'-AGATGAACTTGCTCTTGTTGATGTCAT-3' | (SEQ ID NO: 1353)<br>(SEQ ID NO: 3367)<br>(SEQ ID NO: 5381) |
| LDHA-434 Target: | 5'-UGAACUUGCUCUUGUUGAUGUCAtc-3'<br>3'-CUACUUGAACGAGAACAACUACAGUAG-5'<br>5'-GATGAACTTGCTCTTGTTGATGTCATC-3' | (SEQ ID NO: 1354)<br>(SEQ ID NO: 3368)<br>(SEQ ID NO: 5382) |
| LDHA-435 Target: | 5'-GAACUUGCUCUUGUUGAUGUCAUcg-3'<br>3'-UACUUGAACGAGAACAACUACAGUAGC-5'<br>5'-ATGAACTTGCTCTTGTTGATGTCATCG-3' | (SEQ ID NO: 1355)<br>(SEQ ID NO: 3369)<br>(SEQ ID NO: 5383) |
| LDHA-436 Target: | 5'-AACUUGCUCUUGUUGAUGUCAUCga-3'<br>3'-ACUUGAACGAGAACAACUACAGUAGCU-5'<br>5'-TGAACTTGCTCTTGTTGATGTCATCGA-3' | (SEQ ID NO: 1356)<br>(SEQ ID NO: 3370)<br>(SEQ ID NO: 5384) |
| LDHA-437 Target: | 5'-ACUUGCUCUUGUUGAUGUCAUCGaa-3'<br>3'-CUUGAACGAGAACAACUACAGUAGCUU-5'<br>5'-GAACTTGCTCTTGTTGATGTCATCGAA-3' | (SEQ ID NO: 1357)<br>(SEQ ID NO: 3371)<br>(SEQ ID NO: 5385) |
| LDHA-438 Target: | 5'-CUUGCUCUUGUUGAUGUCAUCGAag-3'<br>3'-UUGAACGAGAACAACUACAGUAGCUUC-5'<br>5'-AACTTGCTCTTGTTGATGTCATCGAAG-3' | (SEQ ID NO: 1358)<br>(SEQ ID NO: 3372)<br>(SEQ ID NO: 5386) |
| LDHA-439 Target: | 5'-UUGCUCUUGUUGAUGUCAUCGAAga-3'<br>3'-UGAACGAGAACAACUACAGUAGCUUCU-5'<br>5'-ACTTGCTCTTGTTGATGTCATCGAAGA-3' | (SEQ ID NO: 1359)<br>(SEQ ID NO: 3373)<br>(SEQ ID NO: 5387) |
| LDHA-440 Target: | 5'-UGCUCUUGUUGAUGUCAUCGAAGac-3'<br>3'-GAACGAGAACAACUACAGUAGCUUCUG-5'<br>5'-CTTGCTCTTGTTGATGTCATCGAAGAC-3' | (SEQ ID NO: 1360)<br>(SEQ ID NO: 3374)<br>(SEQ ID NO: 5388) |
| LDHA-441 Target: | 5'-GCUCUUGUUGAUGUCAUCGAAGAca-3'<br>3'-AACGAGAACAACUACAGUAGCUUCUGU-5'<br>5'-TTGCTCTTGTTGATGTCATCGAAGACA-3' | (SEQ ID NO: 1361)<br>(SEQ ID NO: 3375)<br>(SEQ ID NO: 5389) |
| LDHA-442 Target: | 5'-CUCUUGUUGAUGUCAUCGAAGACaa-3'<br>3'-ACGAGAACAACUACAGUAGCUUCUGUU-5'<br>5'-TGCTCTTGTTGATGTCATCGAAGACAA-3' | (SEQ ID NO: 1362)<br>(SEQ ID NO: 3376)<br>(SEQ ID NO: 5390) |
| LDHA-443 Target: | 5'-UCUUGUUGAUGUCAUCGAAGACAaa-3'<br>3'-CGAGAACAACUACAGUAGCUUCUGUUU-5'<br>5'-GCTCTTGTTGATGTCATCGAAGACAAA-3' | (SEQ ID NO: 1363)<br>(SEQ ID NO: 3377)<br>(SEQ ID NO: 5391) |
| LDHA-444 Target: | 5'-CUUGUUGAUGUCAUCGAAGACAAat-3'<br>3'-GAGAACAACUACAGUAGCUUCUGUUUA-5'<br>5'-CTCTTGTTGATGTCATCGAAGACAAAT-3' | (SEQ ID NO: 1364)<br>(SEQ ID NO: 3378)<br>(SEQ ID NO: 5392) |
| LDHA-445 Target: | 5'-UUGUUGAUGUCAUCGAAGACAAAtt-3'<br>3'-AGAACAACUACAGUAGCUUCUGUUUAA-5'<br>5'-TCTTGTTGATGTCATCGAAGACAAATT-3' | (SEQ ID NO: 1365)<br>(SEQ ID NO: 3379)<br>(SEQ ID NO: 5393) |

TABLE 12-continued

Additional Selected Human Anti-Lactate Dehydrogenase DsiRNA Agents (Asymmetrics)

| | | |
|---|---|---|
| LDHA-446 Target: | 5'-UGUUGAUGUCAUCGAAGACAAAUtg-3'<br>3'-GAACAACUACAGUAGCUUCUGUUUAAC-5'<br>5'-CTTGTTGATGTCATCGAAGACAAATTG-3' | (SEQ ID NO: 1366)<br>(SEQ ID NO: 3380)<br>(SEQ ID NO: 5394) |
| LDHA-447 Target: | 5'-GUUGAUGUCAUCGAAGACAAAUUga-3'<br>3'-AACAACUACAGUAGCUUCUGUUUAACU-5'<br>5'-TTGTTGATGTCATCGAAGACAAATTGA-3' | (SEQ ID NO: 1367)<br>(SEQ ID NO: 3381)<br>(SEQ ID NO: 5395) |
| LDHA-448 Target: | 5'-UUGAUGUCAUCGAAGACAAAUUGaa-3'<br>3'-ACAACUACAGUAGCUUCUGUUUAACUU-5'<br>5'-TGTTGATGTCATCGAAGACAAATTGAA-3' | (SEQ ID NO: 1368)<br>(SEQ ID NO: 3382)<br>(SEQ ID NO: 5396) |
| LDHA-449 Target: | 5'-UGAUGUCAUCGAAGACAAAUUGAag-3'<br>3'-CAACUACAGUAGCUUCUGUUUAACUUC-5'<br>5'-GTTGATGTCATCGAAGACAAATTGAAG-3' | (SEQ ID NO: 1369)<br>(SEQ ID NO: 3383)<br>(SEQ ID NO: 5397) |
| LDHA-450 Target: | 5'-GAUGUCAUCGAAGACAAAUUGAAgg-3'<br>3'-AACUACAGUAGCUUCUGUUUAACUUCC-5'<br>5'-TTGATGTCATCGAAGACAAATTGAAGG-3' | (SEQ ID NO: 1370)<br>(SEQ ID NO: 3384)<br>(SEQ ID NO: 5398) |
| LDHA-451 Target: | 5'-AUGUCAUCGAAGACAAAUUGAAGgg-3'<br>3'-ACUACAGUAGCUUCUGUUUAACUUCCC-5'<br>5'-TGATGTCATCGAAGACAAATTGAAGGG-3' | (SEQ ID NO: 1371)<br>(SEQ ID NO: 3385)<br>(SEQ ID NO: 5399) |
| LDHA-452 Target: | 5'-UGUCAUCGAAGACAAAUUGAAGGga-3'<br>3'-CUACAGUAGCUUCUGUUUAACUUCCCU-5'<br>5'-GATGTCATCGAAGACAAATTGAAGGGA-3' | (SEQ ID NO: 1372)<br>(SEQ ID NO: 3386)<br>(SEQ ID NO: 5400) |
| LDHA-453 Target: | 5'-GUCAUCGAAGACAAAUUGAAGGGag-3'<br>3'-UACAGUAGCUUCUGUUUAACUUCCCUC-5'<br>5'-ATGTCATCGAAGACAAATTGAAGGGAG-3' | (SEQ ID NO: 1373)<br>(SEQ ID NO: 3387)<br>(SEQ ID NO: 5401) |
| LDHA-454 Target: | 5'-UCAUCGAAGACAAAUUGAAGGGAga-3'<br>3'-ACAGUAGCUUCUGUUUAACUUCCCUCU-5'<br>5'-TGTCATCGAAGACAAATTGAAGGGAGA-3' | (SEQ ID NO: 1374)<br>(SEQ ID NO: 3388)<br>(SEQ ID NO: 5402) |
| LDHA-455 Target: | 5'-CAUCGAAGACAAAUUGAAGGGAGag-3'<br>3'-CAGUAGCUUCUGUUUAACUUCCCUCUC-5'<br>5'-GTCATCGAAGACAAATTGAAGGGAGAG-3' | (SEQ ID NO: 1375)<br>(SEQ ID NO: 3389)<br>(SEQ ID NO: 5403) |
| LDHA-456 Target: | 5'-AUCGAAGACAAAUUGAAGGGAGAga-3'<br>3'-AGUAGCUUCUGUUUAACUUCCCUCUCU-5'<br>5'-TCATCGAAGACAAATTGAAGGGAGAGA-3' | (SEQ ID NO: 1376)<br>(SEQ ID NO: 3390)<br>(SEQ ID NO: 5404) |
| LDHA-457 Target: | 5'-UCGAAGACAAAUUGAAGGGAGAGat-3'<br>3'-GUAGCUUCUGUUUAACUUCCCUCUCUA-5'<br>5'-CATCGAAGACAAATTGAAGGGAGAGAT-3' | (SEQ ID NO: 1377)<br>(SEQ ID NO: 3391)<br>(SEQ ID NO: 5405) |
| LDHA-458 Target: | 5'-CGAAGACAAAUUGAAGGGAGAGAtg-3'<br>3'-UAGCUUCUGUUUAACUUCCCUCUCUAC-5'<br>5'-ATCGAAGACAAATTGAAGGGAGAGATG-3' | (SEQ ID NO: 1378)<br>(SEQ ID NO: 3392)<br>(SEQ ID NO: 5406) |
| LDHA-459 Target: | 5'-GAAGACAAAUUGAAGGGAGAGAUga-3'<br>3'-AGCUUCUGUUUAACUUCCCUCUCUACU-5'<br>5'-TCGAAGACAAATTGAAGGGAGAGATGA-3' | (SEQ ID NO: 1379)<br>(SEQ ID NO: 3393)<br>(SEQ ID NO: 5407) |
| LDHA-460 Target: | 5'-AAGACAAAUUGAAGGGAGAGAUGat-3'<br>3'-GCUUCUGUUUAACUUCCCUCUCUACUA-5'<br>5'-CGAAGACAAATTGAAGGGAGAGATGAT-3' | (SEQ ID NO: 1380)<br>(SEQ ID NO: 3394)<br>(SEQ ID NO: 5408) |
| LDHA-461 Target: | 5'-AGACAAAUUGAAGGGAGAGAUGAtg-3'<br>3'-CUUCUGUUUAACUUCCCUCUCUACUAC-5'<br>5'-GAAGACAAATTGAAGGGAGAGATGATG-3' | (SEQ ID NO: 1381)<br>(SEQ ID NO: 3395)<br>(SEQ ID NO: 5409) |
| LDHA-462 Target: | 5'-GACAAAUUGAAGGGAGAGAUGAUgg-3'<br>3'-UUCUGUUUAACUUCCCUCUCUACUACC-5'<br>5'-AAGACAAATTGAAGGGAGAGATGATGG-3' | (SEQ ID NO: 1382)<br>(SEQ ID NO: 3396)<br>(SEQ ID NO: 5410) |
| LDHA-463 Target: | 5'-ACAAAUUGAAGGGAGAGAUGAUGga-3'<br>3'-UCUGUUUAACUUCCCUCUCUACUACCU-5'<br>5'-AGACAAATTGAAGGGAGAGATGATGGA-3' | (SEQ ID NO: 1383)<br>(SEQ ID NO: 3397)<br>(SEQ ID NO: 5411) |
| LDHA-464 Target: | 5'-CAAAUUGAAGGGAGAGAUGAUGGat-3'<br>3'-CUGUUUAACUUCCCUCUCUACUACCUA-5'<br>5'-GACAAATTGAAGGGAGAGATGATGGAT-3' | (SEQ ID NO: 1384)<br>(SEQ ID NO: 3398)<br>(SEQ ID NO: 5412) |

TABLE 12-continued

Additional Selected Human Anti-Lactate Dehydrogenase DsiRNA Agents (Asymmetrics)

|  |  |  |
|---|---|---|
| LDHA-465 Target: | 5'-AAAUUGAAGGGAGAGAUGAUGGAtc-3'<br>3'-UGUUUAACUUCCCUCUCUACUACCUAG-5'<br>5'-ACAAATTGAAGGGAGAGATGATGGATC-3' | (SEQ ID NO: 1385)<br>(SEQ ID NO: 3399)<br>(SEQ ID NO: 5413) |
| LDHA-466 Target: | 5'-AAUUGAAGGGAGAGAUGAUGGAUct-3'<br>3'-GUUUAACUUCCCUCUCUACUACCUAGA-5'<br>5'-CAAATTGAAGGGAGAGATGATGGATCT-3' | (SEQ ID NO: 1386)<br>(SEQ ID NO: 3400)<br>(SEQ ID NO: 5414) |
| LDHA-467 Target: | 5'-AUUGAAGGGAGAGAUGAUGGAUCtc-3'<br>3'-UUUAACUUCCCUCUCUACUACCUAGAG-5'<br>5'-AAATTGAAGGGAGAGATGATGGATCTC-3' | (SEQ ID NO: 1387)<br>(SEQ ID NO: 3401)<br>(SEQ ID NO: 5415) |
| LDHA-468 Target: | 5'-UUGAAGGGAGAGAUGAUGGAUCUcc-3'<br>3'-UUAACUUCCCUCUCUACUACCUAGAGG-5'<br>5'-AATTGAAGGGAGAGATGATGGATCTCC-3' | (SEQ ID NO: 1388)<br>(SEQ ID NO: 3402)<br>(SEQ ID NO: 5416) |
| LDHA-469 Target: | 5'-UGAAGGGAGAGAUGAUGGAUCUCca-3'<br>3'-UAACUUCCCUCUCUACUACCUAGAGGU-5'<br>5'-ATTGAAGGGAGAGATGATGGATCTCCA-3' | (SEQ ID NO: 1389)<br>(SEQ ID NO: 3403)<br>(SEQ ID NO: 5417) |
| LDHA-470 Target: | 5'-GAAGGGAGAGAUGAUGGAUCUCCaa-3'<br>3'-AACUUCCCUCUCUACUACCUAGAGGUU-5'<br>5'-TTGAAGGGAGAGATGATGGATCTCCAA-3' | (SEQ ID NO: 1390)<br>(SEQ ID NO: 3404)<br>(SEQ ID NO: 5418) |
| LDHA-471 Target: | 5'-AAGGGAGAGAUGAUGGAUCUCCAac-3'<br>3'-ACUUCCCUCUCUACUACCUAGAGGUUG-5'<br>5'-TGAAGGGAGAGATGATGGATCTCCAAC-3' | (SEQ ID NO: 1391)<br>(SEQ ID NO: 3405)<br>(SEQ ID NO: 5419) |
| LDHA-472 Target: | 5'-AGGGAGAGAUGAUGGAUCUCCAAca-3'<br>3'-CUUCCCUCUCUACUACCUAGAGGUUGU-5'<br>5'-GAAGGGAGAGATGATGGATCTCCAACA-3' | (SEQ ID NO: 1392)<br>(SEQ ID NO: 3406)<br>(SEQ ID NO: 5420) |
| LDHA-473 Target: | 5'-GGGAGAGAUGAUGGAUCUCCAACat-3'<br>3'-UUCCCUCUCUACUACCUAGAGGUUGUA-5'<br>5'-AAGGGAGAGATGATGGATCTCCAACAT-3' | (SEQ ID NO: 1393)<br>(SEQ ID NO: 3407)<br>(SEQ ID NO: 5421) |
| LDHA-474 Target: | 5'-GGAGAGAUGAUGGAUCUCCAACAtg-3'<br>3'-UCCCUCUCUACUACCUAGAGGUUGUAC-5'<br>5'-AGGGAGAGATGATGGATCTCCAACATG-3' | (SEQ ID NO: 1394)<br>(SEQ ID NO: 3408)<br>(SEQ ID NO: 5422) |
| LDHA-475 Target: | 5'-GAGAGAUGAUGGAUCUCCAACAUgg-3'<br>3'-CCCUCUCUACUACCUAGAGGUUGUACC-5'<br>5'-GGGAGAGATGATGGATCTCCAACATGG-3' | (SEQ ID NO: 1395)<br>(SEQ ID NO: 3409)<br>(SEQ ID NO: 5423) |
| LDHA-476 Target: | 5'-AGAGAUGAUGGAUCUCCAACAUGgc-3'<br>3'-CCUCUCUACUACCUAGAGGUUGUACCG-5'<br>5'-GGAGAGATGATGGATCTCCAACATGGC-3' | (SEQ ID NO: 1396)<br>(SEQ ID NO: 3410)<br>(SEQ ID NO: 5424) |
| LDHA-477 Target: | 5'-GAGAUGAUGGAUCUCCAACAUGGca-3'<br>3'-CUCUCUACUACCUAGAGGUUGUACCGU-5'<br>5'-GAGAGATGATGGATCTCCAACATGGCA-3' | (SEQ ID NO: 1397)<br>(SEQ ID NO: 3411)<br>(SEQ ID NO: 5425) |
| LDHA-478 Target: | 5'-AGAUGAUGGAUCUCCAACAUGGCag-3'<br>3'-UCUCUACUACCUAGAGGUUGUACCGUC-5'<br>5'-AGAGATGATGGATCTCCAACATGGCAG-3' | (SEQ ID NO: 1398)<br>(SEQ ID NO: 3412)<br>(SEQ ID NO: 5426) |
| LDHA-479 Target: | 5'-GAUGAUGGAUCUCCAACAUGGCAgc-3'<br>3'-CUCUACUACCUAGAGGUUGUACCGUCG-5'<br>5'-GAGATGATGGATCTCCAACATGGCAGC-3' | (SEQ ID NO: 1399)<br>(SEQ ID NO: 3413)<br>(SEQ ID NO: 5427) |
| LDHA-480 Target: | 5'-AUGAUGGAUCUCCAACAUGGCAGcc-3'<br>3'-UCUACUACCUAGAGGUUGUACCGUCGG-5'<br>5'-AGATGATGGATCTCCAACATGGCAGCC-3' | (SEQ ID NO: 1400)<br>(SEQ ID NO: 3414)<br>(SEQ ID NO: 5428) |
| LDHA-481 Target: | 5'-UGAUGGAUCUCCAACAUGGCAGCct-3'<br>3'-CUACUACCUAGAGGUUGUACCGUCGGA-5'<br>5'-GATGATGGATCTCCAACATGGCAGCCT-3' | (SEQ ID NO: 1401)<br>(SEQ ID NO: 3415)<br>(SEQ ID NO: 5429) |
| LDHA-482 Target: | 5'-GAUGGAUCUCCAACAUGGCAGCCtt-3'<br>3'-UACUACCUAGAGGUUGUACCGUCGGAA-5'<br>5'-ATGATGGATCTCCAACATGGCAGCCTT-3' | (SEQ ID NO: 1402)<br>(SEQ ID NO: 3416)<br>(SEQ ID NO: 5430) |
| LDHA-483 Target: | 5'-AUGGAUCUCCAACAUGGCAGCCUtt-3'<br>3'-ACUACCUAGAGGUUGUACCGUCGGAAA-5'<br>5'-TGATGGATCTCCAACATGGCAGCCTTT-3' | (SEQ ID NO: 1403)<br>(SEQ ID NO: 3417)<br>(SEQ ID NO: 5431) |

TABLE 12-continued

Additional Selected Human Anti-Lactate Dehydrogenase DsiRNA Agents (Asymmetrics)

|  |  |  |
|---|---|---|
| LDHA-484 Target: | 5'-UGGAUCUCCAACAUGGCAGCCUUtt-3'<br>3'-CUACCUAGAGGUUGUACCGUCGGAAAA-5'<br>5'-GATGGATCTCCAACATGGCAGCCTTTT-3' | (SEQ ID NO: 1404)<br>(SEQ ID NO: 3418)<br>(SEQ ID NO: 5432) |
| LDHA-485 Target: | 5'-GGAUCUCCAACAUGGCAGCCUUUtc-3'<br>3'-UACCUAGAGGUUGUACCGUCGGAAAAG-5'<br>5'-ATGGATCTCCAACATGGCAGCCTTTTC-3' | (SEQ ID NO: 1405)<br>(SEQ ID NO: 3419)<br>(SEQ ID NO: 5433) |
| LDHA-486 Target: | 5'-GAUCUCCAACAUGGCAGCCUUUUcc-3'<br>3'-ACCUAGAGGUUGUACCGUCGGAAAAGG-5'<br>5'-TGGATCTCCAACATGGCAGCCTTTTCC-3' | (SEQ ID NO: 1406)<br>(SEQ ID NO: 3420)<br>(SEQ ID NO: 5434) |
| LDHA-487 Target: | 5'-AUCUCCAACAUGGCAGCCUUUUCct-3'<br>3'-CCUAGAGGUUGUACCGUCGGAAAAGGA-5'<br>5'-GGATCTCCAACATGGCAGCCTTTTCCT-3' | (SEQ ID NO: 1407)<br>(SEQ ID NO: 3421)<br>(SEQ ID NO: 5435) |
| LDHA-488 Target: | 5'-UCUCCAACAUGGCAGCCUUUUCCtt-3'<br>3'-CUAGAGGUUGUACCGUCGGAAAAGGAA-5'<br>5'-GATCTCCAACATGGCAGCCTTTTCCTT-3' | (SEQ ID NO: 1408)<br>(SEQ ID NO: 3422)<br>(SEQ ID NO: 5436) |
| LDHA-489 Target: | 5'-CUCCAACAUGGCAGCCUUUUCCUta-3'<br>3'-UAGAGGUUGUACCGUCGGAAAAGGAAU-5'<br>5'-ATCTCCAACATGGCAGCCTTTTCCTTA-3' | (SEQ ID NO: 1409)<br>(SEQ ID NO: 3423)<br>(SEQ ID NO: 5437) |
| LDHA-490 Target: | 5'-UCCAACAUGGCAGCCUUUUCCUUag-3'<br>3'-AGAGGUUGUACCGUCGGAAAAGGAAUC-5'<br>5'-TCTCCAACATGGCAGCCTTTTCCTTAG-3' | (SEQ ID NO: 1410)<br>(SEQ ID NO: 3424)<br>(SEQ ID NO: 5438) |
| LDHA-491 Target: | 5'-CCAACAUGGCAGCCUUUUCCUUAga-3'<br>3'-GAGGUUGUACCGUCGGAAAAGGAAUCU-5'<br>5'-CTCCAACATGGCAGCCTTTTCCTTAGA-3' | (SEQ ID NO: 1411)<br>(SEQ ID NO: 3425)<br>(SEQ ID NO: 5439) |
| LDHA-492 Target: | 5'-CAACAUGGCAGCCUUUUCCUUAGaa-3'<br>3'-AGGUUGUACCGUCGGAAAAGGAAUCUU-5'<br>5'-TCCAACATGGCAGCCTTTTCCTTAGAA-3' | (SEQ ID NO: 1412)<br>(SEQ ID NO: 3426)<br>(SEQ ID NO: 5440) |
| LDHA-493 Target: | 5'-AACAUGGCAGCCUUUUCCUUAGAac-3'<br>3'-GGUUGUACCGUCGGAAAAGGAAUCUUG-5'<br>5'-CCAACATGGCAGCCTTTTCCTTAGAAC-3' | (SEQ ID NO: 1413)<br>(SEQ ID NO: 3427)<br>(SEQ ID NO: 5441) |
| LDHA-494 Target: | 5'-ACAUGGCAGCCUUUUCCUUAGAAca-3'<br>3'-GUUGUACCGUCGGAAAAGGAAUCUUGU-5'<br>5'-CAACATGGCAGCCTTTTCCTTAGAACA-3' | (SEQ ID NO: 1414)<br>(SEQ ID NO: 3428)<br>(SEQ ID NO: 5442) |
| LDHA-495 Target: | 5'-CAUGGCAGCCUUUUCCUUAGAACac-3'<br>3'-UUGUACCGUCGGAAAAGGAAUCUUGUG-5'<br>5'-AACATGGCAGCCTTTTCCTTAGAACAC-3' | (SEQ ID NO: 1415)<br>(SEQ ID NO: 3429)<br>(SEQ ID NO: 5443) |
| LDHA-496 Target: | 5'-AUGGCAGCCUUUUCCUUAGAACAcc-3'<br>3'-UGUACCGUCGGAAAAGGAAUCUUGUGG-5'<br>5'-ACATGGCAGCCTTTTCCTTAGAACACC-3' | (SEQ ID NO: 1416)<br>(SEQ ID NO: 3430)<br>(SEQ ID NO: 5444) |
| LDHA-497 Target: | 5'-UGGCAGCCUUUUCCUUAGAACACca-3'<br>3'-GUACCGUCGGAAAAGGAAUCUUGUGGU-5'<br>5'-CATGGCAGCCTTTTCCTTAGAACACCA-3' | (SEQ ID NO: 1417)<br>(SEQ ID NO: 3431)<br>(SEQ ID NO: 5445) |
| LDHA-498 Target: | 5'-GGCAGCCUUUUCCUUAGAACACCaa-3'<br>3'-UACCGUCGGAAAAGGAAUCUUGUGGUU-5'<br>5'-ATGGCAGCCTTTTCCTTAGAACACCAA-3' | (SEQ ID NO: 1418)<br>(SEQ ID NO: 3432)<br>(SEQ ID NO: 5446) |
| LDHA-499 Target: | 5'-GCAGCCUUUUCCUUAGAACACCAaa-3'<br>3'-ACCGUCGGAAAAGGAAUCUUGUGGUUU-5'<br>5'-TGGCAGCCTTTTCCTTAGAACACCAAA-3' | (SEQ ID NO: 1419)<br>(SEQ ID NO: 3433)<br>(SEQ ID NO: 5447) |
| LDHA-500 Target: | 5'-CAGCCUUUUCCUUAGAACACCAAag-3'<br>3'-CCGUCGGAAAAGGAAUCUUGUGGUUUC-5'<br>5'-GGCAGCCTTTTCCTTAGAACACCAAAG-3' | (SEQ ID NO: 1420)<br>(SEQ ID NO: 3434)<br>(SEQ ID NO: 5448) |
| LDHA-501 Target: | 5'-AGCCUUUUCCUUAGAACACCAAAga-3'<br>3'-CGUCGGAAAAGGAAUCUUGUGGUUUCU-5'<br>5'-GCAGCCTTTTCCTTAGAACACCAAAGA-3' | (SEQ ID NO: 1421)<br>(SEQ ID NO: 3435)<br>(SEQ ID NO: 5449) |
| LDHA-502 Target: | 5'-GCCUUUUCCUUAGAACACCAAAGat-3'<br>3'-GUCGGAAAAGGAAUCUUGUGGUUUCUA-5'<br>5'-CAGCCTTTTCCTTAGAACACCAAAGAT-3' | (SEQ ID NO: 1422)<br>(SEQ ID NO: 3436)<br>(SEQ ID NO: 5450) |

TABLE 12-continued

Additional Selected Human Anti-Lactate Dehydrogenase DsiRNA Agents (Asymmetrics)

|  |  |  |
|---|---|---|
| LDHA-503 Target: | 5'-CCUUUCCUUAGAACACCAAAGAtt-3'<br>3'-UCGGAAAAGGAAUCUUGUGGUUUCUAA-5'<br>5'-AGCCTTTTCCTTAGAACACCAAAGATT-3' | (SEQ ID NO: 1423)<br>(SEQ ID NO: 3437)<br>(SEQ ID NO: 5451) |
| LDHA-504 Target: | 5'-CUUUCCUUAGAACACCAAAGAUtg-3'<br>3'-CGGAAAAGGAAUCUUGUGGUUUCUAAC-5'<br>5'-GCCTTTTCCTTAGAACACCAAAGATTG-3' | (SEQ ID NO: 1424)<br>(SEQ ID NO: 3438)<br>(SEQ ID NO: 5452) |
| LDHA-505 Target: | 5'-UUUCCUUAGAACACCAAAGAUUgt-3'<br>3'-GGAAAAGGAAUCUUGUGGUUUCUAACA-5'<br>5'-CCTTTTCCTTAGAACACCAAAGATTGT-3' | (SEQ ID NO: 1425)<br>(SEQ ID NO: 3439)<br>(SEQ ID NO: 5453) |
| LDHA-506 Target: | 5'-UUUCCUUAGAACACCAAAGAUUGtc-3'<br>3'-GAAAAGGAAUCUUGUGGUUUCUAACAG-5'<br>5'-CTTTTCCTTAGAACACCAAAGATTGTC-3' | (SEQ ID NO: 1426)<br>(SEQ ID NO: 3440)<br>(SEQ ID NO: 5454) |
| LDHA-507 Target: | 5'-UUCCUUAGAACACCAAAGAUUGUct-3'<br>3'-AAAAGGAAUCUUGUGGUUUCUAACAGA-5'<br>5'-TTTTCCTTAGAACACCAAAGATTGTCT-3' | (SEQ ID NO: 1427)<br>(SEQ ID NO: 3441)<br>(SEQ ID NO: 5455) |
| LDHA-508 Target: | 5'-UCCUUAGAACACCAAAGAUUGUCtc-3'<br>3'-AAAGGAAUCUUGUGGUUUCUAACAGAG-5'<br>5'-TTTCCTTAGAACACCAAAGATTGTCTC-3' | (SEQ ID NO: 1428)<br>(SEQ ID NO: 3442)<br>(SEQ ID NO: 5456) |
| LDHA-509 Target: | 5'-CCUUAGAACACCAAAGAUUGUCUct-3'<br>3'-AAGGAAUCUUGUGGUUUCUAACAGAGA-5'<br>5'-TTCCTTAGAACACCAAAGATTGTCTCT-3' | (SEQ ID NO: 1429)<br>(SEQ ID NO: 3443)<br>(SEQ ID NO: 5457) |
| LDHA-510 Target: | 5'-CUUAGAACACCAAAGAUUGUCUCtg-3'<br>3'-AGGAAUCUUGUGGUUUCUAACAGAGAC-5'<br>5'-TCCTTAGAACACCAAAGATTGTCTCTG-3' | (SEQ ID NO: 1430)<br>(SEQ ID NO: 3444)<br>(SEQ ID NO: 5458) |
| LDHA-511 Target: | 5'-UUAGAACACCAAAGAUUGUCUCUgg-3'<br>3'-GGAAUCUUGUGGUUUCUAACAGAGACC-5'<br>5'-CCTTAGAACACCAAAGATTGTCTCTGG-3' | (SEQ ID NO: 1431)<br>(SEQ ID NO: 3445)<br>(SEQ ID NO: 5459) |
| LDHA-512 Target: | 5'-UAGAACACCAAAGAUUGUCUCUGgc-3'<br>3'-GAAUCUUGUGGUUUCUAACAGAGACCG-5'<br>5'-CTTAGAACACCAAAGATTGTCTCTGGC-3' | (SEQ ID NO: 1432)<br>(SEQ ID NO: 3446)<br>(SEQ ID NO: 5460) |
| LDHA-513 Target: | 5'-AGAACACCAAAGAUUGUCUCUGGca-3'<br>3'-AAUCUUGUGGUUUCUAACAGAGACCGU-5'<br>5'-TTAGAACACCAAAGATTGTCTCTGGCA-3' | (SEQ ID NO: 1433)<br>(SEQ ID NO: 3447)<br>(SEQ ID NO: 5461) |
| LDHA-514 Target: | 5'-GAACACCAAAGAUUGUCUCUGGCaa-3'<br>3'-AUCUUGUGGUUUCUAACAGAGACCGUU-5'<br>5'-TAGAACACCAAAGATTGTCTCTGGCAA-3' | (SEQ ID NO: 1434)<br>(SEQ ID NO: 3448)<br>(SEQ ID NO: 5462) |
| LDHA-515 Target: | 5'-AACACCAAAGAUUGUCUCUGGCAaa-3'<br>3'-UCUUGUGGUUUCUAACAGAGACCGUUU-5'<br>5'-AGAACACCAAAGATTGTCTCTGGCAAA-3' | (SEQ ID NO: 1435)<br>(SEQ ID NO: 3449)<br>(SEQ ID NO: 5463) |
| LDHA-516 Target: | 5'-ACACCAAAGAUUGUCUCUGGCAAag-3'<br>3'-CUUGUGGUUUCUAACAGAGACCGUUUC-5'<br>5'-GAACACCAAAGATTGTCTCTGGCAAAG-3' | (SEQ ID NO: 1436)<br>(SEQ ID NO: 3450)<br>(SEQ ID NO: 5464) |
| LDHA-517 Target: | 5'-CACCAAAGAUUGUCUCUGGCAAAga-3'<br>3'-UUGUGGUUUCUAACAGAGACCGUUUCU-5'<br>5'-AACACCAAAGATTGTCTCTGGCAAAGA-3' | (SEQ ID NO: 1437)<br>(SEQ ID NO: 3451)<br>(SEQ ID NO: 5465) |
| LDHA-518 Target: | 5'-ACCAAAGAUUGUCUCUGGCAAAGac-3'<br>3'-UGUGGUUUCUAACAGAGACCGUUUCUG-5'<br>5'-ACACCAAAGATTGTCTCTGGCAAAGAC-3' | (SEQ ID NO: 1438)<br>(SEQ ID NO: 3452)<br>(SEQ ID NO: 5466) |
| LDHA-519 Target: | 5'-CCAAAGAUUGUCUCUGGCAAAGAct-3'<br>3'-GUGGUUUCUAACAGAGACCGUUUCUGA-5'<br>5'-CACCAAAGATTGTCTCTGGCAAAGACT-3' | (SEQ ID NO: 1439)<br>(SEQ ID NO: 3453)<br>(SEQ ID NO: 5467) |
| LDHA-520 Target: | 5'-CAAAGAUUGUCUCUGGCAAAGACta-3'<br>3'-UGGUUUCUAACAGAGACCGUUUCUGAU-5'<br>5'-ACCAAAGATTGTCTCTGGCAAAGACTA-3' | (SEQ ID NO: 1440)<br>(SEQ ID NO: 3454)<br>(SEQ ID NO: 5468) |
| LDHA-521 Target: | 5'-AAAGAUUGUCUCUGGCAAAGACUat-3'<br>3'-GGUUUCUAACAGAGACCGUUUCUGAUA-5'<br>5'-CCAAAGATTGTCTCTGGCAAAGACTAT-3' | (SEQ ID NO: 1441)<br>(SEQ ID NO: 3455)<br>(SEQ ID NO: 5469) |

TABLE 12-continued

Additional Selected Human Anti-Lactate Dehydrogenase DsiRNA Agents (Asymmetrics)

| | | |
|---|---|---|
| LDHA-522 | 5'-AAGAUUGUCUCUGGCAAAGACUAta-3'<br>3'-GUUUCUAACAGAGACCGUUUCUGAUAUAU-5'<br>Target: 5'-CAAAGATTGTCTCTGGCAAAGACTATA-3' | (SEQ ID NO: 1442)<br>(SEQ ID NO: 3456)<br>(SEQ ID NO: 5470) |
| LDHA-523 | 5'-AGAUUGUCUCUGGCAAAGACUAUaa-3'<br>3'-UUUCUAACAGAGACCGUUUCUGAUAUU-5'<br>Target: 5'-AAAGATTGTCTCTGGCAAAGACTATAA-3' | (SEQ ID NO: 1443)<br>(SEQ ID NO: 3457)<br>(SEQ ID NO: 5471) |
| LDHA-524 | 5'-GAUUGUCUCUGGCAAAGACUAUAat-3'<br>3'-UUCUAACAGAGACCGUUUCUGAUAUUA-5'<br>Target: 5'-AAGATTGTCTCTGGCAAAGACTATAAT-3' | (SEQ ID NO: 1444)<br>(SEQ ID NO: 3458)<br>(SEQ ID NO: 5472) |
| LDHA-525 | 5'-AUUGUCUCUGGCAAAGACUAUAAtg-3'<br>3'-UCUAACAGAGACCGUUUCUGAUAUUAC-5'<br>Target: 5'-AGATTGTCTCTGGCAAAGACTATAATG-3' | (SEQ ID NO: 1445)<br>(SEQ ID NO: 3459)<br>(SEQ ID NO: 5473) |
| LDHA-526 | 5'-UUGUCUCUGGCAAAGACUAUAAUgt-3'<br>3'-CUAACAGAGACCGUUUCUGAUAUUACA-5'<br>Target: 5'-GATTGTCTCTGGCAAAGACTATAATGT-3' | (SEQ ID NO: 1446)<br>(SEQ ID NO: 3460)<br>(SEQ ID NO: 5474) |
| LDHA-527 | 5'-UGUCUCUGGCAAAGACUAUAAUGta-3'<br>3'-UAACAGAGACCGUUUCUGAUAUUACAU-5'<br>Target: 5'-ATTGTCTCTGGCAAAGACTATAATGTA-3' | (SEQ ID NO: 1447)<br>(SEQ ID NO: 3461)<br>(SEQ ID NO: 5475) |
| LDHA-528 | 5'-GUCUCUGGCAAAGACUAUAAUGUaa-3'<br>3'-AACAGAGACCGUUUCUGAUAUUACAUU-5'<br>Target: 5'-TTGTCTCTGGCAAAGACTATAATGTAA-3' | (SEQ ID NO: 1448)<br>(SEQ ID NO: 3462)<br>(SEQ ID NO: 5476) |
| LDHA-529 | 5'-UCUCUGGCAAAGACUAUAAUGUAac-3'<br>3'-ACAGAGACCGUUUCUGAUAUUACAUUG-5'<br>Target: 5'-TGTCTCTGGCAAAGACTATAATGTAAC-3' | (SEQ ID NO: 1449)<br>(SEQ ID NO: 3463)<br>(SEQ ID NO: 5477) |
| LDHA-530 | 5'-CUCUGGCAAAGACUAUAAUGUAAct-3'<br>3'-CAGAGACCGUUUCUGAUAUUACAUUGA-5'<br>Target: 5'-GTCTCTGGCAAAGACTATAATGTAACT-3' | (SEQ ID NO: 1450)<br>(SEQ ID NO: 3464)<br>(SEQ ID NO: 5478) |
| LDHA-531 | 5'-UCUGGCAAAGACUAUAAUGUAACtg-3'<br>3'-AGAGACCGUUUCUGAUAUUACAUUGAC-5'<br>Target: 5'-TCTCTGGCAAAGACTATAATGTAACTG-3' | (SEQ ID NO: 1451)<br>(SEQ ID NO: 3465)<br>(SEQ ID NO: 5479) |
| LDHA-532 | 5'-CUGGCAAAGACUAUAAUGUAACUgc-3'<br>3'-GAGACCGUUUCUGAUAUUACAUUGACG-5'<br>Target: 5'-CTCTGGCAAAGACTATAATGTAACTGC-3' | (SEQ ID NO: 1452)<br>(SEQ ID NO: 3466)<br>(SEQ ID NO: 5480) |
| LDHA-533 | 5'-UGGCAAAGACUAUAAUGUAACUGca-3'<br>3'-AGACCGUUUCUGAUAUUACAUUGACGU-5'<br>Target: 5'-TCTGGCAAAGACTATAATGTAACTGCA-3' | (SEQ ID NO: 1453)<br>(SEQ ID NO: 3467)<br>(SEQ ID NO: 5481) |
| LDHA-534 | 5'-GGCAAAGACUAUAAUGUAACUGCaa-3'<br>3'-GACCGUUUCUGAUAUUACAUUGACGUU-5'<br>Target: 5'-CTGGCAAAGACTATAATGTAACTGCAA-3' | (SEQ ID NO: 1454)<br>(SEQ ID NO: 3468)<br>(SEQ ID NO: 5482) |
| LDHA-535 | 5'-GCAAAGACUAUAAUGUAACUGCAaa-3'<br>3'-ACCGUUUCUGAUAUUACAUUGACGUUU-5'<br>Target: 5'-TGGCAAAGACTATAATGTAACTGCAAA-3' | (SEQ ID NO: 1455)<br>(SEQ ID NO: 3469)<br>(SEQ ID NO: 5483) |
| LDHA-536 | 5'-CAAAGACUAUAAUGUAACUGCAAac-3'<br>3'-CCGUUUCUGAUAUUACAUUGACGUUUG-5'<br>Target: 5'-GGCAAAGACTATAATGTAACTGCAAAC-3' | (SEQ ID NO: 1456)<br>(SEQ ID NO: 3470)<br>(SEQ ID NO: 5484) |
| LDHA-537 | 5'-AAAGACUAUAAUGUAACUGCAAAct-3'<br>3'-CGUUUCUGAUAUUACAUUGACGUUUGA-5'<br>Target: 5'-GCAAAGACTATAATGTAACTGCAAACT-3' | (SEQ ID NO: 1457)<br>(SEQ ID NO: 3471)<br>(SEQ ID NO: 5485) |
| LDHA-538 | 5'-AAGACUAUAAUGUAACUGCAAACtc-3'<br>3'-GUUUCUGAUAUUACAUUGACGUUUGAG-5'<br>Target: 5'-CAAAGACTATAATGTAACTGCAAACTC-3' | (SEQ ID NO: 1458)<br>(SEQ ID NO: 3472)<br>(SEQ ID NO: 5486) |
| LDHA-539 | 5'-AGACUAUAAUGUAACUGCAAACUcc-3'<br>3'-UUUCUGAUAUUACAUUGACGUUUGAGG-5'<br>Target: 5'-AAAGACTATAATGTAACTGCAAACTCC-3' | (SEQ ID NO: 1459)<br>(SEQ ID NO: 3473)<br>(SEQ ID NO: 5487) |
| LDHA-540 | 5'-GACUAUAAUGUAACUGCAAACUCca-3'<br>3'-UUCUGAUAUUACAUUGACGUUUGAGGU-5'<br>Target: 5'-AAGACTATAATGTAACTGCAAACTCCA-3' | (SEQ ID NO: 1460)<br>(SEQ ID NO: 3474)<br>(SEQ ID NO: 5488) |

TABLE 12-continued

Additional Selected Human Anti-Lactate Dehydrogenase DsiRNA Agents (Asymmetrics)

| | | |
|---|---|---|
| LDHA-541 Target: | 5'-ACUAUAAUGUAACUGCAAACUCCaa-3'<br>3'-UCUGAUAUUACAUUGACGUUUGAGGUU-5'<br>5'-AGACTATAATGTAACTGCAAACTCCAA-3' | (SEQ ID NO: 1461)<br>(SEQ ID NO: 3475)<br>(SEQ ID NO: 5489) |
| LDHA-542 Target: | 5'-CUAUAAUGUAACUGCAAACUCCAag-3'<br>3'-CUGAUAUUACAUUGACGUUUGAGGUUC-5'<br>5'-GACTATAATGTAACTGCAAACTCCAAG-3' | (SEQ ID NO: 1462)<br>(SEQ ID NO: 3476)<br>(SEQ ID NO: 5490) |
| LDHA-543 Target: | 5'-UAUAAUGUAACUGCAAACUCCAAgc-3'<br>3'-UGAUAUUACAUUGACGUUUGAGGUUCG-5'<br>5'-ACTATAATGTAACTGCAAACTCCAAGC-3' | (SEQ ID NO: 1463)<br>(SEQ ID NO: 3477)<br>(SEQ ID NO: 5491) |
| LDHA-544 Target: | 5'-AUAAUGUAACUGCAAACUCCAAGct-3'<br>3'-GAUAUUACAUUGACGUUUGAGGUUCGA-5'<br>5'-CTATAATGTAACTGCAAACTCCAAGCT-3' | (SEQ ID NO: 1464)<br>(SEQ ID NO: 3478)<br>(SEQ ID NO: 5492) |
| LDHA-545 Target: | 5'-UAAUGUAACUGCAAACUCCAAGCtg-3'<br>3'-AUAUUACAUUGACGUUUGAGGUUCGAC-5'<br>5'-TATAATGTAACTGCAAACTCCAAGCTG-3' | (SEQ ID NO: 1465)<br>(SEQ ID NO: 3479)<br>(SEQ ID NO: 5493) |
| LDHA-546 Target: | 5'-AAUGUAACUGCAAACUCCAAGCUgg-3'<br>3'-UAUUACAUUGACGUUUGAGGUUCGACC-5'<br>5'-ATAATGTAACTGCAAACTCCAAGCTGG-3' | (SEQ ID NO: 1466)<br>(SEQ ID NO: 3480)<br>(SEQ ID NO: 5494) |
| LDHA-547 Target: | 5'-AUGUAACUGCAAACUCCAAGCUGgt-3'<br>3'-AUUACAUUGACGUUUGAGGUUCGACCA-5'<br>5'-TAATGTAACTGCAAACTCCAAGCTGGT-3' | (SEQ ID NO: 1467)<br>(SEQ ID NO: 3481)<br>(SEQ ID NO: 5495) |
| LDHA-548 Target: | 5'-UGUAACUGCAAACUCCAAGCUGGtc-3'<br>3'-UUACAUUGACGUUUGAGGUUCGACCAG-5'<br>5'-AATGTAACTGCAAACTCCAAGCTGGTC-3' | (SEQ ID NO: 1468)<br>(SEQ ID NO: 3482)<br>(SEQ ID NO: 5496) |
| LDHA-549 Target: | 5'-GUAACUGCAAACUCCAAGCUGGUca-3'<br>3'-UACAUUGACGUUUGAGGUUCGACCAGU-5'<br>5'-ATGTAACTGCAAACTCCAAGCTGGTCA-3' | (SEQ ID NO: 1469)<br>(SEQ ID NO: 3483)<br>(SEQ ID NO: 5497) |
| LDHA-550 Target: | 5'-UAACUGCAAACUCCAAGCUGGUCat-3'<br>3'-ACAUUGACGUUUGAGGUUCGACCAGUA-5'<br>5'-TGTAACTGCAAACTCCAAGCTGGTCAT-3' | (SEQ ID NO: 1470)<br>(SEQ ID NO: 3484)<br>(SEQ ID NO: 5498) |
| LDHA-551 Target: | 5'-AACUGCAAACUCCAAGCUGGUCAtt-3'<br>3'-CAUUGACGUUUGAGGUUCGACCAGUAA-5'<br>5'-GTAACTGCAAACTCCAAGCTGGTCATT-3' | (SEQ ID NO: 1471)<br>(SEQ ID NO: 3485)<br>(SEQ ID NO: 5499) |
| LDHA-552 Target: | 5'-ACUGCAAACUCCAAGCUGGUCAUta-3'<br>3'-AUUGACGUUUGAGGUUCGACCAGUAAU-5'<br>5'-TAACTGCAAACTCCAAGCTGGTCATTA-3' | (SEQ ID NO: 1472)<br>(SEQ ID NO: 3486)<br>(SEQ ID NO: 5500) |
| LDHA-553 Target: | 5'-CUGCAAACUCCAAGCUGGUCAUUat-3'<br>3'-UUGACGUUUGAGGUUCGACCAGUAAUA-5'<br>5'-AACTGCAAACTCCAAGCTGGTCATTAT-3' | (SEQ ID NO: 1473)<br>(SEQ ID NO: 3487)<br>(SEQ ID NO: 5501) |
| LDHA-554 Target: | 5'-UGCAAACUCCAAGCUGGUCAUUAtc-3'<br>3'-UGACGUUUGAGGUUCGACCAGUAAUAG-5'<br>5'-ACTGCAAACTCCAAGCTGGTCATTATC-3' | (SEQ ID NO: 1474)<br>(SEQ ID NO: 3488)<br>(SEQ ID NO: 5502) |
| LDHA-555 Target: | 5'-GCAAACUCCAAGCUGGUCAUUAUca-3'<br>3'-GACGUUUGAGGUUCGACCAGUAAUAGU-5'<br>5'-CTGCAAACTCCAAGCTGGTCATTATCA-3' | (SEQ ID NO: 1475)<br>(SEQ ID NO: 3489)<br>(SEQ ID NO: 5503) |
| LDHA-556 Target: | 5'-CAAACUCCAAGCUGGUCAUUAUCac-3'<br>3'-ACGUUUGAGGUUCGACCAGUAAUAGUG-5'<br>5'-TGCAAACTCCAAGCTGGTCATTATCAC-3' | (SEQ ID NO: 1476)<br>(SEQ ID NO: 3490)<br>(SEQ ID NO: 5504) |
| LDHA-557 Target: | 5'-AAACUCCAAGCUGGUCAUUAUCAcg-3'<br>3'-CGUUUGAGGUUCGACCAGUAAUAGUGC-5'<br>5'-GCAAACTCCAAGCTGGTCATTATCACG-3' | (SEQ ID NO: 1477)<br>(SEQ ID NO: 3491)<br>(SEQ ID NO: 5505) |
| LDHA-558 Target: | 5'-AACUCCAAGCUGGUCAUUAUCACgg-3'<br>3'-GUUUGAGGUUCGACCAGUAAUAGUGCC-5'<br>5'-CAAACTCCAAGCTGGTCATTATCACGG-3' | (SEQ ID NO: 1478)<br>(SEQ ID NO: 3492)<br>(SEQ ID NO: 5506) |
| LDHA-559 Target: | 5'-ACUCCAAGCUGGUCAUUAUCACGgc-3'<br>3'-UUUGAGGUUCGACCAGUAAUAGUGCCG-5'<br>5'-AAACTCCAAGCTGGTCATTATCACGGC-3' | (SEQ ID NO: 1479)<br>(SEQ ID NO: 3493)<br>(SEQ ID NO: 5507) |

TABLE 12-continued

Additional Selected Human Anti-Lactate Dehydrogenase DsiRNA Agents (Asymmetrics)

| | | |
|---|---|---|
| LDHA-560 Target: | 5'-CUCCAAGCUGGUCAUUAUCACGGct-3'<br>3'-UUGAGGUUCGACCAGUAAUAGUGCCGA-5'<br>5'-AACTCCAAGCTGGTCATTATCACGGCT-3' | (SEQ ID NO: 1480)<br>(SEQ ID NO: 3494)<br>(SEQ ID NO: 5508) |
| LDHA-561 Target: | 5'-UCCAAGCUGGUCAUUAUCACGGCtg-3'<br>3'-UGAGGUUCGACCAGUAAUAGUGCCGAC-5'<br>5'-ACTCCAAGCTGGTCATTATCACGGCTG-3' | (SEQ ID NO: 1481)<br>(SEQ ID NO: 3495)<br>(SEQ ID NO: 5509) |
| LDHA-562 Target: | 5'-CCAAGCUGGUCAUUAUCACGGCUgg-3'<br>3'-GAGGUUCGACCAGUAAUAGUGCCGACC-5'<br>5'-CTCCAAGCTGGTCATTATCACGGCTGG-3' | (SEQ ID NO: 1482)<br>(SEQ ID NO: 3496)<br>(SEQ ID NO: 5510) |
| LDHA-563 Target: | 5'-CAAGCUGGUCAUUAUCACGGCUGgg-3'<br>3'-AGGUUCGACCAGUAAUAGUGCCGACCC-5'<br>5'-TCCAAGCTGGTCATTATCACGGCTGGG-3' | (SEQ ID NO: 1483)<br>(SEQ ID NO: 3497)<br>(SEQ ID NO: 5511) |
| LDHA-564 Target: | 5'-AAGCUGGUCAUUAUCACGGCUGGgg-3'<br>3'-GGUUCGACCAGUAAUAGUGCCGACCCC-5'<br>5'-CCAAGCTGGTCATTATCACGGCTGGGG-3' | (SEQ ID NO: 1484)<br>(SEQ ID NO: 3498)<br>(SEQ ID NO: 5512) |
| LDHA-565 Target: | 5'-AGCUGGUCAUUAUCACGGCUGGGgc-3'<br>3'-GUUCGACCAGUAAUAGUGCCGACCCCG-5'<br>5'-CAAGCTGGTCATTATCACGGCTGGGGC-3' | (SEQ ID NO: 1485)<br>(SEQ ID NO: 3499)<br>(SEQ ID NO: 5513) |
| LDHA-566 Target: | 5'-GCUGGUCAUUAUCACGGCUGGGGca-3'<br>3'-UUCGACCAGUAAUAGUGCCGACCCCGU-5'<br>5'-AAGCTGGTCATTATCACGGCTGGGGCA-3' | (SEQ ID NO: 1486)<br>(SEQ ID NO: 3500)<br>(SEQ ID NO: 5514) |
| LDHA-567 Target: | 5'-CUGGUCAUUAUCACGGCUGGGGCac-3'<br>3'-UCGACCAGUAAUAGUGCCGACCCCGUG-5'<br>5'-AGCTGGTCATTATCACGGCTGGGGCAC-3' | (SEQ ID NO: 1487)<br>(SEQ ID NO: 3501)<br>(SEQ ID NO: 5515) |
| LDHA-568 Target: | 5'-UGGUCAUUAUCACGGCUGGGGCAcg-3'<br>3'-CGACCAGUAAUAGUGCCGACCCCGUGC-5'<br>5'-GCTGGTCATTATCACGGCTGGGGCACG-3' | (SEQ ID NO: 1488)<br>(SEQ ID NO: 3502)<br>(SEQ ID NO: 5516) |
| LDHA-569 Target: | 5'-GGUCAUUAUCACGGCUGGGGCACgt-3'<br>3'-GACCAGUAAUAGUGCCGACCCCGUGCA-5'<br>5'-CTGGTCATTATCACGGCTGGGGCACGT-3' | (SEQ ID NO: 1489)<br>(SEQ ID NO: 3503)<br>(SEQ ID NO: 5517) |
| LDHA-570 Target: | 5'-GUCAUUAUCACGGCUGGGGCACGtc-3'<br>3'-ACCAGUAAUAGUGCCGACCCCGUGCAG-5'<br>5'-TGGTCATTATCACGGCTGGGGCACGTC-3' | (SEQ ID NO: 1490)<br>(SEQ ID NO: 3504)<br>(SEQ ID NO: 5518) |
| LDHA-571 Target: | 5'-UCAUUAUCACGGCUGGGGCACGUca-3'<br>3'-CCAGUAAUAGUGCCGACCCCGUGCAGU-5'<br>5'-GGTCATTATCACGGCTGGGGCACGTCA-3' | (SEQ ID NO: 1491)<br>(SEQ ID NO: 3505)<br>(SEQ ID NO: 5519) |
| LDHA-572 Target: | 5'-CAUUAUCACGGCUGGGGCACGUCag-3'<br>3'-CAGUAAUAGUGCCGACCCCGUGCAGUC-5'<br>5'-GTCATTATCACGGCTGGGGCACGTCAG-3' | (SEQ ID NO: 1492)<br>(SEQ ID NO: 3506)<br>(SEQ ID NO: 5520) |
| LDHA-573 Target: | 5'-AUUAUCACGGCUGGGGCACGUCAgc-3'<br>3'-AGUAAUAGUGCCGACCCCGUGCAGUCG-5'<br>5'-TCATTATCACGGCTGGGGCACGTCAGC-3' | (SEQ ID NO: 1493)<br>(SEQ ID NO: 3507)<br>(SEQ ID NO: 5521) |
| LDHA-574 Target: | 5'-UUAUCACGGCUGGGGCACGUCAGca-3'<br>3'-GUAAUAGUGCCGACCCCGUGCAGUCGU-5'<br>5'-CATTATCACGGCTGGGGCACGTCAGCA-3' | (SEQ ID NO: 1494)<br>(SEQ ID NO: 3508)<br>(SEQ ID NO: 5522) |
| LDHA-575 Target: | 5'-UAUCACGGCUGGGGCACGUCAGCaa-3'<br>3'-UAAUAGUGCCGACCCCGUGCAGUCGUU-5'<br>5'-ATTATCACGGCTGGGGCACGTCAGCAA-3' | (SEQ ID NO: 1495)<br>(SEQ ID NO: 3509)<br>(SEQ ID NO: 5523) |
| LDHA-576 Target: | 5'-AUCACGGCUGGGGCACGUCAGCAag-3'<br>3'-AAUAGUGCCGACCCCGUGCAGUCGUUC-5'<br>5'-TTATCACGGCTGGGGCACGTCAGCAAG-3' | (SEQ ID NO: 1496)<br>(SEQ ID NO: 3510)<br>(SEQ ID NO: 5524) |
| LDHA-577 Target: | 5'-UCACGGCUGGGGCACGUCAGCAAga-3'<br>3'-AUAGUGCCGACCCCGUGCAGUCGUUCU-5'<br>5'-TATCACGGCTGGGGCACGTCAGCAAGA-3' | (SEQ ID NO: 1497)<br>(SEQ ID NO: 3511)<br>(SEQ ID NO: 5525) |
| LDHA-578 Target: | 5'-CACGGCUGGGGCACGUCAGCAAGag-3'<br>3'-UAGUGCCGACCCCGUGCAGUCGUUCUC-5'<br>5'-ATCACGGCTGGGGCACGTCAGCAAGAG-3' | (SEQ ID NO: 1498)<br>(SEQ ID NO: 3512)<br>(SEQ ID NO: 5526) |

TABLE 12-continued

Additional Selected Human Anti-Lactate Dehydrogenase DsiRNA Agents (Asymmetrics)

| | | |
|---|---|---|
| LDHA-579 Target: | 5'-ACGGCUGGGGCACGUCAGCAAGAgg-3'<br>3'-AGUGCCGACCCCGUGCAGUCGUUCUCCC-5'<br>5'-TCACGGCTGGGGCACGTCAGCAAGAGG-3' | (SEQ ID NO: 1499)<br>(SEQ ID NO: 3513)<br>(SEQ ID NO: 5527) |
| LDHA-580 Target: | 5'-CGGCUGGGGCACGUCAGCAAGAGgg-3'<br>3'-GUGCCGACCCCGUGCAGUCGUUCUCCC-5'<br>5'-CACGGCTGGGGCACGTCAGCAAGAGGG-3' | (SEQ ID NO: 1500)<br>(SEQ ID NO: 3514)<br>(SEQ ID NO: 5528) |
| LDHA-581 Target: | 5'-GGCUGGGGCACGUCAGCAAGAGGga-3'<br>3'-UGCCGACCCCGUGCAGUCGUUCUCCCU-5'<br>5'-ACGGCTGGGGCACGTCAGCAAGAGGGA-3' | (SEQ ID NO: 1501)<br>(SEQ ID NO: 3515)<br>(SEQ ID NO: 5529) |
| LDHA-582 Target: | 5'-GCUGGGGCACGUCAGCAAGAGGGag-3'<br>3'-GCCGACCCCGUGCAGUCGUUCUCCCUC-5'<br>5'-CGGCTGGGGCACGTCAGCAAGAGGGAG-3' | (SEQ ID NO: 1502)<br>(SEQ ID NO: 3516)<br>(SEQ ID NO: 5530) |
| LDHA-583 Target: | 5'-CUGGGGCACGUCAGCAAGAGGGAga-3'<br>3'-CCGACCCCGUGCAGUCGUUCUCCCUCU-5'<br>5'-GGCTGGGGCACGTCAGCAAGAGGGAGA-3' | (SEQ ID NO: 1503)<br>(SEQ ID NO: 3517)<br>(SEQ ID NO: 5531) |
| LDHA-584 Target: | 5'-UGGGGCACGUCAGCAAGAGGGAGaa-3'<br>3'-CGACCCCGUGCAGUCGUUCUCCCUCUU-5'<br>5'-GCTGGGGCACGTCAGCAAGAGGGAGAA-3' | (SEQ ID NO: 1504)<br>(SEQ ID NO: 3518)<br>(SEQ ID NO: 5532) |
| LDHA-585 Target: | 5'-GGGGCACGUCAGCAAGAGGGAGAaa-3'<br>3'-GACCCCGUGCAGUCGUUCUCCCUCUUU-5'<br>5'-CTGGGGCACGTCAGCAAGAGGGAGAAA-3' | (SEQ ID NO: 1505)<br>(SEQ ID NO: 3519)<br>(SEQ ID NO: 5533) |
| LDHA-586 Target: | 5'-GGGCACGUCAGCAAGAGGGAGAAag-3'<br>3'-ACCCCGUGCAGUCGUUCUCCCUCUUUC-5'<br>5'-TGGGGCACGTCAGCAAGAGGGAGAAAG-3' | (SEQ ID NO: 1506)<br>(SEQ ID NO: 3520)<br>(SEQ ID NO: 5534) |
| LDHA-587 Target: | 5'-GGCACGUCAGCAAGAGGGAGAAAgc-3'<br>3'-CCCCGUGCAGUCGUUCUCCCUCUUUCG-5'<br>5'-GGGGCACGTCAGCAAGAGGGAGAAAGC-3' | (SEQ ID NO: 1507)<br>(SEQ ID NO: 3521)<br>(SEQ ID NO: 5535) |
| LDHA-588 Target: | 5'-GCACGUCAGCAAGAGGGAGAAAGcc-3'<br>3'-CCCGUGCAGUCGUUCUCCCUCUUUCGG-5'<br>5'-GGGCACGTCAGCAAGAGGGAGAAAGCC-3' | (SEQ ID NO: 1508)<br>(SEQ ID NO: 3522)<br>(SEQ ID NO: 5536) |
| LDHA-589 Target: | 5'-CACGUCAGCAAGAGGGAGAAAGCcg-3'<br>3'-CCGUGCAGUCGUUCUCCCUCUUUCGGC-5'<br>5'-GGCACGTCAGCAAGAGGGAGAAAGCCG-3' | (SEQ ID NO: 1509)<br>(SEQ ID NO: 3523)<br>(SEQ ID NO: 5537) |
| LDHA-590 Target: | 5'-ACGUCAGCAAGAGGGAGAAAGCCgt-3'<br>3'-CGUGCAGUCGUUCUCCCUCUUUCGGCA-5'<br>5'-GCACGTCAGCAAGAGGGAGAAAGCCGT-3' | (SEQ ID NO: 1510)<br>(SEQ ID NO: 3524)<br>(SEQ ID NO: 5538) |
| LDHA-591 Target: | 5'-CGUCAGCAAGAGGGAGAAAGCCGtc-3'<br>3'-GUGCAGUCGUUCUCCCUCUUUCGGCAG-5'<br>5'-CACGTCAGCAAGAGGGAGAAAGCCGTC-3' | (SEQ ID NO: 1511)<br>(SEQ ID NO: 3525)<br>(SEQ ID NO: 5539) |
| LDHA-592 Target: | 5'-GUCAGCAAGAGGGAGAAAGCCGUct-3'<br>3'-UGCAGUCGUUCUCCCUCUUUCGGCAGA-5'<br>5'-ACGTCAGCAAGAGGGAGAAAGCCGTCT-3' | (SEQ ID NO: 1512)<br>(SEQ ID NO: 3526)<br>(SEQ ID NO: 5540) |
| LDHA-593 Target: | 5'-UCAGCAAGAGGGAGAAAGCCGUCtt-3'<br>3'-GCAGUCGUUCUCCCUCUUUCGGCAGAA-5'<br>5'-CGTCAGCAAGAGGGAGAAAGCCGTCTT-3' | (SEQ ID NO: 1513)<br>(SEQ ID NO: 3527)<br>(SEQ ID NO: 5541) |
| LDHA-594 Target: | 5'-CAGCAAGAGGGAGAAAGCCGUCUta-3'<br>3'-CAGUCGUUCUCCCUCUUUCGGCAGAAU-5'<br>5'-GTCAGCAAGAGGGAGAAAGCCGTCTTA-3' | (SEQ ID NO: 1514)<br>(SEQ ID NO: 3528)<br>(SEQ ID NO: 5542) |
| LDHA-595 Target: | 5'-AGCAAGAGGGAGAAAGCCGUCUUaa-3'<br>3'-AGUCGUUCUCCCUCUUUCGGCAGAAUU-5'<br>5'-TCAGCAAGAGGGAGAAAGCCGTCTTAA-3' | (SEQ ID NO: 1515)<br>(SEQ ID NO: 3529)<br>(SEQ ID NO: 5543) |
| LDHA-596 Target: | 5'-GCAAGAGGGAGAAAGCCGUCUUAat-3'<br>3'-GUCGUUCUCCCUCUUUCGGCAGAAUUA-5'<br>5'-CAGCAAGAGGGAGAAAGCCGTCTTAAT-3' | (SEQ ID NO: 1516)<br>(SEQ ID NO: 3530)<br>(SEQ ID NO: 5544) |
| LDHA-597 Target: | 5'-CAAGAGGGAGAAAGCCGUCUUAatt-3'<br>3'-UCGUUCUCCCUCUUUCGGCAGAAUUAA-5'<br>5'-AGCAAGAGGGAGAAAGCCGTCTTAATT-3' | (SEQ ID NO: 1517)<br>(SEQ ID NO: 3531)<br>(SEQ ID NO: 5545) |

TABLE 12-continued

Additional Selected Human Anti-Lactate Dehydrogenase DsiRNA Agents (Asymmetrics)

| | | |
|---|---|---|
| LDHA-598 Target: | 5'-A<u>AGAGG</u>GAGAAAGC<u>CG</u>UCUUAAUtt-3'<br>3'-<u>CGUUCUCCC</u>UCUUU<u>CGG</u>CAGAAUU<u>AAAA</u>-5'<br>5'-GCAAGAGGGAGAAAGCCGTCTTAATTT-3' | (SEQ ID NO: 1518)<br>(SEQ ID NO: 3532)<br>(SEQ ID NO: 5546) |
| LDHA-599 Target: | 5'-A<u>GA</u>GGGAGAAAGC<u>CG</u>UCUUAAUUtg-3'<br>3'-<u>GUUCUCCC</u>UCUUU<u>CGG</u>CAGAAUU<u>AAAC</u>-5'<br>5'-CAAGAGGGAGAAAGCCGTCTTAATTTG-3' | (SEQ ID NO: 1519)<br>(SEQ ID NO: 3533)<br>(SEQ ID NO: 5547) |
| LDHA-600 Target: | 5'-<u>GA</u>GGGAGAAAGCC<u>GU</u>CUUAAUUUgg-3'<br>3'-<u>UUCUCCC</u>UCUUUCGG<u>C</u>AGAAUU<u>AAACC</u>-5'<br>5'-AAGAGGGAGAAAGCCGTCTTAATTTGG-3' | (SEQ ID NO: 1520)<br>(SEQ ID NO: 3534)<br>(SEQ ID NO: 5548) |
| LDHA-601 Target: | 5'-<u>A</u>GGGAGAAAGCCG<u>UC</u>UUAAUUUGgt-3'<br>3'-<u>UCUCCC</u>UCUUUCGGCAGAAUU<u>AAACCA</u>-5'<br>5'-AGAGGGAGAAAGCCGTCTTAATTTGGT-3' | (SEQ ID NO: 1521)<br>(SEQ ID NO: 3535)<br>(SEQ ID NO: 5549) |
| LDHA-602 Target: | 5'-GGGAGAAAGCCGU<u>C</u>UUAAUUUGGtc-3'<br>3'-<u>CUCCC</u>UCUUUCGGC<u>A</u>GAAUUAAAC<u>CAG</u>-5'<br>5'-GAGGGAGAAAGCCGTCTTAATTTGGTC-3' | (SEQ ID NO: 1522)<br>(SEQ ID NO: 3536)<br>(SEQ ID NO: 5550) |
| LDHA-603 Target: | 5'-GG<u>A</u>GAAAGCCGUC<u>UU</u>A<u>A</u>UUUGGUcc-3'<br>3'-<u>UCCC</u>UCUUUCGGC<u>A</u>G<u>A</u>AUUAAACCA<u>GG</u>-5'<br>5'-AGGGAGAAAGCCGTCTTAATTTGGTCC-3' | (SEQ ID NO: 1523)<br>(SEQ ID NO: 3537)<br>(SEQ ID NO: 5551) |
| LDHA-604 Target: | 5'-GAGAAAGCCGUCUU<u>AA</u>UUUGGUCca-3'<br>3'-<u>CCCU</u>CUUUCGGCAG<u>AA</u>UUAAACCAG<u>GU</u>-5'<br>5'-GGGAGAAAGCCGTCTTAATTTGGTCCA-3' | (SEQ ID NO: 1524)<br>(SEQ ID NO: 3538)<br>(SEQ ID NO: 5552) |
| LDHA-605 Target: | 5'-AGAAAGCCGUCUU<u>A</u>AU<u>UU</u>GGUCCag-3'<br>3'-<u>CCU</u>CUUUCGGCAGA<u>A</u>UU<u>AAA</u>CCAGG<u>UC</u>-5'<br>5'-GGAGAAAGCCGTCTTAATTTGGTCCAG-3' | (SEQ ID NO: 1525)<br>(SEQ ID NO: 3539)<br>(SEQ ID NO: 5553) |
| LDHA-606 Target: | 5'-G<u>AA</u>AGCCGUCUUA<u>AU</u>UUGGUCCAgc-3'<br>3'-<u>CUCU</u>UUCGGCAGAAUU<u>AAACC</u>AGG<u>UCG</u>-5'<br>5'-GAGAAAGCCGTCTTAATTTGGTCCAGC-3' | (SEQ ID NO: 1526)<br>(SEQ ID NO: 3540)<br>(SEQ ID NO: 5554) |
| LDHA-607 Target: | 5'-A<u>AA</u>GCCGUCUUA<u>AU</u>UUGGUCCAGcg-3'<br>3'-<u>UCUU</u>UCGGCAGAAUU<u>AAA</u>CCAGG<u>UCGC</u>-5'<br>5'-AGAAAGCCGTCTTAATTTGGTCCAGCG-3' | (SEQ ID NO: 1527)<br>(SEQ ID NO: 3541)<br>(SEQ ID NO: 5555) |
| LDHA-608 Target: | 5'-A<u>A</u>GCCGUCUUAAU<u>UU</u>GGUCCAGCgt-3'<br>3'-<u>CUUU</u>CGGCAGAAUU<u>AAA</u>CCAGGUCG<u>CA</u>-5'<br>5'-GAAAGCCGTCTTAATTTGGTCCAGCGT-3' | (SEQ ID NO: 1528)<br>(SEQ ID NO: 3542)<br>(SEQ ID NO: 5556) |
| LDHA-609 Target: | 5'-A<u>G</u>CCGUCUUAAUU<u>UG</u>GUCCAGCGta-3'<br>3'-<u>UUUC</u>GGCAGAAUUA<u>AA</u>CCAGGUCG<u>CAU</u>-5'<br>5'-AAAGCCGTCTTAATTTGGTCCAGCGTA-3' | (SEQ ID NO: 1529)<br>(SEQ ID NO: 3543)<br>(SEQ ID NO: 5557) |
| LDHA-610 Target: | 5'-G<u>CC</u>GUCUAUUUG<u>GU</u>CCAGCGUaa-3'<br>3'-<u>UUCG</u>GCAGAAUUA<u>AAC</u>CAGGUCG<u>CAUU</u>-5'<br>5'-AAGCCGTCTTAATTTGGTCCAGCGTAA-3' | (SEQ ID NO: 1530)<br>(SEQ ID NO: 3544)<br>(SEQ ID NO: 5558) |
| LDHA-611 Target: | 5'-C<u>C</u>GUCUUAAUUUGG<u>UC</u>CAGCGUAac-3'<br>3'-<u>UCGG</u>CAGAAUUAAA<u>CC</u>AGGUCGC<u>AUUG</u>-5'<br>5'-AGCCGTCTTAATTTGGTCCAGCGTAAC-3' | (SEQ ID NO: 1531)<br>(SEQ ID NO: 3545)<br>(SEQ ID NO: 5559) |
| LDHA-612 Target: | 5'-C<u>GU</u>CUUAAUUUGG<u>UCC</u>AGCGUAAcg-3'<br>3'-<u>CGG</u>CAGAAUUAAA<u>CC</u>AGGUCGC<u>AUUGC</u>-5'<br>5'-GCCGTCTTAATTTGGTCCAGCGTAACG-3' | (SEQ ID NO: 1532)<br>(SEQ ID NO: 3546)<br>(SEQ ID NO: 5560) |
| LDHA-613 Target: | 5'-G<u>U</u>CUUAAUUUGGUC<u>C</u>AGCGUAACgt-3'<br>3'-<u>GG</u>CAGAAUUAAACCAGGUCGCAUU<u>GCA</u>-5'<br>5'-CCGTCTTAATTTGGTCCAGCGTAACGT-3' | (SEQ ID NO: 1533)<br>(SEQ ID NO: 3547)<br>(SEQ ID NO: 5561) |
| LDHA-614 Target: | 5'-<u>U</u>CUUAAUUUGGUCC<u>A</u>GCGUAACGtg-3'<br>3'-<u>GCA</u>GAAUUAAACCAGGUCGCAUUG<u>CAC</u>-5'<br>5'-CGTCTTAATTTGGTCCAGCGTAACGTG-3' | (SEQ ID NO: 1534)<br>(SEQ ID NO: 3548)<br>(SEQ ID NO: 5562) |
| LDHA-615 Target: | 5'-C<u>UU</u>AAUUUGGUCC<u>AG</u>CGUAACGUga-3'<br>3'-<u>CAGA</u>AUUAAACCAGG<u>U</u>CGCAUUG<u>CACU</u>-5'<br>5'-GTCTTAATTTGGTCCAGCGTAACGTGA-3' | (SEQ ID NO: 1535)<br>(SEQ ID NO: 3549)<br>(SEQ ID NO: 5563) |
| LDHA-616 Target: | 5'-U<u>UA</u>AUUUGGUCC<u>AG</u>CGUAACGUGaa-3'<br>3'-<u>AGAA</u>UUAAACCAGG<u>UC</u>GCAUUGC<u>ACUU</u>-5'<br>5'-TCTTAATTTGGTCCAGCGTAACGTGAA-3' | (SEQ ID NO: 1536)<br>(SEQ ID NO: 3550)<br>(SEQ ID NO: 5564) |

TABLE 12-continued

Additional Selected Human Anti-Lactate Dehydrogenase DsiRNA Agents (Asymmetrics)

|  |  |  |
| --- | --- | --- |
| LDHA-617 Target: | 5'-UAAUUUGGUCCAGCGUAACGUGAac-3'<br>3'-GAAUUAAACCAGGUCGCAUUGCACUUG-5'<br>5'-CTTAATTTGGTCCAGCGTAACGTGAAC-3' | (SEQ ID NO: 1537)<br>(SEQ ID NO: 3551)<br>(SEQ ID NO: 5565) |
| LDHA-618 Target: | 5'-AAUUUGGUCCAGCGUAACGUGAAca-3'<br>3'-AAUUAAACCAGGUCGCAUUGCACUUGU-5'<br>5'-TTAATTTGGTCCAGCGTAACGTGAACA-3' | (SEQ ID NO: 1538)<br>(SEQ ID NO: 3552)<br>(SEQ ID NO: 5566) |
| LDHA-619 Target: | 5'-AUUUGGUCCAGCGUAACGUGAACat-3'<br>3'-AUUAAACCAGGUCGCAUUGCACUUGUA-5'<br>5'-TAATTTGGTCCAGCGTAACGTGAACAT-3' | (SEQ ID NO: 1539)<br>(SEQ ID NO: 3553)<br>(SEQ ID NO: 5567) |
| LDHA-620 Target: | 5'-UUUGGUCCAGCGUAACGUGAACAtc-3'<br>3'-UUAAACCAGGUCGCAUUGCACUUGUAG-5'<br>5'-AATTTGGTCCAGCGTAACGTGAACATC-3' | (SEQ ID NO: 1540)<br>(SEQ ID NO: 3554)<br>(SEQ ID NO: 5568) |
| LDHA-621 Target: | 5'-UUGGUCCAGCGUAACGUGAACAUct-3'<br>3'-UAAACCAGGUCGCAUUGCACUUGUAGA-5'<br>5'-ATTTGGTCCAGCGTAACGTGAACATCT-3' | (SEQ ID NO: 1541)<br>(SEQ ID NO: 3555)<br>(SEQ ID NO: 5569) |
| LDHA-622 Target: | 5'-UGGUCCAGCGUAACGUGAACAUCtt-3'<br>3'-AAACCAGGUCGCAUUGCACUUGUAGAA-5'<br>5'-TTTGGTCCAGCGTAACGTGAACATCTT-3' | (SEQ ID NO: 1542)<br>(SEQ ID NO: 3556)<br>(SEQ ID NO: 5570) |
| LDHA-623 Target: | 5'-GGUCCAGCGUAACGUGAACAUCUtt-3'<br>3'-AACCAGGUCGCAUUGCACUUGUAGAAA-5'<br>5'-TTGGTCCAGCGTAACGTGAACATCTTT-3' | (SEQ ID NO: 1543)<br>(SEQ ID NO: 3557)<br>(SEQ ID NO: 5571) |
| LDHA-624 Target: | 5'-GUCCAGCGUAACGUGAACAUCUUta-3'<br>3'-ACCAGGUCGCAUUGCACUUGUAGAAAU-5'<br>5'-TGGTCCAGCGTAACGTGAACATCTTTA-3' | (SEQ ID NO: 1544)<br>(SEQ ID NO: 3558)<br>(SEQ ID NO: 5572) |
| LDHA-625 Target: | 5'-UCCAGCGUAACGUGAACAUCUUUaa-3'<br>3'-CCAGGUCGCAUUGCACUUGUAGAAAUU-5'<br>5'-GGTCCAGCGTAACGTGAACATCTTTAA-3' | (SEQ ID NO: 1545)<br>(SEQ ID NO: 3559)<br>(SEQ ID NO: 5573) |
| LDHA-626 Target: | 5'-CCAGCGUAACGUGAACAUCUUUAaa-3'<br>3'-CAGGUCGCAUUGCACUUGUAGAAAUUU-5'<br>5'-GTCCAGCGTAACGTGAACATCTTTAAA-3' | (SEQ ID NO: 1546)<br>(SEQ ID NO: 3560)<br>(SEQ ID NO: 5574) |
| LDHA-627 Target: | 5'-CAGCGUAACGUGAACAUCUUUAAat-3'<br>3'-AGGUCGCAUUGCACUUGUAGAAAUUUA-5'<br>5'-TCCAGCGTAACGTGAACATCTTTAAAT-3' | (SEQ ID NO: 1547)<br>(SEQ ID NO: 3561)<br>(SEQ ID NO: 5575) |
| LDHA-628 Target: | 5'-AGCGUAACGUGAACAUCUUUAAAtt-3'<br>3'-GGUCGCAUUGCACUUGUAGAAAUUUAA-5'<br>5'-CCAGCGTAACGTGAACATCTTTAAATT-3' | (SEQ ID NO: 1548)<br>(SEQ ID NO: 3562)<br>(SEQ ID NO: 5576) |
| LDHA-629 Target: | 5'-GCGUAACGUGAACAUCUUUAAAUtc-3'<br>3'-GUCGCAUUGCACUUGUAGAAAUUUAAG-5'<br>5'-CAGCGTAACGTGAACATCTTTAAATTC-3' | (SEQ ID NO: 1549)<br>(SEQ ID NO: 3563)<br>(SEQ ID NO: 5577) |
| LDHA-630 Target: | 5'-CGUAACGUGAACAUCUUUAAAUUca-3'<br>3'-UCGCAUUGCACUUGUAGAAAUUUAAGU-5'<br>5'-AGCGTAACGTGAACATCTTTAAATTCA-3' | (SEQ ID NO: 1550)<br>(SEQ ID NO: 3564)<br>(SEQ ID NO: 5578) |
| LDHA-631 Target: | 5'-GUAACGUGAACAUCUUUAAAUUCat-3'<br>3'-CGCAUUGCACUUGUAGAAAUUUAAGUA-5'<br>5'-GCGTAACGTGAACATCTTTAAATTCAT-3' | (SEQ ID NO: 1551)<br>(SEQ ID NO: 3565)<br>(SEQ ID NO: 5579) |
| LDHA-632 Target: | 5'-UAACGUGAACAUCUUUAAAUUCAtc-3'<br>3'-GCAUUGCACUUGUAGAAAUUUAAGUAG-5'<br>5'-CGTAACGTGAACATCTTTAAATTCATC-3' | (SEQ ID NO: 1552)<br>(SEQ ID NO: 3566)<br>(SEQ ID NO: 5580) |
| LDHA-633 Target: | 5'-AACGUGAACAUCUUUAAAUUCAUca-3'<br>3'-CAUUGCACUUGUAGAAAUUUAAGUAGU-5'<br>5'-GTAACGTGAACATCTTTAAATTCATCA-3' | (SEQ ID NO: 1553)<br>(SEQ ID NO: 3567)<br>(SEQ ID NO: 5581) |
| LDHA-634 Target: | 5'-ACGUGAACAUCUUUAAAUUCAUCat-3'<br>3'-AUUGCACUUGUAGAAAUUUAAGUAGUA-5'<br>5'-TAACGTGAACATCTTTAAATTCATCAT-3' | (SEQ ID NO: 1554)<br>(SEQ ID NO: 3568)<br>(SEQ ID NO: 5582) |
| LDHA-635 Target: | 5'-CGUGAACAUCUUUAAAUUCAUCAtt-3'<br>3'-UUGCACUUGUAGAAAUUUAAGUAGUAA-5'<br>5'-AACGTGAACATCTTTAAATTCATCATT-3' | (SEQ ID NO: 1555)<br>(SEQ ID NO: 3569)<br>(SEQ ID NO: 5583) |

TABLE 12-continued

Additional Selected Human Anti-Lactate Dehydrogenase DsiRNA Agents (Asymmetrics)

| | | |
|---|---|---|
| LDHA-636 Target: | 5'-GUGAACAUCUUUAAAUUCAUCAUtc-3'<br>3'-UGCACUUGUAGAAAUUUAAGUAGUAAG-5'<br>5'-ACGTGAACATCTTTAAATTCATCATTC-3' | (SEQ ID NO: 1556)<br>(SEQ ID NO: 3570)<br>(SEQ ID NO: 5584) |
| LDHA-637 Target: | 5'-UGAACAUCUUUAAAUUCAUCAUUcc-3'<br>3'-GCACUUGUAGAAAUUUAAGUAGUAAGG-5'<br>5'-CGTGAACATCTTTAAATTCATCATTCC-3' | (SEQ ID NO: 1557)<br>(SEQ ID NO: 3571)<br>(SEQ ID NO: 5585) |
| LDHA-638 Target: | 5'-GAACAUCUUUAAAUUCAUCAUUCct-3'<br>3'-CACUUGUAGAAAUUUAAGUAGUAAGGA-5'<br>5'-GTGAACATCTTTAAATTCATCATTCCT-3' | (SEQ ID NO: 1558)<br>(SEQ ID NO: 3572)<br>(SEQ ID NO: 5586) |
| LDHA-639 Target: | 5'-AACAUCUUUAAAUUCAUCAUUCCta-3'<br>3'-ACUUGUAGAAAUUUAAGUAGUAAGGAU-5'<br>5'-TGAACATCTTTAAATTCATCATTCCTA-3' | (SEQ ID NO: 1559)<br>(SEQ ID NO: 3573)<br>(SEQ ID NO: 5587) |
| LDHA-640 Target: | 5'-ACAUCUUUAAAUUCAUCAUUCCUaa-3'<br>3'-CUUGUAGAAAUUUAAGUAGUAAGGAUU-5'<br>5'-GAACATCTTTAAATTCATCATTCCTAA-3' | (SEQ ID NO: 1560)<br>(SEQ ID NO: 3574)<br>(SEQ ID NO: 5588) |
| LDHA-641 Target: | 5'-CAUCUUUAAAUUCAUCAUUCCUAat-3'<br>3'-UUGUAGAAAUUUAAGUAGUAAGGAUUA-5'<br>5'-AACATCTTTAAATTCATCATTCCTAAT-3' | (SEQ ID NO: 1561)<br>(SEQ ID NO: 3575)<br>(SEQ ID NO: 5589) |
| LDHA-642 Target: | 5'-AUCUUUAAAUUCAUCAUUCCUAAtg-3'<br>3'-UGUAGAAAUUUAAGUAGUAAGGAUUAC-5'<br>5'-ACATCTTTAAATTCATCATTCCTAATG-3' | (SEQ ID NO: 1562)<br>(SEQ ID NO: 3576)<br>(SEQ ID NO: 5590) |
| LDHA-643 Target: | 5'-UCUUUAAAUUCAUCAUUCCUAAUgt-3'<br>3'-GUAGAAAUUUAAGUAGUAAGGAUUACA-5'<br>5'-CATCTTTAAATTCATCATTCCTAATGT-3' | (SEQ ID NO: 1563)<br>(SEQ ID NO: 3577)<br>(SEQ ID NO: 5591) |
| LDHA-644 Target: | 5'-CUUUAAAUUCAUCAUUCCUAAUGtt-3'<br>3'-UAGAAAUUUAAGUAGUAAGGAUUACAA-5'<br>5'-ATCTTTAAATTCATCATTCCTAATGTT-3' | (SEQ ID NO: 1564)<br>(SEQ ID NO: 3578)<br>(SEQ ID NO: 5592) |
| LDHA-645 Target: | 5'-UUUAAAUUCAUCAUUCCUAAUGUtg-3'<br>3'-AGAAAUUUAAGUAGUAAGGAUUACAAC-5'<br>5'-TCTTTAAATTCATCATTCCTAATGTTG-3' | (SEQ ID NO: 1565)<br>(SEQ ID NO: 3579)<br>(SEQ ID NO: 5593) |
| LDHA-646 Target: | 5'-UUAAAUUCAUCAUUCCUAAUGUUgt-3'<br>3'-GAAAUUUAAGUAGUAAGGAUUACAACA-5'<br>5'-CTTTAAATTCATCATTCCTAATGTTGT-3' | (SEQ ID NO: 1566)<br>(SEQ ID NO: 3580)<br>(SEQ ID NO: 5594) |
| LDHA-647 Target: | 5'-UAAAUUCAUCAUUCCUAAUGUUGta-3'<br>3'-AAAUUUAAGUAGUAAGGAUUACAACAU-5'<br>5'-TTTAAATTCATCATTCCTAATGTTGTA-3' | (SEQ ID NO: 1567)<br>(SEQ ID NO: 3581)<br>(SEQ ID NO: 5595) |
| LDHA-648 Target: | 5'-AAAUUCAUCAUUCCUAAUGUUGUaa-3'<br>3'-AAUUUAAGUAGUAAGGAUUACAACAUU-5'<br>5'-TTAAATTCATCATTCCTAATGTTGTAA-3' | (SEQ ID NO: 1568)<br>(SEQ ID NO: 3582)<br>(SEQ ID NO: 5596) |
| LDHA-649 Target: | 5'-AAUUCAUCAUUCCUAAUGUUGUAaa-3'<br>3'-AUUUAAGUAGUAAGGAUUACAACAUUU-5'<br>5'-TAAATTCATCATTCCTAATGTTGTAAA-3' | (SEQ ID NO: 1569)<br>(SEQ ID NO: 3583)<br>(SEQ ID NO: 5597) |
| LDHA-650 Target: | 5'-AUUCAUCAUUCCUAAUGUUGUAAaa-3'<br>3'-UUUAAGUAGUAAGGAUUACAACAUUUU-5'<br>5'-AAATTCATCATTCCTAATGTTGTAAAA-3' | (SEQ ID NO: 1570)<br>(SEQ ID NO: 3584)<br>(SEQ ID NO: 5598) |
| LDHA-651 Target: | 5'-UUCAUCAUUCCUAAUGUUGUAAAat-3'<br>3'-UUAAGUAGUAAGGAUUACAACAUUUUA-5'<br>5'-AATTCATCATTCCTAATGTTGTAAAAT-3' | (SEQ ID NO: 1571)<br>(SEQ ID NO: 3585)<br>(SEQ ID NO: 5599) |
| LDHA-652 Target: | 5'-UCAUCAUUCCUAAUGUUGUAAAAta-3'<br>3'-UAAGUAGUAAGGAUUACAACAUUUUAU-5'<br>5'-ATTCATCATTCCTAATGTTGTAAAATA-3' | (SEQ ID NO: 1572)<br>(SEQ ID NO: 3586)<br>(SEQ ID NO: 5600) |
| LDHA-653 Target: | 5'-CAUCAUUCCUAAUGUUGUAAAAUac-3'<br>3'-AAGUAGUAAGGAUUACAACAUUUUAUG-5'<br>5'-TTCATCATTCCTAATGTTGTAAAATAC-3' | (SEQ ID NO: 1573)<br>(SEQ ID NO: 3587)<br>(SEQ ID NO: 5601) |
| LDHA-654 Target: | 5'-AUCAUUCCUAAUGUUGUAAAAUAca-3'<br>3'-AGUAGUAAGGAUUACAACAUUUUAUGU-5'<br>5'-TCATCATTCCTAATGTTGTAAAATACA-3' | (SEQ ID NO: 1574)<br>(SEQ ID NO: 3588)<br>(SEQ ID NO: 5602) |

TABLE 12-continued

Additional Selected Human Anti-Lactate Dehydrogenase DsiRNA Agents (Asymmetrics)

| | | |
|---|---|---|
| LDHA-655 | 5'-UCAUUCCUAAUGUUGUAAAAUACag-3'<br>3'-GUAGUAAGGAUUACAACAUUUUAUGUC-5'<br>Target: 5'-CATCATTCCTAATGTTGTAAAATACAG-3' | (SEQ ID NO: 1575)<br>(SEQ ID NO: 3589)<br>(SEQ ID NO: 5603) |
| LDHA-656 | 5'-CAUUCCUAAUGUUGUAAAAUACAgc-3'<br>3'-UAGUAAGGAUUACAACAUUUUAUGUCG-5'<br>Target: 5'-ATCATTCCTAATGTTGTAAAATACAGC-3' | (SEQ ID NO: 1576)<br>(SEQ ID NO: 3590)<br>(SEQ ID NO: 5604) |
| LDHA-657 | 5'-AUUCCUAAUGUUGUAAAAUACAGcc-3'<br>3'-AGUAAGGAUUACAACAUUUUAUGUCGG-5'<br>Target: 5'-TCATTCCTAATGTTGTAAAATACAGCC-3' | (SEQ ID NO: 1577)<br>(SEQ ID NO: 3591)<br>(SEQ ID NO: 5605) |
| LDHA-658 | 5'-UUCCUAAUGUUGUAAAAUACAGCcc-3'<br>3'-GUAAGGAUUACAACAUUUUAUGUCGGG-5'<br>Target: 5'-CATTCCTAATGTTGTAAAATACAGCCC-3' | (SEQ ID NO: 1578)<br>(SEQ ID NO: 3592)<br>(SEQ ID NO: 5606) |
| LDHA-659 | 5'-UCCUAAUGUUGUAAAAUACAGCCcg-3'<br>3'-UAAGGAUUACAACAUUUUAUGUCGGGC-5'<br>Target: 5'-ATTCCTAATGTTGTAAAATACAGCCCG-3' | (SEQ ID NO: 1579)<br>(SEQ ID NO: 3593)<br>(SEQ ID NO: 5607) |
| LDHA-660 | 5'-CCUAAUGUUGUAAAAUACAGCCCga-3'<br>3'-AAGGAUUACAACAUUUUAUGUCGGGCU-5'<br>Target: 5'-TTCCTAATGTTGTAAAATACAGCCCGA-3' | (SEQ ID NO: 1580)<br>(SEQ ID NO: 3594)<br>(SEQ ID NO: 5608) |
| LDHA-661 | 5'-CUAAUGUUGUAAAAUACAGCCCGaa-3'<br>3'-AGGAUUACAACAUUUUAUGUCGGGCUU-5'<br>Target: 5'-TCCTAATGTTGTAAAATACAGCCCGAA-3' | (SEQ ID NO: 1581)<br>(SEQ ID NO: 3595)<br>(SEQ ID NO: 5609) |
| LDHA-662 | 5'-UAAUGUUGUAAAAUACAGCCCGAac-3'<br>3'-GGAUUACAACAUUUUAUGUCGGGCUUG-5'<br>Target: 5'-CCTAATGTTGTAAAATACAGCCCGAAC-3' | (SEQ ID NO: 1582)<br>(SEQ ID NO: 3596)<br>(SEQ ID NO: 5610) |
| LDHA-663 | 5'-AAUGUUGUAAAAUACAGCCCGAAct-3'<br>3'-GAUUACAACAUUUUAUGUCGGGCUUGA-5'<br>Target: 5'-CTAATGTTGTAAAATACAGCCCGAACT-3' | (SEQ ID NO: 1583)<br>(SEQ ID NO: 3597)<br>(SEQ ID NO: 5611) |
| LDHA-664 | 5'-AUGUUGUAAAAUACAGCCCGAACtg-3'<br>3'-AUUACAACAUUUUAUGUCGGGCUUGAC-5'<br>Target: 5'-TAATGTTGTAAAATACAGCCCGAACTG-3' | (SEQ ID NO: 1584)<br>(SEQ ID NO: 3598)<br>(SEQ ID NO: 5612) |
| LDHA-665 | 5'-UGUUGUAAAAUACAGCCCGAACUgc-3'<br>3'-UUACAACAUUUUAUGUCGGGCUUGACG-5'<br>Target: 5'-AATGTTGTAAAATACAGCCCGAACTGC-3' | (SEQ ID NO: 1585)<br>(SEQ ID NO: 3599)<br>(SEQ ID NO: 5613) |
| LDHA-666 | 5'-GUUGUAAAAUACAGCCCGAACUGca-3'<br>3'-UACAACAUUUUAUGUCGGGCUUGACGU-5'<br>Target: 5'-ATGTTGTAAAATACAGCCCGAACTGCA-3' | (SEQ ID NO: 1586)<br>(SEQ ID NO: 3600)<br>(SEQ ID NO: 5614) |
| LDHA-667 | 5'-UUGUAAAAUACAGCCCGAACUGCaa-3'<br>3'-ACAACAUUUUAUGUCGGGCUUGACGUU-5'<br>Target: 5'-TGTTGTAAAATACAGCCCGAACTGCAA-3' | (SEQ ID NO: 1587)<br>(SEQ ID NO: 3601)<br>(SEQ ID NO: 5615) |
| LDHA-668 | 5'-UGUAAAAUACAGCCCGAACUGCAag-3'<br>3'-CAACAUUUUAUGUCGGGCUUGACGUUC-5'<br>Target: 5'-GTTGTAAAATACAGCCCGAACTGCAAG-3' | (SEQ ID NO: 1588)<br>(SEQ ID NO: 3602)<br>(SEQ ID NO: 5616) |
| LDHA-669 | 5'-GUAAAAUACAGCCCGAACUGCAAgt-3'<br>3'-AACAUUUUAUGUCGGGCUUGACGUUCA-5'<br>Target: 5'-TTGTAAAATACAGCCCGAACTGCAAGT-3' | (SEQ ID NO: 1589)<br>(SEQ ID NO: 3603)<br>(SEQ ID NO: 5617) |
| LDHA-670 | 5'-UAAAAUACAGCCCGAACUGCAAGtt-3'<br>3'-ACAUUUUAUGUCGGGCUUGACGUUCAA-5'<br>Target: 5'-TGTAAAATACAGCCCGAACTGCAAGTT-3' | (SEQ ID NO: 1590)<br>(SEQ ID NO: 3604)<br>(SEQ ID NO: 5618) |
| LDHA-671 | 5'-AAAAUACAGCCCGAACUGCAAGUtg-3'<br>3'-CAUUUUAUGUCGGGCUUGACGUUCAAC-5'<br>Target: 5'-GTAAAATACAGCCCGAACTGCAAGTTG-3' | (SEQ ID NO: 1591)<br>(SEQ ID NO: 3605)<br>(SEQ ID NO: 5619) |
| LDHA-672 | 5'-AAAUACAGCCCGAACUGCAAGUUgc-3'<br>3'-AUUUUAUGUCGGGCUUGACGUUCAACG-5'<br>Target: 5'-TAAAATACAGCCCGAACTGCAAGTTGC-3' | (SEQ ID NO: 1592)<br>(SEQ ID NO: 3606)<br>(SEQ ID NO: 5620) |
| LDHA-673 | 5'-AAUACAGCCCGAACUGCAAGUUGct-3'<br>3'-UUUUAUGUCGGGCUUGACGUUCAACGA-5'<br>Target: 5'-AAAATACAGCCCGAACTGCAAGTTGCT-3' | (SEQ ID NO: 1593)<br>(SEQ ID NO: 3607)<br>(SEQ ID NO: 5621) |

TABLE 12-continued

Additional Selected Human Anti-Lactate Dehydrogenase DsiRNA Agents (Asymmetrics)

| | | |
|---|---|---|
| LDHA-674 | 5'-A<u>U</u>A<u>C</u>AGCCCGAACU<u>GC</u>AAGUUGCtt-3'<br>3'-<u>UUUAUGUC</u>GGGCUUGA<u>C</u>GUUCAA<u>C</u>GAA-5'<br>Target: 5'-AAATACAGCCCGAACTGCAAGTTGCTT-3' | (SEQ ID NO: 1594)<br>(SEQ ID NO: 3608)<br>(SEQ ID NO: 5622) |
| LDHA-675 | 5'-<u>U</u>A<u>C</u>AGCCCGAACU<u>GC</u>AAGUUGCUta-3'<br>3'-<u>UUAUGUC</u>GGGCUUGA<u>C</u>GUUCAAC<u>G</u>AAU-5'<br>Target: 5'-AATACAGCCCGAACTGCAAGTTGCTTA-3' | (SEQ ID NO: 1595)<br>(SEQ ID NO: 3609)<br>(SEQ ID NO: 5623) |
| LDHA-676 | 5'-<u>A</u>C<u>A</u>GCCCGAACUGC<u>A</u>AGUUGCUUat-3'<br>3'-<u>UAUGUC</u>GGGCUUGA<u>C</u>GUUCAACG<u>AAUA</u>-5'<br>Target: 5'-ATACAGCCCGAACTGCAAGTTGCTTAT-3' | (SEQ ID NO: 1596)<br>(SEQ ID NO: 3610)<br>(SEQ ID NO: 5624) |
| LDHA-677 | 5'-<u>C</u>AGCCCGAACUGC<u>A</u>AGUUGCUUAtt-3'<br>3'-<u>AUGUC</u>GGGCUUGAC<u>G</u>UUCAACGA<u>AUAA</u>-5'<br>Target: 5'-TACAGCCCGAACTGCAAGTTGCTTATT-3' | (SEQ ID NO: 1597)<br>(SEQ ID NO: 3611)<br>(SEQ ID NO: 5625) |
| LDHA-678 | 5'-A<u>GCCC</u>GAACUGCA<u>A</u>GUUGCUUAUtg-3'<br>3'-<u>UGUC</u>GGGCUUGAC<u>GUU</u>CAACGAAU<u>AAC</u>-5'<br>Target: 5'-ACAGCCCGAACTGCAAGTTGCTTATTG-3' | (SEQ ID NO: 1598)<br>(SEQ ID NO: 3612)<br>(SEQ ID NO: 5626) |
| LDHA-679 | 5'-<u>GCCC</u>GAACUGCAA<u>G</u>UUGCUUAUUgt-3'<br>3'-<u>GUC</u>GGGCUUGACGUU<u>C</u>AACGAAUA<u>ACA</u>-5'<br>Target: 5'-CAGCCCGAACTGCAAGTTGCTTATTGT-3' | (SEQ ID NO: 1599)<br>(SEQ ID NO: 3613)<br>(SEQ ID NO: 5627) |
| LDHA-680 | 5'-<u>CCC</u>GAACUGCAAGU<u>U</u>GCUUAUUGtt-3'<br>3'-<u>UC</u>GGGCUUGACGUU<u>C</u>AACGAAUA<u>ACAA</u>-5'<br>Target: 5'-AGCCCGAACTGCAAGTTGCTTATTGTT-3' | (SEQ ID NO: 1600)<br>(SEQ ID NO: 3614)<br>(SEQ ID NO: 5628) |
| LDHA-681 | 5'-<u>CC</u>GAACUGCAAGUU<u>GC</u>UUAUUGUtt-3'<br>3'-<u>C</u>GGGCUUGACGUUC<u>AA</u>CGAAUAAC<u>AAA</u>-5'<br>Target: 5'-GCCCGAACTGCAAGTTGCTTATTGTTT-3' | (SEQ ID NO: 1601)<br>(SEQ ID NO: 3615)<br>(SEQ ID NO: 5629) |
| LDHA-682 | 5'-<u>C</u>G<u>A</u>ACUGCAAGUUG<u>C</u>UUAUUGUUtc-3'<br>3'-<u>GGG</u>CUUGACGUUCA<u>C</u>GAAUAACA<u>AAG</u>-5'<br>Target: 5'-CCCGAACTGCAAGTTGCTTATTGTTTC-3' | (SEQ ID NO: 1602)<br>(SEQ ID NO: 3616)<br>(SEQ ID NO: 5630) |
| LDHA-683 | 5'-G<u>A</u>ACUGCAAGUUGC<u>UU</u>AUUGUUUca-3'<br>3'-<u>GG</u>CUUGACGUUCAA<u>C</u>GAAUAACA<u>AAGU</u>-5'<br>Target: 5'-CCGAACTGCAAGTTGCTTATTGTTTCA-3' | (SEQ ID NO: 1603)<br>(SEQ ID NO: 3617)<br>(SEQ ID NO: 5631) |
| LDHA-684 | 5'-<u>A</u>ACUGCAAGUUGC<u>UU</u>AUUGUUUCaa-3'<br>3'-<u>GC</u>UUGACGUUCAAC<u>G</u>AAUAACAAA<u>GUU</u>-5'<br>Target: 5'-CGAACTGCAAGTTGCTTATTGTTTCAA-3' | (SEQ ID NO: 1604)<br>(SEQ ID NO: 3618)<br>(SEQ ID NO: 5632) |
| LDHA-685 | 5'-<u>AC</u>UGCAAGUUGCU<u>UA</u>UUGUUUCAaa-3'<br>3'-<u>C</u>UUGACGUUCAACGAAUAACAAA<u>GUU</u>-5'<br>Target: 5'-GAACTGCAAGTTGCTTATTGTTTCAAA-3' | (SEQ ID NO: 1605)<br>(SEQ ID NO: 3619)<br>(SEQ ID NO: 5633) |
| LDHA-686 | 5'-C<u>UGC</u>AAGUUGCUU<u>AUU</u>GUUUCAAat-3'<br>3'-<u>UU</u>GACGUUCAACGA<u>A</u>UAACAAAGU<u>UUA</u>-5'<br>Target: 5'-AACTGCAAGTTGCTTATTGTTTCAAAT-3' | (SEQ ID NO: 1606)<br>(SEQ ID NO: 3620)<br>(SEQ ID NO: 5634) |
| LDHA-687 | 5'-<u>UGC</u>AAGUUGCUUA<u>UU</u>GUUUCAAAtc-3'<br>3'-<u>UGA</u>CGUUCAACGAA<u>U</u>AACAAAGUU<u>UAG</u>-5'<br>Target: 5'-ACTGCAAGTTGCTTATTGTTTCAAATC-3' | (SEQ ID NO: 1607)<br>(SEQ ID NO: 3621)<br>(SEQ ID NO: 5635) |
| LDHA-688 | 5'-<u>GC</u>AAGUUGCUUAU<u>UG</u>UUUCAAAUcc-3'<br>3'-<u>GAC</u>GUUCAACGAAU<u>AA</u>CAAAGUUU<u>AGG</u>-5'<br>Target: 5'-CTGCAAGTTGCTTATTGTTTCAAATCC-3' | (SEQ ID NO: 1608)<br>(SEQ ID NO: 3622)<br>(SEQ ID NO: 5636) |
| LDHA-689 | 5'-C<u>A</u>AGUUGCUUAUU<u>G</u>UUUCAAAUCca-3'<br>3'-<u>AC</u>GUUCAACGAAUA<u>AC</u>AAAGUUUA<u>GGU</u>-5'<br>Target: 5'-TGCAAGTTGCTTATTGTTTCAAATCCA-3' | (SEQ ID NO: 1609)<br>(SEQ ID NO: 3623)<br>(SEQ ID NO: 5637) |
| LDHA-690 | 5'-<u>A</u>AGUUGCUUAUUG<u>UUU</u>CAAAUCCag-3'<br>3'-<u>C</u>GUUCAACGAAUAACAAAGUUUAG<u>GUC</u>-5'<br>Target: 5'-GCAAGTTGCTTATTGTTTCAAATCCAG-3' | (SEQ ID NO: 1610)<br>(SEQ ID NO: 3624)<br>(SEQ ID NO: 5638) |
| LDHA-691 | 5'-<u>A</u>GUUGCUUAUUGU<u>UU</u>CAAAUCCAgt-3'<br>3'-<u>GUU</u>CAACGAAUAACA<u>A</u>AGUUUAGG<u>UCA</u>-5'<br>Target: 5'-CAAGTTGCTTATTGTTTCAAATCCAGT-3' | (SEQ ID NO: 1611)<br>(SEQ ID NO: 3625)<br>(SEQ ID NO: 5639) |
| LDHA-692 | 5'-G<u>UUG</u>CUUAUUGUU<u>U</u>CAAAUCCAGtg-3'<br>3'-<u>UUCA</u>ACGAAUAACA<u>AA</u>GUUUAGGU<u>CAC</u>-5'<br>Target: 5'-AAGTTGCTTATTGTTTCAAATCCAGTG-3' | (SEQ ID NO: 1612)<br>(SEQ ID NO: 3626)<br>(SEQ ID NO: 5640) |

TABLE 12-continued

Additional Selected Human Anti-Lactate Dehydrogenase DsiRNA Agents (Asymmetrics)

| | | |
|---|---|---|
| LDHA-693 Target: | 5'-UUGCUUAUUGUUUCAAAUCCAGUGgg-3'<br>3'-UCAACGAAUAACAAAGUUUAGGUCACC-5'<br>5'-AGTTGCTTATTGTTTCAAATCCAGTGG-3' | (SEQ ID NO: 1613)<br>(SEQ ID NO: 3627)<br>(SEQ ID NO: 5641) |
| LDHA-694 Target: | 5'-UGCUUAUUGUUUCAAAUCCAGUGga-3'<br>3'-CAACGAAUAACAAAGUUUAGGUCACCU-5'<br>5'-GTTGCTTATTGTTTCAAATCCAGTGGA-3' | (SEQ ID NO: 1614)<br>(SEQ ID NO: 3628)<br>(SEQ ID NO: 5642) |
| LDHA-695 Target: | 5'-GCUUAUUGUUUCAAAUCCAGUGGat-3'<br>3'-AACGAAUAACAAAGUUUAGGUCACCUA-5'<br>5'-TTGCTTATTGTTTCAAATCCAGTGGAT-3' | (SEQ ID NO: 1615)<br>(SEQ ID NO: 3629)<br>(SEQ ID NO: 5643) |
| LDHA-696 Target: | 5'-CUUAUUGUUUCAAAUCCAGUGGAta-3'<br>3'-ACGAAUAACAAAGUUUAGGUCACCUAU-5'<br>5'-TGCTTATTGTTTCAAATCCAGTGGATA-3' | (SEQ ID NO: 1616)<br>(SEQ ID NO: 3630)<br>(SEQ ID NO: 5644) |
| LDHA-697 Target: | 5'-UUAUUGUUUCAAAUCCAGUGGAUat-3'<br>3'-CGAAUAACAAAGUUUAGGUCACCUAUA-5'<br>5'-GCTTATTGTTTCAAATCCAGTGGATAT-3' | (SEQ ID NO: 1617)<br>(SEQ ID NO: 3631)<br>(SEQ ID NO: 5645) |
| LDHA-698 Target: | 5'-UAUUGUUUCAAAUCCAGUGGAUAtc-3'<br>3'-GAAUAACAAAGUUUAGGUCACCUAUAG-5'<br>5'-CTTATTGTTTCAAATCCAGTGGATATC-3' | (SEQ ID NO: 1618)<br>(SEQ ID NO: 3632)<br>(SEQ ID NO: 5646) |
| LDHA-699 Target: | 5'-AUUGUUUCAAAUCCAGUGGAUAUct-3'<br>3'-AAUAACAAAGUUUAGGUCACCUAUAGA-5'<br>5'-TTATTGTTTCAAATCCAGTGGATATCT-3' | (SEQ ID NO: 1619)<br>(SEQ ID NO: 3633)<br>(SEQ ID NO: 5647) |
| LDHA-700 Target: | 5'-UUGUUUCAAAUCCAGUGGAUAUCtt-3'<br>3'-AUAACAAAGUUUAGGUCACCUAUAGAA-5'<br>5'-TATTGTTTCAAATCCAGTGGATATCTT-3' | (SEQ ID NO: 1620)<br>(SEQ ID NO: 3634)<br>(SEQ ID NO: 5648) |
| LDHA-701 Target: | 5'-UGUUUCAAAUCCAGUGGAUAUCUtg-3'<br>3'-UAACAAAGUUUAGGUCACCUAUAGAAC-5'<br>5'-ATTGTTTCAAATCCAGTGGATATCTTG-3' | (SEQ ID NO: 1621)<br>(SEQ ID NO: 3635)<br>(SEQ ID NO: 5649) |
| LDHA-702 Target: | 5'-GUUUCAAAUCCAGUGGAUAUCUUga-3'<br>3'-AACAAAGUUUAGGUCACCUAUAGAACU-5'<br>5'-TTGTTTCAAATCCAGTGGATATCTTGA-3' | (SEQ ID NO: 1622)<br>(SEQ ID NO: 3636)<br>(SEQ ID NO: 5650) |
| LDHA-703 Target: | 5'-UUUCAAAUCCAGUGGAUAUCUUGac-3'<br>3'-ACAAAGUUUAGGUCACCUAUAGAACUG-5'<br>5'-TGTTTCAAATCCAGTGGATATCTTGAC-3' | (SEQ ID NO: 1623)<br>(SEQ ID NO: 3637)<br>(SEQ ID NO: 5651) |
| LDHA-704 Target: | 5'-UUCAAAUCCAGUGGAUAUCUUGAcc-3'<br>3'-CAAAGUUUAGGUCACCUAUAGAACUGG-5'<br>5'-GTTTCAAATCCAGTGGATATCTTGACC-3' | (SEQ ID NO: 1624)<br>(SEQ ID NO: 3638)<br>(SEQ ID NO: 5652) |
| LDHA-705 Target: | 5'-UCAAAUCCAGUGGAUAUCUUGACct-3'<br>3'-AAAGUUUAGGUCACCUAUAGAACUGGA-5'<br>5'-TTTCAAATCCAGTGGATATCTTGACCT-3' | (SEQ ID NO: 1625)<br>(SEQ ID NO: 3639)<br>(SEQ ID NO: 5653) |
| LDHA-706 Target: | 5'-CAAAUCCAGUGGAUAUCUUGACCta-3'<br>3'-AAGUUUAGGUCACCUAUAGAACUGGAU-5'<br>5'-TTCAAATCCAGTGGATATCTTGACCTA-3' | (SEQ ID NO: 1626)<br>(SEQ ID NO: 3640)<br>(SEQ ID NO: 5654) |
| LDHA-707 Target: | 5'-AAAUCCAGUGGAUAUCUUGACCUac-3'<br>3'-AGUUUAGGUCACCUAUAGAACUGGAUG-5'<br>5'-TCAAATCCAGTGGATATCTTGACCTAC-3' | (SEQ ID NO: 1627)<br>(SEQ ID NO: 3641)<br>(SEQ ID NO: 5655) |
| LDHA-708 Target: | 5'-AAUCCAGUGGAUAUCUUGACCUAcg-3'<br>3'-GUUUAGGUCACCUAUAGAACUGGAUGC-5'<br>5'-CAAATCCAGTGGATATCTTGACCTACG-3' | (SEQ ID NO: 1628)<br>(SEQ ID NO: 3642)<br>(SEQ ID NO: 5656) |
| LDHA-709 Target: | 5'-AUCCAGUGGAUAUCUUGACCUACgt-3'<br>3'-UUUAGGUCACCUAUAGAACUGGAUGCA-5'<br>5'-AAATCCAGTGGATATCTTGACCTACGT-3' | (SEQ ID NO: 1629)<br>(SEQ ID NO: 3643)<br>(SEQ ID NO: 5657) |
| LDHA-710 Target: | 5'-UCCAGUGGAUAUCUUGACCUACGtg-3'<br>3'-UUAGGUCACCUAUAGAACUGGAUGCAC-5'<br>5'-AATCCAGTGGATATCTTGACCTACGTG-3' | (SEQ ID NO: 1630)<br>(SEQ ID NO: 3644)<br>(SEQ ID NO: 5658) |
| LDHA-711 Target: | 5'-CCAGUGGAUAUCUUGACCUACGUgg-3'<br>3'-UAGGUCACCUAUAGAACUGGAUGCACC-5'<br>5'-ATCCAGTGGATATCTTGACCTACGTGG-3' | (SEQ ID NO: 1631)<br>(SEQ ID NO: 3645)<br>(SEQ ID NO: 5659) |

TABLE 12-continued

Additional Selected Human Anti-Lactate Dehydrogenase DsiRNA Agents (Asymmetrics)

| | | |
|---|---|---|
| LDHA-712 | 5'-CAGUGGAUAUCUUGACCUACGUGGgc-3'<br>3'-AGGUCACCUAUAGAACUGGAUGCACCG-5'<br>Target: 5'-TCCAGTGGATATCTTGACCTACGTGGC-3' | (SEQ ID NO: 1632)<br>(SEQ ID NO: 3646)<br>(SEQ ID NO: 5660) |
| LDHA-713 | 5'-AGUGGAUAUCUUGACCUACGUGGct-3'<br>3'-GGUCACCUAUAGAACUGGAUGCACCGA-5'<br>Target: 5'-CCAGTGGATATCTTGACCTACGTGGCT-3' | (SEQ ID NO: 1633)<br>(SEQ ID NO: 3647)<br>(SEQ ID NO: 5661) |
| LDHA-715 | 5'-UGGAUAUCUUGACCUACGUGGCUtg-3'<br>3'-UCACCUAUAGAACUGGAUGCACCGAAC-5'<br>Target: 5'-AGTGGATATCTTGACCTACGTGGCTTG-3' | (SEQ ID NO: 1634)<br>(SEQ ID NO: 3648)<br>(SEQ ID NO: 5662) |
| LDHA-716 | 5'-GGAUAUCUUGACCUACGUGGCUUgg-3'<br>3'-CACCUAUAGAACUGGAUGCACCGAACC-5'<br>Target: 5'-GTGGATATCTTGACCTACGTGGCTTGG-3' | (SEQ ID NO: 1635)<br>(SEQ ID NO: 3649)<br>(SEQ ID NO: 5663) |
| LDHA-721 | 5'-UCUUGACCUACGUGGCUUGGAAGat-3'<br>3'-AUAGAACUGGAUGCACCGAACCUUCUA-5'<br>Target: 5'-TATCTTGACCTACGTGGCTTGGAAGAT-3' | (SEQ ID NO: 1636)<br>(SEQ ID NO: 3650)<br>(SEQ ID NO: 5664) |
| LDHA-725 | 5'-GACCUACGUGGCUUGGAAGAUAAgt-3'<br>3'-AACUGGAUGCACCGAACCUUCUAUUCA-5'<br>Target: 5'-TTGACCTACGTGGCTTGGAAGATAAGT-3' | (SEQ ID NO: 1637)<br>(SEQ ID NO: 3651)<br>(SEQ ID NO: 5665) |
| LDHA-726 | 5'-ACCUACGUGGCUUGGAAGAUAAGtg-3'<br>3'-ACUGGAUGCACCGAACCUUCUAUUCAC-5'<br>Target: 5'-TGACCTACGTGGCTTGGAAGATAAGTG-3' | (SEQ ID NO: 1638)<br>(SEQ ID NO: 3652)<br>(SEQ ID NO: 5666) |
| LDHA-727 | 5'-CCUACGUGGCUUGGAAGAUAAGUgg-3'<br>3'-CUGGAUGCACCGAACCUUCUAUUCACC-5'<br>Target: 5'-GACCTACGTGGCTTGGAAGATAAGTGG-3' | (SEQ ID NO: 1639)<br>(SEQ ID NO: 3653)<br>(SEQ ID NO: 5667) |
| LDHA-728 | 5'-CUACGUGGCUUGGAAGAUAAGUGgt-3'<br>3'-UGGAUGCACCGAACCUUCUAUUCACCA-5'<br>Target: 5'-ACCTACGTGGCTTGGAAGATAAGTGGT-3' | (SEQ ID NO: 1640)<br>(SEQ ID NO: 3654)<br>(SEQ ID NO: 5668) |
| LDHA-729 | 5'-UACGUGGCUUGGAAGAUAAGUGGtt-3'<br>3'-GGAUGCACCGAACCUUCUAUUCACCAA-5'<br>Target: 5'-CCTACGTGGCTTGGAAGATAAGTGGTT-3' | (SEQ ID NO: 1641)<br>(SEQ ID NO: 3655)<br>(SEQ ID NO: 5669) |
| LDHA-730 | 5'-ACGUGGCUUGGAAGAUAAGUGGUtt-3'<br>3'-GAUGCACCGAACCUUCUAUUCACCAAA-5'<br>Target: 5'-CTACGTGGCTTGGAAGATAAGTGGTTT-3' | (SEQ ID NO: 1642)<br>(SEQ ID NO: 3656)<br>(SEQ ID NO: 5670) |
| LDHA-731 | 5'-CGUGGCUUGGAAGAUAAGUGGUUtt-3'<br>3'-AUGCACCGAACCUUCUAUUCACCAAAA-5'<br>Target: 5'-TACGTGGCTTGGAAGATAAGTGGTTTT-3' | (SEQ ID NO: 1643)<br>(SEQ ID NO: 3657)<br>(SEQ ID NO: 5671) |
| LDHA-732 | 5'-GUGGCUUGGAAGAUAAGUGGUUUtc-3'<br>3'-UGCACCGAACCUUCUAUUCACCAAAAG-5'<br>Target: 5'-ACGTGGCTTGGAAGATAAGTGGTTTTC-3' | (SEQ ID NO: 1644)<br>(SEQ ID NO: 3658)<br>(SEQ ID NO: 5672) |
| LDHA-733 | 5'-UGGCUUGGAAGAUAAGUGGUUUUcc-3'<br>3'-GCACCGAACCUUCUAUUCACCAAAAGG-5'<br>Target: 5'-CGTGGCTTGGAAGATAAGTGGTTTTCC-3' | (SEQ ID NO: 1645)<br>(SEQ ID NO: 3659)<br>(SEQ ID NO: 5673) |
| LDHA-734 | 5'-GGCUUGGAAGAUAAGUGGUUUUCcc-3'<br>3'-CACCGAACCUUCUAUUCACCAAAAGGG-5'<br>Target: 5'-GTGGCTTGGAAGATAAGTGGTTTTCCC-3' | (SEQ ID NO: 1646)<br>(SEQ ID NO: 3660)<br>(SEQ ID NO: 5674) |
| LDHA-735 | 5'-GCUUGGAAGAUAAGUGGUUUUCCca-3'<br>3'-ACCGAACCUUCUAUUCACCAAAAGGGU-5'<br>Target: 5'-TGGCTTGGAAGATAAGTGGTTTTCCCA-3' | (SEQ ID NO: 1647)<br>(SEQ ID NO: 3661)<br>(SEQ ID NO: 5675) |
| LDHA-736 | 5'-CUUGGAAGAUAAGUGGUUUUCCCaa-3'<br>3'-CCGAACCUUCUAUUCACCAAAAGGGUU-5'<br>Target: 5'-GGCTTGGAAGATAAGTGGTTTTCCCAA-3' | (SEQ ID NO: 1648)<br>(SEQ ID NO: 3662)<br>(SEQ ID NO: 5676) |
| LDHA-737 | 5'-UUGGAAGAUAAGUGGUUUUCCCAaa-3'<br>3'-CGAACCUUCUAUUCACCAAAAGGGUUU-5'<br>Target: 5'-GCTTGGAAGATAAGTGGTTTTCCCAAA-3' | (SEQ ID NO: 1649)<br>(SEQ ID NO: 3663)<br>(SEQ ID NO: 5677) |
| LDHA-738 | 5'-UGGAAGAUAAGUGGUUUUCCCAAaa-3'<br>3'-GAACCUUCUAUUCACCAAAAGGGUUUU-5'<br>Target: 5'-CTTGGAAGATAAGTGGTTTTCCCAAAA-3' | (SEQ ID NO: 1650)<br>(SEQ ID NO: 3664)<br>(SEQ ID NO: 5678) |

TABLE 12-continued

Additional Selected Human Anti-Lactate Dehydrogenase DsiRNA Agents (Asymmetrics)

| | | |
|---|---|---|
| LDHA-741 Target: | 5'-AAGAUAAGUGGUUUUCCCAAAAAcc-3'<br>3'-CCUUCUAUUCACCAAAAGGGUUUUUGG-5'<br>5'-GGAAGATAAGTGGTTTTCCCAAAAACC-3' | (SEQ ID NO: 1651)<br>(SEQ ID NO: 3665)<br>(SEQ ID NO: 5679) |
| LDHA-742 Target: | 5'-AGAUAAGUGGUUUUCCCAAAAACcg-3'<br>3'-CUUCUAUUCACCAAAAGGGUUUUUGGC-5'<br>5'-GAAGATAAGTGGTTTTCCCAAAAACCG-3' | (SEQ ID NO: 1652)<br>(SEQ ID NO: 3666)<br>(SEQ ID NO: 5680) |
| LDHA-743 Target: | 5'-GAUAAGUGGUUUUCCCAAAAACCgt-3'<br>3'-UUCUAUUCACCAAAAGGGUUUUUGGCA-5'<br>5'-AAGATAAGTGGTTTTCCCAAAAACCGT-3' | (SEQ ID NO: 1653)<br>(SEQ ID NO: 3667)<br>(SEQ ID NO: 5681) |
| LDHA-744 Target: | 5'-AUAAGUGGUUUUCCCAAAAACCGtg-3'<br>3'-UCUAUUCACCAAAAGGGUUUUUGGCAC-5'<br>5'-AGATAAGTGGTTTTCCCAAAAACCGTG-3' | (SEQ ID NO: 1654)<br>(SEQ ID NO: 3668)<br>(SEQ ID NO: 5682) |
| LDHA-745 Target: | 5'-UAAGUGGUUUUCCCAAAAACCGUgt-3'<br>3'-CUAUUCACCAAAAGGGUUUUUGGCACA-5'<br>5'-GATAAGTGGTTTTCCCAAAAACCGTGT-3' | (SEQ ID NO: 1655)<br>(SEQ ID NO: 3669)<br>(SEQ ID NO: 5683) |
| LDHA-746 Target: | 5'-AAGUGGUUUUCCCAAAAACCGUGtt-3'<br>3'-UAUUCACCAAAAGGGUUUUUGGCACAA-5'<br>5'-ATAAGTGGTTTTCCCAAAAACCGTGTT-3' | (SEQ ID NO: 1656)<br>(SEQ ID NO: 3670)<br>(SEQ ID NO: 5684) |
| LDHA-747 Target: | 5'-AGUGGUUUUCCCAAAAACCGUGUta-3'<br>3'-AUUCACCAAAAGGGUUUUUGGCACAAU-5'<br>5'-TAAGTGGTTTTCCCAAAAACCGTGTTA-3' | (SEQ ID NO: 1657)<br>(SEQ ID NO: 3671)<br>(SEQ ID NO: 5685) |
| LDHA-748 Target: | 5'-GUGGUUUUCCCAAAAACCGUGUUat-3'<br>3'-UUCACCAAAAGGGUUUUUGGCACAAUA-5'<br>5'-AAGTGGTTTTCCCAAAAACCGTGTTAT-3' | (SEQ ID NO: 1658)<br>(SEQ ID NO: 3672)<br>(SEQ ID NO: 5686) |
| LDHA-749 Target: | 5'-UGGUUUUCCCAAAAACCGUGUUAtt-3'<br>3'-UCACCAAAAGGGUUUUUGGCACAAUAA-5'<br>5'-AGTGGTTTTCCCAAAAACCGTGTTATT-3' | (SEQ ID NO: 1659)<br>(SEQ ID NO: 3673)<br>(SEQ ID NO: 5687) |
| LDHA-750 Target: | 5'-GGUUUUCCCAAAAACCGUGUUAUtg-3'<br>3'-CACCAAAAGGGUUUUUGGCACAAUAAC-5'<br>5'-GTGGTTTTCCCAAAAACCGTGTTATTG-3' | (SEQ ID NO: 1660)<br>(SEQ ID NO: 3674)<br>(SEQ ID NO: 5688) |
| LDHA-751 Target: | 5'-GUUUUCCCAAAAACCGUGUUAUUgg-3'<br>3'-ACCAAAAGGGUUUUUGGCACAAUAACC-5'<br>5'-TGGTTTTCCCAAAAACCGTGTTATTGG-3' | (SEQ ID NO: 1661)<br>(SEQ ID NO: 3675)<br>(SEQ ID NO: 5689) |
| LDHA-752 Target: | 5'-UUUUCCCAAAAACCGUGUUAUUGga-3'<br>3'-CCAAAAGGGUUUUUGGCACAAUAACCU-5'<br>5'-GGTTTTCCCAAAAACCGTGTTATTGGA-3' | (SEQ ID NO: 1662)<br>(SEQ ID NO: 3676)<br>(SEQ ID NO: 5690) |
| LDHA-753 Target: | 5'-UUUCCCAAAAACCGUGUUAUUGGaa-3'<br>3'-CAAAAGGGUUUUUGGCACAAUAACCUU-5'<br>5'-GTTTTCCCAAAAACCGTGTTATTGGAA-3' | (SEQ ID NO: 1663)<br>(SEQ ID NO: 3677)<br>(SEQ ID NO: 5691) |
| LDHA-754 Target: | 5'-UUCCCAAAAACCGUGUUAUUGGAag-3'<br>3'-AAAAGGGUUUUUGGCACAAUAACCUUC-5'<br>5'-TTTTCCCAAAAACCGTGTTATTGGAAG-3' | (SEQ ID NO: 1664)<br>(SEQ ID NO: 3678)<br>(SEQ ID NO: 5692) |
| LDHA-755 Target: | 5'-UCCCAAAAACCGUGUUAUUGGAAgc-3'<br>3'-AAAGGGUUUUUGGCACAAUAACCUUCG-5'<br>5'-TTTCCCAAAAACCGTGTTATTGGAAGC-3' | (SEQ ID NO: 1665)<br>(SEQ ID NO: 3679)<br>(SEQ ID NO: 5693) |
| LDHA-756 Target: | 5'-CCCAAAAACCGUGUUAUUGGAAGcg-3'<br>3'-AAGGGUUUUUGGCACAAUAACCUUCGC-5'<br>5'-TTCCCAAAAACCGTGTTATTGGAAGCG-3' | (SEQ ID NO: 1666)<br>(SEQ ID NO: 3680)<br>(SEQ ID NO: 5694) |
| LDHA-757 Target: | 5'-CCAAAAACCGUGUUAUUGGAAGCgg-3'<br>3'-AGGGUUUUUGGCACAAUAACCUUCGCC-5'<br>5'-TCCCAAAAACCGTGTTATTGGAAGCGG-3' | (SEQ ID NO: 1667)<br>(SEQ ID NO: 3681)<br>(SEQ ID NO: 5695) |
| LDHA-758 Target: | 5'-CAAAAACCGUGUUAUUGGAAGCGgt-3'<br>3'-GGGUUUUUGGCACAAUAACCUUCGCCA-5'<br>5'-CCCAAAAACCGTGTTATTGGAAGCGGT-3' | (SEQ ID NO: 1668)<br>(SEQ ID NO: 3682)<br>(SEQ ID NO: 5696) |
| LDHA-759 Target: | 5'-AAAAACCGUGUUAUUGGAAGCGGtt-3'<br>3'-GGUUUUUGGCACAAUAACCUUCGCCAA-5'<br>5'-CCAAAAACCGTGTTATTGGAAGCGGTT-3' | (SEQ ID NO: 1669)<br>(SEQ ID NO: 3683)<br>(SEQ ID NO: 5697) |

TABLE 12-continued

Additional Selected Human Anti-Lactate Dehydrogenase DsiRNA Agents (Asymmetrics)

| | | |
|---|---|---|
| | 5'-AAAACCGUGUUAUUGGAAGCGGUtg-3' | (SEQ ID NO: 1670) |
| | 3'-GUUUUUGGCACAAUAACCUUCGCCAAC-5' | (SEQ ID NO: 3684) |
| LDHA-760 Target: | 5'-CAAAAACCGTGTTATTGGAAGCGGTTG-3' | (SEQ ID NO: 5698) |
| | 5'-AAACCGUGUUAUUGGAAGCGGUUgc-3' | (SEQ ID NO: 1671) |
| | 3'-UUUUUGGCACAAUAACCUUCGCCAACG-5' | (SEQ ID NO: 3685) |
| LDHA-761 Target: | 5'-AAAAACCGTGTTATTGGAAGCGGTTGC-3' | (SEQ ID NO: 5699) |
| | 5'-AACCGUGUUAUUGGAAGCGGUUGca-3' | (SEQ ID NO: 1672) |
| | 3'-UUUUGGCACAAUAACCUUCGCCAACGU-5' | (SEQ ID NO: 3686) |
| LDHA-762 Target: | 5'-AAAACCGTGTTATTGGAAGCGGTTGCA-3' | (SEQ ID NO: 5700) |
| | 5'-ACCGUGUUAUUGGAAGCGGUUGCaa-3' | (SEQ ID NO: 1673) |
| | 3'-UUUGGCACAAUAACCUUCGCCAACGUU-5' | (SEQ ID NO: 3687) |
| LDHA-763 Target: | 5'-AAACCGTGTTATTGGAAGCGGTTGCAA-3' | (SEQ ID NO: 5701) |
| | 5'-CCGUGUUAUUGGAAGCGGUUGCAat-3' | (SEQ ID NO: 1674) |
| | 3'-UUGGCACAAUAACCUUCGCCAACGUUA-5' | (SEQ ID NO: 3688) |
| LDHA-764 Target: | 5'-AACCGTGTTATTGGAAGCGGTTGCAAT-3' | (SEQ ID NO: 5702) |
| | 5'-CGUGUUAUUGGAAGCGGUUGCAAtc-3' | (SEQ ID NO: 1675) |
| | 3'-UGGCACAAUAACCUUCGCCAACGUUAG-5' | (SEQ ID NO: 3689) |
| LDHA-765 Target: | 5'-ACCGTGTTATTGGAAGCGGTTGCAATC-3' | (SEQ ID NO: 5703) |
| | 5'-GUGUUAUUGGAAGCGGUUGCAAUct-3' | (SEQ ID NO: 1676) |
| | 3'-GGCACAAUAACCUUCGCCAACGUUAGA-5' | (SEQ ID NO: 3690) |
| LDHA-766 Target: | 5'-CCGTGTTATTGGAAGCGGTTGCAATCT-3' | (SEQ ID NO: 5704) |
| | 5'-UGUUAUUGGAAGCGGUUGCAAUCtg-3' | (SEQ ID NO: 1677) |
| | 3'-GCACAAUAACCUUCGCCAACGUUAGAC-5' | (SEQ ID NO: 3691) |
| LDHA-767 Target: | 5'-CGTGTTATTGGAAGCGGTTGCAATCTG-3' | (SEQ ID NO: 5705) |
| | 5'-GUUAUUGGAAGCGGUUGCAAUCUgg-3' | (SEQ ID NO: 1678) |
| | 3'-CACAAUAACCUUCGCCAACGUUAGACC-5' | (SEQ ID NO: 3692) |
| LDHA-768 Target: | 5'-GTGTTATTGGAAGCGGTTGCAATCTGG-3' | (SEQ ID NO: 5706) |
| | 5'-UUAUUGGAAGCGGUUGCAAUCUGga-3' | (SEQ ID NO: 1679) |
| | 3'-ACAAUAACCUUCGCCAACGUUAGACCU-5' | (SEQ ID NO: 3693) |
| LDHA-769 Target: | 5'-TGTTATTGGAAGCGGTTGCAATCTGGA-3' | (SEQ ID NO: 5707) |
| | 5'-UAUUGGAAGCGGUUGCAAUCUGGat-3' | (SEQ ID NO: 1680) |
| | 3'-CAAUAACCUUCGCCAACGUUAGACCUA-5' | (SEQ ID NO: 3694) |
| LDHA-770 Target: | 5'-GTTATTGGAAGCGGTTGCAATCTGGAT-3' | (SEQ ID NO: 5708) |
| | 5'-AUUGGAAGCGGUUGCAAUCUGGAtt-3' | (SEQ ID NO: 1681) |
| | 3'-AAUAACCUUCGCCAACGUUAGACCUAA-5' | (SEQ ID NO: 3695) |
| LDHA-771 Target: | 5'-TTATTGGAAGCGGTTGCAATCTGGATT-3' | (SEQ ID NO: 5709) |
| | 5'-UUGGAAGCGGUUGCAAUCUGGAUtc-3' | (SEQ ID NO: 1682) |
| | 3'-AUAACCUUCGCCAACGUUAGACCUAAG-5' | (SEQ ID NO: 3696) |
| LDHA-772 Target: | 5'-TATTGGAAGCGGTTGCAATCTGGATTC-3' | (SEQ ID NO: 5710) |
| | 5'-UGGAAGCGGUUGCAAUCUGGAUUca-3' | (SEQ ID NO: 1683) |
| | 3'-UAACCUUCGCCAACGUUAGACCUAAGU-5' | (SEQ ID NO: 3697) |
| LDHA-773 Target: | 5'-ATTGGAAGCGGTTGCAATCTGGATTCA-3' | (SEQ ID NO: 5711) |
| | 5'-GGAAGCGGUUGCAAUCUGGAUUCag-3' | (SEQ ID NO: 1684) |
| | 3'-AACCUUCGCCAACGUUAGACCUAAGUC-5' | (SEQ ID NO: 3698) |
| LDHA-774 Target: | 5'-TTGGAAGCGGTTGCAATCTGGATTCAG-3' | (SEQ ID NO: 5712) |
| | 5'-GAAGCGGUUGCAAUCUGGAUUCAgc-3' | (SEQ ID NO: 1685) |
| | 3'-ACCUUCGCCAACGUUAGACCUAAGUCG-5' | (SEQ ID NO: 3699) |
| LDHA-775 Target: | 5'-TGGAAGCGGTTGCAATCTGGATTCAGC-3' | (SEQ ID NO: 5713) |
| | 5'-AAGCGGUUGCAAUCUGGAUUCAGcc-3' | (SEQ ID NO: 1686) |
| | 3'-CCUUCGCCAACGUUAGACCUAAGUCGG-5' | (SEQ ID NO: 3700) |
| LDHA-776 Target: | 5'-GGAAGCGGTTGCAATCTGGATTCAGCC-3' | (SEQ ID NO: 5714) |
| | 5'-AGCGGUUGCAAUCUGGAUUCAGCcc-3' | (SEQ ID NO: 1687) |
| | 3'-CUUCGCCAACGUUAGACCUAAGUCGGG-5' | (SEQ ID NO: 3701) |
| LDHA-777 Target: | 5'-GAAGCGGTTGCAATCTGGATTCAGCCC-3' | (SEQ ID NO: 5715) |
| | 5'-GCGGUUGCAAUCUGGAUUCAGCCcg-3' | (SEQ ID NO: 1688) |
| | 3'-UUCGCCAACGUUAGACCUAAGUCGGGC-5' | (SEQ ID NO: 3702) |
| LDHA-778 Target: | 5'-AAGCGGTTGCAATCTGGATTCAGCCCG-3' | (SEQ ID NO: 5716) |

TABLE 12-continued

Additional Selected Human Anti-Lactate Dehydrogenase DsiRNA Agents (Asymmetrics)

| | | |
|---|---|---|
| LDHA-779 Target: | 5'-CGGUUGCAAUCUGGAUUCAGCCCga-3'<br>3'-UCGCCAACGUUAGACCUAAGUCGGGCU-5'<br>5'-AGCGGTTGCAATCTGGATTCAGCCCGA-3' | (SEQ ID NO: 1689)<br>(SEQ ID NO: 3703)<br>(SEQ ID NO: 5717) |
| LDHA-780 Target: | 5'-GGUUGCAAUCUGGAUUCAGCCCGat-3'<br>3'-CGCCAACGUUAGACCUAAGUCGGGCUA-5'<br>5'-GCGGTTGCAATCTGGATTCAGCCCGAT-3' | (SEQ ID NO: 1690)<br>(SEQ ID NO: 3704)<br>(SEQ ID NO: 5718) |
| LDHA-781 Target: | 5'-GUUGCAAUCUGGAUUCAGCCCGAtt-3'<br>3'-GCCAACGUUAGACCUAAGUCGGGCUAA-5'<br>5'-CGGTTGCAATCTGGATTCAGCCCGATT-3' | (SEQ ID NO: 1691)<br>(SEQ ID NO: 3705)<br>(SEQ ID NO: 5719) |
| LDHA-782 Target: | 5'-UUGCAAUCUGGAUUCAGCCCGAUtc-3'<br>3'-CCAACGUUAGACCUAAGUCGGGCUAAG-5'<br>5'-GGTTGCAATCTGGATTCAGCCCGATTC-3' | (SEQ ID NO: 1692)<br>(SEQ ID NO: 3706)<br>(SEQ ID NO: 5720) |
| LDHA-783 Target: | 5'-UGCAAUCUGGAUUCAGCCCGAUUcc-3'<br>3'-CAACGUUAGACCUAAGUCGGGCUAAGG-5'<br>5'-GTTGCAATCTGGATTCAGCCCGATTCC-3' | (SEQ ID NO: 1693)<br>(SEQ ID NO: 3707)<br>(SEQ ID NO: 5721) |
| LDHA-784 Target: | 5'-GCAAUCUGGAUUCAGCCCGAUUCcg-3'<br>3'-AACGUUAGACCUAAGUCGGGCUAAGGC-5'<br>5'-TTGCAATCTGGATTCAGCCCGATTCCG-3' | (SEQ ID NO: 1694)<br>(SEQ ID NO: 3708)<br>(SEQ ID NO: 5722) |
| LDHA-785 Target: | 5'-CAAUCUGGAUUCAGCCCGAUUCCgt-3'<br>3'-ACGUUAGACCUAAGUCGGGCUAAGGCA-5'<br>5'-TGCAATCTGGATTCAGCCCGATTCCGT-3' | (SEQ ID NO: 1695)<br>(SEQ ID NO: 3709)<br>(SEQ ID NO: 5723) |
| LDHA-786 Target: | 5'-AAUCUGGAUUCAGCCCGAUUCCGtt-3'<br>3'-CGUUAGACCUAAGUCGGGCUAAGGCAA-5'<br>5'-GCAATCTGGATTCAGCCCGATTCCGTT-3' | (SEQ ID NO: 1696)<br>(SEQ ID NO: 3710)<br>(SEQ ID NO: 5724) |
| LDHA-787 Target: | 5'-AUCUGGAUUCAGCCCGAUUCCGUta-3'<br>3'-GUUAGACCUAAGUCGGGCUAAGGCAAU-5'<br>5'-CAATCTGGATTCAGCCCGATTCCGTTA-3' | (SEQ ID NO: 1697)<br>(SEQ ID NO: 3711)<br>(SEQ ID NO: 5725) |
| LDHA-788 Target: | 5'-UCUGGAUUCAGCCCGAUUCCGUUac-3'<br>3'-UUAGACCUAAGUCGGGCUAAGGCAAUG-5'<br>5'-AATCTGGATTCAGCCCGATTCCGTTAC-3' | (SEQ ID NO: 1698)<br>(SEQ ID NO: 3712)<br>(SEQ ID NO: 5726) |
| LDHA-789 Target: | 5'-CUGGAUUCAGCCCGAUUCCGUUAcc-3'<br>3'-UAGACCUAAGUCGGGCUAAGGCAAUGG-5'<br>5'-ATCTGGATTCAGCCCGATTCCGTTACC-3' | (SEQ ID NO: 1699)<br>(SEQ ID NO: 3713)<br>(SEQ ID NO: 5727) |
| LDHA-790 Target: | 5'-UGGAUUCAGCCCGAUUCCGUUACct-3'<br>3'-AGACCUAAGUCGGGCUAAGGCAAUGGA-5'<br>5'-TCTGGATTCAGCCCGATTCCGTTACCT-3' | (SEQ ID NO: 1700)<br>(SEQ ID NO: 3714)<br>(SEQ ID NO: 5728) |
| LDHA-791 Target: | 5'-GGAUUCAGCCCGAUUCCGUUACCta-3'<br>3'-GACCUAAGUCGGGCUAAGGCAAUGGAU-5'<br>5'-CTGGATTCAGCCCGATTCCGTTACCTA-3' | (SEQ ID NO: 1701)<br>(SEQ ID NO: 3715)<br>(SEQ ID NO: 5729) |
| LDHA-792 Target: | 5'-GAUUCAGCCCGAUUCCGUUACCUaa-3'<br>3'-ACCUAAGUCGGGCUAAGGCAAUGGAUU-5'<br>5'-TGGATTCAGCCCGATTCCGTTACCTAA-3' | (SEQ ID NO: 1702)<br>(SEQ ID NO: 3716)<br>(SEQ ID NO: 5730) |
| LDHA-793 Target: | 5'-AUUCAGCCCGAUUCCGUUACCUAat-3'<br>3'-CCUAAGUCGGGCUAAGGCAAUGGAUUA-5'<br>5'-GGATTCAGCCCGATTCCGTTACCTAAT-3' | (SEQ ID NO: 1703)<br>(SEQ ID NO: 3717)<br>(SEQ ID NO: 5731) |
| LDHA-794 Target: | 5'-UUCAGCCCGAUUCCGUUACCUAAtg-3'<br>3'-CUAAGUCGGGCUAAGGCAAUGGAUUAC-5'<br>5'-GATTCAGCCCGATTCCGTTACCTAATG-3' | (SEQ ID NO: 1704)<br>(SEQ ID NO: 3718)<br>(SEQ ID NO: 5732) |
| LDHA-795 Target: | 5'-UCAGCCCGAUUCCGUUACCUAAUgg-3'<br>3'-UAAGUCGGGCUAAGGCAAUGGAUUACC-5'<br>5'-ATTCAGCCCGATTCCGTTACCTAATGG-3' | (SEQ ID NO: 1705)<br>(SEQ ID NO: 3719)<br>(SEQ ID NO: 5733) |
| LDHA-796 Target: | 5'-CAGCCCGAUUCCGUUACCUAAUGgg-3'<br>3'-AAGUCGGGCUAAGGCAAUGGAUUACCC-5'<br>5'-TTCAGCCCGATTCCGTTACCTAATGGG-3' | (SEQ ID NO: 1706)<br>(SEQ ID NO: 3720)<br>(SEQ ID NO: 5734) |
| LDHA-797 Target: | 5'-AGCCCGAUUCCGUUACCUAAUGGg-3'<br>3'-AGUCGGGCUAAGGCAAUGGAUUACCCC-5'<br>5'-TCAGCCCGATTCCGTTACCTAATGGGG-3' | (SEQ ID NO: 1707)<br>(SEQ ID NO: 3721)<br>(SEQ ID NO: 5735) |

TABLE 12-continued

Additional Selected Human Anti-Lactate Dehydrogenase DsiRNA Agents (Asymmetrics)

|  |  |  |
| --- | --- | --- |
|  | 5'-GCCCGAUUCCGUUACCUAAUGGGgg-3' | (SEQ ID NO: 1708) |
|  | 3'-GUCGGGCUAAGGCAAUGGAUUACCCCC-5' | (SEQ ID NO: 3722) |
| LDHA-798 Target: | 5'-CAGCCCGATTCCGTTACCTAATGGGGG-3' | (SEQ ID NO: 5736) |
|  | 5'-CCCGAUUCCGUUACCUAAUGGGGga-3' | (SEQ ID NO: 1709) |
|  | 3'-UCGGGCUAAGGCAAUGGAUUACCCCCU-5' | (SEQ ID NO: 3723) |
| LDHA-799 Target: | 5'-AGCCCGATTCCGTTACCTAATGGGGGA-3' | (SEQ ID NO: 5737) |
|  | 5'-CCGAUUCCGUUACCUAAUGGGGaa-3' | (SEQ ID NO: 1710) |
|  | 3'-CGGGCUAAGGCAAUGGAUUACCCCCUU-5' | (SEQ ID NO: 3724) |
| LDHA-800 Target: | 5'-GCCCGATTCCGTTACCTAATGGGGGAA-3' | (SEQ ID NO: 5738) |
|  | 5'-CGAUUCCGUUACCUAAUGGGGGAaa-3' | (SEQ ID NO: 1711) |
|  | 3'-GGGCUAAGGCAAUGGAUUACCCCCUUU-5' | (SEQ ID NO: 3725) |
| LDHA-801 Target: | 5'-CCCGATTCCGTTACCTAATGGGGGAAA-3' | (SEQ ID NO: 5739) |
|  | 5'-GAUUCCGUUACCUAAUGGGGGAAag-3' | (SEQ ID NO: 1712) |
|  | 3'-GGCUAAGGCAAUGGAUUACCCCCUUUC-5' | (SEQ ID NO: 3726) |
| LDHA-802 Target: | 5'-CCGATTCCGTTACCTAATGGGGGAAAG-3' | (SEQ ID NO: 5740) |
|  | 5'-AUUCCGUUACCUAAUGGGGGAAAgg-3' | (SEQ ID NO: 1713) |
|  | 3'-GCUAAGGCAAUGGAUUACCCCCUUUCC-5' | (SEQ ID NO: 3727) |
| LDHA-803 Target: | 5'-CGATTCCGTTACCTAATGGGGGAAAGG-3' | (SEQ ID NO: 5741) |
|  | 5'-UUCCGUUACCUAAUGGGGGAAAGgc-3' | (SEQ ID NO: 1714) |
|  | 3'-CUAAGGCAAUGGAUUACCCCCUUUCCG-5' | (SEQ ID NO: 3728) |
| LDHA-804 Target: | 5'-GATTCCGTTACCTAATGGGGGAAAGGC-3' | (SEQ ID NO: 5742) |
|  | 5'-UCCGUUACCUAAUGGGGGAAAGGct-3' | (SEQ ID NO: 1715) |
|  | 3'-UAAGGCAAUGGAUUACCCCCUUUCCGA-5' | (SEQ ID NO: 3729) |
| LDHA-805 Target: | 5'-ATTCCGTTACCTAATGGGGGAAAGGCT-3' | (SEQ ID NO: 5743) |
|  | 5'-CCGUUACCUAAUGGGGGAAAGGCtg-3' | (SEQ ID NO: 1716) |
|  | 3'-AAGGCAAUGGAUUACCCCCUUUCCGAC-5' | (SEQ ID NO: 3730) |
| LDHA-806 Target: | 5'-TTCCGTTACCTAATGGGGGAAAGGCTG-3' | (SEQ ID NO: 5744) |
|  | 5'-CGUUACCUAAUGGGGGAAAGGCUgg-3' | (SEQ ID NO: 1717) |
|  | 3'-AGGCAAUGGAUUACCCCCUUUCCGACC-5' | (SEQ ID NO: 3731) |
| LDHA-807 Target: | 5'-TCCGTTACCTAATGGGGGAAAGGCTGG-3' | (SEQ ID NO: 5745) |
|  | 5'-GUUACCUAAUGGGGGAAAGGCUGgg-3' | (SEQ ID NO: 1718) |
|  | 3'-GGCAAUGGAUUACCCCCUUUCCGACCC-5' | (SEQ ID NO: 3732) |
| LDHA-808 Target: | 5'-CCGTTACCTAATGGGGGAAAGGCTGGG-3' | (SEQ ID NO: 5746) |
|  | 5'-UUACCUAAUGGGGGAAAGGCUGGga-3' | (SEQ ID NO: 1719) |
|  | 3'-GCAAUGGAUUACCCCCUUUCCGACCCU-5' | (SEQ ID NO: 3733) |
| LDHA-809 Target: | 5'-CGTTACCTAATGGGGGAAAGGCTGGGA-3' | (SEQ ID NO: 5747) |
|  | 5'-UACCUAAUGGGGGAAAGGCUGGGag-3' | (SEQ ID NO: 1720) |
|  | 3'-CAAUGGAUUACCCCCUUUCCGACCCUC-5' | (SEQ ID NO: 3734) |
| LDHA-810 Target: | 5'-GTTACCTAATGGGGGAAAGGCTGGGAG-3' | (SEQ ID NO: 5748) |
|  | 5'-ACCUAAUGGGGGAAAGGCUGGGAgt-3' | (SEQ ID NO: 1721) |
|  | 3'-AAUGGAUUACCCCCUUUCCGACCCUCA-5' | (SEQ ID NO: 3735) |
| LDHA-811 Target: | 5'-TTACCTAATGGGGGAAAGGCTGGGAGT-3' | (SEQ ID NO: 5749) |
|  | 5'-CCUAAUGGGGGAAAGGCUGGGAGtt-3' | (SEQ ID NO: 1722) |
|  | 3'-AUGGAUUACCCCCUUUCCGACCCUCAA-5' | (SEQ ID NO: 3736) |
| LDHA-812 Target: | 5'-TACCTAATGGGGGAAAGGCTGGGAGTT-3' | (SEQ ID NO: 5750) |
|  | 5'-CUAAUGGGGGAAAGGCUGGGAGUtc-3' | (SEQ ID NO: 1723) |
|  | 3'-UGGAUUACCCCCUUUCCGACCCUCAAG-5' | (SEQ ID NO: 3737) |
| LDHA-813 Target: | 5'-ACCTAATGGGGGAAAGGCTGGGAGTTC-3' | (SEQ ID NO: 5751) |
|  | 5'-UAAUGGGGGAAAGGCUGGGAGUUca-3' | (SEQ ID NO: 1724) |
|  | 3'-GGAUUACCCCCUUUCCGACCCUCAAGU-5' | (SEQ ID NO: 3738) |
| LDHA-814 Target: | 5'-CCTAATGGGGGAAAGGCTGGGAGTTCA-3' | (SEQ ID NO: 5752) |
|  | 5'-AAUGGGGGAAAGGCUGGGAGUUCac-3' | (SEQ ID NO: 1725) |
|  | 3'-GAUUACCCCCUUUCCGACCCUCAAGUG-5' | (SEQ ID NO: 3739) |
| LDHA-815 Target: | 5'-CTAATGGGGGAAAGGCTGGGAGTTCAC-3' | (SEQ ID NO: 5753) |
|  | 5'-AUGGGGGAAAGGCUGGGAGUUCAcc-3' | (SEQ ID NO: 1726) |
|  | 3'-AUUACCCCCUUUCCGACCCUCAAGUGG-5' | (SEQ ID NO: 3740) |
| LDHA-816 Target: | 5'-TAATGGGGGAAAGGCTGGGAGTTCACC-3' | (SEQ ID NO: 5754) |

TABLE 12-continued

Additional Selected Human Anti-Lactate Dehydrogenase DsiRNA
Agents (Asymmetrics)

```
                  5'-UGGGGGAAAGGCUGGGAGUUCACcc-3'      (SEQ ID NO: 1727)
                  3'-UUACCCCCUUUCCGACCCUCAAGUGGG-5'    (SEQ ID NO: 3741)
LDHA-817 Target:  5'-AATGGGGGAAAGGCTGGGAGTTCACCC-3'    (SEQ ID NO: 5755)

5'-GGGGGAAAGGCUGGGAGUUCACCca-3'      (SEQ ID NO: 1728)
                  3'-UACCCCCUUUCCGACCCUCAAGUGGGU-5'    (SEQ ID NO: 3742)
LDHA-818 Target:  5'-ATGGGGGAAAGGCTGGGAGTTCACCCA-3'    (SEQ ID NO: 5756)

5'-GGGGAAAGGCUGGGAGUUCACCCat-3'      (SEQ ID NO: 1729)
                  3'-ACCCCCUUUCCGACCCUCAAGUGGGUA-5'    (SEQ ID NO: 3743)
LDHA-819 Target:  5'-TGGGGGAAAGGCTGGGAGTTCACCCAT-3'    (SEQ ID NO: 5757)

5'-GGGAAAGGCUGGGAGUUCACCCAtt-3'      (SEQ ID NO: 1730)
                  3'-CCCCCUUUCCGACCCUCAAGUGGGUAA-5'    (SEQ ID NO: 3744)
LDHA-820 Target:  5'-GGGGGAAAGGCTGGGAGTTCACCCATT-3'    (SEQ ID NO: 5758)

5'-GGAAAGGCUGGGAGUUCACCCAUta-3'      (SEQ ID NO: 1731)
                  3'-CCCCUUUCCGACCCUCAAGUGGGUAAU-5'    (SEQ ID NO: 3745)
LDHA-821 Target:  5'-GGGGAAAGGCTGGGAGTTCACCCATTA-3'    (SEQ ID NO: 5759)

5'-GAAAGGCUGGGAGUUCACCCAUUaa-3'      (SEQ ID NO: 1732)
                  3'-CCCUUUCCGACCCUCAAGUGGGUAAUU-5'    (SEQ ID NO: 3746)
LDHA-822 Target:  5'-GGGAAAGGCTGGGAGTTCACCCATTAA-3'    (SEQ ID NO: 5760)

5'-AAAGGCUGGGAGUUCACCCAUUAag-3'      (SEQ ID NO: 1733)
                  3'-CCUUUCCGACCCUCAAGUGGGUAAUUC-5'    (SEQ ID NO: 3747)
LDHA-823 Target:  5'-GGAAAGGCTGGGAGTTCACCCATTAAG-3'    (SEQ ID NO: 5761)

5'-AAGGCUGGGAGUUCACCCAUUAAgc-3'      (SEQ ID NO: 1734)
                  3'-CUUUCCGACCCUCAAGUGGGUAAUUCG-5'    (SEQ ID NO: 3748)
LDHA-824 Target:  5'-GAAAGGCTGGGAGTTCACCCATTAAGC-3'    (SEQ ID NO: 5762)

5'-AGGCUGGGAGUUCACCCAUUAAGct-3'      (SEQ ID NO: 1735)
                  3'-UUUCCGACCCUCAAGUGGGUAAUUCGA-5'    (SEQ ID NO: 3749)
LDHA-825 Target:  5'-AAAGGCTGGGAGTTCACCCATTAAGCT-3'    (SEQ ID NO: 5763)

5'-GGCUGGGAGUUCACCCAUUAAGCtg-3'      (SEQ ID NO: 1736)
                  3'-UUCCGACCCUCAAGUGGGUAAUUCGAC-5'    (SEQ ID NO: 3750)
LDHA-826 Target:  5'-AAGGCTGGGAGTTCACCCATTAAGCTG-3'    (SEQ ID NO: 5764)

5'-GCUGGGAGUUCACCCAUUAAGCUgt-3'      (SEQ ID NO: 1737)
                  3'-UCCGACCCUCAAGUGGGUAAUUCGACA-5'    (SEQ ID NO: 3751)
LDHA-827 Target:  5'-AGGCTGGGAGTTCACCCATTAAGCTGT-3'    (SEQ ID NO: 5765)

5'-CUGGGAGUUCACCCAUUAAGCUGtc-3'      (SEQ ID NO: 1738)
                  3'-CCGACCCUCAAGUGGGUAAUUCGACAG-5'    (SEQ ID NO: 3752)
LDHA-828 Target:  5'-GGCTGGGAGTTCACCCATTAAGCTGTC-3'    (SEQ ID NO: 5766)

5'-UGGGAGUUCACCCAUUAAGCUGUca-3'      (SEQ ID NO: 1739)
                  3'-CGACCCUCAAGUGGGUAAUUCGACAGU-5'    (SEQ ID NO: 3753)
LDHA-829 Target:  5'-GCTGGGAGTTCACCCATTAAGCTGTCA-3'    (SEQ ID NO: 5767)

5'-GGGAGUUCACCCAUUAAGCUGUCat-3'      (SEQ ID NO: 1740)
                  3'-GACCCUCAAGUGGGUAAUUCGACAGUA-5'    (SEQ ID NO: 3754)
LDHA-830 Target:  5'-CTGGGAGTTCACCCATTAAGCTGTCAT-3'    (SEQ ID NO: 5768)

5'-GGAGUUCACCCAUUAAGCUGUCAtg-3'      (SEQ ID NO: 1741)
                  3'-ACCCUCAAGUGGGUAAUUCGACAGUAC-5'    (SEQ ID NO: 3755)
LDHA-831 Target:  5'-TGGGAGTTCACCCATTAAGCTGTCATG-3'    (SEQ ID NO: 5769)

5'-GAGUUCACCCAUUAAGCUGUCAUgg-3'      (SEQ ID NO: 1742)
                  3'-CCCUCAAGUGGGUAAUUCGACAGUACC-5'    (SEQ ID NO: 3756)
LDHA-832 Target:  5'-GGGAGTTCACCCATTAAGCTGTCATGG-3'    (SEQ ID NO: 5770)

5'-AGUUCACCCAUUAAGCUGUCAUGgg-3'      (SEQ ID NO: 1743)
                  3'-CCUCAAGUGGGUAAUUCGACAGUACCC-5'    (SEQ ID NO: 3757)
LDHA-833 Target:  5'-GGAGTTCACCCATTAAGCTGTCATGGG-3'    (SEQ ID NO: 5771)

5'-GUUCACCCAUUAAGCUGUCAUGGgt-3'      (SEQ ID NO: 1744)
                  3'-CUCAAGUGGGUAAUUCGACAGUACCCA-5'    (SEQ ID NO: 3758)
LDHA-834 Target:  5'-GAGTTCACCCATTAAGCTGTCATGGGT-3'    (SEQ ID NO: 5772)

5'-UUCACCCAUUAAGCUGUCAUGGGtg-3'      (SEQ ID NO: 1745)
                  3'-UCAAGUGGGUAAUUCGACAGUACCCAC-5'    (SEQ ID NO: 3759)
LDHA-835 Target:  5'-AGTTCACCCATTAAGCTGTCATGGGTG-3'    (SEQ ID NO: 5773)
```

TABLE 12-continued

Additional Selected Human Anti-Lactate Dehydrogenase DsiRNA Agents (Asymmetrics)

| | | |
|---|---|---|
| | 5'-UCACCCAUUAAGCUGUCAUGGGUgg-3' | (SEQ ID NO: 1746) |
| | 3'-CAAGUGGGUAAUUCGACAGUACCCACC-5' | (SEQ ID NO: 3760) |
| LDHA-836 Target: | 5'-GTTCACCCATTAAGCTGTCATGGGTGG-3' | (SEQ ID NO: 5774) |
| | 5'-CACCCAUUAAGCUGUCAUGGGUGgg-3' | (SEQ ID NO: 1747) |
| | 3'-AAGUGGGUAAUUCGACAGUACCCACCC-5' | (SEQ ID NO: 3761) |
| LDHA-837 Target: | 5'-TTCACCCATTAAGCTGTCATGGGTGGG-3' | (SEQ ID NO: 5775) |
| | 5'-ACCCAUUAAGCUGUCAUGGGUGGgt-3' | (SEQ ID NO: 1748) |
| | 3'-AGUGGGUAAUUCGACAGUACCCACCCA-5' | (SEQ ID NO: 3762) |
| LDHA-838 Target: | 5'-TCACCCATTAAGCTGTCATGGGTGGGT-3' | (SEQ ID NO: 5776) |
| | 5'-CCCAUUAAGCUGUCAUGGGUGGGtc-3' | (SEQ ID NO: 1749) |
| | 3'-GUGGGUAAUUCGACAGUACCCACCCAG-5' | (SEQ ID NO: 3763) |
| LDHA-839 Target: | 5'-CACCCATTAAGCTGTCATGGGTGGGTC-3' | (SEQ ID NO: 5777) |
| | 5'-CCAUUAAGCUGUCAUGGGUGGGUcc-3' | (SEQ ID NO: 1750) |
| | 3'-UGGGUAAUUCGACAGUACCCACCCAGG-5' | (SEQ ID NO: 3764) |
| LDHA-840 Target: | 5'-ACCCATTAAGCTGTCATGGGTGGGTCC-3' | (SEQ ID NO: 5778) |
| | 5'-CAUUAAGCUGUCAUGGGUGGGUCct-3' | (SEQ ID NO: 1751) |
| | 3'-GGGUAAUUCGACAGUACCCACCCAGGA-5' | (SEQ ID NO: 3765) |
| LDHA-841 Target: | 5'-CCCATTAAGCTGTCATGGGTGGGTCCT-3' | (SEQ ID NO: 5779) |
| | 5'-AUUAAGCUGUCAUGGGUGGGUCCtt-3' | (SEQ ID NO: 1752) |
| | 3'-GGUAAUUCGACAGUACCCACCCAGGAA-5' | (SEQ ID NO: 3766) |
| LDHA-842 Target: | 5'-CCATTAAGCTGTCATGGGTGGGTCCTT-3' | (SEQ ID NO: 5780) |
| | 5'-UUAAGCUGUCAUGGGUGGGUCCUtg-3' | (SEQ ID NO: 1753) |
| | 3'-GUAAUUCGACAGUACCCACCCAGGAAC-5' | (SEQ ID NO: 3767) |
| LDHA-843 Target: | 5'-CATTAAGCTGTCATGGGTGGGTCCTTG-3' | (SEQ ID NO: 5781) |
| | 5'-UAAGCUGUCAUGGGUGGGUCCUUgg-3' | (SEQ ID NO: 1754) |
| | 3'-UAAUUCGACAGUACCCACCCAGGAACC-5' | (SEQ ID NO: 3768) |
| LDHA-844 Target: | 5'-ATTAAGCTGTCATGGGTGGGTCCTTGG-3' | (SEQ ID NO: 5782) |
| | 5'-AAGCUGUCAUGGGUGGGUCCUUGgg-3' | (SEQ ID NO: 1755) |
| | 3'-AAUUCGACAGUACCCACCCAGGAACCC-5' | (SEQ ID NO: 3769) |
| LDHA-845 Target: | 5'-TTAAGCTGTCATGGGTGGGTCCTTGGG-3' | (SEQ ID NO: 5783) |
| | 5'-AGCUGUCAUGGGUGGGUCCUUGGgg-3' | (SEQ ID NO: 1756) |
| | 3'-AUUCGACAGUACCCACCCAGGAACCCC-5' | (SEQ ID NO: 3770) |
| LDHA-846 Target: | 5'-TAAGCTGTCATGGGTGGGTCCTTGGGG-3' | (SEQ ID NO: 5784) |
| | 5'-GCUGUCAUGGGUGGGUCCUUGGGga-3' | (SEQ ID NO: 1757) |
| | 3'-UUCGACAGUACCCACCCAGGAACCCCU-5' | (SEQ ID NO: 3771) |
| LDHA-847 Target: | 5'-AAGCTGTCATGGGTGGGTCCTTGGGGA-3' | (SEQ ID NO: 5785) |
| | 5'-CUGUCAUGGGUGGGUCCUUGGGGaa-3' | (SEQ ID NO: 1758) |
| | 3'-UCGACAGUACCCACCCAGGAACCCCUU-5' | (SEQ ID NO: 3772) |
| LDHA-848 Target: | 5'-AGCTGTCATGGGTGGGTCCTTGGGGAA-3' | (SEQ ID NO: 5786) |
| | 5'-UGUCAUGGGUGGGUCCUUGGGGAac-3' | (SEQ ID NO: 1759) |
| | 3'-CGACAGUACCCACCCAGGAACCCCUUG-5' | (SEQ ID NO: 3773) |
| LDHA-849 Target: | 5'-GCTGTCATGGGTGGGTCCTTGGGGAAC-3' | (SEQ ID NO: 5787) |
| | 5'-GUCAUGGGUGGGUCCUUGGGGAAca-3' | (SEQ ID NO: 1760) |
| | 3'-GACAGUACCCACCCAGGAACCCCUUGU-5' | (SEQ ID NO: 3774) |
| LDHA-850 Target: | 5'-CTGTCATGGGTGGGTCCTTGGGGAACA-3' | (SEQ ID NO: 5788) |
| | 5'-UCAUGGGUGGGUCCUUGGGGAACat-3' | (SEQ ID NO: 1761) |
| | 3'-ACAGUACCCACCCAGGAACCCCUUGUA-5' | (SEQ ID NO: 3775) |
| LDHA-851 Target: | 5'-TGTCATGGGTGGGTCCTTGGGGAACAT-3' | (SEQ ID NO: 5789) |
| | 5'-CAUGGGUGGGUCCUUGGGGAACAtg-3' | (SEQ ID NO: 1762) |
| | 3'-CAGUACCCACCCAGGAACCCCUUGUAC-5' | (SEQ ID NO: 3776) |
| LDHA-852 Target: | 5'-GTCATGGGTGGGTCCTTGGGGAACATG-3' | (SEQ ID NO: 5790) |
| | 5'-AUGGGUGGGUCCUUGGGGAACAUgg-3' | (SEQ ID NO: 1763) |
| | 3'-AGUACCCACCCAGGAACCCCUUGUACC-5' | (SEQ ID NO: 3777) |
| LDHA-853 Target: | 5'-TCATGGGTGGGTCCTTGGGGAACATGG-3' | (SEQ ID NO: 5791) |
| | 5'-UGGGUGGGUCCUUGGGGAACAUGga-3' | (SEQ ID NO: 1764) |
| | 3'-GUACCCACCCAGGAACCCCUUGUACCU-5' | (SEQ ID NO: 3778) |
| LDHA-854 Target: | 5'-CATGGGTGGGTCCTTGGGGAACATGGA-3' | (SEQ ID NO: 5792) |

TABLE 12-continued

Additional Selected Human Anti-Lactate Dehydrogenase DsiRNA Agents (Asymmetrics)

| | | |
|---|---|---|
| LDHA-855 Target: | 5'-GGGUGGGUCCUUGGGGAACAUGGAg-3'<br>3'-UACCCACCCAGGAACCCCUUGUACCUC-5'<br>5'-ATGGGTGGGTCCTTGGGGAACATGGAG-3' | (SEQ ID NO: 1765)<br>(SEQ ID NO: 3779)<br>(SEQ ID NO: 5793) |
| LDHA-856 Target: | 5'-GGUGGGUCCUUGGGGAACAUGGAga-3'<br>3'-ACCCACCCAGGAACCCCUUGUACCUCU-5'<br>5'-TGGGTGGGTCCTTGGGGAACATGGAGA-3' | (SEQ ID NO: 1766)<br>(SEQ ID NO: 3780)<br>(SEQ ID NO: 5794) |
| LDHA-857 Target: | 5'-GUGGGUCCUUGGGGAACAUGGAGat-3'<br>3'-CCCACCCAGGAACCCCUUGUACCUCUA-5'<br>5'-GGGTGGGTCCTTGGGGAACATGGAGAT-3' | (SEQ ID NO: 1767)<br>(SEQ ID NO: 3781)<br>(SEQ ID NO: 5795) |
| LDHA-858 Target: | 5'-UGGGUCCUUGGGGAACAUGGAGAtt-3'<br>3'-CCACCCAGGAACCCCUUGUACCUCUAA-5'<br>5'-GGTGGGTCCTTGGGGAACATGGAGATT-3' | (SEQ ID NO: 1768)<br>(SEQ ID NO: 3782)<br>(SEQ ID NO: 5796) |
| LDHA-859 Target: | 5'-GGGUCCUUGGGGAACAUGGAGAUtc-3'<br>3'-CACCCAGGAACCCCUUGUACCUCUAAG-5'<br>5'-GTGGGTCCTTGGGGAACATGGAGATTC-3' | (SEQ ID NO: 1769)<br>(SEQ ID NO: 3783)<br>(SEQ ID NO: 5797) |
| LDHA-860 Target: | 5'-GGUCCUUGGGGAACAUGGAGAUUcc-3'<br>3'-ACCCAGGAACCCCUUGUACCUCUAAGG-5'<br>5'-TGGGTCCTTGGGGAACATGGAGATTCC-3' | (SEQ ID NO: 1770)<br>(SEQ ID NO: 3784)<br>(SEQ ID NO: 5798) |
| LDHA-861 Target: | 5'-GUCCUUGGGGAACAUGGAGAUUCca-3'<br>3'-CCCAGGAACCCCUUGUACCUCUAAGGU-5'<br>5'-GGGTCCTTGGGGAACATGGAGATTCCA-3' | (SEQ ID NO: 1771)<br>(SEQ ID NO: 3785)<br>(SEQ ID NO: 5799) |
| LDHA-862 Target: | 5'-UCCUUGGGGAACAUGGAGAUUCCag-3'<br>3'-CCAGGAACCCCUUGUACCUCUAAGGUC-5'<br>5'-GGTCCTTGGGGAACATGGAGATTCCAG-3' | (SEQ ID NO: 1772)<br>(SEQ ID NO: 3786)<br>(SEQ ID NO: 5800) |
| LDHA-863 Target: | 5'-CCUUGGGGAACAUGGAGAUUCCAgt-3'<br>3'-CAGGAACCCCUUGUACCUCUAAGGUCA-5'<br>5'-GTCCTTGGGGAACATGGAGATTCCAGT-3' | (SEQ ID NO: 1773)<br>(SEQ ID NO: 3787)<br>(SEQ ID NO: 5801) |
| LDHA-864 Target: | 5'-CUUGGGGAACAUGGAGAUUCCAGtg-3'<br>3'-AGGAACCCCUUGUACCUCUAAGGUCAC-5'<br>5'-TCCTTGGGGAACATGGAGATTCCAGTG-3' | (SEQ ID NO: 1774)<br>(SEQ ID NO: 3788)<br>(SEQ ID NO: 5802) |
| LDHA-865 Target: | 5'-UUGGGGAACAUGGAGAUUCCAGUgt-3'<br>3'-GGAACCCCUUGUACCUCUAAGGUCACA-5'<br>5'-CCTTGGGGAACATGGAGATTCCAGTGT-3' | (SEQ ID NO: 1775)<br>(SEQ ID NO: 3789)<br>(SEQ ID NO: 5803) |
| LDHA-866 Target: | 5'-UGGGGAACAUGGAGAUUCCAGUGtg-3'<br>3'-GAACCCCUUGUACCUCUAAGGUCACAC-5'<br>5'-CTTGGGGAACATGGAGATTCCAGTGTG-3' | (SEQ ID NO: 1776)<br>(SEQ ID NO: 3790)<br>(SEQ ID NO: 5804) |
| LDHA-867 Target: | 5'-GGGGAACAUGGAGAUUCCAGUGUgc-3'<br>3'-AACCCCUUGUACCUCUAAGGUCACACG-5'<br>5'-TTGGGGAACATGGAGATTCCAGTGTGC-3' | (SEQ ID NO: 1777)<br>(SEQ ID NO: 3791)<br>(SEQ ID NO: 5805) |
| LDHA-868 Target: | 5'-GGGAACAUGGAGAUUCCAGUGUGcc-3'<br>3'-ACCCCUUGUACCUCUAAGGUCACACGG-5'<br>5'-TGGGGAACATGGAGATTCCAGTGTGCC-3' | (SEQ ID NO: 1778)<br>(SEQ ID NO: 3792)<br>(SEQ ID NO: 5806) |
| LDHA-869 Target: | 5'-GGAACAUGGAGAUUCCAGUGUGCct-3'<br>3'-CCCCUUGUACCUCUAAGGUCACACGGA-5'<br>5'-GGGGAACATGGAGATTCCAGTGTGCCT-3' | (SEQ ID NO: 1779)<br>(SEQ ID NO: 3793)<br>(SEQ ID NO: 5807) |
| LDHA-870 Target: | 5'-GAACAUGGAGAUUCCAGUGUGCCtg-3'<br>3'-CCCUUGUACCUCUAAGGUCACACGGAC-5'<br>5'-GGGAACATGGAGATTCCAGTGTGCCTG-3' | (SEQ ID NO: 1780)<br>(SEQ ID NO: 3794)<br>(SEQ ID NO: 5808) |
| LDHA-871 Target: | 5'-AACAUGGAGAUUCCAGUGUGCCUgt-3'<br>3'-CCUUGUACCUCUAAGGUCACACGGACA-5'<br>5'-GGAACATGGAGATTCCAGTGTGCCTGT-3' | (SEQ ID NO: 1781)<br>(SEQ ID NO: 3795)<br>(SEQ ID NO: 5809) |
| LDHA-872 Target: | 5'-ACAUGGAGAUUCCAGUGUGCCUGta-3'<br>3'-CUUGUACCUCUAAGGUCACACGGACAU-5'<br>5'-GAACATGGAGATTCCAGTGTGCCTGTA-3' | (SEQ ID NO: 1782)<br>(SEQ ID NO: 3796)<br>(SEQ ID NO: 5810) |
| LDHA-873 Target: | 5'-CAUGGAGAUUCCAGUGUGCCUGUat-3'<br>3'-UUGUACCUCUAAGGUCACACGGACAUA-5'<br>5'-AACATGGAGATTCCAGTGTGCCTGTAT-3' | (SEQ ID NO: 1783)<br>(SEQ ID NO: 3797)<br>(SEQ ID NO: 5811) |

TABLE 12-continued

Additional Selected Human Anti-Lactate Dehydrogenase DsiRNA Agents (Asymmetrics)

| | | |
|---|---|---|
| LDHA-874 | 5'-AUGGAGAUUCCAGUGUGCCUGUAtg-3'<br>3'-UGUACCUCUAAGGUCACACGGACAUAC-5'<br>Target: 5'-ACATGGAGATTCCAGTGTGCCTGTATG-3' | (SEQ ID NO: 1784)<br>(SEQ ID NO: 3798)<br>(SEQ ID NO: 5812) |
| LDHA-875 | 5'-UGGAGAUUCCAGUGUGCCUGUAUgg-3'<br>3'-GUACCUCUAAGGUCACACGGACAUACC-5'<br>Target: 5'-CATGGAGATTCCAGTGTGCCTGTATGG-3' | (SEQ ID NO: 1785)<br>(SEQ ID NO: 3799)<br>(SEQ ID NO: 5813) |
| LDHA-876 | 5'-GGAGAUUCCAGUGUGCCUGUAUGga-3'<br>3'-UACCUCUAAGGUCACACGGACAUACCU-5'<br>Target: 5'-ATGGAGATTCCAGTGTGCCTGTATGGA-3' | (SEQ ID NO: 1786)<br>(SEQ ID NO: 3800)<br>(SEQ ID NO: 5814) |
| LDHA-877 | 5'-GAGAUUCCAGUGUGCCUGUAUGGag-3'<br>3'-ACCUCUAAGGUCACACGGACAUACCUC-5'<br>Target: 5'-TGGAGATTCCAGTGTGCCTGTATGGAG-3' | (SEQ ID NO: 1787)<br>(SEQ ID NO: 3801)<br>(SEQ ID NO: 5815) |
| LDHA-878 | 5'-AGAUUCCAGUGUGCCUGUAUGGAgt-3'<br>3'-CCUCUAAGGUCACACGGACAUACCUCA-5'<br>Target: 5'-GGAGATTCCAGTGTGCCTGTATGGAGT-3' | (SEQ ID NO: 1788)<br>(SEQ ID NO: 3802)<br>(SEQ ID NO: 5816) |
| LDHA-879 | 5'-GAUUCCAGUGUGCCUGUAUGGAGtg-3'<br>3'-CUCUAAGGUCACACGGACAUACCUCAC-5'<br>Target: 5'-GAGATTCCAGTGTGCCTGTATGGAGTG-3' | (SEQ ID NO: 1789)<br>(SEQ ID NO: 3803)<br>(SEQ ID NO: 5817) |
| LDHA-880 | 5'-AUUCCAGUGUGCCUGUAUGGAGUgg-3'<br>3'-UCUAAGGUCACACGGACAUACCUCACC-5'<br>Target: 5'-AGATTCCAGTGTGCCTGTATGGAGTGG-3' | (SEQ ID NO: 1790)<br>(SEQ ID NO: 3804)<br>(SEQ ID NO: 5818) |
| LDHA-881 | 5'-UUCCAGUGUGCCUGUAUGGAGUGga-3'<br>3'-CUAAGGUCACACGGACAUACCUCACCU-5'<br>Target: 5'-GATTCCAGTGTGCCTGTATGGAGTGGA-3' | (SEQ ID NO: 1791)<br>(SEQ ID NO: 3805)<br>(SEQ ID NO: 5819) |
| LDHA-882 | 5'-UCCAGUGUGCCUGUAUGGAGUGGaa-3'<br>3'-UAAGGUCACACGGACAUACCUCACCUU-5'<br>Target: 5'-ATTCCAGTGTGCCTGTATGGAGTGGAA-3' | (SEQ ID NO: 1792)<br>(SEQ ID NO: 3806)<br>(SEQ ID NO: 5820) |
| LDHA-883 | 5'-CCAGUGUGCCUGUAUGGAGUGGAat-3'<br>3'-AAGGUCACACGGACAUACCUCACCUUA-5'<br>Target: 5'-TTCCAGTGTGCCTGTATGGAGTGGAAT-3' | (SEQ ID NO: 1793)<br>(SEQ ID NO: 3807)<br>(SEQ ID NO: 5821) |
| LDHA-884 | 5'-CAGUGUGCCUGUAUGGAGUGGAAtg-3'<br>3'-AGGUCACACGGACAUACCUCACCUUAC-5'<br>Target: 5'-TCCAGTGTGCCTGTATGGAGTGGAATG-3' | (SEQ ID NO: 1794)<br>(SEQ ID NO: 3808)<br>(SEQ ID NO: 5822) |
| LDHA-885 | 5'-AGUGUGCCUGUAUGGAGUGGAAUga-3'<br>3'-GGUCACACGGACAUACCUCACCUUACU-5'<br>Target: 5'-CCAGTGTGCCTGTATGGAGTGGAATGA-3' | (SEQ ID NO: 1795)<br>(SEQ ID NO: 3809)<br>(SEQ ID NO: 5823) |
| LDHA-886 | 5'-GUGUGCCUGUAUGGAGUGGAAUGaa-3'<br>3'-GUCACACGGACAUACCUCACCUUACUU-5'<br>Target: 5'-CAGTGTGCCTGTATGGAGTGGAATGAA-3' | (SEQ ID NO: 1796)<br>(SEQ ID NO: 3810)<br>(SEQ ID NO: 5824) |
| LDHA-887 | 5'-UGUGCCUGUAUGGAGUGGAAUGAat-3'<br>3'-UCACACGGACAUACCUCACCUUACUUA-5'<br>Target: 5'-AGTGTGCCTGTATGGAGTGGAATGAAT-3' | (SEQ ID NO: 1797)<br>(SEQ ID NO: 3811)<br>(SEQ ID NO: 5825) |
| LDHA-888 | 5'-GUGCCUGUAUGGAGUGGAAUGAAtg-3'<br>3'-CACACGGACAUACCUCACCUUACUUAC-5'<br>Target: 5'-GTGTGCCTGTATGGAGTGGAATGAATG-3' | (SEQ ID NO: 1798)<br>(SEQ ID NO: 3812)<br>(SEQ ID NO: 5826) |
| LDHA-889 | 5'-UGCCUGUAUGGAGUGGAAUGAAUgt-3'<br>3'-ACACGGACAUACCUCACCUUACUUACA-5'<br>Target: 5'-TGTGCCTGTATGGAGTGGAATGAATGT-3' | (SEQ ID NO: 1799)<br>(SEQ ID NO: 3813)<br>(SEQ ID NO: 5827) |
| LDHA-890 | 5'-GCCUGUAUGGAGUGGAAUGAAUGtt-3'<br>3'-CACGGACAUACCUCACCUUACUUACAA-5'<br>Target: 5'-GTGCCTGTATGGAGTGGAATGAATGTT-3' | (SEQ ID NO: 1800)<br>(SEQ ID NO: 3814)<br>(SEQ ID NO: 5828) |
| LDHA-893 | 5'-UGUAUGGAGUGGAAUGAAUGUUGct-3'<br>3'-GGACAUACCUCACCUUACUUACAACGA-5'<br>Target: 5'-CCTGTATGGAGTGGAATGAATGTTGCT-3' | (SEQ ID NO: 1801)<br>(SEQ ID NO: 3815)<br>(SEQ ID NO: 5829) |
| LDHA-894 | 5'-GUAUGGAGUGGAAUGAAUGUUGCtg-3'<br>3'-GACAUACCUCACCUUACUUACAACGAC-5'<br>Target: 5'-CTGTATGGAGTGGAATGAATGTTGCTG-3' | (SEQ ID NO: 1802)<br>(SEQ ID NO: 3816)<br>(SEQ ID NO: 5830) |

TABLE 12-continued

Additional Selected Human Anti-Lactate Dehydrogenase DsiRNA Agents (Asymmetrics)

| | | |
|---|---|---|
| LDHA-895 Target: | 5'-UAUGGAGUGGAAUGAAUGUUGCUgg-3'<br>3'-ACAUACCUCACCUUACUUACAACGACC-5'<br>5'-TGTATGGAGTGGAATGAATGTTGCTGG-3' | (SEQ ID NO: 1803)<br>(SEQ ID NO: 3817)<br>(SEQ ID NO: 5831) |
| LDHA-896 Target: | 5'-AUGGAGUGGAAUGAAUGUUGCUGgt-3'<br>3'-CAUACCUCACCUUACUUACAACGACCA-5'<br>5'-GTATGGAGTGGAATGAATGTTGCTGGT-3' | (SEQ ID NO: 1804)<br>(SEQ ID NO: 3818)<br>(SEQ ID NO: 5832) |
| LDHA-897 Target: | 5'-UGGAGUGGAAUGAAUGUUGCUGGtg-3'<br>3'-AUACCUCACCUUACUUACAACGACCAC-5'<br>5'-TATGGAGTGGAATGAATGTTGCTGGTG-3' | (SEQ ID NO: 1805)<br>(SEQ ID NO: 3819)<br>(SEQ ID NO: 5833) |
| LDHA-898 Target: | 5'-GGAGUGGAAUGAAUGUUGCUGGUgt-3'<br>3'-UACCUCACCUUACUUACAACGACCACA-5'<br>5'-ATGGAGTGGAATGAATGTTGCTGGTGT-3' | (SEQ ID NO: 1806)<br>(SEQ ID NO: 3820)<br>(SEQ ID NO: 5834) |
| LDHA-899 Target: | 5'-GAGUGGAAUGAAUGUUGCUGGUGtc-3'<br>3'-ACCUCACCUUACUUACAACGACCACAG-5'<br>5'-TGGAGTGGAATGAATGTTGCTGGTGTC-3' | (SEQ ID NO: 1807)<br>(SEQ ID NO: 3821)<br>(SEQ ID NO: 5835) |
| LDHA-900 Target: | 5'-AGUGGAAUGAAUGUUGCUGGUGUct-3'<br>3'-CCUCACCUUACUUACAACGACCACAGA-5'<br>5'-GGAGTGGAATGAATGTTGCTGGTGTCT-3' | (SEQ ID NO: 1808)<br>(SEQ ID NO: 3822)<br>(SEQ ID NO: 5836) |
| LDHA-901 Target: | 5'-GUGGAAUGAAUGUUGCUGGUGUCtc-3'<br>3'-CUCACCUUACUUACAACGACCACAGAG-5'<br>5'-GAGTGGAATGAATGTTGCTGGTGTCTC-3' | (SEQ ID NO: 1809)<br>(SEQ ID NO: 3823)<br>(SEQ ID NO: 5837) |
| LDHA-902 Target: | 5'-UGGAAUGAAUGUUGCUGGUGUCUct-3'<br>3'-UCACCUUACUUACAACGACCACAGAGA-5'<br>5'-AGTGGAATGAATGTTGCTGGTGTCTCT-3' | (SEQ ID NO: 1810)<br>(SEQ ID NO: 3824)<br>(SEQ ID NO: 5838) |
| LDHA-903 Target: | 5'-GGAAUGAAUGUUGCUGGUGUCUCtc-3'<br>3'-CACCUUACUUACAACGACCACAGAGAG-5'<br>5'-GTGGAATGAATGTTGCTGGTGTCTCTC-3' | (SEQ ID NO: 1811)<br>(SEQ ID NO: 3825)<br>(SEQ ID NO: 5839) |
| LDHA-904 Target: | 5'-GAAUGAAUGUUGCUGGUGUCUCUct-3'<br>3'-ACCUUACUUACAACGACCACAGAGAGA-5'<br>5'-TGGAATGAATGTTGCTGGTGTCTCTCT-3' | (SEQ ID NO: 1812)<br>(SEQ ID NO: 3826)<br>(SEQ ID NO: 5840) |
| LDHA-905 Target: | 5'-AAUGAAUGUUGCUGGUGUCUCUCtg-3'<br>3'-CCUUACUUACAACGACCACAGAGAGAC-5'<br>5'-GGAATGAATGTTGCTGGTGTCTCTCTG-3' | (SEQ ID NO: 1813)<br>(SEQ ID NO: 3827)<br>(SEQ ID NO: 5841) |
| LDHA-906 Target: | 5'-AUGAAUGUUGCUGGUGUCUCUCUga-3'<br>3'-CUUACUUACAACGACCACAGAGAGACU-5'<br>5'-GAATGAATGTTGCTGGTGTCTCTCTGA-3' | (SEQ ID NO: 1814)<br>(SEQ ID NO: 3828)<br>(SEQ ID NO: 5842) |
| LDHA-908 Target: | 5'-GAAUGUUGCUGGUGUCUCUCUGAag-3'<br>3'-UACUUACAACGACCACAGAGAGACUUC-5'<br>5'-ATGAATGTTGCTGGTGTCTCTCTGAAG-3' | (SEQ ID NO: 1815)<br>(SEQ ID NO: 3829)<br>(SEQ ID NO: 5843) |
| LDHA-909 Target: | 5'-AAUGUUGCUGGUGUCUCUCUGAAga-3'<br>3'-ACUUACAACGACCACAGAGAGACUUCU-5'<br>5'-TGAATGTTGCTGGTGTCTCTCTGAAGA-3' | (SEQ ID NO: 1816)<br>(SEQ ID NO: 3830)<br>(SEQ ID NO: 5844) |
| LDHA-910 Target: | 5'-AUGUUGCUGGUGUCUCUCUGAAGac-3'<br>3'-CUUACAACGACCACAGAGAGACUUCUG-5'<br>5'-GAATGTTGCTGGTGTCTCTCTGAAGAC-3' | (SEQ ID NO: 1817)<br>(SEQ ID NO: 3831)<br>(SEQ ID NO: 5845) |
| LDHA-911 Target: | 5'-UGUUGCUGGUGUCUCUCUGAAGAct-3'<br>3'-UUACAACGACCACAGAGAGACUUCUGA-5'<br>5'-AATGTTGCTGGTGTCTCTCTGAAGACT-3' | (SEQ ID NO: 1818)<br>(SEQ ID NO: 3832)<br>(SEQ ID NO: 5846) |
| LDHA-912 Target: | 5'-GUUGCUGGUGUCUCUCUGAAGACtc-3'<br>3'-UACAACGACCACAGAGAGACUUCUGAG-5'<br>5'-ATGTTGCTGGTGTCTCTCTGAAGACTC-3' | (SEQ ID NO: 1819)<br>(SEQ ID NO: 3833)<br>(SEQ ID NO: 5847) |
| LDHA-913 Target: | 5'-UUGCUGGUGUCUCUCUGAAGACUct-3'<br>3'-ACAACGACCACAGAGAGACUUCUGAGA-5'<br>5'-TGTTGCTGGTGTCTCTCTGAAGACTCT-3' | (SEQ ID NO: 1820)<br>(SEQ ID NO: 3834)<br>(SEQ ID NO: 5848) |
| LDHA-914 Target: | 5'-UGCUGGUGUCUCUCUGAAGACUCtg-3'<br>3'-CAACGACCACAGAGAGACUUCUGAGAC-5'<br>5'-GTTGCTGGTGTCTCTCTGAAGACTCTG-3' | (SEQ ID NO: 1821)<br>(SEQ ID NO: 3835)<br>(SEQ ID NO: 5849) |

TABLE 12-continued

Additional Selected Human Anti-Lactate Dehydrogenase DsiRNA Agents (Asymmetrics)

| | | |
|---|---|---|
| LDHA-915 | 5'-GCUGGUGUCUCUCUGAAGACUCUGgc-3'<br>3'-AACGACCACAGAGAGACUUCUGAGACG-5'<br>Target: 5'-TTGCTGGTGTCTCTCTGAAGACTCTGC-3' | (SEQ ID NO: 1822)<br>(SEQ ID NO: 3836)<br>(SEQ ID NO: 5850) |
| LDHA-916 | 5'-CUGGUGUCUCUCUGAAGACUCUGca-3'<br>3'-ACGACCACAGAGAGACUUCUGAGACGU-5'<br>Target: 5'-TGCTGGTGTCTCTCTGAAGACTCTGCA-3' | (SEQ ID NO: 1823)<br>(SEQ ID NO: 3837)<br>(SEQ ID NO: 5851) |
| LDHA-917 | 5'-UGGUGUCUCUCUGAAGACUCUGCac-3'<br>3'-CGACCACAGAGAGACUUCUGAGACGUG-5'<br>Target: 5'-GCTGGTGTCTCTCTGAAGACTCTGCAC-3' | (SEQ ID NO: 1824)<br>(SEQ ID NO: 3838)<br>(SEQ ID NO: 5852) |
| LDHA-918 | 5'-GGUGUCUCUCUGAAGACUCUGCAcc-3'<br>3'-GACCACAGAGAGACUUCUGAGACGUGG-5'<br>Target: 5'-CTGGTGTCTCTCTGAAGACTCTGCACC-3' | (SEQ ID NO: 1825)<br>(SEQ ID NO: 3839)<br>(SEQ ID NO: 5853) |
| LDHA-919 | 5'-GUGUCUCUCUGAAGACUCUGCACcc-3'<br>3'-ACCACAGAGAGACUUCUGAGACGUGGG-5'<br>Target: 5'-TGGTGTCTCTCTGAAGACTCTGCACCC-3' | (SEQ ID NO: 1826)<br>(SEQ ID NO: 3840)<br>(SEQ ID NO: 5854) |
| LDHA-920 | 5'-UGUCUCUCUGAAGACUCUGCACCca-3'<br>3'-CCACAGAGAGACUUCUGAGACGUGGGU-5'<br>Target: 5'-GGTGTCTCTCTGAAGACTCTGCACCCA-3' | (SEQ ID NO: 1827)<br>(SEQ ID NO: 3841)<br>(SEQ ID NO: 5855) |
| LDHA-921 | 5'-GUCUCUCUGAAGACUCUGCACCCag-3'<br>3'-CACAGAGAGACUUCUGAGACGUGGGUC-5'<br>Target: 5'-GTGTCTCTCTGAAGACTCTGCACCCAG-3' | (SEQ ID NO: 1828)<br>(SEQ ID NO: 3842)<br>(SEQ ID NO: 5856) |
| LDHA-922 | 5'-UCUCUCUGAAGACUCUGCACCCAga-3'<br>3'-ACAGAGAGACUUCUGAGACGUGGGUCU-5'<br>Target: 5'-TGTCTCTCTGAAGACTCTGCACCCAGA-3' | (SEQ ID NO: 1829)<br>(SEQ ID NO: 3843)<br>(SEQ ID NO: 5857) |
| LDHA-923 | 5'-CUCUCUGAAGACUCUGCACCCAGat-3'<br>3'-CAGAGAGACUUCUGAGACGUGGGUCUA-5'<br>Target: 5'-GTCTCTCTGAAGACTCTGCACCCAGAT-3' | (SEQ ID NO: 1830)<br>(SEQ ID NO: 3844)<br>(SEQ ID NO: 5858) |
| LDHA-924 | 5'-UCUCUGAAGACUCUGCACCCAGAtt-3'<br>3'-AGAGAGACUUCUGAGACGUGGGUCUAA-5'<br>Target: 5'-TCTCTCTGAAGACTCTGCACCCAGATT-3' | (SEQ ID NO: 1831)<br>(SEQ ID NO: 3845)<br>(SEQ ID NO: 5859) |
| LDHA-925 | 5'-CUCUGAAGACUCUGCACCCAGAUtt-3'<br>3'-GAGAGACUUCUGAGACGUGGGUCUAAA-5'<br>Target: 5'-CTCTCTGAAGACTCTGCACCCAGATTT-3' | (SEQ ID NO: 1832)<br>(SEQ ID NO: 3846)<br>(SEQ ID NO: 5860) |
| LDHA-926 | 5'-UCUGAAGACUCUGCACCCAGAUUta-3'<br>3'-AGAGACUUCUGAGACGUGGGUCUAAAU-5'<br>Target: 5'-TCTCTGAAGACTCTGCACCCAGATTTA-3' | (SEQ ID NO: 1833)<br>(SEQ ID NO: 3847)<br>(SEQ ID NO: 5861) |
| LDHA-927 | 5'-CUGAAGACUCUGCACCCAGAUUUag-3'<br>3'-GAGACUUCUGAGACGUGGGUCUAAAUC-5'<br>Target: 5'-CTCTGAAGACTCTGCACCCAGATTTAG-3' | (SEQ ID NO: 1834)<br>(SEQ ID NO: 3848)<br>(SEQ ID NO: 5862) |
| LDHA-928 | 5'-UGAAGACUCUGCACCCAGAUUUAgg-3'<br>3'-AGACUUCUGAGACGUGGGUCUAAAUCC-5'<br>Target: 5'-TCTGAAGACTCTGCACCCAGATTTAGG-3' | (SEQ ID NO: 1835)<br>(SEQ ID NO: 3849)<br>(SEQ ID NO: 5863) |
| LDHA-929 | 5'-GAAGACUCUGCACCCAGAUUUAGgg-3'<br>3'-GACUUCUGAGACGUGGGUCUAAAUCCC-5'<br>Target: 5'-CTGAAGACTCTGCACCCAGATTTAGGG-3' | (SEQ ID NO: 1836)<br>(SEQ ID NO: 3850)<br>(SEQ ID NO: 5864) |
| LDHA-930 | 5'-AAGACUCUGCACCCAGAUUUAGGga-3'<br>3'-ACUUCUGAGACGUGGGUCUAAAUCCCU-5'<br>Target: 5'-TGAAGACTCTGCACCCAGATTTAGGGA-3' | (SEQ ID NO: 1837)<br>(SEQ ID NO: 3851)<br>(SEQ ID NO: 5865) |
| LDHA-931 | 5'-AGACUCUGCACCCAGAUUUAGGGac-3'<br>3'-CUUCUGAGACGUGGGUCUAAAUCCCUG-5'<br>Target: 5'-GAAGACTCTGCACCCAGATTTAGGGAC-3' | (SEQ ID NO: 1838)<br>(SEQ ID NO: 3852)<br>(SEQ ID NO: 5866) |
| LDHA-932 | 5'-GACUCUGCACCCAGAUUUAGGGAct-3'<br>3'-UUCUGAGACGUGGGUCUAAAUCCCUGA-5'<br>Target: 5'-AAGACTCTGCACCCAGATTTAGGGACT-3' | (SEQ ID NO: 1839)<br>(SEQ ID NO: 3853)<br>(SEQ ID NO: 5867) |
| LDHA-933 | 5'-ACUCUGCACCCAGAUUUAGGGACtg-3'<br>3'-UCUGAGACGUGGGUCUAAAUCCCUGAC-5'<br>Target: 5'-AGACTCTGCACCCAGATTTAGGGACTG-3' | (SEQ ID NO: 1840)<br>(SEQ ID NO: 3854)<br>(SEQ ID NO: 5868) |

TABLE 12-continued

Additional Selected Human Anti-Lactate Dehydrogenase DsiRNA Agents (Asymmetrics)

| | | |
|---|---|---|
| LDHA-934 Target: | 5'-CUCUGCACCCAGAUUUAGGGACUga-3'<br>3'-CUGAGACGUGGGUCUAAAUCCCUGACU-5'<br>5'-GACTCTGCACCCAGATTTAGGGACTGA-3' | (SEQ ID NO: 1841)<br>(SEQ ID NO: 3855)<br>(SEQ ID NO: 5869) |
| LDHA-935 Target: | 5'-UCUGCACCCAGAUUUAGGGACUGat-3'<br>3'-UGAGACGUGGGUCUAAAUCCCUGACUA-5'<br>5'-ACTCTGCACCCAGATTTAGGGACTGAT-3' | (SEQ ID NO: 1842)<br>(SEQ ID NO: 3856)<br>(SEQ ID NO: 5870) |
| LDHA-936 Target: | 5'-CUGCACCCAGAUUUAGGGACUGAta-3'<br>3'-GAGACGUGGGUCUAAAUCCCUGACUAU-5'<br>5'-CTCTGCACCCAGATTTAGGGACTGATA-3' | (SEQ ID NO: 1843)<br>(SEQ ID NO: 3857)<br>(SEQ ID NO: 5871) |
| LDHA-937 Target: | 5'-UGCACCCAGAUUUAGGGACUGAUaa-3'<br>3'-AGACGUGGGUCUAAAUCCCUGACUAUU-5'<br>5'-TCTGCACCCAGATTTAGGGACTGATAA-3' | (SEQ ID NO: 1844)<br>(SEQ ID NO: 3858)<br>(SEQ ID NO: 5872) |
| LDHA-938 Target: | 5'-GCACCCAGAUUUAGGGACUGAUAaa-3'<br>3'-GACGUGGGUCUAAAUCCCUGACUAUUU-5'<br>5'-CTGCACCCAGATTTAGGGACTGATAAA-3' | (SEQ ID NO: 1845)<br>(SEQ ID NO: 3859)<br>(SEQ ID NO: 5873) |
| LDHA-939 Target: | 5'-CACCCAGAUUUAGGGACUGAUAAag-3'<br>3'-ACGUGGGUCUAAAUCCCUGACUAUUUC-5'<br>5'-TGCACCCAGATTTAGGGACTGATAAAG-3' | (SEQ ID NO: 1846)<br>(SEQ ID NO: 3860)<br>(SEQ ID NO: 5874) |
| LDHA-940 Target: | 5'-ACCCAGAUUUAGGGACUGAUAAAga-3'<br>3'-CGUGGGUCUAAAUCCCUGACUAUUUCU-5'<br>5'-GCACCCAGATTTAGGGACTGATAAAGA-3' | (SEQ ID NO: 1847)<br>(SEQ ID NO: 3861)<br>(SEQ ID NO: 5875) |
| LDHA-941 Target: | 5'-CCCAGAUUUAGGGACUGAUAAAGat-3'<br>3'-GUGGGUCUAAAUCCCUGACUAUUUCUA-5'<br>5'-CACCCAGATTTAGGGACTGATAAAGAT-3' | (SEQ ID NO: 1848)<br>(SEQ ID NO: 3862)<br>(SEQ ID NO: 5876) |
| LDHA-942 Target: | 5'-CCAGAUUUAGGGACUGAUAAAGAta-3'<br>3'-UGGGUCUAAAUCCCUGACUAUUUCUAU-5'<br>5'-ACCCAGATTTAGGGACTGATAAAGATA-3' | (SEQ ID NO: 1849)<br>(SEQ ID NO: 3863)<br>(SEQ ID NO: 5877) |
| LDHA-943 Target: | 5'-CAGAUUUAGGGACUGAUAAAGAUaa-3'<br>3'-GGGUCUAAAUCCCUGACUAUUUCUAUU-5'<br>5'-CCCAGATTTAGGGACTGATAAAGATAA-3' | (SEQ ID NO: 1850)<br>(SEQ ID NO: 3864)<br>(SEQ ID NO: 5878) |
| LDHA-944 Target: | 5'-AGAUUUAGGGACUGAUAAAGAUAag-3'<br>3'-GGUCUAAAUCCCUGACUAUUUCUAUUC-5'<br>5'-CCAGATTTAGGGACTGATAAAGATAAG-3' | (SEQ ID NO: 1851)<br>(SEQ ID NO: 3865)<br>(SEQ ID NO: 5879) |
| LDHA-945 Target: | 5'-GAUUUAGGGACUGAUAAAGAUAAgg-3'<br>3'-GUCUAAAUCCCUGACUAUUUCUAUUCC-5'<br>5'-CAGATTTAGGGACTGATAAAGATAAGG-3' | (SEQ ID NO: 1852)<br>(SEQ ID NO: 3866)<br>(SEQ ID NO: 5880) |
| LDHA-946 Target: | 5'-AUUUAGGGACUGAUAAAGAUAAGga-3'<br>3'-UCUAAAUCCCUGACUAUUUCUAUUCCU-5'<br>5'-AGATTTAGGGACTGATAAAGATAAGGA-3' | (SEQ ID NO: 1853)<br>(SEQ ID NO: 3867)<br>(SEQ ID NO: 5881) |
| LDHA-947 Target: | 5'-UUUAGGGACUGAUAAAGAUAAGGaa-3'<br>3'-CUAAAUCCCUGACUAUUUCUAUUCCUU-5'<br>5'-GATTTAGGGACTGATAAAGATAAGGAA-3' | (SEQ ID NO: 1854)<br>(SEQ ID NO: 3868)<br>(SEQ ID NO: 5882) |
| LDHA-948 Target: | 5'-UUAGGGACUGAUAAAGAUAAGGAac-3'<br>3'-UAAAUCCCUGACUAUUUCUAUUCCUUG-5'<br>5'-ATTTAGGGACTGATAAAGATAAGGAAC-3' | (SEQ ID NO: 1855)<br>(SEQ ID NO: 3869)<br>(SEQ ID NO: 5883) |
| LDHA-949 Target: | 5'-UAGGGACUGAUAAAGAUAAGGAAca-3'<br>3'-AAAUCCCUGACUAUUUCUAUUCCUUGU-5'<br>5'-TTTAGGGACTGATAAAGATAAGGAACA-3' | (SEQ ID NO: 1856)<br>(SEQ ID NO: 3870)<br>(SEQ ID NO: 5884) |
| LDHA-950 Target: | 5'-AGGGACUGAUAAAGAUAAGGAACag-3'<br>3'-AAUCCCUGACUAUUUCUAUUCCUUGUC-5'<br>5'-TTAGGGACTGATAAAGATAAGGAACAG-3' | (SEQ ID NO: 1857)<br>(SEQ ID NO: 3871)<br>(SEQ ID NO: 5885) |
| LDHA-951 Target: | 5'-GGGACUGAUAAAGAUAAGGAACAgt-3'<br>3'-AUCCCUGACUAUUUCUAUUCCUUGUCA-5'<br>5'-TAGGGACTGATAAAGATAAGGAACAGT-3' | (SEQ ID NO: 1858)<br>(SEQ ID NO: 3872)<br>(SEQ ID NO: 5886) |
| LDHA-953 Target: | 5'-GACUGAUAAAGAUAAGGAACAGUgg-3'<br>3'-CCCUGACUAUUUCUAUUCCUUGUCACC-5'<br>5'-GGGACTGATAAAGATAAGGAACAGTGG-3' | (SEQ ID NO: 1859)<br>(SEQ ID NO: 3873)<br>(SEQ ID NO: 5887) |

TABLE 12-continued

Additional Selected Human Anti-Lactate Dehydrogenase DsiRNA Agents (Asymmetrics)

| | | |
|---|---|---|
| LDHA-954 Target: | 5'-ACUGAUAAAGAUAAGGAACAGUGGa-3'<br>3'-CCUGACUAUUUCUAUUCCUUGUCACCU-5'<br>5'-GGACTGATAAAGATAAGGAACAGTGGA-3' | (SEQ ID NO: 1860)<br>(SEQ ID NO: 3874)<br>(SEQ ID NO: 5888) |
| LDHA-955 Target: | 5'-CUGAUAAAGAUAAGGAACAGUGGaa-3'<br>3'-CUGACUAUUUCUAUUCCUUGUCACCUU-5'<br>5'-GACTGATAAAGATAAGGAACAGTGGAA-3' | (SEQ ID NO: 1861)<br>(SEQ ID NO: 3875)<br>(SEQ ID NO: 5889) |
| LDHA-956 Target: | 5'-UGAUAAAGAUAAGGAACAGUGGAaa-3'<br>3'-UGACUAUUUCUAUUCCUUGUCACCUUU-5'<br>5'-ACTGATAAAGATAAGGAACAGTGGAAA-3' | (SEQ ID NO: 1862)<br>(SEQ ID NO: 3876)<br>(SEQ ID NO: 5890) |
| LDHA-957 Target: | 5'-GAUAAAGAUAAGGAACAGUGGAAag-3'<br>3'-GACUAUUUCUAUUCCUUGUCACCUUUC-5'<br>5'-CTGATAAAGATAAGGAACAGTGGAAAG-3' | (SEQ ID NO: 1863)<br>(SEQ ID NO: 3877)<br>(SEQ ID NO: 5891) |
| LDHA-958 Target: | 5'-AUAAAGAUAAGGAACAGUGGAAAga-3'<br>3'-ACUAUUUCUAUUCCUUGUCACCUUUCU-5'<br>5'-TGATAAAGATAAGGAACAGTGGAAAGA-3' | (SEQ ID NO: 1864)<br>(SEQ ID NO: 3878)<br>(SEQ ID NO: 5892) |
| LDHA-959 Target: | 5'-UAAAGAUAAGGAACAGUGGAAAGag-3'<br>3'-CUAUUUCUAUUCCUUGUCACCUUUCUC-5'<br>5'-GATAAAGATAAGGAACAGTGGAAAGAG-3' | (SEQ ID NO: 1865)<br>(SEQ ID NO: 3879)<br>(SEQ ID NO: 5893) |
| LDHA-960 Target: | 5'-AAAGAUAAGGAACAGUGGAAAGAgg-3'<br>3'-UAUUUCUAUUCCUUGUCACCUUUCUCC-5'<br>5'-ATAAAGATAAGGAACAGTGGAAAGAGG-3' | (SEQ ID NO: 1866)<br>(SEQ ID NO: 3880)<br>(SEQ ID NO: 5894) |
| LDHA-961 Target: | 5'-AAGAUAAGGAACAGUGGAAAGAGgt-3'<br>3'-AUUUCUAUUCCUUGUCACCUUUCUCCA-5'<br>5'-TAAAGATAAGGAACAGTGGAAAGAGGT-3' | (SEQ ID NO: 1867)<br>(SEQ ID NO: 3881)<br>(SEQ ID NO: 5895) |
| LDHA-962 Target: | 5'-AGAUAAGGAACAGUGGAAAGAGGtt-3'<br>3'-UUUCUAUUCCUUGUCACCUUUCUCCAA-5'<br>5'-AAAGATAAGGAACAGTGGAAAGAGGTT-3' | (SEQ ID NO: 1868)<br>(SEQ ID NO: 3882)<br>(SEQ ID NO: 5896) |
| LDHA-963 Target: | 5'-GAUAAGGAACAGUGGAAAGAGGUtc-3'<br>3'-UUCUAUUCCUUGUCACCUUUCUCCAAG-5'<br>5'-AAGATAAGGAACAGTGGAAAGAGGTTC-3' | (SEQ ID NO: 1869)<br>(SEQ ID NO: 3883)<br>(SEQ ID NO: 5897) |
| LDHA-964 Target: | 5'-AUAAGGAACAGUGGAAAGAGGUUca-3'<br>3'-UCUAUUCCUUGUCACCUUUCUCCAAGU-5'<br>5'-AGATAAGGAACAGTGGAAAGAGGTTCA-3' | (SEQ ID NO: 1870)<br>(SEQ ID NO: 3884)<br>(SEQ ID NO: 5898) |
| LDHA-965 Target: | 5'-UAAGGAACAGUGGAAAGAGGUUCac-3'<br>3'-CUAUUCCUUGUCACCUUUCUCCAAGUG-5'<br>5'-GATAAGGAACAGTGGAAAGAGGTTCAC-3' | (SEQ ID NO: 1871)<br>(SEQ ID NO: 3885)<br>(SEQ ID NO: 5899) |
| LDHA-966 Target: | 5'-AAGGAACAGUGGAAAGAGGUUCAca-3'<br>3'-UAUUCCUUGUCACCUUUCUCCAAGUGU-5'<br>5'-ATAAGGAACAGTGGAAAGAGGTTCACA-3' | (SEQ ID NO: 1872)<br>(SEQ ID NO: 3886)<br>(SEQ ID NO: 5900) |
| LDHA-967 Target: | 5'-AGGAACAGUGGAAAGAGGUUCACaa-3'<br>3'-AUUCCUUGUCACCUUUCUCCAAGUGUU-5'<br>5'-TAAGGAACAGTGGAAAGAGGTTCACAA-3' | (SEQ ID NO: 1873)<br>(SEQ ID NO: 3887)<br>(SEQ ID NO: 5901) |
| LDHA-968 Target: | 5'-GGAACAGUGGAAAGAGGUUCACAag-3'<br>3'-UUCCUUGUCACCUUUCUCCAAGUGUUC-5'<br>5'-AAGGAACAGTGGAAAGAGGTTCACAAG-3' | (SEQ ID NO: 1874)<br>(SEQ ID NO: 3888)<br>(SEQ ID NO: 5902) |
| LDHA-969 Target: | 5'-GAACAGUGGAAAGAGGUUCACAAgc-3'<br>3'-UCCUUGUCACCUUUCUCCAAGUGUUCG-5'<br>5'-AGGAACAGTGGAAAGAGGTTCACAAGC-3' | (SEQ ID NO: 1875)<br>(SEQ ID NO: 3889)<br>(SEQ ID NO: 5903) |
| LDHA-970 Target: | 5'-AACAGUGGAAAGAGGUUCACAAGca-3'<br>3'-CCUUGUCACCUUUCUCCAAGUGUUCGU-5'<br>5'-GGAACAGTGGAAAGAGGTTCACAAGCA-3' | (SEQ ID NO: 1876)<br>(SEQ ID NO: 3890)<br>(SEQ ID NO: 5904) |
| LDHA-971 Target: | 5'-ACAGUGGAAAGAGGUUCACAAGCag-3'<br>3'-CUUGUCACCUUUCUCCAAGUGUUCGUC-5'<br>5'-GAACAGTGGAAAGAGGTTCACAAGCAG-3' | (SEQ ID NO: 1877)<br>(SEQ ID NO: 3891)<br>(SEQ ID NO: 5905) |
| LDHA-972 Target: | 5'-CAGUGGAAAGAGGUUCACAAGCAgg-3'<br>3'-UUGUCACCUUUCUCCAAGUGUUCGUCC-5'<br>5'-AACAGTGGAAAGAGGTTCACAAGCAGG-3' | (SEQ ID NO: 1878)<br>(SEQ ID NO: 3892)<br>(SEQ ID NO: 5906) |

TABLE 12-continued

Additional Selected Human Anti-Lactate Dehydrogenase DsiRNA
Agents (Asymmetrics)

|  |  |  |
|---|---|---|
| LDHA-973 Target: | 5'-AGUGGAAAGAGGUUCACAAGCAGgt-3'<br>3'-UGUCACCUUUCUCCAAGUGUUCGUCCA-5'<br>5'-ACAGTGGAAAGAGGTTCACAAGCAGGT-3' | (SEQ ID NO: 1879)<br>(SEQ ID NO: 3893)<br>(SEQ ID NO: 5907) |
| LDHA-974 Target: | 5'-GUGGAAAGAGGUUCACAAGCAGGtg-3'<br>3'-GUCACCUUUCUCCAAGUGUUCGUCCAC-5'<br>5'-CAGTGGAAAGAGGTTCACAAGCAGGTG-3' | (SEQ ID NO: 1880)<br>(SEQ ID NO: 3894)<br>(SEQ ID NO: 5908) |
| LDHA-975 Target: | 5'-UGGAAAGAGGUUCACAAGCAGGUgg-3'<br>3'-UCACCUUUCUCCAAGUGUUCGUCCACC-5'<br>5'-AGTGGAAAGAGGTTCACAAGCAGGTGG-3' | (SEQ ID NO: 1881)<br>(SEQ ID NO: 3895)<br>(SEQ ID NO: 5909) |
| LDHA-976 Target: | 5'-GGAAAGAGGUUCACAAGCAGGUGgt-3'<br>3'-CACCUUUCUCCAAGUGUUCGUCCACCA-5'<br>5'-GTGGAAAGAGGTTCACAAGCAGGTGGT-3' | (SEQ ID NO: 1882)<br>(SEQ ID NO: 3896)<br>(SEQ ID NO: 5910) |
| LDHA-977 Target: | 5'-GAAAGAGGUUCACAAGCAGGUGGtt-3'<br>3'-ACCUUUCUCCAAGUGUUCGUCCACCAA-5'<br>5'-TGGAAAGAGGTTCACAAGCAGGTGGTT-3' | (SEQ ID NO: 1883)<br>(SEQ ID NO: 3897)<br>(SEQ ID NO: 5911) |
| LDHA-978 Target: | 5'-AAAGAGGUUCACAAGCAGGUGGUtg-3'<br>3'-CCUUUCUCCAAGUGUUCGUCCACCAAC-5'<br>5'-GGAAAGAGGTTCACAAGCAGGTGGTTG-3' | (SEQ ID NO: 1884)<br>(SEQ ID NO: 3898)<br>(SEQ ID NO: 5912) |
| LDHA-979 Target: | 5'-AAGAGGUUCACAAGCAGGUGGUUga-3'<br>3'-CUUUCUCCAAGUGUUCGUCCACCAACU-5'<br>5'-GAAAGAGGTTCACAAGCAGGTGGTTGA-3' | (SEQ ID NO: 1885)<br>(SEQ ID NO: 3899)<br>(SEQ ID NO: 5913) |
| LDHA-980 Target: | 5'-AGAGGUUCACAAGCAGGUGGUUGag-3'<br>3'-UUUCUCCAAGUGUUCGUCCACCAACUC-5'<br>5'-AAAGAGGTTCACAAGCAGGTGGTTGAG-3' | (SEQ ID NO: 1886)<br>(SEQ ID NO: 3900)<br>(SEQ ID NO: 5914) |
| LDHA-981 Target: | 5'-GAGGUUCACAAGCAGGUGGUUGAga-3'<br>3'-UUCUCCAAGUGUUCGUCCACCAACUCU-5'<br>5'-AAGAGGTTCACAAGCAGGTGGTTGAGA-3' | (SEQ ID NO: 1887)<br>(SEQ ID NO: 3901)<br>(SEQ ID NO: 5915) |
| LDHA-982 Target: | 5'-AGGUUCACAAGCAGGUGGUUGAGag-3'<br>3'-UCUCCAAGUGUUCGUCCACCAACUCUC-5'<br>5'-AGAGGTTCACAAGCAGGTGGTTGAGAG-3' | (SEQ ID NO: 1888)<br>(SEQ ID NO: 3902)<br>(SEQ ID NO: 5916) |
| LDHA-983 Target: | 5'-GGUUCACAAGCAGGUGGUUGAGAgt-3'<br>3'-CUCCAAGUGUUCGUCCACCAACUCUCA-5'<br>5'-GAGGTTCACAAGCAGGTGGTTGAGAGT-3' | (SEQ ID NO: 1889)<br>(SEQ ID NO: 3903)<br>(SEQ ID NO: 5917) |
| LDHA-984 Target: | 5'-GUUCACAAGCAGGUGGUUGAGAGtg-3'<br>3'-UCCAAGUGUUCGUCCACCAACUCUCAC-5'<br>5'-AGGTTCACAAGCAGGTGGTTGAGAGTG-3' | (SEQ ID NO: 1890)<br>(SEQ ID NO: 3904)<br>(SEQ ID NO: 5918) |
| LDHA-985 Target: | 5'-UUCACAAGCAGGUGGUUGAGAGUgc-3'<br>3'-CCAAGUGUUCGUCCACCAACUCUCACG-5'<br>5'-GGTTCACAAGCAGGTGGTTGAGAGTGC-3' | (SEQ ID NO: 1891)<br>(SEQ ID NO: 3905)<br>(SEQ ID NO: 5919) |
| LDHA-986 Target: | 5'-UCACAAGCAGGUGGUUGAGAGUGct-3'<br>3'-CAAGUGUUCGUCCACCAACUCUCACGA-5'<br>5'-GTTCACAAGCAGGTGGTTGAGAGTGCT-3' | (SEQ ID NO: 1892)<br>(SEQ ID NO: 3906)<br>(SEQ ID NO: 5920) |
| LDHA-987 Target: | 5'-CACAAGCAGGUGGUUGAGAGUGCtt-3'<br>3'-AAGUGUUCGUCCACCAACUCUCACGAA-5'<br>5'-TTCACAAGCAGGTGGTTGAGAGTGCTT-3' | (SEQ ID NO: 1893)<br>(SEQ ID NO: 3907)<br>(SEQ ID NO: 5921) |
| LDHA-988 Target: | 5'-ACAAGCAGGUGGUUGAGAGUGCUta-3'<br>3'-AGUGUUCGUCCACCAACUCUCACGAAU-5'<br>5'-TCACAAGCAGGTGGTTGAGAGTGCTTA-3' | (SEQ ID NO: 1894)<br>(SEQ ID NO: 3908)<br>(SEQ ID NO: 5922) |
| LDHA-989 Target: | 5'-CAAGCAGGUGGUUGAGAGUGCUUat-3'<br>3'-GUGUUCGUCCACCAACUCUCACGAAUA-5'<br>5'-CACAAGCAGGTGGTTGAGAGTGCTTAT-3' | (SEQ ID NO: 1895)<br>(SEQ ID NO: 3909)<br>(SEQ ID NO: 5923) |
| LDHA-990 Target: | 5'-AAGCAGGUGGUUGAGAGUGCUUAtg-3'<br>3'-UGUUCGUCCACCAACUCUCACGAAUAC-5'<br>5'-ACAAGCAGGTGGTTGAGAGTGCTTATG-3' | (SEQ ID NO: 1896)<br>(SEQ ID NO: 3910)<br>(SEQ ID NO: 5924) |
| LDHA-991 Target: | 5'-AGCAGGUGGUUGAGAGUGCUUAUga-3'<br>3'-GUUCGUCCACCAACUCUCACGAAUACU-5'<br>5'-CAAGCAGGTGGTTGAGAGTGCTTATGA-3' | (SEQ ID NO: 1897)<br>(SEQ ID NO: 3911)<br>(SEQ ID NO: 5925) |

TABLE 12-continued

Additional Selected Human Anti-Lactate Dehydrogenase DsiRNA Agents (Asymmetrics)

```
                5'-GCAGGUGGUUGAGAGUGCUUAUGag-3'      (SEQ ID NO: 1898)
                3'-UUCGUCCACCAACUCUCACGAAUACUC-5'    (SEQ ID NO: 3912)
LDHA-992 Target: 5'-AAGCAGGTGGTTGAGAGTGCTTATGAG-3'   (SEQ ID NO: 5926)

5'-CAGGUGGUUGAGAGUGCUUAUGAgg-3'      (SEQ ID NO: 1899)
                3'-UCGUCCACCAACUCUCACGAAUACUCC-5'    (SEQ ID NO: 3913)
LDHA-993 Target: 5'-AGCAGGTGGTTGAGAGTGCTTATGAGG-3'   (SEQ ID NO: 5927)

5'-AGGUGGUUGAGAGUGCUUAUGAGgt-3'      (SEQ ID NO: 1900)
                3'-CGUCCACCAACUCUCACGAAUACUCCA-5'    (SEQ ID NO: 3914)
LDHA-994 Target: 5'-GCAGGTGGTTGAGAGTGCTTATGAGGT-3'   (SEQ ID NO: 5928)

5'-GGUGGUUGAGAGUGCUUAUGAGGtg-3'      (SEQ ID NO: 1901)
                3'-GUCCACCAACUCUCACGAAUACUCCAC-5'    (SEQ ID NO: 3915)
LDHA-995 Target: 5'-CAGGTGGTTGAGAGTGCTTATGAGGTG-3'   (SEQ ID NO: 5929)

5'-GUGGUUGAGAGUGCUUAUGAGGUga-3'      (SEQ ID NO: 1902)
                3'-UCCACCAACUCUCACGAAUACUCCACU-5'    (SEQ ID NO: 3916)
LDHA-996 Target: 5'-AGGTGGTTGAGAGTGCTTATGAGGTGA-3'   (SEQ ID NO: 5930)

5'-UGGUUGAGAGUGCUUAUGAGGUGat-3'      (SEQ ID NO: 1903)
                3'-CCACCAACUCUCACGAAUACUCCACUA-5'    (SEQ ID NO: 3917)
LDHA-997 Target: 5'-GGTGGTTGAGAGTGCTTATGAGGTGAT-3'   (SEQ ID NO: 5931)

5'-GGUUGAGAGUGCUUAUGAGGUGAtc-3'      (SEQ ID NO: 1904)
                3'-CACCAACUCUCACGAAUACUCCACUAG-5'    (SEQ ID NO: 3918)
LDHA-998 Target: 5'-GTGGTTGAGAGTGCTTATGAGGTGATC-3'   (SEQ ID NO: 5932)

5'-GUUGAGAGUGCUUAUGAGGUGAUca-3'      (SEQ ID NO: 1905)
                3'-ACCAACUCUCACGAAUACUCCACUAGU-5'    (SEQ ID NO: 3919)
LDHA-999 Target: 5'-TGGTTGAGAGTGCTTATGAGGTGATCA-3'   (SEQ ID NO: 5933)

5'-UUGAGAGUGCUUAUGAGGUGAUCaa-3'     (SEQ ID NO: 1906)
                 3'-CCAACUCUCACGAAUACUCCACUAGUU-5'   (SEQ ID NO: 3920)
LDHA-1000 Target: 5'-GGTTGAGAGTGCTTATGAGGTGATCAA-3'  (SEQ ID NO: 5934)

5'-UGAGAGUGCUUAUGAGGUGAUCAaa-3'     (SEQ ID NO: 1907)
                 3'-CAACUCUCACGAAUACUCCACUAGUUU-5'   (SEQ ID NO: 3921)
LDHA-1001 Target: 5'-GTTGAGAGTGCTTATGAGGTGATCAAA-3'  (SEQ ID NO: 5935)

5'-GAGAGUGCUUAUGAGGUGAUCAAac-3'     (SEQ ID NO: 1908)
                 3'-AACUCUCACGAAUACUCCACUAGUUUG-5'   (SEQ ID NO: 3922)
LDHA-1002 Target: 5'-TTGAGAGTGCTTATGAGGTGATCAAAC-3'  (SEQ ID NO: 5936)

5'-AGAGUGCUUAUGAGGUGAUCAAACt-3'     (SEQ ID NO: 1909)
                 3'-ACUCUCACGAAUACUCCACUAGUUUGA-5'   (SEQ ID NO: 3923)
LDHA-1003 Target: 5'-TGAGAGTGCTTATGAGGTGATCAAACT-3'  (SEQ ID NO: 5937)

5'-GAGUGCUUAUGAGGUGAUCAAACtc-3'     (SEQ ID NO: 1910)
                 3'-CUCUCACGAAUACUCCACUAGUUUGAG-5'   (SEQ ID NO: 3924)
LDHA-1004 Target: 5'-GAGAGTGCTTATGAGGTGATCAAACTC-3'  (SEQ ID NO: 5938)

5'-AGUGCUUAUGAGGUGAUCAAACUca-3'     (SEQ ID NO: 1911)
                 3'-UCUCACGAAUACUCCACUAGUUUGAGU-5'   (SEQ ID NO: 3925)
LDHA-1005 Target: 5'-AGAGTGCTTATGAGGTGATCAAACTCA-3'  (SEQ ID NO: 5939)

5'-GUGCUUAUGAGGUGAUCAAACUCaa-3'     (SEQ ID NO: 1912)
                 3'-CUCACGAAUACUCCACUAGUUUGAGUU-5'   (SEQ ID NO: 3926)
LDHA-1006 Target: 5'-GAGTGCTTATGAGGTGATCAAACTCAA-3'  (SEQ ID NO: 5940)

5'-UGCUUAUGAGGUGAUCAAACUCAaa-3'     (SEQ ID NO: 1913)
                 3'-UCACGAAUACUCCACUAGUUUGAGUUU-5'   (SEQ ID NO: 3927)
LDHA-1007 Target: 5'-AGTGCTTATGAGGTGATCAAACTCAAA-3'  (SEQ ID NO: 5941)

5'-GCUUAUGAGGUGAUCAAACUCAAag-3'     (SEQ ID NO: 1914)
                 3'-CACGAAUACUCCACUAGUUUGAGUUUC-5'   (SEQ ID NO: 3928)
LDHA-1008 Target: 5'-GTGCTTATGAGGTGATCAAACTCAAAG-3'  (SEQ ID NO: 5942)

5'-CUUAUGAGGUGAUCAAACUCAAAgg-3'     (SEQ ID NO: 1915)
                 3'-ACGAAUACUCCACUAGUUUGAGUUUCC-5'   (SEQ ID NO: 3929)
LDHA-1009 Target: 5'-TGCTTATGAGGTGATCAAACTCAAAGG-3'  (SEQ ID NO: 5943)

5'-UUAUGAGGUGAUCAAACUCAAAGgc-3'     (SEQ ID NO: 1916)
                 3'-CGAAUACUCCACUAGUUUGAGUUUCCG-5'   (SEQ ID NO: 3930)
LDHA-1010 Target: 5'-GCTTATGAGGTGATCAAACTCAAAGGC-3'  (SEQ ID NO: 5944)
```

TABLE 12-continued

Additional Selected Human Anti-Lactate Dehydrogenase DsiRNA Agents (Asymmetrics)

| | | |
|---|---|---|
| LDHA-1011 Target: | 5'-UAUGAGGUGAUCAAACUCAAAGGct-3'<br>3'-GAAUACUCCACUAGUUUGAGUUUCCGA-5'<br>5'-CTTATGAGGTGATCAAACTCAAAGGCT-3' | (SEQ ID NO: 1917)<br>(SEQ ID NO: 3931)<br>(SEQ ID NO: 5945) |
| LDHA-1012 Target: | 5'-AUGAGGUGAUCAAACUCAAAGGCta-3'<br>3'-AAUACUCCACUAGUUUGAGUUUCCGAU-5'<br>5'-TTATGAGGTGATCAAACTCAAAGGCTA-3' | (SEQ ID NO: 1918)<br>(SEQ ID NO: 3932)<br>(SEQ ID NO: 5946) |
| LDHA-1013 Target: | 5'-UGAGGUGAUCAAACUCAAAGGCUac-3'<br>3'-AUACUCCACUAGUUUGAGUUUCCGAUG-5'<br>5'-TATGAGGTGATCAAACTCAAAGGCTAC-3' | (SEQ ID NO: 1919)<br>(SEQ ID NO: 3933)<br>(SEQ ID NO: 5947) |
| LDHA-1014 Target: | 5'-GAGGUGAUCAAACUCAAAGGCUAca-3'<br>3'-UACUCCACUAGUUUGAGUUUCCGAUGU-5'<br>5'-ATGAGGTGATCAAACTCAAAGGCTACA-3' | (SEQ ID NO: 1920)<br>(SEQ ID NO: 3934)<br>(SEQ ID NO: 5948) |
| LDHA-1015 Target: | 5'-AGGUGAUCAAACUCAAAGGCUACac-3'<br>3'-ACUCCACUAGUUUGAGUUUCCGAUGUG-5'<br>5'-TGAGGTGATCAAACTCAAAGGCTACAC-3' | (SEQ ID NO: 1921)<br>(SEQ ID NO: 3935)<br>(SEQ ID NO: 5949) |
| LDHA-1016 Target: | 5'-GGUGAUCAAACUCAAAGGCUACAca-3'<br>3'-CUCCACUAGUUUGAGUUUCCGAUGUGU-5'<br>5'-GAGGTGATCAAACTCAAAGGCTACACA-3' | (SEQ ID NO: 1922)<br>(SEQ ID NO: 3936)<br>(SEQ ID NO: 5950) |
| LDHA-1017 Target: | 5'-GUGAUCAAACUCAAAGGCUACACat-3'<br>3'-UCCACUAGUUUGAGUUUCCGAUGUGUA-5'<br>5'-AGGTGATCAAACTCAAAGGCTACACAT-3' | (SEQ ID NO: 1923)<br>(SEQ ID NO: 3937)<br>(SEQ ID NO: 5951) |
| LDHA-1018 Target: | 5'-UGAUCAAACUCAAAGGCUACACAtc-3'<br>3'-CCACUAGUUUGAGUUUCCGAUGUGUAG-5'<br>5'-GGTGATCAAACTCAAAGGCTACACATC-3' | (SEQ ID NO: 1924)<br>(SEQ ID NO: 3938)<br>(SEQ ID NO: 5952) |
| LDHA-1019 Target: | 5'-GAUCAAACUCAAAGGCUACACAUcc-3'<br>3'-CACUAGUUUGAGUUUCCGAUGUGUAGG-5'<br>5'-GTGATCAAACTCAAAGGCTACACATCC-3' | (SEQ ID NO: 1925)<br>(SEQ ID NO: 3939)<br>(SEQ ID NO: 5953) |
| LDHA-1020 Target: | 5'-AUCAAACUCAAAGGCUACACAUCct-3'<br>3'-ACUAGUUUGAGUUUCCGAUGUGUAGGA-5'<br>5'-TGATCAAACTCAAAGGCTACACATCCT-3' | (SEQ ID NO: 1926)<br>(SEQ ID NO: 3940)<br>(SEQ ID NO: 5954) |
| LDHA-1021 Target: | 5'-UCAAACUCAAAGGCUACACAUCCtg-3'<br>3'-CUAGUUUGAGUUUCCGAUGUGUAGGAC-5'<br>5'-GATCAAACTCAAAGGCTACACATCCTG-3' | (SEQ ID NO: 1927)<br>(SEQ ID NO: 3941)<br>(SEQ ID NO: 5955) |
| LDHA-1022 Target: | 5'-CAAACUCAAAGGCUACACAUCCUgg-3'<br>3'-UAGUUUGAGUUUCCGAUGUGUAGGACC-5'<br>5'-ATCAAACTCAAAGGCTACACATCCTGG-3' | (SEQ ID NO: 1928)<br>(SEQ ID NO: 3942)<br>(SEQ ID NO: 5956) |
| LDHA-1023 Target: | 5'-AAACUCAAAGGCUACACAUCCUGgg-3'<br>3'-AGUUUGAGUUUCCGAUGUGUAGGACCC-5'<br>5'-TCAAACTCAAAGGCTACACATCCTGGG-3' | (SEQ ID NO: 1929)<br>(SEQ ID NO: 3943)<br>(SEQ ID NO: 5957) |
| LDHA-1024 Target: | 5'-AACUCAAAGGCUACACAUCCUGGgc-3'<br>3'-GUUUGAGUUUCCGAUGUGUAGGACCCG-5'<br>5'-CAAACTCAAAGGCTACACATCCTGGGC-3' | (SEQ ID NO: 1930)<br>(SEQ ID NO: 3944)<br>(SEQ ID NO: 5958) |
| LDHA-1025 Target: | 5'-ACUCAAAGGCUACACAUCCUGGGct-3'<br>3'-UUUGAGUUUCCGAUGUGUAGGACCCGA-5'<br>5'-AAACTCAAAGGCTACACATCCTGGGCT-3' | (SEQ ID NO: 1931)<br>(SEQ ID NO: 3945)<br>(SEQ ID NO: 5959) |
| LDHA-1026 Target: | 5'-CUCAAAGGCUACACAUCCUGGGCta-3'<br>3'-UUGAGUUUCCGAUGUGUAGGACCCGAU-5'<br>5'-AACTCAAAGGCTACACATCCTGGGCTA-3' | (SEQ ID NO: 1932)<br>(SEQ ID NO: 3946)<br>(SEQ ID NO: 5960) |
| LDHA-1027 Target: | 5'-UCAAAGGCUACACAUCCUGGGCUat-3'<br>3'-UGAGUUUCCGAUGUGUAGGACCCGAUA-5'<br>5'-ACTCAAAGGCTACACATCCTGGGCTAT-3' | (SEQ ID NO: 1933)<br>(SEQ ID NO: 3947)<br>(SEQ ID NO: 5961) |
| LDHA-1028 Target: | 5'-CAAAGGCUACACAUCCUGGGCUAtt-3'<br>3'-GAGUUUCCGAUGUGUAGGACCCGAUAA-5'<br>5'-CTCAAAGGCTACACATCCTGGGCTATT-3' | (SEQ ID NO: 1934)<br>(SEQ ID NO: 3948)<br>(SEQ ID NO: 5962) |
| LDHA-1029 Target: | 5'-AAAGGCUACACAUCCUGGGCUAUtg-3'<br>3'-AGUUUCCGAUGUGUAGGACCCGAUAAC-5'<br>5'-TCAAAGGCTACACATCCTGGGCTATTG-3' | (SEQ ID NO: 1935)<br>(SEQ ID NO: 3949)<br>(SEQ ID NO: 5963) |

TABLE 12-continued

Additional Selected Human Anti-Lactate Dehydrogenase DsiRNA Agents (Asymmetrics)

|  |  |  |
|---|---|---|
| LDHA-1030 | 5'-AAGGCUACACAUCCUGGGCUAUUgg-3'<br>3'-GUUUCCGAUGUGUAGGACCCGAUAACC-5'<br>Target: 5'-CAAAGGCTACACATCCTGGGCTATTGG-3' | (SEQ ID NO: 1936)<br>(SEQ ID NO: 3950)<br>(SEQ ID NO: 5964) |
| LDHA-1031 | 5'-AGGCUACACAUCCUGGGCUAUUGga-3'<br>3'-UUUCCGAUGUGUAGGACCCGAUAACCU-5'<br>Target: 5'-AAAGGCTACACATCCTGGGCTATTGGA-3' | (SEQ ID NO: 1937)<br>(SEQ ID NO: 3951)<br>(SEQ ID NO: 5965) |
| LDHA-1032 | 5'-GGCUACACAUCCUGGGCUAUUGGac-3'<br>3'-UUCCGAUGUGUAGGACCCGAUAACCUG-5'<br>Target: 5'-AAGGCTACACATCCTGGGCTATTGGAC-3' | (SEQ ID NO: 1938)<br>(SEQ ID NO: 3952)<br>(SEQ ID NO: 5966) |
| LDHA-1033 | 5'-GCUACACAUCCUGGGCUAUUGGAct-3'<br>3'-UCCGAUGUGUAGGACCCGAUAACCUGA-5'<br>Target: 5'-AGGCTACACATCCTGGGCTATTGGACT-3' | (SEQ ID NO: 1939)<br>(SEQ ID NO: 3953)<br>(SEQ ID NO: 5967) |
| LDHA-1034 | 5'-CUACACAUCCUGGGCUAUUGGACtc-3'<br>3'-CCGAUGUGUAGGACCCGAUAACCUGAG-5'<br>Target: 5'-GGCTACACATCCTGGGCTATTGGACTC-3' | (SEQ ID NO: 1940)<br>(SEQ ID NO: 3954)<br>(SEQ ID NO: 5968) |
| LDHA-1035 | 5'-UACACAUCCUGGGCUAUUGGACUct-3'<br>3'-CGAUGUGUAGGACCCGAUAACCUGAGA-5'<br>Target: 5'-GCTACACATCCTGGGCTATTGGACTCT-3' | (SEQ ID NO: 1941)<br>(SEQ ID NO: 3955)<br>(SEQ ID NO: 5969) |
| LDHA-1036 | 5'-ACACAUCCUGGGCUAUUGGACUCtc-3'<br>3'-GAUGUGUAGGACCCGAUAACCUGAGAG-5'<br>Target: 5'-CTACACATCCTGGGCTATTGGACTCTC-3' | (SEQ ID NO: 1942)<br>(SEQ ID NO: 3956)<br>(SEQ ID NO: 5970) |
| LDHA-1037 | 5'-CACAUCCUGGGCUAUUGGACUCUct-3'<br>3'-AUGUGUAGGACCCGAUAACCUGAGAGA-5'<br>Target: 5'-TACACATCCTGGGCTATTGGACTCTCT-3' | (SEQ ID NO: 1943)<br>(SEQ ID NO: 3957)<br>(SEQ ID NO: 5971) |
| LDHA-1038 | 5'-ACAUCCUGGGCUAUUGGACUCUCtg-3'<br>3'-UGUGUAGGACCCGAUAACCUGAGAGAC-5'<br>Target: 5'-ACACATCCTGGGCTATTGGACTCTCTG-3' | (SEQ ID NO: 1944)<br>(SEQ ID NO: 3958)<br>(SEQ ID NO: 5972) |
| LDHA-1039 | 5'-CAUCCUGGGCUAUUGGACUCUCUgt-3'<br>3'-GUGUAGGACCCGAUAACCUGAGAGACA-5'<br>Target: 5'-CACATCCTGGGCTATTGGACTCTCTGT-3' | (SEQ ID NO: 1945)<br>(SEQ ID NO: 3959)<br>(SEQ ID NO: 5973) |
| LDHA-1040 | 5'-AUCCUGGGCUAUUGGACUCUCUGta-3'<br>3'-UGUAGGACCCGAUAACCUGAGAGACAU-5'<br>Target: 5'-ACATCCTGGGCTATTGGACTCTCTGTA-3' | (SEQ ID NO: 1946)<br>(SEQ ID NO: 3960)<br>(SEQ ID NO: 5974) |
| LDHA-1041 | 5'-UCCUGGGCUAUUGGACUCUCUGUag-3'<br>3'-GUAGGACCCGAUAACCUGAGAGACAUC-5'<br>Target: 5'-CATCCTGGGCTATTGGACTCTCTGTAG-3' | (SEQ ID NO: 1947)<br>(SEQ ID NO: 3961)<br>(SEQ ID NO: 5975) |
| LDHA-1042 | 5'-CCUGGGCUAUUGGACUCUCUGUAgc-3'<br>3'-UAGGACCCGAUAACCUGAGAGACAUCG-5'<br>Target: 5'-ATCCTGGGCTATTGGACTCTCTGTAGC-3' | (SEQ ID NO: 1948)<br>(SEQ ID NO: 3962)<br>(SEQ ID NO: 5976) |
| LDHA-1043 | 5'-CUGGGCUAUUGGACUCUCUGUAGca-3'<br>3'-AGGACCCGAUAACCUGAGAGACAUCGU-5'<br>Target: 5'-TCCTGGGCTATTGGACTCTCTGTAGCA-3' | (SEQ ID NO: 1949)<br>(SEQ ID NO: 3963)<br>(SEQ ID NO: 5977) |
| LDHA-1044 | 5'-UGGGCUAUUGGACUCUCUGUAGCag-3'<br>3'-GGACCCGAUAACCUGAGAGACAUCGUC-5'<br>Target: 5'-CCTGGGCTATTGGACTCTCTGTAGCAG-3' | (SEQ ID NO: 1950)<br>(SEQ ID NO: 3964)<br>(SEQ ID NO: 5978) |
| LDHA-1045 | 5'-GGGCUAUUGGACUCUCUGUAGCAga-3'<br>3'-GACCCGAUAACCUGAGAGACAUCGUCU-5'<br>Target: 5'-CTGGGCTATTGGACTCTCTGTAGCAGA-3' | (SEQ ID NO: 1951)<br>(SEQ ID NO: 3965)<br>(SEQ ID NO: 5979) |
| LDHA-1046 | 5'-GGCUAUUGGACUCUCUGUAGCAGat-3'<br>3'-ACCCGAUAACCUGAGAGACAUCGUCUA-5'<br>Target: 5'-TGGGCTATTGGACTCTCTGTAGCAGAT-3' | (SEQ ID NO: 1952)<br>(SEQ ID NO: 3966)<br>(SEQ ID NO: 5980) |
| LDHA-1047 | 5'-GCUAUUGGACUCUCUGUAGCAGAtt-3'<br>3'-CCCGAUAACCUGAGAGACAUCGUCUAA-5'<br>Target: 5'-GGGCTATTGGACTCTCTGTAGCAGATT-3' | (SEQ ID NO: 1953)<br>(SEQ ID NO: 3967)<br>(SEQ ID NO: 5981) |
| LDHA-1048 | 5'-CUAUUGGACUCUCUGUAGCAGAUtt-3'<br>3'-CCGAUAACCUGAGAGACAUCGUCUAAA-5'<br>Target: 5'-GGCTATTGGACTCTCTGTAGCAGATTT-3' | (SEQ ID NO: 1954)<br>(SEQ ID NO: 3968)<br>(SEQ ID NO: 5982) |

TABLE 12-continued

Additional Selected Human Anti-Lactate Dehydrogenase DsiRNA Agents (Asymmetrics)

```
                5'-UAUUGGACUCUCUGUAGCAGAUUtg-3'    (SEQ ID NO: 1955)
                3'-CGAUAACCUGAGAGACAUCGUCUAAAC-5'  (SEQ ID NO: 3969)
LDHA-1049 Target: 5'-GCTATTGGACTCTCTGTAGCAGATTTG-3'  (SEQ ID NO: 5983)

5'-AUUGGACUCUCUGUAGCAGAUUUgg-3'    (SEQ ID NO: 1956)
                3'-GAUAACCUGAGAGACAUCGUCUAAACC-5'  (SEQ ID NO: 3970)
LDHA-1050 Target: 5'-CTATTGGACTCTCTGTAGCAGATTTGG-3' (SEQ ID NO: 5984)

5'-UUGGACUCUCUGUAGCAGAUUUGgc-3'    (SEQ ID NO: 1957)
                3'-AUAACCUGAGAGACAUCGUCUAAACCG-5'  (SEQ ID NO: 3971)
LDHA-1051 Target: 5'-TATTGGACTCTCTGTAGCAGATTTGGC-3' (SEQ ID NO: 5985)

5'-UGGACUCUCUGUAGCAGAUUUGGca-3'    (SEQ ID NO: 1958)
                3'-UAACCUGAGAGACAUCGUCUAAACCGU-5'  (SEQ ID NO: 3972)
LDHA-1052 Target: 5'-ATTGGACTCTCTGTAGCAGATTTGGCA-3' (SEQ ID NO: 5986)

5'-GGACUCUCUGUAGCAGAUUUGGCag-3'    (SEQ ID NO: 1959)
                3'-AACCUGAGAGACAUCGUCUAAACCGUC-5'  (SEQ ID NO: 3973)
LDHA-1053 Target: 5'-TTGGACTCTCTGTAGCAGATTTGGCAG-3' (SEQ ID NO: 5987)

5'-GACUCUCUGUAGCAGAUUUGGCAga-3'    (SEQ ID NO: 1960)
                3'-ACCUGAGAGACAUCGUCUAAACCGUCU-5'  (SEQ ID NO: 3974)
LDHA-1054 Target: 5'-TGGACTCTCTGTAGCAGATTTGGCAGA-3' (SEQ ID NO: 5988)

5'-ACUCUCUGUAGCAGAUUUGGCAGag-3'    (SEQ ID NO: 1961)
                3'-CCUGAGAGACAUCGUCUAAACCGUCUC-5'  (SEQ ID NO: 3975)
LDHA-1055 Target: 5'-GGACTCTCTGTAGCAGATTTGGCAGAG-3' (SEQ ID NO: 5989)

5'-CUCUCUGUAGCAGAUUUGGCAGAga-3'    (SEQ ID NO: 1962)
                3'-CUGAGAGACAUCGUCUAAACCGUCUCU-5'  (SEQ ID NO: 3976)
LDHA-1056 Target: 5'-GACTCTCTGTAGCAGATTTGGCAGAGA-3' (SEQ ID NO: 5990)

5'-UCUCUGUAGCAGAUUUGGCAGAGag-3'    (SEQ ID NO: 1963)
                3'-UGAGAGACAUCGUCUAAACCGUCUCUC-5'  (SEQ ID NO: 3977)
LDHA-1057 Target: 5'-ACTCTCTGTAGCAGATTTGGCAGAGAG-3' (SEQ ID NO: 5991)

5'-CUCUGUAGCAGAUUUGGCAGAGAgt-3'    (SEQ ID NO: 1964)
                3'-GAGAGACAUCGUCUAAACCGUCUCUCA-5'  (SEQ ID NO: 3978)
LDHA-1058 Target: 5'-CTCTCTGTAGCAGATTTGGCAGAGAGT-3' (SEQ ID NO: 5992)

5'-UCUGUAGCAGAUUUGGCAGAGAGta-3'    (SEQ ID NO: 1965)
                3'-AGAGACAUCGUCUAAACCGUCUCUCAU-5'  (SEQ ID NO: 3979)
LDHA-1059 Target: 5'-TCTCTGTAGCAGATTTGGCAGAGAGTA-3' (SEQ ID NO: 5993)

5'-CUGUAGCAGAUUUGGCAGAGAGUat-3'    (SEQ ID NO: 1966)
                3'-GAGACAUCGUCUAAACCGUCUCUCAUA-5'  (SEQ ID NO: 3980)
LDHA-1060 Target: 5'-CTCTGTAGCAGATTTGGCAGAGAGTAT-3' (SEQ ID NO: 5994)

5'-UGUAGCAGAUUUGGCAGAGAGUAta-3'    (SEQ ID NO: 1967)
                3'-AGACAUCGUCUAAACCGUCUCUCAUAU-5'  (SEQ ID NO: 3981)
LDHA-1061 Target: 5'-TCTGTAGCAGATTTGGCAGAGAGTATA-3' (SEQ ID NO: 5995)

5'-GUAGCAGAUUUGGCAGAGAGUAUaa-3'    (SEQ ID NO: 1968)
                3'-GACAUCGUCUAAACCGUCUCUCAUAUU-5'  (SEQ ID NO: 3982)
LDHA-1062 Target: 5'-CTGTAGCAGATTTGGCAGAGAGTATAA-3' (SEQ ID NO: 5996)

5'-UAGCAGAUUUGGCAGAGAGUAUAat-3'    (SEQ ID NO: 1969)
                3'-ACAUCGUCUAAACCGUCUCUCAUAUUA-5'  (SEQ ID NO: 3983)
LDHA-1063 Target: 5'-TGTAGCAGATTTGGCAGAGAGTATAAT-3' (SEQ ID NO: 5997)

5'-AGCAGAUUUGGCAGAGAGUAUAAtg-3'    (SEQ ID NO: 1970)
                3'-CAUCGUCUAAACCGUCUCUCAUAUUAC-5'  (SEQ ID NO: 3984)
LDHA-1064 Target: 5'-GTAGCAGATTTGGCAGAGAGTATAATG-3' (SEQ ID NO: 5998)

5'-GCAGAUUUGGCAGAGAGUAUAAUga-3'    (SEQ ID NO: 1971)
                3'-AUCGUCUAAACCGUCUCUCAUAUUACU-5'  (SEQ ID NO: 3985)
LDHA-1065 Target: 5'-TAGCAGATTTGGCAGAGAGTATAATGA-3' (SEQ ID NO: 5999)

5'-CAGAUUUGGCAGAGAGUAUAAUGaa-3'    (SEQ ID NO: 1972)
                3'-UCGUCUAAACCGUCUCUCAUAUUACUU-5'  (SEQ ID NO: 3986)
LDHA-1066 Target: 5'-AGCAGATTTGGCAGAGAGTATAATGAA-3' (SEQ ID NO: 6000)

5'-AGAUUUGGCAGAGAGUAUAAUGAag-3'    (SEQ ID NO: 1973)
                3'-CGUCUAAACCGUCUCUCAUAUUACUUC-5'  (SEQ ID NO: 3987)
LDHA-1067 Target: 5'-GCAGATTTGGCAGAGAGTATAATGAAG-3' (SEQ ID NO: 6001)
```

TABLE 12-continued

Additional Selected Human Anti-Lactate Dehydrogenase DsiRNA Agents (Asymmetrics)

```
                5'-GAUUUGGCAGAGAGUAUAAUGAAga-3'        (SEQ ID NO: 1974)
                3'-GUCUAAACCGUCUCUCAUAUUACUUCU-5'      (SEQ ID NO: 3988)
LDHA-1068 Target: 5'-CAGATTTGGCAGAGAGTATAATGAAGA-3'    (SEQ ID NO: 6002)

5'-AUUUGGCAGAGAGUAUAAUGAAGaa-3'        (SEQ ID NO: 1975)
                3'-UCUAAACCGUCUCUCAUAUUACUUCUU-5'      (SEQ ID NO: 3989)
LDHA-1069 Target: 5'-AGATTTGGCAGAGAGTATAATGAAGAA-3'    (SEQ ID NO: 6003)

5'-UUUGGCAGAGAGUAUAAUGAAGAat-3'        (SEQ ID NO: 1976)
                3'-CUAAACCGUCUCUCAUAUUACUUCUUA-5'      (SEQ ID NO: 3990)
LDHA-1070 Target: 5'-GATTTGGCAGAGAGTATAATGAAGAAT-3'    (SEQ ID NO: 6004)

5'-UUGGCAGAGAGUAUAAUGAAGAAtc-3'        (SEQ ID NO: 1977)
                3'-UAAACCGUCUCUCAUAUUACUUCUUAG-5'      (SEQ ID NO: 3991)
LDHA-1071 Target: 5'-ATTTGGCAGAGAGTATAATGAAGAATC-3'    (SEQ ID NO: 6005)

5'-UGGCAGAGAGUAUAAUGAAGAAUct-3'        (SEQ ID NO: 1978)
                3'-AAACCGUCUCUCAUAUUACUUCUUAGA-5'      (SEQ ID NO: 3992)
LDHA-1072 Target: 5'-TTTGGCAGAGAGTATAATGAAGAATCT-3'    (SEQ ID NO: 6006)

5'-GGCAGAGAGUAUAAUGAAGAAUCtt-3'        (SEQ ID NO: 1979)
                3'-AACCGUCUCUCAUAUUACUUCUUAGAA-5'      (SEQ ID NO: 3993)
LDHA-1073 Target: 5'-TTGGCAGAGAGTATAATGAAGAATCTT-3'    (SEQ ID NO: 6007)

5'-GCAGAGAGUAUAAUGAAGAAUCUta-3'        (SEQ ID NO: 1980)
                3'-ACCGUCUCUCAUAUUACUUCUUAGAAU-5'      (SEQ ID NO: 3994)
LDHA-1074 Target: 5'-TGGCAGAGAGTATAATGAAGAATCTTA-3'    (SEQ ID NO: 6008)

5'-CAGAGAGUAUAAUGAAGAAUCUUag-3'        (SEQ ID NO: 1981)
                3'-CCGUCUCUCAUAUUACUUCUUAGAAUC-5'      (SEQ ID NO: 3995)
LDHA-1075 Target: 5'-GGCAGAGAGTATAATGAAGAATCTTAG-3'    (SEQ ID NO: 6009)

5'-AGAGAGUAUAAUGAAGAAUCUUAgg-3'        (SEQ ID NO: 1982)
                3'-CGUCUCUCAUAUUACUUCUUAGAAUCC-5'      (SEQ ID NO: 3996)
LDHA-1076 Target: 5'-GCAGAGAGTATAATGAAGAATCTTAGG-3'    (SEQ ID NO: 6010)

5'-GAGAGUAUAAUGAAGAAUCUUAGgc-3'        (SEQ ID NO: 1983)
                3'-GUCUCUCAUAUUACUUCUUAGAAUCCG-5'      (SEQ ID NO: 3997)
LDHA-1077 Target: 5'-CAGAGAGTATAATGAAGAATCTTAGGC-3'    (SEQ ID NO: 6011)

5'-AGAGUAUAAUGAAGAAUCUUAGGcg-3'        (SEQ ID NO: 1984)
                3'-UCUCUCAUAUUACUUCUUAGAAUCCGC-5'      (SEQ ID NO: 3998)
LDHA-1078 Target: 5'-AGAGAGTATAATGAAGAATCTTAGGCG-3'    (SEQ ID NO: 6012)

5'-GAGUAUAAUGAAGAAUCUUAGGCgg-3'        (SEQ ID NO: 1985)
                3'-CUCUCAUAUUACUUCUUAGAAUCCGCC-5'      (SEQ ID NO: 3999)
LDHA-1079 Target: 5'-GAGAGTATAATGAAGAATCTTAGGCGG-3'    (SEQ ID NO: 6013)

5'-AGUAUAAUGAAGAAUCUUAGGCGgg-3'        (SEQ ID NO: 1986)
                3'-UCUCAUAUUACUUCUUAGAAUCCGCCC-5'      (SEQ ID NO: 4000)
LDHA-1080 Target: 5'-AGAGTATAATGAAGAATCTTAGGCGGG-3'    (SEQ ID NO: 6014)

5'-GUAUAAUGAAGAAUCUUAGGCGGgt-3'        (SEQ ID NO: 1987)
                3'-CUCAUAUUACUUCUUAGAAUCCGCCCA-5'      (SEQ ID NO: 4001)
LDHA-1081 Target: 5'-GAGTATAATGAAGAATCTTAGGCGGGT-3'    (SEQ ID NO: 6015)

5'-UAUAAUGAAGAAUCUUAGGCGGGtg-3'        (SEQ ID NO: 1988)
                3'-UCAUAUUACUUCUUAGAAUCCGCCCAC-5'      (SEQ ID NO: 4002)
LDHA-1082 Target: 5'-AGTATAATGAAGAATCTTAGGCGGGTG-3'    (SEQ ID NO: 6016)

5'-AUAAUGAAGAAUCUUAGGCGGGUgc-3'        (SEQ ID NO: 1989)
                3'-CAUAUUACUUCUUAGAAUCCGCCCACG-5'      (SEQ ID NO: 4003)
LDHA-1083 Target: 5'-GTATAATGAAGAATCTTAGGCGGGTGC-3'    (SEQ ID NO: 6017)

5'-UAAUGAAGAAUCUUAGGCGGGUGca-3'        (SEQ ID NO: 1990)
                3'-AUAUUACUUCUUAGAAUCCGCCCACGU-5'      (SEQ ID NO: 4004)
LDHA-1084 Target: 5'-TATAATGAAGAATCTTAGGCGGGTGCA-3'    (SEQ ID NO: 6018)

5'-AAUGAAGAAUCUUAGGCGGGUGCac-3'        (SEQ ID NO: 1991)
                3'-UAUUACUUCUUAGAAUCCGCCCACGUG-5'      (SEQ ID NO: 4005)
LDHA-1085 Target: 5'-ATAATGAAGAATCTTAGGCGGGTGCAC-3'    (SEQ ID NO: 6019)

5'-AUGAAGAAUCUUAGGCGGGUGCAcc-3'        (SEQ ID NO: 1992)
                3'-AUUACUUCUUAGAAUCCGCCCACGUGG-5'      (SEQ ID NO: 4006)
LDHA-1086 Target: 5'-TAATGAAGAATCTTAGGCGGGTGCACC-3'    (SEQ ID NO: 6020)
```

TABLE 12-continued

Additional Selected Human Anti-Lactate Dehydrogenase DsiRNA Agents (Asymmetrics)

|               |                                                                                                                                                       |                                                  |
|---------------|-------------------------------------------------------------------------------------------------------------------------------------------------------|--------------------------------------------------|
| LDHA-1087 Target: | 5'-UGAAGAAUCUUAGGCGGGUGCACcc-3'<br>3'-UUACUUCUUAGAAUCCGCCCACGUGGG-5'<br>5'-AATGAAGAATCTTAGGCGGGTGCACCC-3'                                              | (SEQ ID NO: 1993)<br>(SEQ ID NO: 4007)<br>(SEQ ID NO: 6021) |
| LDHA-1088 Target: | 5'-GAAGAAUCUUAGGCGGGUGCACCca-3'<br>3'-UACUUCUUAGAAUCCGCCCACGUGGGU-5'<br>5'-ATGAAGAATCTTAGGCGGGTGCACCCA-3'                                              | (SEQ ID NO: 1994)<br>(SEQ ID NO: 4008)<br>(SEQ ID NO: 6022) |
| LDHA-1089 Target: | 5'-AAGAAUCUUAGGCGGGUGCACCCag-3'<br>3'-ACUUCUUAGAAUCCGCCCACGUGGGUC-5'<br>5'-TGAAGAATCTTAGGCGGGTGCACCCAG-3'                                              | (SEQ ID NO: 1995)<br>(SEQ ID NO: 4009)<br>(SEQ ID NO: 6023) |
| LDHA-1090 Target: | 5'-AGAAUCUUAGGCGGGUGCACCCAgt-3'<br>3'-CUUCUUAGAAUCCGCCCACGUGGGUCA-5'<br>5'-GAAGAATCTTAGGCGGGTGCACCCAGT-3'                                              | (SEQ ID NO: 1996)<br>(SEQ ID NO: 4010)<br>(SEQ ID NO: 6024) |
| LDHA-1091 Target: | 5'-GAAUCUUAGGCGGGUGCACCCAGtt-3'<br>3'-UUCUUAGAAUCCGCCCACGUGGGUCAA-5'<br>5'-AAGAATCTTAGGCGGGTGCACCCAGTT-3'                                              | (SEQ ID NO: 1997)<br>(SEQ ID NO: 4011)<br>(SEQ ID NO: 6025) |
| LDHA-1092 Target: | 5'-AAUCUUAGGCGGGUGCACCCAGUtt-3'<br>3'-UCUUAGAAUCCGCCCACGUGGGUCAAA-5'<br>5'-AGAATCTTAGGCGGGTGCACCCAGTTT-3'                                              | (SEQ ID NO: 1998)<br>(SEQ ID NO: 4012)<br>(SEQ ID NO: 6026) |
| LDHA-1093 Target: | 5'-AUCUUAGGCGGGUGCACCCAGUUtc-3'<br>3'-CUUAGAAUCCGCCCACGUGGGUCAAAG-5'<br>5'-GAATCTTAGGCGGGTGCACCCAGTTTC-3'                                              | (SEQ ID NO: 1999)<br>(SEQ ID NO: 4013)<br>(SEQ ID NO: 6027) |
| LDHA-1094 Target: | 5'-UCUUAGGCGGGUGCACCCAGUUUcc-3'<br>3'-UUAGAAUCCGCCCACGUGGGUCAAAGG-5'<br>5'-AATCTTAGGCGGGTGCACCCAGTTTCC-3'                                              | (SEQ ID NO: 2000)<br>(SEQ ID NO: 4014)<br>(SEQ ID NO: 6028) |
| LDHA-1095 Target: | 5'-CUUAGGCGGGUGCACCCAGUUUCca-3'<br>3'-UAGAAUCCGCCCACGUGGGUCAAAGGU-5'<br>5'-ATCTTAGGCGGGTGCACCCAGTTTCCA-3'                                              | (SEQ ID NO: 2001)<br>(SEQ ID NO: 4015)<br>(SEQ ID NO: 6029) |
| LDHA-1096 Target: | 5'-UUAGGCGGGUGCACCCAGUUUCCac-3'<br>3'-AGAAUCCGCCCACGUGGGUCAAAGGUG-5'<br>5'-TCTTAGGCGGGTGCACCCAGTTTCCAC-3'                                              | (SEQ ID NO: 2002)<br>(SEQ ID NO: 4016)<br>(SEQ ID NO: 6030) |
| LDHA-1097 Target: | 5'-UAGGCGGGUGCACCCAGUUUCCAcc-3'<br>3'-GAAUCCGCCCACGUGGGUCAAAGGUGG-5'<br>5'-CTTAGGCGGGTGCACCCAGTTTCCACC-3'                                              | (SEQ ID NO: 2003)<br>(SEQ ID NO: 4017)<br>(SEQ ID NO: 6031) |
| LDHA-1098 Target: | 5'-AGGCGGGUGCACCCAGUUUCCACca-3'<br>3'-AAUCCGCCCACGUGGGUCAAAGGUGGU-5'<br>5'-TTAGGCGGGTGCACCCAGTTTCCACCA-3'                                              | (SEQ ID NO: 2004)<br>(SEQ ID NO: 4018)<br>(SEQ ID NO: 6032) |
| LDHA-1099 Target: | 5'-GGCGGGUGCACCCAGUUUCCACCat-3'<br>3'-AUCCGCCCACGUGGGUCAAAGGUGGUA-5'<br>5'-TAGGCGGGTGCACCCAGTTTCCACCAT-3'                                              | (SEQ ID NO: 2005)<br>(SEQ ID NO: 4019)<br>(SEQ ID NO: 6033) |
| LDHA-1100 Target: | 5'-GCGGGUGCACCCAGUUUCCACCAtg-3'<br>3'-UCCGCCCACGUGGGUCAAAGGUGGUAC-5'<br>5'-AGGCGGGTGCACCCAGTTTCCACCATG-3'                                              | (SEQ ID NO: 2006)<br>(SEQ ID NO: 4020)<br>(SEQ ID NO: 6034) |
| LDHA-1101 Target: | 5'-CGGGUGCACCCAGUUUCCACCAUga-3'<br>3'-CCGCCCACGUGGGUCAAAGGUGGUACU-5'<br>5'-GGCGGGTGCACCCAGTTTCCACCATGA-3'                                              | (SEQ ID NO: 2007)<br>(SEQ ID NO: 4021)<br>(SEQ ID NO: 6035) |
| LDHA-1102 Target: | 5'-GGGUGCACCCAGUUUCCACCAUGat-3'<br>3'-CGCCCACGUGGGUCAAAGGUGGUACUA-5'<br>5'-GCGGGTGCACCCAGTTTCCACCATGAT-3'                                              | (SEQ ID NO: 2008)<br>(SEQ ID NO: 4022)<br>(SEQ ID NO: 6036) |
| LDHA-1103 Target: | 5'-GGUGCACCCAGUUUCCACCAUGAtt-3'<br>3'-GCCCACGUGGGUCAAAGGUGGUACUAA-5'<br>5'-CGGGTGCACCCAGTTTCCACCATGATT-3'                                              | (SEQ ID NO: 2009)<br>(SEQ ID NO: 4023)<br>(SEQ ID NO: 6037) |
| LDHA-1104 Target: | 5'-GUGCACCCAGUUUCCACCAUGAUta-3'<br>3'-CCCACGUGGGUCAAAGGUGGUACUAAU-5'<br>5'-GGGTGCACCCAGTTTCCACCATGATTA-3'                                              | (SEQ ID NO: 2010)<br>(SEQ ID NO: 4024)<br>(SEQ ID NO: 6038) |
| LDHA-1105 Target: | 5'-UGCACCCAGUUUCCACCAUGAUUaa-3'<br>3'-CCACGUGGGUCAAAGGUGGUACUAAUU-5'<br>5'-GGTGCACCCAGTTTCCACCATGATTAA-3'                                              | (SEQ ID NO: 2011)<br>(SEQ ID NO: 4025)<br>(SEQ ID NO: 6039) |

TABLE 12-continued

Additional Selected Human Anti-Lactate Dehydrogenase DsiRNA Agents (Asymmetrics)

| | | |
|---|---|---|
| LDHA-1106 | 5'-GCACCCAGUUUCCACCAUGAUUAag-3'<br>3'-CACGUGGGUCAAAGGUGGUACUAAUUC-5'<br>Target: 5'-GTGCACCCAGTTTCCACCATGATTAAG-3' | (SEQ ID NO: 2012)<br>(SEQ ID NO: 4026)<br>(SEQ ID NO: 6040) |
| LDHA-1107 | 5'-CACCCAGUUUCCACCAUGAUUAAgg-3'<br>3'-ACGUGGGUCAAAGGUGGUACUAAUUCC-5'<br>Target: 5'-TGCACCCAGTTTCCACCATGATTAAGG-3' | (SEQ ID NO: 2013)<br>(SEQ ID NO: 4027)<br>(SEQ ID NO: 6041) |
| LDHA-1108 | 5'-ACCCAGUUUCCACCAUGAUUAAGgg-3'<br>3'-CGUGGGUCAAAGGUGGUACUAAUUCCC-5'<br>Target: 5'-GCACCCAGTTTCCACCATGATTAAGGG-3' | (SEQ ID NO: 2014)<br>(SEQ ID NO: 4028)<br>(SEQ ID NO: 6042) |
| LDHA-1109 | 5'-CCCAGUUUCCACCAUGAUUAAGGgt-3'<br>3'-GUGGGUCAAAGGUGGUACUAAUUCCCA-5'<br>Target: 5'-CACCCAGTTTCCACCATGATTAAGGGT-3' | (SEQ ID NO: 2015)<br>(SEQ ID NO: 4029)<br>(SEQ ID NO: 6043) |
| LDHA-1110 | 5'-CCAGUUUCCACCAUGAUUAAGGGtc-3'<br>3'-UGGGUCAAAGGUGGUACUAAUUCCCAG-5'<br>Target: 5'-ACCCAGTTTCCACCATGATTAAGGGTC-3' | (SEQ ID NO: 2016)<br>(SEQ ID NO: 4030)<br>(SEQ ID NO: 6044) |
| LDHA-1111 | 5'-CAGUUUCCACCAUGAUUAAGGGUct-3'<br>3'-GGGUCAAAGGUGGUACUAAUUCCCAGA-5'<br>Target: 5'-CCCAGTTTCCACCATGATTAAGGGTCT-3' | (SEQ ID NO: 2017)<br>(SEQ ID NO: 4031)<br>(SEQ ID NO: 6045) |
| LDHA-1112 | 5'-AGUUUCCACCAUGAUUAAGGGUCtt-3'<br>3'-GGUCAAAGGUGGUACUAAUUCCCAGAA-5'<br>Target: 5'-CCAGTTTCCACCATGATTAAGGGTCTT-3' | (SEQ ID NO: 2018)<br>(SEQ ID NO: 4032)<br>(SEQ ID NO: 6046) |
| LDHA-1113 | 5'-GUUUCCACCAUGAUUAAGGGUCUtt-3'<br>3'-GUCAAAGGUGGUACUAAUUCCCAGAAA-5'<br>Target: 5'-CAGTTTCCACCATGATTAAGGGTCTTT-3' | (SEQ ID NO: 2019)<br>(SEQ ID NO: 4033)<br>(SEQ ID NO: 6047) |
| LDHA-1114 | 5'-UUUCCACCAUGAUUAAGGGUCUUta-3'<br>3'-UCAAAGGUGGUACUAAUUCCCAGAAAU-5'<br>Target: 5'-AGTTTCCACCATGATTAAGGGTCTTTA-3' | (SEQ ID NO: 2020)<br>(SEQ ID NO: 4034)<br>(SEQ ID NO: 6048) |
| LDHA-1115 | 5'-UUCCACCAUGAUUAAGGGUCUUUac-3'<br>3'-CAAAGGUGGUACUAAUUCCCAGAAAUG-5'<br>Target: 5'-GTTTCCACCATGATTAAGGGTCTTTAC-3' | (SEQ ID NO: 2021)<br>(SEQ ID NO: 4035)<br>(SEQ ID NO: 6049) |
| LDHA-1116 | 5'-UCCACCAUGAUUAAGGGUCUUUAcg-3'<br>3'-AAAGGUGGUACUAAUUCCCAGAAAUGC-5'<br>Target: 5'-TTTCCACCATGATTAAGGGTCTTTACG-3' | (SEQ ID NO: 2022)<br>(SEQ ID NO: 4036)<br>(SEQ ID NO: 6050) |
| LDHA-1117 | 5'-CCACCAUGAUUAAGGGUCUUUACgg-3'<br>3'-AAGGUGGUACUAAUUCCCAGAAAUGCC-5'<br>Target: 5'-TTCCACCATGATTAAGGGTCTTTACGG-3' | (SEQ ID NO: 2023)<br>(SEQ ID NO: 4037)<br>(SEQ ID NO: 6051) |
| LDHA-1118 | 5'-CACCAUGAUUAAGGGUCUUUACGga-3'<br>3'-AGGUGGUACUAAUUCCCAGAAAUGCCU-5'<br>Target: 5'-TCCACCATGATTAAGGGTCTTTACGGA-3' | (SEQ ID NO: 2024)<br>(SEQ ID NO: 4038)<br>(SEQ ID NO: 6052) |
| LDHA-1119 | 5'-ACCAUGAUUAAGGGUCUUUACGGaa-3'<br>3'-GGUGGUACUAAUUCCCAGAAAUGCCUU-5'<br>Target: 5'-CCACCATGATTAAGGGTCTTTACGGAA-3' | (SEQ ID NO: 2025)<br>(SEQ ID NO: 4039)<br>(SEQ ID NO: 6053) |
| LDHA-1120 | 5'-CCAUGAUUAAGGGUCUUUACGGAat-3'<br>3'-GUGGUACUAAUUCCCAGAAAUGCCUUA-5'<br>Target: 5'-CACCATGATTAAGGGTCTTTACGGAAT-3' | (SEQ ID NO: 2026)<br>(SEQ ID NO: 4040)<br>(SEQ ID NO: 6054) |
| LDHA-1121 | 5'-CAUGAUUAAGGGUCUUUACGGAAta-3'<br>3'-UGGUACUAAUUCCCAGAAAUGCCUUAU-5'<br>Target: 5'-ACCATGATTAAGGGTCTTTACGGAATA-3' | (SEQ ID NO: 2027)<br>(SEQ ID NO: 4041)<br>(SEQ ID NO: 6055) |
| LDHA-1122 | 5'-AUGAUUAAGGGUCUUUACGGAAUaa-3'<br>3'-GGUACUAAUUCCCAGAAAUGCCUUAUU-5'<br>Target: 5'-CCATGATTAAGGGTCTTTACGGAATAA-3' | (SEQ ID NO: 2028)<br>(SEQ ID NO: 4042)<br>(SEQ ID NO: 6056) |
| LDHA-1123 | 5'-UGAUUAAGGGUCUUUACGGAAUAaa-3'<br>3'-GUACUAAUUCCCAGAAAUGCCUUAUUU-5'<br>Target: 5'-CATGATTAAGGGTCTTTACGGAATAAA-3' | (SEQ ID NO: 2029)<br>(SEQ ID NO: 4043)<br>(SEQ ID NO: 6057) |
| LDHA-1124 | 5'-GAUUAAGGGUCUUUACGGAAUAAag-3'<br>3'-UACUAAUUCCCAGAAAUGCCUUAUUUC-5'<br>Target: 5'-ATGATTAAGGGTCTTTACGGAATAAAG-3' | (SEQ ID NO: 2030)<br>(SEQ ID NO: 4044)<br>(SEQ ID NO: 6058) |

TABLE 12-continued

Additional Selected Human Anti-Lactate Dehydrogenase DsiRNA Agents (Asymmetrics)

|  |  |  |
|---|---|---|
| LDHA-1125 Target: | 5'-AUUAAGGGUCUUUACGGAAUAAAGg-3'<br>3'-ACUAAUUCCCAGAAAUGCCUUAUUUCC-5'<br>5'-TGATTAAGGGTCTTTACGGAATAAAGG-3' | (SEQ ID NO: 2031)<br>(SEQ ID NO: 4045)<br>(SEQ ID NO: 6059) |
| LDHA-1126 Target: | 5'-UUAAGGGUCUUUACGGAAUAAAGga-3'<br>3'-CUAAUUCCCAGAAAUGCCUUAUUUCCU-5'<br>5'-GATTAAGGGTCTTTACGGAATAAAGGA-3' | (SEQ ID NO: 2032)<br>(SEQ ID NO: 4046)<br>(SEQ ID NO: 6060) |
| LDHA-1127 Target: | 5'-UAAGGGUCUUUACGGAAUAAAGGat-3'<br>3'-UAAUUCCCAGAAAUGCCUUAUUUCCUA-5'<br>5'-ATTAAGGGTCTTTACGGAATAAAGGAT-3' | (SEQ ID NO: 2033)<br>(SEQ ID NO: 4047)<br>(SEQ ID NO: 6061) |
| LDHA-1128 Target: | 5'-AAGGGUCUUUACGGAAUAAAGGAtg-3'<br>3'-AAUUCCCAGAAAUGCCUUAUUUCCUAC-5'<br>5'-TTAAGGGTCTTTACGGAATAAAGGATG-3' | (SEQ ID NO: 2034)<br>(SEQ ID NO: 4048)<br>(SEQ ID NO: 6062) |
| LDHA-1129 Target: | 5'-AGGGUCUUUACGGAAUAAAGGAUga-3'<br>3'-AUUCCCAGAAAUGCCUUAUUUCCUACU-5'<br>5'-TAAGGGTCTTTACGGAATAAAGGATGA-3' | (SEQ ID NO: 2035)<br>(SEQ ID NO: 4049)<br>(SEQ ID NO: 6063) |
| LDHA-1130 Target: | 5'-GGGUCUUUACGGAAUAAAGGAUGat-3'<br>3'-UUCCCAGAAAUGCCUUAUUUCCUACUA-5'<br>5'-AAGGGTCTTTACGGAATAAAGGATGAT-3' | (SEQ ID NO: 2036)<br>(SEQ ID NO: 4050)<br>(SEQ ID NO: 6064) |
| LDHA-1131 Target: | 5'-GGUCUUUACGGAAUAAAGGAUGAtg-3'<br>3'-UCCCAGAAAUGCCUUAUUUCCUACUAC-5'<br>5'-AGGGTCTTTACGGAATAAAGGATGATG-3' | (SEQ ID NO: 2037)<br>(SEQ ID NO: 4051)<br>(SEQ ID NO: 6065) |
| LDHA-1132 Target: | 5'-GUCUUUACGGAAUAAAGGAUGAUgt-3'<br>3'-CCCAGAAAUGCCUUAUUUCCUACUACA-5'<br>5'-GGGTCTTTACGGAATAAAGGATGATGT-3' | (SEQ ID NO: 2038)<br>(SEQ ID NO: 4052)<br>(SEQ ID NO: 6066) |
| LDHA-1133 Target: | 5'-UCUUUACGGAAUAAAGGAUGAUGtc-3'<br>3'-CCAGAAAUGCCUUAUUUCCUACUACAG-5'<br>5'-GGTCTTTACGGAATAAAGGATGATGTC-3' | (SEQ ID NO: 2039)<br>(SEQ ID NO: 4053)<br>(SEQ ID NO: 6067) |
| LDHA-1134 Target: | 5'-CUUUACGGAAUAAAGGAUGAUGUct-3'<br>3'-CAGAAAUGCCUUAUUUCCUACUACAGA-5'<br>5'-GTCTTTACGGAATAAAGGATGATGTCT-3' | (SEQ ID NO: 2040)<br>(SEQ ID NO: 4054)<br>(SEQ ID NO: 6068) |
| LDHA-1135 Target: | 5'-UUUACGGAAUAAAGGAUGAUGUCtt-3'<br>3'-AGAAAUGCCUUAUUUCCUACUACAGAA-5'<br>5'-TCTTTACGGAATAAAGGATGATGTCTT-3' | (SEQ ID NO: 2041)<br>(SEQ ID NO: 4055)<br>(SEQ ID NO: 6069) |
| LDHA-1136 Target: | 5'-UUACGGAAUAAAGGAUGAUGUCUtc-3'<br>3'-GAAAUGCCUUAUUUCCUACUACAGAAG-5'<br>5'-CTTTACGGAATAAAGGATGATGTCTTC-3' | (SEQ ID NO: 2042)<br>(SEQ ID NO: 4056)<br>(SEQ ID NO: 6070) |
| LDHA-1137 Target: | 5'-UACGGAAUAAAGGAUGAUGUCUUcc-3'<br>3'-AAAUGCCUUAUUUCCUACUACAGAAGG-5'<br>5'-TTTACGGAATAAAGGATGATGTCTTCC-3' | (SEQ ID NO: 2043)<br>(SEQ ID NO: 4057)<br>(SEQ ID NO: 6071) |
| LDHA-1138 Target: | 5'-ACGGAAUAAAGGAUGAUGUCUUCct-3'<br>3'-AAUGCCUUAUUUCCUACUACAGAAGGA-5'<br>5'-TTACGGAATAAAGGATGATGTCTTCCT-3' | (SEQ ID NO: 2044)<br>(SEQ ID NO: 4058)<br>(SEQ ID NO: 6072) |
| LDHA-1139 Target: | 5'-CGGAAUAAAGGAUGAUGUCUUCCtt-3'<br>3'-AUGCCUUAUUUCCUACUACAGAAGGAA-5'<br>5'-TACGGAATAAAGGATGATGTCTTCCTT-3' | (SEQ ID NO: 2045)<br>(SEQ ID NO: 4059)<br>(SEQ ID NO: 6073) |
| LDHA-1140 Target: | 5'-GGAAUAAAGGAUGAUGUCUUCCUta-3'<br>3'-UGCCUUAUUUCCUACUACAGAAGGAAU-5'<br>5'-ACGGAATAAAGGATGATGTCTTCCTTA-3' | (SEQ ID NO: 2046)<br>(SEQ ID NO: 4060)<br>(SEQ ID NO: 6074) |
| LDHA-1141 Target: | 5'-GAAUAAAGGAUGAUGUCUUCCUUag-3'<br>3'-GCCUUAUUUCCUACUACAGAAGGAAUC-5'<br>5'-CGGAATAAAGGATGATGTCTTCCTTAG-3' | (SEQ ID NO: 2047)<br>(SEQ ID NO: 4061)<br>(SEQ ID NO: 6075) |
| LDHA-1142 Target: | 5'-AAUAAAGGAUGAUGUCUUCCUUAgt-3'<br>3'-CCUUAUUUCCUACUACAGAAGGAAUCA-5'<br>5'-GGAATAAAGGATGATGTCTTCCTTAGT-3' | (SEQ ID NO: 2048)<br>(SEQ ID NO: 4062)<br>(SEQ ID NO: 6076) |
| LDHA-1143 Target: | 5'-AUAAAGGAUGAUGUCUUCCUUAGtg-3'<br>3'-CUUAUUUCCUACUACAGAAGGAAUCAC-5'<br>5'-GAATAAAGGATGATGTCTTCCTTAGTG-3' | (SEQ ID NO: 2049)<br>(SEQ ID NO: 4063)<br>(SEQ ID NO: 6077) |

TABLE 12-continued

Additional Selected Human Anti-Lactate Dehydrogenase DsiRNA Agents (Asymmetrics)

|  | | |
|---|---|---|
| LDHA-1144 | 5'-U<u>AA</u>AGGAUGAUGU<u>C</u>UU<u>CC</u>UUAGUGt-3'<br>3'-<u>UUAUUU</u>CCUACUAC<u>AG</u>AAGGAAUC<u>ACA</u>-5'<br>Target: 5'-AATAAAGGATGATGTCTTCCTTAGTGT-3' | (SEQ ID NO: 2050)<br>(SEQ ID NO: 4064)<br>(SEQ ID NO: 6078) |
| LDHA-1145 | 5'-A<u>AA</u>GGAUGAUGUC<u>UU</u>C<u>C</u>UUAGUGtt-3'<br>3'-<u>UAUUU</u>CCUACUACAG<u>A</u>AGGAAUC<u>ACAA</u>-5'<br>Target: 5'-ATAAAGGATGATGTCTTCCTTAGTGTT-3' | (SEQ ID NO: 2051)<br>(SEQ ID NO: 4065)<br>(SEQ ID NO: 6079) |
| LDHA-1146 | 5'-<u>AA</u>GGAUGAUGUCUU<u>CC</u>UUAGUGUtc-3'<br>3'-<u>AUUU</u>CCUACUACAG<u>A</u>AGGAAUCA<u>CAAG</u>-5'<br>Target: 5'-TAAAGGATGATGTCTTCCTTAGTGTTC-3' | (SEQ ID NO: 2052)<br>(SEQ ID NO: 4066)<br>(SEQ ID NO: 6080) |
| LDHA-1147 | 5'-<u>A</u>GGAUGAUGUCUU<u>CC</u>UUAGUGUUcc-3'<br>3'-<u>UUU</u>CCUACUACAGA<u>A</u>GGAAUCAC<u>AAGG</u>-5'<br>Target: 5'-AAAGGATGATGTCTTCCTTAGTGTTCC-3' | (SEQ ID NO: 2053)<br>(SEQ ID NO: 4067)<br>(SEQ ID NO: 6081) |
| LDHA-1148 | 5'-GGAUGAUGUCUUCC<u>U</u>UAGUGUUCct-3'<br>3'-<u>UU</u>CCUACUACAGAA<u>GG</u>AAUCACAA<u>GGA</u>-5'<br>Target: 5'-AAGGATGATGTCTTCCTTAGTGTTCCT-3' | (SEQ ID NO: 2054)<br>(SEQ ID NO: 4068)<br>(SEQ ID NO: 6082) |
| LDHA-1149 | 5'-GAUGAUGUCUUCC<u>UU</u>AGUGUUCCtt-3'<br>3'-<u>U</u>CCUACUACAGAAG<u>GA</u>AUCACAAG<u>GAA</u>-5'<br>Target: 5'-AGGATGATGTCTTCCTTAGTGTTCCTT-3' | (SEQ ID NO: 2055)<br>(SEQ ID NO: 4069)<br>(SEQ ID NO: 6083) |
| LDHA-1150 | 5'-AUGAUGUCUUCC<u>UUA</u>GUGUUCCUtg-3'<br>3'-<u>CC</u>UACUACAGAAGG<u>AA</u>UCACAAGG<u>AAC</u>-5'<br>Target: 5'-GGATGATGTCTTCCTTAGTGTTCCTTG-3' | (SEQ ID NO: 2056)<br>(SEQ ID NO: 4070)<br>(SEQ ID NO: 6084) |
| LDHA-1151 | 5'-UGAUGUCUUCCUU<u>A</u>GUGUUCCUUgc-3'<br>3'-<u>C</u>UACUACAGAAGGA<u>AU</u>CACAAGGA<u>ACG</u>-5'<br>Target: 5'-GATGATGTCTTCCTTAGTGTTCCTTGC-3' | (SEQ ID NO: 2057)<br>(SEQ ID NO: 4071)<br>(SEQ ID NO: 6085) |
| LDHA-1152 | 5'-GA<u>U</u>GUCUUCCUUA<u>G</u>U<u>G</u>UUCCUUGca-3'<br>3'-<u>U</u>ACUACAGAAGGAA<u>UC</u>ACAAGGAA<u>CGU</u>-5'<br>Target: 5'-ATGATGTCTTCCTTAGTGTTCCTTGCA-3' | (SEQ ID NO: 2058)<br>(SEQ ID NO: 4072)<br>(SEQ ID NO: 6086) |
| LDHA-1153 | 5'-A<u>U</u>GUCUUCCUUAG<u>U</u>GUUCCUUGCat-3'<br>3'-<u>A</u>CUACAGAAGGAAUC<u>A</u>CAAGGAAC<u>GUA</u>-5'<br>Target: 5'-TGATGTCTTCCTTAGTGTTCCTTGCAT-3' | (SEQ ID NO: 2059)<br>(SEQ ID NO: 4073)<br>(SEQ ID NO: 6087) |
| LDHA-1154 | 5'-U<u>GU</u>CUUCCUUAGU<u>G</u>U<u>U</u>CCUUGCAtt-3'<br>3'-<u>CUAC</u>AGAAGGAAUC<u>AC</u>AAGGAACG<u>UAA</u>-5'<br>Target: 5'-GATGTCTTCCTTAGTGTTCCTTGCATT-3' | (SEQ ID NO: 2060)<br>(SEQ ID NO: 4074)<br>(SEQ ID NO: 6088) |
| LDHA-1155 | 5'-G<u>U</u>C<u>UU</u>CCUUAGUGU<u>U</u>CC<u>U</u>UGCAUtt-3'<br>3'-<u>UAC</u>AGAAGGAAUCA<u>C</u>AAGGAACGU<u>AAA</u>-5'<br>Target: 5'-ATGTCTTCCTTAGTGTTCCTTGCATTT-3' | (SEQ ID NO: 2061)<br>(SEQ ID NO: 4075)<br>(SEQ ID NO: 6089) |
| LDHA-1156 | 5'-U<u>CUU</u>CCUUAGUGUU<u>CC</u>UUGCAUUtt-3'<br>3'-<u>AC</u>AGAAGGAAUCAC<u>AA</u>GGAACGU<u>AAAA</u>-5'<br>Target: 5'-TGTCTTCCTTAGTGTTCCTTGCATTTT-3' | (SEQ ID NO: 2062)<br>(SEQ ID NO: 4076)<br>(SEQ ID NO: 6090) |
| LDHA-1157 | 5'-C<u>UU</u>CCUUAGUGUUCC<u>U</u>UGCAUUUtg-3'<br>3'-<u>CA</u>GAAGGAAUCACAA<u>GG</u>AACGUAA<u>AAC</u>-5'<br>Target: 5'-GTCTTCCTTAGTGTTCCTTGCATTTTG-3' | (SEQ ID NO: 2063)<br>(SEQ ID NO: 4077)<br>(SEQ ID NO: 6091) |
| LDHA-1158 | 5'-U<u>U</u>CCUUAGUGUUCC<u>U</u>UGCAUUUUgg-3'<br>3'-<u>A</u>GAAGGAAUCACAAGG<u>A</u>ACGUAAA<u>ACC</u>-5'<br>Target: 5'-TCTTCCTTAGTGTTCCTTGCATTTTGG-3' | (SEQ ID NO: 2064)<br>(SEQ ID NO: 4078)<br>(SEQ ID NO: 6092) |
| LDHA-1159 | 5'-U<u>C</u>CUUAGUGUUCC<u>UU</u>GCAUUUUGgg-3'<br>3'-<u>GA</u>AGGAAUCACAAGG<u>AA</u>CGUAAAA<u>CCC</u>-5'<br>Target: 5'-CTTCCTTAGTGTTCCTTGCATTTTGGG-3' | (SEQ ID NO: 2065)<br>(SEQ ID NO: 4079)<br>(SEQ ID NO: 6093) |
| LDHA-1160 | 5'-<u>CC</u>UUAGUGUUCC<u>UUG</u>C<u>A</u>UUUUGGga-3'<br>3'-<u>AAGG</u>AAUCACAAGGA<u>A</u>CGUAAAA<u>CCCU</u>-5'<br>Target: 5'-TTCCTTAGTGTTCCTTGCATTTTGGGA-3' | (SEQ ID NO: 2066)<br>(SEQ ID NO: 4080)<br>(SEQ ID NO: 6094) |
| LDHA-1161 | 5'-C<u>UU</u>AGUGUUCCUUG<u>C</u>AUUUUGGGac-3'<br>3'-<u>A</u>GGAAUCACAAGGAAC<u>G</u>UAAAACC<u>CUG</u>-5'<br>Target: 5'-TCCTTAGTGTTCCTTGCATTTTGGGAC-3' | (SEQ ID NO: 2067)<br>(SEQ ID NO: 4081)<br>(SEQ ID NO: 6095) |
| LDHA-1162 | 5'-UU<u>A</u>GUGUUCCUUGC<u>A</u>UUUUGGGAca-3'<br>3'-<u>GG</u>AAUCACAAGGAAC<u>G</u>UAAAACCC<u>UGU</u>-5'<br>Target: 5'-CCTTAGTGTTCCTTGCATTTTGGGACA-3' | (SEQ ID NO: 2068)<br>(SEQ ID NO: 4082)<br>(SEQ ID NO: 6096) |

TABLE 12-continued

Additional Selected Human Anti-Lactate Dehydrogenase DsiRNA Agents (Asymmetrics)

| | | |
|---|---|---|
| | 5'-UAGUGUUCCUUGCAUUUUGGGACag-3' | (SEQ ID NO: 2069) |
| | 3'-GAAUCACAAGGAACGUAAAACCCUGUC-5' | (SEQ ID NO: 4083) |
| LDHA-1163 Target: | 5'-CTTAGTGTTCCTTGCATTTTGGGACAG-3' | (SEQ ID NO: 6097) |
| | 5'-AGUGUUCCUUGCAUUUUGGGACAga-3' | (SEQ ID NO: 2070) |
| | 3'-AAUCACAAGGAACGUAAAACCCUGUCU-5' | (SEQ ID NO: 4084) |
| LDHA-1164 Target: | 5'-TTAGTGTTCCTTGCATTTTGGGACAGA-3' | (SEQ ID NO: 6098) |
| | 5'-GUGUUCCUUGCAUUUUGGGACAGaa-3' | (SEQ ID NO: 2071) |
| | 3'-AUCACAAGGAACGUAAAACCCUGUCUU-5' | (SEQ ID NO: 4085) |
| LDHA-1165 Target: | 5'-TAGTGTTCCTTGCATTTTGGGACAGAA-3' | (SEQ ID NO: 6099) |
| | 5'-UGUUCCUUGCAUUUUGGGACAGAat-3' | (SEQ ID NO: 2072) |
| | 3'-UCACAAGGAACGUAAAACCCUGUCUUA-5' | (SEQ ID NO: 4086) |
| LDHA-1166 Target: | 5'-AGTGTTCCTTGCATTTTGGGACAGAAT-3' | (SEQ ID NO: 6100) |
| | 5'-GUUCCUUGCAUUUUGGGACAGAAtg-3' | (SEQ ID NO: 2073) |
| | 3'-CACAAGGAACGUAAAACCCUGUCUUAC-5' | (SEQ ID NO: 4087) |
| LDHA-1167 Target: | 5'-GTGTTCCTTGCATTTTGGGACAGAATG-3' | (SEQ ID NO: 6101) |
| | 5'-UUCCUUGCAUUUUGGGACAGAAUgg-3' | (SEQ ID NO: 2074) |
| | 3'-ACAAGGAACGUAAAACCCUGUCUUACC-5' | (SEQ ID NO: 4088) |
| LDHA-1168 Target: | 5'-TGTTCCTTGCATTTTGGGACAGAATGG-3' | (SEQ ID NO: 6102) |
| | 5'-UCCUUGCAUUUUGGGACAGAAUGga-3' | (SEQ ID NO: 2075) |
| | 3'-CAAGGAACGUAAAACCCUGUCUUACCU-5' | (SEQ ID NO: 4089) |
| LDHA-1169 Target: | 5'-GTTCCTTGCATTTTGGGACAGAATGGA-3' | (SEQ ID NO: 6103) |
| | 5'-CCUUGCAUUUUGGGACAGAAUGGaa-3' | (SEQ ID NO: 2076) |
| | 3'-AAGGAACGUAAAACCCUGUCUUACCUU-5' | (SEQ ID NO: 4090) |
| LDHA-1170 Target: | 5'-TTCCTTGCATTTTGGGACAGAATGGAA-3' | (SEQ ID NO: 6104) |
| | 5'-CUUGCAUUUUGGGACAGAAUGGAat-3' | (SEQ ID NO: 2077) |
| | 3'-AGGAACGUAAAACCCUGUCUUACCUUA-5' | (SEQ ID NO: 4091) |
| LDHA-1171 Target: | 5'-TCCTTGCATTTTGGGACAGAATGGAAT-3' | (SEQ ID NO: 6105) |
| | 5'-UUGCAUUUUGGGACAGAAUGGAAtc-3' | (SEQ ID NO: 2078) |
| | 3'-GGAACGUAAAACCCUGUCUUACCUUAG-5' | (SEQ ID NO: 4092) |
| LDHA-1172 Target: | 5'-CCTTGCATTTTGGGACAGAATGGAATC-3' | (SEQ ID NO: 6106) |
| | 5'-UGCAUUUUGGGACAGAAUGGAAUct-3' | (SEQ ID NO: 2079) |
| | 3'-GAACGUAAAACCCUGUCUUACCUUAGA-5' | (SEQ ID NO: 4093) |
| LDHA-1173 Target: | 5'-CTTGCATTTTGGGACAGAATGGAATCT-3' | (SEQ ID NO: 6107) |
| | 5'-GCAUUUUGGGACAGAAUGGAAUCtc-3' | (SEQ ID NO: 2080) |
| | 3'-AACGUAAAACCCUGUCUUACCUUAGAG-5' | (SEQ ID NO: 4094) |
| LDHA-1174 Target: | 5'-TTGCATTTTGGGACAGAATGGAATCTC-3' | (SEQ ID NO: 6108) |
| | 5'-CAUUUUGGGACAGAAUGGAAUCUca-3' | (SEQ ID NO: 2081) |
| | 3'-ACGUAAAACCCUGUCUUACCUUAGAGU-5' | (SEQ ID NO: 4095) |
| LDHA-1175 Target: | 5'-TGCATTTTGGGACAGAATGGAATCTCA-3' | (SEQ ID NO: 6109) |
| | 5'-AUUUUGGGACAGAAUGGAAUCUCag-3' | (SEQ ID NO: 2082) |
| | 3'-CGUAAAACCCUGUCUUACCUUAGAGUC-5' | (SEQ ID NO: 4096) |
| LDHA-1176 Target: | 5'-GCATTTTGGGACAGAATGGAATCTCAG-3' | (SEQ ID NO: 6110) |
| | 5'-UUUUGGGACAGAAUGGAAUCUCAga-3' | (SEQ ID NO: 2083) |
| | 3'-GUAAAACCCUGUCUUACCUUAGAGUCU-5' | (SEQ ID NO: 4097) |
| LDHA-1177 Target: | 5'-CATTTTGGGACAGAATGGAATCTCAGA-3' | (SEQ ID NO: 6111) |
| | 5'-UUUGGGACAGAAUGGAAUCUCAGac-3' | (SEQ ID NO: 2084) |
| | 3'-UAAAACCCUGUCUUACCUUAGAGUCUG-5' | (SEQ ID NO: 4098) |
| LDHA-1178 Target: | 5'-ATTTTGGGACAGAATGGAATCTCAGAC-3' | (SEQ ID NO: 6112) |
| | 5'-UUGGGACAGAAUGGAAUCUCAGAcc-3' | (SEQ ID NO: 2085) |
| | 3'-AAAACCCUGUCUUACCUUAGAGUCUGG-5' | (SEQ ID NO: 4099) |
| LDHA-1179 Target: | 5'-TTTTGGGACAGAATGGAATCTCAGACC-3' | (SEQ ID NO: 6113) |
| | 5'-UGGGACAGAAUGGAAUCUCAGACct-3' | (SEQ ID NO: 2086) |
| | 3'-AAACCCUGUCUUACCUUAGAGUCUGGA-5' | (SEQ ID NO: 4100) |
| LDHA-1180 Target: | 5'-TTTGGGACAGAATGGAATCTCAGACCT-3' | (SEQ ID NO: 6114) |
| | 5'-GGGACAGAAUGGAAUCUCAGACCtt-3' | (SEQ ID NO: 2087) |
| | 3'-AACCCUGUCUUACCUUAGAGUCUGGAA-5' | (SEQ ID NO: 4101) |
| LDHA-1181 Target: | 5'-TTGGGACAGAATGGAATCTCAGACCTT-3' | (SEQ ID NO: 6115) |

TABLE 12-continued

Additional Selected Human Anti-Lactate Dehydrogenase DsiRNA Agents (Asymmetrics)

|  |  |  |
|---|---|---|
| LDHA-1182 | 5'-GGACAGAAUGGAAUCUCAGACCUtg-3'<br>3'-ACCCUGUCUUACCUUAGAGUCUGGAAC-5'<br>Target: 5'-TGGGACAGAATGGAATCTCAGACCTTG-3' | (SEQ ID NO: 2088)<br>(SEQ ID NO: 4102)<br>(SEQ ID NO: 6116) |
| LDHA-1183 | 5'-GACAGAAUGGAAUCUCAGACCUUgt-3'<br>3'-CCCUGUCUUACCUUAGAGUCUGGAACA-5'<br>Target: 5'-GGGACAGAATGGAATCTCAGACCTTGT-3' | (SEQ ID NO: 2089)<br>(SEQ ID NO: 4103)<br>(SEQ ID NO: 6117) |
| LDHA-1184 | 5'-ACAGAAUGGAAUCUCAGACCUUGtg-3'<br>3'-CCUGUCUUACCUUAGAGUCUGGAACAC-5'<br>Target: 5'-GGACAGAATGGAATCTCAGACCTTGTG-3' | (SEQ ID NO: 2090)<br>(SEQ ID NO: 4104)<br>(SEQ ID NO: 6118) |
| LDHA-1185 | 5'-CAGAAUGGAAUCUCAGACCUUGUga-3'<br>3'-CUGUCUUACCUUAGAGUCUGGAACACU-5'<br>Target: 5'-GACAGAATGGAATCTCAGACCTTGTGA-3' | (SEQ ID NO: 2091)<br>(SEQ ID NO: 4105)<br>(SEQ ID NO: 6119) |
| LDHA-1186 | 5'-AGAAUGGAAUCUCAGACCUUGUGaa-3'<br>3'-UGUCUUACCUUAGAGUCUGGAACACUU-5'<br>Target: 5'-ACAGAATGGAATCTCAGACCTTGTGAA-3' | (SEQ ID NO: 2092)<br>(SEQ ID NO: 4106)<br>(SEQ ID NO: 6120) |
| LDHA-1187 | 5'-GAAUGGAAUCUCAGACCUUGUGAag-3'<br>3'-GUCUUACCUUAGAGUCUGGAACACUUC-5'<br>Target: 5'-CAGAATGGAATCTCAGACCTTGTGAAG-3' | (SEQ ID NO: 2093)<br>(SEQ ID NO: 4107)<br>(SEQ ID NO: 6121) |
| LDHA-1188 | 5'-AAUGGAAUCUCAGACCUUGUGAAgg-3'<br>3'-UCUUACCUUAGAGUCUGGAACACUUCC-5'<br>Target: 5'-AGAATGGAATCTCAGACCTTGTGAAGG-3' | (SEQ ID NO: 2094)<br>(SEQ ID NO: 4108)<br>(SEQ ID NO: 6122) |
| LDHA-1189 | 5'-AUGGAAUCUCAGACCUUGUGAAGgt-3'<br>3'-CUUACCUUAGAGUCUGGAACACUUCCA-5'<br>Target: 5'-GAATGGAATCTCAGACCTTGTGAAGGT-3' | (SEQ ID NO: 2095)<br>(SEQ ID NO: 4109)<br>(SEQ ID NO: 6123) |
| LDHA-1190 | 5'-UGGAAUCUCAGACCUUGUGAAGGtg-3'<br>3'-UUACCUUAGAGUCUGGAACACUUCCAC-5'<br>Target: 5'-AATGGAATCTCAGACCTTGTGAAGGTG-3' | (SEQ ID NO: 2096)<br>(SEQ ID NO: 4110)<br>(SEQ ID NO: 6124) |
| LDHA-1191 | 5'-GGAAUCUCAGACCUUGUGAAGGUga-3'<br>3'-UACCUUAGAGUCUGGAACACUUCCACU-5'<br>Target: 5'-ATGGAATCTCAGACCTTGTGAAGGTGA-3' | (SEQ ID NO: 2097)<br>(SEQ ID NO: 4111)<br>(SEQ ID NO: 6125) |
| LDHA-1192 | 5'-GAAUCUCAGACCUUGUGAAGGUGac-3'<br>3'-ACCUUAGAGUCUGGAACACUUCCACUG-5'<br>Target: 5'-TGGAATCTCAGACCTTGTGAAGGTGAC-3' | (SEQ ID NO: 2098)<br>(SEQ ID NO: 4112)<br>(SEQ ID NO: 6126) |
| LDHA-1193 | 5'-AAUCUCAGACCUUGUGAAGGUGAct-3'<br>3'-CCUUAGAGUCUGGAACACUUCCACUGA-5'<br>Target: 5'-GGAATCTCAGACCTTGTGAAGGTGACT-3' | (SEQ ID NO: 2099)<br>(SEQ ID NO: 4113)<br>(SEQ ID NO: 6127) |
| LDHA-1194 | 5'-AUCUCAGACCUUGUGAAGGUGACtc-3'<br>3'-CUUAGAGUCUGGAACACUUCCACUGAG-5'<br>Target: 5'-GAATCTCAGACCTTGTGAAGGTGACTC-3' | (SEQ ID NO: 2100)<br>(SEQ ID NO: 4114)<br>(SEQ ID NO: 6128) |
| LDHA-1195 | 5'-UCUCAGACCUUGUGAAGGUGACUct-3'<br>3'-UUAGAGUCUGGAACACUUCCACUGAGA-5'<br>Target: 5'-AATCTCAGACCTTGTGAAGGTGACTCT-3' | (SEQ ID NO: 2101)<br>(SEQ ID NO: 4115)<br>(SEQ ID NO: 6129) |
| LDHA-1196 | 5'-CUCAGACCUUGUGAAGGUGACUCtg-3'<br>3'-UAGAGUCUGGAACACUUCCACUGAGAC-5'<br>Target: 5'-ATCTCAGACCTTGTGAAGGTGACTCTG-3' | (SEQ ID NO: 2102)<br>(SEQ ID NO: 4116)<br>(SEQ ID NO: 6130) |
| LDHA-1197 | 5'-UCAGACCUUGUGAAGGUGACUCUga-3'<br>3'-AGAGUCUGGAACACUUCCACUGAGACU-5'<br>Target: 5'-TCTCAGACCTTGTGAAGGTGACTCTGA-3' | (SEQ ID NO: 2103)<br>(SEQ ID NO: 4117)<br>(SEQ ID NO: 6131) |
| LDHA-1198 | 5'-CAGACCUUGUGAAGGUGACUCUGac-3'<br>3'-GAGUCUGGAACACUUCCACUGAGACUG-5'<br>Target: 5'-CTCAGACCTTGTGAAGGTGACTCTGAC-3' | (SEQ ID NO: 2104)<br>(SEQ ID NO: 4118)<br>(SEQ ID NO: 6132) |
| LDHA-1199 | 5'-AGACCUUGUGAAGGUGACUCUGAct-3'<br>3'-AGUCUGGAACACUUCCACUGAGACUGA-5'<br>Target: 5'-TCAGACCTTGTGAAGGTGACTCTGACT-3' | (SEQ ID NO: 2105)<br>(SEQ ID NO: 4119)<br>(SEQ ID NO: 6133) |
| LDHA-1200 | 5'-GACCUUGUGAAGGUGACUCUGACtt-3'<br>3'-GUCUGGAACACUUCCACUGAGACUGAA-5'<br>Target: 5'-CAGACCTTGTGAAGGTGACTCTGACTT-3' | (SEQ ID NO: 2106)<br>(SEQ ID NO: 4120)<br>(SEQ ID NO: 6134) |

TABLE 12-continued

Additional Selected Human Anti-Lactate Dehydrogenase DsiRNA Agents (Asymmetrics)

|  |  |  |
|---|---|---|
| LDHA-1201 | 5'-ACCUUGUGAAGGUGACUCUGACUtc-3'<br>3'-UCUGGAACACUUCCACUGAGACUGAAG-5'<br>Target: 5'-AGACCTTGTGAAGGTGACTCTGACTTC-3' | (SEQ ID NO: 2107)<br>(SEQ ID NO: 4121)<br>(SEQ ID NO: 6135) |
| LDHA-1202 | 5'-CCUUGUGAAGGUGACUCUGACUUct-3'<br>3'-CUGGAACACUUCCACUGAGACUGAAGA-5'<br>Target: 5'-GACCTTGTGAAGGTGACTCTGACTTCT-3' | (SEQ ID NO: 2108)<br>(SEQ ID NO: 4122)<br>(SEQ ID NO: 6136) |
| LDHA-1203 | 5'-CUUGUGAAGGUGACUCUGACUUCtg-3'<br>3'-UGGAACACUUCCACUGAGACUGAAGAC-5'<br>Target: 5'-ACCTTGTGAAGGTGACTCTGACTTCTG-3' | (SEQ ID NO: 2109)<br>(SEQ ID NO: 4123)<br>(SEQ ID NO: 6137) |
| LDHA-1204 | 5'-UUGUGAAGGUGACUCUGACUUCUga-3'<br>3'-GGAACACUUCCACUGAGACUGAAGACU-5'<br>Target: 5'-CCTTGTGAAGGTGACTCTGACTTCTGA-3' | (SEQ ID NO: 2110)<br>(SEQ ID NO: 4124)<br>(SEQ ID NO: 6138) |
| LDHA-1205 | 5'-UGUGAAGGUGACUCUGACUUCUGag-3'<br>3'-GAACACUUCCACUGAGACUGAAGACUC-5'<br>Target: 5'-CTTGTGAAGGTGACTCTGACTTCTGAG-3' | (SEQ ID NO: 2111)<br>(SEQ ID NO: 4125)<br>(SEQ ID NO: 6139) |
| LDHA-1206 | 5'-GUGAAGGUGACUCUGACUUCUGAgg-3'<br>3'-AACACUUCCACUGAGACUGAAGACUCC-5'<br>Target: 5'-TTGTGAAGGTGACTCTGACTTCTGAGG-3' | (SEQ ID NO: 2112)<br>(SEQ ID NO: 4126)<br>(SEQ ID NO: 6140) |
| LDHA-1207 | 5'-UGAAGGUGACUCUGACUUCUGAGga-3'<br>3'-ACACUUCCACUGAGACUGAAGACUCCU-5'<br>Target: 5'-TGTGAAGGTGACTCTGACTTCTGAGGA-3' | (SEQ ID NO: 2113)<br>(SEQ ID NO: 4127)<br>(SEQ ID NO: 6141) |
| LDHA-1208 | 5'-GAAGGUGACUCUGACUUCUGAGGaa-3'<br>3'-CACUUCCACUGAGACUGAAGACUCCUU-5'<br>Target: 5'-GTGAAGGTGACTCTGACTTCTGAGGAA-3' | (SEQ ID NO: 2114)<br>(SEQ ID NO: 4128)<br>(SEQ ID NO: 6142) |
| LDHA-1209 | 5'-AAGGUGACUCUGACUUCUGAGGAag-3'<br>3'-ACUUCCACUGAGACUGAAGACUCCUUC-5'<br>Target: 5'-TGAAGGTGACTCTGACTTCTGAGGAAG-3' | (SEQ ID NO: 2115)<br>(SEQ ID NO: 4129)<br>(SEQ ID NO: 6143) |
| LDHA-1210 | 5'-AGGUGACUCUGACUUCUGAGGAAga-3'<br>3'-CUUCCACUGAGACUGAAGACUCCUUCU-5'<br>Target: 5'-GAAGGTGACTCTGACTTCTGAGGAAGA-3' | (SEQ ID NO: 2116)<br>(SEQ ID NO: 4130)<br>(SEQ ID NO: 6144) |
| LDHA-1211 | 5'-GGUGACUCUGACUUCUGAGGAAGag-3'<br>3'-UUCCACUGAGACUGAAGACUCCUUCUC-5'<br>Target: 5'-AAGGTGACTCTGACTTCTGAGGAAGAG-3' | (SEQ ID NO: 2117)<br>(SEQ ID NO: 4131)<br>(SEQ ID NO: 6145) |
| LDHA-1212 | 5'-GUGACUCUGACUUCUGAGGAAGAgg-3'<br>3'-UCCACUGAGACUGAAGACUCCUUCUCC-5'<br>Target: 5'-AGGTGACTCTGACTTCTGAGGAAGAGG-3' | (SEQ ID NO: 2118)<br>(SEQ ID NO: 4132)<br>(SEQ ID NO: 6146) |
| LDHA-1213 | 5'-UGACUCUGACUUCUGAGGAAGAGgc-3'<br>3'-CCACUGAGACUGAAGACUCCUUCUCCG-5'<br>Target: 5'-GGTGACTCTGACTTCTGAGGAAGAGGC-3' | (SEQ ID NO: 2119)<br>(SEQ ID NO: 4133)<br>(SEQ ID NO: 6147) |
| LDHA-1214 | 5'-GACUCUGACUUCUGAGGAAGAGGcc-3'<br>3'-CACUGAGACUGAAGACUCCUUCUCCGG-5'<br>Target: 5'-GTGACTCTGACTTCTGAGGAAGAGGCC-3' | (SEQ ID NO: 2120)<br>(SEQ ID NO: 4134)<br>(SEQ ID NO: 6148) |
| LDHA-1215 | 5'-ACUCUGACUUCUGAGGAAGAGGCcc-3'<br>3'-ACUGAGACUGAAGACUCCUUCUCCGGG-5'<br>Target: 5'-TGACTCTGACTTCTGAGGAAGAGGCCC-3' | (SEQ ID NO: 2121)<br>(SEQ ID NO: 4135)<br>(SEQ ID NO: 6149) |
| LDHA-1216 | 5'-CUCUGACUUCUGAGGAAGAGGCCcg-3'<br>3'-CUGAGACUGAAGACUCCUUCUCCGGGC-5'<br>Target: 5'-GACTCTGACTTCTGAGGAAGAGGCCCG-3' | (SEQ ID NO: 2122)<br>(SEQ ID NO: 4136)<br>(SEQ ID NO: 6150) |
| LDHA-1217 | 5'-UCUGACUUCUGAGGAAGAGGCCCgt-3'<br>3'-UGAGACUGAAGACUCCUUCUCCGGGCA-5'<br>Target: 5'-ACTCTGACTTCTGAGGAAGAGGCCCGT-3' | (SEQ ID NO: 2123)<br>(SEQ ID NO: 4137)<br>(SEQ ID NO: 6151) |
| LDHA-1218 | 5'-CUGACUUCUGAGGAAGAGGCCCGtt-3'<br>3'-GAGACUGAAGACUCCUUCUCCGGGCAA-5'<br>Target: 5'-CTCTGACTTCTGAGGAAGAGGCCCGTT-3' | (SEQ ID NO: 2124)<br>(SEQ ID NO: 4138)<br>(SEQ ID NO: 6152) |
| LDHA-1219 | 5'-UGACUUCUGAGGAAGAGGCCCGUtt-3'<br>3'-AGACUGAAGACUCCUUCUCCGGGCAAA-5'<br>Target: 5'-TCTGACTTCTGAGGAAGAGGCCCGTTT-3' | (SEQ ID NO: 2125)<br>(SEQ ID NO: 4139)<br>(SEQ ID NO: 6153) |

TABLE 12-continued

Additional Selected Human Anti-Lactate Dehydrogenase DsiRNA Agents (Asymmetrics)

| | | |
|---|---|---|
| LDHA-1220 | 5'-GACUUCUGAGGAAGAGGCCCGUUtg-3'<br>3'-GACUGAAGACUCCUUCUCCGGGCAAAC-5'<br>Target: 5'-CTGACTTCTGAGGAAGAGGCCCGTTTG-3' | (SEQ ID NO: 2126)<br>(SEQ ID NO: 4140)<br>(SEQ ID NO: 6154) |
| LDHA-1221 | 5'-ACUUCUGAGGAAGAGGCCCGUUUga-3'<br>3'-ACUGAAGACUCCUUCUCCGGGCAAACU-5'<br>Target: 5'-TGACTTCTGAGGAAGAGGCCCGTTTGA-3' | (SEQ ID NO: 2127)<br>(SEQ ID NO: 4141)<br>(SEQ ID NO: 6155) |
| LDHA-1222 | 5'-CUUCUGAGGAAGAGGCCCGUUUGaa-3'<br>3'-CUGAAGACUCCUUCUCCGGGCAAACUU-5'<br>Target: 5'-GACTTCTGAGGAAGAGGCCCGTTTGAA-3' | (SEQ ID NO: 2128)<br>(SEQ ID NO: 4142)<br>(SEQ ID NO: 6156) |
| LDHA-1223 | 5'-UUCUGAGGAAGAGGCCCGUUUGAag-3'<br>3'-UGAAGACUCCUUCUCCGGGCAAACUUC-5'<br>Target: 5'-ACTTCTGAGGAAGAGGCCCGTTTGAAG-3' | (SEQ ID NO: 2129)<br>(SEQ ID NO: 4143)<br>(SEQ ID NO: 6157) |
| LDHA-1224 | 5'-UCUGAGGAAGAGGCCCGUUUGAAga-3'<br>3'-GAAGACUCCUUCUCCGGGCAAACUUCU-5'<br>Target: 5'-CTTCTGAGGAAGAGGCCCGTTTGAAGA-3' | (SEQ ID NO: 2130)<br>(SEQ ID NO: 4144)<br>(SEQ ID NO: 6158) |
| LDHA-1225 | 5'-CUGAGGAAGAGGCCCGUUUGAAGaa-3'<br>3'-AAGACUCCUUCUCCGGGCAAACUUCUU-5'<br>Target: 5'-TTCTGAGGAAGAGGCCCGTTTGAAGAA-3' | (SEQ ID NO: 2131)<br>(SEQ ID NO: 4145)<br>(SEQ ID NO: 6159) |
| LDHA-1226 | 5'-UGAGGAAGAGGCCCGUUUGAAGAag-3'<br>3'-AGACUCCUUCUCCGGGCAAACUUCUUC-5'<br>Target: 5'-TCTGAGGAAGAGGCCCGTTTGAAGAAG-3' | (SEQ ID NO: 2132)<br>(SEQ ID NO: 4146)<br>(SEQ ID NO: 6160) |
| LDHA-1227 | 5'-GAGGAAGAGGCCCGUUUGAAGAAga-3'<br>3'-GACUCCUUCUCCGGGCAAACUUCUUCU-5'<br>Target: 5'-CTGAGGAAGAGGCCCGTTTGAAGAAGA-3' | (SEQ ID NO: 2133)<br>(SEQ ID NO: 4147)<br>(SEQ ID NO: 6161) |
| LDHA-1228 | 5'-AGGAAGAGGCCCGUUUGAAGAAGag-3'<br>3'-ACUCCUUCUCCGGGCAAACUUCUUCUC-5'<br>Target: 5'-TGAGGAAGAGGCCCGTTTGAAGAAGAG-3' | (SEQ ID NO: 2134)<br>(SEQ ID NO: 4148)<br>(SEQ ID NO: 6162) |
| LDHA-1229 | 5'-GGAAGAGGCCCGUUUGAAGAAGAgt-3'<br>3'-CUCCUUCUCCGGGCAAACUUCUUCUCA-5'<br>Target: 5'-GAGGAAGAGGCCCGTTTGAAGAAGAGT-3' | (SEQ ID NO: 2135)<br>(SEQ ID NO: 4149)<br>(SEQ ID NO: 6163) |
| LDHA-1230 | 5'-GAAGAGGCCCGUUUGAAGAAGAGtg-3'<br>3'-UCCUUCUCCGGGCAAACUUCUUCUCAC-5'<br>Target: 5'-AGGAAGAGGCCCGTTTGAAGAAGAGTG-3' | (SEQ ID NO: 2136)<br>(SEQ ID NO: 4150)<br>(SEQ ID NO: 6164) |
| LDHA-1231 | 5'-AAGAGGCCCGUUUGAAGAAGAGUgc-3'<br>3'-CCUUCUCCGGGCAAACUUCUUCUCACG-5'<br>Target: 5'-GGAAGAGGCCCGTTTGAAGAAGAGTGC-3' | (SEQ ID NO: 2137)<br>(SEQ ID NO: 4151)<br>(SEQ ID NO: 6165) |
| LDHA-1232 | 5'-AGAGGCCCGUUUGAAGAAGAGUGca-3'<br>3'-CUUCUCCGGGCAAACUUCUUCUCACGU-5'<br>Target: 5'-GAAGAGGCCCGTTTGAAGAAGAGTGCA-3' | (SEQ ID NO: 2138)<br>(SEQ ID NO: 4152)<br>(SEQ ID NO: 6166) |
| LDHA-1233 | 5'-GAGGCCCGUUUGAAGAAGAGUGCag-3'<br>3'-UUCUCCGGGCAAACUUCUUCUCACGUC-5'<br>Target: 5'-AAGAGGCCCGTTTGAAGAAGAGTGCAG-3' | (SEQ ID NO: 2139)<br>(SEQ ID NO: 4153)<br>(SEQ ID NO: 6167) |
| LDHA-1234 | 5'-AGGCCCGUUUGAAGAAGAGUGCAga-3'<br>3'-UCUCCGGGCAAACUUCUUCUCACGUCU-5'<br>Target: 5'-AGAGGCCCGTTTGAAGAAGAGTGCAGA-3' | (SEQ ID NO: 2140)<br>(SEQ ID NO: 4154)<br>(SEQ ID NO: 6168) |
| LDHA-1235 | 5'-GGCCCGUUUGAAGAAGAGUGCAGat-3'<br>3'-CUCCGGGCAAACUUCUUCUCACGUCUA-5'<br>Target: 5'-GAGGCCCGTTTGAAGAAGAGTGCAGAT-3' | (SEQ ID NO: 2141)<br>(SEQ ID NO: 4155)<br>(SEQ ID NO: 6169) |
| LDHA-1236 | 5'-GCCCGUUUGAAGAAGAGUGCAGAta-3'<br>3'-UCCGGGCAAACUUCUUCUCACGUCUAU-5'<br>Target: 5'-AGGCCCGTTTGAAGAAGAGTGCAGATA-3' | (SEQ ID NO: 2142)<br>(SEQ ID NO: 4156)<br>(SEQ ID NO: 6170) |
| LDHA-1237 | 5'-CCCGUUUGAAGAAGAGUGCAGAUac-3'<br>3'-CCGGGCAAACUUCUUCUCACGUCUAUG-5'<br>Target: 5'-GGCCCGTTTGAAGAAGAGTGCAGATAC-3' | (SEQ ID NO: 2143)<br>(SEQ ID NO: 4157)<br>(SEQ ID NO: 6171) |
| LDHA-1238 | 5'-CCGUUUGAAGAAGAGUGCAGAUAca-3'<br>3'-CGGGCAAACUUCUUCUCACGUCUAUGU-5'<br>Target: 5'-GCCCGTTTGAAGAAGAGTGCAGATACA-3' | (SEQ ID NO: 2144)<br>(SEQ ID NO: 4158)<br>(SEQ ID NO: 6172) |

TABLE 12-continued

Additional Selected Human Anti-Lactate Dehydrogenase DsiRNA Agents (Asymmetrics)

|  |  |  |
| --- | --- | --- |
| LDHA-1239 Target: | 5'-CGUUUGAAGAAGAGUGCAGAUACAc-3'<br>3'-GGGCAAACUUCUUCUCACGUCUAUGUG-5'<br>5'-CCCGTTTGAAGAAGAGTGCAGATACAC-3' | (SEQ ID NO: 2145)<br>(SEQ ID NO: 4159)<br>(SEQ ID NO: 6173) |
| LDHA-1240 Target: | 5'-GUUUGAAGAAGAGUGCAGAUACAct-3'<br>3'-GGCAAACUUCUUCUCACGUCUAUGUGA-5'<br>5'-CCGTTTGAAGAAGAGTGCAGATACACT-3' | (SEQ ID NO: 2146)<br>(SEQ ID NO: 4160)<br>(SEQ ID NO: 6174) |
| LDHA-1241 Target: | 5'-UUUGAAGAAGAGUGCAGAUACACtt-3'<br>3'-GCAAACUUCUUCUCACGUCUAUGUGAA-5'<br>5'-CGTTTGAAGAAGAGTGCAGATACACTT-3' | (SEQ ID NO: 2147)<br>(SEQ ID NO: 4161)<br>(SEQ ID NO: 6175) |
| LDHA-1242 Target: | 5'-UUGAAGAAGAGUGCAGAUACACUtt-3'<br>3'-CAAACUUCUUCUCACGUCUAUGUGAAA-5'<br>5'-GTTTGAAGAAGAGTGCAGATACACTTT-3' | (SEQ ID NO: 2148)<br>(SEQ ID NO: 4162)<br>(SEQ ID NO: 6176) |
| LDHA-1243 Target: | 5'-UGAAGAAGAGUGCAGAUACACUUtg-3'<br>3'-AAACUUCUUCUCACGUCUAUGUGAAAC-5'<br>5'-TTTGAAGAAGAGTGCAGATACACTTTG-3' | (SEQ ID NO: 2149)<br>(SEQ ID NO: 4163)<br>(SEQ ID NO: 6177) |
| LDHA-1244 Target: | 5'-GAAGAAGAGUGCAGAUACACUUUgg-3'<br>3'-AACUUCUUCUCACGUCUAUGUGAAACC-5'<br>5'-TTGAAGAAGAGTGCAGATACACTTTGG-3' | (SEQ ID NO: 2150)<br>(SEQ ID NO: 4164)<br>(SEQ ID NO: 6178) |
| LDHA-1245 Target: | 5'-AAGAAGAGUGCAGAUACACUUUGgg-3'<br>3'-ACUUCUUCUCACGUCUAUGUGAAACCC-5'<br>5'-TGAAGAAGAGTGCAGATACACTTTGGG-3' | (SEQ ID NO: 2151)<br>(SEQ ID NO: 4165)<br>(SEQ ID NO: 6179) |
| LDHA-1246 Target: | 5'-AGAAGAGUGCAGAUACACUUUGGgg-3'<br>3'-CUUCUUCUCACGUCUAUGUGAAACCCC-5'<br>5'-GAAGAAGAGTGCAGATACACTTTGGGG-3' | (SEQ ID NO: 2152)<br>(SEQ ID NO: 4166)<br>(SEQ ID NO: 6180) |
| LDHA-1247 Target: | 5'-GAAGAGUGCAGAUACACUUUGGGgg-3'<br>3'-UUCUUCUCACGUCUAUGUGAAACCCCC-5'<br>5'-AAGAAGAGTGCAGATACACTTTGGGGG-3' | (SEQ ID NO: 2153)<br>(SEQ ID NO: 4167)<br>(SEQ ID NO: 6181) |
| LDHA-1248 Target: | 5'-AAGAGUGCAGAUACACUUUGGGGga-3'<br>3'-UCUUCUCACGUCUAUGUGAAACCCCCU-5'<br>5'-AGAAGAGTGCAGATACACTTTGGGGGA-3' | (SEQ ID NO: 2154)<br>(SEQ ID NO: 4168)<br>(SEQ ID NO: 6182) |
| LDHA-1249 Target: | 5'-AGAGUGCAGAUACACUUUGGGGGat-3'<br>3'-CUUCUCACGUCUAUGUGAAACCCCCUA-5'<br>5'-GAAGAGTGCAGATACACTTTGGGGGAT-3' | (SEQ ID NO: 2155)<br>(SEQ ID NO: 4169)<br>(SEQ ID NO: 6183) |
| LDHA-1250 Target: | 5'-GAGUGCAGAUACACUUUGGGGGAtc-3'<br>3'-UUCUCACGUCUAUGUGAAACCCCCUAG-5'<br>5'-AAGAGTGCAGATACACTTTGGGGGATC-3' | (SEQ ID NO: 2156)<br>(SEQ ID NO: 4170)<br>(SEQ ID NO: 6184) |
| LDHA-1251 Target: | 5'-AGUGCAGAUACACUUUGGGGGAUcc-3'<br>3'-UCUCACGUCUAUGUGAAACCCCCUAGG-5'<br>5'-AGAGTGCAGATACACTTTGGGGGATCC-3' | (SEQ ID NO: 2157)<br>(SEQ ID NO: 4171)<br>(SEQ ID NO: 6185) |
| LDHA-1252 Target: | 5'-GUGCAGAUACACUUUGGGGGAUCca-3'<br>3'-CUCACGUCUAUGUGAAACCCCCUAGGU-5'<br>5'-GAGTGCAGATACACTTTGGGGGATCCA-3' | (SEQ ID NO: 2158)<br>(SEQ ID NO: 4172)<br>(SEQ ID NO: 6186) |
| LDHA-1253 Target: | 5'-UGCAGAUACACUUUGGGGGAUCCaa-3'<br>3'-UCACGUCUAUGUGAAACCCCCUAGGUU-5'<br>5'-AGTGCAGATACACTTTGGGGGATCCAA-3' | (SEQ ID NO: 2159)<br>(SEQ ID NO: 4173)<br>(SEQ ID NO: 6187) |
| LDHA-1254 Target: | 5'-GCAGAUACACUUUGGGGGAUCCAaa-3'<br>3'-CACGUCUAUGUGAAACCCCCUAGGUUU-5'<br>5'-GTGCAGATACACTTTGGGGGATCCAAA-3' | (SEQ ID NO: 2160)<br>(SEQ ID NO: 4174)<br>(SEQ ID NO: 6188) |
| LDHA-1255 Target: | 5'-CAGAUACACUUUGGGGGAUCCAAaa-3'<br>3'-ACGUCUAUGUGAAACCCCCUAGGUUUU-5'<br>5'-TGCAGATACACTTTGGGGGATCCAAAA-3' | (SEQ ID NO: 2161)<br>(SEQ ID NO: 4175)<br>(SEQ ID NO: 6189) |
| LDHA-1256 Target: | 5'-AGAUACACUUUGGGGGAUCCAAAag-3'<br>3'-CGUCUAUGUGAAACCCCCUAGGUUUUC-5'<br>5'-GCAGATACACTTTGGGGGATCCAAAAG-3' | (SEQ ID NO: 2162)<br>(SEQ ID NO: 4176)<br>(SEQ ID NO: 6190) |
| LDHA-1257 Target: | 5'-GAUACACUUUGGGGGAUCCAAAAgg-3'<br>3'-GUCUAUGUGAAACCCCCUAGGUUUUCC-5'<br>5'-CAGATACACTTTGGGGGATCCAAAAGG-3' | (SEQ ID NO: 2163)<br>(SEQ ID NO: 4177)<br>(SEQ ID NO: 6191) |

TABLE 12-continued

Additional Selected Human Anti-Lactate Dehydrogenase DsiRNA Agents (Asymmetrics)

|  |  |  |
| --- | --- | --- |
| LDHA-1258 | 5'-AUACACUUUGGGGGAUCCAAAAGGa-3'<br>3'-UCUAUGUGAAACCCCCUAGGUUUUCCU-5'<br>Target: 5'-AGATACACTTTGGGGGATCCAAAAGGA-3' | (SEQ ID NO: 2164)<br>(SEQ ID NO: 4178)<br>(SEQ ID NO: 6192) |
| LDHA-1259 | 5'-UACACUUUGGGGGAUCCAAAAGGag-3'<br>3'-CUAUGUGAAACCCCCUAGGUUUUCCUC-5'<br>Target: 5'-GATACACTTTGGGGGATCCAAAAGGAG-3' | (SEQ ID NO: 2165)<br>(SEQ ID NO: 4179)<br>(SEQ ID NO: 6193) |
| LDHA-1260 | 5'-ACACUUUGGGGGAUCCAAAAGGAgc-3'<br>3'-UAUGUGAAACCCCCUAGGUUUUCCUCG-5'<br>Target: 5'-ATACACTTTGGGGGATCCAAAAGGAGC-3' | (SEQ ID NO: 2166)<br>(SEQ ID NO: 4180)<br>(SEQ ID NO: 6194) |
| LDHA-1261 | 5'-CACUUUGGGGGAUCCAAAAGGAGct-3'<br>3'-AUGUGAAACCCCCUAGGUUUUCCUCGA-5'<br>Target: 5'-TACACTTTGGGGGATCCAAAAGGAGCT-3' | (SEQ ID NO: 2167)<br>(SEQ ID NO: 4181)<br>(SEQ ID NO: 6195) |
| LDHA-1262 | 5'-ACUUUGGGGGAUCCAAAAGGAGCtg-3'<br>3'-UGUGAAACCCCCUAGGUUUUCCUCGAC-5'<br>Target: 5'-ACACTTTGGGGGATCCAAAAGGAGCTG-3' | (SEQ ID NO: 2168)<br>(SEQ ID NO: 4182)<br>(SEQ ID NO: 6196) |
| LDHA-1263 | 5'-CUUUGGGGGAUCCAAAAGGAGCUgc-3'<br>3'-GUGAAACCCCCUAGGUUUUCCUCGACG-5'<br>Target: 5'-CACTTTGGGGGATCCAAAAGGAGCTGC-3' | (SEQ ID NO: 2169)<br>(SEQ ID NO: 4183)<br>(SEQ ID NO: 6197) |
| LDHA-1264 | 5'-UUUGGGGGAUCCAAAAGGAGCUGca-3'<br>3'-UGAAACCCCCUAGGUUUUCCUCGACGU-5'<br>Target: 5'-ACTTTGGGGGATCCAAAAGGAGCTGCA-3' | (SEQ ID NO: 2170)<br>(SEQ ID NO: 4184)<br>(SEQ ID NO: 6198) |
| LDHA-1265 | 5'-UUGGGGGAUCCAAAAGGAGCUGCaa-3'<br>3'-GAAACCCCCUAGGUUUUCCUCGACGUU-5'<br>Target: 5'-CTTTGGGGGATCCAAAAGGAGCTGCAA-3' | (SEQ ID NO: 2171)<br>(SEQ ID NO: 4185)<br>(SEQ ID NO: 6199) |
| LDHA-1266 | 5'-UGGGGGAUCCAAAAGGAGCUGCAat-3'<br>3'-AAACCCCCUAGGUUUUCCUCGACGUUA-5'<br>Target: 5'-TTTGGGGGATCCAAAAGGAGCTGCAAT-3' | (SEQ ID NO: 2172)<br>(SEQ ID NO: 4186)<br>(SEQ ID NO: 6200) |
| LDHA-1267 | 5'-GGGGGAUCCAAAAGGAGCUGCAAtt-3'<br>3'-AACCCCCUAGGUUUUCCUCGACGUUAA-5'<br>Target: 5'-TTGGGGGATCCAAAAGGAGCTGCAATT-3' | (SEQ ID NO: 2173)<br>(SEQ ID NO: 4187)<br>(SEQ ID NO: 6201) |
| LDHA-1268 | 5'-GGGGAUCCAAAAGGAGCUGCAAUtt-3'<br>3'-ACCCCCUAGGUUUUCCUCGACGUUAAA-5'<br>Target: 5'-TGGGGGATCCAAAAGGAGCTGCAATTT-3' | (SEQ ID NO: 2174)<br>(SEQ ID NO: 4188)<br>(SEQ ID NO: 6202) |
| LDHA-1269 | 5'-GGGAUCCAAAAGGAGCUGCAAUUtt-3'<br>3'-CCCCCUAGGUUUUCCUCGACGUUAAAA-5'<br>Target: 5'-GGGGGATCCAAAAGGAGCTGCAATTTT-3' | (SEQ ID NO: 2175)<br>(SEQ ID NO: 4189)<br>(SEQ ID NO: 6203) |
| LDHA-1270 | 5'-GGAUCCAAAAGGAGCUGCAAUUUta-3'<br>3'-CCCCUAGGUUUUCCUCGACGUUAAAAU-5'<br>Target: 5'-GGGGATCCAAAAGGAGCTGCAATTTTA-3' | (SEQ ID NO: 2176)<br>(SEQ ID NO: 4190)<br>(SEQ ID NO: 6204) |
| LDHA-1271 | 5'-GAUCCAAAAGGAGCUGCAAUUUUaa-3'<br>3'-CCCUAGGUUUUCCUCGACGUUAAAAUU-5'<br>Target: 5'-GGGATCCAAAAGGAGCTGCAATTTTAA-3' | (SEQ ID NO: 2177)<br>(SEQ ID NO: 4191)<br>(SEQ ID NO: 6205) |
| LDHA-1272 | 5'-AUCCAAAAGGAGCUGCAAUUUUAaa-3'<br>3'-CCUAGGUUUUCCUCGACGUUAAAAUUU-5'<br>Target: 5'-GGATCCAAAAGGAGCTGCAATTTTAAA-3' | (SEQ ID NO: 2178)<br>(SEQ ID NO: 4192)<br>(SEQ ID NO: 6206) |
| LDHA-1273 | 5'-UCCAAAAGGAGCUGCAAUUUUAAag-3'<br>3'-CUAGGUUUUCCUCGACGUUAAAAUUUC-5'<br>Target: 5'-GATCCAAAAGGAGCTGCAATTTTAAAG-3' | (SEQ ID NO: 2179)<br>(SEQ ID NO: 4193)<br>(SEQ ID NO: 6207) |
| LDHA-1274 | 5'-CCAAAAGGAGCUGCAAUUUUAAAgt-3'<br>3'-UAGGUUUUCCUCGACGUUAAAAUUUCA-5'<br>Target: 5'-ATCCAAAAGGAGCTGCAATTTTAAAGT-3' | (SEQ ID NO: 2180)<br>(SEQ ID NO: 4194)<br>(SEQ ID NO: 6208) |
| LDHA-1275 | 5'-CAAAAGGAGCUGCAAUUUUAAAGtc-3'<br>3'-AGGUUUUCCUCGACGUUAAAAUUUCAG-5'<br>Target: 5'-TCCAAAAGGAGCTGCAATTTTAAAGTC-3' | (SEQ ID NO: 2181)<br>(SEQ ID NO: 4195)<br>(SEQ ID NO: 6209) |
| LDHA-1276 | 5'-AAAAGGAGCUGCAAUUUUAAAGUct-3'<br>3'-GGUUUUCCUCGACGUUAAAAUUUCAGA-5'<br>Target: 5'-CCAAAAGGAGCTGCAATTTTAAAGTCT-3' | (SEQ ID NO: 2182)<br>(SEQ ID NO: 4196)<br>(SEQ ID NO: 6210) |

TABLE 12-continued

Additional Selected Human Anti-Lactate Dehydrogenase DsiRNA Agents (Asymmetrics)

|  |  |  |
|---|---|---|
| LDHA-1277 | 5'-AAAGGAGCUGCAAUUUUAAAGUCtt-3'<br>3'-GUUUUCCUCGACGUUAAAAUUUCAGAA-5'<br>Target: 5'-CAAAAGGAGCTGCAATTTTAAAGTCTT-3' | (SEQ ID NO: 2183)<br>(SEQ ID NO: 4197)<br>(SEQ ID NO: 6211) |
| LDHA-1278 | 5'-AAGGAGCUGCAAUUUUAAAGUCUtc-3'<br>3'-UUUUCCUCGACGUUAAAAUUUCAGAAG-5'<br>Target: 5'-AAAAGGAGCTGCAATTTTAAAGTCTTC-3' | (SEQ ID NO: 2184)<br>(SEQ ID NO: 4198)<br>(SEQ ID NO: 6212) |
| LDHA-1279 | 5'-AGGAGCUGCAAUUUUAAAGUCUUct-3'<br>3'-UUUCCUCGACGUUAAAAUUUCAGAAGA-5'<br>Target: 5'-AAAGGAGCTGCAATTTTAAAGTCTTCT-3' | (SEQ ID NO: 2185)<br>(SEQ ID NO: 4199)<br>(SEQ ID NO: 6213) |
| LDHA-1280 | 5'-GGAGCUGCAAUUUUAAAGUCUUCtg-3'<br>3'-UUCCUCGACGUUAAAAUUUCAGAAGAC-5'<br>Target: 5'-AAGGAGCTGCAATTTTAAAGTCTTCTG-3' | (SEQ ID NO: 2186)<br>(SEQ ID NO: 4200)<br>(SEQ ID NO: 6214) |
| LDHA-1281 | 5'-GAGCUGCAAUUUUAAAGUCUUCUga-3'<br>3'-UCCUCGACGUUAAAAUUUCAGAAGACU-5'<br>Target: 5'-AGGAGCTGCAATTTTAAAGTCTTCTGA-3' | (SEQ ID NO: 2187)<br>(SEQ ID NO: 4201)<br>(SEQ ID NO: 6215) |
| LDHA-1282 | 5'-AGCUGCAAUUUUAAAGUCUUCUGat-3'<br>3'-CCUCGACGUUAAAAUUUCAGAAGACUA-5'<br>Target: 5'-GGAGCTGCAATTTTAAAGTCTTCTGAT-3' | (SEQ ID NO: 2188)<br>(SEQ ID NO: 4202)<br>(SEQ ID NO: 6216) |
| LDHA-1283 | 5'-GCUGCAAUUUUAAAGUCUUCUGAtg-3'<br>3'-CUCGACGUUAAAAUUUCAGAAGACUAC-5'<br>Target: 5'-GAGCTGCAATTTTAAAGTCTTCTGATG-3' | (SEQ ID NO: 2189)<br>(SEQ ID NO: 4203)<br>(SEQ ID NO: 6217) |
| LDHA-1284 | 5'-CUGCAAUUUUAAAGUCUUCUGAUgt-3'<br>3'-UCGACGUUAAAAUUUCAGAAGACUACA-5'<br>Target: 5'-AGCTGCAATTTTAAAGTCTTCTGATGT-3' | (SEQ ID NO: 2190)<br>(SEQ ID NO: 4204)<br>(SEQ ID NO: 6218) |
| LDHA-1285 | 5'-UGCAAUUUUAAAGUCUUCUGAUGtc-3'<br>3'-CGACGUUAAAAUUUCAGAAGACUACAG-5'<br>Target: 5'-GCTGCAATTTTAAAGTCTTCTGATGTC-3' | (SEQ ID NO: 2191)<br>(SEQ ID NO: 4205)<br>(SEQ ID NO: 6219) |
| LDHA-1288 | 5'-AAUUUUAAAGUCUUCUGAUGUCAta-3'<br>3'-CGUUAAAAUUUCAGAAGACUACAGUAU-5'<br>Target: 5'-GCAATTTTAAAGTCTTCTGATGTCATA-3' | (SEQ ID NO: 2192)<br>(SEQ ID NO: 4206)<br>(SEQ ID NO: 6220) |
| LDHA-1289 | 5'-AUUUUAAAGUCUUCUGAUGUCAUat-3'<br>3'-GUUAAAAUUUCAGAAGACUACAGUAUA-5'<br>Target: 5'-CAATTTTAAAGTCTTCTGATGTCATAT-3' | (SEQ ID NO: 2193)<br>(SEQ ID NO: 4207)<br>(SEQ ID NO: 6221) |
| LDHA-1290 | 5'-UUUUAAAGUCUUCUGAUGUCAUAtc-3'<br>3'-UUAAAAUUUCAGAAGACUACAGUAUAG-5'<br>Target: 5'-AATTTTAAAGTCTTCTGATGTCATATC-3' | (SEQ ID NO: 2194)<br>(SEQ ID NO: 4208)<br>(SEQ ID NO: 6222) |
| LDHA-1291 | 5'-UUUAAAGUCUUCUGAUGUCAUAUca-3'<br>3'-UAAAAUUUCAGAAGACUACAGUAUAGU-5'<br>Target: 5'-ATTTTAAAGTCTTCTGATGTCATATCA-3' | (SEQ ID NO: 2195)<br>(SEQ ID NO: 4209)<br>(SEQ ID NO: 6223) |
| LDHA-1295 | 5'-AAGUCUUCUGAUGUCAUAUCAUUtc-3'<br>3'-AUUUCAGAAGACUACAGUAUAGUAAAG-5'<br>Target: 5'-TAAAGTCTTCTGATGTCATATCATTTC-3' | (SEQ ID NO: 2196)<br>(SEQ ID NO: 4210)<br>(SEQ ID NO: 6224) |
| LDHA-1296 | 5'-AGUCUUCUGAUGUCAUAUCAUUUca-3'<br>3'-UUUCAGAAGACUACAGUAUAGUAAAGU-5'<br>Target: 5'-AAAGTCTTCTGATGTCATATCATTTCA-3' | (SEQ ID NO: 2197)<br>(SEQ ID NO: 4211)<br>(SEQ ID NO: 6225) |
| LDHA-1297 | 5'-GUCUUCUGAUGUCAUAUCAUUUCac-3'<br>3'-UUCAGAAGACUACAGUAUAGUAAAGUG-5'<br>Target: 5'-AAGTCTTCTGATGTCATATCATTTCAC-3' | (SEQ ID NO: 2198)<br>(SEQ ID NO: 4212)<br>(SEQ ID NO: 6226) |
| LDHA-1298 | 5'-UCUUCUGAUGUCAUAUCAUUUCAct-3'<br>3'-UCAGAAGACUACAGUAUAGUAAAGUGA-5'<br>Target: 5'-AGTCTTCTGATGTCATATCATTTCACT-3' | (SEQ ID NO: 2199)<br>(SEQ ID NO: 4213)<br>(SEQ ID NO: 6227) |
| LDHA-1299 | 5'-CUUCUGAUGUCAUAUCAUUUCACtg-3'<br>3'-CAGAAGACUACAGUAUAGUAAAGUGAC-5'<br>Target: 5'-GTCTTCTGATGTCATATCATTTCACTG-3' | (SEQ ID NO: 2200)<br>(SEQ ID NO: 4214)<br>(SEQ ID NO: 6228) |
| LDHA-1300 | 5'-UUCUGAUGUCAUAUCAUUUCACUgt-3'<br>3'-AGAAGACUACAGUAUAGUAAAGUGACA-5'<br>Target: 5'-TCTTCTGATGTCATATCATTTCACTGT-3' | (SEQ ID NO: 2201)<br>(SEQ ID NO: 4215)<br>(SEQ ID NO: 6229) |

TABLE 12-continued

Additional Selected Human Anti-Lactate Dehydrogenase DsiRNA Agents (Asymmetrics)

| | | |
|---|---|---|
| | 5'-UCUGAUGUCAUAUCAUUUCACUGtc-3' | (SEQ ID NO: 2202) |
| | 3'-GAAGACUACAGUAUAGUAAAGUGACAG-5' | (SEQ ID NO: 4216) |
| LDHA-1301 Target: | 5'-CTTCTGATGTCATATCATTTCACTGTC-3' | (SEQ ID NO: 6230) |
| | 5'-CUGAUGUCAUAUCAUUUCACUGUct-3' | (SEQ ID NO: 2203) |
| | 3'-AAGACUACAGUAUAGUAAAGUGACAGA-5' | (SEQ ID NO: 4217) |
| LDHA-1302 Target: | 5'-TTCTGATGTCATATCATTTCACTGTCT-3' | (SEQ ID NO: 6231) |
| | 5'-UGAUGUCAUAUCAUUUCACUGUCta-3' | (SEQ ID NO: 2204) |
| | 3'-AGACUACAGUAUAGUAAAGUGACAGAU-5' | (SEQ ID NO: 4218) |
| LDHA-1303 Target: | 5'-TCTGATGTCATATCATTTCACTGTCTA-3' | (SEQ ID NO: 6232) |
| | 5'-GAUGUCAUAUCAUUUCACUGUCUag-3' | (SEQ ID NO: 2205) |
| | 3'-GACUACAGUAUAGUAAAGUGACAGAUC-5' | (SEQ ID NO: 4219) |
| LDHA-1304 Target: | 5'-CTGATGTCATATCATTTCACTGTCTAG-3' | (SEQ ID NO: 6233) |
| | 5'-AUGUCAUAUCAUUUCACUGUCUAgg-3' | (SEQ ID NO: 2206) |
| | 3'-ACUACAGUAUAGUAAAGUGACAGAUCC-5' | (SEQ ID NO: 4220) |
| LDHA-1305 Target: | 5'-TGATGTCATATCATTTCACTGTCTAGG-3' | (SEQ ID NO: 6234) |
| | 5'-UGUCAUAUCAUUUCACUGUCUAGgc-3' | (SEQ ID NO: 2207) |
| | 3'-CUACAGUAUAGUAAAGUGACAGAUCCG-5' | (SEQ ID NO: 4221) |
| LDHA-1306 Target: | 5'-GATGTCATATCATTTCACTGTCTAGGC-3' | (SEQ ID NO: 6235) |
| | 5'-GUCAUAUCAUUUCACUGUCUAGGct-3' | (SEQ ID NO: 2208) |
| | 3'-UACAGUAUAGUAAAGUGACAGAUCCGA-5' | (SEQ ID NO: 4222) |
| LDHA-1307 Target: | 5'-ATGTCATATCATTTCACTGTCTAGGCT-3' | (SEQ ID NO: 6236) |
| | 5'-UCAUAUCAUUUCACUGUCUAGGCta-3' | (SEQ ID NO: 2209) |
| | 3'-ACAGUAUAGUAAAGUGACAGAUCCGAU-5' | (SEQ ID NO: 4223) |
| LDHA-1308 Target: | 5'-TGTCATATCATTTCACTGTCTAGGCTA-3' | (SEQ ID NO: 6237) |
| | 5'-CAUAUCAUUUCACUGUCUAGGCUac-3' | (SEQ ID NO: 2210) |
| | 3'-CAGUAUAGUAAAGUGACAGAUCCGAUG-5' | (SEQ ID NO: 4224) |
| LDHA-1309 Target: | 5'-GTCATATCATTTCACTGTCTAGGCTAC-3' | (SEQ ID NO: 6238) |
| | 5'-AUAUCAUUUCACUGUCUAGGCUAca-3' | (SEQ ID NO: 2211) |
| | 3'-AGUAUAGUAAAGUGACAGAUCCGAUGU-5' | (SEQ ID NO: 4225) |
| LDHA-1310 Target: | 5'-TCATATCATTTCACTGTCTAGGCTACA-3' | (SEQ ID NO: 6239) |
| | 5'-UAUCAUUUCACUGUCUAGGCUACaa-3' | (SEQ ID NO: 2212) |
| | 3'-GUAUAGUAAAGUGACAGAUCCGAUGUU-5' | (SEQ ID NO: 4226) |
| LDHA-1311 Target: | 5'-CATATCATTTCACTGTCTAGGCTACAA-3' | (SEQ ID NO: 6240) |
| | 5'-AUCAUUUCACUGUCUAGGCUACAac-3' | (SEQ ID NO: 2213) |
| | 3'-UAUAGUAAAGUGACAGAUCCGAUGUUG-5' | (SEQ ID NO: 4227) |
| LDHA-1312 Target: | 5'-ATATCATTTCACTGTCTAGGCTACAAC-3' | (SEQ ID NO: 6241) |
| | 5'-UCAUUUCACUGUCUAGGCUACAAca-3' | (SEQ ID NO: 2214) |
| | 3'-AUAGUAAAGUGACAGAUCCGAUGUUGU-5' | (SEQ ID NO: 4228) |
| LDHA-1313 Target: | 5'-TATCATTTCACTGTCTAGGCTACAACA-3' | (SEQ ID NO: 6242) |
| | 5'-CAUUUCACUGUCUAGGCUACAACag-3' | (SEQ ID NO: 2215) |
| | 3'-UAGUAAAGUGACAGAUCCGAUGUUGUC-5' | (SEQ ID NO: 4229) |
| LDHA-1314 Target: | 5'-ATCATTTCACTGTCTAGGCTACAACAG-3' | (SEQ ID NO: 6243) |
| | 5'-AUUUCACUGUCUAGGCUACAACAgg-3' | (SEQ ID NO: 2216) |
| | 3'-AGUAAAGUGACAGAUCCGAUGUUGUCC-5' | (SEQ ID NO: 4230) |
| LDHA-1315 Target: | 5'-TCATTTCACTGTCTAGGCTACAACAGG-3' | (SEQ ID NO: 6244) |
| | 5'-UUUCACUGUCUAGGCUACAACAGga-3' | (SEQ ID NO: 2217) |
| | 3'-GUAAAGUGACAGAUCCGAUGUUGUCCU-5' | (SEQ ID NO: 4231) |
| LDHA-1316 Target: | 5'-CATTTCACTGTCTAGGCTACAACAGGA-3' | (SEQ ID NO: 6245) |
| | 5'-UUCACUGUCUAGGCUACAACAGGat-3' | (SEQ ID NO: 2218) |
| | 3'-UAAAGUGACAGAUCCGAUGUUGUCCUA-5' | (SEQ ID NO: 4232) |
| LDHA-1317 Target: | 5'-ATTTCACTGTCTAGGCTACAACAGGAT-3' | (SEQ ID NO: 6246) |
| | 5'-UCACUGUCUAGGCUACAACAGGAtt-3' | (SEQ ID NO: 2219) |
| | 3'-AAAGUGACAGAUCCGAUGUUGUCCUAA-5' | (SEQ ID NO: 4233) |
| LDHA-1318 Target: | 5'-TTTCACTGTCTAGGCTACAACAGGATT-3' | (SEQ ID NO: 6247) |
| | 5'-CACUGUCUAGGCUACAACAGGAUtc-3' | (SEQ ID NO: 2220) |
| | 3'-AAGUGACAGAUCCGAUGUUGUCCUAAG-5' | (SEQ ID NO: 4234) |
| LDHA-1319 Target: | 5'-TTCACTGTCTAGGCTACAACAGGATTC-3' | (SEQ ID NO: 6248) |

TABLE 12-continued

Additional Selected Human Anti-Lactate Dehydrogenase DsiRNA Agents (Asymmetrics)

| | | |
|---|---|---|
| | 5'-ACUGUCUAGGCUACAACAGGAUUct-3' | (SEQ ID NO: 2221) |
| | 3'-AGUGACAGAUCCGAUGUUGUCCUAAGA-5' | (SEQ ID NO: 4235) |
| LDHA-1320 Target: | 5'-TCACTGTCTAGGCTACAACAGGATTCT-3' | (SEQ ID NO: 6249) |
| | 5'-CUGUCUAGGCUACAACAGGAUUCta-3' | (SEQ ID NO: 2222) |
| | 3'-GUGACAGAUCCGAUGUUGUCCUAAGAU-5' | (SEQ ID NO: 4236) |
| LDHA-1321 Target: | 5'-CACTGTCTAGGCTACAACAGGATTCTA-3' | (SEQ ID NO: 6250) |
| | 5'-UGUCUAGGCUACAACAGGAUUCUag-3' | (SEQ ID NO: 2223) |
| | 3'-UGACAGAUCCGAUGUUGUCCUAAGAUC-5' | (SEQ ID NO: 4237) |
| LDHA-1322 Target: | 5'-ACTGTCTAGGCTACAACAGGATTCTAG-3' | (SEQ ID NO: 6251) |
| | 5'-GUCUAGGCUACAACAGGAUUCUAgg-3' | (SEQ ID NO: 2224) |
| | 3'-GACAGAUCCGAUGUUGUCCUAAGAUCC-5' | (SEQ ID NO: 4238) |
| LDHA-1323 Target: | 5'-CTGTCTAGGCTACAACAGGATTCTAGG-3' | (SEQ ID NO: 6252) |
| | 5'-UCUAGGCUACAACAGGAUUCUAGgt-3' | (SEQ ID NO: 2225) |
| | 3'-ACAGAUCCGAUGUUGUCCUAAGAUCCA-5' | (SEQ ID NO: 4239) |
| LDHA-1324 Target: | 5'-TGTCTAGGCTACAACAGGATTCTAGGT-3' | (SEQ ID NO: 6253) |
| | 5'-CUAGGCUACAACAGGAUUCUAGGtg-3' | (SEQ ID NO: 2226) |
| | 3'-CAGAUCCGAUGUUGUCCUAAGAUCCAC-5' | (SEQ ID NO: 4240) |
| LDHA-1325 Target: | 5'-GTCTAGGCTACAACAGGATTCTAGGTG-3' | (SEQ ID NO: 6254) |
| | 5'-UAGGCUACAACAGGAUUCUAGGUgg-3' | (SEQ ID NO: 2227) |
| | 3'-AGAUCCGAUGUUGUCCUAAGAUCCACC-5' | (SEQ ID NO: 4241) |
| LDHA-1326 Target: | 5'-TCTAGGCTACAACAGGATTCTAGGTGG-3' | (SEQ ID NO: 6255) |
| | 5'-AGGCUACAACAGGAUUCUAGGUGga-3' | (SEQ ID NO: 2228) |
| | 3'-GAUCCGAUGUUGUCCUAAGAUCCACCU-5' | (SEQ ID NO: 4242) |
| LDHA-1327 Target: | 5'-CTAGGCTACAACAGGATTCTAGGTGGA-3' | (SEQ ID NO: 6256) |
| | 5'-GGCUACAACAGGAUUCUAGGUGGag-3' | (SEQ ID NO: 2229) |
| | 3'-AUCCGAUGUUGUCCUAAGAUCCACCUC-5' | (SEQ ID NO: 4243) |
| LDHA-1328 Target: | 5'-TAGGCTACAACAGGATTCTAGGTGGAG-3' | (SEQ ID NO: 6257) |
| | 5'-GCUACAACAGGAUUCUAGGUGGAgg-3' | (SEQ ID NO: 2230) |
| | 3'-UCCGAUGUUGUCCUAAGAUCCACCUCC-5' | (SEQ ID NO: 4244) |
| LDHA-1329 Target: | 5'-AGGCTACAACAGGATTCTAGGTGGAGG-3' | (SEQ ID NO: 6258) |
| | 5'-CUACAACAGGAUUCUAGGUGGAGgt-3' | (SEQ ID NO: 2231) |
| | 3'-CCGAUGUUGUCCUAAGAUCCACCUCCA-5' | (SEQ ID NO: 4245) |
| LDHA-1330 Target: | 5'-GGCTACAACAGGATTCTAGGTGGAGGT-3' | (SEQ ID NO: 6259) |
| | 5'-UACAACAGGAUUCUAGGUGGAGGtt-3' | (SEQ ID NO: 2232) |
| | 3'-CGAUGUUGUCCUAAGAUCCACCUCCAA-5' | (SEQ ID NO: 4246) |
| LDHA-1331 Target: | 5'-GCTACAACAGGATTCTAGGTGGAGGTT-3' | (SEQ ID NO: 6260) |
| | 5'-ACAACAGGAUUCUAGGUGGAGGUtg-3' | (SEQ ID NO: 2233) |
| | 3'-GAUGUUGUCCUAAGAUCCACCUCCAAC-5' | (SEQ ID NO: 4247) |
| LDHA-1332 Target: | 5'-CTACAACAGGATTCTAGGTGGAGGTTG-3' | (SEQ ID NO: 6261) |
| | 5'-CAACAGGAUUCUAGGUGGAGGUUgt-3' | (SEQ ID NO: 2234) |
| | 3'-AUGUUGUCCUAAGAUCCACCUCCAACA-5' | (SEQ ID NO: 4248) |
| LDHA-1333 Target: | 5'-TACAACAGGATTCTAGGTGGAGGTTGT-3' | (SEQ ID NO: 6262) |
| | 5'-AACAGGAUUCUAGGUGGAGGUUGtg-3' | (SEQ ID NO: 2235) |
| | 3'-UGUUGUCCUAAGAUCCACCUCCAACAC-5' | (SEQ ID NO: 4249) |
| LDHA-1334 Target: | 5'-ACAACAGGATTCTAGGTGGAGGTTGTG-3' | (SEQ ID NO: 6263) |
| | 5'-ACAGGAUUCUAGGUGGAGGUUGUgc-3' | (SEQ ID NO: 2236) |
| | 3'-GUUGUCCUAAGAUCCACCUCCAACACG-5' | (SEQ ID NO: 4250) |
| LDHA-1335 Target: | 5'-CAACAGGATTCTAGGTGGAGGTTGTGC-3' | (SEQ ID NO: 6264) |
| | 5'-CAGGAUUCUAGGUGGAGGUUGUGca-3' | (SEQ ID NO: 2237) |
| | 3'-UUGUCCUAAGAUCCACCUCCAACACGU-5' | (SEQ ID NO: 4251) |
| LDHA-1336 Target: | 5'-AACAGGATTCTAGGTGGAGGTTGTGCA-3' | (SEQ ID NO: 6265) |
| | 5'-AGGAUUCUAGGUGGAGGUUGUGCat-3' | (SEQ ID NO: 2238) |
| | 3'-UGUCCUAAGAUCCACCUCCAACACGUA-5' | (SEQ ID NO: 4252) |
| LDHA-1337 Target: | 5'-ACAGGATTCTAGGTGGAGGTTGTGCAT-3' | (SEQ ID NO: 6266) |
| | 5'-GGAUUCUAGGUGGAGGUUGUGCAtg-3' | (SEQ ID NO: 2239) |
| | 3'-GUCCUAAGAUCCACCUCCAACACGUAC-5' | (SEQ ID NO: 4253) |
| LDHA-1338 Target: | 5'-CAGGATTCTAGGTGGAGGTTGTGCATG-3' | (SEQ ID NO: 6267) |

TABLE 12-continued

Additional Selected Human Anti-Lactate Dehydrogenase DsiRNA Agents (Asymmetrics)

|  |  |  |  |
|---|---|---|---|
| LDHA-1339 | 5'-GAUUCUAGGUGGAGGUUGUGCAUgt-3'<br>3'-UCCUAAGAUCCACCUCCAACACGUACA-5'<br>Target: 5'-AGGATTCTAGGTGGAGGTTGTGCATGT-3' | (SEQ ID NO: 2240)<br>(SEQ ID NO: 4254)<br>(SEQ ID NO: 6268) | |
| LDHA-1340 | 5'-AUUCUAGGUGGAGGUUGUGCAUGtt-3'<br>3'-CCUAAGAUCCACCUCCAACACGUACAA-5'<br>Target: 5'-GGATTCTAGGTGGAGGTTGTGCATGTT-3' | (SEQ ID NO: 2241)<br>(SEQ ID NO: 4255)<br>(SEQ ID NO: 6269) | |
| LDHA-1341 | 5'-UUCUAGGUGGAGGUUGUGCAUGUtg-3'<br>3'-CUAAGAUCCACCUCCAACACGUACAAC-5'<br>Target: 5'-GATTCTAGGTGGAGGTTGTGCATGTTG-3' | (SEQ ID NO: 2242)<br>(SEQ ID NO: 4256)<br>(SEQ ID NO: 6270) | |
| LDHA-1342 | 5'-UCUAGGUGGAGGUUGUGCAUGUUgt-3'<br>3'-UAAGAUCCACCUCCAACACGUACAACA-5'<br>Target: 5'-ATTCTAGGTGGAGGTTGTGCATGTTGT-3' | (SEQ ID NO: 2243)<br>(SEQ ID NO: 4257)<br>(SEQ ID NO: 6271) | |
| LDHA-1343 | 5'-CUAGGUGGAGGUUGUGCAUGUUGtc-3'<br>3'-AAGAUCCACCUCCAACACGUACAACAG-5'<br>Target: 5'-TTCTAGGTGGAGGTTGTGCATGTTGTC-3' | (SEQ ID NO: 2244)<br>(SEQ ID NO: 4258)<br>(SEQ ID NO: 6272) | |
| LDHA-1344 | 5'-UAGGUGGAGGUUGUGCAUGUUGUcc-3'<br>3'-AGAUCCACCUCCAACACGUACAACAGG-5'<br>Target: 5'-TCTAGGTGGAGGTTGTGCATGTTGTCC-3' | (SEQ ID NO: 2245)<br>(SEQ ID NO: 4259)<br>(SEQ ID NO: 6273) | |
| LDHA-1345 | 5'-AGGUGGAGGUUGUGCAUGUUGUCct-3'<br>3'-GAUCCACCUCCAACACGUACAACAGGA-5'<br>Target: 5'-CTAGGTGGAGGTTGTGCATGTTGTCCT-3' | (SEQ ID NO: 2246)<br>(SEQ ID NO: 4260)<br>(SEQ ID NO: 6274) | |
| LDHA-1346 | 5'-GGUGGAGGUUGUGCAUGUUGUCCtt-3'<br>3'-AUCCACCUCCAACACGUACAACAGGAA-5'<br>Target: 5'-TAGGTGGAGGTTGTGCATGTTGTCCTT-3' | (SEQ ID NO: 2247)<br>(SEQ ID NO: 4261)<br>(SEQ ID NO: 6275) | |
| LDHA-1347 | 5'-GUGGAGGUUGUGCAUGUUGUCCUtt-3'<br>3'-UCCACCUCCAACACGUACAACAGGAAA-5'<br>Target: 5'-AGGTGGAGGTTGTGCATGTTGTCCTTT-3' | (SEQ ID NO: 2248)<br>(SEQ ID NO: 4262)<br>(SEQ ID NO: 6276) | |
| LDHA-1348 | 5'-UGGAGGUUGUGCAUGUUGUCCUUtt-3'<br>3'-CCACCUCCAACACGUACAACAGGAAAA-5'<br>Target: 5'-GGTGGAGGTTGTGCATGTTGTCCTTTT-3' | (SEQ ID NO: 2249)<br>(SEQ ID NO: 4263)<br>(SEQ ID NO: 6277) | |
| LDHA-1349 | 5'-GGAGGUUGUGCAUGUUGUCCUUUtt-3'<br>3'-CACCUCCAACACGUACAACAGGAAAAA-5'<br>Target: 5'-GTGGAGGTTGTGCATGTTGTCCTTTTT-3' | (SEQ ID NO: 2250)<br>(SEQ ID NO: 4264)<br>(SEQ ID NO: 6278) | |
| LDHA-1350 | 5'-GAGGUUGUGCAUGUUGUCCUUUUta-3'<br>3'-ACCUCCAACACGUACAACAGGAAAAAU-5'<br>Target: 5'-TGGAGGTTGTGCATGTTGTCCTTTTTA-3' | (SEQ ID NO: 2251)<br>(SEQ ID NO: 4265)<br>(SEQ ID NO: 6279) | |
| LDHA-1351 | 5'-AGGUUGUGCAUGUUGUCCUUUUUat-3'<br>3'-CCUCCAACACGUACAACAGGAAAAAUA-5'<br>Target: 5'-GGAGGTTGTGCATGTTGTCCTTTTTAT-3' | (SEQ ID NO: 2252)<br>(SEQ ID NO: 4266)<br>(SEQ ID NO: 6280) | |
| LDHA-1352 | 5'-GGUUGUGCAUGUUGUCCUUUUUAtc-3'<br>3'-CUCCAACACGUACAACAGGAAAAAUAG-5'<br>Target: 5'-GAGGTTGTGCATGTTGTCCTTTTTATC-3' | (SEQ ID NO: 2253)<br>(SEQ ID NO: 4267)<br>(SEQ ID NO: 6281) | |
| LDHA-1353 | 5'-GUUGUGCAUGUUGUCCUUUUUAUct-3'<br>3'-UCCAACACGUACAACAGGAAAAAUAGA-5'<br>Target: 5'-AGGTTGTGCATGTTGTCCTTTTTATCT-3' | (SEQ ID NO: 2254)<br>(SEQ ID NO: 4268)<br>(SEQ ID NO: 6282) | |
| LDHA-1354 | 5'-UUGUGCAUGUUGUCCUUUUUAUCtg-3'<br>3'-CCAACACGUACAACAGGAAAAAUAGAC-5'<br>Target: 5'-GGTTGTGCATGTTGTCCTTTTTATCTG-3' | (SEQ ID NO: 2255)<br>(SEQ ID NO: 4269)<br>(SEQ ID NO: 6283) | |
| LDHA-1355 | 5'-UGUGCAUGUUGUCCUUUUUAUCUga-3'<br>3'-CAACACGUACAACAGGAAAAAUAGACU-5'<br>Target: 5'-GTTGTGCATGTTGTCCTTTTTATCTGA-3' | (SEQ ID NO: 2256)<br>(SEQ ID NO: 4270)<br>(SEQ ID NO: 6284) | |
| LDHA-1356 | 5'-GUGCAUGUUGUCCUUUUUAUCUGat-3'<br>3'-AACACGUACAACAGGAAAAAUAGACUA-5'<br>Target: 5'-TTGTGCATGTTGTCCTTTTTATCTGAT-3' | (SEQ ID NO: 2257)<br>(SEQ ID NO: 4271)<br>(SEQ ID NO: 6285) | |
| LDHA-1357 | 5'-UGCAUGUUGUCCUUUUUAUCUGAtc-3'<br>3'-ACACGUACAACAGGAAAAAUAGACUAG-5'<br>Target: 5'-TGTGCATGTTGTCCTTTTTATCTGATC-3' | (SEQ ID NO: 2258)<br>(SEQ ID NO: 4272)<br>(SEQ ID NO: 6286) | |

TABLE 12-continued

Additional Selected Human Anti-Lactate Dehydrogenase DsiRNA Agents (Asymmetrics)

| | | |
|---|---|---|
| | 5'-GCAUGUUGUCCUUUUUAUCUGAUct-3' | (SEQ ID NO: 2259) |
| | 3'-CACGUACAACAGGAAAAAUAGACUAGA-5' | (SEQ ID NO: 4273) |
| LDHA-1358 Target: | 5'-GTGCATGTTGTCCTTTTTATCTGATCT-3' | (SEQ ID NO: 6287) |
| | 5'-UGUCCUUUUUAUCUGAUCUGUGAtt-3' | (SEQ ID NO: 2260) |
| | 3'-CAACAGGAAAAAUAGACUAGACACUAA-5' | (SEQ ID NO: 4274) |
| LDHA-1364 Target: | 5'-GTTGTCCTTTTTATCTGATCTGTGATT-3' | (SEQ ID NO: 6288) |
| | 5'-UUUUUAUCUGAUCUGUGAUUAAAgc-3' | (SEQ ID NO: 2261) |
| | 3'-GGAAAAAUAGACUAGACACUAAUUUCG-5' | (SEQ ID NO: 4275) |
| LDHA-1369 Target: | 5'-CCTTTTTATCTGATCTGTGATTAAAGC-3' | (SEQ ID NO: 6289) |
| | 5'-UAUCUGAUCUGUGAUUAAAGCAGta-3' | (SEQ ID NO: 2262) |
| | 3'-AAAUAGACUAGACACUAAUUUCGUCAU-5' | (SEQ ID NO: 4276) |
| LDHA-1373 Target: | 5'-TTTATCTGATCTGTGATTAAAGCAGTA-3' | (SEQ ID NO: 6290) |
| | 5'-AUCUGAUCUGUGAUUAAAGCAGUaa-3' | (SEQ ID NO: 2263) |
| | 3'-AAUAGACUAGACACUAAUUUCGUCAUU-5' | (SEQ ID NO: 4277) |
| LDHA-1374 Target: | 5'-TTATCTGATCTGTGATTAAAGCAGTAA-3' | (SEQ ID NO: 6291) |
| | 5'-UCUGAUCUGUGAUUAAAGCAGUAat-3' | (SEQ ID NO: 2264) |
| | 3'-AUAGACUAGACACUAAUUUCGUCAUUA-5' | (SEQ ID NO: 4278) |
| LDHA-1375 Target: | 5'-TATCTGATCTGTGATTAAAGCAGTAAT-3' | (SEQ ID NO: 6292) |
| | 5'-CUGAUCUGUGAUUAAAGCAGUAAta-3' | (SEQ ID NO: 2265) |
| | 3'-UAGACUAGACACUAAUUUCGUCAUUAU-5' | (SEQ ID NO: 4279) |
| LDHA-1376 Target: | 5'-ATCTGATCTGTGATTAAAGCAGTAATA-3' | (SEQ ID NO: 6293) |
| | 5'-UGAUCUGUGAUUAAAGCAGUAAUat-3' | (SEQ ID NO: 2266) |
| | 3'-AGACUAGACACUAAUUUCGUCAUUAUA-5' | (SEQ ID NO: 4280) |
| LDHA-1377 Target: | 5'-TCTGATCTGTGATTAAAGCAGTAATAT-3' | (SEQ ID NO: 6294) |
| | 5'-GAUCUGUGAUUAAAGCAGUAAUAtt-3' | (SEQ ID NO: 2267) |
| | 3'-GACUAGACACUAAUUUCGUCAUUAUAA-5' | (SEQ ID NO: 4281) |
| LDHA-1378 Target: | 5'-CTGATCTGTGATTAAAGCAGTAATATT-3' | (SEQ ID NO: 6295) |
| | 5'-AUCUGUGAUUAAAGCAGUAAUAUtt-3' | (SEQ ID NO: 2268) |
| | 3'-ACUAGACACUAAUUUCGUCAUUAUAAA-5' | (SEQ ID NO: 4282) |
| LDHA-1379 Target: | 5'-TGATCTGTGATTAAAGCAGTAATATTT-3' | (SEQ ID NO: 6296) |
| | 5'-UCUGUGAUUAAAGCAGUAAUAUUtt-3' | (SEQ ID NO: 2269) |
| | 3'-CUAGACACUAAUUUCGUCAUUAUAAAA-5' | (SEQ ID NO: 4283) |
| LDHA-1380 Target: | 5'-GATCTGTGATTAAAGCAGTAATATTTT-3' | (SEQ ID NO: 6297) |
| | 5'-CUGUGAUUAAAGCAGUAAUAUUUta-3' | (SEQ ID NO: 2270) |
| | 3'-UAGACACUAAUUUCGUCAUUAUAAAAU-5' | (SEQ ID NO: 4284) |
| LDHA-1381 Target: | 5'-ATCTGTGATTAAAGCAGTAATATTTTA-3' | (SEQ ID NO: 6298) |
| | 5'-UGUGAUUAAAGCAGUAAUAUUUUaa-3' | (SEQ ID NO: 2271) |
| | 3'-AGACACUAAUUUCGUCAUUAUAAAAUU-5' | (SEQ ID NO: 4285) |
| LDHA-1382 Target: | 5'-TCTGTGATTAAAGCAGTAATATTTTAA-3' | (SEQ ID NO: 6299) |
| | 5'-GUGAUUAAAGCAGUAAUAUUUUAag-3' | (SEQ ID NO: 2272) |
| | 3'-GACACUAAUUUCGUCAUUAUAAAAUUC-5' | (SEQ ID NO: 4286) |
| LDHA-1383 Target: | 5'-CTGTGATTAAAGCAGTAATATTTTAAG-3' | (SEQ ID NO: 6300) |
| | 5'-UGAUUAAAGCAGUAAUAUUUUAAga-3' | (SEQ ID NO: 2273) |
| | 3'-ACACUAAUUUCGUCAUUAUAAAAUUCU-5' | (SEQ ID NO: 4287) |
| LDHA-1384 Target: | 5'-TGTGATTAAAGCAGTAATATTTTAAGA-3' | (SEQ ID NO: 6301) |
| | 5'-GAUUAAAGCAGUAAUAUUUUAAGat-3' | (SEQ ID NO: 2274) |
| | 3'-CACUAAUUUCGUCAUUAUAAAAUUCUA-5' | (SEQ ID NO: 4288) |
| LDHA-1385 Target: | 5'-GTGATTAAAGCAGTAATATTTTAAGAT-3' | (SEQ ID NO: 6302) |
| | 5'-AUUAAAGCAGUAAUAUUUUAAGAtg-3' | (SEQ ID NO: 2275) |
| | 3'-ACUAAUUUCGUCAUUAUAAAAUUCUAC-5' | (SEQ ID NO: 4289) |
| LDHA-1386 Target: | 5'-TGATTAAAGCAGTAATATTTTAAGATG-3' | (SEQ ID NO: 6303) |
| | 5'-UUAAAGCAGUAAUAUUUUAAGAUgg-3' | (SEQ ID NO: 2276) |
| | 3'-CUAAUUUCGUCAUUAUAAAAUUCUACC-5' | (SEQ ID NO: 4290) |
| LDHA-1387 Target: | 5'-GATTAAAGCAGTAATATTTTAAGATGG-3' | (SEQ ID NO: 6304) |
| | 5'-UAAAGCAGUAAUAUUUUAAGAUGga-3' | (SEQ ID NO: 2277) |
| | 3'-UAAUUUCGUCAUUAUAAAAUUCUACCU-5' | (SEQ ID NO: 4291) |
| LDHA-1388 Target: | 5'-ATTAAAGCAGTAATATTTTAAGATGGA-3' | (SEQ ID NO: 6305) |

TABLE 12-continued

Additional Selected Human Anti-Lactate Dehydrogenase DsiRNA Agents (Asymmetrics)

|  |  |  |
|---|---|---|
|  | 5'-A<u>AA</u>GCAGUAAUAU<u>UUU</u>AAGAUGGac-3' | (SEQ ID NO: 2278) |
|  | 3'-<u>AAUUU</u>CGUCAUUAU<u>AAAA</u>UUCUA<u>CCUG</u>-5' | (SEQ ID NO: 4292) |
| LDHA-1389 Target: | 5'-TTAAAGCAGTAATATTTTAAGATGGAC-3' | (SEQ ID NO: 6306) |
|  | 5'-A<u>AG</u>CAGUAAUAUUU<u>U</u>AAGAUGGAct-3' | (SEQ ID NO: 2279) |
|  | 3'-<u>AUUU</u>CGUCAUUAUA<u>AAA</u>UUCUA<u>CUGA</u>-5' | (SEQ ID NO: 4293) |
| LDHA-1390 Target: | 5'-TAAAGCAGTAATATTTTAAGATGGACT-3' | (SEQ ID NO: 6307) |
|  | 5'-A<u>G</u>CAGUAAUAUUUU<u>AA</u>GAUGGACtg-3' | (SEQ ID NO: 2280) |
|  | 3'-<u>UUU</u>CGUCAUUAUAA<u>AA</u>UUCUACC<u>UGAC</u>-5' | (SEQ ID NO: 4294) |
| LDHA-1391 Target: | 5'-AAAGCAGTAATATTTTAAGATGGACTG-3' | (SEQ ID NO: 6308) |
|  | 5'-G<u>CA</u>GUAAUAUUUU<u>AA</u>GAUGGACUgg-3' | (SEQ ID NO: 2281) |
|  | 3'-<u>UUC</u>GUCAUUAUAAA<u>A</u>UUCUACCUG<u>ACC</u>-5' | (SEQ ID NO: 4295) |
| LDHA-1392 Target: | 5'-AAGCAGTAATATTTTAAGATGGACTGG-3' | (SEQ ID NO: 6309) |
|  | 5'-A<u>GU</u>AAUAUUUUAA<u>GA</u>UGGACUGGga-3' | (SEQ ID NO: 2282) |
|  | 3'-<u>C</u>GUC<u>A</u>UUAUAAAAU<u>U</u>C<u>U</u>ACCUGA<u>CCCU</u>-5' | (SEQ ID NO: 4296) |
| LDHA-1394 Target: | 5'-GCAGTAATATTTTAAGATGGACTGGGA-3' | (SEQ ID NO: 6310) |
|  | 5'-G<u>UA</u>AUAUUUAAGA<u>U</u>GGACUGGGaa-3' | (SEQ ID NO: 2283) |
|  | 3'-<u>GUC</u>AUUAUAAAAUU<u>C</u>UACCUGA<u>CCUU</u>-5' | (SEQ ID NO: 4297) |
| LDHA-1395 Target: | 5'-CAGTAATATTTTAAGATGGACTGGGAA-3' | (SEQ ID NO: 6311) |
|  | 5'-U<u>AA</u>UAUUUUAAGAU<u>GG</u>ACUGGGAaa-3' | (SEQ ID NO: 2284) |
|  | 3'-<u>UCA</u>UU<u>AUAAAAUUCU</u>ACCUGA<u>CCCUUU</u>-5' | (SEQ ID NO: 4298) |
| LDHA-1396 Target: | 5'-AGTAATATTTTAAGATGGACTGGGAAA-3' | (SEQ ID NO: 6312) |
|  | 5'-A<u>AU</u>AUUUUAAGAUGG<u>A</u>CUGGGAAaa-3' | (SEQ ID NO: 2285) |
|  | 3'-<u>CAUU</u>AUAAAAUUCUA<u>C</u>CUGACCC<u>UUUU</u>-5' | (SEQ ID NO: 4299) |
| LDHA-1397 Target: | 5'-GTAATATTTTAAGATGGACTGGGAAAA-3' | (SEQ ID NO: 6313) |
|  | 5'-A<u>UA</u>UUUUAAGAUGG<u>A</u>CUGGGAAAaa-3' | (SEQ ID NO: 2286) |
|  | 3'-<u>AUUA</u>UA<u>AAAUUCUA</u>CCUGACCC<u>UUUUU</u>-5' | (SEQ ID NO: 4300) |
| LDHA-1398 Target: | 5'-TAATATTTTAAGATGGACTGGGAAAAA-3' | (SEQ ID NO: 6314) |
|  | 5'-U<u>A</u>UUUUAAGAUGGA<u>CU</u>GGGAAAAac-3' | (SEQ ID NO: 2287) |
|  | 3'-<u>UUAU</u>AAAAUUCUA<u>CC</u>UGACCCUU<u>UUUG</u>-5' | (SEQ ID NO: 4301) |
| LDHA-1399 Target: | 5'-AATATTTTAAGATGGACTGGGAAAAAC-3' | (SEQ ID NO: 6315) |
|  | 5'-A<u>U</u>UUUAAGAUGGAC<u>U</u>GGGAAAAAca-3' | (SEQ ID NO: 2288) |
|  | 3'-<u>UAU</u>AAAAUUCUA<u>CC</u>UGACCCUUU<u>UUGU</u>-5' | (SEQ ID NO: 4302) |
| LDHA-1400 Target: | 5'-ATATTTTAAGATGGACTGGGAAAAACA-3' | (SEQ ID NO: 6316) |
|  | 5'-U<u>UUU</u>AAGAUGGACU<u>G</u>GGAAAAACat-3' | (SEQ ID NO: 2289) |
|  | 3'-<u>AUAAAA</u>UUCUACCUGA<u>C</u>CCUUUUU<u>GUA</u>-5' | (SEQ ID NO: 4303) |
| LDHA-1401 Target: | 5'-TATTTTAAGATGGACTGGGAAAAACAT-3' | (SEQ ID NO: 6317) |
|  | 5'-U<u>UU</u>AAGAUGGACU<u>GGG</u>AAAAACAtc-3' | (SEQ ID NO: 2290) |
|  | 3'-<u>UAAAA</u>UUCUACCUGA<u>CCC</u>UUUUUG<u>UAG</u>-5' | (SEQ ID NO: 4304) |
| LDHA-1402 Target: | 5'-ATTTTAAGATGGACTGGGAAAAACATC-3' | (SEQ ID NO: 6318) |
|  | 5'-U<u>U</u>AAGAUGGACUGG<u>G</u>AAAAACAUca-3' | (SEQ ID NO: 2291) |
|  | 3'-<u>AAAA</u>UUCUACCUGA<u>CCC</u>UUUUUGU<u>AGU</u>-5' | (SEQ ID NO: 4305) |
| LDHA-1403 Target: | 5'-TTTTAAGATGGACTGGGAAAAACATCA-3' | (SEQ ID NO: 6319) |
|  | 5'-U<u>AA</u>GAUGGACUGGG<u>A</u>AAAACAUCaa-3' | (SEQ ID NO: 2292) |
|  | 3'-<u>AAA</u>UUCUACCUGA<u>CCC</u>UUUUUGU<u>AGUU</u>-5' | (SEQ ID NO: 4306) |
| LDHA-1404 Target: | 5'-TTTAAGATGGACTGGGAAAAACATCAA-3' | (SEQ ID NO: 6320) |
|  | 5'-A<u>AG</u>AUGGACUGGG<u>AAA</u>AACAUCAac-3' | (SEQ ID NO: 2293) |
|  | 3'-<u>AA</u>UUCUACCUGACC<u>C</u>UUUUUGUA<u>GUUG</u>-5' | (SEQ ID NO: 4307) |
| LDHA-1405 Target: | 5'-TTAAGATGGACTGGGAAAAACATCAAC-3' | (SEQ ID NO: 6321) |
|  | 5'-A<u>GA</u>UGGACUGGGA<u>AAAA</u>CAUCAAct-3' | (SEQ ID NO: 2294) |
|  | 3'-<u>AU</u>UCUACCUGACCC<u>UUUUU</u>GUAG<u>UUGA</u>-5' | (SEQ ID NO: 4308) |
| LDHA-1406 Target: | 5'-TAAGATGGACTGGGAAAAACATCAACT-3' | (SEQ ID NO: 6322) |
|  | 5'-G<u>A</u>UGGACUGGGAAAAA<u>C</u>AUCAACtc-3' | (SEQ ID NO: 2295) |
|  | 3'-<u>UUC</u>U<u>A</u>CCUGACCCUUUUUGUAGUU<u>GAG</u>-5' | (SEQ ID NO: 4309) |
| LDHA-1407 Target: | 5'-AAGATGGACTGGGAAAAACATCAACTC-3' | (SEQ ID NO: 6323) |
|  | 5'-A<u>U</u>GGACUGGG<u>AAAA</u>CAUCAACUcc-3' | (SEQ ID NO: 2296) |
|  | 3'-<u>UCUA</u>CCUGACCC<u>UUUUU</u>GUAGUU<u>GAGG</u>-5' | (SEQ ID NO: 4310) |
| LDHA-1408 Target: | 5'-AGATGGACTGGGAAAAACATCAACTCC-3' | (SEQ ID NO: 6324) |

TABLE 12-continued

Additional Selected Human Anti-Lactate Dehydrogenase DsiRNA Agents (Asymmetrics)

|  |  |  |
|---|---|---|
| LDHA-1409 Target: | 5'-UGGACUGGGAAAAACAUCAACUCCct-3'<br>3'-CUACCUGACCCUUUUUGUAGUUGAGGA-5'<br>5'-GATGGACTGGGAAAAACATCAACTCCT-3' | (SEQ ID NO: 2297)<br>(SEQ ID NO: 4311)<br>(SEQ ID NO: 6325) |
| LDHA-1410 Target: | 5'-GGACUGGGAAAAACAUCAACUCCtg-3'<br>3'-UACCUGACCCUUUUUGUAGUUGAGGAC-5'<br>5'-ATGGACTGGGAAAAACATCAACTCCTG-3' | (SEQ ID NO: 2298)<br>(SEQ ID NO: 4312)<br>(SEQ ID NO: 6326) |
| LDHA-1411 Target: | 5'-GACUGGGAAAAACAUCAACUCCUga-3'<br>3'-ACCUGACCCUUUUUGUAGUUGAGGACU-5'<br>5'-TGGACTGGGAAAAACATCAACTCCTGA-3' | (SEQ ID NO: 2299)<br>(SEQ ID NO: 4313)<br>(SEQ ID NO: 6327) |
| LDHA-1412 Target: | 5'-ACUGGGAAAAACAUCAACUCCUGaa-3'<br>3'-CCUGACCCUUUUUGUAGUUGAGGACUU-5'<br>5'-GGACTGGGAAAAACATCAACTCCTGAA-3' | (SEQ ID NO: 2300)<br>(SEQ ID NO: 4314)<br>(SEQ ID NO: 6328) |
| LDHA-1413 Target: | 5'-CUGGGAAAAACAUCAACUCCUGAag-3'<br>3'-CUGACCCUUUUUGUAGUUGAGGACUUC-5'<br>5'-GACTGGGAAAAACATCAACTCCTGAAG-3' | (SEQ ID NO: 2301)<br>(SEQ ID NO: 4315)<br>(SEQ ID NO: 6329) |
| LDHA-1414 Target: | 5'-UGGGAAAAACAUCAACUCCUGAAgt-3'<br>3'-UGACCCUUUUUGUAGUUGAGGACUUCA-5'<br>5'-ACTGGGAAAAACATCAACTCCTGAAGT-3' | (SEQ ID NO: 2302)<br>(SEQ ID NO: 4316)<br>(SEQ ID NO: 6330) |
| LDHA-1415 Target: | 5'-GGGAAAAACAUCAACUCCUGAAGtt-3'<br>3'-GACCCUUUUUGUAGUUGAGGACUUCAA-5'<br>5'-CTGGGAAAAACATCAACTCCTGAAGTT-3' | (SEQ ID NO: 2303)<br>(SEQ ID NO: 4317)<br>(SEQ ID NO: 6331) |
| LDHA-1416 Target: | 5'-GGAAAAACAUCAACUCCUGAAGUta-3'<br>3'-ACCCUUUUUGUAGUUGAGGACUUCAAU-5'<br>5'-TGGAAAAACATCAACTCCTGAAGTTA-3' | (SEQ ID NO: 2304)<br>(SEQ ID NO: 4318)<br>(SEQ ID NO: 6332) |
| LDHA-1417 Target: | 5'-GAAAAACAUCAACUCCUGAAGUUag-3'<br>3'-CCCUUUUUGUAGUUGAGGACUUCAAUC-5'<br>5'-GGGAAAAACATCAACTCCTGAAGTTAG-3' | (SEQ ID NO: 2305)<br>(SEQ ID NO: 4319)<br>(SEQ ID NO: 6333) |
| LDHA-1418 Target: | 5'-AAAAACAUCAACUCCUGAAGUUAga-3'<br>3'-CCUUUUUGUAGUUGAGGACUUCAAUCU-5'<br>5'-GGAAAAACATCAACTCCTGAAGTTAGA-3' | (SEQ ID NO: 2306)<br>(SEQ ID NO: 4320)<br>(SEQ ID NO: 6334) |
| LDHA-1419 Target: | 5'-AAAACAUCAACUCCUGAAGUUAGaa-3'<br>3'-CUUUUUGUAGUUGAGGACUUCAAUCUU-5'<br>5'-GAAAAACATCAACTCCTGAAGTTAGAA-3' | (SEQ ID NO: 2307)<br>(SEQ ID NO: 4321)<br>(SEQ ID NO: 6335) |
| LDHA-1420 Target: | 5'-AAACAUCAACUCCUGAAGUUAGAaa-3'<br>3'-UUUUUGUAGUUGAGGACUUCAAUCUUU-5'<br>5'-AAAAACATCAACTCCTGAAGTTAGAAA-3' | (SEQ ID NO: 2308)<br>(SEQ ID NO: 4322)<br>(SEQ ID NO: 6336) |
| LDHA-1421 Target: | 5'-AACAUCAACUCCUGAAGUUAGAAat-3'<br>3'-UUUUGUAGUUGAGGACUUCAAUCUUUA-5'<br>5'-AAAACATCAACTCCTGAAGTTAGAAAT-3' | (SEQ ID NO: 2309)<br>(SEQ ID NO: 4323)<br>(SEQ ID NO: 6337) |
| LDHA-1422 Target: | 5'-ACAUCAACUCCUGAAGUUAGAAAta-3'<br>3'-UUUGUAGUUGAGGACUUCAAUCUUUAU-5'<br>5'-AAACATCAACTCCTGAAGTTAGAAATA-3' | (SEQ ID NO: 2310)<br>(SEQ ID NO: 4324)<br>(SEQ ID NO: 6338) |
| LDHA-1423 Target: | 5'-CAUCAACUCCUGAAGUUAGAAAUaa-3'<br>3'-UUGUAGUUGAGGACUUCAAUCUUUAUU-5'<br>5'-AACATCAACTCCTGAAGTTAGAAATAA-3' | (SEQ ID NO: 2311)<br>(SEQ ID NO: 4325)<br>(SEQ ID NO: 6339) |
| LDHA-1424 Target: | 5'-AUCAACUCCUGAAGUUAGAAAUAag-3'<br>3'-UGUAGUUGAGGACUUCAAUCUUUAUUC-5'<br>5'-ACATCAACTCCTGAAGTTAGAAATAAG-3' | (SEQ ID NO: 2312)<br>(SEQ ID NO: 4326)<br>(SEQ ID NO: 6340) |
| LDHA-1425 Target: | 5'-UCAACUCCUGAAGUUAGAAAUAAga-3'<br>3'-GUAGUUGAGGACUUCAAUCUUUAUUCU-5'<br>5'-CATCAACTCCTGAAGTTAGAAATAAGA-3' | (SEQ ID NO: 2313)<br>(SEQ ID NO: 4327)<br>(SEQ ID NO: 6341) |
| LDHA-1426 Target: | 5'-CAACUCCUGAAGUUAGAAAUAAGaa-3'<br>3'-UAGUUGAGGACUUCAAUCUUUAUUCUU-5'<br>5'-ATCAACTCCTGAAGTTAGAAATAAGAA-3' | (SEQ ID NO: 2314)<br>(SEQ ID NO: 4328)<br>(SEQ ID NO: 6342) |
| LDHA-1429 Target: | 5'-CUCCUGAAGUUAGAAAUAAGAAUgg-3'<br>3'-UUGAGGACUUCAAUCUUUAUUCUUACC-5'<br>5'-AACTCCTGAAGTTAGAAATAAGAATGG-3' | (SEQ ID NO: 2315)<br>(SEQ ID NO: 4329)<br>(SEQ ID NO: 6343) |

TABLE 12-continued

Additional Selected Human Anti-Lactate Dehydrogenase DsiRNA Agents (Asymmetrics)

```
                 5'-UCCUGAAGUUAGAAAUAAGAAUGgt-3'     (SEQ ID NO: 2316)
                 3'-UGAGGACUUCAAUCUUUAUUCUUACCA-5'   (SEQ ID NO: 4330)
LDHA-1430 Target: 5'-ACTCCTGAAGTTAGAAATAAGAATGGT-3'  (SEQ ID NO: 6344)

5'-CCUGAAGUUAGAAAUAAGAAUGGtt-3'     (SEQ ID NO: 2317)
                 3'-GAGGACUUCAAUCUUUAUUCUUACCAA-5'   (SEQ ID NO: 4331)
LDHA-1431 Target: 5'-CTCCTGAAGTTAGAAATAAGAATGGTT-3'  (SEQ ID NO: 6345)

5'-CUGAAGUUAGAAAUAAGAAUGGUtt-3'     (SEQ ID NO: 2318)
                 3'-AGGACUUCAAUCUUUAUUCUUACCAAA-5'   (SEQ ID NO: 4332)
LDHA-1432 Target: 5'-TCCTGAAGTTAGAAATAAGAATGGTTT-3'  (SEQ ID NO: 6346)

5'-UGAAGUUAGAAAUAAGAAUGGUUtg-3'     (SEQ ID NO: 2319)
                 3'-GGACUUCAAUCUUUAUUCUUACCAAAC-5'   (SEQ ID NO: 4333)
LDHA-1433 Target: 5'-CCTGAAGTTAGAAATAAGAATGGTTTG-3'  (SEQ ID NO: 6347)

5'-GAAGUUAGAAAUAAGAAUGGUUUgt-3'     (SEQ ID NO: 2320)
                 3'-GACUUCAAUCUUUAUUCUUACCAAACA-5'   (SEQ ID NO: 4334)
LDHA-1434 Target: 5'-CTGAAGTTAGAAATAAGAATGGTTTGT-3'  (SEQ ID NO: 6348)

5'-AAGUUAGAAAUAAGAAUGGUUUGta-3'     (SEQ ID NO: 2321)
                 3'-ACUUCAAUCUUUAUUCUUACCAAACAU-5'   (SEQ ID NO: 4335)
LDHA-1435 Target: 5'-TGAAGTTAGAAATAAGAATGGTTTGTA-3'  (SEQ ID NO: 6349)

5'-AGUUAGAAAUAAGAAUGGUUUGUaa-3'     (SEQ ID NO: 2322)
                 3'-CUUCAAUCUUUAUUCUUACCAAACAUU-5'   (SEQ ID NO: 4336)
LDHA-1436 Target: 5'-GAAGTTAGAAATAAGAATGGTTTGTAA-3'  (SEQ ID NO: 6350)

5'-GUUAGAAAUAAGAAUGGUUUGUAaa-3'     (SEQ ID NO: 2323)
                 3'-UUCAAUCUUUAUUCUUACCAAACAUUU-5'   (SEQ ID NO: 4337)
LDHA-1437 Target: 5'-AAGTTAGAAATAAGAATGGTTTGTAAA-3'  (SEQ ID NO: 6351)

5'-UUAGAAAUAAGAAUGGUUUGUAAaa-3'     (SEQ ID NO: 2324)
                 3'-UCAAUCUUUAUUCUUACCAAACAUUUU-5'   (SEQ ID NO: 4338)
LDHA-1438 Target: 5'-AGTTAGAAATAAGAATGGTTTGTAAAA-3' (SEQ ID NO: 6352)

5'-UAGAAAUAAGAAUGGUUUGUAAAat-3'     (SEQ ID NO: 2325)
                 3'-CAAUCUUUAUUCUUACCAAACAUUUUA-5'   (SEQ ID NO: 4339)
LDHA-1439 Target: 5'-GTTAGAAATAAGAATGGTTTGTAAAAT-3' (SEQ ID NO: 6353)

5'-AGAAAUAAGAAUGGUUUGUAAAAtc-3'     (SEQ ID NO: 2326)
                 3'-AAUCUUUAUUCUUACCAAACAUUUUAG-5'   (SEQ ID NO: 4340)
LDHA-1440 Target: 5'-TTAGAAATAAGAATGGTTTGTAAAATC-3' (SEQ ID NO: 6354)

5'-GAAAUAAGAAUGGUUUGUAAAAUcc-3'     (SEQ ID NO: 2327)
                 3'-AUCUUUAUUCUUACCAAACAUUUUAGG-5'   (SEQ ID NO: 4341)
LDHA-1441 Target: 5'-TAGAAATAAGAATGGTTTGTAAAATCC-3' (SEQ ID NO: 6355)

5'-AAAUAAGAAUGGUUUGUAAAAUCca-3'     (SEQ ID NO: 2328)
                 3'-UCUUUAUUCUUACCAAACAUUUUAGGU-5'   (SEQ ID NO: 4342)
LDHA-1442 Target: 5'-AGAAATAAGAATGGTTTGTAAAATCCA-3' (SEQ ID NO: 6356)

5'-AAUAAGAAUGGUUUGUAAAAUCCac-3'     (SEQ ID NO: 2329)
                 3'-CUUUAUUCUUACCAAACAUUUUAGGUG-5'   (SEQ ID NO: 4343)
LDHA-1443 Target: 5'-GAAATAAGAATGGTTTGTAAAATCCAC-3' (SEQ ID NO: 6357)

5'-AUAAGAAUGGUUUGUAAAAUCCAca-3'     (SEQ ID NO: 2330)
                 3'-UUUAUUCUUACCAAACAUUUUAGGUGU-5'   (SEQ ID NO: 4344)
LDHA-1444 Target: 5'-AAATAAGAATGGTTTGTAAAATCCACA-3' (SEQ ID NO: 6358)

5'-UAAGAAUGGUUUGUAAAAUCCACag-3'     (SEQ ID NO: 2331)
                 3'-UUAUUCUUACCAAACAUUUUAGGUGUC-5'   (SEQ ID NO: 4345)
LDHA-1445 Target: 5'-AATAAGAATGGTTTGTAAAATCCACAG-3' (SEQ ID NO: 6359)

5'-AAGAAUGGUUUGUAAAAUCCACAgc-3'     (SEQ ID NO: 2332)
                 3'-UAUUCUUACCAAACAUUUUAGGUGUCG-5'   (SEQ ID NO: 4346)
LDHA-1446 Target: 5'-ATAAGAATGGTTTGTAAAATCCACAGC-3' (SEQ ID NO: 6360)

5'-AGAAUGGUUUGUAAAAUCCACAGct-3'     (SEQ ID NO: 2333)
                 3'-AUUCUUACCAAACAUUUUAGGUGUCGA-5'   (SEQ ID NO: 4347)
LDHA-1447 Target: 5'-TAAGAATGGTTTGTAAAATCCACAGCT-3' (SEQ ID NO: 6361)

5'-GAAUGGUUUGUAAAAUCCACAGCta-3'     (SEQ ID NO: 2334)
                 3'-UUCUUACCAAACAUUUUAGGUGUCGAU-5'   (SEQ ID NO: 4348)
LDHA-1448 Target: 5'-AAGAATGGTTTGTAAAATCCACAGCTA-3' (SEQ ID NO: 6362)
```

TABLE 12-continued

Additional Selected Human Anti-Lactate Dehydrogenase DsiRNA Agents (Asymmetrics)

```
                 5'-AAUGGUUUGUAAAAUCCACAGCUat-3'      (SEQ ID NO: 2335)
                 3'-UCUUACCAAACAUUUUAGGUGUCGAUA-5'    (SEQ ID NO: 4349)
LDHA-1449 Target: 5'-AGAATGGTTTGTAAAATCCACAGCTAT-3'   (SEQ ID NO: 6363)

5'-AUGGUUUGUAAAAUCCACAGCUAta-3'      (SEQ ID NO: 2336)
                 3'-CUUUACCAAACAUUUUAGGUGUCGAUAU-5'   (SEQ ID NO: 4350)
LDHA-1450 Target: 5'-GAATGGTTTGTAAAATCCACAGCTATA-3'   (SEQ ID NO: 6364)

5'-UGGUUUGUAAAAUCCACAGCUAUat-3'      (SEQ ID NO: 2337)
                 3'-UUACCAAACAUUUUAGGUGUCGAUAUA-5'    (SEQ ID NO: 4351)
LDHA-1451 Target: 5'-AATGGTTTGTAAAATCCACAGCTATAT-3'   (SEQ ID NO: 6365)

5'-GGUUUGUAAAAUCCACAGCUAUAtc-3'      (SEQ ID NO: 2338)
                 3'-UACCAAACAUUUUAGGUGUCGAUAUAG-5'    (SEQ ID NO: 4352)
LDHA-1452 Target: 5'-ATGGTTTGTAAAATCCACAGCTATATC-3'   (SEQ ID NO: 6366)

5'-GUUUGUAAAAUCCACAGCUAUAUcc-3'      (SEQ ID NO: 2339)
                 3'-ACCAAACAUUUUAGGUGUCGAUAUAGG-5'    (SEQ ID NO: 4353)
LDHA-1453 Target: 5'-TGGTTTGTAAAATCCACAGCTATATCC-3'   (SEQ ID NO: 6367)

5'-UUUGUAAAAUCCACAGCUAUAUCct-3'      (SEQ ID NO: 2340)
                 3'-CCAAACAUUUUAGGUGUCGAUAUAGGA-5'    (SEQ ID NO: 4354)
LDHA-1454 Target: 5'-GGTTTGTAAAATCCACAGCTATATCCT-3'   (SEQ ID NO: 6368)

5'-UUGUAAAAUCCACAGCUAUAUCCtg-3'      (SEQ ID NO: 2341)
                 3'-CAAACAUUUUAGGUGUCGAUAUAGGAC-5'    (SEQ ID NO: 4355)
LDHA-1455 Target: 5'-GTTTGTAAAATCCACAGCTATATCCTG-3'   (SEQ ID NO: 6369)

5'-UGUAAAAUCCACAGCUAUAUCCUga-3'      (SEQ ID NO: 2342)
                 3'-AAACAUUUUAGGUGUCGAUAUAGGACU-5'    (SEQ ID NO: 4356)
LDHA-1456 Target: 5'-TTTGTAAAATCCACAGCTATATCCTGA-3'   (SEQ ID NO: 6370)

5'-GUAAAAUCCACAGCUAUAUCCUGat-3'      (SEQ ID NO: 2343)
                 3'-AACAUUUUAGGUGUCGAUAUAGGACUA-5'    (SEQ ID NO: 4357)
LDHA-1457 Target: 5'-TTGTAAAATCCACAGCTATATCCTGAT-3'   (SEQ ID NO: 6371)

5'-UAAAAUCCACAGCUAUAUCCUGAtg-3'      (SEQ ID NO: 2344)
                 3'-ACAUUUUAGGUGUCGAUAUAGGACUAC-5'    (SEQ ID NO: 4358)
LDHA-1458 Target: 5'-TGTAAAATCCACAGCTATATCCTGATG-3'   (SEQ ID NO: 6372)

5'-AAAAUCCACAGCUAUAUCCUGAUgc-3'      (SEQ ID NO: 2345)
                 3'-CAUUUUAGGUGUCGAUAUAGGACUACG-5'    (SEQ ID NO: 4359)
LDHA-1459 Target: 5'-GTAAAATCCACAGCTATATCCTGATGC-3'   (SEQ ID NO: 6373)

5'-AAAUCCACAGCUAUAUCCUGAUGct-3'      (SEQ ID NO: 2346)
                 3'-AUUUUAGGUGUCGAUAUAGGACUACGA-5'    (SEQ ID NO: 4360)
LDHA-1460 Target: 5'-TAAAATCCACAGCTATATCCTGATGCT-3'   (SEQ ID NO: 6374)

5'-AAUCCACAGCUAUAUCCUGAUGCtg-3'      (SEQ ID NO: 2347)
                 3'-UUUUAGGUGUCGAUAUAGGACUACGAC-5'    (SEQ ID NO: 4361)
LDHA-1461 Target: 5'-AAAATCCACAGCTATATCCTGATGCTG-3'   (SEQ ID NO: 6375)

5'-AUCCACAGCUAUAUCCUGAUGCUgg-3'      (SEQ ID NO: 2348)
                 3'-UUUAGGUGUCGAUAUAGGACUACGACC-5'    (SEQ ID NO: 4362)
LDHA-1462 Target: 5'-AAATCCACAGCTATATCCTGATGCTGG-3'   (SEQ ID NO: 6376)

5'-UCCACAGCUAUAUCCUGAUGCUGga-3'      (SEQ ID NO: 2349)
                 3'-UUAGGUGUCGAUAUAGGACUACGACCU-5'    (SEQ ID NO: 4363)
LDHA-1463 Target: 5'-AATCCACAGCTATATCCTGATGCTGGA-3'   (SEQ ID NO: 6377)

5'-CCACAGCUAUAUCCUGAUGCUGGat-3'      (SEQ ID NO: 2350)
                 3'-UAGGUGUCGAUAUAGGACUACGACCUA-5'    (SEQ ID NO: 4364)
LDHA-1464 Target: 5'-ATCCACAGCTATATCCTGATGCTGGAT-3'   (SEQ ID NO: 6378)

5'-CACAGCUAUAUCCUGAUGCUGGAtg-3'      (SEQ ID NO: 2351)
                 3'-AGGUGUCGAUAUAGGACUACGACCUAC-5'    (SEQ ID NO: 4365)
LDHA-1465 Target: 5'-TCCACAGCTATATCCTGATGCTGGATG-3'   (SEQ ID NO: 6379)

5'-ACAGCUAUAUCCUGAUGCUGGAUgg-3'      (SEQ ID NO: 2352)
                 3'-GGUGUCGAUAUAGGACUACGACCUACC-5'    (SEQ ID NO: 4366)
LDHA-1466 Target: 5'-CCACAGCTATATCCTGATGCTGGATGG-3'   (SEQ ID NO: 6380)

5'-CAGCUAUAUCCUGAUGCUGGAUGgt-3'      (SEQ ID NO: 2353)
                 3'-GUGUCGAUAUAGGACUACGACCUACCA-5'    (SEQ ID NO: 4367)
LDHA-1467 Target: 5'-CACAGCTATATCCTGATGCTGGATGGT-3'   (SEQ ID NO: 6381)
```

TABLE 12-continued

Additional Selected Human Anti-Lactate Dehydrogenase DsiRNA Agents (Asymmetrics)

```
              5'-AGCUAUAUCCUGAUGCUGGAUGGta-3'      (SEQ ID NO: 2354)
              3'-UGUCGAUAUAGGACUACGACCUACCAU-5'    (SEQ ID NO: 4368)
LDHA-1468 Target: 5'-ACAGCTATATCCTGATGCTGGATGGTA-3' (SEQ ID NO: 6382)

5'-GCUAUAUCCUGAUGCUGGAUGGUat-3'      (SEQ ID NO: 2355)
              3'-GUCGAUAUAGGACUACGACCUACCAUA-5'    (SEQ ID NO: 4369)
LDHA-1469 Target: 5'-CAGCTATATCCTGATGCTGGATGGTAT-3' (SEQ ID NO: 6383)

5'-CUAUAUCCUGAUGCUGGAUGGUAtt-3'     (SEQ ID NO: 2356)
              3'-UCGAUAUAGGACUACGACCUACCAUAA-5'   (SEQ ID NO: 4370)
LDHA-1470 Target: 5'-AGCTATATCCTGATGCTGGATGGTATT-3' (SEQ ID NO: 6384)

5'-UAUAUCCUGAUGCUGGAUGGUAUta-3'     (SEQ ID NO: 2357)
              3'-CGAUAUAGGACUACGACCUACCAUAAU-5'   (SEQ ID NO: 4371)
LDHA-1471 Target: 5'-GCTATATCCTGATGCTGGATGGTATTA-3' (SEQ ID NO: 6385)

5'-AUAUCCUGAUGCUGGAUGGUAUUaa-3'     (SEQ ID NO: 2358)
              3'-GAUAUAGGACUACGACCUACCAUAAUU-5'   (SEQ ID NO: 4372)
LDHA-1472 Target: 5'-CTATATCCTGATGCTGGATGGTATTAA-3' (SEQ ID NO: 6386)

5'-UAUCCUGAUGCUGGAUGGUAUUAat-3'     (SEQ ID NO: 2359)
              3'-AUAUAGGACUACGACCUACCAUAAUUA-5'   (SEQ ID NO: 4373)
LDHA-1473 Target: 5'-TATATCCTGATGCTGGATGGTATTAAT-3' (SEQ ID NO: 6387)

5'-AUCCUGAUGCUGGAUGGUAUUAAtc-3'     (SEQ ID NO: 2360)
              3'-UAUAGGACUACGACCUACCAUAAUUAG-5'   (SEQ ID NO: 4374)
LDHA-1474 Target: 5'-ATATCCTGATGCTGGATGGTATTAATC-3' (SEQ ID NO: 6388)

5'-UCCUGAUGCUGGAUGGUAUUAAUct-3'     (SEQ ID NO: 2361)
              3'-AUAGGACUACGACCUACCAUAAUUAGA-5'   (SEQ ID NO: 4375)
LDHA-1475 Target: 5'-TATCCTGATGCTGGATGGTATTAATCT-3' (SEQ ID NO: 6389)

5'-CCUGAUGCUGGAUGGUAUUAAUCtt-3'     (SEQ ID NO: 2362)
              3'-UAGGACUACGACCUACCAUAAUUAGAA-5'   (SEQ ID NO: 4376)
LDHA-1476 Target: 5'-ATCCTGATGCTGGATGGTATTAATCTT-3' (SEQ ID NO: 6390)

5'-CUGAUGCUGGAUGGUAUUAAUCUtg-3'     (SEQ ID NO: 2363)
              3'-AGGACUACGACCUACCAUAAUUAGAAC-5'   (SEQ ID NO: 4377)
LDHA-1477 Target: 5'-TCCTGATGCTGGATGGTATTAATCTTG-3' (SEQ ID NO: 6391)

5'-UGAUGCUGGAUGGUAUUAAUCUUgt-3'     (SEQ ID NO: 2364)
              3'-GGACUACGACCUACCAUAAUUAGAACA-5'   (SEQ ID NO: 4378)
LDHA-1478 Target: 5'-CCTGATGCTGGATGGTATTAATCTTGT-3' (SEQ ID NO: 6392)

5'-GAUGCUGGAUGGUAUUAAUCUUGtg-3'     (SEQ ID NO: 2365)
              3'-GACUACGACCUACCAUAAUUAGAACAC-5'   (SEQ ID NO: 4379)
LDHA-1479 Target: 5'-CTGATGCTGGATGGTATTAATCTTGTG-3' (SEQ ID NO: 6393)

5'-AUGCUGGAUGGUAUUAAUCUUGUgt-3'     (SEQ ID NO: 2366)
              3'-ACUACGACCUACCAUAAUUAGAACACA-5'   (SEQ ID NO: 4380)
LDHA-1480 Target: 5'-TGATGCTGGATGGTATTAATCTTGTGT-3' (SEQ ID NO: 6394)

5'-UGCUGGAUGGUAUUAAUCUUGUGta-3'     (SEQ ID NO: 2367)
              3'-CUACGACCUACCAUAAUUAGAACACAU-5'   (SEQ ID NO: 4381)
LDHA-1481 Target: 5'-GATGCTGGATGGTATTAATCTTGTGTA-3' (SEQ ID NO: 6395)

5'-GCUGGAUGGUAUUAAUCUUGUGUag-3'     (SEQ ID NO: 2368)
              3'-UACGACCUACCAUAAUUAGAACACAUC-5'   (SEQ ID NO: 4382)
LDHA-1482 Target: 5'-ATGCTGGATGGTATTAATCTTGTGTAG-3' (SEQ ID NO: 6396)

5'-CUGGAUGGUAUUAAUCUUGUGUAgt-3'     (SEQ ID NO: 2369)
              3'-ACGACCUACCAUAAUUAGAACACAUCA-5'   (SEQ ID NO: 4383)
LDHA-1483 Target: 5'-TGCTGGATGGTATTAATCTTGTGTAGT-3' (SEQ ID NO: 6397)

5'-UGGAUGGUAUUAAUCUUGUGUAGtc-3'     (SEQ ID NO: 2370)
              3'-CGACCUACCAUAAUUAGAACACAUCAG-5'   (SEQ ID NO: 4384)
LDHA-1484 Target: 5'-GCTGGATGGTATTAATCTTGTGTAGTC-3' (SEQ ID NO: 6398)

5'-GGAUGGUAUUAAUCUUGUGUAGUct-3'     (SEQ ID NO: 2371)
              3'-GACCUACCAUAAUUAGAACACAUCAGA-5'   (SEQ ID NO: 4385)
LDHA-1485 Target: 5'-CTGGATGGTATTAATCTTGTGTAGTCT-3' (SEQ ID NO: 6399)

5'-GAUGGUAUUAAUCUUGUGUAGUCtt-3'     (SEQ ID NO: 2372)
              3'-ACCUACCAUAAUUAGAACACAUCAGAA-5'   (SEQ ID NO: 4386)
LDHA-1486 Target: 5'-TGGATGGTATTAATCTTGTGTAGTCTT-3' (SEQ ID NO: 6400)
```

TABLE 12-continued

Additional Selected Human Anti-Lactate Dehydrogenase DsiRNA Agents (Asymmetrics)

|  |  |  |
|---|---|---|
|  | 5'-AUGGUAUUAAUCUUGUGUAGUCUtc-3' | (SEQ ID NO: 2373) |
|  | 3'-CCUACCAUAAUUAGAACACAUCAGAAG-5' | (SEQ ID NO: 4387) |
| LDHA-1487 Target: | 5'-GGATGGTATTAATCTTGTGTAGTCTTC-3' | (SEQ ID NO: 6401) |
|  | 5'-UGGUAUUAAUCUUGUGUAGUCUUca-3' | (SEQ ID NO: 2374) |
|  | 3'-CUACCAUAAUUAGAACACAUCAGAAGU-5' | (SEQ ID NO: 4388) |
| LDHA-1488 Target: | 5'-GATGGTATTAATCTTGTGTAGTCTTCA-3' | (SEQ ID NO: 6402) |
|  | 5'-GGUAUUAAUCUUGUGUAGUCUUCaa-3' | (SEQ ID NO: 2375) |
|  | 3'-UACCAUAAUUAGAACACAUCAGAAGUU-5' | (SEQ ID NO: 4389) |
| LDHA-1489 Target: | 5'-ATGGTATTAATCTTGTGTAGTCTTCAA-3' | (SEQ ID NO: 6403) |
|  | 5'-GUAUUAAUCUUGUGUAGUCUUCAac-3' | (SEQ ID NO: 2376) |
|  | 3'-ACCAUAAUUAGAACACAUCAGAAGUUG-5' | (SEQ ID NO: 4390) |
| LDHA-1490 Target: | 5'-TGGTATTAATCTTGTGTAGTCTTCAAC-3' | (SEQ ID NO: 6404) |
|  | 5'-UAUUAAUCUUGUGUAGUCUUCAAct-3' | (SEQ ID NO: 2377) |
|  | 3'-CCAUAAUUAGAACACAUCAGAAGUUGA-5' | (SEQ ID NO: 4391) |
| LDHA-1491 Target: | 5'-GGTATTAATCTTGTGTAGTCTTCAACT-3' | (SEQ ID NO: 6405) |
|  | 5'-AUUAAUCUUGUGUAGUCUUCAACtg-3' | (SEQ ID NO: 2378) |
|  | 3'-CAUAAUUAGAACACAUCAGAAGUUGAC-5' | (SEQ ID NO: 4392) |
| LDHA-1492 Target: | 5'-GTATTAATCTTGTGTAGTCTTCAACTG-3' | (SEQ ID NO: 6406) |
|  | 5'-UUAAUCUUGUGUAGUCUUCAACUgg-3' | (SEQ ID NO: 2379) |
|  | 3'-AUAAUUAGAACACAUCAGAAGUUGACC-5' | (SEQ ID NO: 4393) |
| LDHA-1493 Target: | 5'-TATTAATCTTGTGTAGTCTTCAACTGG-3' | (SEQ ID NO: 6407) |
|  | 5'-UAAUCUUGUGUAGUCUUCAACUGgt-3' | (SEQ ID NO: 2380) |
|  | 3'-UAAUUAGAACACAUCAGAAGUUGACCA-5' | (SEQ ID NO: 4394) |
| LDHA-1494 Target: | 5'-ATTAATCTTGTGTAGTCTTCAACTGGT-3' | (SEQ ID NO: 6408) |
|  | 5'-AAUCUUGUGUAGUCUUCAACUGGtt-3' | (SEQ ID NO: 2381) |
|  | 3'-AAUUAGAACACAUCAGAAGUUGACCAA-5' | (SEQ ID NO: 4395) |
| LDHA-1495 Target: | 5'-TTAATCTTGTGTAGTCTTCAACTGGTT-3' | (SEQ ID NO: 6409) |
|  | 5'-AUCUUGUGUAGUCUUCAACUGGUta-3' | (SEQ ID NO: 2382) |
|  | 3'-AUUAGAACACAUCAGAAGUUGACCAAU-5' | (SEQ ID NO: 4396) |
| LDHA-1496 Target: | 5'-TAATCTTGTGTAGTCTTCAACTGGTTA-3' | (SEQ ID NO: 6410) |
|  | 5'-UCUUGUGUAGUCUUCAACUGGUUag-3' | (SEQ ID NO: 2383) |
|  | 3'-UUAGAACACAUCAGAAGUUGACCAAUC-5' | (SEQ ID NO: 4397) |
| LDHA-1497 Target: | 5'-AATCTTGTGTAGTCTTCAACTGGTTAG-3' | (SEQ ID NO: 6411) |
|  | 5'-CUUGUGUAGUCUUCAACUGGUUAgt-3' | (SEQ ID NO: 2384) |
|  | 3'-UAGAACACAUCAGAAGUUGACCAAUCA-5' | (SEQ ID NO: 4398) |
| LDHA-1498 Target: | 5'-ATCTTGTGTAGTCTTCAACTGGTTAGT-3' | (SEQ ID NO: 6412) |
|  | 5'-UUGUGUAGUCUUCAACUGGUUAGtg-3' | (SEQ ID NO: 2385) |
|  | 3'-AGAACACAUCAGAAGUUGACCAAUCAC-5' | (SEQ ID NO: 4399) |
| LDHA-1499 Target: | 5'-TCTTGTGTAGTCTTCAACTGGTTAGTG-3' | (SEQ ID NO: 6413) |
|  | 5'-UGUGUAGUCUUCAACUGGUUAGUgt-3' | (SEQ ID NO: 2386) |
|  | 3'-GAACACAUCAGAAGUUGACCAAUCACA-5' | (SEQ ID NO: 4400) |
| LDHA-1500 Target: | 5'-CTTGTGTAGTCTTCAACTGGTTAGTGT-3' | (SEQ ID NO: 6414) |
|  | 5'-GUGUAGUCUUCAACUGGUUAGUGtg-3' | (SEQ ID NO: 2387) |
|  | 3'-AACACAUCAGAAGUUGACCAAUCACAC-5' | (SEQ ID NO: 4401) |
| LDHA-1501 Target: | 5'-TTGTGTAGTCTTCAACTGGTTAGTGTG-3' | (SEQ ID NO: 6415) |
|  | 5'-UGUAGUCUUCAACUGGUUAGUGUga-3' | (SEQ ID NO: 2388) |
|  | 3'-ACACAUCAGAAGUUGACCAAUCACACU-5' | (SEQ ID NO: 4402) |
| LDHA-1502 Target: | 5'-TGTGTAGTCTTCAACTGGTTAGTGTGA-3' | (SEQ ID NO: 6416) |
|  | 5'-GUAGUCUUCAACUGGUUAGUGUGaa-3' | (SEQ ID NO: 2389) |
|  | 3'-CACAUCAGAAGUUGACCAAUCACACUU-5' | (SEQ ID NO: 4403) |
| LDHA-1503 Target: | 5'-GTGTAGTCTTCAACTGGTTAGTGTGAA-3' | (SEQ ID NO: 6417) |
|  | 5'-UAGUCUUCAACUGGUUAGUGUGAaa-3' | (SEQ ID NO: 2390) |
|  | 3'-ACAUCAGAAGUUGACCAAUCACACUUU-5' | (SEQ ID NO: 4404) |
| LDHA-1504 Target: | 5'-TGTAGTCTTCAACTGGTTAGTGTGAAA-3' | (SEQ ID NO: 6418) |
|  | 5'-AGUCUUCAACUGGUUAGUGUGAAat-3' | (SEQ ID NO: 2391) |
|  | 3'-CAUCAGAAGUUGACCAAUCACACUUUA-5' | (SEQ ID NO: 4405) |
| LDHA-1505 Target: | 5'-GTAGTCTTCAACTGGTTAGTGTGAAAT-3' | (SEQ ID NO: 6419) |

TABLE 12-continued

Additional Selected Human Anti-Lactate Dehydrogenase DsiRNA Agents (Asymmetrics)

| | | |
|---|---|---|
| LDHA-1506 | 5'-GUCUUCAACUGGUUAGUGUGAAAta-3'<br>3'-AUCAGAAGUUGACCAAUCACACUUUAU-5'<br>Target: 5'-TAGTCTTCAACTGGTTAGTGTGAAATA-3' | (SEQ ID NO: 2392)<br>(SEQ ID NO: 4406)<br>(SEQ ID NO: 6420) |
| LDHA-1507 | 5'-UCUUCAACUGGUUAGUGUGAAAUag-3'<br>3'-UCAGAAGUUGACCAAUCACACUUUAUC-5'<br>Target: 5'-AGTCTTCAACTGGTTAGTGTGAAATAG-3' | (SEQ ID NO: 2393)<br>(SEQ ID NO: 4407)<br>(SEQ ID NO: 6421) |
| LDHA-1508 | 5'-CUUCAACUGGUUAGUGUGAAAUAgt-3'<br>3'-CAGAAGUUGACCAAUCACACUUUAUCA-5'<br>Target: 5'-GTCTTCAACTGGTTAGTGTGAAATAGT-3' | (SEQ ID NO: 2394)<br>(SEQ ID NO: 4408)<br>(SEQ ID NO: 6422) |
| LDHA-1509 | 5'-UUCAACUGGUUAGUGUGAAAUAGtt-3'<br>3'-AGAAGUUGACCAAUCACACUUUAUCAA-5'<br>Target: 5'-TCTTCAACTGGTTAGTGTGAAATAGTT-3' | (SEQ ID NO: 2395)<br>(SEQ ID NO: 4409)<br>(SEQ ID NO: 6423) |
| LDHA-1510 | 5'-UCAACUGGUUAGUGUGAAAUAGUtc-3'<br>3'-GAAGUUGACCAAUCACACUUUAUCAAG-5'<br>Target: 5'-CTTCAACTGGTTAGTGTGAAATAGTTC-3' | (SEQ ID NO: 2396)<br>(SEQ ID NO: 4410)<br>(SEQ ID NO: 6424) |
| LDHA-1511 | 5'-CAACUGGUUAGUGUGAAAUAGUUct-3'<br>3'-AAGUUGACCAAUCACACUUUAUCAAGA-5'<br>Target: 5'-TTCAACTGGTTAGTGTGAAATAGTTCT-3' | (SEQ ID NO: 2397)<br>(SEQ ID NO: 4411)<br>(SEQ ID NO: 6425) |
| LDHA-1515 | 5'-UGGUUAGUGUGAAAUAGUUCUGCca-3'<br>3'-UGACCAAUCACACUUUAUCAAGACGGU-5'<br>Target: 5'-ACTGGTTAGTGTGAAATAGTTCTGCCA-3' | (SEQ ID NO: 2398)<br>(SEQ ID NO: 4412)<br>(SEQ ID NO: 6426) |
| LDHA-1517 | 5'-GUUAGUGUGAAAUAGUUCUGCCAcc-3'<br>3'-ACCAAUCACACUUUAUCAAGACGGUGG-5'<br>Target: 5'-TGGTTAGTGTGAAATAGTTCTGCCACC-3' | (SEQ ID NO: 2399)<br>(SEQ ID NO: 4413)<br>(SEQ ID NO: 6427) |
| LDHA-1518 | 5'-UUAGUGUGAAAUAGUUCUGCCACct-3'<br>3'-CCAAUCACACUUUAUCAAGACGGUGGA-5'<br>Target: 5'-GGTTAGTGTGAAATAGTTCTGCCACCT-3' | (SEQ ID NO: 2400)<br>(SEQ ID NO: 4414)<br>(SEQ ID NO: 6428) |
| LDHA-1519 | 5'-UAGUGUGAAAUAGUUCUGCCACCtc-3'<br>3'-CAAUCACACUUUAUCAAGACGGUGGAG-5'<br>Target: 5'-GTTAGTGTGAAATAGTTCTGCCACCTC-3' | (SEQ ID NO: 2401)<br>(SEQ ID NO: 4415)<br>(SEQ ID NO: 6429) |
| LDHA-1520 | 5'-AGUGUGAAAUAGUUCUGCCACCUct-3'<br>3'-AAUCACACUUUAUCAAGACGGUGGAGA-5'<br>Target: 5'-TTAGTGTGAAATAGTTCTGCCACCTCT-3' | (SEQ ID NO: 2402)<br>(SEQ ID NO: 4416)<br>(SEQ ID NO: 6430) |
| LDHA-1521 | 5'-GUGUGAAAUAGUUCUGCCACCUCtg-3'<br>3'-AUCACACUUUAUCAAGACGGUGGAGAC-5'<br>Target: 5'-TAGTGTGAAATAGTTCTGCCACCTCTG-3' | (SEQ ID NO: 2403)<br>(SEQ ID NO: 4417)<br>(SEQ ID NO: 6431) |
| LDHA-1522 | 5'-UGUGAAAUAGUUCUGCCACCUCUga-3'<br>3'-UCACACUUUAUCAAGACGGUGGAGACU-5'<br>Target: 5'-AGTGTGAAATAGTTCTGCCACCTCTGA-3' | (SEQ ID NO: 2404)<br>(SEQ ID NO: 4418)<br>(SEQ ID NO: 6432) |
| LDHA-1523 | 5'-GUGAAAUAGUUCUGCCACCUCUGac-3'<br>3'-CACACUUUAUCAAGACGGUGGAGACUG-5'<br>Target: 5'-GTGTGAAATAGTTCTGCCACCTCTGAC-3' | (SEQ ID NO: 2405)<br>(SEQ ID NO: 4419)<br>(SEQ ID NO: 6433) |
| LDHA-1524 | 5'-UGAAAUAGUUCUGCCACCUCUGAcg-3'<br>3'-ACACUUUAUCAAGACGGUGGAGACUGC-5'<br>Target: 5'-TGTGAAATAGTTCTGCCACCTCTGACG-3' | (SEQ ID NO: 2406)<br>(SEQ ID NO: 4420)<br>(SEQ ID NO: 6434) |
| LDHA-1525 | 5'-GAAAUAGUUCUGCCACCUCUGACgc-3'<br>3'-CACUUUAUCAAGACGGUGGAGACUGCG-5'<br>Target: 5'-GTGAAATAGTTCTGCCACCTCTGACGC-3' | (SEQ ID NO: 2407)<br>(SEQ ID NO: 4421)<br>(SEQ ID NO: 6435) |
| LDHA-1526 | 5'-AAAUAGUUCUGCCACCUCUGACGca-3'<br>3'-ACUUUAUCAAGACGGUGGAGACUGCGU-5'<br>Target: 5'-TGAAATAGTTCTGCCACCTCTGACGCA-3' | (SEQ ID NO: 2408)<br>(SEQ ID NO: 4422)<br>(SEQ ID NO: 6436) |
| LDHA-1527 | 5'-AAUAGUUCUGCCACCUCUGACGCac-3'<br>3'-CUUUAUCAAGACGGUGGAGACUGCGUG-5'<br>Target: 5'-GAAATAGTTCTGCCACCTCTGACGCAC-3' | (SEQ ID NO: 2409)<br>(SEQ ID NO: 4423)<br>(SEQ ID NO: 6437) |
| LDHA-1528 | 5'-AUAGUUCUGCCACCUCUGACGCAcc-3'<br>3'-UUUAUCAAGACGGUGGAGACUGCGUGG-5'<br>Target: 5'-AAATAGTTCTGCCACCTCTGACGCACC-3' | (SEQ ID NO: 2410)<br>(SEQ ID NO: 4424)<br>(SEQ ID NO: 6438) |

TABLE 12-continued

Additional Selected Human Anti-Lactate Dehydrogenase DsiRNA Agents (Asymmetrics)

|  |  |  |
|---|---|---|
| LDHA-1529 Target: | 5'-UAGUUCUGCCACCUCUGACGCACca-3'<br>3'-UUAUCAAGACGGUGGAGACUGCGUGGU-5'<br>5'-AATAGTTCTGCCACCTCTGACGCACCA-3' | (SEQ ID NO: 2411)<br>(SEQ ID NO: 4425)<br>(SEQ ID NO: 6439) |
| LDHA-1530 Target: | 5'-AGUUCUGCCACCUCUGACGCACCac-3'<br>3'-UAUCAAGACGGUGGAGACUGCGUGGUG-5'<br>5'-ATAGTTCTGCCACCTCTGACGCACCAC-3' | (SEQ ID NO: 2412)<br>(SEQ ID NO: 4426)<br>(SEQ ID NO: 6440) |
| LDHA-1531 Target: | 5'-GUUCUGCCACCUCUGACGCACCAct-3'<br>3'-AUCAAGACGGUGGAGACUGCGUGGUGA-5'<br>5'-TAGTTCTGCCACCTCTGACGCACCACT-3' | (SEQ ID NO: 2413)<br>(SEQ ID NO: 4427)<br>(SEQ ID NO: 6441) |
| LDHA-1532 Target: | 5'-UUCUGCCACCUCUGACGCACCACtg-3'<br>3'-UCAAGACGGUGGAGACUGCGUGGUGAC-5'<br>5'-AGTTCTGCCACCTCTGACGCACCACTG-3' | (SEQ ID NO: 2414)<br>(SEQ ID NO: 4428)<br>(SEQ ID NO: 6442) |
| LDHA-1533 Target: | 5'-UCUGCCACCUCUGACGCACCACUgc-3'<br>3'-CAAGACGGUGGAGACUGCGUGGUGACG-5'<br>5'-GTTCTGCCACCTCTGACGCACCACTGC-3' | (SEQ ID NO: 2415)<br>(SEQ ID NO: 4429)<br>(SEQ ID NO: 6443) |
| LDHA-1534 Target: | 5'-CUGCCACCUCUGACGCACCACUGcc-3'<br>3'-AAGACGGUGGAGACUGCGUGGUGACGG-5'<br>5'-TTCTGCCACCTCTGACGCACCACTGCC-3' | (SEQ ID NO: 2416)<br>(SEQ ID NO: 4430)<br>(SEQ ID NO: 6444) |
| LDHA-1535 Target: | 5'-UGCCACCUCUGACGCACCACUGCca-3'<br>3'-AGACGGUGGAGACUGCGUGGUGACGGU-5'<br>5'-TCTGCCACCTCTGACGCACCACTGCCA-3' | (SEQ ID NO: 2417)<br>(SEQ ID NO: 4431)<br>(SEQ ID NO: 6445) |
| LDHA-1536 Target: | 5'-GCCACCUCUGACGCACCACUGCCaa-3'<br>3'-GACGGUGGAGACUGCGUGGUGACGGUU-5'<br>5'-CTGCCACCTCTGACGCACCACTGCCAA-3' | (SEQ ID NO: 2418)<br>(SEQ ID NO: 4432)<br>(SEQ ID NO: 6446) |
| LDHA-1537 Target: | 5'-CCACCUCUGACGCACCACUGCCAat-3'<br>3'-ACGGUGGAGACUGCGUGGUGACGGUUA-5'<br>5'-TGCCACCTCTGACGCACCACTGCCAAT-3' | (SEQ ID NO: 2419)<br>(SEQ ID NO: 4433)<br>(SEQ ID NO: 6447) |
| LDHA-1538 Target: | 5'-CACCUCUGACGCACCACUGCCAAtg-3'<br>3'-CGGUGGAGACUGCGUGGUGACGGUUAC-5'<br>5'-GCCACCTCTGACGCACCACTGCCAATG-3' | (SEQ ID NO: 2420)<br>(SEQ ID NO: 4434)<br>(SEQ ID NO: 6448) |
| LDHA-1539 Target: | 5'-ACCUCUGACGCACCACUGCCAAUgc-3'<br>3'-GGUGGAGACUGCGUGGUGACGGUUACG-5'<br>5'-CCACCTCTGACGCACCACTGCCAATGC-3' | (SEQ ID NO: 2421)<br>(SEQ ID NO: 4435)<br>(SEQ ID NO: 6449) |
| LDHA-1540 Target: | 5'-CCUCUGACGCACCACUGCCAAUGct-3'<br>3'-GUGGAGACUGCGUGGUGACGGUUACGA-5'<br>5'-CACCTCTGACGCACCACTGCCAATGCT-3' | (SEQ ID NO: 2422)<br>(SEQ ID NO: 4436)<br>(SEQ ID NO: 6450) |
| LDHA-1541 Target: | 5'-CUCUGACGCACCACUGCCAAUGCtg-3'<br>3'-UGGAGACUGCGUGGUGACGGUUACGAC-5'<br>5'-ACCTCTGACGCACCACTGCCAATGCTG-3' | (SEQ ID NO: 2423)<br>(SEQ ID NO: 4437)<br>(SEQ ID NO: 6451) |
| LDHA-1542 Target: | 5'-UCUGACGCACCACUGCCAAUGCUgt-3'<br>3'-GGAGACUGCGUGGUGACGGUUACGACA-5'<br>5'-CCTCTGACGCACCACTGCCAATGCTGT-3' | (SEQ ID NO: 2424)<br>(SEQ ID NO: 4438)<br>(SEQ ID NO: 6452) |
| LDHA-1543 Target: | 5'-CUGACGCACCACUGCCAAUGCUGta-3'<br>3'-GAGACUGCGUGGUGACGGUUACGACAU-5'<br>5'-CTCTGACGCACCACTGCCAATGCTGTA-3' | (SEQ ID NO: 2425)<br>(SEQ ID NO: 4439)<br>(SEQ ID NO: 6453) |
| LDHA-1544 Target: | 5'-UGACGCACCACUGCCAAUGCUGUac-3'<br>3'-AGACUGCGUGGUGACGGUUACGACAUG-5'<br>5'-TCTGACGCACCACTGCCAATGCTGTAC-3' | (SEQ ID NO: 2426)<br>(SEQ ID NO: 4440)<br>(SEQ ID NO: 6454) |
| LDHA-1545 Target: | 5'-GACGCACCACUGCCAAUGCUGUAcg-3'<br>3'-GACUGCGUGGUGACGGUUACGACAUGC-5'<br>5'-CTGACGCACCACTGCCAATGCTGTACG-3' | (SEQ ID NO: 2427)<br>(SEQ ID NO: 4441)<br>(SEQ ID NO: 6455) |
| LDHA-1546 Target: | 5'-ACGCACCACUGCCAAUGCUGUACgt-3'<br>3'-ACUGCGUGGUGACGGUUACGACAUGCA-5'<br>5'-TGACGCACCACTGCCAATGCTGTACGT-3' | (SEQ ID NO: 2428)<br>(SEQ ID NO: 4442)<br>(SEQ ID NO: 6456) |
| LDHA-1547 Target: | 5'-CGCACCACUGCCAAUGCUGUACGta-3'<br>3'-CUGCGUGGUGACGGUUACGACAUGCAU-5'<br>5'-GACGCACCACTGCCAATGCTGTACGTA-3' | (SEQ ID NO: 2429)<br>(SEQ ID NO: 4443)<br>(SEQ ID NO: 6457) |

TABLE 12-continued

Additional Selected Human Anti-Lactate Dehydrogenase DsiRNA Agents (Asymmetrics)

|  |  |  |
| --- | --- | --- |
| LDHA-1548 Target: | 5'-GCACCACUGCCAAUGCUGUACGUac-3'<br>3'-UGCGUGGUGACGGUUACGACAUGCAUG-5'<br>5'-ACGCACCACTGCCAATGCTGTACGTAC-3' | (SEQ ID NO: 2430)<br>(SEQ ID NO: 4444)<br>(SEQ ID NO: 6458) |
| LDHA-1549 Target: | 5'-CACCACUGCCAAUGCUGUACGUAct-3'<br>3'-GCGUGGUGACGGUUACGACAUGCAUGA-5'<br>5'-CGCACCACTGCCAATGCTGTACGTACT-3' | (SEQ ID NO: 2431)<br>(SEQ ID NO: 4445)<br>(SEQ ID NO: 6459) |
| LDHA-1550 Target: | 5'-ACCACUGCCAAUGCUGUACGUACtg-3'<br>3'-CGUGGUGACGGUUACGACAUGCAUGAC-5'<br>5'-GCACCACTGCCAATGCTGTACGTACTG-3' | (SEQ ID NO: 2432)<br>(SEQ ID NO: 4446)<br>(SEQ ID NO: 6460) |
| LDHA-1551 Target: | 5'-CCACUGCCAAUGCUGUACGUACUgc-3'<br>3'-GUGGUGACGGUUACGACAUGCAUGACG-5'<br>5'-CACCACTGCCAATGCTGTACGTACTGC-3' | (SEQ ID NO: 2433)<br>(SEQ ID NO: 4447)<br>(SEQ ID NO: 6461) |
| LDHA-1552 Target: | 5'-CACUGCCAAUGCUGUACGUACUGca-3'<br>3'-UGGUGACGGUUACGACAUGCAUGACGU-5'<br>5'-ACCACTGCCAATGCTGTACGTACTGCA-3' | (SEQ ID NO: 2434)<br>(SEQ ID NO: 4448)<br>(SEQ ID NO: 6462) |
| LDHA-1553 Target: | 5'-ACUGCCAAUGCUGUACGUACUGCat-3'<br>3'-GGUGACGGUUACGACAUGCAUGACGUA-5'<br>5'-CCACTGCCAATGCTGTACGTACTGCAT-3' | (SEQ ID NO: 2435)<br>(SEQ ID NO: 4449)<br>(SEQ ID NO: 6463) |
| LDHA-1554 Target: | 5'-CUGCCAAUGCUGUACGUACUGCAtt-3'<br>3'-GUGACGGUUACGACAUGCAUGACGUAA-5'<br>5'-CACTGCCAATGCTGTACGTACTGCATT-3' | (SEQ ID NO: 2436)<br>(SEQ ID NO: 4450)<br>(SEQ ID NO: 6464) |
| LDHA-1555 Target: | 5'-UGCCAAUGCUGUACGUACUGCAUtt-3'<br>3'-UGACGGUUACGACAUGCAUGACGUAAA-5'<br>5'-ACTGCCAATGCTGTACGTACTGCATTT-3' | (SEQ ID NO: 2437)<br>(SEQ ID NO: 4451)<br>(SEQ ID NO: 6465) |
| LDHA-1556 Target: | 5'-GCCAAUGCUGUACGUACUGCAUUtg-3'<br>3'-GACGGUUACGACAUGCAUGACGUAAAC-5'<br>5'-CTGCCAATGCTGTACGTACTGCATTTG-3' | (SEQ ID NO: 2438)<br>(SEQ ID NO: 4452)<br>(SEQ ID NO: 6466) |
| LDHA-1557 Target: | 5'-CCAAUGCUGUACGUACUGCAUUUgc-3'<br>3'-ACGGUUACGACAUGCAUGACGUAAACG-5'<br>5'-TGCCAATGCTGTACGTACTGCATTTGC-3' | (SEQ ID NO: 2439)<br>(SEQ ID NO: 4453)<br>(SEQ ID NO: 6467) |
| LDHA-1558 Target: | 5'-CAAUGCUGUACGUACUGCAUUUGcc-3'<br>3'-CGGUUACGACAUGCAUGACGUAAACGG-5'<br>5'-GCCAATGCTGTACGTACTGCATTTGCC-3' | (SEQ ID NO: 2440)<br>(SEQ ID NO: 4454)<br>(SEQ ID NO: 6468) |
| LDHA-1559 Target: | 5'-AAUGCUGUACGUACUGCAUUUGCcc-3'<br>3'-GGUUACGACAUGCAUGACGUAAACGGG-5'<br>5'-CCAATGCTGTACGTACTGCATTTGCCC-3' | (SEQ ID NO: 2441)<br>(SEQ ID NO: 4455)<br>(SEQ ID NO: 6469) |
| LDHA-1560 Target: | 5'-AUGCUGUACGUACUGCAUUUGCCcc-3'<br>3'-GUUACGACAUGCAUGACGUAAACGGGG-5'<br>5'-CAATGCTGTACGTACTGCATTTGCCCC-3' | (SEQ ID NO: 2442)<br>(SEQ ID NO: 4456)<br>(SEQ ID NO: 6470) |
| LDHA-1561 Target: | 5'-UGCUGUACGUACUGCAUUUGCCCct-3'<br>3'-UUACGACAUGCAUGACGUAAACGGGGA-5'<br>5'-AATGCTGTACGTACTGCATTTGCCCCT-3' | (SEQ ID NO: 2443)<br>(SEQ ID NO: 4457)<br>(SEQ ID NO: 6471) |
| LDHA-1562 Target: | 5'-GCUGUACGUACUGCAUUUGCCCCtt-3'<br>3'-UACGACAUGCAUGACGUAAACGGGGAA-5'<br>5'-ATGCTGTACGTACTGCATTTGCCCCTT-3' | (SEQ ID NO: 2444)<br>(SEQ ID NO: 4458)<br>(SEQ ID NO: 6472) |
| LDHA-1563 Target: | 5'-CUGUACGUACUGCAUUUGCCCCUtg-3'<br>3'-ACGACAUGCAUGACGUAAACGGGGAAC-5'<br>5'-TGCTGTACGTACTGCATTTGCCCCTTG-3' | (SEQ ID NO: 2445)<br>(SEQ ID NO: 4459)<br>(SEQ ID NO: 6473) |
| LDHA-1564 Target: | 5'-UGUACGUACUGCAUUUGCCCCUUga-3'<br>3'-CGACAUGCAUGACGUAAACGGGGAACU-5'<br>5'-GCTGTACGTACTGCATTTGCCCCTTGA-3' | (SEQ ID NO: 2446)<br>(SEQ ID NO: 4460)<br>(SEQ ID NO: 6474) |
| LDHA-1565 Target: | 5'-GUACGUACUGCAUUUGCCCCUUGag-3'<br>3'-GACAUGCAUGACGUAAACGGGGAACUC-5'<br>5'-CTGTACGTACTGCATTTGCCCCTTGAG-3' | (SEQ ID NO: 2447)<br>(SEQ ID NO: 4461)<br>(SEQ ID NO: 6475) |
| LDHA-1566 Target: | 5'-UACGUACUGCAUUUGCCCCUUGAgc-3'<br>3'-ACAUGCAUGACGUAAACGGGGAACUCG-5'<br>5'-TGTACGTACTGCATTTGCCCCTTGAGC-3' | (SEQ ID NO: 2448)<br>(SEQ ID NO: 4462)<br>(SEQ ID NO: 6476) |

TABLE 12-continued

Additional Selected Human Anti-Lactate Dehydrogenase DsiRNA Agents (Asymmetrics)

|               |         |                                                  |                    |
|---------------|---------|--------------------------------------------------|--------------------|
| LDHA-1567     |         | 5'-ACGUACUGCAUUUGCCCCUUGAGCcc-3'                 | (SEQ ID NO: 2449)  |
|               |         | 3'-CAUGCAUGACGUAAACGGGGAACUCGG-5'                | (SEQ ID NO: 4463)  |
|               | Target: | 5'-GTACGTACTGCATTTGCCCCTTGAGCC-3'                | (SEQ ID NO: 6477)  |
| LDHA-1568     |         | 5'-CGUACUGCAUUUGCCCCUUGAGCca-3'                  | (SEQ ID NO: 2450)  |
|               |         | 3'-AUGCAUGACGUAAACGGGGAACUCGGU-5'                | (SEQ ID NO: 4464)  |
|               | Target: | 5'-TACGTACTGCATTTGCCCCTTGAGCCA-3'                | (SEQ ID NO: 6478)  |
| LDHA-1569     |         | 5'-GUACUGCAUUUGCCCCUUGAGCCag-3'                  | (SEQ ID NO: 2451)  |
|               |         | 3'-UGCAUGACGUAAACGGGGAACUCGGUC-5'                | (SEQ ID NO: 4465)  |
|               | Target: | 5'-ACGTACTGCATTTGCCCCTTGAGCCAG-3'                | (SEQ ID NO: 6479)  |
| LDHA-1570     |         | 5'-UACUGCAUUUGCCCCUUGAGCCAgg-3'                  | (SEQ ID NO: 2452)  |
|               |         | 3'-GCAUGACGUAAACGGGGAACUCGGUCC-5'                | (SEQ ID NO: 4466)  |
|               | Target: | 5'-CGTACTGCATTTGCCCCTTGAGCCAGG-3'                | (SEQ ID NO: 6480)  |
| LDHA-1571     |         | 5'-ACUGCAUUUGCCCCUUGAGCCAGgt-3'                  | (SEQ ID NO: 2453)  |
|               |         | 3'-CAUGACGUAAACGGGGAACUCGGUCCA-5'                | (SEQ ID NO: 4467)  |
|               | Target: | 5'-GTACTGCATTTGCCCCTTGAGCCAGGT-3'                | (SEQ ID NO: 6481)  |
| LDHA-1572     |         | 5'-CUGCAUUUGCCCCUUGAGCCAGGtg-3'                  | (SEQ ID NO: 2454)  |
|               |         | 3'-AUGACGUAAACGGGGAACUCGGUCCAC-5'                | (SEQ ID NO: 4468)  |
|               | Target: | 5'-TACTGCATTTGCCCCTTGAGCCAGGTG-3'                | (SEQ ID NO: 6482)  |
| LDHA-1573     |         | 5'-UGCAUUUGCCCCUUGAGCCAGGUgg-3'                  | (SEQ ID NO: 2455)  |
|               |         | 3'-UGACGUAAACGGGGAACUCGGUCCACC-5'                | (SEQ ID NO: 4469)  |
|               | Target: | 5'-ACTGCATTTGCCCCTTGAGCCAGGTGG-3'                | (SEQ ID NO: 6483)  |
| LDHA-1574     |         | 5'-GCAUUUGCCCCUUGAGCCAGGUGga-3'                  | (SEQ ID NO: 2456)  |
|               |         | 3'-GACGUAAACGGGGAACUCGGUCCACCU-5'                | (SEQ ID NO: 4470)  |
|               | Target: | 5'-CTGCATTTGCCCCTTGAGCCAGGTGGA-3'                | (SEQ ID NO: 6484)  |
| LDHA-1575     |         | 5'-CAUUUGCCCCUUGAGCCAGGUGGat-3'                  | (SEQ ID NO: 2457)  |
|               |         | 3'-ACGUAAACGGGGAACUCGGUCCACCUA-5'                | (SEQ ID NO: 4471)  |
|               | Target: | 5'-TGCATTTGCCCCTTGAGCCAGGTGGAT-3'                | (SEQ ID NO: 6485)  |
| LDHA-1576     |         | 5'-AUUUGCCCCUUGAGCCAGGUGGAtg-3'                  | (SEQ ID NO: 2458)  |
|               |         | 3'-CGUAAACGGGGAACUCGGUCCACCUAC-5'                | (SEQ ID NO: 4472)  |
|               | Target: | 5'-GCATTTGCCCCTTGAGCCAGGTGGATG-3'                | (SEQ ID NO: 6486)  |
| LDHA-1577     |         | 5'-UUUGCCCCUUGAGCCAGGUGGAUgt-3'                  | (SEQ ID NO: 2459)  |
|               |         | 3'-GUAAACGGGGAACUCGGUCCACCUACA-5'                | (SEQ ID NO: 4473)  |
|               | Target: | 5'-CATTTGCCCCTTGAGCCAGGTGGATGT-3'                | (SEQ ID NO: 6487)  |
| LDHA-1578     |         | 5'-UUGCCCCUUGAGCCAGGUGGAUGtt-3'                  | (SEQ ID NO: 2460)  |
|               |         | 3'-UAAACGGGGAACUCGGUCCACCUACAA-5'                | (SEQ ID NO: 4474)  |
|               | Target: | 5'-ATTTGCCCCTTGAGCCAGGTGGATGTT-3'                | (SEQ ID NO: 6488)  |
| LDHA-1579     |         | 5'-UGCCCCUUGAGCCAGGUGGAUGUtt-3'                  | (SEQ ID NO: 2461)  |
|               |         | 3'-AAACGGGGAACUCGGUCCACCUACAAA-5'                | (SEQ ID NO: 4475)  |
|               | Target: | 5'-TTTGCCCCTTGAGCCAGGTGGATGTTT-3'                | (SEQ ID NO: 6489)  |
| LDHA-1580     |         | 5'-GCCCCUUGAGCCAGGUGGAUGUUta-3'                  | (SEQ ID NO: 2462)  |
|               |         | 3'-AACGGGGAACUCGGUCCACCUACAAAU-5'                | (SEQ ID NO: 4476)  |
|               | Target: | 5'-TTGCCCCTTGAGCCAGGTGGATGTTTA-3'                | (SEQ ID NO: 6490)  |
| LDHA-1581     |         | 5'-CCCCUUGAGCCAGGUGGAUGUUUac-3'                  | (SEQ ID NO: 2463)  |
|               |         | 3'-ACGGGGAACUCGGUCCACCUACAAAUG-5'                | (SEQ ID NO: 4477)  |
|               | Target: | 5'-TGCCCCTTGAGCCAGGTGGATGTTTAC-3'                | (SEQ ID NO: 6491)  |
| LDHA-1582     |         | 5'-CCCUUGAGCCAGGUGGAUGUUUAcc-3'                  | (SEQ ID NO: 2464)  |
|               |         | 3'-CGGGGAACUCGGUCCACCUACAAAUGG-5'                | (SEQ ID NO: 4478)  |
|               | Target: | 5'-GCCCCTTGAGCCAGGTGGATGTTTACC-3'                | (SEQ ID NO: 6492)  |
| LDHA-1583     |         | 5'-CCUUGAGCCAGGUGGAUGUUUACcg-3'                  | (SEQ ID NO: 2465)  |
|               |         | 3'-GGGGAACUCGGUCCACCUACAAAUGGC-5'                | (SEQ ID NO: 4479)  |
|               | Target: | 5'-CCCCTTGAGCCAGGTGGATGTTTACCG-3'                | (SEQ ID NO: 6493)  |
| LDHA-1584     |         | 5'-CUUGAGCCAGGUGGAUGUUUACCgt-3'                  | (SEQ ID NO: 2466)  |
|               |         | 3'-GGGAACUCGGUCCACCUACAAAUGGCA-5'                | (SEQ ID NO: 4480)  |
|               | Target: | 5'-CCCTTGAGCCAGGTGGATGTTTACCGT-3'                | (SEQ ID NO: 6494)  |
| LDHA-1585     |         | 5'-UUGAGCCAGGUGGAUGUUUACCGtg-3'                  | (SEQ ID NO: 2467)  |
|               |         | 3'-GGAACUCGGUCCACCUACAAAUGGCAC-5'                | (SEQ ID NO: 4481)  |
|               | Target: | 5'-CCTTGAGCCAGGTGGATGTTTACCGTG-3'                | (SEQ ID NO: 6495)  |

TABLE 12-continued

Additional Selected Human Anti-Lactate Dehydrogenase DsiRNA Agents (Asymmetrics)

```
                   5'-UGAGCCAGGUGGAUGUUUACCGUgt-3'        (SEQ ID NO: 2468)
                   3'-GAACUCGGUCCACCUACAAAUGGCACA-5'      (SEQ ID NO: 4482)
LDHA-1586 Target:  5'-CTTGAGCCAGGTGGATGTTTACCGTGT-3'      (SEQ ID NO: 6496)

5'-GAGCCAGGUGGAUGUUUACCGUGtg-3'        (SEQ ID NO: 2469)
                   3'-AACUCGGUCCACCUACAAAUGGCACAC-5'      (SEQ ID NO: 4483)
LDHA-1587 Target:  5'-TTGAGCCAGGTGGATGTTTACCGTGTG-3'     (SEQ ID NO: 6497)

5'-AGCCAGGUGGAUGUUUACCGUGUgt-3'        (SEQ ID NO: 2470)
                   3'-ACUCGGUCCACCUACAAAUGGCACACA-5'      (SEQ ID NO: 4484)
LDHA-1588 Target:  5'-TGAGCCAGGTGGATGTTTACCGTGTGT-3'     (SEQ ID NO: 6498)

5'-GCCAGGUGGAUGUUUACCGUGUGtt-3'        (SEQ ID NO: 2471)
                   3'-CUCGGUCCACCUACAAAUGGCACACAA-5'      (SEQ ID NO: 4485)
LDHA-1589 Target:  5'-GAGCCAGGTGGATGTTTACCGTGTGTT-3'     (SEQ ID NO: 6499)

5'-CCAGGUGGAUGUUUACCGUGUGUta-3'        (SEQ ID NO: 2472)
                   3'-UCGGUCCACCUACAAAUGGCACACAAU-5'      (SEQ ID NO: 4486)
LDHA-1590 Target:  5'-AGCCAGGTGGATGTTTACCGTGTGTTA-3'     (SEQ ID NO: 6500)

5'-CAGGUGGAUGUUUACCGUGUGUUat-3'        (SEQ ID NO: 2473)
                   3'-CGGUCCACCUACAAAUGGCACACAAUA-5'      (SEQ ID NO: 4487)
LDHA-1591 Target:  5'-GCCAGGTGGATGTTTACCGTGTGTTAT-3'     (SEQ ID NO: 6501)

5'-AGGUGGAUGUUUACCGUGUGUUAta-3'        (SEQ ID NO: 2474)
                   3'-GGUCCACCUACAAAUGGCACACAAUAU-5'      (SEQ ID NO: 4488)
LDHA-1592 Target:  5'-CCAGGTGGATGTTTACCGTGTGTTATA-3'     (SEQ ID NO: 6502)

5'-GGUGGAUGUUUACCGUGUGUUAUat-3'        (SEQ ID NO: 2475)
                   3'-GUCCACCUACAAAUGGCACACAAUAUA-5'      (SEQ ID NO: 4489)
LDHA-1593 Target:  5'-CAGGTGGATGTTTACCGTGTGTTATAT-3'     (SEQ ID NO: 6503)

5'-GUGGAUGUUUACCGUGUGUUAUAta-3'        (SEQ ID NO: 2476)
                   3'-UCCACCUACAAAUGGCACACAAUAUAU-5'      (SEQ ID NO: 4490)
LDHA-1594 Target:  5'-AGGTGGATGTTTACCGTGTGTTATATA-3'     (SEQ ID NO: 6504)

5'-UGGAUGUUUACCGUGUGUUAUAUaa-3'        (SEQ ID NO: 2477)
                   3'-CCACCUACAAAUGGCACACAAUAUAUU-5'      (SEQ ID NO: 4491)
LDHA-1595 Target:  5'-GGTGGATGTTTACCGTGTGTTATATAA-3'     (SEQ ID NO: 6505)

5'-GGAUGUUUACCGUGUGUUAUAUAac-3'        (SEQ ID NO: 2478)
                   3'-CACCUACAAAUGGCACACAAUAUAUUG-5'      (SEQ ID NO: 4492)
LDHA-1596 Target:  5'-GTGGATGTTTACCGTGTGTTATATAAC-3'     (SEQ ID NO: 6506)

5'-GAUGUUUACCGUGUGUUAUAUAAct-3'        (SEQ ID NO: 2479)
                   3'-ACCUACAAAUGGCACACAAUAUAUUGA-5'      (SEQ ID NO: 4493)
LDHA-1597 Target:  5'-TGGATGTTTACCGTGTGTTATATAACT-3'     (SEQ ID NO: 6507)

5'-AUGUUUACCGUGUGUUAUAUAACtt-3'        (SEQ ID NO: 2480)
                   3'-CCUACAAAUGGCACACAAUAUAUUGAA-5'      (SEQ ID NO: 4494)
LDHA-1598 Target:  5'-GGATGTTTACCGTGTGTTATATAACTT-3'     (SEQ ID NO: 6508)

5'-UGUUUACCGUGUGUUAUAUAACUtc-3'        (SEQ ID NO: 2481)
                   3'-CUACAAAUGGCACACAAUAUAUUGAAG-5'      (SEQ ID NO: 4495)
LDHA-1599 Target:  5'-GATGTTTACCGTGTGTTATATAACTTC-3'     (SEQ ID NO: 6509)

5'-GUUUACCGUGUGUUAUAUAACUUcc-3'        (SEQ ID NO: 2482)
                   3'-UACAAAUGGCACACAAUAUAUUGAAGG-5'      (SEQ ID NO: 4496)
LDHA-1600 Target:  5'-ATGTTTACCGTGTGTTATATAACTTCC-3'     (SEQ ID NO: 6510)

5'-UUUACCGUGUGUUAUAUAACUUCct-3'        (SEQ ID NO: 2483)
                   3'-ACAAAUGGCACACAAUAUAUUGAAGGA-5'      (SEQ ID NO: 4497)
LDHA-1601 Target:  5'-TGTTTACCGTGTGTTATATAACTTCCT-3'     (SEQ ID NO: 6511)

5'-UUACCGUGUGUUAUAUAACUUCCtg-3'        (SEQ ID NO: 2484)
                   3'-CAAAUGGCACACAAUAUAUUGAAGGAC-5'      (SEQ ID NO: 4498)
LDHA-1602 Target:  5'-GTTTACCGTGTGTTATATAACTTCCTG-3'     (SEQ ID NO: 6512)

5'-UACCGUGUGUUAUAUAACUUCCUgg-3'        (SEQ ID NO: 2485)
                   3'-AAAUGGCACACAAUAUAUUGAAGGACC-5'      (SEQ ID NO: 4499)
LDHA-1603 Target:  5'-TTTACCGTGTGTTATATAACTTCCTGG-3'     (SEQ ID NO: 6513)

5'-ACCGUGUGUUAUAUAACUUCCUGgc-3'        (SEQ ID NO: 2486)
                   3'-AAUGGCACACAAUAUAUUGAAGGACCG-5'      (SEQ ID NO: 4500)
LDHA-1604 Target:  5'-TTACCGTGTGTTATATAACTTCCTGGC-3'     (SEQ ID NO: 6514)
```

TABLE 12-continued

Additional Selected Human Anti-Lactate Dehydrogenase DsiRNA Agents (Asymmetrics)

| | | |
|---|---|---|
| | 5'-CCGUGUGUUAUAUAACUUCCUGGct-3' | (SEQ ID NO: 2487) |
| | 3'-AUGGCACACAAUAUAUUGAAGGACCGA-5' | (SEQ ID NO: 4501) |
| LDHA-1605 Target: | 5'-TACCGTGTGTTATATAACTTCCTGGCT-3' | (SEQ ID NO: 6515) |
| | 5'-CGUGUGUUAUAUAACUUCCUGGCtc-3' | (SEQ ID NO: 2488) |
| | 3'-UGGCACACAAUAUAUUGAAGGACCGAG-5' | (SEQ ID NO: 4502) |
| LDHA-1606 Target: | 5'-ACCGTGTGTTATATAACTTCCTGGCTC-3' | (SEQ ID NO: 6516) |
| | 5'-GUGUGUUAUAUAACUUCCUGGCUcc-3' | (SEQ ID NO: 2489) |
| | 3'-GGCACACAAUAUAUUGAAGGACCGAGG-5' | (SEQ ID NO: 4503) |
| LDHA-1607 Target: | 5'-CCGTGTGTTATATAACTTCCTGGCTCC-3' | (SEQ ID NO: 6517) |
| | 5'-UGUGUUAUAUAACUUCCUGGCUCct-3' | (SEQ ID NO: 2490) |
| | 3'-GCACACAAUAUAUUGAAGGACCGAGGA-5' | (SEQ ID NO: 4504) |
| LDHA-1608 Target: | 5'-CGTGTGTTATATAACTTCCTGGCTCCT-3' | (SEQ ID NO: 6518) |
| | 5'-GUGUUAUAUAACUUCCUGGCUCCtt-3' | (SEQ ID NO: 2491) |
| | 3'-CACACAAUAUAUUGAAGGACCGAGGAA-5' | (SEQ ID NO: 4505) |
| LDHA-1609 Target: | 5'-GTGTGTTATATAACTTCCTGGCTCCTT-3' | (SEQ ID NO: 6519) |
| | 5'-UGUUAUAUAACUUCCUGGCUCCUtc-3' | (SEQ ID NO: 2492) |
| | 3'-ACACAAUAUAUUGAAGGACCGAGGAAG-5' | (SEQ ID NO: 4506) |
| LDHA-1610 Target: | 5'-TGTGTTATATAACTTCCTGGCTCCTTC-3' | (SEQ ID NO: 6520) |
| | 5'-GUUAUAUAACUUCCUGGCUCCUUca-3' | (SEQ ID NO: 2493) |
| | 3'-CACAAUAUAUUGAAGGACCGAGGAAGU-5' | (SEQ ID NO: 4507) |
| LDHA-1611 Target: | 5'-GTGTTATATAACTTCCTGGCTCCTTCA-3' | (SEQ ID NO: 6521) |
| | 5'-UUAUAUAACUUCCUGGCUCCUUCac-3' | (SEQ ID NO: 2494) |
| | 3'-ACAAUAUAUUGAAGGACCGAGGAAGUG-5' | (SEQ ID NO: 4508) |
| LDHA-1612 Target: | 5'-TGTTATATAACTTCCTGGCTCCTTCAC-3' | (SEQ ID NO: 6522) |
| | 5'-UAUAUAACUUCCUGGCUCCUUCAct-3' | (SEQ ID NO: 2495) |
| | 3'-CAAUAUAUUGAAGGACCGAGGAAGUGA-5' | (SEQ ID NO: 4509) |
| LDHA-1613 Target: | 5'-GTTATATAACTTCCTGGCTCCTTCACT-3' | (SEQ ID NO: 6523) |
| | 5'-AUAUAACUUCCUGGCUCCUUCACtg-3' | (SEQ ID NO: 2496) |
| | 3'-AAUAUAUUGAAGGACCGAGGAAGUGAC-5' | (SEQ ID NO: 4510) |
| LDHA-1614 Target: | 5'-TTATATAACTTCCTGGCTCCTTCACTG-3' | (SEQ ID NO: 6524) |
| | 5'-UAUAACUUCCUGGCUCCUUCACUga-3' | (SEQ ID NO: 2497) |
| | 3'-AUAUAUUGAAGGACCGAGGAAGUGACU-5' | (SEQ ID NO: 4511) |
| LDHA-1615 Target: | 5'-TATATAACTTCCTGGCTCCTTCACTGA-3' | (SEQ ID NO: 6525) |
| | 5'-AUAACUUCCUGGCUCCUUCACUGaa-3' | (SEQ ID NO: 2498) |
| | 3'-UAUAUUGAAGGACCGAGGAAGUGACUU-5' | (SEQ ID NO: 4512) |
| LDHA-1616 Target: | 5'-ATATAACTTCCTGGCTCCTTCACTGAA-3' | (SEQ ID NO: 6526) |
| | 5'-UAACUUCCUGGCUCCUUCACUGAac-3' | (SEQ ID NO: 2499) |
| | 3'-AUAUUGAAGGACCGAGGAAGUGACUUG-5' | (SEQ ID NO: 4513) |
| LDHA-1617 Target: | 5'-TATAACTTCCTGGCTCCTTCACTGAAC-3' | (SEQ ID NO: 6527) |
| | 5'-AACUUCCUGGCUCCUUCACUGAAca-3' | (SEQ ID NO: 2500) |
| | 3'-UAUUGAAGGACCGAGGAAGUGACUUGU-5' | (SEQ ID NO: 4514) |
| LDHA-1618 Target: | 5'-ATAACTTCCTGGCTCCTTCACTGAACA-3' | (SEQ ID NO: 6528) |
| | 5'-ACUUCCUGGCUCCUUCACUGAACat-3' | (SEQ ID NO: 2501) |
| | 3'-AUUGAAGGACCGAGGAAGUGACUUGUA-5' | (SEQ ID NO: 4515) |
| LDHA-1619 Target: | 5'-TAACTTCCTGGCTCCTTCACTGAACAT-3' | (SEQ ID NO: 6529) |
| | 5'-CUUCCUGGCUCCUUCACUGAACAtg-3' | (SEQ ID NO: 2502) |
| | 3'-UUGAAGGACCGAGGAAGUGACUUGUAC-5' | (SEQ ID NO: 4516) |
| LDHA-1620 Target: | 5'-AACTTCCTGGCTCCTTCACTGAACATG-3' | (SEQ ID NO: 6530) |
| | 5'-UUCCUGGCUCCUUCACUGAACAUgc-3' | (SEQ ID NO: 2503) |
| | 3'-UGAAGGACCGAGGAAGUGACUUGUACG-5' | (SEQ ID NO: 4517) |
| LDHA-1621 Target: | 5'-ACTTCCTGGCTCCTTCACTGAACATGC-3' | (SEQ ID NO: 6531) |
| | 5'-UCCUGGCUCCUUCACUGAACAUGcc-3' | (SEQ ID NO: 2504) |
| | 3'-GAAGGACCGAGGAAGUGACUUGUACGG-5' | (SEQ ID NO: 4518) |
| LDHA-1622 Target: | 5'-CTTCCTGGCTCCTTCACTGAACATGCC-3' | (SEQ ID NO: 6532) |
| | 5'-CCUGGCUCCUUCACUGAACAUGCct-3' | (SEQ ID NO: 2505) |
| | 3'-AAGGACCGAGGAAGUGACUUGUACGGA-5' | (SEQ ID NO: 4519) |
| LDHA-1623 Target: | 5'-TTCCTGGCTCCTTCACTGAACATGCCT-3' | (SEQ ID NO: 6533) |

TABLE 12-continued

Additional Selected Human Anti-Lactate Dehydrogenase DsiRNA Agents (Asymmetrics)

|   |   |   |
|---|---|---|
| | 5'-CUGGCUCCUUCACUGAACAUGCCta-3' | (SEQ ID NO: 2506) |
| | 3'-AGGACCGAGGAAGUGACUUGUACGGAU-5' | (SEQ ID NO: 4520) |
| LDHA-1624 Target: | 5'-TCCTGGCTCCTTCACTGAACATGCCTA-3' | (SEQ ID NO: 6534) |
| | 5'-UGGCUCCUUCACUGAACAUGCCUag-3' | (SEQ ID NO: 2507) |
| | 3'-GGACCGAGGAAGUGACUUGUACGGAUC-5' | (SEQ ID NO: 4521) |
| LDHA-1625 Target: | 5'-CCTGGCTCCTTCACTGAACATGCCTAG-3' | (SEQ ID NO: 6535) |
| | 5'-GGCUCCUUCACUGAACAUGCCUAgt-3' | (SEQ ID NO: 2508) |
| | 3'-GACCGAGGAAGUGACUUGUACGGAUCA-5' | (SEQ ID NO: 4522) |
| LDHA-1626 Target: | 5'-CTGGCTCCTTCACTGAACATGCCTAGT-3' | (SEQ ID NO: 6536) |
| | 5'-GCUCCUUCACUGAACAUGCCUAGtc-3' | (SEQ ID NO: 2509) |
| | 3'-ACCGAGGAAGUGACUUGUACGGAUCAG-5' | (SEQ ID NO: 4523) |
| LDHA-1627 Target: | 5'-TGGCTCCTTCACTGAACATGCCTAGTC-3' | (SEQ ID NO: 6537) |
| | 5'-CUCCUUCACUGAACAUGCCUAGUcc-3' | (SEQ ID NO: 2510) |
| | 3'-CCGAGGAAGUGACUUGUACGGAUCAGG-5' | (SEQ ID NO: 4524) |
| LDHA-1628 Target: | 5'-GGCTCCTTCACTGAACATGCCTAGTCC-3' | (SEQ ID NO: 6538) |
| | 5'-UCCUUCACUGAACAUGCCUAGUCca-3' | (SEQ ID NO: 2511) |
| | 3'-CGAGGAAGUGACUUGUACGGAUCAGGU-5' | (SEQ ID NO: 4525) |
| LDHA-1629 Target: | 5'-GCTCCTTCACTGAACATGCCTAGTCCA-3' | (SEQ ID NO: 6539) |
| | 5'-CCUUCACUGAACAUGCCUAGUCCaa-3' | (SEQ ID NO: 2512) |
| | 3'-GAGGAAGUGACUUGUACGGAUCAGGUU-5' | (SEQ ID NO: 4526) |
| LDHA-1630 Target: | 5'-CTCCTTCACTGAACATGCCTAGTCCAA-3' | (SEQ ID NO: 6540) |
| | 5'-CUUCACUGAACAUGCCUAGUCCAac-3' | (SEQ ID NO: 2513) |
| | 3'-AGGAAGUGACUUGUACGGAUCAGGUUG-5' | (SEQ ID NO: 4527) |
| LDHA-1631 Target: | 5'-TCCTTCACTGAACATGCCTAGTCCAAC-3' | (SEQ ID NO: 6541) |
| | 5'-UUCACUGAACAUGCCUAGUCCAAca-3' | (SEQ ID NO: 2514) |
| | 3'-GGAAGUGACUUGUACGGAUCAGGUUGU-5' | (SEQ ID NO: 4528) |
| LDHA-1632 Target: | 5'-CCTTCACTGAACATGCCTAGTCCAACA-3' | (SEQ ID NO: 6542) |
| | 5'-UCACUGAACAUGCCUAGUCCAACat-3' | (SEQ ID NO: 2515) |
| | 3'-GAAGUGACUUGUACGGAUCAGGUUGUA-5' | (SEQ ID NO: 4529) |
| LDHA-1633 Target: | 5'-CTTCACTGAACATGCCTAGTCCAACAT-3' | (SEQ ID NO: 6543) |
| | 5'-CACUGAACAUGCCUAGUCCAACAtt-3' | (SEQ ID NO: 2516) |
| | 3'-AAGUGACUUGUACGGAUCAGGUUGUAA-5' | (SEQ ID NO: 4530) |
| LDHA-1634 Target: | 5'-TTCACTGAACATGCCTAGTCCAACATT-3' | (SEQ ID NO: 6544) |
| | 5'-ACUGAACAUGCCUAGUCCAACAUtt-3' | (SEQ ID NO: 2517) |
| | 3'-AGUGACUUGUACGGAUCAGGUUGUAAA-5' | (SEQ ID NO: 4531) |
| LDHA-1635 Target: | 5'-TCACTGAACATGCCTAGTCCAACATTT-3' | (SEQ ID NO: 6545) |
| | 5'-CUGAACAUGCCUAGUCCAACAUUtt-3' | (SEQ ID NO: 2518) |
| | 3'-GUGACUUGUACGGAUCAGGUUGUAAAA-5' | (SEQ ID NO: 4532) |
| LDHA-1636 Target: | 5'-CACTGAACATGCCTAGTCCAACATTTT-3' | (SEQ ID NO: 6546) |
| | 5'-UGAACAUGCCUAGUCCAACAUUUtt-3' | (SEQ ID NO: 2519) |
| | 3'-UGACUUGUACGGAUCAGGUUGUAAAAA-5' | (SEQ ID NO: 4533) |
| LDHA-1637 Target: | 5'-ACTGAACATGCCTAGTCCAACATTTTT-3' | (SEQ ID NO: 6547) |
| | 5'-GAACAUGCCUAGUCCAACAUUUUtt-3' | (SEQ ID NO: 2520) |
| | 3'-GACUUGUACGGAUCAGGUUGUAAAAAA-5' | (SEQ ID NO: 4534) |
| LDHA-1638 Target: | 5'-CTGAACATGCCTAGTCCAACATTTTTT-3' | (SEQ ID NO: 6548) |
| | 5'-AACAUGCCUAGUCCAACAUUUUUtc-3' | (SEQ ID NO: 2521) |
| | 3'-ACUUGUACGGAUCAGGUUGUAAAAAAG-5' | (SEQ ID NO: 4535) |
| LDHA-1639 Target: | 5'-TGAACATGCCTAGTCCAACATTTTTTC-3' | (SEQ ID NO: 6549) |
| | 5'-ACAUGCCUAGUCCAACAUUUUUUcc-3' | (SEQ ID NO: 2522) |
| | 3'-CUUGUACGGAUCAGGUUGUAAAAAAGG-5' | (SEQ ID NO: 4536) |
| LDHA-1640 Target: | 5'-GAACATGCCTAGTCCAACATTTTTTCC-3' | (SEQ ID NO: 6550) |
| | 5'-CAUGCCUAGUCCAACAUUUUUUCcc-3' | (SEQ ID NO: 2523) |
| | 3'-UUGUACGGAUCAGGUUGUAAAAAAGGG-5' | (SEQ ID NO: 4537) |
| LDHA-1641 Target: | 5'-AACATGCCTAGTCCAACATTTTTTCCC-3' | (SEQ ID NO: 6551) |
| | 5'-AUGCCUAGUCCAACAUUUUUUCCca-3' | (SEQ ID NO: 2524) |
| | 3'-UGUACGGAUCAGGUUGUAAAAAAGGGU-5' | (SEQ ID NO: 4538) |
| LDHA-1642 Target: | 5'-ACATGCCTAGTCCAACATTTTTTCCCA-3' | (SEQ ID NO: 6552) |

TABLE 12-continued

Additional Selected Human Anti-Lactate Dehydrogenase DsiRNA Agents (Asymmetrics)

|  |  |  |
| --- | --- | --- |
| LDHA-1643 | 5'-UGCCUAGUCCAACAUUUUUUCCCag-3'<br>3'-GUACGGAUCAGGUUGUAAAAAAGGGUC-5'<br>Target: 5'-CATGCCTAGTCCAACATTTTTTCCCAG-3' | (SEQ ID NO: 2525)<br>(SEQ ID NO: 4539)<br>(SEQ ID NO: 6553) |
| LDHA-1644 | 5'-GCCUAGUCCAACAUUUUUUCCCAgt-3'<br>3'-UACGGAUCAGGUUGUAAAAAAGGGUCA-5'<br>Target: 5'-ATGCCTAGTCCAACATTTTTTCCCAGT-3' | (SEQ ID NO: 2526)<br>(SEQ ID NO: 4540)<br>(SEQ ID NO: 6554) |
| LDHA-1645 | 5'-CCUAGUCCAACAUUUUUUCCCAGtg-3'<br>3'-ACGGAUCAGGUUGUAAAAAAGGGUCAC-5'<br>Target: 5'-TGCCTAGTCCAACATTTTTTCCCAGTG-3' | (SEQ ID NO: 2527)<br>(SEQ ID NO: 4541)<br>(SEQ ID NO: 6555) |
| LDHA-1646 | 5'-CUAGUCCAACAUUUUUUCCCAGUga-3'<br>3'-CGGAUCAGGUUGUAAAAAAGGGUCACU-5'<br>Target: 5'-GCCTAGTCCAACATTTTTTCCCAGTGA-3' | (SEQ ID NO: 2528)<br>(SEQ ID NO: 4542)<br>(SEQ ID NO: 6556) |
| LDHA-1647 | 5'-UAGUCCAACAUUUUUUCCCAGUGag-3'<br>3'-GGAUCAGGUUGUAAAAAAGGGUCACUC-5'<br>Target: 5'-CCTAGTCCAACATTTTTTCCCAGTGAG-3' | (SEQ ID NO: 2529)<br>(SEQ ID NO: 4543)<br>(SEQ ID NO: 6557) |
| LDHA-1648 | 5'-AGUCCAACAUUUUUUCCCAGUGAgt-3'<br>3'-GAUCAGGUUGUAAAAAAGGGUCACUCA-5'<br>Target: 5'-CTAGTCCAACATTTTTTCCCAGTGAGT-3' | (SEQ ID NO: 2530)<br>(SEQ ID NO: 4544)<br>(SEQ ID NO: 6558) |
| LDHA-1649 | 5'-GUCCAACAUUUUUUCCCAGUGAgtc-3'<br>3'-AUCAGGUUGUAAAAAAGGGUCACUCAG-5'<br>Target: 5'-TAGTCCAACATTTTTTCCCAGTGAGTC-3' | (SEQ ID NO: 2531)<br>(SEQ ID NO: 4545)<br>(SEQ ID NO: 6559) |
| LDHA-1650 | 5'-UCCAACAUUUUUUCCCAGUGAGUca-3'<br>3'-UCAGGUUGUAAAAAAGGGUCACUCAGU-5'<br>Target: 5'-AGTCCAACATTTTTTCCCAGTGAGTCA-3' | (SEQ ID NO: 2532)<br>(SEQ ID NO: 4546)<br>(SEQ ID NO: 6560) |
| LDHA-1651 | 5'-CCAACAUUUUUUCCCAGUGAGUCac-3'<br>3'-CAGGUUGUAAAAAAGGGUCACUCAGUG-5'<br>Target: 5'-GTCCAACATTTTTTCCCAGTGAGTCAC-3' | (SEQ ID NO: 2533)<br>(SEQ ID NO: 4547)<br>(SEQ ID NO: 6561) |
| LDHA-1652 | 5'-CAACAUUUUUUCCCAGUGAGUCAca-3'<br>3'-AGGUUGUAAAAAAGGGUCACUCAGUGU-5'<br>Target: 5'-TCCAACATTTTTTCCCAGTGAGTCACA-3' | (SEQ ID NO: 2534)<br>(SEQ ID NO: 4548)<br>(SEQ ID NO: 6562) |
| LDHA-1653 | 5'-AACAUUUUUUCCCAGUGAGUCACat-3'<br>3'-GGUUGUAAAAAAGGGUCACUCAGUGUA-5'<br>Target: 5'-CCAACATTTTTTCCCAGTGAGTCACAT-3' | (SEQ ID NO: 2535)<br>(SEQ ID NO: 4549)<br>(SEQ ID NO: 6563) |
| LDHA-1654 | 5'-ACAUUUUUUCCCAGUGAGUCACAtc-3'<br>3'-GUUGUAAAAAAGGGUCACUCAGUGUAG-5'<br>Target: 5'-CAACATTTTTTCCCAGTGAGTCACATC-3' | (SEQ ID NO: 2536)<br>(SEQ ID NO: 4550)<br>(SEQ ID NO: 6564) |
| LDHA-1655 | 5'-CAUUUUUUCCCAGUGAGUCACAUcc-3'<br>3'-UUGUAAAAAAGGGUCACUCAGUGUAGG-5'<br>Target: 5'-AACATTTTTTCCCAGTGAGTCACATCC-3' | (SEQ ID NO: 2537)<br>(SEQ ID NO: 4551)<br>(SEQ ID NO: 6565) |
| LDHA-1656 | 5'-AUUUUUUCCCAGUGAGUCACAUCct-3'<br>3'-UGUAAAAAAGGGUCACUCAGUGUAGGA-5'<br>Target: 5'-ACATTTTTTCCCAGTGAGTCACATCCT-3' | (SEQ ID NO: 2538)<br>(SEQ ID NO: 4552)<br>(SEQ ID NO: 6566) |
| LDHA-1657 | 5'-UUUUUUCCCAGUGAGUCACAUCCtg-3'<br>3'-GUAAAAAAGGGUCACUCAGUGUAGGAC-5'<br>Target: 5'-CATTTTTTCCCAGTGAGTCACATCCTG-3' | (SEQ ID NO: 2539)<br>(SEQ ID NO: 4553)<br>(SEQ ID NO: 6567) |
| LDHA-1658 | 5'-UUUUUCCCAGUGAGUCACAUCCUgg-3'<br>3'-UAAAAAAGGGUCACUCAGUGUAGGACC-5'<br>Target: 5'-ATTTTTTCCCAGTGAGTCACATCCTGG-3' | (SEQ ID NO: 2540)<br>(SEQ ID NO: 4554)<br>(SEQ ID NO: 6568) |
| LDHA-1659 | 5'-UUUUCCCAGUGAGUCACAUCCUGgg-3'<br>3'-AAAAAAGGGUCACUCAGUGUAGGACCC-5'<br>Target: 5'-TTTTTTCCCAGTGAGTCACATCCTGGG-3' | (SEQ ID NO: 2541)<br>(SEQ ID NO: 4555)<br>(SEQ ID NO: 6569) |
| LDHA-1660 | 5'-UUUCCCAGUGAGUCACAUCCUGGga-3'<br>3'-AAAAAGGGUCACUCAGUGUAGGACCCU-5'<br>Target: 5'-TTTTTCCCAGTGAGTCACATCCTGGGA-3' | (SEQ ID NO: 2542)<br>(SEQ ID NO: 4556)<br>(SEQ ID NO: 6570) |
| LDHA-1661 | 5'-UUCCCAGUGAGUCACAUCCUGGGat-3'<br>3'-AAAAGGGUCACUCAGUGUAGGACCCUA-5'<br>Target: 5'-TTTTCCCAGTGAGTCACATCCTGGGAT-3' | (SEQ ID NO: 2543)<br>(SEQ ID NO: 4557)<br>(SEQ ID NO: 6571) |

TABLE 12-continued

Additional Selected Human Anti-Lactate Dehydrogenase DsiRNA Agents (Asymmetrics)

|  |  |  |
|---|---|---|
| LDHA-1662 | 5'-UCCCAGUGAGUCACAUCCUGGGAtc-3'<br>3'-AAAGGGUCACUCAGUGUAGGACCCUAG-5'<br>Target: 5'-TTTCCCAGTGAGTCACATCCTGGGATC-3' | (SEQ ID NO: 2544)<br>(SEQ ID NO: 4558)<br>(SEQ ID NO: 6572) |
| LDHA-1663 | 5'-CCCAGUGAGUCACAUCCUGGGAUcc-3'<br>3'-AAGGGUCACUCAGUGUAGGACCCUAGG-5'<br>Target: 5'-TTCCCAGTGAGTCACATCCTGGGATCC-3' | (SEQ ID NO: 2545)<br>(SEQ ID NO: 4559)<br>(SEQ ID NO: 6573) |
| LDHA-1664 | 5'-CCAGUGAGUCACAUCCUGGGAUCca-3'<br>3'-AGGGUCACUCAGUGUAGGACCCUAGGU-5'<br>Target: 5'-TCCCAGTGAGTCACATCCTGGGATCCA-3' | (SEQ ID NO: 2546)<br>(SEQ ID NO: 4560)<br>(SEQ ID NO: 6574) |
| LDHA-1665 | 5'-CAGUGAGUCACAUCCUGGGAUCCag-3'<br>3'-GGGUCACUCAGUGUAGGACCCUAGGUC-5'<br>Target: 5'-CCCAGTGAGTCACATCCTGGGATCCAG-3' | (SEQ ID NO: 2547)<br>(SEQ ID NO: 4561)<br>(SEQ ID NO: 6575) |
| LDHA-1666 | 5'-AGUGAGUCACAUCCUGGGAUCCAgt-3'<br>3'-GGUCACUCAGUGUAGGACCCUAGGUCA-5'<br>Target: 5'-CCAGTGAGTCACATCCTGGGATCCAGT-3' | (SEQ ID NO: 2548)<br>(SEQ ID NO: 4562)<br>(SEQ ID NO: 6576) |
| LDHA-1667 | 5'-GUGAGUCACAUCCUGGGAUCCAGtg-3'<br>3'-GUCACUCAGUGUAGGACCCUAGGUCAC-5'<br>Target: 5'-CAGTGAGTCACATCCTGGGATCCAGTG-3' | (SEQ ID NO: 2549)<br>(SEQ ID NO: 4563)<br>(SEQ ID NO: 6577) |
| LDHA-1668 | 5'-UGAGUCACAUCCUGGGAUCCAGUgt-3'<br>3'-UCACUCAGUGUAGGACCCUAGGUCACA-5'<br>Target: 5'-AGTGAGTCACATCCTGGGATCCAGTGT-3' | (SEQ ID NO: 2550)<br>(SEQ ID NO: 4564)<br>(SEQ ID NO: 6578) |
| LDHA-1669 | 5'-GAGUCACAUCCUGGGAUCCAGUGta-3'<br>3'-CACUCAGUGUAGGACCCUAGGUCACAU-5'<br>Target: 5'-GTGAGTCACATCCTGGGATCCAGTGTA-3' | (SEQ ID NO: 2551)<br>(SEQ ID NO: 4565)<br>(SEQ ID NO: 6579) |
| LDHA-1670 | 5'-AGUCACAUCCUGGGAUCCAGUGUat-3'<br>3'-ACUCAGUGUAGGACCCUAGGUCACAUA-5'<br>Target: 5'-TGAGTCACATCCTGGGATCCAGTGTAT-3' | (SEQ ID NO: 2552)<br>(SEQ ID NO: 4566)<br>(SEQ ID NO: 6580) |
| LDHA-1671 | 5'-GUCACAUCCUGGGAUCCAGUGUAta-3'<br>3'-CUCAGUGUAGGACCCUAGGUCACAUAU-5'<br>Target: 5'-GAGTCACATCCTGGGATCCAGTGTATA-3' | (SEQ ID NO: 2553)<br>(SEQ ID NO: 4567)<br>(SEQ ID NO: 6581) |
| LDHA-1672 | 5'-UCACAUCCUGGGAUCCAGUGUAUaa-3'<br>3'-UCAGUGUAGGACCCUAGGUCACAUAUU-5'<br>Target: 5'-AGTCACATCCTGGGATCCAGTGTATAA-3' | (SEQ ID NO: 2554)<br>(SEQ ID NO: 4568)<br>(SEQ ID NO: 6582) |
| LDHA-1673 | 5'-CACAUCCUGGGAUCCAGUGUAUAaa-3'<br>3'-CAGUGUAGGACCCUAGGUCACAUAUUU-5'<br>Target: 5'-GTCACATCCTGGGATCCAGTGTATAAA-3' | (SEQ ID NO: 2555)<br>(SEQ ID NO: 4569)<br>(SEQ ID NO: 6583) |
| LDHA-1674 | 5'-ACAUCCUGGGAUCCAGUGUAUAAat-3'<br>3'-AGUGUAGGACCCUAGGUCACAUAUUUA-5'<br>Target: 5'-TCACATCCTGGGATCCAGTGTATAAAT-3' | (SEQ ID NO: 2556)<br>(SEQ ID NO: 4570)<br>(SEQ ID NO: 6584) |
| LDHA-1675 | 5'-CAUCCUGGGAUCCAGUGUAUAAAtc-3'<br>3'-GUGUAGGACCCUAGGUCACAUAUUUAG-5'<br>Target: 5'-CACATCCTGGGATCCAGTGTATAAATC-3' | (SEQ ID NO: 2557)<br>(SEQ ID NO: 4571)<br>(SEQ ID NO: 6585) |
| LDHA-1676 | 5'-AUCCUGGGAUCCAGUGUAUAAAUcc-3'<br>3'-UGUAGGACCCUAGGUCACAUAUUUAGG-5'<br>Target: 5'-ACATCCTGGGATCCAGTGTATAAATCC-3' | (SEQ ID NO: 2558)<br>(SEQ ID NO: 4572)<br>(SEQ ID NO: 6586) |
| LDHA-1677 | 5'-UCCUGGGAUCCAGUGUAUAAAUCca-3'<br>3'-GUAGGACCCUAGGUCACAUAUUUAGGU-5'<br>Target: 5'-CATCCTGGGATCCAGTGTATAAATCCA-3' | (SEQ ID NO: 2559)<br>(SEQ ID NO: 4573)<br>(SEQ ID NO: 6587) |
| LDHA-1678 | 5'-CCUGGGAUCCAGUGUAUAAAUCCaa-3'<br>3'-UAGGACCCUAGGUCACAUAUUUAGGUU-5'<br>Target: 5'-ATCCTGGGATCCAGTGTATAAATCCAA-3' | (SEQ ID NO: 2560)<br>(SEQ ID NO: 4574)<br>(SEQ ID NO: 6588) |
| LDHA-1679 | 5'-CUGGGAUCCAGUGUAUAAAUCCAat-3'<br>3'-AGGACCCUAGGUCACAUAUUUAGGUUA-5'<br>Target: 5'-TCCTGGGATCCAGTGTATAAATCCAAT-3' | (SEQ ID NO: 2561)<br>(SEQ ID NO: 4575)<br>(SEQ ID NO: 6589) |
| LDHA-1680 | 5'-UGGGAUCCAGUGUAUAAAUCCAAta-3'<br>3'-GGACCCUAGGUCACAUAUUUAGGUUAU-5'<br>Target: 5'-CCTGGGATCCAGTGTATAAATCCAATA-3' | (SEQ ID NO: 2562)<br>(SEQ ID NO: 4576)<br>(SEQ ID NO: 6590) |

TABLE 12-continued

Additional Selected Human Anti-Lactate Dehydrogenase DsiRNA Agents (Asymmetrics)

|  |  |  |
|---|---|---|
| LDHA-1681 | 5'-GGGAUCCAGUGUAUAAAUCCAAUat-3'<br>3'-GACCCUAGGUCACAUAUUUAGGUUAUA-5'<br>Target: 5'-CTGGGATCCAGTGTATAAATCCAATAT-3' | (SEQ ID NO: 2563)<br>(SEQ ID NO: 4577)<br>(SEQ ID NO: 6591) |
| LDHA-1682 | 5'-GGAUCCAGUGUAUAAAUCCAAUAtc-3'<br>3'-ACCCUAGGUCACAUAUUUAGGUUAUAG-5'<br>Target: 5'-TGGGATCCAGTGTATAAATCCAATATC-3' | (SEQ ID NO: 2564)<br>(SEQ ID NO: 4578)<br>(SEQ ID NO: 6592) |
| LDHA-1683 | 5'-GAUCCAGUGUAUAAAUCCAAUAUca-3'<br>3'-CCCUAGGUCACAUAUUUAGGUUAUAGU-5'<br>Target: 5'-GGGATCCAGTGTATAAATCCAATATCA-3' | (SEQ ID NO: 2565)<br>(SEQ ID NO: 4579)<br>(SEQ ID NO: 6593) |
| LDHA-1685 | 5'-UCCAGUGUAUAAAUCCAAUAUCAtg-3'<br>3'-CUAGGUCACAUAUUUAGGUUAUAGUAC-5'<br>Target: 5'-GATCCAGTGTATAAATCCAATATCATG-3' | (SEQ ID NO: 2566)<br>(SEQ ID NO: 4580)<br>(SEQ ID NO: 6594) |
| LDHA-1686 | 5'-CCAGUGUAUAAAUCCAAUAUCAUgt-3'<br>3'-UAGGUCACAUAUUUAGGUUAUAGUACA-5'<br>Target: 5'-ATCCAGTGTATAAATCCAATATCATGT-3' | (SEQ ID NO: 2567)<br>(SEQ ID NO: 4581)<br>(SEQ ID NO: 6595) |
| LDHA-1687 | 5'-CAGUGUAUAAAUCCAAUAUCAUGtc-3'<br>3'-AGGUCACAUAUUUAGGUUAUAGUACAG-5'<br>Target: 5'-TCCAGTGTATAAATCCAATATCATGTC-3' | (SEQ ID NO: 2568)<br>(SEQ ID NO: 4582)<br>(SEQ ID NO: 6596) |
| LDHA-1689 | 5'-GUGUAUAAAUCCAAUAUCAUGUCtt-3'<br>3'-GUCACAUAUUUAGGUUAUAGUACAGAA-5'<br>Target: 5'-CAGTGTATAAATCCAATATCATGTCTT-3' | (SEQ ID NO: 2569)<br>(SEQ ID NO: 4583)<br>(SEQ ID NO: 6597) |
| LDHA-1690 | 5'-UGUAUAAAUCCAAUAUCAUGUCUtg-3'<br>3'-UCACAUAUUUAGGUUAUAGUACAGAAC-5'<br>Target: 5'-AGTGTATAAATCCAATATCATGTCTTG-3' | (SEQ ID NO: 2570)<br>(SEQ ID NO: 4584)<br>(SEQ ID NO: 6598) |
| LDHA-1691 | 5'-GUAUAAAUCCAAUAUCAUGUCUUgt-3'<br>3'-CACAUAUUUAGGUUAUAGUACAGAACA-5'<br>Target: 5'-GTGTATAAATCCAATATCATGTCTTGT-3' | (SEQ ID NO: 2571)<br>(SEQ ID NO: 4585)<br>(SEQ ID NO: 6599) |
| LDHA-1692 | 5'-UAUAAAUCCAAUAUCAUGUCUUGtg-3'<br>3'-ACAUAUUUAGGUUAUAGUACAGAACAC-5'<br>Target: 5'-TGTATAAATCCAATATCATGTCTTGTG-3' | (SEQ ID NO: 2572)<br>(SEQ ID NO: 4586)<br>(SEQ ID NO: 6600) |
| LDHA-1693 | 5'-AUAAAUCCAAUAUCAUGUCUUGUgc-3'<br>3'-CAUAUUUAGGUUAUAGUACAGAACACG-5'<br>Target: 5'-GTATAAATCCAATATCATGTCTTGTGC-3' | (SEQ ID NO: 2573)<br>(SEQ ID NO: 4587)<br>(SEQ ID NO: 6601) |
| LDHA-1694 | 5'-UAAAUCCAAUAUCAUGUCUUGUGca-3'<br>3'-AUAUUUAGGUUAUAGUACAGAACACGU-5'<br>Target: 5'-TATAAATCCAATATCATGTCTTGTGCA-3' | (SEQ ID NO: 2574)<br>(SEQ ID NO: 4588)<br>(SEQ ID NO: 6602) |
| LDHA-1695 | 5'-AAAUCCAAUAUCAUGUCUUGUGCat-3'<br>3'-UAUUUAGGUUAUAGUACAGAACACGUA-5'<br>Target: 5'-ATAAATCCAATATCATGTCTTGTGCAT-3' | (SEQ ID NO: 2575)<br>(SEQ ID NO: 4589)<br>(SEQ ID NO: 6603) |
| LDHA-1696 | 5'-AAUCCAAUAUCAUGUCUUGUGCAta-3'<br>3'-AUUUAGGUUAUAGUACAGAACACGUAU-5'<br>Target: 5'-TAAATCCAATATCATGTCTTGTGCATA-3' | (SEQ ID NO: 2576)<br>(SEQ ID NO: 4590)<br>(SEQ ID NO: 6604) |
| LDHA-1697 | 5'-AUCCAAUAUCAUGUCUUGUGCAUaa-3'<br>3'-UUUAGGUUAUAGUACAGAACACGUAUU-5'<br>Target: 5'-AAATCCAATATCATGTCTTGTGCATAA-3' | (SEQ ID NO: 2577)<br>(SEQ ID NO: 4591)<br>(SEQ ID NO: 6605) |
| LDHA-1698 | 5'-UCCAAUAUCAUGUCUUGUGCAUAat-3'<br>3'-UUAGGUUAUAGUACAGAACACGUAUUA-5'<br>Target: 5'-AATCCAATATCATGTCTTGTGCATAAT-3' | (SEQ ID NO: 2578)<br>(SEQ ID NO: 4592)<br>(SEQ ID NO: 6606) |
| LDHA-1699 | 5'-CCAAUAUCAUGUCUUGUGCAUAAtt-3'<br>3'-UAGGUUAUAGUACAGAACACGUAUUAA-5'<br>Target: 5'-ATCCAATATCATGTCTTGTGCATAATT-3' | (SEQ ID NO: 2579)<br>(SEQ ID NO: 4593)<br>(SEQ ID NO: 6607) |
| LDHA-1700 | 5'-CAAUAUCAUGUCUUGUGCAUAAUtc-3'<br>3'-AGGUUAUAGUACAGAACACGUAUUAAG-5'<br>Target: 5'-TCCAATATCATGTCTTGTGCATAATTC-3' | (SEQ ID NO: 2580)<br>(SEQ ID NO: 4594)<br>(SEQ ID NO: 6608) |
| LDHA-1701 | 5'-AAUAUCAUGUCUUGUGCAUAAUUct-3'<br>3'-GGUUAUAGUACAGAACACGUAUUAAGA-5'<br>Target: 5'-CCAATATCATGTCTTGTGCATAATTCT-3' | (SEQ ID NO: 2581)<br>(SEQ ID NO: 4595)<br>(SEQ ID NO: 6609) |

TABLE 12-continued

Additional Selected Human Anti-Lactate Dehydrogenase DsiRNA Agents (Asymmetrics)

|  |  |  |
|---|---|---|
| LDHA-1702 | 5'-AUAUCAUGUCUUGUGCAUAAUUCtt-3'<br>3'-GUUAUAGUACAGAACACGUAUUAAGAA-5'<br>Target: 5'-CAATATCATGTCTTGTGCATAATTCTT-3' | (SEQ ID NO: 2582)<br>(SEQ ID NO: 4596)<br>(SEQ ID NO: 6610) |
| LDHA-1703 | 5'-UAUCAUGUCUUGUGCAUAAUUCUtc-3'<br>3'-UUAUAGUACAGAACACGUAUUAAGAAG-5'<br>Target: 5'-AATATCATGTCTTGTGCATAATTCTTC-3' | (SEQ ID NO: 2583)<br>(SEQ ID NO: 4597)<br>(SEQ ID NO: 6611) |
| LDHA-1704 | 5'-AUCAUGUCUUGUGCAUAAUUCUUcc-3'<br>3'-UAUAGUACAGAACACGUAUUAAGAAGG-5'<br>Target: 5'-ATATCATGTCTTGTGCATAATTCTTCC-3' | (SEQ ID NO: 2584)<br>(SEQ ID NO: 4598)<br>(SEQ ID NO: 6612) |
| LDHA-1705 | 5'-UCAUGUCUUGUGCAUAAUUCUUCca-3'<br>3'-AUAGUACAGAACACGUAUUAAGAAGGU-5'<br>Target: 5'-TATCATGTCTTGTGCATAATTCTTCCA-3' | (SEQ ID NO: 2585)<br>(SEQ ID NO: 4599)<br>(SEQ ID NO: 6613) |
| LDHA-1706 | 5'-CAUGUCUUGUGCAUAAUUCUUCCaa-3'<br>3'-UAGUACAGAACACGUAUUAAGAAGGUU-5'<br>Target: 5'-ATCATGTCTTGTGCATAATTCTTCCAA-3' | (SEQ ID NO: 2586)<br>(SEQ ID NO: 4600)<br>(SEQ ID NO: 6614) |
| LDHA-1707 | 5'-AUGUCUUGUGCAUAAUUCUUCCAaa-3'<br>3'-AGUACAGAACACGUAUUAAGAAGGUUU-5'<br>Target: 5'-TCATGTCTTGTGCATAATTCTTCCAAA-3' | (SEQ ID NO: 2587)<br>(SEQ ID NO: 4601)<br>(SEQ ID NO: 6615) |
| LDHA-1708 | 5'-UGUCUUGUGCAUAAUUCUUCCAAag-3'<br>3'-GUACAGAACACGUAUUAAGAAGGUUUC-5'<br>Target: 5'-CATGTCTTGTGCATAATTCTTCCAAAG-3' | (SEQ ID NO: 2588)<br>(SEQ ID NO: 4602)<br>(SEQ ID NO: 6616) |
| LDHA-1709 | 5'-GUCUUGUGCAUAAUUCUUCCAAAgg-3'<br>3'-UACAGAACACGUAUUAAGAAGGUUUCC-5'<br>Target: 5'-ATGTCTTGTGCATAATTCTTCCAAAGG-3' | (SEQ ID NO: 2589)<br>(SEQ ID NO: 4603)<br>(SEQ ID NO: 6617) |
| LDHA-1710 | 5'-UCUUGUGCAUAAUUCUUCCAAAGga-3'<br>3'-ACAGAACACGUAUUAAGAAGGUUUCCU-5'<br>Target: 5'-TGTCTTGTGCATAATTCTTCCAAAGGA-3' | (SEQ ID NO: 2590)<br>(SEQ ID NO: 4604)<br>(SEQ ID NO: 6618) |
| LDHA-1711 | 5'-CUUGUGCAUAAUUCUUCCAAAGGat-3'<br>3'-CAGAACACGUAUUAAGAAGGUUUCCUA-5'<br>Target: 5'-GTCTTGTGCATAATTCTTCCAAAGGAT-3' | (SEQ ID NO: 2591)<br>(SEQ ID NO: 4605)<br>(SEQ ID NO: 6619) |
| LDHA-1712 | 5'-UUGUGCAUAAUUCUUCCAAAGGAtc-3'<br>3'-AGAACACGUAUUAAGAAGGUUUCCUAG-5'<br>Target: 5'-TCTTGTGCATAATTCTTCCAAAGGATC-3' | (SEQ ID NO: 2592)<br>(SEQ ID NO: 4606)<br>(SEQ ID NO: 6620) |
| LDHA-1713 | 5'-UGUGCAUAAUUCUUCCAAAGGAUct-3'<br>3'-GAACACGUAUUAAGAAGGUUUCCUAGA-5'<br>Target: 5'-CTTGTGCATAATTCTTCCAAAGGATCT-3' | (SEQ ID NO: 2593)<br>(SEQ ID NO: 4607)<br>(SEQ ID NO: 6621) |
| LDHA-1714 | 5'-GUGCAUAAUUCUUCCAAAGGAUCtt-3'<br>3'-AACACGUAUUAAGAAGGUUUCCUAGAA-5'<br>Target: 5'-TTGTGCATAATTCTTCCAAAGGATCTT-3' | (SEQ ID NO: 2594)<br>(SEQ ID NO: 4608)<br>(SEQ ID NO: 6622) |
| LDHA-1715 | 5'-UGCAUAAUUCUUCCAAAGGAUCUta-3'<br>3'-ACACGUAUUAAGAAGGUUUCCUAGAAU-5'<br>Target: 5'-TGTGCATAATTCTTCCAAAGGATCTTA-3' | (SEQ ID NO: 2595)<br>(SEQ ID NO: 4609)<br>(SEQ ID NO: 6623) |
| LDHA-1716 | 5'-GCAUAAUUCUUCCAAAGGAUCUUat-3'<br>3'-CACGUAUUAAGAAGGUUUCCUAGAAUA-5'<br>Target: 5'-GTGCATAATTCTTCCAAAGGATCTTAT-3' | (SEQ ID NO: 2596)<br>(SEQ ID NO: 4610)<br>(SEQ ID NO: 6624) |
| LDHA-1717 | 5'-CAUAAUUCUUCCAAAGGAUCUUAtt-3'<br>3'-ACGUAUUAAGAAGGUUUCCUAGAAUAA-5'<br>Target: 5'-TGCATAATTCTTCCAAAGGATCTTATT-3' | (SEQ ID NO: 2597)<br>(SEQ ID NO: 4611)<br>(SEQ ID NO: 6625) |
| LDHA-1718 | 5'-AUAAUUCUUCCAAAGGAUCUUAUtt-3'<br>3'-CGUAUUAAGAAGGUUUCCUAGAAUAAA-5'<br>Target: 5'-GCATAATTCTTCCAAAGGATCTTATTT-3' | (SEQ ID NO: 2598)<br>(SEQ ID NO: 4612)<br>(SEQ ID NO: 6626) |
| LDHA-1719 | 5'-UAAUUCUUCCAAAGGAUCUUAUUtt-3'<br>3'-GUAUUAAGAAGGUUUCCUAGAAUAAAA-5'<br>Target: 5'-CATAATTCTTCCAAAGGATCTTATTTT-3' | (SEQ ID NO: 2599)<br>(SEQ ID NO: 4613)<br>(SEQ ID NO: 6627) |
| LDHA-1720 | 5'-AAUUCUUCCAAAGGAUCUUAUUUtg-3'<br>3'-UAUUAAGAAGGUUUCCUAGAAUAAAAC-5'<br>Target: 5'-ATAATTCTTCCAAAGGATCTTATTTTG-3' | (SEQ ID NO: 2600)<br>(SEQ ID NO: 4614)<br>(SEQ ID NO: 6628) |

TABLE 12-continued

Additional Selected Human Anti-Lactate Dehydrogenase DsiRNA Agents (Asymmetrics)

|  |  |  |
| --- | --- | --- |
| LDHA-1721 Target: | 5'-AUUCUUCCAAAGGAUCUUAUUUUGgt-3'<br>3'-AUUAAGAAGGUUUCCUAGAAUAAAACA-5'<br>5'-TAATTCTTCCAAAGGATCTTATTTTGT-3' | (SEQ ID NO: 2601)<br>(SEQ ID NO: 4615)<br>(SEQ ID NO: 6629) |
| LDHA-1722 Target: | 5'-UUCUUCCAAAGGAUCUUAUUUUGtg-3'<br>3'-UUAAGAAGGUUUCCUAGAAUAAAACAC-5'<br>5'-AATTCTTCCAAAGGATCTTATTTTGTG-3' | (SEQ ID NO: 2602)<br>(SEQ ID NO: 4616)<br>(SEQ ID NO: 6630) |
| LDHA-1723 Target: | 5'-UCUUCCAAAGGAUCUUAUUUUGUga-3'<br>3'-UAAGAAGGUUUCCUAGAAUAAAACACU-5'<br>5'-ATTCTTCCAAAGGATCTTATTTTGTGA-3' | (SEQ ID NO: 2603)<br>(SEQ ID NO: 4617)<br>(SEQ ID NO: 6631) |
| LDHA-1724 Target: | 5'-CUUCCAAAGGAUCUUAUUUUGUGaa-3'<br>3'-AAGAAGGUUUCCUAGAAUAAAACACUU-5'<br>5'-TTCTTCCAAAGGATCTTATTTTGTGAA-3' | (SEQ ID NO: 2604)<br>(SEQ ID NO: 4618)<br>(SEQ ID NO: 6632) |
| LDHA-1725 Target: | 5'-UUCCAAAGGAUCUUAUUUUGUGAac-3'<br>3'-AGAAGGUUUCCUAGAAUAAAACACUUG-5'<br>5'-TCTTCCAAAGGATCTTATTTTGTGAAC-3' | (SEQ ID NO: 2605)<br>(SEQ ID NO: 4619)<br>(SEQ ID NO: 6633) |
| LDHA-1726 Target: | 5'-UCCAAAGGAUCUUAUUUUGUGAAct-3'<br>3'-GAAGGUUUCCUAGAAUAAAACACUUGA-5'<br>5'-CTTCCAAAGGATCTTATTTTGTGAACT-3' | (SEQ ID NO: 2606)<br>(SEQ ID NO: 4620)<br>(SEQ ID NO: 6634) |
| LDHA-1727 Target: | 5'-CCAAAGGAUCUUAUUUUGUGAACta-3'<br>3'-AAGGUUUCCUAGAAUAAAACACUUGAU-5'<br>5'-TTCCAAAGGATCTTATTTTGTGAACTA-3' | (SEQ ID NO: 2607)<br>(SEQ ID NO: 4621)<br>(SEQ ID NO: 6635) |
| LDHA-1728 Target: | 5'-CAAAGGAUCUUAUUUUGUGAACUat-3'<br>3'-AGGUUUCCUAGAAUAAAACACUUGAUA-5'<br>5'-TCCAAAGGATCTTATTTTGTGAACTAT-3' | (SEQ ID NO: 2608)<br>(SEQ ID NO: 4622)<br>(SEQ ID NO: 6636) |
| LDHA-1729 Target: | 5'-AAAGGAUCUUAUUUUGUGAACUAta-3'<br>3'-GGUUUCCUAGAAUAAAACACUUGAUAU-5'<br>5'-CCAAAGGATCTTATTTTGTGAACTATA-3' | (SEQ ID NO: 2609)<br>(SEQ ID NO: 4623)<br>(SEQ ID NO: 6637) |
| LDHA-1730 Target: | 5'-AAGGAUCUUAUUUUGUGAACUAUat-3'<br>3'-GUUUCCUAGAAUAAAACACUUGAUAUA-5'<br>5'-CAAAGGATCTTATTTTGTGAACTATAT-3' | (SEQ ID NO: 2610)<br>(SEQ ID NO: 4624)<br>(SEQ ID NO: 6638) |
| LDHA-1731 Target: | 5'-AGGAUCUUAUUUUGUGAACUAUAtc-3'<br>3'-UUUCCUAGAAUAAAACACUUGAUAUAG-5'<br>5'-AAAGGATCTTATTTTGTGAACTATATC-3' | (SEQ ID NO: 2611)<br>(SEQ ID NO: 4625)<br>(SEQ ID NO: 6639) |
| LDHA-1732 Target: | 5'-GGAUCUUAUUUUGUGAACUAUAUca-3'<br>3'-UUCCUAGAAUAAAACACUUGAUAUAGU-5'<br>5'-AAGGATCTTATTTTGTGAACTATATCA-3' | (SEQ ID NO: 2612)<br>(SEQ ID NO: 4626)<br>(SEQ ID NO: 6640) |
| LDHA-1733 Target: | 5'-GAUCUUAUUUUGUGAACUAUAUCag-3'<br>3'-UCCUAGAAUAAAACACUUGAUAUAGUC-5'<br>5'-AGGATCTTATTTTGTGAACTATATCAG-3' | (SEQ ID NO: 2613)<br>(SEQ ID NO: 4627)<br>(SEQ ID NO: 6641) |
| LDHA-1734 Target: | 5'-AUCUUAUUUUGUGAACUAUAUCAgt-3'<br>3'-CCUAGAAUAAAACACUUGAUAUAGUCA-5'<br>5'-GGATCTTATTTTGTGAACTATATCAGT-3' | (SEQ ID NO: 2614)<br>(SEQ ID NO: 4628)<br>(SEQ ID NO: 6642) |
| LDHA-1735 Target: | 5'-UCUUAUUUUGUGAACUAUAUCAGta-3'<br>3'-CUAGAAUAAAACACUUGAUAUAGUCAU-5'<br>5'-GATCTTATTTTGTGAACTATATCAGTA-3' | (SEQ ID NO: 2615)<br>(SEQ ID NO: 4629)<br>(SEQ ID NO: 6643) |
| LDHA-1737 Target: | 5'-UUAUUUUGUGAACUAUAUCAGUAgt-3'<br>3'-AGAAUAAAACACUUGAUAUAGUCAUCA-5'<br>5'-TCTTATTTTGTGAACTATATCAGTAGT-3' | (SEQ ID NO: 2616)<br>(SEQ ID NO: 4630)<br>(SEQ ID NO: 6644) |
| LDHA-1738 Target: | 5'-UAUUUUGUGAACUAUAUCAGUAGtg-3'<br>3'-GAAUAAAACACUUGAUAUAGUCAUCAC-5'<br>5'-CTTATTTTGTGAACTATATCAGTAGTG-3' | (SEQ ID NO: 2617)<br>(SEQ ID NO: 4631)<br>(SEQ ID NO: 6645) |
| LDHA-1739 Target: | 5'-AUUUUGUGAACUAUAUCAGUAGUgt-3'<br>3'-AAUAAAACACUUGAUAUAGUCAUCACA-5'<br>5'-TTATTTTGTGAACTATATCAGTAGTGT-3' | (SEQ ID NO: 2618)<br>(SEQ ID NO: 4632)<br>(SEQ ID NO: 6646) |
| LDHA-1740 Target: | 5'-UUUUGUGAACUAUAUCAGUAGUGta-3'<br>3'-AUAAAACACUUGAUAUAGUCAUCACAU-5'<br>5'-TATTTTGTGAACTATATCAGTAGTGTA-3' | (SEQ ID NO: 2619)<br>(SEQ ID NO: 4633)<br>(SEQ ID NO: 6647) |

TABLE 12-continued

Additional Selected Human Anti-Lactate Dehydrogenase DsiRNA Agents (Asymmetrics)

|  |  |  |
|---|---|---|
| LDHA-1741 | 5'-UUUGUGAACUAUAUCAGUAGUGUAc-3'<br>3'-UAAAACACUUGAUAUAGUCAUCACAUG-5'<br>Target: 5'-ATTTTGTGAACTATATCAGTAGTGTAC-3' | (SEQ ID NO: 2620)<br>(SEQ ID NO: 4634)<br>(SEQ ID NO: 6648) |
| LDHA-1742 | 5'-UUGUGAACUAUAUCAGUAGUGUAca-3'<br>3'-AAAACACUUGAUAUAGUCAUCACAUGU-5'<br>Target: 5'-TTTTGTGAACTATATCAGTAGTGTACA-3' | (SEQ ID NO: 2621)<br>(SEQ ID NO: 4635)<br>(SEQ ID NO: 6649) |
| LDHA-1743 | 5'-UGUGAACUAUAUCAGUAGUGUACat-3'<br>3'-AAACACUUGAUAUAGUCAUCACAUGUA-5'<br>Target: 5'-TTTGTGAACTATATCAGTAGTGTACAT-3' | (SEQ ID NO: 2622)<br>(SEQ ID NO: 4636)<br>(SEQ ID NO: 6650) |
| LDHA-1744 | 5'-GUGAACUAUAUCAGUAGUGUACAtt-3'<br>3'-AACACUUGAUAUAGUCAUCACAUGUAA-5'<br>Target: 5'-TTGTGAACTATATCAGTAGTGTACATT-3' | (SEQ ID NO: 2623)<br>(SEQ ID NO: 4637)<br>(SEQ ID NO: 6651) |
| LDHA-1745 | 5'-UGAACUAUAUCAGUAGUGUACAUta-3'<br>3'-ACACUUGAUAUAGUCAUCACAUGUAAU-5'<br>Target: 5'-TGTGAACTATATCAGTAGTGTACATTA-3' | (SEQ ID NO: 2624)<br>(SEQ ID NO: 4638)<br>(SEQ ID NO: 6652) |
| LDHA-1746 | 5'-GAACUAUAUCAGUAGUGUACAUUac-3'<br>3'-CACUUGAUAUAGUCAUCACAUGUAAUG-5'<br>Target: 5'-GTGAACTATATCAGTAGTGTACATTAC-3' | (SEQ ID NO: 2625)<br>(SEQ ID NO: 4639)<br>(SEQ ID NO: 6653) |
| LDHA-1747 | 5'-AACUAUAUCAGUAGUGUACAUUAcc-3'<br>3'-ACUUGAUAUAGUCAUCACAUGUAAUGG-5'<br>Target: 5'-TGAACTATATCAGTAGTGTACATTACC-3' | (SEQ ID NO: 2626)<br>(SEQ ID NO: 4640)<br>(SEQ ID NO: 6654) |
| LDHA-1748 | 5'-ACUAUAUCAGUAGUGUACAUUACca-3'<br>3'-CUUGAUAUAGUCAUCACAUGUAAUGGU-5'<br>Target: 5'-GAACTATATCAGTAGTGTACATTACCA-3' | (SEQ ID NO: 2627)<br>(SEQ ID NO: 4641)<br>(SEQ ID NO: 6655) |
| LDHA-1749 | 5'-CUAUAUCAGUAGUGUACAUUACCat-3'<br>3'-UUGAUAUAGUCAUCACAUGUAAUGGUA-5'<br>Target: 5'-AACTATATCAGTAGTGTACATTACCAT-3' | (SEQ ID NO: 2628)<br>(SEQ ID NO: 4642)<br>(SEQ ID NO: 6656) |
| LDHA-1751 | 5'-AUAUCAGUAGUGUACAUUACCAUat-3'<br>3'-GAUAUAGUCAUCACAUGUAAUGGUAUA-5'<br>Target: 5'-CTATATCAGTAGTGTACATTACCATAT-3' | (SEQ ID NO: 2629)<br>(SEQ ID NO: 4643)<br>(SEQ ID NO: 6657) |
| LDHA-1752 | 5'-UAUCAGUAGUGUACAUUACCAUAta-3'<br>3'-AUAUAGUCAUCACAUGUAAUGGUAUAU-5'<br>Target: 5'-TATATCAGTAGTGTACATTACCATATA-3' | (SEQ ID NO: 2630)<br>(SEQ ID NO: 4644)<br>(SEQ ID NO: 6658) |
| LDHA-1755 | 5'-CAGUAGUGUACAUUACCAUAUAAtg-3'<br>3'-UAGUCAUCACAUGUAAUGGUAUAUUAC-5'<br>Target: 5'-ATCAGTAGTGTACATTACCATATAATG-3' | (SEQ ID NO: 2631)<br>(SEQ ID NO: 4645)<br>(SEQ ID NO: 6659) |
| LDHA-1756 | 5'-AGUAGUGUACAUUACCAUAUAAUgt-3'<br>3'-AGUCAUCACAUGUAAUGGUAUAUUACA-5'<br>Target: 5'-TCAGTAGTGTACATTACCATATAATGT-3' | (SEQ ID NO: 2632)<br>(SEQ ID NO: 4646)<br>(SEQ ID NO: 6660) |
| LDHA-1757 | 5'-GUAGUGUACAUUACCAUAUAAUGta-3'<br>3'-GUCAUCACAUGUAAUGGUAUAUUACAU-5'<br>Target: 5'-CAGTAGTGTACATTACCATATAATGTA-3' | (SEQ ID NO: 2633)<br>(SEQ ID NO: 4647)<br>(SEQ ID NO: 6661) |
| LDHA-1758 | 5'-UAGUGUACAUUACCAUAUAAUGUaa-3'<br>3'-UCAUCACAUGUAAUGGUAUAUUACAUU-5'<br>Target: 5'-AGTAGTGTACATTACCATATAATGTAA-3' | (SEQ ID NO: 2634)<br>(SEQ ID NO: 4648)<br>(SEQ ID NO: 6662) |
| LDHA-1759 | 5'-AGUGUACAUUACCAUAUAAUGUAaa-3'<br>3'-CAUCACAUGUAAUGGUAUAUUACAUUU-5'<br>Target: 5'-GTAGTGTACATTACCATATAATGTAAA-3' | (SEQ ID NO: 2635)<br>(SEQ ID NO: 4649)<br>(SEQ ID NO: 6663) |
| LDHA-1760 | 5'-GUGUACAUUACCAUAUAAUGUAAaa-3'<br>3'-AUCACAUGUAAUGGUAUAUUACAUUUU-5'<br>Target: 5'-TAGTGTACATTACCATATAATGTAAAA-3' | (SEQ ID NO: 2636)<br>(SEQ ID NO: 4650)<br>(SEQ ID NO: 6664) |
| LDHA-1761 | 5'-UGUACAUUACCAUAUAAUGUAAAa-3'<br>3'-UCACAUGUAAUGGUAUAUUACAUUUUU-5'<br>Target: 5'-AGTGTACATTACCATATAATGTAAAAA-3' | (SEQ ID NO: 2637)<br>(SEQ ID NO: 4651)<br>(SEQ ID NO: 6665) |
| LDHA-1762 | 5'-GUACAUUACCAUAUAAUGUAAAAg-3'<br>3'-CACAUGUAAUGGUAUAUUACAUUUUUC-5'<br>Target: 5'-GTGTACATTACCATATAATGTAAAAAG-3' | (SEQ ID NO: 2638)<br>(SEQ ID NO: 4652)<br>(SEQ ID NO: 6666) |

TABLE 12-continued

Additional Selected Human Anti-Lactate Dehydrogenase DsiRNA
Agents (Asymmetrics)

```
                   5'-UACAUUACCAUAUAAUGUAAAAAga-3'      (SEQ ID NO: 2639)
                   3'-ACAUGUAAUGGUAUAUUACAUUUUUCU-5'    (SEQ ID NO: 4653)
LDHA-1763 Target:  5'-TGTACATTACCATATAATGTAAAAAGA-3'    (SEQ ID NO: 6667)

5'-ACAUUACCAUAUAAUGUAAAAAGat-3'      (SEQ ID NO: 2640)
                   3'-CAUGUAAUGGUAUAUUACAUUUUUCUA-5'    (SEQ ID NO: 4654)
LDHA-1764 Target:  5'-GTACATTACCATATAATGTAAAAAGAT-3'    (SEQ ID NO: 6668)

5'-CAUUACCAUAUAAUGUAAAAAGAtc-3'      (SEQ ID NO: 2641)
                   3'-AUGUAAUGGUAUAUUACAUUUUUCUAG-5'    (SEQ ID NO: 4655)
LDHA-1765 Target:  5'-TACATTACCATATAATGTAAAAAGATC-3'    (SEQ ID NO: 6669)

5'-AUUACCAUAUAAUGUAAAAAGAUct-3'      (SEQ ID NO: 2642)
                   3'-UGUAAUGGUAUAUUACAUUUUUCUAGA-5'    (SEQ ID NO: 4656)
LDHA-1766 Target:  5'-ACATTACCATATAATGTAAAAAGATCT-3'    (SEQ ID NO: 6670)

5'-UUACCAUAUAAUGUAAAAAGAUCta-3'      (SEQ ID NO: 2643)
                   3'-GUAAUGGUAUAUUACAUUUUUCUAGAU-5'    (SEQ ID NO: 4657)
LDHA-1767 Target:  5'-CATTACCATATAATGTAAAAAGATCTA-3'    (SEQ ID NO: 6671)

5'-UACCAUAUAAUGUAAAAAGAUCUac-3'      (SEQ ID NO: 2644)
                   3'-UAAUGGUAUAUUACAUUUUUCUAGAUG-5'    (SEQ ID NO: 4658)
LDHA-1768 Target:  5'-ATTACCATATAATGTAAAAAGATCTAC-3'    (SEQ ID NO: 6672)

5'-ACCAUAUAAUGUAAAAAGAUCUACa-3'      (SEQ ID NO: 2645)
                   3'-AAUGGUAUAUUACAUUUUUCUAGAUGU-5'    (SEQ ID NO: 4659)
LDHA-1769 Target:  5'-TTACCATATAATGTAAAAAGATCTACA-3'    (SEQ ID NO: 6673)

5'-CCAUAUAAUGUAAAAAGAUCUACat-3'      (SEQ ID NO: 2646)
                   3'-AUGGUAUAUUACAUUUUUCUAGAUGUA-5'    (SEQ ID NO: 4660)
LDHA-1770 Target:  5'-TACCATATAATGTAAAAAGATCTACAT-3'    (SEQ ID NO: 6674)

5'-CAUAUAAUGUAAAAAGAUCUACAta-3'      (SEQ ID NO: 2647)
                   3'-UGGUAUAUUACAUUUUUCUAGAUGUAU-5'    (SEQ ID NO: 4661)
LDHA-1771 Target:  5'-ACCATATAATGTAAAAAGATCTACATA-3'    (SEQ ID NO: 6675)

5'-AUAUAAUGUAAAAAGAUCUACAUac-3'      (SEQ ID NO: 2648)
                   3'-GGUAUAUUACAUUUUUCUAGAUGUAUG-5'    (SEQ ID NO: 4662)
LDHA-1772 Target:  5'-CCATATAATGTAAAAAGATCTACATAC-3'    (SEQ ID NO: 6676)

5'-UAUAAUGUAAAAAGAUCUACAUAca-3'      (SEQ ID NO: 2649)
                   3'-GUAUAUUACAUUUUUCUAGAUGUAUGU-5'    (SEQ ID NO: 4663)
LDHA-1773 Target:  5'-CATATAATGTAAAAAGATCTACATACA-3'    (SEQ ID NO: 6677)

5'-AUAAUGUAAAAAGAUCUACAUACaa-3'      (SEQ ID NO: 2650)
                   3'-UAUAUUACAUUUUUCUAGAUGUAUGUU-5'    (SEQ ID NO: 4664)
LDHA-1774 Target:  5'-ATATAATGTAAAAAGATCTACATACAA-3'    (SEQ ID NO: 6678)

5'-UAAUGUAAAAAGAUCUACAUACAaa-3'      (SEQ ID NO: 2651)
                   3'-AUAUUACAUUUUUCUAGAUGUAUGUUU-5'    (SEQ ID NO: 4665)
LDHA-1775 Target:  5'-TATAATGTAAAAAGATCTACATACAAA-3'    (SEQ ID NO: 6679)

5'-AAUGUAAAAAGAUCUACAUACAAac-3'      (SEQ ID NO: 2652)
                   3'-UAUUACAUUUUUCUAGAUGUAUGUUUG-5'    (SEQ ID NO: 4666)
LDHA-1776 Target:  5'-ATAATGTAAAAAGATCTACATACAAAC-3'    (SEQ ID NO: 6680)

5'-AUGUAAAAAGAUCUACAUACAAAca-3'      (SEQ ID NO: 2653)
                   3'-AUUACAUUUUUCUAGAUGUAUGUUUGU-5'    (SEQ ID NO: 4667)
LDHA-1777 Target:  5'-TAATGTAAAAAGATCTACATACAAACA-3'    (SEQ ID NO: 6681)

5'-UGUAAAAAGAUCUACAUACAAACaa-3'      (SEQ ID NO: 2654)
                   3'-UUACAUUUUUCUAGAUGUAUGUUUGUU-5'    (SEQ ID NO: 4668)
LDHA-1778 Target:  5'-AATGTAAAAAGATCTACATACAAACAA-3'    (SEQ ID NO: 6682)

5'-GUAAAAAGAUCUACAUACAAACAat-3'      (SEQ ID NO: 2655)
                   3'-UACAUUUUUCUAGAUGUAUGUUUGUUA-5'    (SEQ ID NO: 4669)
LDHA-1779 Target:  5'-ATGTAAAAAGATCTACATACAAACAAT-3'    (SEQ ID NO: 6683)

5'-UAAAAAGAUCUACAUACAAACAAtg-3'      (SEQ ID NO: 2656)
                   3'-ACAUUUUUCUAGAUGUAUGUUUGUUAC-5'    (SEQ ID NO: 4670)
LDHA-1780 Target:  5'-TGTAAAAAGATCTACATACAAACAATG-3'    (SEQ ID NO: 6684)

5'-AAAAAGAUCUACAUACAAACAAUgc-3'      (SEQ ID NO: 2657)
                   3'-CAUUUUUCUAGAUGUAUGUUUGUUACG-5'    (SEQ ID NO: 4671)
LDHA-1781 Target:  5'-GTAAAAAGATCTACATACAAACAATGC-3'    (SEQ ID NO: 6685)
```

TABLE 12-continued

Additional Selected Human Anti-Lactate Dehydrogenase DsiRNA Agents (Asymmetrics)

| | | |
|---|---|---|
| | 5'-A<u>AA</u>AGAUCUACAUA<u>AC</u>AAACAAUGca-3' | (SEQ ID NO: 2658) |
| | 3'-<u>AUUU</u>UUCUAGAUGUAU<u>GU</u>UUGUUA<u>CGU</u>-5' | (SEQ ID NO: 4672) |
| LDHA-1782 Target: | 5'-TAAAAAGATCTACATACAAACAATGCA-3' | (SEQ ID NO: 6686) |
| | 5'-A<u>AA</u>GAUCUACAUA<u>C</u>AAACAAUGCaa-3' | (SEQ ID NO: 2659) |
| | 3'-<u>UUUUU</u>CUAGAUGUAU<u>GU</u>UUGUUA<u>CGU</u>U-5' | (SEQ ID NO: 4673) |
| LDHA-1783 Target: | 5'-AAAAAGATCTACATACAAACAATGCAA-3' | (SEQ ID NO: 6687) |
| | 5'-A<u>A</u>GAUCUACAUAC<u>AA</u>ACAAUGCAac-3' | (SEQ ID NO: 2660) |
| | 3'-<u>UUUU</u>CUAGAUGUAUG<u>UU</u>UGUUACG<u>UUG</u>-5' | (SEQ ID NO: 4674) |
| LDHA-1784 Target: | 5'-AAAAGATCTACATACAAACAATGCAAC-3' | (SEQ ID NO: 6688) |
| | 5'-A<u>G</u>AUCUACAUACA<u>AA</u>CAAUGCAcc-3' | (SEQ ID NO: 2661) |
| | 3'-<u>UUU</u>CUAGAUGUAUG<u>UU</u>UGUUACG<u>UUGG</u>-5' | (SEQ ID NO: 4675) |
| LDHA-1785 Target: | 5'-AAAGATCTACATACAAACAATGCAACC-3' | (SEQ ID NO: 6689) |
| | 5'-G<u>A</u>UCUACAUACAA<u>AC</u>AAUGCAACca-3' | (SEQ ID NO: 2662) |
| | 3'-<u>UUC</u>UAGAUGUAUGU<u>UU</u>GUUACGUU<u>GGU</u>-5' | (SEQ ID NO: 4676) |
| LDHA-1786 Target: | 5'-AAGATCTACATACAAACAATGCAACCA-3' | (SEQ ID NO: 6690) |
| | 5'-A<u>U</u>CUACAUACAAA<u>C</u>AAUGCAACCaa-3' | (SEQ ID NO: 2663) |
| | 3'-<u>UC</u>UAGAUGUAUGUU<u>U</u>GUUACGUUG<u>GUU</u>-5' | (SEQ ID NO: 4677) |
| LDHA-1787 Target: | 5'-AGATCTACATACAAACAATGCAACCAA-3' | (SEQ ID NO: 6691) |
| | 5'-U<u>C</u>UACAUACAAAC<u>A</u>AUGCAACCAac-3' | (SEQ ID NO: 2664) |
| | 3'-<u>C</u>UAGAUGUAUGUUU<u>G</u>UUACGUUGG<u>UUG</u>-5' | (SEQ ID NO: 4678) |
| LDHA-1788 Target: | 5'-GATCTACATACAAACAATGCAACCAAC-3' | (SEQ ID NO: 6692) |
| | 5'-C<u>U</u>ACAUACAAACA<u>AU</u>GCAACCAAct-3' | (SEQ ID NO: 2665) |
| | 3'-<u>UA</u>GAUGUAUGUUUG<u>UU</u>ACGUUGGU<u>UGA</u>-5' | (SEQ ID NO: 4679) |
| LDHA-1789 Target: | 5'-ATCTACATACAAACAATGCAACCAACT-3' | (SEQ ID NO: 6693) |
| | 5'-U<u>A</u>CAUACAAACAAUG<u>C</u>AACCAACta-3' | (SEQ ID NO: 2666) |
| | 3'-<u>AG</u>AUGUAUGUUUGUU<u>AC</u>GUUGGU<u>UGAU</u>-5' | (SEQ ID NO: 4680) |
| LDHA-1790 Target: | 5'-TCTACATACAAACAATGCAACCAACTA-3' | (SEQ ID NO: 6694) |
| | 5'-A<u>C</u>AUACAAACAAUGC<u>A</u>ACCAACUat-3' | (SEQ ID NO: 2667) |
| | 3'-<u>GA</u>UGUAUGUUUGUUA<u>C</u>GUUGGUU<u>GAUA</u>-5' | (SEQ ID NO: 4681) |
| LDHA-1791 Target: | 5'-CTACATACAAACAATGCAACCAACTAT-3' | (SEQ ID NO: 6695) |
| | 5'-C<u>A</u>UACAAACAAUGC<u>A</u>ACCAACUAtc-3' | (SEQ ID NO: 2668) |
| | 3'-<u>AU</u>GUAUGUUUGUUAC<u>G</u>UUGGUUG<u>AUAG</u>-5' | (SEQ ID NO: 4682) |
| LDHA-1792 Target: | 5'-TACATACAAACAATGCAACCAACTATC-3' | (SEQ ID NO: 6696) |
| | 5'-A<u>U</u>ACAAACAAUGCA<u>AC</u>CAACUAUcc-3' | (SEQ ID NO: 2669) |
| | 3'-<u>UG</u>UAUGUUUGUUACG<u>UU</u>GGUUGA<u>UAGG</u>-5' | (SEQ ID NO: 4683) |
| LDHA-1793 Target: | 5'-ACATACAAACAATGCAACCAACTATCC-3' | (SEQ ID NO: 6697) |
| | 5'-U<u>A</u>CAAACAAUGCA<u>AC</u>CAACUAUCca-3' | (SEQ ID NO: 2670) |
| | 3'-<u>GU</u>AUGUUUGUUACG<u>UU</u>GGUUGAU<u>AGGU</u>-5' | (SEQ ID NO: 4684) |
| LDHA-1794 Target: | 5'-CATACAAACAATGCAACCAACTATCCA-3' | (SEQ ID NO: 6698) |
| | 5'-A<u>C</u>AAACAAUGCAAC<u>C</u>AACUAUCCaa-3' | (SEQ ID NO: 2671) |
| | 3'-<u>UA</u>UGUUUGUUACGU<u>UG</u>GUUGAUA<u>GGUU</u>-5' | (SEQ ID NO: 4685) |
| LDHA-1795 Target: | 5'-ATACAAACAATGCAACCAACTATCCAA-3' | (SEQ ID NO: 6699) |
| | 5'-C<u>AA</u>ACAAUGCAACC<u>A</u>ACUAUCCAag-3' | (SEQ ID NO: 2672) |
| | 3'-<u>AU</u>GUUUGUUACGUU<u>GG</u>UUGAUAG<u>GUUC</u>-5' | (SEQ ID NO: 4686) |
| LDHA-1796 Target: | 5'-TACAAACAATGCAACCAACTATCCAAG-3' | (SEQ ID NO: 6700) |
| | 5'-A<u>AA</u>CAAUGCAACCA<u>AC</u>UAUCCAAgt-3' | (SEQ ID NO: 2673) |
| | 3'-<u>UG</u>UUUGUUACGUUG<u>G</u>UUGAUAGG<u>UUCA</u>-5' | (SEQ ID NO: 4687) |
| LDHA-1797 Target: | 5'-ACAAACAATGCAACCAACTATCCAAGT-3' | (SEQ ID NO: 6701) |
| | 5'-A<u>A</u>CAAUGCAACCA<u>AC</u>UAUCCAAGtg-3' | (SEQ ID NO: 2674) |
| | 3'-<u>GU</u>UUGUUACGUUGG<u>UU</u>GAUAGGUU<u>CAC</u>-5' | (SEQ ID NO: 4688) |
| LDHA-1798 Target: | 5'-CAAACAATGCAACCAACTATCCAAGTG-3' | (SEQ ID NO: 6702) |
| | 5'-A<u>C</u>AAUGCAACCAAC<u>U</u>AUCCAAGUgt-3' | (SEQ ID NO: 2675) |
| | 3'-<u>UUU</u>GUUACGUUGGU<u>UG</u>AUAGGUU<u>CACA</u>-5' | (SEQ ID NO: 4689) |
| LDHA-1799 Target: | 5'-AAACAATGCAACCAACTATCCAAGTGT-3' | (SEQ ID NO: 6703) |
| | 5'-C<u>AA</u>UGCAACCAACU<u>AU</u>CCAAGUGtt-3' | (SEQ ID NO: 2676) |
| | 3'-<u>UU</u>GUUACGUUGGUU<u>GA</u>UAGGUUC<u>ACAA</u>-5' | (SEQ ID NO: 4690) |
| LDHA-1800 Target: | 5'-AACAATGCAACCAACTATCCAAGTGTT-3' | (SEQ ID NO: 6704) |

TABLE 12-continued

Additional Selected Human Anti-Lactate Dehydrogenase DsiRNA Agents (Asymmetrics)

|  |  |  |
|---|---|---|
| LDHA-1801 Target: | 5'-AAUGCAACCAACUAUCCAAGUGUta-3'<br>3'-UGUUACGUUGGUUGAUAGGUUCACAAU-5'<br>5'-ACAATGCAACCAACTATCCAAGTGTTA-3' | (SEQ ID NO: 2677)<br>(SEQ ID NO: 4691)<br>(SEQ ID NO: 6705) |
| LDHA-1802 Target: | 5'-AUGCAACCAACUAUCCAAGUGUUat-3'<br>3'-GUUACGUUGGUUGAUAGGUUCACAAUA-5'<br>5'-CAATGCAACCAACTATCCAAGTGTTAT-3' | (SEQ ID NO: 2678)<br>(SEQ ID NO: 4692)<br>(SEQ ID NO: 6706) |
| LDHA-1803 Target: | 5'-UGCAACCAACUAUCCAAGUGUUAta-3'<br>3'-UUACGUUGGUUGAUAGGUUCACAAUAU-5'<br>5'-AATGCAACCAACTATCCAAGTGTTATA-3' | (SEQ ID NO: 2679)<br>(SEQ ID NO: 4693)<br>(SEQ ID NO: 6707) |
| LDHA-1804 Target: | 5'-GCAACCAACUAUCCAAGUGUUAUac-3'<br>3'-UACGUUGGUUGAUAGGUUCACAAUAUG-5'<br>5'-ATGCAACCAACTATCCAAGTGTTATAC-3' | (SEQ ID NO: 2680)<br>(SEQ ID NO: 4694)<br>(SEQ ID NO: 6708) |
| LDHA-1809 Target: | 5'-CAACUAUCCAAGUGUUAUACCAAct-3'<br>3'-UGGUUGAUAGGUUCACAAUAUGGUUGA-5'<br>5'-ACCAACTATCCAAGTGTTATACCAACT-3' | (SEQ ID NO: 2681)<br>(SEQ ID NO: 4695)<br>(SEQ ID NO: 6709) |
| LDHA-1810 Target: | 5'-AACUAUCCAAGUGUUAUACCAACta-3'<br>3'-GGUUGAUAGGUUCACAAUAUGGUUGAU-5'<br>5'-CCAACTATCCAAGTGTTATACCAACTA-3' | (SEQ ID NO: 2682)<br>(SEQ ID NO: 4696)<br>(SEQ ID NO: 6710) |
| LDHA-1813 Target: | 5'-UAUCCAAGUGUUAUACCAACUAAaa-3'<br>3'-UGAUAGGUUCACAAUAUGGUUGAUUUU-5'<br>5'-ACTATCCAAGTGTTATACCAACTAAAA-3' | (SEQ ID NO: 2683)<br>(SEQ ID NO: 4697)<br>(SEQ ID NO: 6711) |
| LDHA-1814 Target: | 5'-AUCCAAGUGUUAUACCAACUAAAac-3'<br>3'-GAUAGGUUCACAAUAUGGUUGAUUUUG-5'<br>5'-CTATCCAAGTGTTATACCAACTAAAAC-3' | (SEQ ID NO: 2684)<br>(SEQ ID NO: 4698)<br>(SEQ ID NO: 6712) |
| LDHA-1817 Target: | 5'-CAAGUGUUAUACCAACUAAAACCcc-3'<br>3'-AGGUUCACAAUAUGGUUGAUUUUGGGG-5'<br>5'-TCCAAGTGTTATACCAACTAAAACCCC-3' | (SEQ ID NO: 2685)<br>(SEQ ID NO: 4699)<br>(SEQ ID NO: 6713) |
| LDHA-1818 Target: | 5'-AAGUGUUAUACCAACUAAAACCCcc-3'<br>3'-GGUUCACAAUAUGGUUGAUUUUGGGGG-5'<br>5'-CCAAGTGTTATACCAACTAAAACCCCC-3' | (SEQ ID NO: 2686)<br>(SEQ ID NO: 4700)<br>(SEQ ID NO: 6714) |
| LDHA-1819 Target: | 5'-AGUGUUAUACCAACUAAAACCCCca-3'<br>3'-GUUCACAAUAUGGUUGAUUUUGGGGGU-5'<br>5'-CAAGTGTTATACCAACTAAAACCCCCA-3' | (SEQ ID NO: 2687)<br>(SEQ ID NO: 4701)<br>(SEQ ID NO: 6715) |
| LDHA-1820 Target: | 5'-GUGUUAUACCAACUAAAACCCCCaa-3'<br>3'-UUCACAAUAUGGUUGAUUUUGGGGGUU-5'<br>5'-AAGTGTTATACCAACTAAAACCCCCAA-3' | (SEQ ID NO: 2688)<br>(SEQ ID NO: 4702)<br>(SEQ ID NO: 6716) |
| LDHA-1821 Target: | 5'-UGUUAUACCAACUAAAACCCCCAat-3'<br>3'-UCACAAUAUGGUUGAUUUUGGGGGUUA-5'<br>5'-AGTGTTATACCAACTAAAACCCCCAAT-3' | (SEQ ID NO: 2689)<br>(SEQ ID NO: 4703)<br>(SEQ ID NO: 6717) |
| LDHA-1822 Target: | 5'-GUUAUACCAACUAAAACCCCCAAta-3'<br>3'-CACAAUAUGGUUGAUUUUGGGGGUUAU-5'<br>5'-GTGTTATACCAACTAAAACCCCCAATA-3' | (SEQ ID NO: 2690)<br>(SEQ ID NO: 4704)<br>(SEQ ID NO: 6718) |
| LDHA-1823 Target: | 5'-UUAUACCAACUAAAACCCCCAAUaa-3'<br>3'-ACAAUAUGGUUGAUUUUGGGGGUUAUU-5'<br>5'-TGTTATACCAACTAAAACCCCCAATAA-3' | (SEQ ID NO: 2691)<br>(SEQ ID NO: 4705)<br>(SEQ ID NO: 6719) |
| LDHA-1824 Target: | 5'-UAUACCAACUAAAACCCCCAAUAaa-3'<br>3'-CAAUAUGGUUGAUUUUGGGGGUUAUUU-5'<br>5'-GTTATACCAACTAAAACCCCCAATAAA-3' | (SEQ ID NO: 2692)<br>(SEQ ID NO: 4706)<br>(SEQ ID NO: 6720) |
| LDHA-1825 Target: | 5'-AUACCAACUAAAACCCCCAAUAAac-3'<br>3'-AAUAUGGUUGAUUUUGGGGGUUAUUUG-5'<br>5'-TTATACCAACTAAAACCCCCAATAAAC-3' | (SEQ ID NO: 2693)<br>(SEQ ID NO: 4707)<br>(SEQ ID NO: 6721) |
| LDHA-1826 Target: | 5'-UACCAACUAAAACCCCCAAUAAAcc-3'<br>3'-AUAUGGUUGAUUUUGGGGGUUAUUUGG-5'<br>5'-TATACCAACTAAAACCCCCAATAAACC-3' | (SEQ ID NO: 2694)<br>(SEQ ID NO: 4708)<br>(SEQ ID NO: 6722) |
| LDHA-1827 Target: | 5'-ACCAACUAAAACCCCCAAUAAACct-3'<br>3'-UAUGGUUGAUUUUGGGGGUUAUUUGGA-5'<br>5'-ATACCAACTAAAACCCCCAATAAACCT-3' | (SEQ ID NO: 2695)<br>(SEQ ID NO: 4709)<br>(SEQ ID NO: 6723) |

TABLE 12-continued

Additional Selected Human Anti-Lactate Dehydrogenase DsiRNA
Agents (Asymmetrics)

|  |  |  |
|---|---|---|
| LDHA-1828 Target: | 5'-CCAACUAAAACCCCCAAUAAACCtt-3'<br>3'-AUGGUUGAUUUUGGGGGUUAUUUGGAA-5'<br>5'-TACCAACTAAAACCCCCAATAAACCTT-3' | (SEQ ID NO: 2696)<br>(SEQ ID NO: 4710)<br>(SEQ ID NO: 6724) |
| LDHA-1829 Target: | 5'-CAACUAAAACCCCCAAUAAACCUtg-3'<br>3'-UGGUUGAUUUUGGGGGUUAUUUGGAAC-5'<br>5'-ACCAACTAAAACCCCCAATAAACCTTG-3' | (SEQ ID NO: 2697)<br>(SEQ ID NO: 4711)<br>(SEQ ID NO: 6725) |
| LDHA-1830 Target: | 5'-AACUAAAACCCCCAAUAAACCUUga-3'<br>3'-GGUUGAUUUUGGGGGUUAUUUGGAACU-5'<br>5'-CCAACTAAAACCCCCAATAAACCTTGA-3' | (SEQ ID NO: 2698)<br>(SEQ ID NO: 4712)<br>(SEQ ID NO: 6726) |
| LDHA-1831 Target: | 5'-ACUAAAACCCCCAAUAAACCUUGaa-3'<br>3'-GUUGAUUUUGGGGGUUAUUUGGAACUU-5'<br>5'-CAACTAAAACCCCCAATAAACCTTGAA-3' | (SEQ ID NO: 2699)<br>(SEQ ID NO: 4713)<br>(SEQ ID NO: 6727) |
| LDHA-1832 Target: | 5'-CUAAAACCCCCAAUAAACCUUGAac-3'<br>3'-UUGAUUUUGGGGGUUAUUUGGAACUUG-5'<br>5'-AACTAAAACCCCCAATAAACCTTGAAC-3' | (SEQ ID NO: 2700)<br>(SEQ ID NO: 4714)<br>(SEQ ID NO: 6728) |
| LDHA-1833 Target: | 5'-UAAAACCCCCAAUAAACCUUGAAca-3'<br>3'-UGAUUUUGGGGGUUAUUUGGAACUUGU-5'<br>5'-ACTAAAACCCCCAATAAACCTTGAACA-3' | (SEQ ID NO: 2701)<br>(SEQ ID NO: 4715)<br>(SEQ ID NO: 6729) |
| LDHA-1834 Target: | 5'-AAAACCCCCAAUAAACCUUGAACag-3'<br>3'-GAUUUUGGGGGUUAUUUGGAACUUGUC-5'<br>5'-CTAAAACCCCCAATAAACCTTGAACAG-3' | (SEQ ID NO: 2702)<br>(SEQ ID NO: 4716)<br>(SEQ ID NO: 6730) |
| LDHA-1835 Target: | 5'-AAACCCCCAAUAAACCUUGAACAgt-3'<br>3'-AUUUUGGGGGUUAUUUGGAACUUGUCA-5'<br>5'-TAAAACCCCCAATAAACCTTGAACAGT-3' | (SEQ ID NO: 2703)<br>(SEQ ID NO: 4717)<br>(SEQ ID NO: 6731) |
| LDHA-1836 Target: | 5'-AACCCCCAAUAAACCUUGAACAGtg-3'<br>3'-UUUUGGGGGUUAUUUGGAACUUGUCAC-5'<br>5'-AAAACCCCCAATAAACCTTGAACAGTG-3' | (SEQ ID NO: 2704)<br>(SEQ ID NO: 4718)<br>(SEQ ID NO: 6732) |
| LDHA-1837 Target: | 5'-ACCCCCAAUAAACCUUGAACAGUga-3'<br>3'-UUUGGGGGUUAUUUGGAACUUGUCACU-5'<br>5'-AAACCCCCAATAAACCTTGAACAGTGA-3' | (SEQ ID NO: 2705)<br>(SEQ ID NO: 4719)<br>(SEQ ID NO: 6733) |
| LDHA-1838 Target: | 5'-CCCCCAAUAAACCUUGAACAGUGac-3'<br>3'-UUGGGGGUUAUUUGGAACUUGUCACUG-5'<br>5'-AACCCCCAATAAACCTTGAACAGTGAC-3' | (SEQ ID NO: 2706)<br>(SEQ ID NO: 4720)<br>(SEQ ID NO: 6734) |
| LDHA-1839 Target: | 5'-CCCCAAUAAACCUUGAACAGUGAct-3'<br>3'-UGGGGGUUAUUUGGAACUUGUCACUGA-5'<br>5'-ACCCCCAATAAACCTTGAACAGTGACT-3' | (SEQ ID NO: 2707)<br>(SEQ ID NO: 4721)<br>(SEQ ID NO: 6735) |
| LDHA-1840 Target: | 5'-CCCAAUAAACCUUGAACAGUGACta-3'<br>3'-GGGGGUUAUUUGGAACUUGUCACUGAU-5'<br>5'-CCCCCAATAAACCTTGAACAGTGACTA-3' | (SEQ ID NO: 2708)<br>(SEQ ID NO: 4722)<br>(SEQ ID NO: 6736) |
| LDHA-1841 Target: | 5'-CCAAUAAACCUUGAACAGUGACUac-3'<br>3'-GGGGUUAUUUGGAACUUGUCACUGAUG-5'<br>5'-CCCCAATAAACCTTGAACAGTGACTAC-3' | (SEQ ID NO: 2709)<br>(SEQ ID NO: 4723)<br>(SEQ ID NO: 6737) |
| LDHA-1842 Target: | 5'-CAAUAAACCUUGAACAGUGACUAct-3'<br>3'-GGGUUAUUUGGAACUUGUCACUGAUGA-5'<br>5'-CCCAATAAACCTTGAACAGTGACTACT-3' | (SEQ ID NO: 2710)<br>(SEQ ID NO: 4724)<br>(SEQ ID NO: 6738) |
| LDHA-1843 Target: | 5'-AAUAAACCUUGAACAGUGACUACtt-3'<br>3'-GGUUAUUUGGAACUUGUCACUGAUGAA-5'<br>5'-CCAATAAACCTTGAACAGTGACTACTT-3' | (SEQ ID NO: 2711)<br>(SEQ ID NO: 4725)<br>(SEQ ID NO: 6739) |
| LDHA-1844 Target: | 5'-AUAAACCUUGAACAGUGACUACUtt-3'<br>3'-GUUAUUUGGAACUUGUCACUGAUGAAA-5'<br>5'-CAATAAACCTTGAACAGTGACTACTTT-3' | (SEQ ID NO: 2712)<br>(SEQ ID NO: 4726)<br>(SEQ ID NO: 6740) |
| LDHA-1845 Target: | 5'-UAAACCUUGAACAGUGACUACUUtg-3'<br>3'-UUAUUUGGAACUUGUCACUGAUGAAAC-5'<br>5'-AATAAACCTTGAACAGTGACTACTTTG-3' | (SEQ ID NO: 2713)<br>(SEQ ID NO: 4727)<br>(SEQ ID NO: 6741) |
| LDHA-1846 Target: | 5'-AAACCUUGAACAGUGACUACUUUgg-3'<br>3'-UAUUUGGAACUUGUCACUGAUGAAACC-5'<br>5'-ATAAACCTTGAACAGTGACTACTTTGG-3' | (SEQ ID NO: 2714)<br>(SEQ ID NO: 4728)<br>(SEQ ID NO: 6742) |

TABLE 12-continued

Additional Selected Human Anti-Lactate Dehydrogenase DsiRNA Agents (Asymmetrics)

```
                5'-AACCUUGAACAGUGACUACUUUGgt-3'      (SEQ ID NO: 2715)
                3'-AUUUGGAACUUGUCACUGAUGAAACCA-5'    (SEQ ID NO: 4729)
LDHA-1847 Target: 5'-TAAACCTTGAACAGTGACTACTTTGGT-3'  (SEQ ID NO: 6743)

5'-ACCUUGAACAGUGACUACUUUGGtt-3'      (SEQ ID NO: 2716)
                3'-UUUGGAACUUGUCACUGAUGAAACCAA-5'    (SEQ ID NO: 4730)
LDHA-1848 Target: 5'-AAACCTTGAACAGTGACTACTTTGGTT-3'  (SEQ ID NO: 6744)

5'-CCUUGAACAGUGACUACUUUGGUta-3'      (SEQ ID NO: 2717)
                3'-UUGGAACUUGUCACUGAUGAAACCAAU-5'    (SEQ ID NO: 4731)
LDHA-1849 Target: 5'-AACCTTGAACAGTGACTACTTTGGTTA-3'  (SEQ ID NO: 6745)

5'-CUUGAACAGUGACUACUUUGGUUaa-3'      (SEQ ID NO: 2718)
                3'-UGGAACUUGUCACUGAUGAAACCAAUU-5'    (SEQ ID NO: 4732)
LDHA-1850 Target: 5'-ACCTTGAACAGTGACTACTTTGGTTAA-3'  (SEQ ID NO: 6746)

5'-UUGAACAGUGACUACUUUGGUUAat-3'      (SEQ ID NO: 2719)
                3'-GGAACUUGUCACUGAUGAAACCAAUUA-5'    (SEQ ID NO: 4733)
LDHA-1851 Target: 5'-CCTTGAACAGTGACTACTTTGGTTAAT-3'  (SEQ ID NO: 6747)

5'-UGAACAGUGACUACUUUGGUUAAtt-3'      (SEQ ID NO: 2720)
                3'-GAACUUGUCACUGAUGAAACCAAUUAA-5'    (SEQ ID NO: 4734)
LDHA-1852 Target: 5'-CTTGAACAGTGACTACTTTGGTTAATT-3'  (SEQ ID NO: 6748)

5'-GAACAGUGACUACUUUGGUUAAUtc-3'      (SEQ ID NO: 2721)
                3'-AACUUGUCACUGAUGAAACCAAUUAAG-5'    (SEQ ID NO: 4735)
LDHA-1853 Target: 5'-TTGAACAGTGACTACTTTGGTTAATTC-3'  (SEQ ID NO: 6749)

5'-AACAGUGACUACUUUGGUUAAUUca-3'      (SEQ ID NO: 2722)
                3'-ACUUGUCACUGAUGAAACCAAUUAAGU-5'    (SEQ ID NO: 4736)
LDHA-1854 Target: 5'-TGAACAGTGACTACTTTGGTTAATTCA-3'  (SEQ ID NO: 6750)

5'-ACAGUGACUACUUUGGUUAAUUCat-3'      (SEQ ID NO: 2723)
                3'-CUUGUCACUGAUGAAACCAAUUAAGUA-5'    (SEQ ID NO: 4737)
LDHA-1855 Target: 5'-GAACAGTGACTACTTTGGTTAATTCAT-3'  (SEQ ID NO: 6751)

5'-CAGUGACUACUUUGGUUAAUUCAtt-3'      (SEQ ID NO: 2724)
                3'-UUGUCACUGAUGAAACCAAUUAAGUAA-5'    (SEQ ID NO: 4738)
LDHA-1856 Target: 5'-AACAGTGACTACTTTGGTTAATTCATT-3'  (SEQ ID NO: 6752)

5'-AGUGACUACUUUGGUUAAUUCAUta-3'      (SEQ ID NO: 2725)
                3'-UGUCACUGAUGAAACCAAUUAAGUAAU-5'    (SEQ ID NO: 4739)
LDHA-1857 Target: 5'-ACAGTGACTACTTTGGTTAATTCATTA-3'  (SEQ ID NO: 6753)

5'-GUGACUACUUUGGUUAAUUCAUUat-3'      (SEQ ID NO: 2726)
                3'-GUCACUGAUGAAACCAAUUAAGUAAUA-5'    (SEQ ID NO: 4740)
LDHA-1858 Target: 5'-CAGTGACTACTTTGGTTAATTCATTAT-3'  (SEQ ID NO: 6754)

5'-UGACUACUUUGGUUAAUUCAUUAta-3'      (SEQ ID NO: 2727)
                3'-UCACUGAUGAAACCAAUUAAGUAAUAU-5'    (SEQ ID NO: 4741)
LDHA-1859 Target: 5'-AGTGACTACTTTGGTTAATTCATTATA-3'  (SEQ ID NO: 6755)

5'-GACUACUUUGGUUAAUUCAUUAUat-3'      (SEQ ID NO: 2728)
                3'-CACUGAUGAAACCAAUUAAGUAAUAUA-5'    (SEQ ID NO: 4742)
LDHA-1860 Target: 5'-GTGACTACTTTGGTTAATTCATTATAT-3'  (SEQ ID NO: 6756)

5'-ACUACUUUGGUUAAUUCAUUAUAtt-3'      (SEQ ID NO: 2729)
                3'-ACUGAUGAAACCAAUUAAGUAAUAUAA-5'    (SEQ ID NO: 4743)
LDHA-1861 Target: 5'-TGACTACTTTGGTTAATTCATTATATT-3'  (SEQ ID NO: 6757)

5'-CUACUUUGGUUAAUUCAUUAUAUta-3'      (SEQ ID NO: 2730)
                3'-CUGAUGAAACCAAUUAAGUAAUAUAAU-5'    (SEQ ID NO: 4744)
LDHA-1862 Target: 5'-GACTACTTTGGTTAATTCATTATATTA-3'  (SEQ ID NO: 6758)

5'-UACUUUGGUUAAUUCAUUAUAUUaa-3'      (SEQ ID NO: 2731)
                3'-UGAUGAAACCAAUUAAGUAAUAUAAUU-5'    (SEQ ID NO: 4745)
LDHA-1863 Target: 5'-ACTACTTTGGTTAATTCATTATATTAA-3'  (SEQ ID NO: 6759)

5'-ACUUUGGUUAAUUCAUUAUAUUAag-3'      (SEQ ID NO: 2732)
                3'-GAUGAAACCAAUUAAGUAAUAUAAUUC-5'    (SEQ ID NO: 4746)
LDHA-1864 Target: 5'-CTACTTTGGTTAATTCATTATATTAAG-3'  (SEQ ID NO: 6760)

5'-CUUUGGUUAAUUCAUUAUAUUAAga-3'      (SEQ ID NO: 2733)
                3'-AUGAAACCAAUUAAGUAAUAUAAUUCU-5'    (SEQ ID NO: 4747)
LDHA-1865 Target: 5'-TACTTTGGTTAATTCATTATATTAAGA-3'  (SEQ ID NO: 6761)
```

TABLE 12-continued

Additional Selected Human Anti-Lactate Dehydrogenase DsiRNA Agents (Asymmetrics)

|  |  |  |
| --- | --- | --- |
|  | 5'-UUUGGUUAAUUCAUUAUAUUAAGat-3' | (SEQ ID NO: 2734) |
|  | 3'-UGAAACCAAUUAAGUAAUAUAAUUCUA-5' | (SEQ ID NO: 4748) |
| LDHA-1866 Target: | 5'-ACTTTGGTTAATTCATTATATTAAGAT-3' | (SEQ ID NO: 6762) |
|  | 5'-UUGGUUAAUUCAUUAUAUUAAGAta-3' | (SEQ ID NO: 2735) |
|  | 3'-GAAACCAAUUAAGUAAUAUAAUUCUAU-5' | (SEQ ID NO: 4749) |
| LDHA-1867 Target: | 5'-CTTTGGTTAATTCATTATATTAAGATA-3' | (SEQ ID NO: 6763) |
|  | 5'-UGGUUAAUUCAUUAUAUUAAGAUat-3' | (SEQ ID NO: 2736) |
|  | 3'-AAACCAAUUAAGUAAUAUAAUUCUAUA-5' | (SEQ ID NO: 4750) |
| LDHA-1868 Target: | 5'-TTTGGTTAATTCATTATATTAAGATAT-3' | (SEQ ID NO: 6764) |
|  | 5'-GGUUAAUUCAUUAUAUUAAGAUAta-3' | (SEQ ID NO: 2737) |
|  | 3'-AACCAAUUAAGUAAUAUAAUUCUAUAU-5' | (SEQ ID NO: 4751) |
| LDHA-1869 Target: | 5'-TTGGTTAATTCATTATATTAAGATATA-3' | (SEQ ID NO: 6765) |
|  | 5'-GUUAAUUCAUUAUAUUAAGAUAUaa-3' | (SEQ ID NO: 2738) |
|  | 3'-ACCAAUUAAGUAAUAUAAUUCUAUAUU-5' | (SEQ ID NO: 4752) |
| LDHA-1870 Target: | 5'-TGGTTAATTCATTATATTAAGATATAA-3' | (SEQ ID NO: 6766) |
|  | 5'-UUAAUUCAUUAUAUUAAGAUAUAaa-3' | (SEQ ID NO: 2739) |
|  | 3'-CCAAUUAAGUAAUAUAAUUCUAUAUUU-5' | (SEQ ID NO: 4753) |
| LDHA-1871 Target: | 5'-GGTTAATTCATTATATTAAGATATAAA-3' | (SEQ ID NO: 6767) |
|  | 5'-UAAUUCAUUAUAUUAAGAUAUAAag-3' | (SEQ ID NO: 2740) |
|  | 3'-CAAUUAAGUAAUAUAAUUCUAUAUUUC-5' | (SEQ ID NO: 4754) |
| LDHA-1872 Target: | 5'-GTTAATTCATTATATTAAGATATAAAG-3' | (SEQ ID NO: 6768) |
|  | 5'-AAUUCAUUAUAUUAAGAUAUAAAgt-3' | (SEQ ID NO: 2741) |
|  | 3'-AAUUAAGUAAUAUAAUUCUAUAUUUCA-5' | (SEQ ID NO: 4755) |
| LDHA-1873 Target: | 5'-TTAATTCATTATATTAAGATATAAAGT-3' | (SEQ ID NO: 6769) |
|  | 5'-AUUCAUUAUAUUAAGAUAUAAAGtc-3' | (SEQ ID NO: 2742) |
|  | 3'-AUUAAGUAAUAUAAUUCUAUAUUUCAG-5' | (SEQ ID NO: 4756) |
| LDHA-1874 Target: | 5'-TAATTCATTATATTAAGATATAAAGTC-3' | (SEQ ID NO: 6770) |
|  | 5'-UUCAUUAUAUUAAGAUAUAAAGUca-3' | (SEQ ID NO: 2743) |
|  | 3'-UUAAGUAAUAUAAUUCUAUAUUUCAGU-5' | (SEQ ID NO: 4757) |
| LDHA-1875 Target: | 5'-AATTCATTATATTAAGATATAAAGTCA-3' | (SEQ ID NO: 6771) |
|  | 5'-UCAUUAUAUUAAGAUAUAAAGUCat-3' | (SEQ ID NO: 2744) |
|  | 3'-UAAGUAAUAUAAUUCUAUAUUUCAGUA-5' | (SEQ ID NO: 4758) |
| LDHA-1876 Target: | 5'-ATTCATTATATTAAGATATAAAGTCAT-3' | (SEQ ID NO: 6772) |
|  | 5'-CAUUAUAUUAAGAUAUAAAGUCAta-3' | (SEQ ID NO: 2745) |
|  | 3'-AAGUAAUAUAAUUCUAUAUUUCAGUAU-5' | (SEQ ID NO: 4759) |
| LDHA-1877 Target: | 5'-TTCATTATATTAAGATATAAAGTCATA-3' | (SEQ ID NO: 6773) |
|  | 5'-AUUAUAUUAAGAUAUAAAGUCAUaa-3' | (SEQ ID NO: 2746) |
|  | 3'-AGUAAUAUAAUUCUAUAUUUCAGUAUU-5' | (SEQ ID NO: 4760) |
| LDHA-1878 Target: | 5'-TCATTATATTAAGATATAAAGTCATAA-3' | (SEQ ID NO: 6774) |
|  | 5'-UUAUAUUAAGAUAUAAAGUCAUAaa-3' | (SEQ ID NO: 2747) |
|  | 3'-GUAAUAUAAUUCUAUAUUUCAGUAUUU-5' | (SEQ ID NO: 4761) |
| LDHA-1879 Target: | 5'-CATTATATTAAGATATAAAGTCATAAA-3' | (SEQ ID NO: 6775) |
|  | 5'-UAUAUUAAGAUAUAAAGUCAUAAag-3' | (SEQ ID NO: 2748) |
|  | 3'-UAAUAUAAUUCUAUAUUUCAGUAUUUC-5' | (SEQ ID NO: 4762) |
| LDHA-1880 Target: | 5'-ATTATATTAAGATATAAAGTCATAAAG-3' | (SEQ ID NO: 6776) |
|  | 5'-AUAUUAAGAUAUAAAGUCAUAAAgc-3' | (SEQ ID NO: 2749) |
|  | 3'-AAUAUAAUUCUAUAUUUCAGUAUUUCG-5' | (SEQ ID NO: 4763) |
| LDHA-1881 Target: | 5'-TTATATTAAGATATAAAGTCATAAAGC-3' | (SEQ ID NO: 6777) |
|  | 5'-UAUUAAGAUAUAAAGUCAUAAAGct-3' | (SEQ ID NO: 2750) |
|  | 3'-AUAUAAUUCUAUAUUUCAGUAUUUCGA-5' | (SEQ ID NO: 4764) |
| LDHA-1882 Target: | 5'-TATATTAAGATATAAAGTCATAAAGCT-3' | (SEQ ID NO: 6778) |
|  | 5'-AUUAAGAUAUAAAGUCAUAAAGCtg-3' | (SEQ ID NO: 2751) |
|  | 3'-UAUAAUUCUAUAUUUCAGUAUUUCGAC-5' | (SEQ ID NO: 4765) |
| LDHA-1883 Target: | 5'-ATATTAAGATATAAAGTCATAAAGCTG-3' | (SEQ ID NO: 6779) |
|  | 5'-UUAAGAUAUAAAGUCAUAAAGCUgc-3' | (SEQ ID NO: 2752) |
|  | 3'-AUAAUUCUAUAUUUCAGUAUUUCGACG-5' | (SEQ ID NO: 4766) |
| LDHA-1884 Target: | 5'-TATTAAGATATAAAGTCATAAAGCTGC-3' | (SEQ ID NO: 6780) |

TABLE 12-continued

Additional Selected Human Anti-Lactate Dehydrogenase DsiRNA Agents (Asymmetrics)

| | | |
|---|---|---|
| LDHA-1885 | 5'-UA<u>A</u>GAUAUAAAGUC<u>A</u>UAAAGCUGct-3'<br>3'-<u>UAAU</u>UCUAUAUUUC<u>A</u>GUAUUUCG<u>ACGA</u>-5'<br>Target: 5'-ATTAAGATATAAAGTCATAAAGCTGCT-3' | (SEQ ID NO: 2753)<br>(SEQ ID NO: 4767)<br>(SEQ ID NO: 6781) |
| LDHA-1886 | 5'-A<u>A</u>GAUAUAAAGUC<u>A</u>UAAAGCUGCta-3'<br>3'-<u>AAUU</u>CUAUAUUUC<u>A</u>GU<u>A</u>UUUCG<u>A</u>C<u>GAU</u>-5'<br>Target: 5'-TTAAGATATAAAGTCATAAAGCTGCTA-3' | (SEQ ID NO: 2754)<br>(SEQ ID NO: 4768)<br>(SEQ ID NO: 6782) |
| LDHA-1887 | 5'-<u>A</u>GAUAUAAAGUCAU<u>A</u>AAGCUGCUag-3'<br>3'-<u>AUUC</u>UAUAUUUCAG<u>U</u>AUUUCGAC<u>GAUC</u>-5'<br>Target: 5'-TAAGATATAAAGTCATAAAGCTGCTAG-3' | (SEQ ID NO: 2755)<br>(SEQ ID NO: 4769)<br>(SEQ ID NO: 6783) |
| LDHA-1888 | 5'-<u>G</u>AUAUAAAGUCAU<u>AAA</u>GCUGCUAgt-3'<br>3'-<u>UUC</u>U<u>A</u>UAUUUCAGUAU<u>U</u>UCGACG<u>AUCA</u>-5'<br>Target: 5'-AAGATATAAAGTCATAAAGCTGCTAGT-3' | (SEQ ID NO: 2756)<br>(SEQ ID NO: 4770)<br>(SEQ ID NO: 6784) |
| LDHA-1889 | 5'-<u>A</u>U<u>A</u>U<u>A</u>AAGUCAU<u>AAA</u>GCUGCUAGtt-3'<br>3'-<u>UC</u>U<u>A</u>UAUUUCAGU<u>A</u>U<u>UU</u>CGACGA<u>UCAA</u>-5'<br>Target: 5'-AGATATAAAGTCATAAAGCTGCTAGTT-3' | (SEQ ID NO: 2757)<br>(SEQ ID NO: 4771)<br>(SEQ ID NO: 6785) |
| LDHA-1890 | 5'-<u>U</u>A<u>U</u>A<u>A</u>AGUCAU<u>AAA</u>G<u>C</u>UGCUAGUta-3'<br>3'-<u>CU</u>AU<u>A</u>UUUCAGU<u>A</u>U<u>UU</u>CGACGA<u>UCAAU</u>-5'<br>Target: 5'-GATATAAAGTCATAAAGCTGCTAGTTA-3' | (SEQ ID NO: 2758)<br>(SEQ ID NO: 4772)<br>(SEQ ID NO: 6786) |
| LDHA-1891 | 5'-<u>A</u>U<u>AAA</u>GUCAU<u>AAA</u>G<u>C</u>UGCUAGUUat-3'<br>3'-<u>UAUAU</u>UUCAGUAU<u>UUC</u>GACGAUC<u>AAUA</u>-5'<br>Target: 5'-ATATAAAGTCATAAAGCTGCTAGTTAT-3' | (SEQ ID NO: 2759)<br>(SEQ ID NO: 4773)<br>(SEQ ID NO: 6787) |
| LDHA-1892 | 5'-<u>U</u>A<u>AA</u>GUCAU<u>AAA</u>GC<u>U</u>GCUAGUUAtt-3'<br>3'-<u>AUAU</u>UUCAGUAU<u>UUC</u>GACGAUC<u>AAUAA</u>-5'<br>Target: 5'-TATAAAGTCATAAAGCTGCTAGTTATT-3' | (SEQ ID NO: 2760)<br>(SEQ ID NO: 4774)<br>(SEQ ID NO: 6788) |
| LDHA-1893 | 5'-<u>AA</u>GUCAU<u>AAA</u>GCUGC<u>U</u>AGUUAUta-3'<br>3'-<u>UAUU</u>UCAGUAUUUC<u>G</u>ACGAUCAA<u>UAAU</u>-5'<br>Target: 5'-ATAAAGTCATAAAGCTGCTAGTTATTA-3' | (SEQ ID NO: 2761)<br>(SEQ ID NO: 4775)<br>(SEQ ID NO: 6789) |
| LDHA-1894 | 5'-<u>A</u>AGUCAU<u>AAA</u>GCUGC<u>U</u>AGUUAUUat-3'<br>3'-<u>AUUU</u>CAGUAUUUCG<u>A</u>CGAUCAAU<u>AAUA</u>-5'<br>Target: 5'-TAAAGTCATAAAGCTGCTAGTTATTAT-3' | (SEQ ID NO: 2762)<br>(SEQ ID NO: 4776)<br>(SEQ ID NO: 6790) |
| LDHA-1895 | 5'-<u>A</u>GU<u>C</u>AU<u>AAA</u>GCUGC<u>U</u>AGUUAUUAta-3'<br>3'-<u>UUUC</u>AGUAUUUCG<u>A</u>CGAUCAAUA<u>AUAU</u>-5'<br>Target: 5'-AAAGTCATAAAGCTGCTAGTTATTATA-3' | (SEQ ID NO: 2763)<br>(SEQ ID NO: 4777)<br>(SEQ ID NO: 6791) |
| LDHA-1896 | 5'-<u>G</u>U<u>C</u>AU<u>AAA</u>GCUGC<u>U</u>A<u>G</u>UUAUUAUat-3'<br>3'-<u>UUC</u>AGUAUUUCG<u>AC</u>G<u>A</u>UCAAUAU<u>AUA</u>-5'<br>Target: 5'-AAGTCATAAAGCTGCTAGTTATTATAT-3' | (SEQ ID NO: 2764)<br>(SEQ ID NO: 4778)<br>(SEQ ID NO: 6792) |
| LDHA-1897 | 5'-<u>U</u>C<u>A</u>U<u>AAA</u>GCUGCUA<u>G</u>UUAUUAUAtt-3'<br>3'-<u>UC</u>AGUAUUUCGACG<u>A</u>UCAAUAUA<u>UAA</u>-5'<br>Target: 5'-AGTCATAAAGCTGCTAGTTATTATATT-3' | (SEQ ID NO: 2765)<br>(SEQ ID NO: 4779)<br>(SEQ ID NO: 6793) |
| LDHA-1898 | 5'-<u>C</u>AU<u>AAA</u>GCUGCUA<u>G</u>U<u>U</u>AUUAUAUta-3'<br>3'-<u>C</u>AGUAUUUCGACG<u>A</u>UCAAUAUAU<u>AAU</u>-5'<br>Target: 5'-GTCATAAAGCTGCTAGTTATTATATTA-3' | (SEQ ID NO: 2766)<br>(SEQ ID NO: 4780)<br>(SEQ ID NO: 6794) |
| LDHA-1899 | 5'-<u>A</u>U<u>AAA</u>GCUGCUA<u>G</u>U<u>U</u>AUUAUAUUaa-3'<br>3'-<u>A</u>GUAUUUCGACGAUC<u>A</u>AUAUAUAUA<u>AUU</u>-5'<br>Target: 5'-TCATAAAGCTGCTAGTTATTATATTAA-3' | (SEQ ID NO: 2767)<br>(SEQ ID NO: 4781)<br>(SEQ ID NO: 6795) |
| LDHA-1900 | 5'-<u>U</u>A<u>AA</u>GCUGCUAGU<u>U</u>AUUAUAUUAat-3'<br>3'-<u>G</u>UAUUUCGACGAUC<u>A</u>AUAUAUAUA<u>AUUA</u>-5'<br>Target: 5'-CATAAAGCTGCTAGTTATTATATTAAT-3' | (SEQ ID NO: 2768)<br>(SEQ ID NO: 4782)<br>(SEQ ID NO: 6796) |
| LDHA-1901 | 5'-<u>AAA</u>GCUGCUAGUU<u>A</u>UUAUAUUAAtt-3'<br>3'-<u>U</u>AUUUCGACGAUCA<u>A</u>UAUAUAAUUAA-5'<br>Target: 5'-ATAAAGCTGCTAGTTATTATATTAATT-3' | (SEQ ID NO: 2769)<br>(SEQ ID NO: 4783)<br>(SEQ ID NO: 6797) |
| LDHA-1902 | 5'-<u>AA</u>GCUGCUAGUU<u>A</u>U<u>U</u>AUAUUAAUtt-3'<br>3'-<u>AUUU</u>CGACGAUCAA<u>U</u>A<u>U</u>AUAAUU<u>AAA</u>-5'<br>Target: 5'-TAAAGCTGCTAGTTATTATATTAATTT-3' | (SEQ ID NO: 2770)<br>(SEQ ID NO: 4784)<br>(SEQ ID NO: 6798) |
| LDHA-1903 | 5'-<u>A</u>GCUGCUAGU<u>U</u>AU<u>U</u>A<u>U</u>AUUAAUUtg-3'<br>3'-<u>UUUC</u>GACGAUCAAU<u>A</u>AUAUAAUU<u>AAAC</u>-5'<br>Target: 5'-AAAGCTGCTAGTTATTATATTAATTTG-3' | (SEQ ID NO: 2771)<br>(SEQ ID NO: 4785)<br>(SEQ ID NO: 6799) |

TABLE 12-continued

Additional Selected Human Anti-Lactate Dehydrogenase DsiRNA Agents (Asymmetrics)

|  |  |  |  |
|---|---|---|---|
| LDHA-1904 | Target: | 5'-GCUGCUAGUUAUUAUAUUAAUUUgg-3'<br>3'-UUCGACGAUCAAUAAUAUAAUUAAACC-5'<br>5'-AAGCTGCTAGTTATTATATTAATTTGG-3' | (SEQ ID NO: 2772)<br>(SEQ ID NO: 4786)<br>(SEQ ID NO: 6800) |
| LDHA-1905 | Target: | 5'-CUGCUAGUUAUUAUAUUAAUUUGga-3'<br>3'-UCGACGAUCAAUAAUAUAAUUAAACCU-5'<br>5'-AGCTGCTAGTTATTATATTAATTTGGA-3' | (SEQ ID NO: 2773)<br>(SEQ ID NO: 4787)<br>(SEQ ID NO: 6801) |
| LDHA-1906 | Target: | 5'-UGCUAGUUAUUAUAUUAAUUUGGaa-3'<br>3'-CGACGAUCAAUAAUAUAAUUAAACCUU-5'<br>5'-GCTGCTAGTTATTATATTAATTTGGAA-3' | (SEQ ID NO: 2774)<br>(SEQ ID NO: 4788)<br>(SEQ ID NO: 6802) |
| LDHA-1907 | Target: | 5'-GCUAGUUAUUAUAUUAAUUUGGAaa-3'<br>3'-GACGAUCAAUAAUAUAAUUAAACCUUU-5'<br>5'-CTGCTAGTTATTATATTAATTTGGAAA-3' | (SEQ ID NO: 2775)<br>(SEQ ID NO: 4789)<br>(SEQ ID NO: 6803) |
| LDHA-1908 | Target: | 5'-CUAGUUAUUAUAUUAAUUUGGAAat-3'<br>3'-ACGAUCAAUAAUAUAAUUAAACCUUUA-5'<br>5'-TGCTAGTTATTATATTAATTTGGAAAT-3' | (SEQ ID NO: 2776)<br>(SEQ ID NO: 4790)<br>(SEQ ID NO: 6804) |
| LDHA-1909 | Target: | 5'-UAGUUAUUAUAUUAAUUUGGAAAta-3'<br>3'-CGAUCAAUAAUAUAAUUAAACCUUUAU-5'<br>5'-GCTAGTTATTATATTAATTTGGAAATA-3' | (SEQ ID NO: 2777)<br>(SEQ ID NO: 4791)<br>(SEQ ID NO: 6805) |
| LDHA-1910 | Target: | 5'-AGUUAUUAUAUUAAUUUGGAAAUat-3'<br>3'-GAUCAAUAAUAUAAUUAAACCUUUAUA-5'<br>5'-CTAGTTATTATATTAATTTGGAAATAT-3' | (SEQ ID NO: 2778)<br>(SEQ ID NO: 4792)<br>(SEQ ID NO: 6806) |
| LDHA-1911 | Target: | 5'-GUUAUUAUAUUAAUUUGGAAAUAtt-3'<br>3'-AUCAAUAAUAUAAUUAAACCUUUAUAA-5'<br>5'-TAGTTATTATATTAATTTGGAAATATT-3' | (SEQ ID NO: 2779)<br>(SEQ ID NO: 4793)<br>(SEQ ID NO: 6807) |
| LDHA-1912 | Target: | 5'-UUAUUAUAUUAAUUUGGAAAUAUta-3'<br>3'-UCAAUAAUAUAAUUAAACCUUUAUAAU-5'<br>5'-AGTTATTATATTAATTTGGAAATATTA-3' | (SEQ ID NO: 2780)<br>(SEQ ID NO: 4794)<br>(SEQ ID NO: 6808) |
| LDHA-1913 | Target: | 5'-UAUUAUAUUAAUUUGGAAAUAUUag-3'<br>3'-CAAUAAUAUAAUUAAACCUUUAUAAUC-5'<br>5'-GTTATTATATTAATTTGGAAATATTAG-3' | (SEQ ID NO: 2781)<br>(SEQ ID NO: 4795)<br>(SEQ ID NO: 6809) |
| LDHA-1914 | Target: | 5'-AUUAUAUUAAUUUGGAAAUAUUAgg-3'<br>3'-AAUAAUAUAAUUAAACCUUUAUAAUCC-5'<br>5'-TTATTATATTAATTTGGAAATATTAGG-3' | (SEQ ID NO: 2782)<br>(SEQ ID NO: 4796)<br>(SEQ ID NO: 6810) |
| LDHA-1915 | Target: | 5'-UUAUUAAUUUGGAAAUAUUAGgc-3'<br>3'-AUAAUAUAAUUAAACCUUUAUAAUCCG-5'<br>5'-TATTATATTAATTTGGAAATATTAGGC-3' | (SEQ ID NO: 2783)<br>(SEQ ID NO: 4797)<br>(SEQ ID NO: 6811) |
| LDHA-1916 | Target: | 5'-UAUUAAUUUGGAAAUAUUAGGct-3'<br>3'-UAAUAAUUAAACCUUUAUAAUCCGA-5'<br>5'-ATTATATTAATTTGGAAATATTAGGCT-3' | (SEQ ID NO: 2784)<br>(SEQ ID NO: 4798)<br>(SEQ ID NO: 6812) |
| LDHA-1917 | Target: | 5'-AUAUUAAUUUGGAAAUAUUAGGCta-3'<br>3'-AAUAUAAUUAAACCUUUAUAAUCCGAU-5'<br>5'-TTATATTAATTTGGAAATATTAGGCTA-3' | (SEQ ID NO: 2785)<br>(SEQ ID NO: 4799)<br>(SEQ ID NO: 6813) |
| LDHA-1918 | Target: | 5'-UAUUAAUUUGGAAAUAUUAGGCUat-3'<br>3'-AUAUAAUUAAACCUUUAUAAUCCGAUA-5'<br>5'-TATATTAATTTGGAAATATTAGGCTAT-3' | (SEQ ID NO: 2786)<br>(SEQ ID NO: 4800)<br>(SEQ ID NO: 6814) |
| LDHA-1919 | Target: | 5'-AUUAAUUUGGAAAUAUUAGGCUAtt-3'<br>3'-UAUAAUUAAACCUUUAUAAUCCGAUAA-5'<br>5'-ATATTAATTTGGAAATATTAGGCTATT-3' | (SEQ ID NO: 2787)<br>(SEQ ID NO: 4801)<br>(SEQ ID NO: 6815) |
| LDHA-1920 | Target: | 5'-UUAAUUUGGAAAUAUUAGGCUAUtc-3'<br>3'-AUAAUUAAACCUUUAUAAUCCGAUAAG-5'<br>5'-TATTAATTTGGAAATATTAGGCTATTC-3' | (SEQ ID NO: 2788)<br>(SEQ ID NO: 4802)<br>(SEQ ID NO: 6816) |
| LDHA-1921 | Target: | 5'-UAAUUUGGAAAUAUUAGGCUAUUct-3'<br>3'-UAAUUAAACCUUUAUAAUCCGAUAAGA-5'<br>5'-ATTAATTTGGAAATATTAGGCTATTCT-3' | (SEQ ID NO: 2789)<br>(SEQ ID NO: 4803)<br>(SEQ ID NO: 6817) |
| LDHA-1922 | Target: | 5'-AAUUUGGAAAUAUUAGGCUAUUCtt-3'<br>3'-AAUUAAACCUUUAUAAUCCGAUAAGAA-5'<br>5'-TTAATTTGGAAATATTAGGCTATTCTT-3' | (SEQ ID NO: 2790)<br>(SEQ ID NO: 4804)<br>(SEQ ID NO: 6818) |

TABLE 12-continued

Additional Selected Human Anti-Lactate Dehydrogenase DsiRNA Agents (Asymmetrics)

```
                    5'-AUUUGGAAAUAUUAGGCUAUUCUtg-3'    (SEQ ID NO: 2791)
                    3'-AUUAAACCUUUAUAAUCCGAUAAGAAC-5'  (SEQ ID NO: 4805)
LDHA-1923 Target:   5'-TAATTTGGAAATATTAGGCTATTCTTG-3'  (SEQ ID NO: 6819)

5'-UUUGGAAAUAUUAGGCUAUUCUUgg-3'    (SEQ ID NO: 2792)
                    3'-UUAAACCUUUAUAAUCCGAUAAGAACC-5'  (SEQ ID NO: 4806)
LDHA-1924 Target:   5'-AATTTGGAAATATTAGGCTATTCTTGG-3' (SEQ ID NO: 6820)

5'-UUGGAAAUAUUAGGCUAUUCUUGgg-3'    (SEQ ID NO: 2793)
                    3'-UAAACCUUUAUAAUCCGAUAAGAACCC-5'  (SEQ ID NO: 4807)
LDHA-1925 Target:   5'-ATTTGGAAATATTAGGCTATTCTTGGG-3' (SEQ ID NO: 6821)

5'-UGGAAAUAUUAGGCUAUUCUUGGgc-3'    (SEQ ID NO: 2794)
                    3'-AAACCUUUAUAAUCCGAUAAGAACCCG-5'  (SEQ ID NO: 4808)
LDHA-1926 Target:   5'-TTTGGAAATATTAGGCTATTCTTGGGC-3' (SEQ ID NO: 6822)

5'-GGAAAUAUUAGGCUAUUCUUGGGca-3'    (SEQ ID NO: 2795)
                    3'-AACCUUUAUAAUCCGAUAAGAACCCGU-5'  (SEQ ID NO: 4809)
LDHA-1927 Target:   5'-TTGGAAATATTAGGCTATTCTTGGGCA-3' (SEQ ID NO: 6823)

5'-GAAAUAUUAGGCUAUUCUUGGGCaa-3'    (SEQ ID NO: 2796)
                    3'-ACCUUUAUAAUCCGAUAAGAACCCGUU-5'  (SEQ ID NO: 4810)
LDHA-1928 Target:   5'-TGGAAATATTAGGCTATTCTTGGGCAA-3' (SEQ ID NO: 6824)

5'-AAAUAUUAGGCUAUUCUUGGGCAac-3'    (SEQ ID NO: 2797)
                    3'-CCUUUAUAAUCCGAUAAGAACCCGUUG-5'  (SEQ ID NO: 4811)
LDHA-1929 Target:   5'-GGAAATATTAGGCTATTCTTGGGCAAC-3' (SEQ ID NO: 6825)

5'-AAUAUUAGGCUAUUCUUGGGCAAcc-3'    (SEQ ID NO: 2798)
                    3'-CUUUAUAAUCCGAUAAGAACCCGUUGG-5'  (SEQ ID NO: 4812)
LDHA-1930 Target:   5'-GAAATATTAGGCTATTCTTGGGCAACC-3' (SEQ ID NO: 6826)

5'-AUAUUAGGCUAUUCUUGGGCAACcc-3'    (SEQ ID NO: 2799)
                    3'-UUUAUAAUCCGAUAAGAACCCGUUGGG-5'  (SEQ ID NO: 4813)
LDHA-1931 Target:   5'-AAATATTAGGCTATTCTTGGGCAACCC-3' (SEQ ID NO: 6827)

5'-UAUUAGGCUAUUCUUGGGCAACCct-3'    (SEQ ID NO: 2800)
                    3'-UUAUAAUCCGAUAAGAACCCGUUGGGA-5'  (SEQ ID NO: 4814)
LDHA-1932 Target:   5'-AATATTAGGCTATTCTTGGGCAACCCT-3' (SEQ ID NO: 6828)

5'-AUUAGGCUAUUCUUGGGCAACCCtg-3'    (SEQ ID NO: 2801)
                    3'-UAUAAUCCGAUAAGAACCCGUUGGGAC-5'  (SEQ ID NO: 4815)
LDHA-1933 Target:   5'-ATATTAGGCTATTCTTGGGCAACCCTG-3' (SEQ ID NO: 6829)

5'-UUAGGCUAUUCUUGGGCAACCCUgc-3'    (SEQ ID NO: 2802)
                    3'-AUAAUCCGAUAAGAACCCGUUGGGACG-5'  (SEQ ID NO: 4816)
LDHA-1934 Target:   5'-TATTAGGCTATTCTTGGGCAACCCTGC-3' (SEQ ID NO: 6830)

5'-UAGGCUAUUCUUGGGCAACCCUGca-3'    (SEQ ID NO: 2803)
                    3'-UAAUCCGAUAAGAACCCGUUGGGACGU-5'  (SEQ ID NO: 4817)
LDHA-1935 Target:   5'-ATTAGGCTATTCTTGGGCAACCCTGCA-3' (SEQ ID NO: 6831)

5'-AGGCUAUUCUUGGGCAACCCUGCaa-3'    (SEQ ID NO: 2804)
                    3'-AAUCCGAUAAGAACCCGUUGGGACGUU-5'  (SEQ ID NO: 4818)
LDHA-1936 Target:   5'-TTAGGCTATTCTTGGGCAACCCTGCAA-3' (SEQ ID NO: 6832)

5'-GGCUAUUCUUGGGCAACCCUGCAac-3'    (SEQ ID NO: 2805)
                    3'-AUCCGAUAAGAACCCGUUGGGACGUUG-5'  (SEQ ID NO: 4819)
LDHA-1937 Target:   5'-TAGGCTATTCTTGGGCAACCCTGCAAC-3' (SEQ ID NO: 6833)

5'-GCUAUUCUUGGGCAACCCUGCAAcg-3'    (SEQ ID NO: 2806)
                    3'-UCCGAUAAGAACCCGUUGGGACGUUGC-5'  (SEQ ID NO: 4820)
LDHA-1938 Target:   5'-AGGCTATTCTTGGGCAACCCTGCAACG-3' (SEQ ID NO: 6834)

5'-CUAUUCUUGGGCAACCCUGCAACga-3'    (SEQ ID NO: 2807)
                    3'-CCGAUAAGAACCCGUUGGGACGUUGCU-5'  (SEQ ID NO: 4821)
LDHA-1939 Target:   5'-GGCTATTCTTGGGCAACCCTGCAACGA-3' (SEQ ID NO: 6835)

5'-UAUUCUUGGGCAACCCUGCAACGat-3'    (SEQ ID NO: 2808)
                    3'-CGAUAAGAACCCGUUGGGACGUUGCUA-5'  (SEQ ID NO: 4822)
LDHA-1940 Target:   5'-GCTATTCTTGGGCAACCCTGCAACGAT-3' (SEQ ID NO: 6836)

5'-AUUCUUGGGCAACCCUGCAACGAtt-3'    (SEQ ID NO: 2809)
                    3'-GAUAAGAACCCGUUGGGACGUUGCUAA-5'  (SEQ ID NO: 4823)
LDHA-1941 Target:   5'-CTATTCTTGGGCAACCCTGCAACGATT-3' (SEQ ID NO: 6837)
```

TABLE 12-continued

Additional Selected Human Anti-Lactate Dehydrogenase DsiRNA Agents (Asymmetrics)

|  |  |  |
| --- | --- | --- |
|  | 5'-UUCUUGGGCAACCCUGCAACGAUtt-3' | (SEQ ID NO: 2810) |
|  | 3'-AUAAGAACCCGUUGGGACGUUGCUAAA-5' | (SEQ ID NO: 4824) |
| LDHA-1942 Target: | 5'-TATTCTTGGGCAACCCTGCAACGATTT-3' | (SEQ ID NO: 6838) |
|  | 5'-UCUUGGGCAACCCUGCAACGAUUt-3' | (SEQ ID NO: 2811) |
|  | 3'-UAAGAACCCGUUGGGACGUUGCUAAAA-5' | (SEQ ID NO: 4825) |
| LDHA-1943 Target: | 5'-ATTCTTGGGCAACCCTGCAACGATTTT-3' | (SEQ ID NO: 6839) |
|  | 5'-CUUGGGCAACCCUGCAACGAUUUtt-3' | (SEQ ID NO: 2812) |
|  | 3'-AAGAACCCGUUGGGACGUUGCUAAAAA-5' | (SEQ ID NO: 4826) |
| LDHA-1944 Target: | 5'-TTCTTGGGCAACCCTGCAACGATTTTT-3' | (SEQ ID NO: 6840) |
|  | 5'-UUGGGCAACCCUGCAACGAUUUUtt-3' | (SEQ ID NO: 2813) |
|  | 3'-AGAACCCGUUGGGACGUUGCUAAAAAA-5' | (SEQ ID NO: 4827) |
| LDHA-1945 Target: | 5'-TCTTGGGCAACCCTGCAACGATTTTTT-3' | (SEQ ID NO: 6841) |
|  | 5'-UGGGCAACCCUGCAACGAUUUUUtc-3' | (SEQ ID NO: 2814) |
|  | 3'-GAACCCGUUGGGACGUUGCUAAAAAAG-5' | (SEQ ID NO: 4828) |
| LDHA-1946 Target: | 5'-CTTGGGCAACCCTGCAACGATTTTTTC-3' | (SEQ ID NO: 6842) |
|  | 5'-GGGCAACCCUGCAACGAUUUUUUct-3' | (SEQ ID NO: 2815) |
|  | 3'-AACCCGUUGGGACGUUGCUAAAAAAGA-5' | (SEQ ID NO: 4829) |
| LDHA-1947 Target: | 5'-TTGGGCAACCCTGCAACGATTTTTTCT-3' | (SEQ ID NO: 6843) |
|  | 5'-GGCAACCCUGCAACGAUUUUUUCta-3' | (SEQ ID NO: 2816) |
|  | 3'-ACCCGUUGGGACGUUGCUAAAAAAGAU-5' | (SEQ ID NO: 4830) |
| LDHA-1948 Target: | 5'-TGGGCAACCCTGCAACGATTTTTTCTA-3' | (SEQ ID NO: 6844) |
|  | 5'-GCAACCCUGCAACGAUUUUUUCUaa-3' | (SEQ ID NO: 2817) |
|  | 3'-CCCGUUGGGACGUUGCUAAAAAAGAUU-5' | (SEQ ID NO: 4831) |
| LDHA-1949 Target: | 5'-GGGCAACCCTGCAACGATTTTTTCTAA-3' | (SEQ ID NO: 6845) |
|  | 5'-CAACCCUGCAACGAUUUUUUCUAac-3' | (SEQ ID NO: 2818) |
|  | 3'-CCGUUGGGACGUUGCUAAAAAAGAUUG-5' | (SEQ ID NO: 4832) |
| LDHA-1950 Target: | 5'-GGCAACCCTGCAACGATTTTTTCTAAC-3' | (SEQ ID NO: 6846) |
|  | 5'-AACCCUGCAACGAUUUUUUCUAAca-3' | (SEQ ID NO: 2819) |
|  | 3'-CGUUGGGACGUUGCUAAAAAAGAUUGU-5' | (SEQ ID NO: 4833) |
| LDHA-1951 Target: | 5'-GCAACCCTGCAACGATTTTTTCTAACA-3' | (SEQ ID NO: 6847) |
|  | 5'-ACCCUGCAACGAUUUUUUCUAACag-3' | (SEQ ID NO: 2820) |
|  | 3'-GUUGGGACGUUGCUAAAAAAGAUUGUC-5' | (SEQ ID NO: 4834) |
| LDHA-1952 Target: | 5'-CAACCCTGCAACGATTTTTTCTAACAG-3' | (SEQ ID NO: 6848) |
|  | 5'-CCCUGCAACGAUUUUUUCUAACAgg-3' | (SEQ ID NO: 2821) |
|  | 3'-UUGGGACGUUGCUAAAAAAGAUUGUCC-5' | (SEQ ID NO: 4835) |
| LDHA-1953 Target: | 5'-AACCCTGCAACGATTTTTTCTAACAGG-3' | (SEQ ID NO: 6849) |
|  | 5'-CCUGCAACGAUUUUUUCUAACAGgg-3' | (SEQ ID NO: 2822) |
|  | 3'-UGGGACGUUGCUAAAAAAGAUUGUCCC-5' | (SEQ ID NO: 4836) |
| LDHA-1954 Target: | 5'-ACCCTGCAACGATTTTTTCTAACAGGG-3' | (SEQ ID NO: 6850) |
|  | 5'-CUGCAACGAUUUUUUCUAACAGGga-3' | (SEQ ID NO: 2823) |
|  | 3'-GGGACGUUGCUAAAAAAGAUUGUCCCU-5' | (SEQ ID NO: 4837) |
| LDHA-1955 Target: | 5'-CCCTGCAACGATTTTTTCTAACAGGGA-3' | (SEQ ID NO: 6851) |
|  | 5'-UGCAACGAUUUUUUCUAACAGGGat-3' | (SEQ ID NO: 2824) |
|  | 3'-GGACGUUGCUAAAAAAGAUUGUCCCUA-5' | (SEQ ID NO: 4838) |
| LDHA-1956 Target: | 5'-CCTGCAACGATTTTTTCTAACAGGGAT-3' | (SEQ ID NO: 6852) |
|  | 5'-GCAACGAUUUUUUCUAACAGGGAta-3' | (SEQ ID NO: 2825) |
|  | 3'-GACGUUGCUAAAAAAGAUUGUCCCUAU-5' | (SEQ ID NO: 4839) |
| LDHA-1957 Target: | 5'-CTGCAACGATTTTTTCTAACAGGGATA-3' | (SEQ ID NO: 6853) |
|  | 5'-CAACGAUUUUUUCUAACAGGGAUat-3' | (SEQ ID NO: 2826) |
|  | 3'-ACGUUGCUAAAAAAGAUUGUCCCUAUA-5' | (SEQ ID NO: 4840) |
| LDHA-1958 Target: | 5'-TGCAACGATTTTTTCTAACAGGGATAT-3' | (SEQ ID NO: 6854) |
|  | 5'-AACGAUUUUUUCUAACAGGGAUAtt-3' | (SEQ ID NO: 2827) |
|  | 3'-CGUUGCUAAAAAAGAUUGUCCCUAUAA-5' | (SEQ ID NO: 4841) |
| LDHA-1959 Target: | 5'-GCAACGATTTTTTCTAACAGGGATATT-3' | (SEQ ID NO: 6855) |
|  | 5'-ACGAUUUUUUCUAACAGGGAUAUta-3' | (SEQ ID NO: 2828) |
|  | 3'-GUUGCUAAAAAAGAUUGUCCCUAUAAU-5' | (SEQ ID NO: 4842) |
| LDHA-1960 Target: | 5'-CAACGATTTTTTCTAACAGGGATATTA-3' | (SEQ ID NO: 6856) |

TABLE 12-continued

Additional Selected Human Anti-Lactate Dehydrogenase DsiRNA Agents (Asymmetrics)

| | | |
|---|---|---|
| LDHA-1961 Target: | 5'-CGAUUUUUCUAACAGGGAUAUUat-3'<br>3'-UUGCUAAAAAGAUUGUCCCUAUAAUA-5'<br>5'-AACGATTTTTCTAACAGGGATATTAT-3' | (SEQ ID NO: 2829)<br>(SEQ ID NO: 4843)<br>(SEQ ID NO: 6857) |
| LDHA-1962 Target: | 5'-GAUUUUUCUAACAGGGAUAUUAtt-3'<br>3'-UGCUAAAAAGAUUGUCCCUAUAAUAA-5'<br>5'-ACGATTTTTCTAACAGGGATATTATT-3' | (SEQ ID NO: 2830)<br>(SEQ ID NO: 4844)<br>(SEQ ID NO: 6858) |
| LDHA-1963 Target: | 5'-AUUUUUCUAACAGGGAUAUUAUtg-3'<br>3'-GCUAAAAAGAUUGUCCCUAUAAUAAC-5'<br>5'-CGATTTTTCTAACAGGGATATTATTG-3' | (SEQ ID NO: 2831)<br>(SEQ ID NO: 4845)<br>(SEQ ID NO: 6859) |
| LDHA-1964 Target: | 5'-UUUUUCUAACAGGGAUAUUAUUga-3'<br>3'-CUAAAAAGAUUGUCCCUAUAAUAACU-5'<br>5'-GATTTTTCTAACAGGGATATTATTGA-3' | (SEQ ID NO: 2832)<br>(SEQ ID NO: 4846)<br>(SEQ ID NO: 6860) |
| LDHA-1965 Target: | 5'-UUUUCUAACAGGGAUAUUAUUGac-3'<br>3'-UAAAAAGAUUGUCCCUAUAAUAACUG-5'<br>5'-ATTTTTCTAACAGGGATATTATTGAC-3' | (SEQ ID NO: 2833)<br>(SEQ ID NO: 4847)<br>(SEQ ID NO: 6861) |
| LDHA-1966 Target: | 5'-UUUUCUAACAGGGAUAUUAUUGAct-3'<br>3'-AAAAAGAUUGUCCCUAUAAUAACUGA-5'<br>5'-TTTTTCTAACAGGGATATTATTGACT-3' | (SEQ ID NO: 2834)<br>(SEQ ID NO: 4848)<br>(SEQ ID NO: 6862) |
| LDHA-1967 Target: | 5'-UUUCUAACAGGGAUAUUAUUGACta-3'<br>3'-AAAAGAUUGUCCCUAUAAUAACUGAU-5'<br>5'-TTTTTCTAACAGGGATATTATTGACTA-3' | (SEQ ID NO: 2835)<br>(SEQ ID NO: 4849)<br>(SEQ ID NO: 6863) |
| LDHA-1968 Target: | 5'-UUCUAACAGGGAUAUUAUUGACUaa-3'<br>3'-AAAGAUUGUCCCUAUAAUAACUGAUU-5'<br>5'-TTTTCTAACAGGGATATTATTGACTAA-3' | (SEQ ID NO: 2836)<br>(SEQ ID NO: 4850)<br>(SEQ ID NO: 6864) |
| LDHA-1969 Target: | 5'-UCUAACAGGGAUAUUAUUGACUAat-3'<br>3'-AAAGAUUGUCCCUAUAAUAACUGAUUA-5'<br>5'-TTTCTAACAGGGATATTATTGACTAAT-3' | (SEQ ID NO: 2837)<br>(SEQ ID NO: 4851)<br>(SEQ ID NO: 6865) |
| LDHA-1970 Target: | 5'-CUAACAGGGAUAUUAUUGACUAAta-3'<br>3'-AAGAUUGUCCCUAUAAUAACUGAUUAU-5'<br>5'-TTCTAACAGGGATATTATTGACTAATA-3' | (SEQ ID NO: 2838)<br>(SEQ ID NO: 4852)<br>(SEQ ID NO: 6866) |
| LDHA-1971 Target: | 5'-UAACAGGGAUAUUAUUGACUAAUag-3'<br>3'-AGAUUGUCCCUAUAAUAACUGAUUAUC-5'<br>5'-TCTAACAGGGATATTATTGACTAATAG-3' | (SEQ ID NO: 2839)<br>(SEQ ID NO: 4853)<br>(SEQ ID NO: 6867) |
| LDHA-1972 Target: | 5'-AACAGGGAUAUUAUUGACUAAUAgc-3'<br>3'-GAUUGUCCCUAUAAUAACUGAUUAUCG-5'<br>5'-CTAACAGGGATATTATTGACTAATAGC-3' | (SEQ ID NO: 2840)<br>(SEQ ID NO: 4854)<br>(SEQ ID NO: 6868) |
| LDHA-1973 Target: | 5'-ACAGGGAUAUUAUUGACUAAUAGca-3'<br>3'-AUUGUCCCUAUAAUAACUGAUUAUCGU-5'<br>5'-TAACAGGGATATTATTGACTAATAGCA-3' | (SEQ ID NO: 2841)<br>(SEQ ID NO: 4855)<br>(SEQ ID NO: 6869) |
| LDHA-1974 Target: | 5'-CAGGGAUAUUAUUGACUAAUAGCag-3'<br>3'-UUGUCCCUAUAAUAACUGAUUAUCGUC-5'<br>5'-AACAGGGATATTATTGACTAATAGCAG-3' | (SEQ ID NO: 2842)<br>(SEQ ID NO: 4856)<br>(SEQ ID NO: 6870) |
| LDHA-1975 Target: | 5'-AGGGAUAUUAUUGACUAAUAGCAga-3'<br>3'-UGUCCCUAUAAUAACUGAUUAUCGUCU-5'<br>5'-ACAGGGATATTATTGACTAATAGCAGA-3' | (SEQ ID NO: 2843)<br>(SEQ ID NO: 4857)<br>(SEQ ID NO: 6871) |
| LDHA-1976 Target: | 5'-GGGAUAUUAUUGACUAAUAGCAGag-3'<br>3'-GUCCCUAUAAUAACUGAUUAUCGUCUC-5'<br>5'-CAGGGATATTATTGACTAATAGCAGAG-3' | (SEQ ID NO: 2844)<br>(SEQ ID NO: 4858)<br>(SEQ ID NO: 6872) |
| LDHA-1977 Target: | 5'-GGAUAUUAUUGACUAAUAGCAGAgg-3'<br>3'-UCCCUAUAAUAACUGAUUAUCGUCUCC-5'<br>5'-AGGGATATTATTGACTAATAGCAGAGG-3' | (SEQ ID NO: 2845)<br>(SEQ ID NO: 4859)<br>(SEQ ID NO: 6873) |
| LDHA-1978 Target: | 5'-GAUAUUAUUGACUAAUAGCAGAGga-3'<br>3'-CCCUAUAAUAACUGAUUAUCGUCUCCU-5'<br>5'-GGGATATTATTGACTAATAGCAGAGGA-3' | (SEQ ID NO: 2846)<br>(SEQ ID NO: 4860)<br>(SEQ ID NO: 6874) |
| LDHA-1979 Target: | 5'-AUAUUAUUGACUAAUAGCAGAGGat-3'<br>3'-CCUAUAAUAACUGAUUAUCGUCUCCUA-5'<br>5'-GGATATTATTGACTAATAGCAGAGGAT-3' | (SEQ ID NO: 2847)<br>(SEQ ID NO: 4861)<br>(SEQ ID NO: 6875) |

TABLE 12-continued

Additional Selected Human Anti-Lactate Dehydrogenase DsiRNA Agents (Asymmetrics)

```
                   5'-UAUUAUUGACUAAUAGCAGAGGAtg-3'      (SEQ ID NO: 2848)
                   3'-CUAUAAUAACUGAUUAUCGUCUCCUAC-5'    (SEQ ID NO: 4862)
LDHA-1980 Target:  5'-GATATTATTGACTAATAGCAGAGGATG-3'    (SEQ ID NO: 6876)

5'-AUUAUUGACUAAUAGCAGAGGAUgt-3'      (SEQ ID NO: 2849)
                   3'-UAUAAUAACUGAUUAUCGUCUCCUACA-5'    (SEQ ID NO: 4863)
LDHA-1981 Target:  5'-ATATTATTGACTAATAGCAGAGGATGT-3'    (SEQ ID NO: 6877)

5'-UUAUUGACUAAUAGCAGAGGAUGta-3'      (SEQ ID NO: 2850)
                   3'-AUAAUAACUGAUUAUCGUCUCCUACAU-5'    (SEQ ID NO: 4864)
LDHA-1982 Target:  5'-TATTATTGACTAATAGCAGAGGATGTA-3'    (SEQ ID NO: 6878)

5'-UAUUGACUAAUAGCAGAGGAUGUaa-3'      (SEQ ID NO: 2851)
                   3'-UAAUAACUGAUUAUCGUCUCCUACAUU-5'    (SEQ ID NO: 4865)
LDHA-1983 Target:  5'-ATTATTGACTAATAGCAGAGGATGTAA-3'    (SEQ ID NO: 6879)

5'-AUUGACUAAUAGCAGAGGAUGUAat-3'      (SEQ ID NO: 2852)
                   3'-AAUAACUGAUUAUCGUCUCCUACAUUA-5'    (SEQ ID NO: 4866)
LDHA-1984 Target:  5'-TTATTGACTAATAGCAGAGGATGTAAT-3'    (SEQ ID NO: 6880)

5'-UUGACUAAUAGCAGAGGAUGUAAta-3'      (SEQ ID NO: 2853)
                   3'-AUAACUGAUUAUCGUCUCCUACAUUAU-5'    (SEQ ID NO: 4867)
LDHA-1985 Target:  5'-TATTGACTAATAGCAGAGGATGTAATA-3'    (SEQ ID NO: 6881)

5'-UGACUAAUAGCAGAGGAUGUAAUag-3'      (SEQ ID NO: 2854)
                   3'-UAACUGAUUAUCGUCUCCUACAUUAUC-5'    (SEQ ID NO: 4868)
LDHA-1986 Target:  5'-ATTGACTAATAGCAGAGGATGTAATAG-3'    (SEQ ID NO: 6882)

5'-GACUAAUAGCAGAGGAUGUAAUAgt-3'      (SEQ ID NO: 2855)
                   3'-AACUGAUUAUCGUCUCCUACAUUAUCA-5'    (SEQ ID NO: 4869)
LDHA-1987 Target:  5'-TTGACTAATAGCAGAGGATGTAATAGT-3'    (SEQ ID NO: 6883)

5'-ACUAAUAGCAGAGGAUGUAAUAGtc-3'      (SEQ ID NO: 2856)
                   3'-ACUGAUUAUCGUCUCCUACAUUAUCAG-5'    (SEQ ID NO: 4870)
LDHA-1988 Target:  5'-TGACTAATAGCAGAGGATGTAATAGTC-3'    (SEQ ID NO: 6884)

5'-CUAAUAGCAGAGGAUGUAAUAGUca-3'      (SEQ ID NO: 2857)
                   3'-CUGAUUAUCGUCUCCUACAUUAUCAGU-5'    (SEQ ID NO: 4871)
LDHA-1989 Target:  5'-GACTAATAGCAGAGGATGTAATAGTCA-3'    (SEQ ID NO: 6885)

5'-UAAUAGCAGAGGAUGUAAUAGUCaa-3'      (SEQ ID NO: 2858)
                   3'-UGAUUAUCGUCUCCUACAUUAUCAGUU-5'    (SEQ ID NO: 4872)
LDHA-1990 Target:  5'-ACTAATAGCAGAGGATGTAATAGTCAA-3'    (SEQ ID NO: 6886)

5'-AAUAGCAGAGGAUGUAAUAGUCAac-3'      (SEQ ID NO: 2859)
                   3'-GAUUAUCGUCUCCUACAUUAUCAGUUG-5'    (SEQ ID NO: 4873)
LDHA-1991 Target:  5'-CTAATAGCAGAGGATGTAATAGTCAAC-3'    (SEQ ID NO: 6887)

5'-AUAGCAGAGGAUGUAAUAGUCAAct-3'      (SEQ ID NO: 2860)
                   3'-AUUAUCGUCUCCUACAUUAUCAGUUGA-5'    (SEQ ID NO: 4874)
LDHA-1992 Target:  5'-TAATAGCAGAGGATGTAATAGTCAACT-3'    (SEQ ID NO: 6888)

5'-UAGCAGAGGAUGUAAUAGUCAACtg-3'      (SEQ ID NO: 2861)
                   3'-UUAUCGUCUCCUACAUUAUCAGUUGAC-5'    (SEQ ID NO: 4875)
LDHA-1993 Target:  5'-AATAGCAGAGGATGTAATAGTCAACTG-3'    (SEQ ID NO: 6889)

5'-AGCAGAGGAUGUAAUAGUCAACUga-3'      (SEQ ID NO: 2862)
                   3'-UAUCGUCUCCUACAUUAUCAGUUGACU-5'    (SEQ ID NO: 4876)
LDHA-1994 Target:  5'-ATAGCAGAGGATGTAATAGTCAACTGA-3'    (SEQ ID NO: 6890)

5'-GCAGAGGAUGUAAUAGUCAACUGag-3'      (SEQ ID NO: 2863)
                   3'-AUCGUCUCCUACAUUAUCAGUUGACUC-5'    (SEQ ID NO: 4877)
LDHA-1995 Target:  5'-TAGCAGAGGATGTAATAGTCAACTGAG-3'    (SEQ ID NO: 6891)

5'-CAGAGGAUGUAAUAGUCAACUGAgt-3'      (SEQ ID NO: 2864)
                   3'-UCGUCUCCUACAUUAUCAGUUGACUCA-5'    (SEQ ID NO: 4878)
LDHA-1996 Target:  5'-AGCAGAGGATGTAATAGTCAACTGAGT-3'    (SEQ ID NO: 6892)

5'-AGAGGAUGUAAUAGUCAACUGAGtt-3'      (SEQ ID NO: 2865)
                   3'-CGUCUCCUACAUUAUCAGUUGACUCAA-5'    (SEQ ID NO: 4879)
LDHA-1997 Target:  5'-GCAGAGGATGTAATAGTCAACTGAGTT-3'    (SEQ ID NO: 6893)

5'-GAGGAUGUAAUAGUCAACUGAGUtg-3'      (SEQ ID NO: 2866)
                   3'-GUCUCCUACAUUAUCAGUUGACUCAAC-5'    (SEQ ID NO: 4880)
LDHA-1998 Target:  5'-CAGAGGATGTAATAGTCAACTGAGTTG-3'    (SEQ ID NO: 6894)
```

TABLE 12-continued

Additional Selected Human Anti-Lactate Dehydrogenase DsiRNA Agents (Asymmetrics)

|  |  |  |
|---|---|---|
| LDHA-1999 | 5'-AGGAUGUAAUAGUCAACUGAGUUGt-3'<br>3'-UCUCCUACAUUAUCAGUUGACUCAACA-5'<br>Target: 5'-AGAGGATGTAATAGTCAACTGAGTTGT-3' | (SEQ ID NO: 2867)<br>(SEQ ID NO: 4881)<br>(SEQ ID NO: 6895) |
| LDHA-2000 | 5'-GGAUGUAAUAGUCAACUGAGUUGta-3'<br>3'-CUCCUACAUUAUCAGUUGACUCAACAU-5'<br>Target: 5'-GAGGATGTAATAGTCAACTGAGTTGTA-3' | (SEQ ID NO: 2868)<br>(SEQ ID NO: 4882)<br>(SEQ ID NO: 6896) |
| LDHA-2001 | 5'-GAUGUAAUAGUCAACUGAGUUGUat-3'<br>3'-UCCUACAUUAUCAGUUGACUCAACAUA-5'<br>Target: 5'-AGGATGTAATAGTCAACTGAGTTGTAT-3' | (SEQ ID NO: 2869)<br>(SEQ ID NO: 4883)<br>(SEQ ID NO: 6897) |
| LDHA-2002 | 5'-AUGUAAUAGUCAACUGAGUUGUAtt-3'<br>3'-CCUACAUUAUCAGUUGACUCAACAUAA-5'<br>Target: 5'-GGATGTAATAGTCAACTGAGTTGTATT-3' | (SEQ ID NO: 2870)<br>(SEQ ID NO: 4884)<br>(SEQ ID NO: 6898) |
| LDHA-2003 | 5'-UGUAAUAGUCAACUGAGUUGUAUtg-3'<br>3'-CUACAUUAUCAGUUGACUCAACAUAAC-5'<br>Target: 5'-GATGTAATAGTCAACTGAGTTGTATTG-3' | (SEQ ID NO: 2871)<br>(SEQ ID NO: 4885)<br>(SEQ ID NO: 6899) |
| LDHA-2004 | 5'-GUAAUAGUCAACUGAGUUGUAUUgg-3'<br>3'-UACAUUAUCAGUUGACUCAACAUAACC-5'<br>Target: 5'-ATGTAATAGTCAACTGAGTTGTATTGG-3' | (SEQ ID NO: 2872)<br>(SEQ ID NO: 4886)<br>(SEQ ID NO: 6900) |
| LDHA-2005 | 5'-UAAUAGUCAACUGAGUUGUAUUGgt-3'<br>3'-ACAUUAUCAGUUGACUCAACAUAACCA-5'<br>Target: 5'-TGTAATAGTCAACTGAGTTGTATTGGT-3' | (SEQ ID NO: 2873)<br>(SEQ ID NO: 4887)<br>(SEQ ID NO: 6901) |
| LDHA-2006 | 5'-AAUAGUCAACUGAGUUGUAUUGGta-3'<br>3'-CAUUAUCAGUUGACUCAACAUAACCAU-5'<br>Target: 5'-GTAATAGTCAACTGAGTTGTATTGGTA-3' | (SEQ ID NO: 2874)<br>(SEQ ID NO: 4888)<br>(SEQ ID NO: 6902) |
| LDHA-2007 | 5'-AUAGUCAACUGAGUUGUAUUGGUac-3'<br>3'-AUUAUCAGUUGACUCAACAUAACCAUG-5'<br>Target: 5'-TAATAGTCAACTGAGTTGTATTGGTAC-3' | (SEQ ID NO: 2875)<br>(SEQ ID NO: 4889)<br>(SEQ ID NO: 6903) |
| LDHA-2008 | 5'-UAGUCAACUGAGUUGUAUUGGUAcc-3'<br>3'-UUAUCAGUUGACUCAACAUAACCAUGG-5'<br>Target: 5'-AATAGTCAACTGAGTTGTATTGGTACC-3' | (SEQ ID NO: 2876)<br>(SEQ ID NO: 4890)<br>(SEQ ID NO: 6904) |
| LDHA-2009 | 5'-AGUCAACUGAGUUGUAUUGGUACca-3'<br>3'-UAUCAGUUGACUCAACAUAACCAUGGU-5'<br>Target: 5'-ATAGTCAACTGAGTTGTATTGGTACCA-3' | (SEQ ID NO: 2877)<br>(SEQ ID NO: 4891)<br>(SEQ ID NO: 6905) |
| LDHA-2010 | 5'-GUCAACUGAGUUGUAUUGGUACCac-3'<br>3'-AUCAGUUGACUCAACAUAACCAUGGUG-5'<br>Target: 5'-TAGTCAACTGAGTTGTATTGGTACCAC-3' | (SEQ ID NO: 2878)<br>(SEQ ID NO: 4892)<br>(SEQ ID NO: 6906) |
| LDHA-2011 | 5'-UCAACUGAGUUGUAUUGGUACCAct-3'<br>3'-UCAGUUGACUCAACAUAACCAUGGUGA-5'<br>Target: 5'-AGTCAACTGAGTTGTATTGGTACCACT-3' | (SEQ ID NO: 2879)<br>(SEQ ID NO: 4893)<br>(SEQ ID NO: 6907) |
| LDHA-2012 | 5'-CAACUGAGUUGUAUUGGUACCActt-3'<br>3'-CAGUUGACUCAACAUAACCAUGGUGAA-5'<br>Target: 5'-GTCAACTGAGTTGTATTGGTACCACTT-3' | (SEQ ID NO: 2880)<br>(SEQ ID NO: 4894)<br>(SEQ ID NO: 6908) |
| LDHA-2013 | 5'-AACUGAGUUGUAUUGGUACCACUtc-3'<br>3'-AGUUGACUCAACAUAACCAUGGUGAAG-5'<br>Target: 5'-TCAACTGAGTTGTATTGGTACCACTTC-3' | (SEQ ID NO: 2881)<br>(SEQ ID NO: 4895)<br>(SEQ ID NO: 6909) |
| LDHA-2014 | 5'-ACUGAGUUGUAUUGGUACCACUUcc-3'<br>3'-GUUGACUCAACAUAACCAUGGUGAAGG-5'<br>Target: 5'-CAACTGAGTTGTATTGGTACCACTTCC-3' | (SEQ ID NO: 2882)<br>(SEQ ID NO: 4896)<br>(SEQ ID NO: 6910) |
| LDHA-2015 | 5'-CUGAGUUGUAUUGGUACCACUUCca-3'<br>3'-UUGACUCAACAUAACCAUGGUGAAGGU-5'<br>Target: 5'-AACTGAGTTGTATTGGTACCACTTCCA-3' | (SEQ ID NO: 2883)<br>(SEQ ID NO: 4897)<br>(SEQ ID NO: 6911) |
| LDHA-2016 | 5'-UGAGUUGUAUUGGUACCACUUCCat-3'<br>3'-UGACUCAACAUAACCAUGGUGAAGGUA-5'<br>Target: 5'-ACTGAGTTGTATTGGTACCACTTCCAT-3' | (SEQ ID NO: 2884)<br>(SEQ ID NO: 4898)<br>(SEQ ID NO: 6912) |
| LDHA-2017 | 5'-GAGUUGUAUUGGUACCACUUCCAtt-3'<br>3'-GACUCAACAUAACCAUGGUGAAGGUAA-5'<br>Target: 5'-CTGAGTTGTATTGGTACCACTTCCATT-3' | (SEQ ID NO: 2885)<br>(SEQ ID NO: 4899)<br>(SEQ ID NO: 6913) |

TABLE 12-continued

Additional Selected Human Anti-Lactate Dehydrogenase DsiRNA Agents (Asymmetrics)

```
              5'-AGUUGUAUUGGUACCACUUCCAUtg-3'       (SEQ ID NO: 2886)
              3'-ACUCAACAUAACCAUGGUGAAGGUAAC-5'     (SEQ ID NO: 4900)
LDHA-2018 Target: 5'-TGAGTTGTATTGGTACCACTTCCATTG-3' (SEQ ID NO: 6914)

5'-GUUGUAUUGGUACCACUUCCAUUgt-3'      (SEQ ID NO: 2887)
              3'-CUCAACAUAACCAUGGUGAAGGUAACA-5'    (SEQ ID NO: 4901)
LDHA-2019 Target: 5'-GAGTTGTATTGGTACCACTTCCATTGT-3' (SEQ ID NO: 6915)

5'-UUGUAUUGGUACCACUUCCAUUGta-3'      (SEQ ID NO: 2888)
              3'-UCAACAUAACCAUGGUGAAGGUAACAU-5'    (SEQ ID NO: 4902)
LDHA-2020 Target: 5'-AGTTGTATTGGTACCACTTCCATTGTA-3' (SEQ ID NO: 6916)

5'-UGUAUUGGUACCACUUCCAUUGUaa-3'      (SEQ ID NO: 2889)
              3'-CAACAUAACCAUGGUGAAGGUAACAUU-5'    (SEQ ID NO: 4903)
LDHA-2021 Target: 5'-GTTGTATTGGTACCACTTCCATTGTAA-3' (SEQ ID NO: 6917)

5'-GUAUUGGUACCACUUCCAUUGUAag-3'      (SEQ ID NO: 2890)
              3'-AACAUAACCAUGGUGAAGGUAACAUUC-5'    (SEQ ID NO: 4904)
LDHA-2022 Target: 5'-TTGTATTGGTACCACTTCCATTGTAAG-3' (SEQ ID NO: 6918)

5'-UAUUGGUACCACUUCCAUUGUAAgt-3'      (SEQ ID NO: 2891)
              3'-ACAUAACCAUGGUGAAGGUAACAUUCA-5'    (SEQ ID NO: 4905)
LDHA-2023 Target: 5'-TGTATTGGTACCACTTCCATTGTAAGT-3' (SEQ ID NO: 6919)

5'-AUUGGUACCACUUCCAUUGUAAGtc-3'      (SEQ ID NO: 2892)
              3'-CAUAACCAUGGUGAAGGUAACAUUCAG-5'    (SEQ ID NO: 4906)
LDHA-2024 Target: 5'-GTATTGGTACCACTTCCATTGTAAGTC-3' (SEQ ID NO: 6920)

5'-UUGGUACCACUUCCAUUGUAAGUcc-3'      (SEQ ID NO: 2893)
              3'-AUAACCAUGGUGAAGGUAACAUUCAGG-5'    (SEQ ID NO: 4907)
LDHA-2025 Target: 5'-TATTGGTACCACTTCCATTGTAAGTCC-3' (SEQ ID NO: 6921)

5'-UGGUACCACUUCCAUUGUAAGUCcc-3'      (SEQ ID NO: 2894)
              3'-UAACCAUGGUGAAGGUAACAUUCAGGG-5'    (SEQ ID NO: 4908)
LDHA-2026 Target: 5'-ATTGGTACCACTTCCATTGTAAGTCCC-3' (SEQ ID NO: 6922)

5'-GGUACCACUUCCAUUGUAAGUCCca-3'      (SEQ ID NO: 2895)
              3'-AACCAUGGUGAAGGUAACAUUCAGGGU-5'    (SEQ ID NO: 4909)
LDHA-2027 Target: 5'-TTGGTACCACTTCCATTGTAAGTCCCA-3' (SEQ ID NO: 6923)

5'-GUACCACUUCCAUUGUAAGUCCCaa-3'      (SEQ ID NO: 2896)
              3'-ACCAUGGUGAAGGUAACAUUCAGGGUU-5'    (SEQ ID NO: 4910)
LDHA-2028 Target: 5'-TGGTACCACTTCCATTGTAAGTCCCAA-3' (SEQ ID NO: 6924)

5'-UACCACUUCCAUUGUAAGUCCCAaa-3'      (SEQ ID NO: 2897)
              3'-CCAUGGUGAAGGUAACAUUCAGGGUUU-5'    (SEQ ID NO: 4911)
LDHA-2029 Target: 5'-GGTACCACTTCCATTGTAAGTCCCAAA-3' (SEQ ID NO: 6925)

5'-ACCACUUCCAUUGUAAGUCCCAAag-3'      (SEQ ID NO: 2898)
              3'-CAUGGUGAAGGUAACAUUCAGGGUUUC-5'    (SEQ ID NO: 4912)
LDHA-2030 Target: 5'-GTACCACTTCCATTGTAAGTCCCAAAG-3' (SEQ ID NO: 6926)

5'-CCACUUCCAUUGUAAGUCCCAAAgt-3'      (SEQ ID NO: 2899)
              3'-AUGGUGAAGGUAACAUUCAGGGUUUCA-5'    (SEQ ID NO: 4913)
LDHA-2031 Target: 5'-TACCACTTCCATTGTAAGTCCCAAAGT-3' (SEQ ID NO: 6927)

5'-CACUUCCAUUGUAAGUCCCAAAGta-3'      (SEQ ID NO: 2900)
              3'-UGGUGAAGGUAACAUUCAGGGUUUCAU-5'    (SEQ ID NO: 4914)
LDHA-2032 Target: 5'-ACCACTTCCATTGTAAGTCCCAAAGTA-3' (SEQ ID NO: 6928)

5'-ACUUCCAUUGUAAGUCCCAAAGUat-3'      (SEQ ID NO: 2901)
              3'-GGUGAAGGUAACAUUCAGGGUUUCAUA-5'    (SEQ ID NO: 4915)
LDHA-2033 Target: 5'-CCACTTCCATTGTAAGTCCCAAAGTAT-3' (SEQ ID NO: 6929)

5'-CUUCCAUUGUAAGUCCCAAAGUAtt-3'      (SEQ ID NO: 2902)
              3'-GUGAAGGUAACAUUCAGGGUUUCAUAA-5'    (SEQ ID NO: 4916)
LDHA-2034 Target: 5'-CACTTCCATTGTAAGTCCCAAAGTATT-3' (SEQ ID NO: 6930)

5'-UUCCAUUGUAAGUCCCAAAGUAUta-3'      (SEQ ID NO: 2903)
              3'-UGAAGGUAACAUUCAGGGUUUCAUAAU-5'    (SEQ ID NO: 4917)
LDHA-2035 Target: 5'-ACTTCCATTGTAAGTCCCAAAGTATTA-3' (SEQ ID NO: 6931)

5'-UCCAUUGUAAGUCCCAAAGUAUUat-3'      (SEQ ID NO: 2904)
              3'-GAAGGUAACAUUCAGGGUUUCAUAAUA-5'    (SEQ ID NO: 4918)
LDHA-2036 Target: 5'-CTTCCATTGTAAGTCCCAAAGTATTAT-3' (SEQ ID NO: 6932)
```

TABLE 12-continued

Additional Selected Human Anti-Lactate Dehydrogenase DsiRNA Agents (Asymmetrics)

```
                5'-CCAUUGUAAGUCCCAAAGUAUUAUa-3'     (SEQ ID NO: 2905)
                3'-AAGGUAACAUUCAGGGUUUCAUAAUAU-5'    (SEQ ID NO: 4919)
LDHA-2037 Target: 5'-TTCCATTGTAAGTCCCAAAGTATTATA-3'   (SEQ ID NO: 6933)

5'-CAUUGUAAGUCCCAAAGUAUUAUat-3'     (SEQ ID NO: 2906)
                3'-AGGUAACAUUCAGGGUUUCAUAAUAUA-5'    (SEQ ID NO: 4920)
LDHA-2038 Target: 5'-TCCATTGTAAGTCCCAAAGTATTATAT-3'   (SEQ ID NO: 6934)

5'-AUUGUAAGUCCCAAAGUAUUAUAta-3'     (SEQ ID NO: 2907)
                3'-GGUAACAUUCAGGGUUUCAUAAUAUAU-5'    (SEQ ID NO: 4921)
LDHA-2039 Target: 5'-CCATTGTAAGTCCCAAAGTATTATATA-3'   (SEQ ID NO: 6935)

5'-UUGUAAGUCCCAAAGUAUUAUAUat-3'     (SEQ ID NO: 2908)
                3'-GUAACAUUCAGGGUUUCAUAAUAUAUA-5'    (SEQ ID NO: 4922)
LDHA-2040 Target: 5'-CATTGTAAGTCCCAAAGTATTATATAT-3'   (SEQ ID NO: 6936)

5'-UGUAAGUCCCAAAGUAUUAUAUAUtt-3'    (SEQ ID NO: 2909)
                3'-UAACAUUCAGGGUUUCAUAAUAUAUAA-5'    (SEQ ID NO: 4923)
LDHA-2041 Target: 5'-ATTGTAAGTCCCAAAGTATTATATATT-3'   (SEQ ID NO: 6937)

5'-GUAAGUCCCAAAGUAUUAUAUAUtt-3'     (SEQ ID NO: 2910)
                3'-AACAUUCAGGGUUUCAUAAUAUAUAAA-5'    (SEQ ID NO: 4924)
LDHA-2042 Target: 5'-TTGTAAGTCCCAAAGTATTATATATTT-3'   (SEQ ID NO: 6938)

5'-UAAGUCCCAAAGUAUUAUAUAUUtg-3'     (SEQ ID NO: 2911)
                3'-ACAUUCAGGGUUUCAUAAUAUAUAAAC-5'    (SEQ ID NO: 4925)
LDHA-2043 Target: 5'-TGTAAGTCCCAAAGTATTATATATTTG-3'   (SEQ ID NO: 6939)

5'-AAGUCCCAAAGUAUUAUAUAUUUga-3'     (SEQ ID NO: 2912)
                3'-CAUUCAGGGUUUCAUAAUAUAUAAACU-5'    (SEQ ID NO: 4926)
LDHA-2044 Target: 5'-GTAAGTCCCAAAGTATTATATATTTGA-3'   (SEQ ID NO: 6940)

5'-AGUCCCAAAGUAUUAUAUAUUUGat-3'     (SEQ ID NO: 2913)
                3'-AUUCAGGGUUUCAUAAUAUAUAAACUA-5'    (SEQ ID NO: 4927)
LDHA-2045 Target: 5'-TAAGTCCCAAAGTATTATATATTTGAT-3'   (SEQ ID NO: 6941)

5'-GUCCCAAAGUAUUAUAUAUUUGAta-3'     (SEQ ID NO: 2914)
                3'-UUCAGGGUUUCAUAAUAUAUAAACUAU-5'    (SEQ ID NO: 4928)
LDHA-2046 Target: 5'-AAGTCCCAAAGTATTATATATTTGATA-3'   (SEQ ID NO: 6942)

5'-UCCCAAAGUAUUAUAUAUUUGAUaa-3'     (SEQ ID NO: 2915)
                3'-UCAGGGUUUCAUAAUAUAUAAACUAUU-5'    (SEQ ID NO: 4929)
LDHA-2047 Target: 5'-AGTCCCAAAGTATTATATATTTGATAA-3'   (SEQ ID NO: 6943)

5'-CCCAAAGUAUUAUAUAUUUGAUAat-3'     (SEQ ID NO: 2916)
                3'-CAGGGUUUCAUAAUAUAUAAACUAUUA-5'    (SEQ ID NO: 4930)
LDHA-2048 Target: 5'-GTCCCAAAGTATTATATATTTGATAAT-3'   (SEQ ID NO: 6944)

5'-CCAAAGUAUUAUAUAUUUGAUAAta-3'     (SEQ ID NO: 2917)
                3'-AGGGUUUCAUAAUAUAUAAACUAUUAU-5'    (SEQ ID NO: 4931)
LDHA-2049 Target: 5'-TCCCAAAGTATTATATATTTGATAATA-3'   (SEQ ID NO: 6945)

5'-CAAAGUAUUAUAUAUUUGAUAAUaa-3'     (SEQ ID NO: 2918)
                3'-GGGUUUCAUAAUAUAUAAACUAUUAUU-5'    (SEQ ID NO: 4932)
LDHA-2050 Target: 5'-CCCAAAGTATTATATATTTGATAATAA-3'   (SEQ ID NO: 6946)

5'-AAAGUAUUAUAUAUUUGAUAAUAat-3'     (SEQ ID NO: 2919)
                3'-GGUUUCAUAAUAUAUAAACUAUUAUUA-5'    (SEQ ID NO: 4933)
LDHA-2051 Target: 5'-CCAAAGTATTATATATTTGATAATAAT-3'   (SEQ ID NO: 6947)

5'-AAGUAUUAUAUAUUUGAUAAUAAtg-3'     (SEQ ID NO: 2920)
                3'-GUUUCAUAAUAUAUAAACUAUUAUUAC-5'    (SEQ ID NO: 4934)
LDHA-2052 Target: 5'-CAAAGTATTATATATTTGATAATAATG-3'   (SEQ ID NO: 6948)

5'-AGUAUUAUAUAUUUGAUAAUAAUgc-3'     (SEQ ID NO: 2921)
                3'-UUUCAUAAUAUAUAAACUAUUAUUACG-5'    (SEQ ID NO: 4935)
LDHA-2053 Target: 5'-AAAGTATTATATATTTGATAATAATGC-3'   (SEQ ID NO: 6949)

5'-GUAUUAUAUAUUUGAUAAUAAUGct-3'     (SEQ ID NO: 2922)
                3'-UUCAUAAUAUAUAAACUAUUAUUACGA-5'    (SEQ ID NO: 4936)
LDHA-2054 Target: 5'-AAGTATTATATATTTGATAATAATGCT-3'   (SEQ ID NO: 6950)

5'-UAUUAUAUAUUUGAUAAUAAUGCta-3'     (SEQ ID NO: 2923)
                3'-UCAUAAUAUAUAAACUAUUAUUACGAU-5'    (SEQ ID NO: 4937)
LDHA-2055 Target: 5'-AGTATTATATATTTGATAATAATGCTA-3'   (SEQ ID NO: 6951)
```

TABLE 12-continued

Additional Selected Human Anti-Lactate Dehydrogenase DsiRNA Agents (Asymmetrics)

| | | |
|---|---|---|
| LDHA-2056 | 5'-A<u>U</u>AUAUA<u>U</u>UUGA<u>U</u>A<u>AU</u>AAUGCUaa-3'<br>3'-<u>C</u>A<u>UA</u>AUAUAUAAA<u>C</u>U<u>A</u>UUA<u>U</u>UACG<u>A</u>UU-5'<br>Target: 5'-GTATTATATATTTGATAATAATGCTAA-3' | (SEQ ID NO: 2924)<br>(SEQ ID NO: 4938)<br>(SEQ ID NO: 6952) |
| LDHA-2057 | 5'-U<u>U</u>AUAU<u>A</u>UUUGA<u>U</u>A<u>AU</u>AAUGCUAat-3'<br>3'-<u>A</u>U<u>A</u>AUAUAUAAAC<u>U</u>A<u>U</u>UA<u>U</u>UACG<u>A</u>UUA-5'<br>Target: 5'-TATTATATATTTGATAATAATGCTAAT-3' | (SEQ ID NO: 2925)<br>(SEQ ID NO: 4939)<br>(SEQ ID NO: 6953) |
| LDHA-2058 | 5'-U<u>A</u>U<u>A</u>UAUUUGA<u>U</u>A<u>AU</u>AAUGCUAAtc-3'<br>3'-<u>U</u>A<u>A</u>U<u>A</u>UAUAAAC<u>U</u>A<u>U</u>UA<u>U</u>UACGA<u>U</u>UAG-5'<br>Target: 5'-ATTATATATTTGATAATAATGCTAATC-3' | (SEQ ID NO: 2926)<br>(SEQ ID NO: 4940)<br>(SEQ ID NO: 6954) |
| LDHA-2059 | 5'-A<u>U</u>AUAUUUGA<u>U</u>A<u>AU</u>AAUGCUAAUca-3'<br>3'-<u>A</u>AU<u>A</u>UAUAAAC<u>U</u>A<u>U</u>UA<u>U</u>UACGA<u>U</u>UAGU-5'<br>Target: 5'-TTATATATTTGATAATAATGCTAATCA-3' | (SEQ ID NO: 2927)<br>(SEQ ID NO: 4941)<br>(SEQ ID NO: 6955) |
| LDHA-2060 | 5'-U<u>A</u>UAU<u>U</u>UGA<u>U</u>AA<u>U</u>A<u>A</u>UGCUAAUCat-3'<br>3'-<u>A</u>U<u>A</u>U<u>A</u>UAAAC<u>U</u>A<u>U</u>UA<u>U</u>UACGA<u>U</u>UAGUA-5'<br>Target: 5'-TATATATTTGATAATAATGCTAATCAT-3' | (SEQ ID NO: 2928)<br>(SEQ ID NO: 4942)<br>(SEQ ID NO: 6956) |
| LDHA-2061 | 5'-A<u>U</u>AU<u>U</u>UGA<u>U</u>AA<u>U</u>A<u>AU</u>GCUAAUCAta-3'<br>3'-<u>U</u>A<u>U</u>A<u>U</u>AAACUA<u>U</u>UA<u>U</u>UACGA<u>U</u>UAGUAU-5'<br>Target: 5'-ATATATTTGATAATAATGCTAATCATA-3' | (SEQ ID NO: 2929)<br>(SEQ ID NO: 4943)<br>(SEQ ID NO: 6957) |
| LDHA-2062 | 5'-U<u>A</u>U<u>U</u>UGA<u>U</u>AA<u>U</u>A<u>A</u>UG<u>C</u>UAAUCAUaa-3'<br>3'-<u>A</u>U<u>A</u>U<u>A</u>AACUA<u>U</u>UA<u>U</u>U<u>A</u>CGA<u>U</u>UAGUA<u>U</u>U-5'<br>Target: 5'-TATATTTGATAATAATGCTAATCATAA-3' | (SEQ ID NO: 2930)<br>(SEQ ID NO: 4944)<br>(SEQ ID NO: 6958) |
| LDHA-2063 | 5'-A<u>U</u>UUGA<u>U</u>AA<u>U</u>A<u>A</u>UG<u>C</u>UAAUCAUAat-3'<br>3'-<u>U</u>A<u>U</u>A<u>A</u>ACUA<u>U</u>UA<u>U</u>UACGA<u>U</u>UAGUA<u>U</u>UA-5'<br>Target: 5'-ATATTTGATAATAATGCTAATCATAAT-3' | (SEQ ID NO: 2931)<br>(SEQ ID NO: 4945)<br>(SEQ ID NO: 6959) |
| LDHA-2064 | 5'-U<u>U</u>UGA<u>U</u>AA<u>U</u>A<u>A</u>UG<u>C</u>UAAUCAUAAtt-3'<br>3'-<u>A</u>U<u>A</u>AACUA<u>U</u>UA<u>U</u>UACGA<u>U</u>UAGUA<u>U</u>UAA-5'<br>Target: 5'-TATTTGATAATAATGCTAATCATAATT-3' | (SEQ ID NO: 2932)<br>(SEQ ID NO: 4946)<br>(SEQ ID NO: 6960) |
| LDHA-2065 | 5'-U<u>U</u>GA<u>U</u>AA<u>U</u>AA<u>U</u>G<u>C</u>UA<u>A</u>UCAUAAUtg-3'<br>3'-<u>U</u>A<u>A</u>ACUA<u>U</u>UA<u>U</u>UACG<u>A</u>UUAGUA<u>U</u>UAAC-5'<br>Target: 5'-ATTTGATAATAATGCTAATCATAATTG-3' | (SEQ ID NO: 2933)<br>(SEQ ID NO: 4947)<br>(SEQ ID NO: 6961) |
| LDHA-2066 | 5'-U<u>G</u>A<u>U</u>AA<u>U</u>AA<u>U</u>GCUA<u>A</u>UCAUAAUUgg-3'<br>3'-<u>A</u>A<u>A</u>CUA<u>U</u>UA<u>U</u>UACG<u>A</u>UUAGUA<u>U</u>UAACC-5'<br>Target: 5'-TTTGATAATAATGCTAATCATAATTGG-3' | (SEQ ID NO: 2934)<br>(SEQ ID NO: 4948)<br>(SEQ ID NO: 6962) |
| LDHA-2067 | 5'-G<u>A</u>UAA<u>U</u>AA<u>U</u>GCUA<u>A</u>U<u>C</u>AUAAUUGga-3'<br>3'-<u>A</u>A<u>C</u>UA<u>U</u>UA<u>U</u>UACG<u>A</u>UUAGUA<u>U</u>UAACC<u>U</u>-5'<br>Target: 5'-TTGATAATAATGCTAATCATAATTGGA-3' | (SEQ ID NO: 2935)<br>(SEQ ID NO: 4949)<br>(SEQ ID NO: 6963) |
| LDHA-2068 | 5'-A<u>U</u>A<u>A</u>UAA<u>U</u>GCUA<u>A</u>U<u>C</u>AUAAUUGGaa-3'<br>3'-<u>A</u>C<u>U</u>A<u>U</u>UA<u>U</u>UACGA<u>U</u>U<u>A</u>GUA<u>U</u>UAACC<u>U</u>U-5'<br>Target: 5'-TGATAATAATGCTAATCATAATTGGAA-3' | (SEQ ID NO: 2936)<br>(SEQ ID NO: 4950)<br>(SEQ ID NO: 6964) |
| LDHA-2069 | 5'-U<u>A</u>A<u>U</u>AAUGCUAAU<u>C</u>AUAAUUGGAaa-3'<br>3'-<u>C</u>U<u>A</u>UUA<u>U</u>UACGA<u>U</u>UAGUA<u>U</u>UAACC<u>U</u>UU-5'<br>Target: 5'-GATAATAATGCTAATCATAATTGGAAA-3' | (SEQ ID NO: 2937)<br>(SEQ ID NO: 4951)<br>(SEQ ID NO: 6965) |
| LDHA-2070 | 5'-A<u>A</u>U<u>A</u>AUGCUAAU<u>C</u>A<u>U</u>AAUUGGAAag-3'<br>3'-<u>U</u>A<u>U</u>UA<u>U</u>UACGAUUAG<u>U</u>A<u>U</u>UAACC<u>U</u>UUC-5'<br>Target: 5'-ATAATAATGCTAATCATAATTGGAAAG-3' | (SEQ ID NO: 2938)<br>(SEQ ID NO: 4952)<br>(SEQ ID NO: 6966) |
| LDHA-2071 | 5'-A<u>U</u>A<u>A</u>UGCUAAUCA<u>U</u>A<u>A</u>UUGGAAAgt-3'<br>3'-<u>A</u>U<u>U</u>A<u>U</u>UACGAUUAG<u>U</u>A<u>U</u>UAACC<u>U</u>UUCA-5'<br>Target: 5'-TAATAATGCTAATCATAATTGGAAAGT-3' | (SEQ ID NO: 2939)<br>(SEQ ID NO: 4953)<br>(SEQ ID NO: 6967) |
| LDHA-2072 | 5'-U<u>A</u>A<u>U</u>GCUAAUCA<u>U</u>A<u>A</u>UUGGAAAGta-3'<br>3'-<u>U</u>U<u>A</u>UUACGAUUAGUA<u>U</u>UAACC<u>U</u>UUC<u>A</u>U-5'<br>Target: 5'-AATAATGCTAATCATAATTGGAAAGTA-3' | (SEQ ID NO: 2940)<br>(SEQ ID NO: 4954)<br>(SEQ ID NO: 6968) |
| LDHA-2073 | 5'-A<u>A</u>UGCUAAUCA<u>U</u>A<u>AU</u>UGGAAAGUaa-3'<br>3'-<u>U</u>A<u>U</u>UACGAUUAGUA<u>U</u>UAACC<u>U</u>UUC<u>A</u>UU-5'<br>Target: 5'-ATAATGCTAATCATAATTGGAAAGTAA-3' | (SEQ ID NO: 2941)<br>(SEQ ID NO: 4955)<br>(SEQ ID NO: 6969) |
| LDHA-2074 | 5'-A<u>U</u>G<u>C</u>UAAUCAUA<u>A</u>U<u>U</u>GGAAAGUac-3'<br>3'-<u>A</u>U<u>U</u>A<u>C</u>GAUUAGUA<u>U</u>UA<u>A</u>CCUUUC<u>A</u>UUG-5'<br>Target: 5'-TAATGCTAATCATAATTGGAAAGTAAC-3' | (SEQ ID NO: 2942)<br>(SEQ ID NO: 4956)<br>(SEQ ID NO: 6970) |

TABLE 12-continued

Additional Selected Human Anti-Lactate Dehydrogenase DsiRNA Agents (Asymmetrics)

| | | |
|---|---|---|
| LDHA-2075 | 5'-UGCUAAUCAUAAUUGGAAAGUAAca-3'<br>3'-UUACGAUUAGUAUUAACCUUUCAUUGU-5'<br>Target: 5'-AATGCTAATCATAATTGGAAAGTAACA-3' | (SEQ ID NO: 2943)<br>(SEQ ID NO: 4957)<br>(SEQ ID NO: 6971) |
| LDHA-2076 | 5'-GCUAAUCAUAAUUGGAAAGUAACat-3'<br>3'-UACGAUUAGUAUUAACCUUUCAUUGUA-5'<br>Target: 5'-ATGCTAATCATAATTGGAAAGTAACAT-3' | (SEQ ID NO: 2944)<br>(SEQ ID NO: 4958)<br>(SEQ ID NO: 6972) |
| LDHA-2077 | 5'-CUAAUCAUAAUUGGAAAGUAACAtt-3'<br>3'-ACGAUUAGUAUUAACCUUUCAUUGUAA-5'<br>Target: 5'-TGCTAATCATAATTGGAAAGTAACATT-3' | (SEQ ID NO: 2945)<br>(SEQ ID NO: 4959)<br>(SEQ ID NO: 6973) |
| LDHA-2078 | 5'-UAAUCAUAAUUGGAAAGUAACAUtc-3'<br>3'-CGAUUAGUAUUAACCUUUCAUUGUAAG-5'<br>Target: 5'-GCTAATCATAATTGGAAAGTAACATTC-3' | (SEQ ID NO: 2946)<br>(SEQ ID NO: 4960)<br>(SEQ ID NO: 6974) |
| LDHA-2079 | 5'-AAUCAUAAUUGGAAAGUAACAUUct-3'<br>3'-GAUUAGUAUUAACCUUUCAUUGUAAGA-5'<br>Target: 5'-CTAATCATAATTGGAAAGTAACATTCT-3' | (SEQ ID NO: 2947)<br>(SEQ ID NO: 4961)<br>(SEQ ID NO: 6975) |
| LDHA-2080 | 5'-AUCAUAAUUGGAAAGUAACAUUCta-3'<br>3'-AUUAGUAUUAACCUUUCAUUGUAAGAU-5'<br>Target: 5'-TAATCATAATTGGAAAGTAACATTCTA-3' | (SEQ ID NO: 2948)<br>(SEQ ID NO: 4962)<br>(SEQ ID NO: 6976) |
| LDHA-2081 | 5'-UCAUAAUUGGAAAGUAACAUUCUat-3'<br>3'-UUAGUAUUAACCUUUCAUUGUAAGAUA-5'<br>Target: 5'-AATCATAATTGGAAAGTAACATTCTAT-3' | (SEQ ID NO: 2949)<br>(SEQ ID NO: 4963)<br>(SEQ ID NO: 6977) |
| LDHA-2082 | 5'-CAUAAUUGGAAAGUAACAUUCUAta-3'<br>3'-UAGUAUUAACCUUUCAUUGUAAGAUAU-5'<br>Target: 5'-ATCATAATTGGAAAGTAACATTCTATA-3' | (SEQ ID NO: 2950)<br>(SEQ ID NO: 4964)<br>(SEQ ID NO: 6978) |
| LDHA-2083 | 5'-AUAAUUGGAAAGUAACAUUCUAUat-3'<br>3'-AGUAUUAACCUUUCAUUGUAAGAUAUA-5'<br>Target: 5'-TCATAATTGGAAAGTAACATTCTATAT-3' | (SEQ ID NO: 2951)<br>(SEQ ID NO: 4965)<br>(SEQ ID NO: 6979) |
| LDHA-2084 | 5'-UAAUUGGAAAGUAACAUUCUAUAtg-3'<br>3'-GUAUUAACCUUUCAUUGUAAGAUAUAC-5'<br>Target: 5'-CATAATTGGAAAGTAACATTCTATATG-3' | (SEQ ID NO: 2952)<br>(SEQ ID NO: 4966)<br>(SEQ ID NO: 6980) |
| LDHA-2085 | 5'-AAUUGGAAAGUAACAUUCUAUAUgt-3'<br>3'-UAUUAACCUUUCAUUGUAAGAUAUACA-5'<br>Target: 5'-ATAATTGGAAAGTAACATTCTATATGT-3' | (SEQ ID NO: 2953)<br>(SEQ ID NO: 4967)<br>(SEQ ID NO: 6981) |
| LDHA-2086 | 5'-AUUGGAAAGUAACAUUCUAUAUGta-3'<br>3'-AUUAACCUUUCAUUGUAAGAUAUACAU-5'<br>Target: 5'-TAATTGGAAAGTAACATTCTATATGTA-3' | (SEQ ID NO: 2954)<br>(SEQ ID NO: 4968)<br>(SEQ ID NO: 6982) |
| LDHA-2087 | 5'-UUGGAAAGUAACAUUCUAUAUGUaa-3'<br>3'-UUAACCUUUCAUUGUAAGAUAUACAUU-5'<br>Target: 5'-AATTGGAAAGTAACATTCTATATGTAA-3' | (SEQ ID NO: 2955)<br>(SEQ ID NO: 4969)<br>(SEQ ID NO: 6983) |
| LDHA-2088 | 5'-UGGAAAGUAACAUUCUAUAUGUAaa-3'<br>3'-UAACCUUUCAUUGUAAGAUAUACAUUU-5'<br>Target: 5'-ATTGGAAAGTAACATTCTATATGTAAA-3' | (SEQ ID NO: 2956)<br>(SEQ ID NO: 4970)<br>(SEQ ID NO: 6984) |
| LDHA-2089 | 5'-GGAAAGUAACAUUCUAUAUGUAAat-3'<br>3'-AACCUUUCAUUGUAAGAUAUACAUUUA-5'<br>Target: 5'-TTGGAAAGTAACATTCTATATGTAAAT-3' | (SEQ ID NO: 2957)<br>(SEQ ID NO: 4971)<br>(SEQ ID NO: 6985) |
| LDHA-2090 | 5'-GAAAGUAACAUUCUAUAUGUAAAtg-3'<br>3'-ACCUUUCAUUGUAAGAUAUACAUUUAC-5'<br>Target: 5'-TGGAAAGTAACATTCTATATGTAAATG-3' | (SEQ ID NO: 2958)<br>(SEQ ID NO: 4972)<br>(SEQ ID NO: 6986) |
| LDHA-2091 | 5'-AAAGUAACAUUCUAUAUGUAAAUgt-3'<br>3'-CCUUUCAUUGUAAGAUAUACAUUUACA-5'<br>Target: 5'-GGAAAGTAACATTCTATATGTAAATGT-3' | (SEQ ID NO: 2959)<br>(SEQ ID NO: 4973)<br>(SEQ ID NO: 6987) |
| LDHA-2092 | 5'-AAGUAACAUUCUAUAUGUAAAUGta-3'<br>3'-CUUUCAUUGUAAGAUAUACAUUUACAU-5'<br>Target: 5'-GAAAGTAACATTCTATATGTAAATGTA-3' | (SEQ ID NO: 2960)<br>(SEQ ID NO: 4974)<br>(SEQ ID NO: 6988) |
| LDHA-2093 | 5'-AGUAACAUUCUAUAUGUAAAUGUaa-3'<br>3'-UUUCAUUGUAAGAUAUACAUUUACAUU-5'<br>Target: 5'-AAAGTAACATTCTATATGTAAATGTAA-3' | (SEQ ID NO: 2961)<br>(SEQ ID NO: 4975)<br>(SEQ ID NO: 6989) |

TABLE 12-continued

Additional Selected Human Anti-Lactate Dehydrogenase DsiRNA Agents (Asymmetrics)

| | | |
|---|---|---|
| LDHA-2094 | 5'-GUAACAUUCUAUAUGUAAAUGUAAaa-3'<br>3'-UUCAUUGUAAGAUAUACAUUUACAUUU-5'<br>Target: 5'-AAGTAACATTCTATATGTAAATGTAAA-3' | (SEQ ID NO: 2962)<br>(SEQ ID NO: 4976)<br>(SEQ ID NO: 6990) |
| LDHA-2095 | 5'-UAACAUUCUAUAUGUAAAUGUAAaa-3'<br>3'-UCAUUGUAAGAUAUACAUUUACAUUUU-5'<br>Target: 5'-AGTAACATTCTATATGTAAATGTAAAA-3' | (SEQ ID NO: 2963)<br>(SEQ ID NO: 4977)<br>(SEQ ID NO: 6991) |
| LDHA-2096 | 5'-AACAUUCUAUAUGUAAAUGUAAAat-3'<br>3'-CAUUGUAAGAUAUACAUUUACAUUUA-5'<br>Target: 5'-GTAACATTCTATATGTAAATGTAAAAT-3' | (SEQ ID NO: 2964)<br>(SEQ ID NO: 4978)<br>(SEQ ID NO: 6992) |
| LDHA-2097 | 5'-ACAUUCUAUAUGUAAAUGUAAAAtt-3'<br>3'-AUUGUAAGAUAUACAUUUACAUUUAA-5'<br>Target: 5'-TAACATTCTATATGTAAATGTAAAATT-3' | (SEQ ID NO: 2965)<br>(SEQ ID NO: 4979)<br>(SEQ ID NO: 6993) |
| LDHA-2098 | 5'-CAUUCUAUAUGUAAAUGUAAAAUtt-3'<br>3'-UUGUAAGAUAUACAUUUACAUUUUAAA-5'<br>Target: 5'-AACATTCTATATGTAAATGTAAAATTT-3' | (SEQ ID NO: 2966)<br>(SEQ ID NO: 4980)<br>(SEQ ID NO: 6994) |
| LDHA-2099 | 5'-AUUCUAUAUGUAAAUGUAAAAUUta-3'<br>3'-UGUAAGAUAUACAUUUACAUUUUAAAU-5'<br>Target: 5'-ACATTCTATATGTAAATGTAAAATTTA-3' | (SEQ ID NO: 2967)<br>(SEQ ID NO: 4981)<br>(SEQ ID NO: 6995) |
| LDHA-2100 | 5'-UUCUAUAUGUAAAUGUAAAAUUUat-3'<br>3'-GUAAGAUAUACAUUUACAUUUUAAAUA-5'<br>Target: 5'-CATTCTATATGTAAATGTAAAATTTAT-3' | (SEQ ID NO: 2968)<br>(SEQ ID NO: 4982)<br>(SEQ ID NO: 6996) |
| LDHA-2101 | 5'-UCUAUAUGUAAAUGUAAAAUUUAtt-3'<br>3'-UAAGAUAUACAUUUACAUUUUAAAUAA-5'<br>Target: 5'-ATTCTATATGTAAATGTAAAATTTATT-3' | (SEQ ID NO: 2969)<br>(SEQ ID NO: 4983)<br>(SEQ ID NO: 6997) |
| LDHA-2102 | 5'-CUAUAUGUAAAUGUAAAAUUUAUtt-3'<br>3'-AAGAUAUACAUUUACAUUUUAAAUAAA-5'<br>Target: 5'-TTCTATATGTAAATGTAAAATTTATTT-3' | (SEQ ID NO: 2970)<br>(SEQ ID NO: 4984)<br>(SEQ ID NO: 6998) |
| LDHA-2103 | 5'-UAUAUGUAAAUGUAAAAUUUAUUtg-3'<br>3'-AGAUAUACAUUUACAUUUUAAAUAAAC-5'<br>Target: 5'-TCTATATGTAAATGTAAAATTTATTTG-3' | (SEQ ID NO: 2971)<br>(SEQ ID NO: 4985)<br>(SEQ ID NO: 6999) |
| LDHA-2104 | 5'-AUAUGUAAAUGUAAAAUUUAUUUgc-3'<br>3'-GAUAUACAUUUACAUUUUAAAUAAACG-5'<br>Target: 5'-CTATATGTAAATGTAAAATTTATTTGC-3' | (SEQ ID NO: 2972)<br>(SEQ ID NO: 4986)<br>(SEQ ID NO: 7000) |
| LDHA-2105 | 5'-UAUGUAAAUGUAAAAUUUAUUUGcc-3'<br>3'-AUAUACAUUUACAUUUUAAAUAAACGG-5'<br>Target: 5'-TATATGTAAATGTAAAATTTATTTGCC-3' | (SEQ ID NO: 2973)<br>(SEQ ID NO: 4987)<br>(SEQ ID NO: 7001) |
| LDHA-2106 | 5'-AUGUAAAUGUAAAAUUUAUUUGCca-3'<br>3'-UAUACAUUUACAUUUUAAAUAAACGGU-5'<br>Target: 5'-ATATGTAAATGTAAAATTTATTTGCCA-3' | (SEQ ID NO: 2974)<br>(SEQ ID NO: 4988)<br>(SEQ ID NO: 7002) |
| LDHA-2107 | 5'-UGUAAAUGUAAAAUUUAUUUGCCaa-3'<br>3'-AUACAUUUACAUUUUAAAUAAACGGUU-5'<br>Target: 5'-TATGTAAATGTAAAATTTATTTGCCAA-3' | (SEQ ID NO: 2975)<br>(SEQ ID NO: 4989)<br>(SEQ ID NO: 7003) |
| LDHA-2108 | 5'-GUAAAUGUAAAAUUUAUUUGCCAac-3'<br>3'-UACAUUUACAUUUUAAAUAAACGGUUG-5'<br>Target: 5'-ATGTAAATGTAAAATTTATTTGCCAAC-3' | (SEQ ID NO: 2976)<br>(SEQ ID NO: 4990)<br>(SEQ ID NO: 7004) |
| LDHA-2109 | 5'-UAAAUGUAAAAUUUAUUUGCCAAct-3'<br>3'-ACAUUUACAUUUUAAAUAAACGGUUGA-5'<br>Target: 5'-TGTAAATGTAAAATTTATTTGCCAACT-3' | (SEQ ID NO: 2977)<br>(SEQ ID NO: 4991)<br>(SEQ ID NO: 7005) |
| LDHA-2110 | 5'-AAAUGUAAAAUUUAUUUGCCAACtg-3'<br>3'-CAUUUACAUUUUAAAUAAACGGUUGAC-5'<br>Target: 5'-GTAAATGTAAAATTTATTTGCCAACTG-3' | (SEQ ID NO: 2978)<br>(SEQ ID NO: 4992)<br>(SEQ ID NO: 7006) |
| LDHA-2111 | 5'-AAUGUAAAAUUUAUUUGCCAACUga-3'<br>3'-AUUUACAUUUUAAAUAAACGGUUGACU-5'<br>Target: 5'-TAAATGTAAAATTTATTTGCCAACTGA-3' | (SEQ ID NO: 2979)<br>(SEQ ID NO: 4993)<br>(SEQ ID NO: 7007) |
| LDHA-2112 | 5'-AUGUAAAAUUUAUUUGCCAACUGaa-3'<br>3'-UUUACAUUUUAAAUAAACGGUUGACUU-5'<br>Target: 5'-AAATGTAAAATTTATTTGCCAACTGAA-3' | (SEQ ID NO: 2980)<br>(SEQ ID NO: 4994)<br>(SEQ ID NO: 7008) |

TABLE 12-continued

Additional Selected Human Anti-Lactate Dehydrogenase DsiRNA Agents (Asymmetrics)

| | | |
|---|---|---|
| LDHA-2113 | 5'-UG<u>U</u>AAAAUUUAUUU<u>G</u>CCAACUGAat-3'<br>3'-<u>UUAC</u>AUUUUAAAUA<u>AA</u>CGGUUGA<u>CUUA</u>-5'<br>Target: 5'-AATGTAAAATTTATTTGCCAACTGAAT-3' | (SEQ ID NO: 2981)<br>(SEQ ID NO: 4995)<br>(SEQ ID NO: 7009) |
| LDHA-2114 | 5'-G<u>U</u>AAAAUUUAUUUGC<u>C</u>AACUGAAta-3'<br>3'-<u>UAC</u>AUUUUAAAUAA<u>AC</u>GGUUGAC<u>UUAU</u>-5'<br>Target: 5'-ATGTAAAATTTATTTGCCAACTGAATA-3' | (SEQ ID NO: 2982)<br>(SEQ ID NO: 4996)<br>(SEQ ID NO: 7010) |
| LDHA-2115 | 5'-U<u>AAA</u>AUUUAUUUGC<u>C</u>AACUGAAUat-3'<br>3'-<u>AC</u>AUUUUAAAUAA<u>AC</u>GGUUGACUUA<u>UA</u>-5'<br>Target: 5'-TGTAAAATTTATTTGCCAACTGAATAT-3' | (SEQ ID NO: 2983)<br>(SEQ ID NO: 4997)<br>(SEQ ID NO: 7011) |
| LDHA-2116 | 5'-<u>AAAA</u>UUUAUUUGCC<u>AA</u>CUGAAUAta-3'<br>3'-<u>C</u>AUUUUAAAUAAACGGUUGACUUA<u>UAU</u>-5'<br>Target: 5'-GTAAAATTTATTTGCCAACTGAATATA-3' | (SEQ ID NO: 2984)<br>(SEQ ID NO: 4998)<br>(SEQ ID NO: 7012) |
| LDHA-2117 | 5'-<u>AAA</u>UUUAUUUGCC<u>AA</u>CUGAAUAUag-3'<br>3'-<u>AUUU</u>AAAUAAACGGUUGACUUA<u>UAUC</u>-5'<br>Target: 5'-TAAAATTTATTTGCCAACTGAATATAG-3' | (SEQ ID NO: 2985)<br>(SEQ ID NO: 4999)<br>(SEQ ID NO: 7013) |
| LDHA-2118 | 5'-A<u>AUU</u>UAUUUGCCA<u>A</u>CUGAAUAUAgg-3'<br>3'-<u>UUUU</u>AAAUAAACGG<u>UU</u>GACUUAUA<u>UCC</u>-5'<br>Target: 5'-AAAATTTATTTGCCAACTGAATATAGG-3' | (SEQ ID NO: 2986)<br>(SEQ ID NO: 5000)<br>(SEQ ID NO: 7014) |
| LDHA-2119 | 5'-A<u>UUU</u>AUUUGCCAA<u>C</u>UGAAUAUAGgc-3'<br>3'-<u>UUUA</u>AAUAAACGGUU<u>GA</u>CUUAUA<u>UCCG</u>-5'<br>Target: 5'-AAATTTATTTGCCAACTGAATATAGGC-3' | (SEQ ID NO: 2987)<br>(SEQ ID NO: 5001)<br>(SEQ ID NO: 7015) |
| LDHA-2120 | 5'-<u>UUU</u>AUUUGCCAACU<u>GA</u>AUAUAGGca-3'<br>3'-<u>UUAA</u>AUAAACGGUUG<u>A</u>CUUAUAU<u>CCGU</u>-5'<br>Target: 5'-AATTTATTTGCCAACTGAATATAGGCA-3' | (SEQ ID NO: 2988)<br>(SEQ ID NO: 5002)<br>(SEQ ID NO: 7016) |
| LDHA-2121 | 5'-UU<u>A</u>UUGCCAACUGA<u>A</u>UAUAGGCaa-3'<br>3'-<u>UAA</u>AUAAACGGUUGA<u>C</u>UUAUAUCC<u>GUU</u>-5'<br>Target: 5'-ATTTATTTGCCAACTGAATATAGGCAA-3' | (SEQ ID NO: 2989)<br>(SEQ ID NO: 5003)<br>(SEQ ID NO: 7017) |
| LDHA-2122 | 5'-U<u>A</u>UUGCCAACUGA<u>AU</u>AUAGGCAat-3'<br>3'-<u>AAA</u>UAAACGGUUGA<u>C</u>UUAUAUCC<u>GUUA</u>-5'<br>Target: 5'-TTTATTTGCCAACTGAATATAGGCAAT-3' | (SEQ ID NO: 2990)<br>(SEQ ID NO: 5004)<br>(SEQ ID NO: 7018) |
| LDHA-2123 | 5'-<u>A</u>UUUGCCAACUGA<u>AU</u>AUAGGCAAtg-3'<br>3'-<u>AAU</u>AAACGGUUGAC<u>U</u>UAUAUCCG<u>UUAC</u>-5'<br>Target: 5'-TTATTTGCCAACTGAATATAGGCAATG-3' | (SEQ ID NO: 2991)<br>(SEQ ID NO: 5005)<br>(SEQ ID NO: 7019) |
| LDHA-2124 | 5'-U<u>UUG</u>CCAACUGAA<u>UA</u>UAGGCAAUga-3'<br>3'-<u>AUAA</u>ACGGUUGACUUA<u>U</u>AUCCGUUA<u>CU</u>-5'<br>Target: 5'-TATTTGCCAACTGAATATAGGCAATGA-3' | (SEQ ID NO: 2992)<br>(SEQ ID NO: 5006)<br>(SEQ ID NO: 7020) |
| LDHA-2125 | 5'-<u>UUG</u>CCAACUGAAU<u>AU</u>AGGCAAUGat-3'<br>3'-<u>UAAA</u>CGGUUGACUUAU<u>A</u>UCCGUUA<u>CUA</u>-5'<br>Target: 5'-ATTTGCCAACTGAATATAGGCAATGAT-3' | (SEQ ID NO: 2993)<br>(SEQ ID NO: 5007)<br>(SEQ ID NO: 7021) |
| LDHA-2126 | 5'-U<u>GCC</u>AACUGAAUA<u>U</u>AGGCAAUGAta-3'<br>3'-<u>AAAC</u>GGUUGACUUAUA<u>U</u>CCGUUAC<u>UAU</u>-5'<br>Target: 5'-TTTGCCAACTGAATATAGGCAATGATA-3' | (SEQ ID NO: 2994)<br>(SEQ ID NO: 5008)<br>(SEQ ID NO: 7022) |
| LDHA-2127 | 5'-<u>G</u>CCAACUGAAUAU<u>A</u>GGCAAUGAUag-3'<br>3'-<u>AACG</u>GUUGACUUAUA<u>U</u>CCGUUACU<u>AUC</u>-5'<br>Target: 5'-TTGCCAACTGAATATAGGCAATGATAG-3' | (SEQ ID NO: 2995)<br>(SEQ ID NO: 5009)<br>(SEQ ID NO: 7023) |
| LDHA-2128 | 5'-CC<u>A</u>ACUGAAUAUA<u>GG</u>CAAUGAUAgt-3'<br>3'-<u>ACG</u>GUUGACUUAU<u>A</u>UC<u>C</u>GUUACUA<u>UCA</u>-5'<br>Target: 5'-TGCCAACTGAATATAGGCAATGATAGT-3' | (SEQ ID NO: 2996)<br>(SEQ ID NO: 5010)<br>(SEQ ID NO: 7024) |
| LDHA-2129 | 5'-C<u>A</u>ACUGAAUAUAGG<u>C</u>AAUGAUAGtg-3'<br>3'-<u>C</u>GGUUGACUUAUAU<u>CC</u>GUUACUA<u>UCAC</u>-5'<br>Target: 5'-GCCAACTGAATATAGGCAATGATAGTG-3' | (SEQ ID NO: 2997)<br>(SEQ ID NO: 5011)<br>(SEQ ID NO: 7025) |
| LDHA-2130 | 5'-<u>A</u>ACUGAAUAUAGG<u>C</u>AAUGAUAGUgt-3'<br>3'-<u>GG</u>UUGACUUAUAUCC<u>G</u>UUACUAU<u>CACA</u>-5'<br>Target: 5'-CCAACTGAATATAGGCAATGATAGTGT-3' | (SEQ ID NO: 2998)<br>(SEQ ID NO: 5012)<br>(SEQ ID NO: 7026) |
| LDHA-2131 | 5'-<u>A</u>CUGAAUAUAGGC<u>AA</u>UGAUAGUGtg-3'<br>3'-<u>GUUG</u>ACUUAUAUCCG<u>U</u>UACUAUC<u>ACAC</u>-5'<br>Target: 5'-CAACTGAATATAGGCAATGATAGTGTG-3' | (SEQ ID NO: 2999)<br>(SEQ ID NO: 5013)<br>(SEQ ID NO: 7027) |

TABLE 12-continued

Additional Selected Human Anti-Lactate Dehydrogenase DsiRNA Agents (Asymmetrics)

|  |  |  |
|---|---|---|
| LDHA-2132 Target: | 5'-CUGAAUAUAGGCAAUGAUAGUGUGt-3'<br>3'-UUGACUUAUAUCCGUUACUAUCACACA-5'<br>5'-AACTGAATATAGGCAATGATAGTGTGT-3' | (SEQ ID NO: 3000)<br>(SEQ ID NO: 5014)<br>(SEQ ID NO: 7028) |
| LDHA-2133 Target: | 5'-UGAAUAUAGGCAAUGAUAGUGUGtc-3'<br>3'-UGACUUAUAUCCGUUACUAUCACACAG-5'<br>5'-ACTGAATATAGGCAATGATAGTGTGTC-3' | (SEQ ID NO: 3001)<br>(SEQ ID NO: 5015)<br>(SEQ ID NO: 7029) |
| LDHA-2134 Target: | 5'-GAAUAUAGGCAAUGAUAGUGUGUca-3'<br>3'-GACUUAUAUCCGUUACUAUCACACAGU-5'<br>5'-CTGAATATAGGCAATGATAGTGTGTCA-3' | (SEQ ID NO: 3002)<br>(SEQ ID NO: 5016)<br>(SEQ ID NO: 7030) |
| LDHA-2135 Target: | 5'-AAUAUAGGCAAUGAUAGUGUGUCac-3'<br>3'-ACUUAUAUCCGUUACUAUCACACAGUG-5'<br>5'-TGAATATAGGCAATGATAGTGTGTCAC-3' | (SEQ ID NO: 3003)<br>(SEQ ID NO: 5017)<br>(SEQ ID NO: 7031) |
| LDHA-2136 Target: | 5'-AUAUAGGCAAUGAUAGUGUGUCAct-3'<br>3'-CUUAUAUCCGUUACUAUCACACAGUGA-5'<br>5'-GAATATAGGCAATGATAGTGTGTCACT-3' | (SEQ ID NO: 3004)<br>(SEQ ID NO: 5018)<br>(SEQ ID NO: 7032) |
| LDHA-2137 Target: | 5'-UAUAGGCAAUGAUAGUGUGUCACta-3'<br>3'-UUUAUAUCCGUUACUAUCACACAGUGAU-5'<br>5'-AATATAGGCAATGATAGTGTGTCACTA-3' | (SEQ ID NO: 3005)<br>(SEQ ID NO: 5019)<br>(SEQ ID NO: 7033) |
| LDHA-2138 Target: | 5'-AUAGGCAAUGAUAGUGUGUCACUat-3'<br>3'-UAUAUCCGUUACUAUCACACAGUGAUA-5'<br>5'-ATATAGGCAATGATAGTGTGTCACTAT-3' | (SEQ ID NO: 3006)<br>(SEQ ID NO: 5020)<br>(SEQ ID NO: 7034) |
| LDHA-2139 Target: | 5'-UAGGCAAUGAUAGUGUGUCACUAta-3'<br>3'-AUAUCCGUUACUAUCACACAGUGAUAU-5'<br>5'-TATAGGCAATGATAGTGTGTCACTATA-3' | (SEQ ID NO: 3007)<br>(SEQ ID NO: 5021)<br>(SEQ ID NO: 7035) |
| LDHA-2140 Target: | 5'-AGGCAAUGAUAGUGUGUCACUAUag-3'<br>3'-UAUCCGUUACUAUCACACAGUGAUAUC-5'<br>5'-ATAGGCAATGATAGTGTGTCACTATAG-3' | (SEQ ID NO: 3008)<br>(SEQ ID NO: 5022)<br>(SEQ ID NO: 7036) |
| LDHA-2141 Target: | 5'-GGCAAUGAUAGUGUGUCACUAUAgg-3'<br>3'-AUCCGUUACUAUCACACAGUGAUAUCC-5'<br>5'-TAGGCAATGATAGTGTGTCACTATAGG-3' | (SEQ ID NO: 3009)<br>(SEQ ID NO: 5023)<br>(SEQ ID NO: 7037) |
| LDHA-2142 Target: | 5'-GCAAUGAUAGUGUGUCACUAUAGgg-3'<br>3'-UCCGUUACUAUCACACAGUGAUAUCCC-5'<br>5'-AGGCAATGATAGTGTGTCACTATAGGG-3' | (SEQ ID NO: 3010)<br>(SEQ ID NO: 5024)<br>(SEQ ID NO: 7038) |
| LDHA-2143 Target: | 5'-CAAUGAUAGUGUGUCACUAUAGGga-3'<br>3'-CCGUUACUAUCACACAGUGAUAUCCCU-5'<br>5'-GGCAATGATAGTGTGTCACTATAGGGA-3' | (SEQ ID NO: 3011)<br>(SEQ ID NO: 5025)<br>(SEQ ID NO: 7039) |
| LDHA-2144 Target: | 5'-AAUGAUAGUGUGUCACUAUAGGGaa-3'<br>3'-CGUUACUAUCACACAGUGAUAUCCCUU-5'<br>5'-GCAATGATAGTGTGTCACTATAGGGAA-3' | (SEQ ID NO: 3012)<br>(SEQ ID NO: 5026)<br>(SEQ ID NO: 7040) |
| LDHA-2145 Target: | 5'-AUGAUAGUGUGUCACUAUAGGGAac-3'<br>3'-GUUACUAUCACACAGUGAUAUCCCUUG-5'<br>5'-CAATGATAGTGTGTCACTATAGGGAAC-3' | (SEQ ID NO: 3013)<br>(SEQ ID NO: 5027)<br>(SEQ ID NO: 7041) |
| LDHA-2146 Target: | 5'-UGAUAGUGUGUCACUAUAGGGAAca-3'<br>3'-UUACUAUCACACAGUGAUAUCCCUUGU-5'<br>5'-AATGATAGTGTGTCACTATAGGGAACA-3' | (SEQ ID NO: 3014)<br>(SEQ ID NO: 5028)<br>(SEQ ID NO: 7042) |
| LDHA-2147 Target: | 5'-GAUAGUGUGUCACUAUAGGGAACac-3'<br>3'-UACUAUCACACAGUGAUAUCCCUUGUG-5'<br>5'-ATGATAGTGTGTCACTATAGGGAACAC-3' | (SEQ ID NO: 3015)<br>(SEQ ID NO: 5029)<br>(SEQ ID NO: 7043) |
| LDHA-2148 Target: | 5'-AUAGUGUGUCACUAUAGGGAACAca-3'<br>3'-ACUAUCACACAGUGAUAUCCCUUGUGU-5'<br>5'-TGATAGTGTGTCACTATAGGGAACACA-3' | (SEQ ID NO: 3016)<br>(SEQ ID NO: 5030)<br>(SEQ ID NO: 7044) |
| LDHA-2149 Target: | 5'-UAGUGUGUCACUAUAGGGAACACag-3'<br>3'-CUAUCACACAGUGAUAUCCCUUGUGUC-5'<br>5'-GATAGTGTGTCACTATAGGGAACACAG-3' | (SEQ ID NO: 3017)<br>(SEQ ID NO: 5031)<br>(SEQ ID NO: 7045) |
| LDHA-2150 Target: | 5'-AGUGUGUCACUAUAGGGAACACAga-3'<br>3'-UAUCACACAGUGAUAUCCCUUGUGUCU-5'<br>5'-ATAGTGTGTCACTATAGGGAACACAGA-3' | (SEQ ID NO: 3018)<br>(SEQ ID NO: 5032)<br>(SEQ ID NO: 7046) |

TABLE 12-continued

Additional Selected Human Anti-Lactate Dehydrogenase DsiRNA Agents (Asymmetrics)

```
                        5'-GUGUGUCACUAUAGGGAACACAGat-3'    (SEQ ID NO: 3019)
                        3'-AUCACACAGUGAUAUCCCUUGUGUCUA-5'  (SEQ ID NO: 5033)
LDHA-2151 Target:       5'-TAGTGTGTCACTATAGGGAACACAGAT-3'  (SEQ ID NO: 7047)

5'-UGUGUCACUAUAGGGAACACAGAtt-3'    (SEQ ID NO: 3020)
                        3'-UCACACAGUGAUAUCCCUUGUGUCUAA-5'  (SEQ ID NO: 5034)
LDHA-2152 Target:       5'-AGTGTGTCACTATAGGGAACACAGATT-3'  (SEQ ID NO: 7048)

5'-GUGUCACUAUAGGGAACACAGAUtt-3'    (SEQ ID NO: 3021)
                        3'-CACACAGUGAUAUCCCUUGUGUCUAAA-5'  (SEQ ID NO: 5035)
LDHA-2153 Target:       5'-GTGTGTCACTATAGGGAACACAGATTT-3'  (SEQ ID NO: 7049)

5'-UGUCACUAUAGGGAACACAGAUUtt-3'    (SEQ ID NO: 3022)
                        3'-ACACAGUGAUAUCCCUUGUGUCUAAAA-5'  (SEQ ID NO: 5036)
LDHA-2154 Target:       5'-TGTGTCACTATAGGGAACACAGATTTT-3'  (SEQ ID NO: 7050)

5'-GUCACUAUAGGGAACACAGAUUUtt-3'    (SEQ ID NO: 3023)
                        3'-CACAGUGAUAUCCCUUGUGUCUAAAAA-5'  (SEQ ID NO: 5037)
LDHA-2155 Target:       5'-GTGTCACTATAGGGAACACAGATTTTT-3'  (SEQ ID NO: 7051)

5'-UCACUAUAGGGAACACAGAUUUUtg-3'    (SEQ ID NO: 3024)
                        3'-ACAGUGAUAUCCCUUGUGUCUAAAAAC-5'  (SEQ ID NO: 5038)
LDHA-2156 Target:       5'-TGTCACTATAGGGAACACAGATTTTTG-3'  (SEQ ID NO: 7052)

5'-CACUAUAGGGAACACAGAUUUUUga-3'    (SEQ ID NO: 3025)
                        3'-CAGUGAUAUCCCUUGUGUCUAAAAACU-5'  (SEQ ID NO: 5039)
LDHA-2157 Target:       5'-GTCACTATAGGGAACACAGATTTTTGA-3'  (SEQ ID NO: 7053)

5'-ACUAUAGGGAACACAGAUUUUUGag-3'    (SEQ ID NO: 3026)
                        3'-AGUGAUAUCCCUUGUGUCUAAAAACUC-5'  (SEQ ID NO: 5040)
LDHA-2158 Target:       5'-TCACTATAGGGAACACAGATTTTTGAG-3'  (SEQ ID NO: 7054)

5'-CUAUAGGGAACACAGAUUUUUGAga-3'    (SEQ ID NO: 3027)
                        3'-GUGAUAUCCCUUGUGUCUAAAAACUCU-5'  (SEQ ID NO: 5041)
LDHA-2159 Target:       5'-CACTATAGGGAACACAGATTTTTGAGA-3'  (SEQ ID NO: 7055)

5'-UAUAGGGAACACAGAUUUUUGAGat-3'    (SEQ ID NO: 3028)
                        3'-UGAUAUCCCUUGUGUCUAAAAACUCUA-5'  (SEQ ID NO: 5042)
LDHA-2160 Target:       5'-ACTATAGGGAACACAGATTTTTGAGAT-3'  (SEQ ID NO: 7056)

5'-AUAGGGAACACAGAUUUUUGAGAtc-3'    (SEQ ID NO: 3029)
                        3'-GAUAUCCCUUGUGUCUAAAAACUCUAG-5'  (SEQ ID NO: 5043)
LDHA-2161 Target:       5'-CTATAGGGAACACAGATTTTTGAGATC-3'  (SEQ ID NO: 7057)

5'-UAGGGAACACAGAUUUUUGAGAUct-3'    (SEQ ID NO: 3030)
                        3'-AUAUCCCUUGUGUCUAAAAACUCUAGA-5'  (SEQ ID NO: 5044)
LDHA-2162 Target:       5'-TATAGGGAACACAGATTTTTGAGATCT-3'  (SEQ ID NO: 7058)

5'-AGGGAACACAGAUUUUUGAGAUCtt-3'    (SEQ ID NO: 3031)
                        3'-UAUCCCUUGUGUCUAAAAACUCUAGAA-5'  (SEQ ID NO: 5045)
LDHA-2163 Target:       5'-ATAGGGAACACAGATTTTTGAGATCTT-3'  (SEQ ID NO: 7059)

5'-GGGAACACAGAUUUUUGAGAUCUtg-3'    (SEQ ID NO: 3032)
                        3'-AUCCCUUGUGUCUAAAAACUCUAGAAC-5'  (SEQ ID NO: 5046)
LDHA-2164 Target:       5'-TAGGGAACACAGATTTTTGAGATCTTG-3'  (SEQ ID NO: 7060)

5'-GGAACACAGAUUUUUGAGAUCUUgt-3'    (SEQ ID NO: 3033)
                        3'-UCCCUUGUGUCUAAAAACUCUAGAACA-5'  (SEQ ID NO: 5047)
LDHA-2165 Target:       5'-AGGGAACACAGATTTTTGAGATCTTGT-3'  (SEQ ID NO: 7061)

5'-GAACACAGAUUUUUGAGAUCUUGtc-3'    (SEQ ID NO: 3034)
                        3'-CCCUUGUGUCUAAAAACUCUAGAACAG-5'  (SEQ ID NO: 5048)
LDHA-2166 Target:       5'-GGGAACACAGATTTTTGAGATCTTGTC-3'  (SEQ ID NO: 7062)

5'-AACACAGAUUUUUGAGAUCUUGUcc-3'    (SEQ ID NO: 3035)
                        3'-CCUUGUGUCUAAAAACUCUAGAACAGG-5'  (SEQ ID NO: 5049)
LDHA-2167 Target:       5'-GGAACACAGATTTTTGAGATCTTGTCC-3'  (SEQ ID NO: 7063)

5'-ACACAGAUUUUUGAGAUCUUGUCct-3'    (SEQ ID NO: 3036)
                        3'-CUUGUGUCUAAAAACUCUAGAACAGGA-5'  (SEQ ID NO: 5050)
LDHA-2168 Target:       5'-GAACACAGATTTTTGAGATCTTGTCCT-3'  (SEQ ID NO: 7064)

5'-CACAGAUUUUUGAGAUCUUGUCCtc-3'    (SEQ ID NO: 3037)
                        3'-UUGUGUCUAAAAACUCUAGAACAGGAG-5'  (SEQ ID NO: 5051)
LDHA-2169 Target:       5'-AACACAGATTTTTGAGATCTTGTCCTC-3'  (SEQ ID NO: 7065)
```

TABLE 12-continued

Additional Selected Human Anti-Lactate Dehydrogenase DsiRNA Agents (Asymmetrics)

|  |  |  |
| --- | --- | --- |
| LDHA-2170 | 5'-ACAGAUUUUGAGAUCUUGUCCUCt-3'<br>3'-UGUGUCUAAAAACUCUAGAACAGGAGA-5'<br>Target: 5'-ACACAGATTTTGAGATCTTGTCCTCT-3' | (SEQ ID NO: 3038)<br>(SEQ ID NO: 5052)<br>(SEQ ID NO: 7066) |
| LDHA-2171 | 5'-CAGAUUUUGAGAUCUUGUCCUCtg-3'<br>3'-GUGUCUAAAAACUCUAGAACAGGAGAC-5'<br>Target: 5'-CACAGATTTTGAGATCTTGTCCTCTG-3' | (SEQ ID NO: 3039)<br>(SEQ ID NO: 5053)<br>(SEQ ID NO: 7067) |
| LDHA-2172 | 5'-AGAUUUUGAGAUCUUGUCCUCUgg-3'<br>3'-UGUCUAAAAACUCUAGAACAGGAGACC-5'<br>Target: 5'-ACAGATTTTGAGATCTTGTCCTCTGG-3' | (SEQ ID NO: 3040)<br>(SEQ ID NO: 5054)<br>(SEQ ID NO: 7068) |
| LDHA-2173 | 5'-GAUUUUGAGAUCUUGUCCUCUGga-3'<br>3'-GUCUAAAAACUCUAGAACAGGAGACCU-5'<br>Target: 5'-CAGATTTTGAGATCTTGTCCTCTGGA-3' | (SEQ ID NO: 3041)<br>(SEQ ID NO: 5055)<br>(SEQ ID NO: 7069) |
| LDHA-2174 | 5'-AUUUUGAGAUCUUGUCCUCUGGaa-3'<br>3'-UCUAAAAACUCUAGAACAGGAGACCUU-5'<br>Target: 5'-AGATTTTGAGATCTTGTCCTCTGGAA-3' | (SEQ ID NO: 3042)<br>(SEQ ID NO: 5056)<br>(SEQ ID NO: 7070) |
| LDHA-2175 | 5'-UUUUGAGAUCUUGUCCUCUGGAag-3'<br>3'-CUAAAAACUCUAGAACAGGAGACCUUC-5'<br>Target: 5'-GATTTTGAGATCTTGTCCTCTGGAAG-3' | (SEQ ID NO: 3043)<br>(SEQ ID NO: 5057)<br>(SEQ ID NO: 7071) |
| LDHA-2176 | 5'-UUUGAGAUCUUGUCCUCUGGAAgc-3'<br>3'-UAAAAACUCUAGAACAGGAGACCUUCG-5'<br>Target: 5'-ATTTTGAGATCTTGTCCTCTGGAAGC-3' | (SEQ ID NO: 3044)<br>(SEQ ID NO: 5058)<br>(SEQ ID NO: 7072) |
| LDHA-2177 | 5'-UUUGAGAUCUUGUCCUCUGGAAGct-3'<br>3'-AAAAACUCUAGAACAGGAGACCUUCGA-5'<br>Target: 5'-TTTTTGAGATCTTGTCCTCTGGAAGCT-3' | (SEQ ID NO: 3045)<br>(SEQ ID NO: 5059)<br>(SEQ ID NO: 7073) |
| LDHA-2178 | 5'-UUGAGAUCUUGUCCUCUGGAAGCtg-3'<br>3'-AAAACUCUAGAACAGGAGACCUUCGAC-5'<br>Target: 5'-TTTTGAGATCTTGTCCTCTGGAAGCTG-3' | (SEQ ID NO: 3046)<br>(SEQ ID NO: 5060)<br>(SEQ ID NO: 7074) |
| LDHA-2179 | 5'-UGAGAUCUUGUCCUCUGGAAGCUgg-3'<br>3'-AAACUCUAGAACAGGAGACCUUCGACC-5'<br>Target: 5'-TTTGAGATCTTGTCCTCTGGAAGCTGG-3' | (SEQ ID NO: 3047)<br>(SEQ ID NO: 5061)<br>(SEQ ID NO: 7075) |
| LDHA-2180 | 5'-GAGAUCUUGUCCUCUGGAAGCUGgt-3'<br>3'-AACUCUAGAACAGGAGACCUUCGACCA-5'<br>Target: 5'-TTGAGATCTTGTCCTCTGGAAGCTGGT-3' | (SEQ ID NO: 3048)<br>(SEQ ID NO: 5062)<br>(SEQ ID NO: 7076) |
| LDHA-2181 | 5'-AGAUCUUGUCCUCUGGAAGCUGGta-3'<br>3'-ACUCUAGAACAGGAGACCUUCGACCAU-5'<br>Target: 5'-TGAGATCTTGTCCTCTGGAAGCTGGTA-3' | (SEQ ID NO: 3049)<br>(SEQ ID NO: 5063)<br>(SEQ ID NO: 7077) |
| LDHA-2182 | 5'-GAUCUUGUCCUCUGGAAGCUGGUaa-3'<br>3'-CUCUAGAACAGGAGACCUUCGACCAUU-5'<br>Target: 5'-GAGATCTTGTCCTCTGGAAGCTGGTAA-3' | (SEQ ID NO: 3050)<br>(SEQ ID NO: 5064)<br>(SEQ ID NO: 7078) |
| LDHA-2183 | 5'-AUCUUGUCCUCUGGAAGCUGGUAac-3'<br>3'-UCUAGAACAGGAGACCUUCGACCAUUG-5'<br>Target: 5'-AGATCTTGTCCTCTGGAAGCTGGTAAC-3' | (SEQ ID NO: 3051)<br>(SEQ ID NO: 5065)<br>(SEQ ID NO: 7079) |
| LDHA-2184 | 5'-UCUUGUCCUCUGGAAGCUGGUAAca-3'<br>3'-CUAGAACAGGAGACCUUCGACCAUUGU-5'<br>Target: 5'-GATCTTGTCCTCTGGAAGCTGGTAACA-3' | (SEQ ID NO: 3052)<br>(SEQ ID NO: 5066)<br>(SEQ ID NO: 7080) |
| LDHA-2185 | 5'-CUUGUCCUCUGGAAGCUGGUAACaa-3'<br>3'-UAGAACAGGAGACCUUCGACCAUUGUU-5'<br>Target: 5'-ATCTTGTCCTCTGGAAGCTGGTAACAA-3' | (SEQ ID NO: 3053)<br>(SEQ ID NO: 5067)<br>(SEQ ID NO: 7081) |
| LDHA-2186 | 5'-UUGUCCUCUGGAAGCUGGUAACAat-3'<br>3'-AGAACAGGAGACCUUCGACCAUUGUUA-5'<br>Target: 5'-TCTTGTCCTCTGGAAGCTGGTAACAAT-3' | (SEQ ID NO: 3054)<br>(SEQ ID NO: 5068)<br>(SEQ ID NO: 7082) |
| LDHA-2187 | 5'-UGUCCUCUGGAAGCUGGUAACAAtt-3'<br>3'-GAACAGGAGACCUUCGACCAUUGUUAA-5'<br>Target: 5'-CTTGTCCTCTGGAAGCTGGTAACAATT-3' | (SEQ ID NO: 3055)<br>(SEQ ID NO: 5069)<br>(SEQ ID NO: 7083) |
| LDHA-2188 | 5'-GUCCUCUGGAAGCUGGUAACAAUta-3'<br>3'-AACAGGAGACCUUCGACCAUUGUUAAU-5'<br>Target: 5'-TTGTCCTCTGGAAGCTGGTAACAATTA-3' | (SEQ ID NO: 3056)<br>(SEQ ID NO: 5070)<br>(SEQ ID NO: 7084) |

TABLE 12-continued

Additional Selected Human Anti-Lactate Dehydrogenase DsiRNA Agents (Asymmetrics)

```
                    5'-UCCUCUGGAAGCUGGUAACAAUUaa-3'      (SEQ ID NO: 3057)
                    3'-ACAGGAGACCUUCGACCAUUGUUAAUU-5'    (SEQ ID NO: 5071)
LDHA-2189 Target:   5'-TGTCCTCTGGAAGCTGGTAACAATTAA-3'    (SEQ ID NO: 7085)

5'-CCUCUGGAAGCUGGUAACAAUUAaa-3'      (SEQ ID NO: 3058)
                    3'-CAGGAGACCUUCGACCAUUGUUAAUUU-5'    (SEQ ID NO: 5072)
LDHA-2190 Target:   5'-GTCCTCTGGAAGCTGGTAACAATTAAA-3'    (SEQ ID NO: 7086)

5'-CUCUGGAAGCUGGUAACAAUUAAaa-3'      (SEQ ID NO: 3059)
                    3'-AGGAGACCUUCGACCAUUGUUAAUUUU-5'    (SEQ ID NO: 5073)
LDHA-2191 Target:   5'-TCCTCTGGAAGCTGGTAACAATTAAAA-3'    (SEQ ID NO: 7087)

5'-UCUGGAAGCUGGUAACAAUUAAAaa-3'      (SEQ ID NO: 3060)
                    3'-GGAGACCUUCGACCAUUGUUAAUUUUU-5'    (SEQ ID NO: 5074)
LDHA-2192 Target:   5'-CCTCTGGAAGCTGGTAACAATTAAAAA-3'    (SEQ ID NO: 7088)

5'-CUGGAAGCUGGUAACAAUUAAAAac-3'      (SEQ ID NO: 3061)
                    3'-GAGACCUUCGACCAUUGUUAAUUUUUG-5'    (SEQ ID NO: 5075)
LDHA-2193 Target:   5'-CTCTGGAAGCTGGTAACAATTAAAAAC-3'    (SEQ ID NO: 7089)

5'-UGGAAGCUGGUAACAAUUAAAAACa-3'      (SEQ ID NO: 3062)
                    3'-AGACCUUCGACCAUUGUUAAUUUUUGU-5'    (SEQ ID NO: 5076)
LDHA-2194 Target:   5'-TCTGGAAGCTGGTAACAATTAAAAACA-3'    (SEQ ID NO: 7090)

5'-GGAAGCUGGUAACAAUUAAAAACaa-3'      (SEQ ID NO: 3063)
                    3'-GACCUUCGACCAUUGUUAAUUUUUGUU-5'    (SEQ ID NO: 5077)
LDHA-2195 Target:   5'-CTGGAAGCTGGTAACAATTAAAAACAA-3'    (SEQ ID NO: 7091)

5'-GAAGCUGGUAACAAUUAAAAACAat-3'      (SEQ ID NO: 3064)
                    3'-ACCUUCGACCAUUGUUAAUUUUUGUUA-5'    (SEQ ID NO: 5078)
LDHA-2196 Target:   5'-TGGAAGCTGGTAACAATTAAAAACAAT-3'    (SEQ ID NO: 7092)

5'-AAGCUGGUAACAAUUAAAAACAAtc-3'      (SEQ ID NO: 3065)
                    3'-CCUUCGACCAUUGUUAAUUUUUGUUAG-5'    (SEQ ID NO: 5079)
LDHA-2197 Target:   5'-GGAAGCTGGTAACAATTAAAAACAATC-3'    (SEQ ID NO: 7093)

5'-AGCUGGUAACAAUUAAAAACAAUct-3'      (SEQ ID NO: 3066)
                    3'-CUUCGACCAUUGUUAAUUUUUGUUAGA-5'    (SEQ ID NO: 5080)
LDHA-2198 Target:   5'-GAAGCTGGTAACAATTAAAAACAATCT-3'    (SEQ ID NO: 7094)

5'-GCUGGUAACAAUUAAAAACAAUCtt-3'      (SEQ ID NO: 3067)
                    3'-UUCGACCAUUGUUAAUUUUUGUUAGAA-5'    (SEQ ID NO: 5081)
LDHA-2199 Target:   5'-AAGCTGGTAACAATTAAAAACAATCTT-3'    (SEQ ID NO: 7095)

5'-CUGGUAACAAUUAAAAACAAUCUta-3'      (SEQ ID NO: 3068)
                    3'-UCGACCAUUGUUAAUUUUUGUUAGAAU-5'    (SEQ ID NO: 5082)
LDHA-2200 Target:   5'-AGCTGGTAACAATTAAAAACAATCTTA-3'    (SEQ ID NO: 7096)

5'-UGGUAACAAUUAAAAACAAUCUUaa-3'      (SEQ ID NO: 3069)
                    3'-CGACCAUUGUUAAUUUUUGUUAGAAUU-5'    (SEQ ID NO: 5083)
LDHA-2201 Target:   5'-GCTGGTAACAATTAAAAACAATCTTAA-3'    (SEQ ID NO: 7097)

5'-GGUAACAAUUAAAAACAAUCUUAag-3'      (SEQ ID NO: 3070)
                    3'-GACCAUUGUUAAUUUUUGUUAGAAUUC-5'    (SEQ ID NO: 5084)
LDHA-2202 Target:   5'-CTGGTAACAATTAAAAACAATCTTAAG-3'    (SEQ ID NO: 7098)

5'-GUAACAAUUAAAAACAAUCUUAAgg-3'      (SEQ ID NO: 3071)
                    3'-ACCAUUGUUAAUUUUUGUUAGAAUUCC-5'    (SEQ ID NO: 5085)
LDHA-2203 Target:   5'-TGGTAACAATTAAAAACAATCTTAAGG-3'    (SEQ ID NO: 7099)

5'-UAACAAUUAAAAACAAUCUUAAGgc-3'      (SEQ ID NO: 3072)
                    3'-CCAUUGUUAAUUUUUGUUAGAAUUCCG-5'    (SEQ ID NO: 5086)
LDHA-2204 Target:   5'-GGTAACAATTAAAAACAATCTTAAGGC-3'    (SEQ ID NO: 7100)

5'-AACAAUUAAAAACAAUCUUAAGGca-3'      (SEQ ID NO: 3073)
                    3'-CAUUGUUAAUUUUUGUUAGAAUUCCGU-5'    (SEQ ID NO: 5087)
LDHA-2205 Target:   5'-GTAACAATTAAAAACAATCTTAAGGCA-3'    (SEQ ID NO: 7101)

5'-ACAAUUAAAAACAAUCUUAAGGCag-3'      (SEQ ID NO: 3074)
                    3'-AUUGUUAAUUUUUGUUAGAAUUCCGUC-5'    (SEQ ID NO: 5088)
LDHA-2206 Target:   5'-TAACAATTAAAAACAATCTTAAGGCAG-3'    (SEQ ID NO: 7102)

5'-CAAUUAAAAACAAUCUUAAGGCAgg-3'      (SEQ ID NO: 3075)
                    3'-UUGUUAAUUUUUGUUAGAAUUCCGUCC-5'    (SEQ ID NO: 5089)
LDHA-2207 Target:   5'-AACAATTAAAAACAATCTTAAGGCAGG-3'    (SEQ ID NO: 7103)
```

TABLE 12-continued

Additional Selected Human Anti-Lactate Dehydrogenase DsiRNA Agents (Asymmetrics)

|  |  |  |
|---|---|---|
| LDHA-2208 Target: | 5'-AAUUAAAAACAAUCUUAAGGCAGgg-3'<br>3'-UGUUAAUUUUUGUUAGAAUUCCGUCCC-5'<br>5'-ACAATTAAAAACAATCTTAAGGCAGGG-3' | (SEQ ID NO: 3076)<br>(SEQ ID NO: 5090)<br>(SEQ ID NO: 7104) |
| LDHA-2209 Target: | 5'-AUUAAAAACAAUCUUAAGGCAGGga-3'<br>3'-GUUAAUUUUUGUUAGAAUUCCGUCCCU-5'<br>5'-CAATTAAAAACAATCTTAAGGCAGGGA-3' | (SEQ ID NO: 3077)<br>(SEQ ID NO: 5091)<br>(SEQ ID NO: 7105) |
| LDHA-2210 Target: | 5'-UUAAAAACAAUCUUAAGGCAGGGaa-3'<br>3'-UUAAUUUUUGUUAGAAUUCCGUCCCUU-5'<br>5'-AATTAAAAACAATCTTAAGGCAGGGAA-3' | (SEQ ID NO: 3078)<br>(SEQ ID NO: 5092)<br>(SEQ ID NO: 7106) |
| LDHA-2211 Target: | 5'-UAAAAACAAUCUUAAGGCAGGGAaa-3'<br>3'-UAAUUUUUGUUAGAAUUCCGUCCCUUU-5'<br>5'-ATTAAAAACAATCTTAAGGCAGGGAAA-3' | (SEQ ID NO: 3079)<br>(SEQ ID NO: 5093)<br>(SEQ ID NO: 7107) |
| LDHA-2212 Target: | 5'-AAAAACAAUCUUAAGGCAGGGAAaa-3'<br>3'-AAUUUUGUUAGAAUUCCGUCCCUUUU-5'<br>5'-TTAAAAACAATCTTAAGGCAGGGAAAA-3' | (SEQ ID NO: 3080)<br>(SEQ ID NO: 5094)<br>(SEQ ID NO: 7108) |
| LDHA-2213 Target: | 5'-AAAACAAUCUUAAGGCAGGGAAAaa-3'<br>3'-AUUUUGUUAGAAUUCCGUCCCUUUUU-5'<br>5'-TAAAAACAATCTTAAGGCAGGGAAAAA-3' | (SEQ ID NO: 3081)<br>(SEQ ID NO: 5095)<br>(SEQ ID NO: 7109) |
| LDHA-2214 Target: | 5'-AAACAAUCUUAAGGCAGGGAAAAaa-3'<br>3'-UUUUGUUAGAAUUCCGUCCCUUUUUU-5'<br>5'-AAAAACAATCTTAAGGCAGGGAAAAAA-3' | (SEQ ID NO: 3082)<br>(SEQ ID NO: 5096)<br>(SEQ ID NO: 7110) |
| LDHA-2215 Target: | 5'-AACAAUCUUAAGGCAGGGAAAAAaa-3'<br>3'-UUUGUUAGAAUUCCGUCCCUUUUUUU-5'<br>5'-AAAACAATCTTAAGGCAGGGAAAAAAA-3' | (SEQ ID NO: 3083)<br>(SEQ ID NO: 5097)<br>(SEQ ID NO: 7111) |
| LDHA-2216 Target: | 5'-ACAAUCUUAAGGCAGGGAAAAAAaa-3'<br>3'-UUUGUUAGAAUUCCGUCCCUUUUUUUU-5'<br>5'-AAACAATCTTAAGGCAGGGAAAAAAAA-3' | (SEQ ID NO: 3084)<br>(SEQ ID NO: 5098)<br>(SEQ ID NO: 7112) |
| LDHA-2217 Target: | 5'-CAAUCUUAAGGCAGGGAAAAAAAaa-3'<br>3'-UUGUUAGAAUUCCGUCCCUUUUUUUUU-5'<br>5'-AACAATCTTAAGGCAGGGAAAAAAAAA-3' | (SEQ ID NO: 3085)<br>(SEQ ID NO: 5099)<br>(SEQ ID NO: 7113) |
| LDHA-2218 Target: | 5'-AAUCUUAAGGCAGGGAAAAAAAAaa-3'<br>3'-UGUUAGAAUUCCGUCCCUUUUUUUUUU-5'<br>5'-ACAATCTTAAGGCAGGGAAAAAAAAAA-3' | (SEQ ID NO: 3086)<br>(SEQ ID NO: 5100)<br>(SEQ ID NO: 7114) |
| LDHA-2219 Target: | 5'-AUCUUAAGGCAGGGAAAAAAAAAaa-3'<br>3'-GUUAGAAUUCCGUCCCUUUUUUUUUUU-5'<br>5'-CAATCTTAAGGCAGGGAAAAAAAAAAA-3' | (SEQ ID NO: 3087)<br>(SEQ ID NO: 5101)<br>(SEQ ID NO: 7115) |
| LDHA-2220 Target: | 5'-UCUUAAGGCAGGGAAAAAAAAAAaa-3'<br>3'-UUAGAAUUCCGUCCCUUUUUUUUUUUU-5'<br>5'-AATCTTAAGGCAGGGAAAAAAAAAAAA-3' | (SEQ ID NO: 3088)<br>(SEQ ID NO: 5102)<br>(SEQ ID NO: 7116) |
| LDHA-2221 Target: | 5'-CUUAAGGCAGGGAAAAAAAAAAAaa-3'<br>3'-UAGAAUUCCGUCCCUUUUUUUUUUUUU-5'<br>5'-ATCTTAAGGCAGGGAAAAAAAAAAAAA-3' | (SEQ ID NO: 3089)<br>(SEQ ID NO: 5103)<br>(SEQ ID NO: 7117) |
| LDHA-2222 Target: | 5'-UUAAGGCAGGGAAAAAAAAAAAAaa-3'<br>3'-AGAAUUCCGUCCCUUUUUUUUUUUUUU-5'<br>5'-TCTTAAGGCAGGGAAAAAAAAAAAAAA-3' | (SEQ ID NO: 3090)<br>(SEQ ID NO: 5104)<br>(SEQ ID NO: 7118) |
| LDHA-2223 Target: | 5'-UAAGGCAGGGAAAAAAAAAAAAAaa-3'<br>3'-GAAUUCCGUCCCUUUUUUUUUUUUUUU-5'<br>5'-CTTAAGGCAGGGAAAAAAAAAAAAAAA-3' | (SEQ ID NO: 3091)<br>(SEQ ID NO: 5105)<br>(SEQ ID NO: 7119) |
| LDHA-2224 Target: | 5'-AAGGCAGGGAAAAAAAAAAAAAAaa-3'<br>3'-AAUUCCGUCCCUUUUUUUUUUUUUUUU-5'<br>5'-TTAAGGCAGGGAAAAAAAAAAAAAAAA-3' | (SEQ ID NO: 3092)<br>(SEQ ID NO: 5106)<br>(SEQ ID NO: 7120) |
| LDHA-2225 Target: | 5'-AGGCAGGGAAAAAAAAAAAAAAAaa-3'<br>3'-AUUCCGUCCCUUUUUUUUUUUUUUUUU-5'<br>5'-TAAGGCAGGGAAAAAAAAAAAAAAAAA-3' | (SEQ ID NO: 3093)<br>(SEQ ID NO: 5107)<br>(SEQ ID NO: 7121) |
| LDHA-2226 Target: | 5'-GGCAGGGAAAAAAAAAAAAAAAAaa-3'<br>3'-UUCCGUCCCUUUUUUUUUUUUUUUUUU-5'<br>5'-AAGGCAGGGAAAAAAAAAAAAAAAAAA-3' | (SEQ ID NO: 3094)<br>(SEQ ID NO: 5108)<br>(SEQ ID NO: 7122) |

Within Tables 2, 3, 5, 7, 8, 10 and 12 above, underlined residues indicate 2'-O-methyl residues, UPPER CASE indicates ribonucleotides, and lower case denotes deoxyribonucleotides. The DsiRNA agents of Tables 2-3, 7-8 and 12 above are 25/27mer agents possessing a blunt end. The structures and/or modification patterning of the agents of Tables 2-3, 7-8 and 12 above can be readily adapted to the above generic sequence structures, e.g., the 3' overhang of the second strand can be extended or contracted, 2'-O-methylation of the second strand can be expanded towards the 5' end of the second strand, optionally at alternating sites, etc. Such further modifications are optional, as 25/27mer DsiRNAs with such modifications can also be readily designed from the above DsiRNA agents and are also expected to be functional inhibitors of lactate dehydrogenase expression. Similarly, the 27mer "blunt/blunt" DsiRNA structures and/or modification patterns of the agents of Tables 5 and 10 above can also be readily adapted to the above generic sequence structures, e.g., for application of modification patterning of the antisense strand to such structures and/or adaptation of such sequences to the above generic structures.

In certain embodiments, 27mer DsiRNAs possessing independent strand lengths each of 27 nucleotides are designed and synthesized for targeting of the same sites within the lactate dehydrogenase transcript as the asymmetric "25/27" structures shown in Tables 2-3, 7-8 and 12 herein. Exemplary "27/27" DsiRNAs are optionally designed with a "blunt/blunt" structure as shown for the DsiRNAs of Tables 5 and 10 above.

In certain embodiments, the dsRNA agents of the invention require, e.g., at least 19, at least 20, at least 21, at least 22, at least 23, at least 24, at least 25 or at least 26 residues of the first strand to be complementary to corresponding residues of the second strand. In certain related embodiments, these first strand residues complementary to corresponding residues of the second strand are optionally consecutive residues.

In certain DsiRNAmm ("DsiRNA mismatch") embodiments of the instant invention, mismatched base pairs are located within a "mismatch-tolerant region" which is defined herein with respect to the location of the projected Ago2 cut site of the corresponding target nucleic acid. The mismatch tolerant region is located "upstream of" the projected Ago2 cut site of the target strand. "Upstream" in this context will be understood as the 5'-most portion of the DsiRNAmm duplex, where 5' refers to the orientation of the sense strand of the DsiRNA duplex. Therefore, the mismatch tolerant region is upstream of the base on the sense (passenger) strand that corresponds to the projected Ago2 cut site of the target nucleic acid (see FIG. 1); alternatively, when referring to the antisense (guide) strand of the DsiRNAmm, the mismatch tolerant region can also be described as positioned downstream of the base that is complementary to the projected Ago2 cut site of the target nucleic acid, that is, the 3'-most portion of the antisense strand of the DsiRNAmm (where position 1 of the antisense strand is the 5' terminal nucleotide of the antisense strand, see FIG. 1).

In one embodiment, for example with numbering as depicted in FIG. 1, the mismatch tolerant region is positioned between and including base pairs 3-9 when numbered from the nucleotide starting at the 5' end of the sense strand of the duplex. Therefore, a DsiRNAmm of the invention possesses a single mismatched base pair at any one of positions 3, 4, 5, 6, 7, 8 or 9 of the sense strand of a right-hand extended DsiRNA (where position 1 is the 5' terminal nucleotide of the sense strand and position 9 is the nucleotide residue of the sense strand that is immediately 5' of the projected Ago2 cut site of the target lactate dehydrogenase RNA sequence corresponding to the sense strand sequence). In certain embodiments, for a DsiRNAmm that possesses a mismatched base pair nucleotide at any of positions 3, 4, 5, 6, 7, 8 or 9 of the sense strand, the corresponding mismatched base pair nucleotide of the antisense strand not only forms a mismatched base pair with the DsiRNAmm sense strand sequence, but also forms a mismatched base pair with a DsiRNAmm target lactate dehydrogenase RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target lactate dehydrogenase RNA sequence). In alternative embodiments, the mismatch base pair nucleotide of the antisense strand of a DsiRNAmm only form a mismatched base pair with a corresponding nucleotide of the sense strand sequence of the DsiRNAmm, yet base pairs with its corresponding target lactate dehydrogenase RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target lactate dehydrogenase RNA sequence).

A DsiRNAmm of the invention that possesses a single mismatched base pair within the mismatch-tolerant region (mismatch region) as described above (e.g., a DsiRNAmm harboring a mismatched nucleotide residue at any one of positions 3, 4, 5, 6, 7, 8 or 9 of the sense strand) can further include one, two or even three additional mismatched base pairs. In preferred embodiments, these one, two or three additional mismatched base pairs of the DsiRNAmm occur at position(s) 3, 4, 5, 6, 7, 8 and/or 9 of the sense strand (and at corresponding residues of the antisense strand). In one embodiment where one additional mismatched base pair is present within a DsiRNAmm, the two mismatched base pairs of the sense strand can occur, e.g., at nucleotides of both position 4 and position 6 of the sense strand (with mismatch also occurring at corresponding nucleotide residues of the antisense strand).

In DsiRNAmm agents possessing two mismatched base pairs, mismatches can occur consecutively (e.g., at consecutive positions along the sense strand nucleotide sequence). Alternatively, nucleotides of the sense strand that form mismatched base pairs with the antisense strand sequence can be interspersed by nucleotides that base pair with the antisense strand sequence (e.g., for a DsiRNAmm possessing mismatched nucleotides at positions 3 and 6, but not at positions 4 and 5, the mismatched residues of sense strand positions 3 and 6 are interspersed by two nucleotides that form matched base pairs with corresponding residues of the antisense strand). For example, two residues of the sense strand (located within the mismatch-tolerant region of the sense strand) that form mismatched base pairs with the corresponding antisense strand sequence can occur with zero, one, two, three, four or five matched base pairs located between these mismatched base pairs.

For certain DsiRNAmm agents possessing three mismatched base pairs, mismatches can occur consecutively (e.g., in a triplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiR- NAmm possessing mismatched nucleotides at positions 3, 4 and 8, but not at positions 5, 6 and 7, the mismatched residues of sense strand positions 3 and 4 are adjacent to one another, while the mismatched residues of sense strand positions 4 and 8 are interspersed by three nucleotides that form matched base pairs with corresponding residues of the antisense strand). For example, three residues of the sense strand (located within the mismatch-tolerant region of the sense strand) that form mismatched base pairs with the corresponding antisense strand sequence can occur with zero, one, two, three or four matched base pairs located between any two of these mismatched base pairs.

For certain DsiRNAmm agents possessing four mismatched base pairs, mismatches can occur consecutively (e.g., in a quadruplet along the sense strand nucleotide sequence). Alternatively, nucleotides of the sense strand that form mismatched base pairs with the antisense strand sequence can be interspersed by nucleotides that form matched base pairs with the antisense strand sequence (e.g., for a DsiRNAmm possessing mismatched nucleotides at positions 3, 5, 7 and 8, but not at positions 4 and 6, the mismatched residues of sense strand positions 7 and 8 are adjacent to one another, while the mismatched residues of sense strand positions 3 and 5 are interspersed by one nucleotide that forms a matched base pair with the corresponding residue of the antisense strand—similarly, the mismatched residues of sense strand positions 5 and 7 are also interspersed by one nucleotide that forms a matched base pair with the corresponding residue of the antisense strand). For example, four residues of the sense strand (located within the mismatch-tolerant region of the sense strand) that form mismatched base pairs with the corresponding antisense strand sequence can occur with zero, one, two or three matched base pairs located between any two of these mismatched base pairs.

In another embodiment, for example with numbering also as depicted in FIG. 1, a DsiRNAmm of the invention comprises a mismatch tolerant region which possesses a single mismatched base pair nucleotide at any one of positions 17, 18, 19, 20, 21, 22 or 23 of the antisense strand of the DsiRNA (where position 1 is the 5' terminal nucleotide of the antisense strand and position 17 is the nucleotide residue of the antisense strand that is immediately 3' (downstream) in the antisense strand of the projected Ago2 cut site of the target lactate dehydrogenase RNA sequence sufficiently complementary to the antisense strand sequence). In certain embodiments, for a DsiRNAmm that possesses a mismatched base pair nucleotide at any of positions 17, 18, 19, 20, 21, 22 or 23 of the antisense strand with respect to the sense strand of the DsiRNAmm, the mismatched base pair nucleotide of the antisense strand not only forms a mismatched base pair with the DsiRNAmm sense strand sequence, but also forms a mismatched base pair with a DsiRNAmm target lactate dehydrogenase RNA sequence (thus, complementarity between the antisense strand sequence and the sense strand sequence is disrupted at the mismatched base pair within the DsiRNAmm, and complementarity is similarly disrupted between the antisense strand sequence of the DsiRNAmm and the target lactate dehydrogenase RNA sequence). In alternative embodiments, the mismatch base pair nucleotide of the antisense strand of a DsiRNAmm only forms a mismatched base pair with a corresponding nucleotide of the sense strand sequence of the DsiRNAmm, yet base pairs with its corresponding target lactate dehydrogenase RNA sequence nucleotide (thus, complementarity between the antisense strand sequence and the sense strand sequence is disrupted at the mismatched base pair within the DsiRNAmm, yet complementarity is maintained between the antisense strand sequence of the DsiRNAmm and the target lactate dehydrogenase RNA sequence).

A DsiRNAmm of the invention that possesses a single mismatched base pair within the mismatch-tolerant region as described above (e.g., a DsiRNAmm harboring a mismatched nucleotide residue at positions 17, 18, 19, 20, 21, 22 or 23 of the antisense strand) can further include one, two or even three additional mismatched base pairs. In preferred embodiments, these one, two or three additional mismatched base pairs of the DsiRNAmm occur at position(s) 17, 18, 19, 20, 21, 22 and/or 23 of the antisense strand (and at corresponding residues of the sense strand). In one embodiment where one additional mismatched base pair is present within a DsiRNAmm, the two mismatched base pairs of the antisense strand can occur, e.g., at nucleotides of both position 18 and position 20 of the antisense strand (with mismatch also occurring at corresponding nucleotide residues of the sense strand).

In DsiRNAmm agents possessing two mismatched base pairs, mismatches can occur consecutively (e.g., at consecutive positions along the antisense strand nucleotide sequence). Alternatively, nucleotides of the antisense strand that form mismatched base pairs with the sense strand sequence can be interspersed by nucleotides that base pair with the sense strand sequence (e.g., for a DsiRNAmm possessing mismatched nucleotides at positions 17 and 20, but not at positions 18 and 19, the mismatched residues of antisense strand positions 17 and 20 are interspersed by two nucleotides that form matched base pairs with corresponding residues of the sense strand). For example, two residues of the antisense strand (located within the mismatch-tolerant region of the sense strand) that form mismatched base pairs with the corresponding sense strand sequence can occur with zero, one, two, three, four, five, six or seven matched base pairs located between these mismatched base pairs.

For certain DsiRNAmm agents possessing three mismatched base pairs, mismatches can occur consecutively (e.g., in a triplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 17, 18 and 22, but not at positions 19, 20 and 21, the mismatched residues of antisense strand positions 17 and 18 are adjacent to one another, while the mismatched residues of antisense strand positions 18 and 122 are interspersed by three nucleotides that form matched base pairs with corresponding residues of the sense strand). For example, three residues of the antisense strand (located within the mismatch-tolerant region of the antisense strand) that form mismatched base pairs with the corresponding sense strand sequence can occur with zero, one, two, three, four, five or six matched base pairs located between any two of these mismatched base pairs.

For certain DsiRNAmm agents possessing four mismatched base pairs, mismatches can occur consecutively (e.g., in a quadruplet along the antisense strand nucleotide sequence). Alternatively, nucleotides of the antisense strand that form mismatched base pairs with the sense strand sequence can be interspersed by nucleotides that form matched base pairs with the sense strand sequence (e.g., for a DsiRNAmm possessing mismatched nucleotides at positions 18, 20, 22 and 23, but not at positions 19 and 21, the mismatched residues of antisense strand positions 22 and 23 are adjacent to one another, while the mismatched residues of antisense strand positions 18 and 20 are interspersed by one nucleotide that forms a matched base pair with the corresponding residue of the sense strand—similarly, the mismatched residues of antisense strand positions 20 and 22 are also interspersed by one nucleotide that forms a matched base pair with the corresponding residue of the sense strand). For example, four residues of the antisense strand (located within the mismatch-tolerant region of the antisense strand) that form mismatched base pairs with the corresponding sense strand sequence can occur with zero, one, two, three, four or five matched base pairs located between any two of these mismatched base pairs.

For reasons of clarity, the location(s) of mismatched nucleotide residues within the above DsiRNAmm agents are numbered in reference to the 5' terminal residue of either sense or antisense strands of the DsiRNAmm. The numbering of positions located within the mismatch-tolerant region (mismatch region) of the antisense strand can shift with variations in the proximity of the 5' terminus of the sense or antisense strand to the projected Ago2 cleavage site. Thus, the location(s) of preferred mismatch sites within either antisense strand or sense strand can also be identified as the permissible proximity of such mismatches to the projected Ago2 cut site. Accordingly, in one preferred embodiment, the position of a mismatch nucleotide of the sense strand of a DsiRNAmm is the nucleotide residue of the sense strand that is located immediately 5' (upstream) of the projected Ago2 cleavage site of the corresponding target lactate dehydrogenase RNA sequence. In other preferred embodiments, a mismatch nucleotide of the sense strand of a DsiRNAmm is positioned at the nucleotide residue of the sense strand that is located two nucleotides 5' (upstream) of the projected Ago2 cleavage site, three nucleotides 5' (upstream) of the projected Ago2 cleavage site, four nucleotides 5' (upstream) of the projected Ago2 cleavage site, five nucleotides 5' (upstream) of the projected Ago2 cleavage site, six nucleotides 5' (upstream) of the projected Ago2 cleavage site, seven nucleotides 5' (upstream) of the projected Ago2 cleavage site, eight nucleotides 5' (upstream) of the projected Ago2 cleavage site, or nine nucleotides 5' (upstream) of the projected Ago2 cleavage site.

Exemplary single mismatch-containing 25/27mer DsiRNAs (DsiRNAmm) include the following structures (such mismatch-containing structures may also be incorporated into other exemplary DsiRNA structures shown herein).

```
5'-XX MXXXXXXXXXXXXXXXXXXXXXDD-3'
3'-XXXX MXXXXXXXXXXXXXXXXXXXXXXX-5'
5'-XXX MXXXXXXXXXXXXXXXXXXXXXDD-3'
3'-XXXXX MXXXXXXXXXXXXXXXXXXXXXXX-5'
```

-continued
```
5'-XXXX MXXXXXXXXXXXXXXXXXXXXDD-3'
3'-XXXXXX MXXXXXXXXXXXXXXXXXXXXX-5'
5'-XXXXX MXXXXXXXXXXXXXXXXXXXDD-3'
3'-XXXXXXX MXXXXXXXXXXXXXXXXXXXX-5'
5'-XXXXXX MXXXXXXXXXXXXXXXXXXDD-3'
3'-XXXXXXXX MXXXXXXXXXXXXXXXXXXX-5'
5'-XXXXXXX MXXXXXXXXXXXXXXXXXDD-3'
3'-XXXXXXXXX MXXXXXXXXXXXXXXXXXX-5'
5'-XXXXXXXX MXXXXXXXXXXXXXXXXDD-3'
3'-XXXXXXXXXX MXXXXXXXXXXXXXXXXX-5'
``` wherein "X"=RNA, "D"=DNA and "M"=Nucleic acid residues (RNA, DNA or non-natural or modified nucleic acids) that do not base pair (hydrogen bond) with corresponding "M" residues of otherwise complementary strand when strands are annealed. Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNAmm agents. For the above mismatch structures, the top strand is the sense strand, and the bottom strand is the antisense strand.

In certain embodiments, a DsiRNA of the invention can contain mismatches that exist in reference to the target lactate dehydrogenase RNA sequence yet do not necessarily exist as mismatched base pairs within the two strands of the DsiRNA—thus, a DsiRNA can possess perfect complementarity between first and second strands of a DsiRNA, yet still possess mismatched residues in reference to a target lactate dehydrogenase RNA (which, in certain embodiments, may be advantageous in promoting efficacy and/or potency and/or duration of effect). In certain embodiments, where mismatches occur between antisense strand and target lactate dehydrogenase RNA sequence, the position of a mismatch is located within the antisense strand at a position(s) that corresponds to a sequence of the sense strand located 5' of the projected Ago2 cut site of the target region—e.g., antisense strand residue(s) positioned within the antisense strand to the 3' of the antisense residue which is complementary to the projected Ago2 cut site of the target sequence.

Exemplary 25/27mer DsiRNAs that harbor a single mismatched residue in reference to target sequences include the following structures.

```
Target RNA Sequence:      5'-...AXXXXXXXXXXXXXXXXXXX...-3'
DsiRNAmm Sense Strand:    5'-XXXXXXXXXXXXXXXXXXXXXXXDD-3'
DsiRNAmm Antisense Strand: 3'-EXXXXXXXXXXXXXXXXXXXXXXXXX-5'

Target RNA Sequence:      5'-...XAXXXXXXXXXXXXXXXXXX...-3'
DsiRNAmm Sense Strand:    5'-XXXXXXXXXXXXXXXXXXXXXXXDD-3'
DsiRNAmm Antisense Strand: 3'-XEXXXXXXXXXXXXXXXXXXXXXXXX-5'

Target RNA Sequence:      5'-...AXXXXXXXXXXXXXXXXXX...-3'
DsiRNAmm Sense Strand:    5'-BXXXXXXXXXXXXXXXXXXXXXXDD-3'
DsiRNAmm Antisense Strand: 3'-XXEXXXXXXXXXXXXXXXXXXXXXXX-5'

Target RNA Sequence:      5'-...XAXXXXXXXXXXXXXXXXX...-3'
```

```
                         -continued
DsiRNAmm Sense Strand:     5'-XBXXXXXXXXXXXXXXXXXXXXXDD-3'
DsiRNAmm Antisense Strand: 3'-XXXEXXXXXXXXXXXXXXXXXXXXXXX-5'

Target RNA Sequence:       5'-...XXAXXXXXXXXXXXXXXXX...-3'
DsiRNAmm Sense Strand:     5'-XXBXXXXXXXXXXXXXXXXXXXXDD-3'
DsiRNAmm Antisense Strand: 3'-XXXXEXXXXXXXXXXXXXXXXXXXXXX-5'

Target RNA Sequence:       5'-...XXXAXXXXXXXXXXXXXXX...-3'
DsiRNAmm Sense Strand:     5'-XXXBXXXXXXXXXXXXXXXXXXXDD-3'
DsiRNAmm Antisense Strand: 3'-XXXXXEXXXXXXXXXXXXXXXXXXXXX-5'

Target RNA Sequence:       5'-...XXXXAXXXXXXXXXXXXXX...-3'
DsiRNAmm Sense Strand:     5'-XXXXBXXXXXXXXXXXXXXXXXXDD-3'
DsiRNAmm Antisense Strand: 3'-XXXXXXEXXXXXXXXXXXXXXXXXXXX-5'

Target RNA Sequence:       5'-...XXXXXAXXXXXXXXXXXXX...-3'
DsiRNAmm Sense Strand:     5'-XXXXXBXXXXXXXXXXXXXXXXXDD-3'
DsiRNAmm Antisense Strand: 3'-XXXXXXXEXXXXXXXXXXXXXXXXXXX-5'

Target RNA Sequence:       5'-...XXXXXXAXXXXXXXXXXXX...-3'
DsiRNAmm Sense Strand:     5'-XXXXXXBXXXXXXXXXXXXXXXXDD-3'
DsiRNAmm Antisense Strand: 3'-XXXXXXXXEXXXXXXXXXXXXXXXXXX-5'

Target RNA Sequence:       5'-...XXXXXXXAXXXXXXXXXXX...-3'
DsiRNAmm Sense Strand:     5'-XXXXXXXBXXXXXXXXXXXXXXXDD-3'
DsiRNAmm Antisense Strand: 3'-XXXXXXXXXEXXXXXXXXXXXXXXXXX-5'

Target RNA Sequence:       5'-...XXXXXXXXAXXXXXXXXXX...-3'
DsiRNAmm Sense Strand:     5'-XXXXXXXXBXXXXXXXXXXXXXXDD-3'
DsiRNAmm Antisense Strand: 3'-XXXXXXXXXXEXXXXXXXXXXXXXXXX-5'
``` wherein "X"=RNA, "D"=DNA and "E"=Nucleic acid residues (RNA, DNA or non-natural or modified nucleic acids) that do not base pair (hydrogen bond) with corresponding "A" RNA residues of otherwise complementary (target) strand when strands are annealed, yet optionally do base pair with corresponding "B" residues ("B" residues are also RNA, DNA or non-natural or modified nucleic acids). Any of the residues of such agents can optionally be 2'-O-methyl RNA monomers—alternating positioning of 2'-O-methyl RNA monomers that commences from the 3'-terminal residue of the bottom (second) strand, as shown above, can also be used in the above DsiRNA agents.

In certain embodiments, the guide strand of a dsRNA of the invention that is sufficiently complementary to a target RNA (e.g., mRNA) along at least 19 nucleotides of the target gene sequence to reduce target gene expression is not perfectly complementary to the at least 19 nucleotide long target gene sequence. Rather, it is appreciated that the guide strand of a dsRNA of the invention that is sufficiently complementary to a target mRNA along at least 19 nucleotides of a target RNA sequence to reduce target gene expression can have one, two, three, or even four or more nucleotides that are mismatched with the 19 nucleotide or longer target strand sequence. Thus, for a 19 nucleotide target RNA sequence, the guide strand of a dsRNA of the invention can be sufficiently complementary to the target RNA sequence to reduce target gene levels while possessing, e.g., only 15/19, 16/19, 17/19 or 18/19 matched nucleotide residues between guide strand and target RNA sequence.

In addition to the above-exemplified structures, dsRNAs of the invention can also possess one, two or three additional residues that form further mismatches with the target lactate dehydrogenase RNA sequence. Such mismatches can be consecutive, or can be interspersed by nucleotides that form matched base pairs with the target lactate dehydrogenase RNA sequence. Where interspersed by nucleotides that form matched base pairs, mismatched residues can be spaced apart from each other within a single strand at an interval of one, two, three, four, five, six, seven or even eight base paired nucleotides between such mismatch-forming residues.

As for the above-described DsiRNAmm agents, a preferred location within dsRNAs (e.g., DsiRNAs) for antisense strand nucleotides that form mismatched base pairs with target lactate dehydrogenase RNA sequence (yet may or may not form mismatches with corresponding sense strand nucleotides) is within the antisense strand region that is located 3' (downstream) of the antisense strand sequence which is complementary to the projected Ago2 cut site of the DsiRNA (e.g., in FIG. 1, the region of the antisense strand which is 3' of the projected Ago2 cut site is preferred for mismatch-forming residues and happens to be located at positions 17-23 of the antisense strand for the 25/27mer agent shown in FIG. 1). Thus, in one embodiment, the position of a mismatch nucleotide (in relation to the target lactate dehydrogenase RNA sequence) of the antisense strand of a DsiRNAmm is the nucleotide residue of the antisense strand that is located immediately 3' (downstream) within the antisense strand sequence of the projected Ago2 cleavage site of the corresponding target lactate dehydrogenase RNA sequence. In other preferred embodiments, a mismatch nucleotide of the antisense strand of a DsiRNAmm (in relation to the target lactate dehydrogenase RNA sequence) is positioned at the nucleotide residue of the antisense strand that is located two nucleotides 3' (downstream) of the corresponding projected Ago2 cleavage site, three nucleotides 3' (downstream) of the corresponding projected Ago2 cleavage site, four nucleotides 3' (downstream) of the corresponding projected Ago2 cleavage site, five nucleotides 3' (downstream) of the corresponding projected Ago2 cleavage site, six nucleotides 3' (downstream) of the projected Ago2 cleavage site, seven nucleotides 3' (downstream) of the projected Ago2 cleavage site, eight nucleotides 3' (downstream) of the projected Ago2 cleavage site, or nine nucleotides 3' (downstream) of the projected Ago2 cleavage site.

In dsRNA agents possessing two mismatch-forming nucleotides of the antisense strand (where mismatch-forming nucleotides are mismatch forming in relation to target lactate dehydrogenase RNA sequence), mismatches can occur consecutively (e.g., at consecutive positions along the antisense strand nucleotide sequence). Alternatively, nucleotides of the antisense strand that form mismatched base pairs with the target lactate dehydrogenase RNA sequence can be interspersed by nucleotides that base pair with the target lactate dehydrogenase RNA sequence (e.g., for a DsiRNA possessing mismatch-forming nucleotides at positions 17 and 20 (starting from the 5' terminus (position 1) of the antisense strand of the 25/27mer agent shown in FIG. 1), but not at positions 18 and 19, the mismatched residues of sense strand positions 17 and 20 are interspersed by two nucleotides that form matched base pairs with corresponding residues of the target lactate dehydrogenase RNA sequence). For example, two residues of the antisense strand (located within the mismatch-tolerant region of the antisense strand) that form mismatched base pairs with the corresponding target lactate dehydrogenase RNA sequence can occur with zero, one, two, three, four or five matched base pairs (with respect to target lactate dehydrogenase RNA sequence) located between these mismatch-forming base pairs.

For certain dsRNAs possessing three mismatch-forming base pairs (mismatch-forming with respect to target lactate dehydrogenase RNA sequence), mismatch-forming nucleotides can occur consecutively (e.g., in a triplet along the antisense strand nucleotide sequence). Alternatively, nucleotides of the antisense strand that form mismatched base pairs with the target lactate dehydrogenase RNA sequence can be interspersed by nucleotides that form matched base pairs with the target lactate dehydrogenase RNA sequence (e.g., for a DsiRNA possessing mismatched nucleotides at positions 17, 18 and 22, but not at positions 19, 20 and 21, the mismatch-forming residues of antisense strand positions 17 and 18 are adjacent to one another, while the mismatch-forming residues of antisense strand positions 18 and 22 are interspersed by three nucleotides that form matched base pairs with corresponding residues of the target lactate dehydrogenase RNA). For example, three residues of the antisense strand (located within the mismatch-tolerant region of the antisense strand) that form mismatched base pairs with the corresponding target lactate dehydrogenase RNA sequence can occur with zero, one, two, three or four matched base pairs located between any two of these mismatch-forming base pairs.

For certain dsRNAs possessing four mismatch-forming base pairs (mismatch-forming with respect to target lactate dehydrogenase RNA sequence), mismatch-forming nucleotides can occur consecutively (e.g., in a quadruplet along the sense strand nucleotide sequence). Alternatively, nucleotides of the antisense strand that form mismatched base pairs with the target lactate dehydrogenase RNA sequence can be interspersed by nucleotides that form matched base pairs with the target lactate dehydrogenase RNA sequence (e.g., for a DsiRNA possessing mismatch-forming nucleotides at positions 17, 19, 21 and 22, but not at positions 18 and 20, the mismatch-forming residues of antisense strand positions 21 and 22 are adjacent to one another, while the mismatch-forming residues of antisense strand positions 17 and 19 are interspersed by one nucleotide that forms a matched base pair with the corresponding residue of the target lactate dehydrogenase RNA sequence—similarly, the mismatch-forming residues of antisense strand positions 19 and 21 are also interspersed by one nucleotide that forms a matched base pair with the corresponding residue of the target lactate dehydrogenase RNA sequence). For example, four residues of the antisense strand (located within the mismatch-tolerant region of the antisense strand) that form mismatched base pairs with the corresponding target lactate dehydrogenase RNA sequence can occur with zero, one, two or three matched base pairs located between any two of these mismatch-forming base pairs.

The above DsiRNAmm and other dsRNA structures are described in order to exemplify certain structures of DsiRNAmm and dsRNA agents. Design of the above DsiRNAmm and dsRNA structures can be adapted to generate, e.g., DsiRNAmm forms of other DsiRNA structures shown infra. As exemplified above, dsRNAs can also be designed that possess single mismatches (or two, three or four mismatches) between the antisense strand of the dsRNA and a target sequence, yet optionally can retain perfect complementarity between sense and antisense strand sequences of a dsRNA.

It is further noted that the dsRNA agents exemplified infra can also possess insertion/deletion (in/del) structures within their double-stranded and/or target lactate dehydrogenase RNA-aligned structures. Accordingly, the dsRNAs of the invention can be designed to possess in/del variations in, e.g., antisense strand sequence as compared to target lactate dehydrogenase RNA sequence and/or antisense strand sequence as compared to sense strand sequence, with preferred location(s) for placement of such in/del nucleotides corresponding to those locations described above for positioning of mismatched and/or mismatch-forming base pairs.

It is also noted that the DsiRNAs of the instant invention can tolerate mismatches within the 3'-terminal region of the sense strand/5'-terminal region of the antisense strand, as this region is modeled to be processed by Dicer and liberated from the guide strand sequence that loads into RISC. Exemplary DsiRNA structures of the invention that harbor such mismatches include the following:

```
Target RNA Sequence:    5'-...XXXXXXXXXXXXXXXXXXXXXHXXX...-3'
DsiRNA Sense Strand:    5'-XXXXXXXXXXXXXXXXXXXXXIXDD-3'
DsiRNA Antisense Strand: 3'-XXXXXXXXXXXXXXXXXXXXXXJXXX-5'

Target RNA Sequence:    5'-...XXXXXXXXXXXXXXXXXXXXXHXX...-3'
DsiRNA Sense Strand:    5'-XXXXXXXXXXXXXXXXXXXXXIDD-3'
DsiRNA Antisense Strand: 3'-XXXXXXXXXXXXXXXXXXXXXXJXX-5'

Target RNA Sequence:    5'-...XXXXXXXXXXXXXXXXXXXXXHX...-3'
DsiRNA Sense Strand:    5'-XXXXXXXXXXXXXXXXXXXXXID-3'
DsiRNA Antisense Strand: 3'-XXXXXXXXXXXXXXXXXXXXXXJX-5'

Target RNA Sequence:    5'-...XXXXXXXXXXXXXXXXXXXXXH...-3'
DsiRNA Sense Strand:    5'-XXXXXXXXXXXXXXXXXXXXXDI-3'
DsiRNA Antisense Strand: 3'-XXXXXXXXXXXXXXXXXXXXXXJ-5'
``` wherein "X"=RNA, "D"=DNA and "I" and "J"=Nucleic acid residues (RNA, DNA or non-natural or modified nucleic acids) that do not base pair (hydrogen bond) with one another, yet optionally "J" is complementary to target RNA sequence nucleotide "H". Any of the residues of such agents can optionally be 2'-O-methyl RNA monomers—alternating positioning of 2'-O-methyl RNA monomers that commences from the 3'-terminal residue of the bottom (second) strand, as shown above—or any of the above-described methylation patterns—can also be used in the above DsiRNA agents. The above mismatches can also be combined within the DsiRNAs of the instant invention.

In the below exemplary structures, such mismatches are introduced within the asymmetric LDHA-1287 DsiRNA (newly-introduced mismatch residues are italicized):

LDHA-1287 25/27mer DsiRNA, mismatch position=19 of sense strand (from 5'-terminus)

```
5'-CAAUUUUAAAGUCUUCUG^UUGUCat-3'   (SEQ ID NO: 7127)
3'-ACGUUAAAAUUUCAGAAGAC_UACAGUA-5' (SEQ ID NO: 108)
```

Optionally, the mismatched 'U' residue of position 19 of the sense strand is alternatively 'C' or 'G'.

LDHA-1287 25/27mer DsiRNA, mismatch position=20 of sense strand (from 5'-terminus)

```
5'-CAAUUUUAAAGUCUUCUGA^AGUCat-3'   (SEQ ID NO: 7128)
3'-ACGUUAAAAUUUCAGAAGACU_ACAGUA-5' (SEQ ID NO: 108)
```

Optionally, the mismatched 'A' residue of position 20 of the sense strand is alternatively 'C' or 'G'.

LDHA-1287 25/27mer DsiRNA, mismatch position=21 of sense strand (from 5'-terminus)

```
5'-CAAUUUUAAAGUCUUCUGAU^AUCat-3'   (SEQ ID NO: 7129)
3'-ACGUUAAAAUUUCAGAAGACUA_CAGUA-5' (SEQ ID NO: 108)
```

Optionally, the mismatched 'A' residue of position 21 of the sense strand is alternatively 'U' or 'C'.

LDHA-1287 25/27mer DsiRNA, mismatch position=22 of sense strand (from 5'-terminus)

```
5'-CAAUUUUAAAGUCUUCUGAUG^GCat-3'   (SEQ ID NO: 7130)
3'-ACGUUAAAAUUUCAGAAGACUAC_AGUA-5' (SEQ ID NO: 108)
```

Optionally, the mismatched 'G' residue of position 22 of the sense strand is alternatively 'A' or 'C'.

LDHA-1287 25/27mer DsiRNA, mismatch position=23 of sense strand (from 5'-terminus)

```
5'-CAAUUUUAAAGUCUUCUGAUGU^Aat-3'   (SEQ ID NO: 7131)
3'-ACGUUAAAAUUUCAGAAGACUACA_GUA-5' (SEQ ID NO: 108)
```

Optionally, the mismatched 'A' residue of position 23 of the sense strand is alternatively 'U' or 'G'.

LDHA-1287 25/27mer DsiRNA, mismatch position=24 of sense strand (from 5'-terminus)

```
5'-CAAUUUUAAAGUCUUCUGAUGUC^t-3'   (SEQ ID NO: 7132)
3'-ACGUUAAAAUUUCAGAAGACUACAG_UA-5' (SEQ ID NO: 108)
```

Optionally, the mismatched 'g' residue of position 24 of the sense strand is alternatively 't' or 'c'.

LDHA-1287 25/27mer DsiRNA, mismatch position=25 of sense strand (from 5'-terminus)

```
5'-CAAUUUUAAAGUCUUCUGAUGUCa-3'    (SEQ ID NO: 7133)
3'-ACGUUAAAAUUUCAGAAGACUACAGU_A-5' (SEQ ID NO: 108)
```

Optionally, the mismatched 'a' residue of position 25 of the sense strand is alternatively 'c' or 'g'.

LDHA-1287 25/27mer DsiRNA, mismatch position=1 of antisense strand (from 5'-terminus)

```
5'-CAAUUUUAAAGUCUUCUGAUGUCa^t-3'  (SEQ ID NO: 252)
3'-ACGUUAAAAUUUCAGAAGACUACAGU_U-5' (SEQ ID NO: 7134)
```

Optionally, the mismatched 'U' residue of position 1 of the antisense strand is alternatively 'G' or 'C'.

LDHA-1287 25/27mer DsiRNA, mismatch position=2 of antisense strand (from 5'-terminus)

```
5'-CAAUUUUAAAGUCUUCUGAUGUC^at-3'  (SEQ ID NO: 252)
3'-ACGUUAAAAUUUCAGAAGACUACAG_CA-5' (SEQ ID NO: 7135)
```

Optionally, the mismatched 'C' residue of position 2 of the antisense strand is alternatively 'A' or 'G'.

LDHA-1287 25/27mer DsiRNA, mismatch position=3 of antisense strand (from 5'-terminus)

```
5'-CAAUUUUAAAGUCUUCUGAUGU^Cat-3'  (SEQ ID NO: 252)
3'-ACGUUAAAAUUUCAGAAGACUACA_UUA-5' (SEQ ID NO: 7136)
```

Optionally, the mismatched 'U' residue of position 3 of the antisense strand is alternatively 'A' or 'C'.

LDHA-1287 25/27mer DsiRNA, mismatch position=4 of antisense strand (from 5'-terminus)

```
5'-CAAUUUUAAAGUCUUCUGAUG^UCat-3'  (SEQ ID NO: 252)
3'-ACGUUAAAAUUUCAGAAGACUAC_CGUA-5' (SEQ ID NO: 7137)
```

Optionally, the mismatched 'C' residue of position 4 of the antisense strand is alternatively 'U' or 'G'.

LDHA-1287 25/27mer DsiRNA, mismatch position=5 of antisense strand (from 5'-terminus)

```
5'-CAAUUUUAAAGUCUUCUGAU^GUCat-3'  (SEQ ID NO: 252)
3'-ACGUUAAAAUUUCAGAAGACUA_GAGUA-5' (SEQ ID NO: 7138)
```

Optionally, the mismatched 'U' residue of position 5 of the antisense strand is alternatively 'A' or 'G'.

LDHA-1287 25/27mer DsiRNA, mismatch position=6 of antisense strand (from 5'-terminus)

```
5'-CAAUUUUAAAGUCUUCUGAUGUCat-3'  (SEQ ID NO: 252)
3'-ACGUUAAAAUUUCAGAAGACUUCAGUA-5' (SEQ ID NO: 7139)
```

Optionally, the mismatched 'U' residue of position 6 of the antisense strand is alternatively 'C' or 'G'.
LDHA-1287 25/27mer DsiRNA, mismatch position=7 of antisense strand (from 5'-terminus)

```
5'-CAAUUUUAAAGUCUUCUGAUGCat-3'  (SEQ ID NO: 252)
3'-ACGUUAAAAUUUCAGAAGACAACAGUA-5' (SEQ ID NO: 7140)
```

Optionally, the mismatched 'A' residue of position 7 of the antisense strand is alternatively 'C' or 'G'.

For the above oligonucleotide strand sequences, it is contemplated that the sense strand sequence of one depicted duplex can be combined with an antisense strand of another depicted duplex, thereby forming a distinct duplex—in certain instances, such duplexes contain a mismatched residue with respect to the lactate dehydrogenase target transcript sequence, while such sense and antisense strand sequences do not present a mismatch at this residue with respect to one another (e.g., duplexes comprising SEQ ID NOs: 7127 and 7140; SEQ ID NOs: 7128 and 7139; SEQ ID NOs: 7129 and 7138, etc., are contemplated as exemplary of such duplexes).

In further exemplary structures, mismatches are introduced within the asymmetric LDHA-370 DsiRNA (newly-introduced mismatch residues are italicized):
LDHA-370 25/27mer DsiRNA, mismatch position=19 of sense strand (from 5'-terminus)

```
5'-UUGUUGGGGUUGGUGCUGAUGGCat-3'  (SEQ ID NO: 7145)
3'-UCAACAACCCCAACCACGACAACCGUA-5' (SEQ ID NO: 84)
```

Optionally, the mismatched 'A' residue of position 19 of the sense strand is alternatively 'C' or 'G'.
LDHA-370 25/27mer DsiRNA, mismatch position=20 of sense strand (from 5'-terminus)

```
5'-UUGUUGGGGUUGGUGCUGUAGGCat-3'  (SEQ ID NO: 7146)
3'-UCAACAACCCCAACCACGACAACCGUA-5' (SEQ ID NO: 84)
```

Optionally, the mismatched 'A' residue of position 20 of the sense strand is alternatively 'C' or 'G'.
LDHA-370 25/27mer DsiRNA, mismatch position=21 of sense strand (from 5'-terminus)

```
5'-UUGUUGGGGUUGGUGCUGUUAGCat-3'  (SEQ ID NO: 7147)
3'-UCAACAACCCCAACCACGACAACCGUA-5' (SEQ ID NO: 84)
```

Optionally, the mismatched 'A' residue of position 21 of the sense strand is alternatively 'U' or 'C'.
LDHA-370 25/27mer DsiRNA, mismatch position=22 of sense strand (from 5'-terminus)

```
5'-UUGUUGGGGUUGGUGCUGUUGUCat-3'  (SEQ ID NO: 7148)
3'-UCAACAACCCCAACCACGACAACCGUA-5' (SEQ ID NO: 84)
```

Optionally, the mismatched 'U' residue of position 22 of the sense strand is alternatively 'A' or 'C'.
LDHA-370 25/27mer DsiRNA, mismatch position=23 of sense strand (from 5'-terminus)

```
5'-UUGUUGGGGUUGGUGCUGUUGGAat-3'  (SEQ ID NO: 7149)
3'-UCAACAACCCCAACCACGACAACCGUA-5' (SEQ ID NO: 84)
```

Optionally, the mismatched 'A' residue of position 23 of the sense strand is alternatively 'U' or 'G'.
LDHA-370 25/27mer DsiRNA, mismatch position=24 of sense strand (from 5'-terminus)

```
5'-UUGUUGGGGUUGGUGCUGUUGGCgt-3'  (SEQ ID NO: 7150)
3'-UCAACAACCCCAACCACGACAACCGUA-5' (SEQ ID NO: 84)
```

Optionally, the mismatched 'g' residue of position 24 of the sense strand is alternatively 't' or 'c'.
LDHA-370 25/27mer DsiRNA, mismatch position=25 of sense strand (from 5'-terminus)

```
5'-UUGUUGGGGUUGGUGCUGUUGGCaa-3'  (SEQ ID NO: 7151)
3'-UCAACAACCCCAACCACGACAACCGUA-5' (SEQ ID NO: 84)
```

Optionally, the mismatched 'a' residue of position 25 of the sense strand is alternatively 'c' or 'g'.
LDHA-370 25/27mer DsiRNA, mismatch position=1 of antisense strand (from 5'-terminus)

```
5'-UUGUUGGGGUUGGUGCUGUUGGCat-3'  (SEQ ID NO: 12)
3'-UCAACAACCCCAACCACGACAACCGUU-5' (SEQ ID NO: 7152)
```

Optionally, the mismatched 'U' residue of position 1 of the antisense strand is alternatively 'G' or 'C'.
LDHA-370 25/27mer DsiRNA, mismatch position=2 of antisense strand (from 5'-terminus)

```
5'-UUGUUGGGGUUGGUGCUGUUGGCat-3'  (SEQ ID NO: 12)
3'-UCAACAACCCCAACCACGACAACCGCA-5' (SEQ ID NO: 7153)
```

Optionally, the mismatched 'C' residue of position 2 of the antisense strand is alternatively 'A' or 'G'.
LDHA-370 25/27mer DsiRNA, mismatch position=3 of antisense strand (from 5'-terminus)

```
5'-UUGUUGGGGUUGGUGCUGUUGGCat-3'  (SEQ ID NO: 12)
3'-UCAACAACCCCAACCACGACAACCUUA-5' (SEQ ID NO: 7154)
```

Optionally, the mismatched 'U' residue of position 3 of the antisense strand is alternatively 'A' or 'C'.
LDHA-370 25/27mer DsiRNA, mismatch position=4 of antisense strand (from 5'-terminus)

```
5'-UUGUUGGGGUUGGUGCUGUUG^GCat-3' (SEQ ID NO: 12)
3'-UCAACAACCCCAACCACGACAAC_AGUA-5' (SEQ ID NO: 7155)
```

Optionally, the mismatched 'A' residue of position 4 of the antisense strand is alternatively 'U' or 'G'.
LDHA-370 25/27mer DsiRNA, mismatch position=5 of antisense strand (from 5'-terminus)

```
5'-UUGUUGGGGUUGGUGCUGUU^GGCat-3' (SEQ ID NO: 12)
3'-UCAACAACCCCAACCACGACAA_UCGUA-5' (SEQ ID NO: 7156)
```

Optionally, the mismatched 'U' residue of position 5 of the antisense strand is alternatively 'A' or 'G'.
LDHA-370 25/27mer DsiRNA, mismatch position=6 of antisense strand (from 5'-terminus)

```
5'-UUGUUGGGGUUGGUGCUGU^UGGCat-3' (SEQ ID NO: 12)
3'-UCAACAACCCCAACCACGACA_UCCGUA-5' (SEQ ID NO: 7157)
```

Optionally, the mismatched 'U' residue of position 6 of the antisense strand is alternatively 'C' or 'G'.
LDHA-370 25/27mer DsiRNA, mismatch position=7 of antisense strand (from 5'-terminus)

```
5'-UUGUUGGGGUUGGUGCUG^UUGGCat-3' (SEQ ID NO: 12)
3'-UCAACAACCCCAACCACGAC_UACCGUA-5' (SEQ ID NO: 7158)
```

Optionally, the mismatched 'U' residue of position 7 of the antisense strand is alternatively 'C' or 'G'.

As another example, in the below structures, such mismatches are introduced within the asymmetric LDHA-402 DsiRNA (newly-introduced mismatch residues are italicized):
LDHA-402 25/27mer DsiRNA, mismatch position=19 of sense strand (from 5'-terminus)

```
5'-GCCAUCAGUAUCUUAAUG^UAGGAct-3' (SEQ ID NO: 7159)
3'-CACGGUAGUCAUAGAAUUAC_UUCCUGA-5' (SEQ ID NO: 90)
```

Optionally, the mismatched 'U' residue of position 19 of the sense strand is alternatively 'C' or 'G'.
LDHA-402 25/27mer DsiRNA, mismatch position=20 of sense strand (from 5'-terminus)

```
5'-GCCAUCAGUAUCUUAAUGA^UGGAct-3' (SEQ ID NO: 7160)
3'-CACGGUAGUCAUAGAAUUACU_UCCUGA-5' (SEQ ID NO: 90)
```

Optionally, the mismatched 'U' residue of position 20 of the sense strand is alternatively 'C' or 'G'.
LDHA-402 25/27mer DsiRNA, mismatch position=21 of sense strand (from 5'-terminus)

```
5'-GCCAUCAGUAUCUUAAUGAA^AGAct-3' (SEQ ID NO: 7161)
3'-CACGGUAGUCAUAGAAUUACUU_CCUGA-5' (SEQ ID NO: 90)
```

Optionally, the mismatched 'A' residue of position 21 of the sense strand is alternatively 'U' or 'C'.
LDHA-402 25/27mer DsiRNA, mismatch position=22 of sense strand (from 5'-terminus)

```
5'-GCCAUCAGUAUCUUAAUGAAGG^UAct-3' (SEQ ID NO: 7162)
3'-CACGGUAGUCAUAGAAUUACUUC_CUGA-5' (SEQ ID NO: 90)
```

Optionally, the mismatched 'U' residue of position 22 of the sense strand is alternatively 'A' or 'C'.
LDHA-402 25/27mer DsiRNA, mismatch position=23 of sense strand (from 5'-terminus)

```
5'-GCCAUCAGUAUCUUAAUGAAGG^Uct-3' (SEQ ID NO: 7163)
3'-CACGGUAGUCAUAGAAUUACUUCC_UGA-5' (SEQ ID NO: 90)
```

Optionally, the mismatched 'U' residue of position 23 of the sense strand is alternatively 'C' or 'G'.
LDHA-402 25/27mer DsiRNA, mismatch position=24 of sense strand (from 5'-terminus)

```
5'-GCCAUCAGUAUCUUAAUGAAGGA^t-3' (SEQ ID NO: 7164)
3'-CACGGUAGUCAUAGAAUUACUUCCU_GA-5' (SEQ ID NO: 90)
```

Optionally, the mismatched 't' residue of position 24 of the sense strand is alternatively 'a' or 'g'.
LDHA-402 25/27mer DsiRNA, mismatch position=25 of sense strand (from 5'-terminus)

```
5'-GCCAUCAGUAUCUUAAUGAAGGAc^a-3' (SEQ ID NO: 7165)
3'-CACGGUAGUCAUAGAAUUACUUCCUG_A-5' (SEQ ID NO: 90)
```

Optionally, the mismatched 'a' residue of position 25 of the sense strand is alternatively 'c' or 'g'.
LDHA-402 25/27mer DsiRNA, mismatch position=1 of antisense strand (from 5'-terminus)

```
5'-GCCAUCAGUAUCUUAAUGAAGGAc^t-3' (SEQ ID NO: 18)
3'-CACGGUAGUCAUAGAAUUACUUCCUG_U-5' (SEQ ID NO: 7166)
```

Optionally, the mismatched 'U' residue of position 1 of the antisense strand is alternatively 'G' or 'C'.
LDHA-402 25/27mer DsiRNA, mismatch position=2 of antisense strand (from 5'-terminus)

```
5'-GCCAUCAGUAUCUUAAUGAAGGA^Ct-3' (SEQ ID NO: 18)
3'-CACGGUAGUCAUAGAAUUACUUCCU_AA-5' (SEQ ID NO: 7167)
```

Optionally, the mismatched 'A' residue of position 2 of the antisense strand is alternatively 'U' or 'C'.
LDHA-402 25/27mer DsiRNA, mismatch position=3 of antisense strand (from 5'-terminus)

```
5'-GCCAUCAGUAUCUUAAUGAAGG^Act-3' (SEQ ID NO: 18)
3'-CACGGUAGUCAUAGAAUUACUUCC_AGA-5' (SEQ ID NO: 7168)
```

Optionally, the mismatched 'A' residue of position 3 of the antisense strand is alternatively 'C' or 'G'.
LDHA-402 25/27mer DsiRNA, mismatch position=4 of antisense strand (from 5'-terminus)

```
5'-GCCAUCAGUAUCUUAAUGAAG^GAct-3' (SEQ ID NO: 18)
3'-CACGGUAGUCAUAGAAUUACUUC_AUGA-5' (SEQ ID NO: 7169)
```

Optionally, the mismatched 'A' residue of position 4 of the antisense strand is alternatively 'U' or 'G'.
LDHA-402 25/27mer DsiRNA, mismatch position=5 of antisense strand (from 5'-terminus)

```
5'-GCCAUCAGUAUCUUAAUGAA^GGAct-3' (SEQ ID NO: 18)
3'-CACGGUAGUCAUAGAAUUACUU_UCUGA-5' (SEQ ID NO: 7170)
```

Optionally, the mismatched 'U' residue of position 5 of the antisense strand is alternatively 'A' or 'G'.
LDHA-402 25/27mer DsiRNA, mismatch position=6 of antisense strand (from 5'-terminus)

```
5'-GCCAUCAGUAUCUUAAUGA^AGGAct-3' (SEQ ID NO: 18)
3'-CACGGUAGUCAUAGAAUUACU_ACCUGA-5' (SEQ ID NO: 7171)
```

Optionally, the mismatched 'A' residue of position 6 of the antisense strand is alternatively 'C' or 'G'.
LDHA-402 25/27mer DsiRNA, mismatch position=7 of antisense strand (from 5'-terminus)

```
5'-GCCAUCAGUAUCUUAAUG^AAGGAct-3' (SEQ ID NO: 18)
3'-CACGGUAGUCAUAGAAUUAC_AUCCUGA-5' (SEQ ID NO: 7172)
```

Optionally, the mismatched 'A' residue of position 7 of the antisense strand is alternatively 'C' or 'G'.
As an additional example, in the below structures, such mismatches are introduced within the asymmetric LDHA-723 DsiRNA (newly-introduced mismatch residues are italicized):
LDHA-723 25/27mer DsiRNA, mismatch position=19 of sense strand (from 5'-terminus)

```
5'-UUGACCUACGUGGCUUGG^UAGAUaa-3'       (SEQ ID NO: 7173)
3'-AGAACUGGAUGCACCGAACC_UUCUAUU-5'     (SEQ ID NO: 99)
```

Optionally, the mismatched 'U' residue of position 19 of the sense strand is alternatively 'C' or 'G'.
LDHA-723 25/27mer DsiRNA, mismatch position=20 of sense strand (from 5'-terminus)

```
5'-UUGACCUACGUGGCUUGGA^UGAUaa-3'       (SEQ ID NO: 7174)
3'-AGAACUGGAUGCACCGAACCU_UCUAUU-5'     (SEQ ID NO: 99)
```

Optionally, the mismatched 'U' residue of position 20 of the sense strand is alternatively 'C' or 'G'.
LDHA-723 25/27mer DsiRNA, mismatch position=21 of sense strand (from 5'-terminus)

```
5'-UUGACCUACGUGGCUUGGAA^AUaa-3'        (SEQ ID NO: 7175)
3'-AGAACUGGAUGCACCGAACCUU_CUAUU-5'     (SEQ ID NO: 99)
```

Optionally, the mismatched 'A' residue of position 21 of the sense strand is alternatively 'U' or 'C'.
LDHA-723 25/27mer DsiRNA, mismatch position=22 of sense strand (from 5'-terminus)

```
5'-UUGACCUACGUGGCUUGGAAG^Uaa-3'        (SEQ ID NO: 7176)
3'-AGAACUGGAUGCACCGAACCUUC_AUU-5'      (SEQ ID NO: 99)
```

Optionally, the mismatched 'G' residue of position 22 of the sense strand is alternatively 'U' or 'C'.
LDHA-723 25/27mer DsiRNA, mismatch position=23 of sense strand (from 5'-terminus)

```
5'-UUGACCUACGUGGCUUGGAAGA^aa-3'        (SEQ ID NO: 7177)
3'-AGAACUGGAUGCACCGAACCUUCU_AUU-5'     (SEQ ID NO: 99)
```

Optionally, the mismatched 'A' residue of position 23 of the sense strand is alternatively 'C' or 'G'.
LDHA-723 25/27mer DsiRNA, mismatch position=24 of sense strand (from 5'-terminus)

```
5'-UUGACCUACGUGGCUUGGAAGAU^a-3'        (SEQ ID NO: 7178)
3'-AGAACUGGAUGCACCGAACCUUCUA_UU-5'     (SEQ ID NO: 99)
```

Optionally, the mismatched 'g' residue of position 24 of the sense strand is alternatively 't' or 'c'.
LDHA-723 25/27mer DsiRNA, mismatch position=25 of sense strand (from 5'-terminus)

```
5'-UUGACCUACGUGGCUUGGAAGAUa^t-3'       (SEQ ID NO: 7179)
3'-AGAACUGGAUGCACCGAACCUUCUAU_u-5'     (SEQ ID NO: 99)
```

Optionally, the mismatched 't' residue of position 25 of the sense strand is alternatively 'c' or 'g'.
LDHA-723 25/27mer DsiRNA, mismatch position=1 of antisense strand (from 5'-terminus)

```
5'-UUGACCUACGUGGCUUGGAAGAUa^a-3'       (SEQ ID NO: 27)
3'-AGAACUGGAUGCACCGAACCUUCUAU_A-5'     (SEQ ID NO: 7180)
```

Optionally, the mismatched 'A' residue of position 1 of the antisense strand is alternatively 'G' or 'C'.
LDHA-723 25/27mer DsiRNA, mismatch position=2 of antisense strand (from 5'-terminus)

5'-UUGACCUACGUGGCUUGGAAGAU$^a$a-3'     (SEQ ID NO: 27)
3'-AGAACUGGAUGCACCGAACCUUCUA$_C$U-5'   (SEQ ID NO: 7181)

Optionally, the mismatched 'C' residue of position 2 of the antisense strand is alternatively 'A' or 'G'.
LDHA-723 25/27mer DsiRNA, mismatch position=3 of antisense strand (from 5'-terminus)

5'-UUGACCUACGUGGCUUGGAAGA$^U$aa-3'     (SEQ ID NO: 27)
3'-AGAACUGGAUGCACCGAACCUUCU$_U$UU-5'   (SEQ ID NO: 7182)

Optionally, the mismatched 'U' residue of position 3 of the antisense strand is alternatively 'C' or 'G'.
LDHA-723 25/27mer DsiRNA, mismatch position=4 of antisense strand (from 5'-terminus)

5'-UUGACCUACGUGGCUUGGAAG$^A$Uaa-3'     (SEQ ID NO: 27)
3'-AGAACUGGAUGCACCGAACCUUC$_G$AUU-5'   (SEQ ID NO: 7183)

Optionally, the mismatched 'C' residue of position 4 of the antisense strand is alternatively 'A' or 'G'.
LDHA-723 25/27mer DsiRNA, mismatch position=5 of antisense strand (from 5'-terminus)

5'-UUGACCUACGUGGCUUGGAA$^G$AUaa-3'     (SEQ ID NO: 27)
3'-AGAACUGGAUGCACCGAACCUU$_U$UAUU-5'   (SEQ ID NO: 7184)

Optionally, the mismatched 'U' residue of position 5 of the antisense strand is alternatively 'A' or 'G'.
LDHA-723 25/27mer DsiRNA, mismatch position=6 of antisense strand (from 5'-terminus)

5'-UUGACCUACGUGGCUUGGA$^A$GAUaa-3'     (SEQ ID NO: 27)
3'-AGAACUGGAUGCACCGAACCU$_A$CUAUU-5'   (SEQ ID NO: 7185)

Optionally, the mismatched 'A' residue of position 6 of the antisense strand is alternatively 'C' or 'G'.
LDHA-723 25/27mer DsiRNA, mismatch position=7 of antisense strand (from 5'-terminus)

5'-UUGACCUACGUGGCUUGG$^A$GAUaa-3'      (SEQ ID NO: 27)
3'-AGAACUGGAUGCACCGAACCU$_A$UCUAUU-5'  (SEQ ID NO: 7186)

Optionally, the mismatched 'A' residue of position 7 of the antisense strand is alternatively 'C' or 'G'.

As noted above, introduction of mismatches can be performed upon any of the DsiRNAs described herein.

The mismatches of such DsiRNA structures can be combined to produce a DsiRNA possessing, e.g., two, three or even four mismatches within the 3'-terminal four to seven nucleotides of the sense strand/5'-terminal four to seven nucleotides of the antisense strand.

Indeed, in view of the flexibility of sequences which can be incorporated into DsiRNAs at the 3'-terminal residues of the sense strand/5'-terminal residues of the antisense strand, in certain embodiments, the sequence requirements of an asymmetric DsiRNA of the instant invention can be represented as the following (minimalist) structure (shown for an exemplary lactate dehydrogenase-1365 DsiRNA sequence):

(SEQ ID NO: 7141)
5'-GUCCUUUUUAUCUGAUCUXXXXXX[X]$_n$-3'

(SEQ ID NO: 7142)
3'-AACAGGAAAAAUAGACUAGAXXXXXX[X]$_n$-5' where n=1 to 5, 1 to 10, 1 to 20, 1 to 30, 1 to 50, or 1 to 80 or more.
lactate dehydrogenase-1365 mRNA Target: 5'-UUGUCCUUUUUAUCUGAUCUXXXXXXX-3' (SEQ ID NO: 7143).

The lactate dehydrogenase target site may also be a site which is targeted by one or more of several oligonucleotides whose complementary target sites overlap with a stated target site. For example, for an exemplary lactate dehydrogenase-1365 DsiRNA, it is noted that certain DsiRNAs targeting overlapping and only slightly offset lactate dehydrogenase sequences could exhibit activity levels similar to that of lactate dehydrogenase-1635 (e.g., lactate dehydrogenase-1359 to 1372 of Table 2 above). Thus, in certain embodiments, a designated target sequence region might be effectively targeted by a series of DsiRNAs possessing largely overlapping sequences. (E.g., if considering DsiRNAs of the lactate dehydrogenase-1359 to lactate dehydrogenase-1372 target site(s), a more encompassing lactate dehydrogenase transcript target sequence might be recited as, e.g., 5'-UGCAUGUUGUCCUUUUUAUCUGAUCUGUGAUUAAAGCAGU-3' (SEQ ID NO: 7144), wherein any given DsiRNA (e.g., a DsiRNA selected from lactate dehydrogenase-1359 to lactate dehydrogenase-1372) only targets a sub-sequence within such a sequence region, yet the entire sequence can be considered a viable target for such a series of DsiRNAs).

Additionally and/or alternatively, mismatches within the 3'-terminal seven nucleotides of the sense strand/5'-terminal seven nucleotides of the antisense strand can be combined with mismatches positioned at other mismatch-tolerant positions, as described above.

In view of the present identification of the above-described Dicer substrate agents (DsiRNAs) as inhibitors of lactate dehydrogenase levels via targeting of specific lactate dehydrogenase sequences, it is also recognized that dsRNAs having structures similar to those described herein can also be synthesized which target other sequences within the lactate dehydrogenase sequence of NM_005566.3, or within variants thereof (e.g., target sequences possessing 80% identity, 90% identity, 95% identity, 96% identity, 97% identity, 98% identity, 99% or more identity to a sequence of NM_005566.3).

Anti-Lactate Dehydrogenase DsiRNA Design/Synthesis

It has been found empirically that longer dsRNA species of from 25 to 35 nucleotides (DsiRNAs) and especially from 25 to 30 nucleotides give unexpectedly effective results in terms of potency and duration of action, as compared to 19-23mer siRNA agents. Without wishing to be bound by the underlying theory of the dsRNA processing mechanism, it is thought that the longer dsRNA species serve as a substrate for the Dicer enzyme in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA (e.g., lactate dehydrogenase RNA) of or derived from the target gene, lactate dehydrogenase (or other gene associated with a lactate dehydrogenase-associated disease or disorder). Prior studies (Rossi et al., U.S. Patent Application No. 2007/0265220) have shown that the cleavability of a dsRNA species (specifically, a DsiRNA agent) by Dicer corresponds with increased potency and duration of action of the dsRNA species.

Certain preferred anti-lactate dehydrogenase DsiRNA agents were selected from a pre-screened population. Design of DsiRNAs can optionally involve use of predictive scoring algorithms that perform in silico assessments of the projected activity/efficacy of a number of possible DsiRNA agents spanning a region of sequence. Information regarding the design of such scoring algorithms can be found, e.g., in Gong et al. (*BMC Bioinformatics* 2006, 7:516), though a more recent "v4.3" algorithm represents a theoretically improved algorithm relative to siRNA scoring algorithms previously available in the art. (E.g., "v3" and "v4" scoring algorithms are machine learning algorithms that are not reliant upon any biases in human sequence. In addition, the "v3" and "v4" algorithms derive from data sets that are many-fold larger than that from which an older "v2" algorithm such as that described in Gong et al. derives.)

The first and second oligonucleotides of the DsiRNA agents of the instant invention are not required to be completely complementary. In fact, in one embodiment, the 3'-terminus of the sense strand contains one or more mismatches. In one aspect, two mismatches are incorporated at the 3' terminus of the sense strand. In another embodiment, the DsiRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003, *Cell* 115: 199-208; Khvorova et al., 2003, *Cell* 115: 209-216), presumably by affecting some rate-limiting unwinding steps that occur with entry of the siRNA into RISC. Thus, terminal base composition has been included in design algorithms for selecting active 21mer siRNA duplexes (Ui-Tei et al., 2004, *Nucleic Acids Res* 32: 936-948; Reynolds et al., 2004, *Nat Biotechnol* 22: 326-330). With Dicer cleavage of the dsRNA of this embodiment, the small end-terminal sequence which contains the mismatches will either be left unpaired with the antisense strand (become part of a 3'-overhang) or be cleaved entirely off the final 21-mer siRNA. These "mismatches", therefore, do not persist as mismatches in the final RNA component of RISC. The finding that base mismatches or destabilization of segments at the 3'-end of the sense strand of Dicer substrate improved the potency of synthetic duplexes in RNAi, presumably by facilitating processing by Dicer, was a surprising finding of past works describing the design and use of 25-30mer dsRNAs (also termed "DsiRNAs" herein; Rossi et al., U.S. Patent Application Nos. 2005/0277610, 2005/0244858 and 2007/0265220).

Modification of Anti-Lactate Dehydrogenase dsRNAs

One major factor that inhibits the effect of double stranded RNAs ("dsRNAs") is the degradation of dsRNAs (e.g., siRNAs and DsiRNAs) by nucleases. A 3'-exonuclease is the primary nuclease activity present in serum and modification of the 3'-ends of antisense DNA oligonucleotides is crucial to prevent degradation (Eder et al., 1991, *Antisense Res Dev*, 1: 141-151). An RNase-T family nuclease has been identified called ERI-1 which has 3' to 5' exonuclease activity that is involved in regulation and degradation of siRNAs (Kennedy et al., 2004, *Nature* 427: 645-649; Hong et al., 2005, *Biochem J*, 390: 675-679). This gene is also known as Thex1 (NM_02067) in mice or THEX1 (NM_153332) in humans and is involved in degradation of histone mRNA; it also mediates degradation of 3'-overhangs in siRNAs, but does not degrade duplex RNA (Yang et al., 2006, *J Biol Chem*, 281: 30447-30454). It is therefore reasonable to expect that 3'-end-stabilization of dsRNAs, including the DsiRNAs of the instant invention, will improve stability.

XRN1 (NM_019001) is a 5' to 3' exonuclease that resides in P-bodies and has been implicated in degradation of mRNA targeted by miRNA (Rehwinkel et al., 2005, *RNA* 11: 1640-1647) and may also be responsible for completing degradation initiated by internal cleavage as directed by a siRNA. XRN2 (NM_012255) is a distinct 5' to 3' exonuclease that is involved in nuclear RNA processing.

RNase A is a major endonuclease activity in mammals that degrades RNAs. It is specific for ssRNA and cleaves at the 3'-end of pyrimidine bases. SiRNA degradation products consistent with RNase A cleavage can be detected by mass spectrometry after incubation in serum (Turner et al., 2007, *Mol Biosyst* 3: 43-50). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006 *Biochem Pharmacol* 71: 702-710). This suggests the possibility that lower stability regions of the duplex may "breathe" and offer transient single-stranded species available for degradation by RNase A. RNase A inhibitors can be added to serum and improve siRNA longevity and potency (Haupenthal et al., 2007, *Int J. Cancer* 121: 206-210).

In 21mers, phosphorothioate or boranophosphate modifications directly stabilize the internucleoside phosphate linkage. Boranophosphate modified RNAs are highly nuclease resistant, potent as silencing agents, and are relatively non-toxic. Boranophosphate modified RNAs cannot be manufactured using standard chemical synthesis methods and instead are made by in vitro transcription (IVT) (Hall et al., 2004, *Nucleic Acids Res* 32: 5991-6000; Hall et al., 2006, *Nucleic Acids Res* 34: 2773-2781). Phosphorothioate (PS) modifications can be easily placed in the RNA duplex at any desired position and can be made using standard chemical synthesis methods. The PS modification shows dose-dependent toxicity, so most investigators have recommended limited incorporation in siRNAs, favoring the 3'-ends where protection from nucleases is most important (Harborth et al., 2003, *Antisense Nucleic Acid Drug Dev* 13: 83-105; Chiu and Rana, 2003, *Mol Cell* 10: 549-561; Braasch et al., 2003, *Biochemistry* 42: 7967-7975; Amarzguioui et al., 2003, *Nucleic Acids Research* 31: 589-595). More extensive PS modification can be compatible with potent RNAi activity; however, use of sugar modifications (such as 2'-O-methyl RNA) may be superior (Choung et al., 2006, *Biochem Biophys Res Commun* 342: 919-927).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung et al., 2006, *Biochem Biophys Res Commun* 342: 919-927; Czauderna et al., 2003, *Nucleic Acids Research* 31: 2705-2716).

The 2'-fluoro (2'-F) modification is also compatible with dsRNA (e.g., siRNA and DsiRNA) function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005, *J Med Chem* 48: 901-904; Prakash et al., 2005, *J Med Chem* 48: 4247-4253; Kraynack and Baker, 2006, *RNA* 12: 163-176) and can improve performance and extend duration of action when used in vivo (Morrissey et al., 2005, *Hepatology* 41: 1349-1356; Morrissey et al., 2005, *Nat Biotechnol* 23: 1002-1007). A highly potent, nuclease stable, blunt 19mer duplex containing alternative 2'-F and 2'-O-Me bases is taught by Allerson. In this design, alternating 2'-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 2'-O-Me RNA and 2'-F RNA, this duplex includes DNA, RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004, *Nature* 432: 173-178) employed a duplex in vivo and was mostly RNA with two 2'-O-Me RNA bases and limited 3'-terminal PS internucleoside linkages.

Locked nucleic acids (LNAs) are a different class of 2'-modification that can be used to stabilize dsRNA (e.g., siRNA and DsiRNA). Patterns of LNA incorporation that retain potency are more restricted than 2'-O-methyl or 2'-F bases, so limited modification is preferred (Braasch et al., 2003, *Biochemistry* 42: 7967-7975; Grunweller et al., 2003, *Nucleic Acids Res* 31: 3185-3193; Elmen et al., 2005, *Nucleic Acids Res* 33: 439-447). Even with limited incorporation, the use of LNA modifications can improve dsRNA performance in vivo and may also alter or improve off target effect profiles (Mook et al., 2007, *Mol Cancer Ther* 6: 833-843).

Synthetic nucleic acids introduced into cells or live animals can be recognized as "foreign" and trigger an immune response. Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005, *Nat Biotechnol* 23: 1399-1405; Schlee et al., 2006, *Mol Ther* 14: 463-470). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005, *Nat Biotechnol* 23: 1002-1007; Sioud and Sorensen, 2003, *Biochem Biophys Res Commun* 312: 1220-1225; Sioud, 2005, *J Mol Biol* 348: 1079-1090; Ma et al., 2005, *Biochem Biophys Res Commun* 330: 755-759). RNAs transcribed within the cell are less immunogenic (Robbins et al., 2006, *Nat Biotechnol* 24: 566-571) and synthetic RNAs that are immunogenic when delivered using lipid-based methods can evade immune stimulation when introduced unto cells by mechanical means, even in vivo (Heidel et al., 2004, *Nat Biotechnol* 22: 1579-1582). However, lipid based delivery methods are convenient, effective, and widely used. Some general strategy to prevent immune responses is needed, especially for in vivo application where all cell types are present and the risk of generating an immune response is highest. Use of chemically modified RNAs may solve most or even all of these problems.

In certain embodiments, modifications can be included in the anti-lactate dehydrogenase dsRNA agents of the present invention so long as the modification does not prevent the dsRNA agent from possessing lactate dehydrogenase inhibitory activity. In one embodiment, one or more modifications are made that enhance Dicer processing of the DsiRNA agent (an assay for determining Dicer processing of a DsiRNA is described elsewhere herein). In a second embodiment, one or more modifications are made that result in more effective lactate dehydrogenase inhibition (as described herein, lactate dehydrogenase inhibition/lactate dehydrogenase inhibitory activity of a dsRNA can be assayed via art-recognized methods for determining RNA levels, or for determining lactate dehydrogenase polypeptide levels, should such levels be assessed in lieu of or in addition to assessment of, e.g., lactate dehydrogenase mRNA levels). In a third embodiment, one or more modifications are made that support greater lactate dehydrogenase inhibitory activity (means of determining lactate dehydrogenase inhibitory activity are described supra). In a fourth embodiment, one or more modifications are made that result in greater potency of lactate dehydrogenase inhibitory activity per each dsRNA agent molecule to be delivered to the cell (potency of lactate dehydrogenase inhibitory activity is described supra). Modifications can be incorporated in the 3'-terminal region, the 5'-terminal region, in both the 3'-terminal and 5'-terminal region or in some instances in various positions within the sequence. With the restrictions noted above in mind, numbers and combinations of modifications can be incorporated into the dsRNA agent. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003, *Nucleic Acids Research* 31: 589-595). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1. Other modifications are disclosed in Herdewijn (2000, *Antisense Nucleic Acid Drug Dev* 10: 297-310), Eckstein (2000, *Antisense Nucleic Acid Drug Dev* 10: 117-21), Rusckowski et al. (2000, *Antisense Nucleic Acid Drug Dev* 10: 333-345), Stein et al. (2001, *Antisense Nucleic Acid Drug Dev* 11: 317-25); Vorobjev et al. (2001, *Antisense Nucleic Acid Drug Dev* 11: 77-85).

One or more modifications contemplated can be incorporated into either strand. The placement of the modifications in the dsRNA agent can greatly affect the characteristics of the dsRNA agent, including conferring greater potency and stability, reducing toxicity, enhance Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides.

In certain embodiments, the anti-lactate dehydrogenase DsiRNA agent of the invention has several properties which enhance its processing by Dicer. According to such embodiments, the DsiRNA agent has a length sufficient such that it is processed by Dicer to produce an siRNA and at least one of the following properties: (i) the DsiRNA agent is asymmetric, e.g., has a 3' overhang on the sense strand and (ii) the DsiRNA agent has a modified 3' end on the antisense strand to direct orientation of Dicer binding and processing of the dsRNA to an active siRNA. According to these embodiments, the longest strand in the DsiRNA agent comprises 25-30 nucleotides. In one embodiment, the sense strand comprises 25-30 nucleotides and the antisense strand comprises 25-28 nucleotides. Thus, the resulting dsRNA has an overhang on the 3' end of the sense strand. The overhang is 1-4 nucleotides, such as 2 nucleotides. The antisense strand may also have a 5' phosphate.

In certain embodiments, the sense strand of a DsiRNA agent is modified for Dicer processing by suitable modifiers located at the 3' end of the sense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the sense strand in place of two ribonucleotides forming a blunt end of the duplex on the 5' end of the antisense strand and the 3' end of the sense strand, and a two-nucleotide RNA overhang is located on the 3'-end of the antisense strand. This is an asymmetric composition with DNA on the blunt end and RNA bases on the overhanging end.

In certain other embodiments, the antisense strand of a DsiRNA agent is modified for Dicer processing by suitable modifiers located at the 3' end of the antisense strand, i.e., the DsiRNA agent is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is also an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the target lactate dehydrogenase RNA.

Additionally, the DsiRNA agent structure can be optimized to ensure that the oligonucleotide segment generated from Dicer's cleavage will be the portion of the oligonucleotide that is most effective in inhibiting gene expression. For example, in one embodiment of the invention, a 27-bp oligonucleotide of the DsiRNA agent structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

US 2007/0265220 discloses that 27mer DsiRNAs showed improved stability in serum over comparable 21mer siRNA compositions, even absent chemical modification. Modifications of DsiRNA agents, such as inclusion of 2'-O-methyl RNA in the antisense strand, in patterns such as detailed above, when coupled with addition of a 5' Phosphate, can improve stability of DsiRNA agents. Addition of 5'-phosphate to all strands in synthetic RNA duplexes may be an inexpensive and physiological method to confer some limited degree of nuclease stability.

The chemical modification patterns of the dsRNA agents of the instant invention are designed to enhance the efficacy of such agents. Accordingly, such modifications are designed to avoid reducing potency of dsRNA agents; to avoid interfering with Dicer processing of DsiRNA agents; to improve stability in biological fluids (reduce nuclease sensitivity) of dsRNA agents; or to block or evade detection by the innate immune system. Such modifications are also designed to avoid being toxic and to avoid increasing the cost or impact the ease of manufacturing the instant dsRNA agents of the invention.

In certain embodiments of the present invention, an anti-lactate dehydrogenase DsiRNA agent has one or more of the following properties: (i) the DsiRNA agent is asymmetric, e.g., has a 3' overhang on the antisense strand and (ii) the DsiRNA agent has a modified 3' end on the sense strand to direct orientation of Dicer binding and processing of the dsRNA to an active siRNA. According to this embodiment, the longest strand in the dsRNA comprises 25-35 nucleotides (e.g., 25, 26, 27, 28, 29, 30, 31, 32, 33, 34 or 35 nucleotides). In certain such embodiments, the DsiRNA agent is asymmetric such that the sense strand comprises 25-34 nucleotides and the 3' end of the sense strand forms a blunt end with the 5' end of the antisense strand while the antisense strand comprises 26-35 nucleotides and forms an overhang on the 3' end of the antisense strand. In one embodiment, the DsiRNA agent is asymmetric such that the sense strand comprises 25-28 nucleotides and the antisense strand comprises 25-30 nucleotides. Thus, the resulting dsRNA has an overhang on the 3' end of the antisense strand. The overhang is 1-4 nucleotides, for example 2 nucleotides. The sense strand may also have a 5' phosphate.

The DsiRNA agent can also have one or more of the following additional properties: (a) the antisense strand has a right shift from the typical 21mer (e.g., the DsiRNA comprises a length of antisense strand nucleotides that extends to the 5' of a projected Dicer cleavage site within the DsiRNA, with such antisense strand nucleotides base paired with corresponding nucleotides of the sense strand extending 3' of a projected Dicer cleavage site in the sense strand), (b) the strands may not be completely complementary, i.e., the strands may contain simple mismatched base pairs (in certain embodiments, the DsiRNAs of the invention possess 1, 2, 3, 4 or even 5 or more mismatched base pairs, provided that lactate dehydrogenase inhibitory activity of the DsiRNA possessing mismatched base pairs is retained at sufficient levels (e.g., retains at least 50% lactate dehydrogenase inhibitory activity or more, at least 60% lactate dehydrogenase inhibitory activity or more, at least 70% lactate dehydrogenase inhibitory activity or more, at least 80% lactate dehydrogenase inhibitory activity or more, at least 90% lactate dehydrogenase inhibitory activity or more or at least 95% lactate dehydrogenase inhibitory activity or more as compared to a corresponding DsiRNA not possessing mismatched base pairs. In certain embodiments, mismatched base pairs exist between the antisense and sense strands of a DsiRNA. In some embodiments, mismatched base pairs exist (or are predicted to exist) between the antisense strand and the target RNA. In certain embodiments, the presence of a mismatched base pair(s) between an antisense strand residue and a corresponding residue within the target RNA that is located 3' in the target RNA sequence of a projected Ago2 cleavage site retains and may even enhance lactate dehydrogenase inhibitory activity of a DsiRNA of the invention) and (c) base modifications such as locked nucleic acid(s) may be included in the 5' end of the sense strand. A "typical" 21mer siRNA is designed using conventional techniques. In one technique, a variety of sites are commonly tested in parallel or pools containing several distinct siRNA duplexes specific to the same target with the hope that one of the reagents will be effective (Ji et al., 2003, *FEBS Lett* 552: 247-252). Other techniques use design rules and algorithms to increase the likelihood of obtaining active RNAi effector molecules (Schwarz et al., 2003, *Cell* 115: 199-208; Khvorova et al., 2003, *Cell* 115: 209-216; Ui-Tei et al., 2004, *Nucleic Acids Res* 32: 936-948; Reynolds et al., 2004, *Nat Biotechnol* 22: 326-330; Krol et al., 2004, *J Biol Chem* 279: 42230-42239; Yuan et al., 2004, *Nucl Acids Res* 32 (Webserver issue):W130-134; Boese et al., 2005, *Methods Enzymol* 392: 73-96). High throughput selection of siRNA has also been developed (U.S. published patent application No. 2005/0042641 A1). Potential target sites can also be analyzed by secondary structure predictions (Heale et al., 2005, *Nucleic Acids Res* 33(3): e30). This 21mer is then used to design a right shift to include 3-9 additional nucleotides on the 5' end of the 21mer. The sequence of these additional nucleotides is not restricted. In one embodiment, the added ribonucleotides are based on the sequence of the target gene. Even in this embodiment, full complementarity between the target sequence and the antisense siRNA is not required.

The first and second oligonucleotides of a DsiRNA agent of the instant invention are not required to be completely complementary. They only need to be sufficiently complementary to anneal under biological conditions and to provide a substrate for Dicer that produces a siRNA sufficiently complementary to the target sequence. Locked nucleic acids, or LNA's, are well known to a skilled artisan (Elmen et al., 2005, *Nucleic Acids Res* 33: 439-447; Kurreck et al., 2002, *Nucleic Acids Res* 30: 1911-1918; Crinelli et al., 2002, *Nucleic Acids Res* 30: 2435-2443; Braasch and Corey, 2001, *Chem Biol* 8: 1-7; Bondensgaard et al., 2000, *Chemistry* 6: 2687-2695; Wahlestedt et al., 2000, *Proc Natl Acad Sci USA* 97: 5633-5638). In one embodiment, an LNA is incorporated at the 5' terminus of the sense strand. In another embodiment, an LNA is incorporated at the 5' terminus of the sense strand in duplexes designed to include a 3' overhang on the antisense strand.

In certain embodiments, the DsiRNA agent of the instant invention has an asymmetric structure, with the sense strand having a 25-base pair length, and the antisense strand having a 27-base pair length with a 2 base 3'-overhang. In other embodiments, this DsiRNA agent having an asymmetric structure further contains 2 deoxynucleotides at the 3' end of the sense strand in place of two of the ribonucleotides.

Certain DsiRNA agent compositions containing two separate oligonucleotides can be linked by a third structure. The third structure will not block Dicer activity on the DsiRNA agent and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the DsiRNA agent in a manner such that a hairpin structure is produced upon annealing of the two oligonucleotides making up the dsRNA composition. The hairpin structure will not block Dicer activity on the DsiRNA agent and will not interfere with the directed destruction of the lactate dehydrogenase RNA.

In Vitro Assay to Assess dsRNA Lactate Dehydrogenase Inhibitory Activity

An in vitro assay that recapitulates RNAi in a cell-free system can be used to evaluate dsRNA constructs targeting lactate dehydrogenase RNA sequence(s), and thus to assess lactate dehydrogenase-specific gene inhibitory activity (also referred to herein as lactate dehydrogenase inhibitory activity) of a dsRNA. The assay comprises the system described by Tuschl et al., 1999, Genes and Development, 13, 3191-3197 and Zamore et al., 2000, Cell, 101, 25-33 adapted for use with dsRNA (e.g., DsiRNA) agents directed against lactate dehydrogenase RNA. A *Drosophila* extract derived from syncytial blastoderm is used to reconstitute RNAi activity in vitro. Target RNA is generated via in vitro transcription from a selected lactate dehydrogenase expressing plasmid using T7 RNA polymerase or via chemical synthesis. Sense and antisense dsRNA strands (for example, 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing dsRNA (10 nM final concentration). The reaction mixture also contains 10 mM creatine phosphate, 10 ug/ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and preincubated at 25° C. for 10 minutes before adding RNA, then incubated at 25° C. for an additional 60 minutes. Reactions are quenched with 4 volumes of 1.25× Passive Lysis Buffer (Promega). Target RNA cleavage is assayed by RT-PCR analysis or other methods known in the art and are compared to control reactions in which dsRNA is omitted from the reaction.

Alternately, internally-labeled target RNA for the assay is prepared by in vitro transcription in the presence of [$\alpha$-$^{32}$P] CTP, passed over a G50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by PHOSPHOR IMAGER® (autoradiography) quantitation of bands representing intact control RNA or RNA from control reactions without dsRNA and the cleavage products generated by the assay.

In one embodiment, this assay is used to determine target sites in the lactate dehydrogenase RNA target for dsRNA mediated RNAi cleavage, wherein a plurality of dsRNA constructs are screened for RNAi mediated cleavage of the lactate dehydrogenase RNA target, for example, by analyzing the assay reaction by electrophoresis of labeled target RNA, or by northern blotting, as well as by other methodology well known in the art.

In certain embodiments, a dsRNA of the invention is deemed to possess lactate dehydrogenase inhibitory activity if, e.g., a 50% reduction in lactate dehydrogenase RNA levels is observed in a system, cell, tissue or organism, relative to a suitable control. Additional metes and bounds for determination of lactate dehydrogenase inhibitory activity of a dsRNA of the invention are described supra.

Conjugation and Delivery of Anti-Lactate Dehydrogenase dsRNA Agents

In certain embodiments the present invention relates to a method for treating a subject having oxalate accumulation, PH1 and/or other lactate dehydrogenase-associated disease or disorder, or is at risk of developing oxalate accumulation, PH1 and/or other lactate dehydrogenase-associated disease or disorder. In such embodiments, the dsRNA can act as novel therapeutic agents for controlling the oxalate accumulation, PH1 and/or other lactate dehydrogenase-associated disease or disorder. The method comprises administering a pharmaceutical composition of the invention to the patient (e.g., human), such that the expression, level and/or activity of a lactate dehydrogenase RNA is reduced. The expression, level and/or activity of a polypeptide encoded by a lactate dehydrogenase RNA might also be reduced by a dsRNA of the instant invention, even where said dsRNA is directed against a non-coding region of the lactate dehydrogenase transcript (e.g., a targeted 5' UTR or 3' UTR sequence). Because of their high specificity, the dsRNAs of the present invention can specifically target lactate dehydrogenase sequences of cells and tissues, optionally in an allele-specific manner where polymorphic alleles exist within an individual and/or population.

In the treatment of oxalate accumulation, PH1 and/or other lactate dehydrogenase-associated disease or disorder, the dsRNA can be brought into contact with the cells or tissue of a subject, e.g., the cells or tissue of a subject targeted for reduction of lactate dehydrogenase levels. For a disease such as PH1 or other disease or disorder of oxalate accumulation treatable or preventable via administration of an anti-LDHA agent (e.g., a dsRNA of the invention), targeted inhibition of LDHA preferentially delivered to the liver can be performed via use of dsRNA therapeutics such as those disclosed herein and delivery modalities for dsRNA known in the art (e.g., lipid nanoparticles and other moieties that preferentially deliver dsRNA to the liver). For example, dsRNA substantially identical to all or part of a lactate dehydrogenase RNA sequence, may be brought into contact with or introduced into such a cell, either in vivo or in vitro. Similarly, dsRNA substantially identical to all or part of a lactate dehydrogenase RNA sequence may administered directly to a subject having or at risk of developing a disease or disorder that could be prevented or treated via administration of an anti-LDHA agent.

Therapeutic use of the dsRNA agents of the instant invention can involve use of formulations of dsRNA agents comprising multiple different dsRNA agent sequences. For example, two or more, three or more, four or more, five or more, etc. of the presently described agents can be combined to produce a formulation that, e.g., targets multiple different regions of the lactate dehydrogenase RNA, or that not only target lactate dehydrogenase RNA but also target, e.g., cellular target genes associated with a lactate dehydrogenase-associated disease or disorder. A dsRNA agent of the instant invention may also be constructed such that either strand of the dsRNA agent independently targets two or more regions of lactate dehydrogenase RNA, or such that one of the strands of the dsRNA agent targets a cellular target gene of lactate dehydrogenase known in the art.

Use of multifunctional dsRNA molecules that target more then one region of a target nucleic acid molecule can also provide potent inhibition of lactate dehydrogenase RNA levels and expression. For example, a single multifunctional dsRNA construct of the invention can target both the lactate dehydrogenase-402 and lactate dehydrogenase-723 sites simultaneously; additionally and/or alternatively, single or multifunctional agents of the invention can be designed to selectively target one splice variant of lactate dehydrogenase over another.

Thus, the dsRNA agents of the instant invention, individually, or in combination or in conjunction with other drugs, can be used to treat, inhibit, reduce, or prevent a lactate dehydrogenase-associated disease or disorder. For example, the dsRNA molecules can be administered to a subject or can be administered to other appropriate cells evident to those skilled in the art, individually or in combination with one or more drugs under conditions suitable for the treatment.

The dsRNA molecules also can be used in combination with other known treatments to treat, inhibit, reduce, or prevent PH1 or other lactate dehydrogenase-associated disease or disorder in a subject or organism. For example, the described molecules could be used in combination with one or more known compounds, treatments, or procedures to treat, inhibit, reduce, or prevent PH1 or other lactate dehydrogenase-associated disease or disorder in a subject or organism as are known in the art.

A dsRNA agent of the invention can be conjugated (e.g., at its 5' or 3' terminus of its sense or antisense strand) or unconjugated to another moiety (e.g. a non-nucleic acid moiety such as a peptide), an organic compound (e.g., a dye, cholesterol, or the like). Modifying dsRNA agents in this way may improve cellular uptake or enhance cellular targeting activities of the resulting dsRNA agent derivative as compared to the corresponding unconjugated dsRNA agent, are useful for tracing the dsRNA agent derivative in the cell, or improve the stability of the dsRNA agent derivative compared to the corresponding unconjugated dsRNA agent.

Methods of Introducing Nucleic Acids, Vectors, and Host Cells dsRNA agents of the invention may be directly introduced into a cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The dsRNA agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target lactate dehydrogenase RNA.

A cell having a target lactate dehydrogenase RNA may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target lactate dehydrogenase RNA sequence and the dose of dsRNA agent material delivered, this process may provide partial or complete loss of function for the lactate dehydrogenase RNA. A reduction or loss of RNA levels or expression (either lactate dehydrogenase RNA expression or encoded polypeptide expression) in at least 50%, 60%, 70%, 80%, 90%, 95% or 99% or more of targeted cells is exemplary. Inhibition of lactate dehydrogenase RNA levels or expression refers to the absence (or observable decrease) in the level of lactate dehydrogenase RNA or lactate dehydrogenase RNA-encoded protein. Specificity refers to the ability to inhibit the lactate dehydrogenase RNA without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). Inhibition of target lactate dehydrogenase RNA sequence(s) by the dsRNA agents of the invention also can be measured based upon the effect of administration of such dsRNA agents upon development/progression of PH1 or other lactate dehydrogenase-associated disease or disorder, either in vivo or in vitro. Treatment of any of these conditions can be assessed by art-recognized tests for PH1 and/or kidney function, e.g., determination of the percentage of kidney function and/or kidney stone formation (e.g., 20%, 30%, 40%, 50%, 60%, 70%, 80% or greater) that is being achieved relative to average healthy kidney function and/or stone formation of an appropriate control population. In certain embodiments, successful treatment results in a decline or halting of stone formation or a decline or halting of reduction in total kidney function associated with PH1 or other lactate dehydrogenase-associated disease or disorder. In some embodiments, kidney function improves with successful treatment.

For RNA-mediated inhibition in a cell line or whole organism, expression a reporter or drug resistance gene whose protein product is easily assayed can be measured. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention.

Lower doses of injected material and longer times after administration of RNA silencing agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target lactate dehydrogenase RNA or translation of target protein. As an example, the efficiency of inhibition may be determined by assessing the amount of gene product in the cell; RNA may be detected with a hybridization probe having a nucleotide sequence outside the region used for the inhibitory dsRNA, or translated polypeptide may be detected with an antibody raised against the polypeptide sequence of that region.

The dsRNA agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

Pharmaceutical Compositions

In certain embodiments, the present invention provides for a pharmaceutical composition comprising the dsRNA agent of the present invention. The dsRNA agent sample can be suitably formulated and introduced into the environment of the cell by any means that allows for a sufficient portion of the sample to enter the cell to induce gene silencing, if it is to occur. Many formulations for dsRNA are known in the art and can be used so long as the dsRNA gains entry to the target cells so that it can act. See, e.g., U.S. published patent application Nos. 2004/0203145 A1 and 2005/0054598 A1. For example, the dsRNA agent of the instant invention can be formulated in buffer solutions such as phosphate buffered saline solutions, liposomes, micellar structures, and capsids. Formulations of dsRNA agent with cationic lipids can be used to facilitate transfection of the dsRNA agent into cells. For example, cationic lipids, such as lipofectin (U.S. Pat. No. 5,705,188), cationic glycerol derivatives, and polycationic molecules, such as polylysine (published PCT International Application WO 97/30731), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The compounds can also be administered by a method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a nucleic acid molecule (i.e., an effective dosage) depends on the nucleic acid selected. For instance, single dose amounts of a dsRNA (or, e.g., a construct(s) encoding for such dsRNA) in the range of approximately 1 µg to 1000 mg may be administered; in some embodiments, 10, 30, 100, or 1000 µg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a nucleic acid (e.g., dsRNA), protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The expression constructs may be constructs suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, e.g., Tuschl (2002, *Nature Biotechnol* 20: 500-505).

It can be appreciated that the method of introducing dsRNA agents into the environment of the cell will depend on the type of cell and the make up of its environment. For example, when the cells are found within a liquid, one preferable formulation is with a lipid formulation such as in lipofectamine and the dsRNA agents can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA agents in a buffer or saline solution and directly inject the formulated dsRNA agents into cells, as in studies with oocytes. The direct injection of dsRNA agent duplexes may also be done. For suitable methods of introducing dsRNA (e.g., DsiRNA agents), see U.S. published patent application No. 2004/0203145 A1.

Suitable amounts of a dsRNA agent must be introduced and these amounts can be empirically determined using standard methods. Typically, effective concentrations of individual dsRNA agent species in the environment of a cell will be 50 nanomolar or less, 10 nanomolar or less, or compositions in which concentrations of 1 nanomolar or less can be used. In another embodiment, methods utilizing a concentration of 200 picomolar or less, 100 picomolar or less, 50 picomolar or less, 20 picomolar or less, and even a concentration of 10 picomolar or less, 5 picomolar or less, 2 picomolar or less or 1 picomolar or less can be used in many circumstances.

The method can be carried out by addition of the dsRNA agent compositions to an extracellular matrix in which cells can live provided that the dsRNA agent composition is formulated so that a sufficient amount of the dsRNA agent can enter the cell to exert its effect. For example, the method is amenable for use with cells present in a liquid such as a liquid culture or cell growth media, in tissue explants, or in whole organisms, including animals, such as mammals and especially humans.

The level or activity of a lactate dehydrogenase RNA can be determined by a suitable method now known in the art or that is later developed. It can be appreciated that the method used to measure a target RNA and/or the expression of a target RNA can depend upon the nature of the target RNA. For example, where the target lactate dehydrogenase RNA sequence encodes a protein, the term "expression" can refer to a protein or the lactate dehydrogenase RNA/transcript derived from the lactate dehydrogenase gene (either genomic or of exogenous origin). In such instances the expression of the target lactate dehydrogenase RNA can be determined by measuring the amount of lactate dehydrogenase RNA/transcript directly or by measuring the amount of lactate dehydrogenase protein. Protein can be measured in protein assays such as by staining or immunoblotting or, if the protein catalyzes a reaction that can be measured, by measuring reaction rates. All such methods are known in the art and can be used. Where target lactate dehydrogenase RNA levels are to be measured, art-recognized methods for detecting RNA levels can be used (e.g., RT-PCR, Northern Blotting, etc.). In targeting lactate dehydrogenase RNAs with the dsRNA agents of the instant invention, it is also anticipated that measurement of the efficacy of a dsRNA agent in reducing levels of lactate dehydrogenase RNA or protein in a subject, tissue, in cells, either in vitro or in vivo, or in cell extracts can also be used to determine the extent of reduction of PH1, oxalate accumulation or other lactate dehydrogenase-associated disease or disorder phenotypes (e.g., kidney function, kidney stones, etc.). The above measurements can be made on cells, cell extracts, tissues, tissue extracts or other suitable source material.

The determination of whether the expression of a lactate dehydrogenase RNA has been reduced can be by a suitable method that can reliably detect changes in RNA levels. Typically, the determination is made by introducing into the environment of a cell undigested dsRNA such that at least a portion of that dsRNA agent enters the cytoplasm, and then measuring the level of the target RNA. The same measurement is made on identical untreated cells and the results obtained from each measurement are compared.

The dsRNA agent can be formulated as a pharmaceutical composition which comprises a pharmacologically effective amount of a dsRNA agent and pharmaceutically acceptable carrier. A pharmacologically or therapeutically effective amount refers to that amount of a dsRNA agent effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

Suitably formulated pharmaceutical compositions of this invention can be administered by means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general, a suitable dosage unit of dsRNA will be in the range of 0.001 to 0.25 milligrams per kilogram body weight of the recipient per day, or in the range of 0.01 to 20 micrograms per kilogram body weight per day, or in the range of 0.001 to 5 micrograms per kilogram of body weight per day, or in the range of 1 to 500 nanograms per kilogram of body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. A pharmaceutical composition comprising the dsRNA can be administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in such a way that the sum of the multiple units of dsRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

The pharmaceutical compositions can be included in a kit, container, pack, or dispenser together with instructions for administration.

Formulations can give trophism, and there are certain benefits to that. Specificity of LDHA, LDHB, LDHC are advantageous. [[Back off of statements re tissue specificity—what if delivery to muscle does not impact negatively]].

Methods of Treatment

The present invention provides for both prophylactic and therapeutic methods of treating a subject at risk of (or susceptible to) a disease or disorder caused, in whole or in part, by lactate dehydrogenase (e.g., misregulation and/or elevation of lactate dehydrogenase transcript and/or lactate dehydrogenase protein levels), or treatable via selective targeting of lactate dehydrogenase.

In certain aspects, the invention provides a method for preventing in a subject, a disease or disorder as described herein (including, e.g., prevention of PH1 within a subject via inhibition of lactate dehydrogenase expression), by administering to the subject a therapeutic agent (e.g., a dsRNA agent or vector or transgene encoding same). Subjects at risk for the disease can be identified by, for example, one or a combination of diagnostic or prognostic assays known in the art (e.g., identification of reduced functionality of AGT, or other altered functioning of the oxalate-producing pathway, in a subject). Administration of a prophylactic agent can occur prior to the detection of, e.g., PH1 in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the dsRNA agent) or, alternatively, in vivo (e.g., by administering the dsRNA agent to a subject).

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target lactate dehydrogenase RNA molecules of the present invention or target lactate dehydrogenase RNA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Example 1: Preparation of Double-Stranded RNA Oligonucleotides

Oligonucleotide Synthesis and Purification

DsiRNA molecules can be designed to interact with various sites in the RNA message, for example, target sequences within the RNA sequences described herein. In presently exemplified agents, 48 DsiRNAs predicted on the basis of homology to uniquely target human lactate dehydrogenase (LDHA) sequences, 48 DsiRNAs predicted on the basis of homology to uniquely target mouse lactate dehydrogenase sequences, and an additional 24 DsiRNAs predicted to target both human and mouse lactate dehydrogenase sequences were selected for evaluation. The sequences of one strand of the DsiRNA molecules were complementary to target lactate dehydrogenase site sequences. The DsiRNA molecules were chemically synthesized using methods described herein. Generally, DsiRNA constructs were synthesized using solid phase oligonucleotide synthesis methods as described for 19-23mer siRNAs (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086).

Individual RNA strands were synthesized and HPLC purified according to standard methods (Integrated DNA Technologies, Coralville, Iowa). For example, RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, 1993, *Methods Mol Biol* 20: 81-114; Wincott et al., 1995, *Nucleic Acids Res* 23: 2677-84). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min step-linear gradient. The gradient varied from 90:10 Buffers A:B to 52:48 Buffers A:B, where Buffer A was 100 mM Tris pH 8.5 and Buffer B was 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 m inner diameter and contained ssDNA 100R Gel (Beckman-Coulter). Typically, about 0.6 nmole of oligonucleotide was injected into a capillary, run in an electric field of 444 V/cm and detected by UV absorbance at 260 nm. Denaturing Tris-Borate-7 M-urea running buffer was purchased from Beckman-Coulter. Oligoribonucleotides were obtained that were at least 90% pure as assessed by CE for use in experiments described below. Compound identity was verified by matrix-assisted laser desorption ionization time-of-flight (MALDI-TOF) mass spectroscopy on a Voyager DE™ Biospectometry Work Station (Applied Biosystems, Foster City, Calif.) following the manufacturer's recommended protocol. Relative molecular masses of all oligomers were obtained, often within 0.2% of expected molecular mass.

Preparation of Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5' in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Nomenclature

For consistency, the following nomenclature has been employed in the instant specification. Names given to duplexes indicate the length of the oligomers and the presence or absence of overhangs. A "25/27" is an asymmetric duplex having a 25 base sense strand and a 27 base antisense strand with a 2-base 3'-overhang. A "27/25" is an asymmetric duplex having a 27 base sense strand and a 25 base antisense strand.

Cell Culture and RNA Transfection

HeLa cells were obtained and maintained in DMEM (HyClone) supplemented with 10% fetal bovine serum (HyClone) at 37° C. under 5% $CO_2$. For RNA transfections, cells were transfected with DsiRNAs at a final concentration of 1 nM, 0.1 nM or 0.03 nM using Lipofectamine™ RNAiMAX (Invitrogen) and following manufacturer's instructions. Briefly, for 0.1 nM transfections, e.g., of Example 3 below, an aliquot of stock solution of each DsiRNA was mixed with Opti-MEM I (Invitrogen) and Lipofectamine™ RNAiMAX to reach a volume of 150 µL (with 0.3 nM DsiRNA). The resulting 150 µL mix was incubated for 20 min at RT to allow DsiRNA:Lipofectamine™ RNAiMAX complexes to form. Meanwhile, target cells were trypsinized and resuspended in medium. At the end of the 20 min of complexation, 50 µL of the DsiRNA:RNAiMAX mixture was added per well into triplicate wells of 96 well plates. Finally, 100 µL of the cell suspension was added to each well (final volume 150 µL) and plates were placed into the incubator for 24 hours.

Assessment of LDHA Inhibition

Lactate Dehydrogenase target gene knockdown was determined by qRT-PCR, with values normalized to HPRT and SFRS9 housekeeping genes, and to transfections with control DsiRNAs and/or mock transfection controls.

RNA Isolation and Analysis

Media was aspirated, and total RNA was extracted using the SV96 kit (Promega). Total RNA was reverse-transcribed using SuperscriptII, Oligo dT, and random hexamers following manufacturer's instructions. Typically, the resulting cDNA was analyzed by qPCR using primers and probes specific for both the lactate dehydrogenase gene and for the human genes HPRT-1 and SFRS9. An ABI 7700 was used for the amplification reactions. Each sample was tested in triplicate. Relative LDHA RNA levels were normalized to HPRT1 and SFRS9 RNA levels and compared with RNA levels obtained in transfection control samples.

Example 2: DsiRNA Inhibition of LDHA

DsiRNA molecules targeting LDHA were designed and synthesized as described above and tested in human HeLa cells (alternatively, HepG2 or other human cells could have been used) and/or mouse B16-F10 cells for inhibitory efficacy. For transfection, annealed DsiRNAs were mixed with the transfection reagent (Lipofectamine™ RNAiMAX, Invitrogen) and incubated for 20 minutes at room temperature. The HeLa (human) or B16-F10 (mouse) cells (alternatively, mouse Hepa 1-6 or other mouse cells could have been used) were trypsinized, resuspended in media, and added to wells (100 uL per well) to give a final DsiRNA concentration of 1 nM in a volume of 150 µl. Each DsiRNA transfection mixture was added to 3 wells for triplicate DsiRNA treatments. Cells were incubated at 37° C. for 24 hours in the continued presence of the DsiRNA transfection mixture. At 24 hours, RNA was prepared from each well of treated cells. The supernatants with the transfection mixtures were first removed and discarded, then the cells were lysed and RNA was prepared from each well. Target LDHA RNA levels following treatment were evaluated by qRT-PCR for the LDHA target gene, with values normalized to those obtained for controls. Triplicate data was averaged and the % error was determined for each treatment. Normalized data were both tabulated and graphed, and the reduction of target mRNA by active DsiRNAs in comparison to controls was determined (see Table 13 below and FIGS. 3A to 3J).

TABLE 13

LDHA Inhibitory Efficacy of DsiRNAs Assayed at 1 nM in Human HeLa and Mouse B16-F10 Cells

| | | | Human - HeLa Normalized HPRT/SFRS9; vs NC1, NC5, NC7 | | Mouse - B16-F10 Normalized HPRT/Rpl23; vs NC1, NC5, NC7 | |
|---|---|---|---|---|---|---|
| Duplex Name | Mm Location | Rhesus Location | Hs 262-396 (FAM) Assay % Remaining | Hs 1304-1419 (HEX) Assay % Remaining | Mm 384-510 (FAM) Assay % Remaining | Mm 1402-1504 (HEX) Assay % Remaining |
| LDHA-355 | | 440 | 2.7 ± 17.5 | 2.8 ± 14.8 | | |
| LDHA-356 | | 441 | 2.6 ± 8.5 | 2.6 ± 9.6 | | |
| LDHA-397 | | 482 | 8.5 ± 12.5 | 8.8 ± 11.1 | | |
| LDHA-398 | | 483 | 2.8 ± 11.5 | 3.1 ± 12.4 | | |
| LDHA-739 | | 824 | 8.7 ± 19.5 | 9.0 ± 17.6 | | |
| LDHA-740 | | 825 | 3.9 ± 11.6 | 3.7 ± 13.2 | | |
| LDHA-891 | | 976 | 3.9 ± 7.0 | 3.8 ± 7.5 | | |
| LDHA-892 | | 977 | 2.5 ± 5.3 | 2.4 ± 3.8 | | |
| LDHA-907 | | 992 | 4.4 ± 8.1 | 4.1 ± 8.5 | | |
| LDHA-952 | | 1037 | 2.9 ± 3.4 | 2.8 ± 6.0 | | |
| LDHA-1286 | | 1371 | 3.7 ± 11.1 | 3.6 ± 2.7 | | |
| LDHA-1287 | | 1372 | 2.0 ± 2.2 | 1.9 ± 4.1 | | |
| LDHA-1292 | | 1377 | 4.3 ± 2.0 | 4.3 ± 5.9 | | |
| LDHA-1293 | | 1378 | 2.2 ± 5.6 | 1.7 ± 1.6 | | |
| LDHA-1294 | | 1379 | 5.2 ± 4.3 | 5.2 ± 3.1 | | |
| LDHA-1359 | | 1444 | 4.5 ± 2.4 | 3.5 ± 3.2 | | |
| LDHA-1360 | | 1445 | 3.8 ± 9.4 | 3.2 ± 10.4 | | |
| LDHA-1361 | | 1446 | 3.0 ± 8.1 | 2.4 ± 8.7 | | |
| LDHA-1362 | | 1447 | 6.1 ± 5.0 | 5.1 ± 5.0 | | |
| LDHA-1363 | | 1448 | 2.5 ± 2.5 | 2.0 ± 4.4 | | |
| LDHA-1365 | | 1450 | 3.3 ± 1.2 | 2.7 ± 1.8 | | |
| LDHA-1366 | | 1451 | 3.4 ± 3.5 | 2.8 ± 2.6 | | |
| LDHA-1367 | | 1452 | 5.8 ± 1.5 | 5.3 ± 1.7 | | |
| LDHA-1368 | | 1453 | 4.5 ± 6.8 | 3.5 ± 8.7 | | |
| LDHA-1370 | | 1455 | 7.3 ± 7.0 | 6.3 ± 8.7 | | |
| LDHA-1371 | | 1456 | 2.5 ± 4.2 | 1.7 ± 7.4 | | |
| LDHA-1372 | | 1457 | 2.6 ± 6.6 | 1.9 ± 9.1 | | |
| LDHA-1393 | | 1478 | 9.1 ± 2.5 | 2.0 ± 5.9 | | |
| LDHA-1427 | | 1512 | 8.7 ± 3.1 | 3.6 ± 7.7 | | |
| LDHA-1428 | | 1513 | 8.5 ± 3.2 | 4.0 ± 12.3 | | |
| LDHA-1512 | | 1597 | 7.8 ± 2.0 | 4.4 ± 3.6 | | |
| LDHA-1513 | | 1598 | 9.4 ± 4.4 | 5.7 ± 4.1 | | |
| LDHA-1514 | | 1599 | 7.0 ± 1.7 | 3.7 ± 1.7 | | |
| LDHA-1516 | | 1601 | 6.7 ± 4.3 | 3.7 ± 5.3 | | |
| LDHA-1684 | | 1760 | 3.9 ± 10.4 | 1.7 ± 14.2 | | |
| LDHA-1688 | | 1764 | 4.7 ± 1.9 | 2.6 ± 3.6 | | |
| LDHA-1736 | | 1814 | 11.4 ± 0.6 | 8.3 ± 1.2 | | |
| LDHA-1750 | | 1832 | 3.9 ± 2.5 | 2.1 ± 3.6 | | |
| LDHA-1753 | | 1835 | 6.5 ± 1.4 | 3.2 ± 3.9 | | |
| LDHA-1754 | | 1836 | 8.0 ± 3.9 | 4.3 ± 4.8 | | |
| LDHA-1805 | | 1887 | 6.3 ± 6.9 | 3.3 ± 4.2 | | |
| LDHA-1806 | | 1888 | 6.4 ± 4.2 | 3.6 ± 4.9 | | |
| LDHA-1807 | | 1889 | 9.5 ± 2.4 | 7.6 ± 2.3 | | |
| LDHA-1808 | | 1890 | 5.7 ± 2.9 | 3.0 ± 3.4 | | |
| LDHA-1811 | | 1893 | 6.4 ± 2.8 | 2.9 ± 3.8 | | |
| LDHA-1812 | | 1894 | 5.9 ± 1.9 | 3.1 ± 1.9 | | |
| LDHA-1815 | | 1897 | 7.3 ± 3.4 | 4.0 ± 4.2 | | |
| LDHA-1816 | | 1898 | 12.2 ± 5.4 | 8.5 ± 6.7 | | |
| LDHA-360 | 419 | 445 | 7.2 ± 4.2 | 7.4 ± 3.3 | 11.2 ± 4.3 | 8.8 ± 8.0 |
| LDHA-361 | 420 | 446 | 3.5 ± 12.0 | 3.7 ± 14.2 | 6.3 ± 9.0 | 4.5 ± 10.9 |
| LDHA-362 | 421 | 447 | 8.4 ± 9.8 | 10.0 ± 9.2 | 11.6 ± 16.0 | 8.5 ± 14.0 |
| LDHA-363 | 422 | 448 | 20.5 ± 11.3 | 23.3 ± 10.4 | 26.0 ± 7.4 | 19.4 ± 11.5 |
| LDHA-364 | 423 | 449 | 7.6 ± 17.3 | 7.7 ± 15.5 | 14.1 ± 25.3 | 9.9 ± 19.4 |
| LDHA-365 | 424 | 450 | 10.4 ± 13.0 | 11.0 ± 10.5 | 13.1 ± 18.0 | 8.5 ± 14.3 |
| LDHA-366 | 425 | 451 | 15.0 ± 2.2 | 22.1 ± 2.5 | 12.6 ± 6.8 | 11.8 ± 2.9 |
| LDHA-367 | 426 | 452 | 7.8 ± 7.6 | 9.1 ± 8.6 | 9.7 ± 5.5 | 9.4 ± 4.6 |
| LDHA-369 | 428 | 454 | 23.7 ± 4.3 | 24.5 ± 3.0 | 12.7 ± 6.1 | 11.3 ± 5.1 |
| LDHA-370 | 429 | 455 | 5.9 ± 2.5 | 5.8 ± 2.2 | 6.1 ± 5.1 | 5.0 ± 9.5 |
| LDHA-399 | 458 | 484 | 3.0 ± 4.9 | 3.3 ± 11.1 | 7.3 ± 7.8 | 7.4 ± 28.4 |

TABLE 13-continued

LDHA Inhibitory Efficacy of DsiRNAs Assayed at 1 nM in Human HeLa and Mouse B16-F10 Cells

| Duplex Name | Mm Location | Rhesus Location | Human - HeLa Normalized HPRT/SFRS9; vs NC1, NC5, NC7 | | Mouse - B16-F10 Normalized HPRT/Rpl23; vs NC1, NC5, NC7 | |
|---|---|---|---|---|---|---|
| | | | Hs 262-396 (FAM) Assay % Remaining | Hs 1304-1419 (HEX) Assay % Remaining | Mm 384-510 (FAM) Assay % Remaining | Mm 1402-1504 (HEX) Assay % Remaining |
| LDHA-400 | 459 | 485 | 7.7 ± 6.2 | 8.4 ± 6.2 | 13.9 ± 1.2 | 10.2 ± 4.6 |
| LDHA-401 | 460 | 486 | 4.1 ± 6.1 | 4.1 ± 5.2 | 8.5 ± 1.8 | 5.5 ± 1.9 |
| LDHA-402 | 461 | 487 | 2.6 ± 5.7 | 3.0 ± 4.1 | 4.3 ± 5.8 | 3.0 ± 7.0 |
| LDHA-403 | 462 | 488 | 7.2 ± 3.4 | 7.2 ± 2.0 | 8.7 ± 4.4 | 7.3 ± 4.0 |
| LDHA-404 | 463 | 489 | 15.7 ± 4.1 | 14.7 ± 5.9 | 14.0 ± 7.7 | 10.8 ± 5.7 |
| LDHA-714 | 773 | 799 | 7.9 ± 11.0 | 8.4 ± 11.3 | 10.8 ± 3.0 | 9.2 ± 8.8 |
| LDHA-717 | 776 | 802 | 6.2 ± 1.4 | 7.4 ± 1.0 | 9.8 ± 7.7 | 8.7 ± 1.1 |
| LDHA-718 | 777 | 803 | 1.8 ± 7.8 | 2.0 ± 5.1 | 2.6 ± 6.8 | 3.7 ± 6.0 |
| LDHA-719 | 778 | 804 | 2.4 ± 1.9 | 2.7 ± 3.6 | 3.4 ± 3.0 | 3.3 ± 3.2 |
| LDHA-720 | 779 | 805 | 3.6 ± 5.5 | 3.6 ± 3.0 | 6.0 ± 3.2 | 5.1 ± 4.6 |
| LDHA-722 | 781 | 807 | 9.6 ± 2.2 | 10.7 ± 1.5 | 29.3 ± 36.2 | 13.8 ± 10.4 |
| LDHA-723 | 782 | 808 | 3.1 ± 5.7 | 3.1 ± 4.5 | 2.1 ± 7.8 | 2.6 ± 6.9 |
| LDHA-724 | 783 | 809 | 7.1 ± 6.4 | 7.4 ± 10.1 | 8.1 ± 7.9 | 7.1 ± 9.6 |
| LDHA-m367 | | | | | 6.7 ± 9.9 | 6.4 ± 11.1 |
| LDHA-m368 | | | | | 3.7 ± 15.8 | 3.4 ± 11.2 |
| LDHA-m372 | | | | | 6.0 ± 23.0 | 5.3 ± 14.6 |
| LDHA-m376 | | | | | 4.8 ± 1.9 | 4.5 ± 0.1 |
| LDHA-m456 | | | | | 38.3 ± 10.4 | 29.6 ± 10.4 |
| LDHA-m501 | | | | | 3.3 ± 5.3 | 3.9 ± 12.5 |
| LDHA-m506 | | | | | 17.3 ± 10.4 | 15.1 ± 11.5 |
| LDHA-m507 | | | | | 17.4 ± 5.1 | 14.4 ± 5.5 |
| LDHA-m584 | | | | | 5.9 ± 11.4 | 6.2 ± 6.0 |
| LDHA-m689 | | | | | 2.3 ± 5.0 | 3.0 ± 4.1 |
| LDHA-m694 | | | | | 2.1 ± 2.0 | 2.7 ± 3.0 |
| LDHA-m695 | | | | | 6.9 ± 1.6 | 6.0 ± 2.5 |
| LDHA-m823 | | | | | 3.6 ± 4.4 | 4.5 ± 3.1 |
| LDHA-m1071 | | | | | 4.5 ± 4.6 | 3.6 ± 4.0 |
| LDHA-m1133 | | | | | 2.8 ± 6.3 | 3.0 ± 5.5 |
| LDHA-m1183 | | | | | 6.5 ± 8.0 | 5.8 ± 7.6 |
| LDHA-m1245 | | | | | 4.9 ± 8.0 | 4.7 ± 3.0 |
| LDHA-m1250 | | | | | 5.8 ± 4.2 | 5.5 ± 4.6 |
| LDHA-m1257 | | | | | 1.7 ± 7.1 | 6.6 ± 4.0 |
| LDHA-m1687 | | | | | 29.7 ± 9.2 | 24.6 ± 10.5 |
| LDHA-m1688 | | | | | 5.6 ± 4.0 | 4.7 ± 5.2 |
| LDHA-m1690 | | | | | 12.9 ± 1.4 | 8.7 ± 1.7 |
| LDHA-m1691 | | | | | 4.2 ± 6.7 | 3.6 ± 4.0 |
| LDHA-m1692 | | | | | 10.8 ± 4.8 | 9.7 ± 6.4 |
| LDHA-m1694 | | | | | 37.2 ± 3.3 | 33.4 ± 2.5 |
| LDHA-m1695 | | | | | 9.8 ± 16.0 | 7.3 ± 16.4 |
| LDHA-m1697 | | | | | 3.6 ± 11.1 | 3.3 ± 12.3 |
| LDHA-m1698 | | | | | 6.6 ± 16.9 | 5.4 ± 18.8 |
| LDHA-m1699 | | | | | 12.3 ± 5.9 | 8.5 ± 4.8 |
| LDHA-m1700 | | | | | 3.1 ± 17.6 | 2.4 ± 14.4 |
| LDHA-m1701 | | | | | 2.1 ± 6.8 | 1.9 ± 5.6 |
| LDHA-m1702 | | | | | 4.2 ± 6.2 | 3.3 ± 3.4 |
| LDHA-m1703 | | | | | 5.2 ± 4.4 | 4.5 ± 3.3 |
| LDHA-m1704 | | | | | 6.7 ± 6.2 | 5.4 ± 5.3 |
| LDHA-m1705 | | | | | 11.5 ± 12.8 | 9.3 ± 14.7 |
| LDHA-m1706 | | | | | 13.6 ± 3.5 | 10.7 ± 2.9 |
| LDHA-m1707 | | | | | 2.8 ± 6.9 | 2.3 ± 4.8 |
| LDHA-m1708 | | | | | 3.1 ± 5.0 | 2.5 ± 3.2 |
| LDHA-m1709 | | | | | 2.2 ± 2.1 | 1.8 ± 3.2 |
| LDHA-m1710 | | | | | 4.1 ± 10.0 | 3.3 ± 9.9 |
| LDHA-m1739 | | | | | 2.9 ± 11.2 | 2.5 ± 6.3 |
| LDHA-m1743 | | | | | 3.8 ± 7.9 | 3.2 ± 7.6 |
| LDHA-m1744 | | | | | 2.2 ± 6.5 | 2.1 ± 4.0 |
| LDHA-m1746 | | | | | 2.5 ± 1.8 | 2.2 ± 3.1 |
| LDHA-m1751 | | | | | 2.5 ± 1.4 | 1.9 ± 3.0 |
| LDHA-m1752 | | | | | 4.3 ± 6.0 | 3.0 ± 4.9 |
| LDHA-m1755 | | | | | 2.9 ± 3.4 | 2.4 ± 3.4 |
| LDHA-m1756 | | | | | 3.0 ± 4.6 | 2.6 ± 7.0 |

Figure 4A:
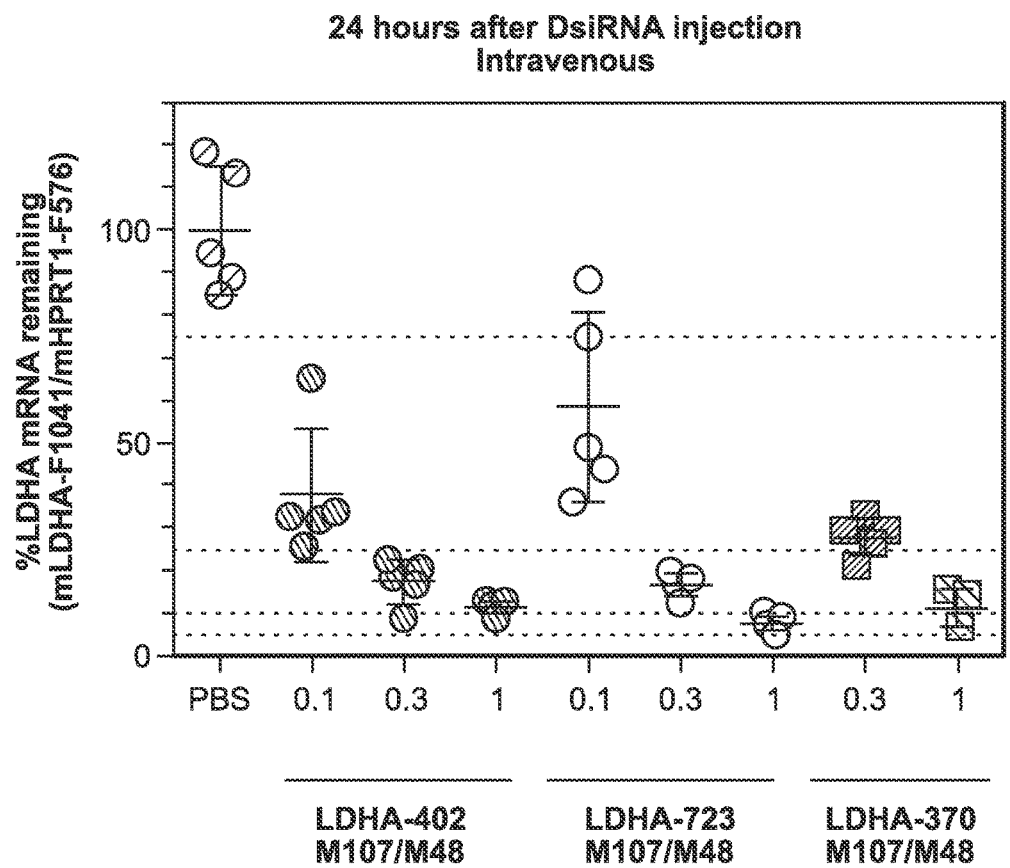
FIGS. 4A to 4C demonstrate that LDHA-targeting DsiRNAs, as well as PRODH2- and HAO1-targeting DsiRNAs potently inhibited mRNA and protein expression in mouse liver, in target-specific fashion. The histogram at the left of FIG. 4A shows that DsiRNAs LDHA-402, LDHA-723 and LDHA-370 (each of which is human-mouse cross-reactive) robustly knocked down LDHA mRNA levels at 24 hours post-DsiRNA injection. The right-hand panels of FIG. 4A show dramatically reduced levels of LDHA protein in mice administered LDHA-402 DsiRNA, even at 14 days post-i.v. injection at 1 mg/kg.
Figure 4A:
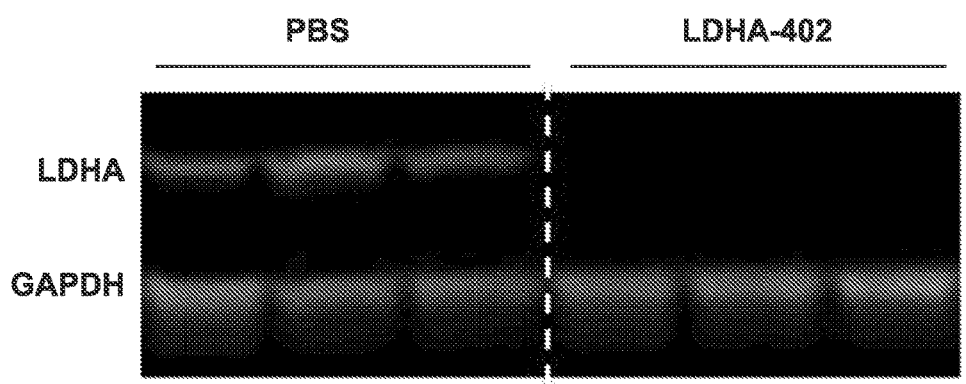
Figure 4B:
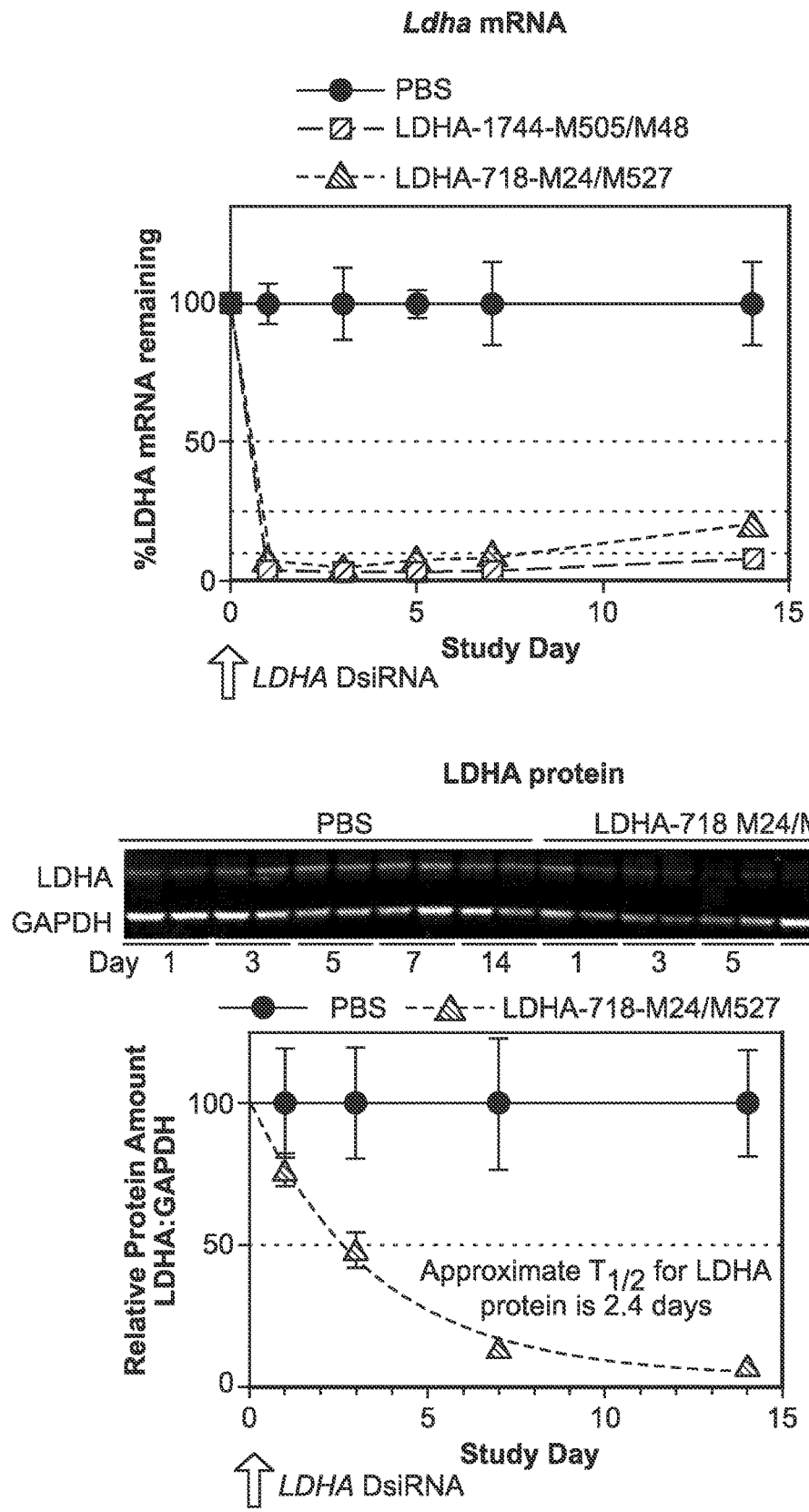
Figure 4C:
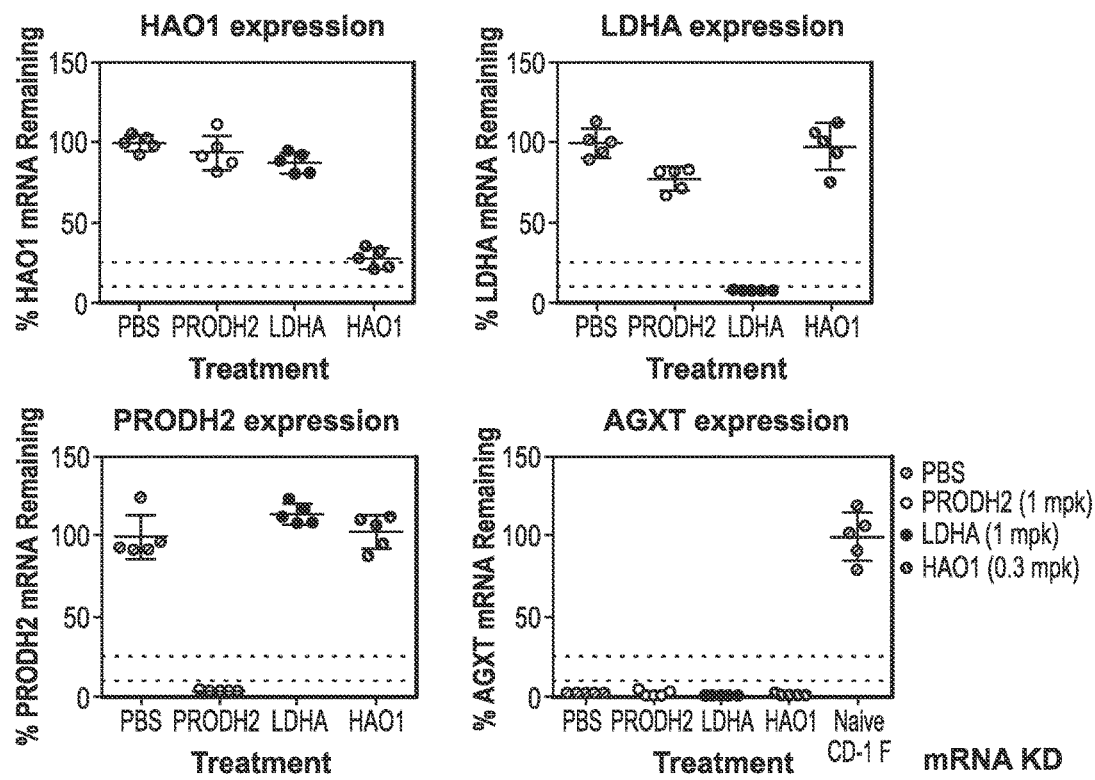
Figure 4C:
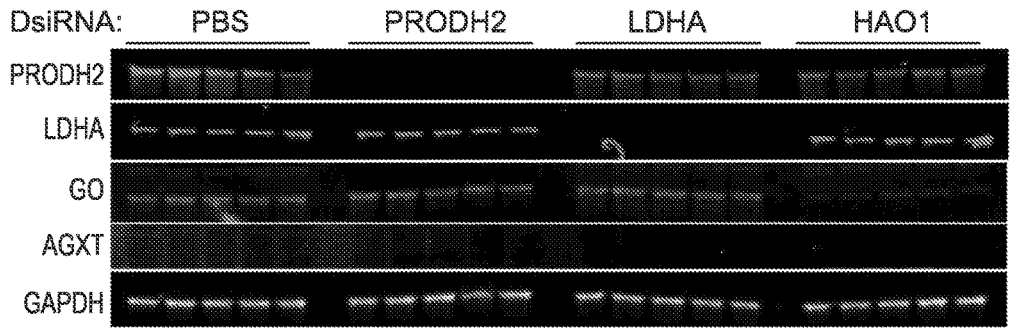
Figure 4C:
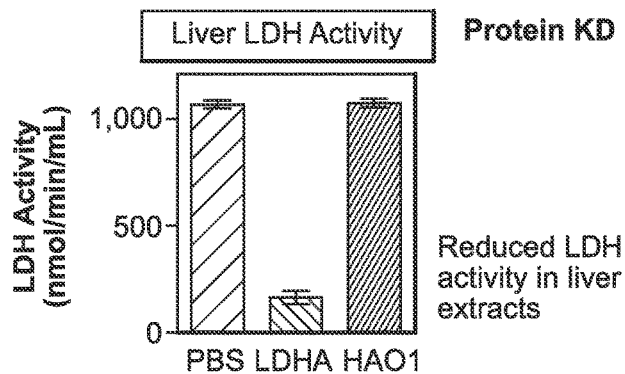

Example 3: Lactate Dehydrogenase-Targeting DsiRNAs were Effective Inhibitors of Both LDHA mRNA and Protein In Vivo The efficacy of LDHA-targeting DsiRNAs to inhibit both LDHA mRNA and protein levels was examined in mice. As shown in FIGS. 4A to 4C, LDHA-targeting DsiRNAs potently inhibited mRNA and protein expression in mouse liver (human-mouse cross-reactive DsiRNAs LDHA-402, LDHA-723 and LDHA-370 possessing M107/M48 modifications were tested for mRNA knockdown, while LDHA-402 protein levels are shown in the right panel of FIG. 4A, relative to a GAPDH control). Specifically, robust knockdown of LDHA mRNA levels was observed at 24 hours post-DsiRNA injection. Meanwhile dramatically reduced levels of LDHA protein were observed in mice administered LDHA-402 DsiRNA, even at 14 days post-i.v. injection at 1 mg/kg.

Example 4: Lactate Dehydrogenase-Targeting DsiRNAs Demonstrated Phenotypic Efficacy in Reducing Oxalate Excretion and in Preventing Ethylene Glycol-Induced Kidney Damage and Calcium Oxalate Crystals in PH1 Model Mice The ability of active lactate dehydrogenase-targeting DsiRNAs to reduce lactate dehydrogenase levels within a mouse model of PH1 was examined, with the specific model employed relying upon pre-treatment of mice with AGXT-targeting DsiRNA (administered with timing of the upper arrows of FIGS. 5A through 5D; alternatively, an AGXT knockout mouse, as described in Hernandez-Fernaud and Salido (*FEBS Journal* 277: 4766-74) or other model of PH1 or other oxalate accumulation disease could have been used).

Figure 5B:
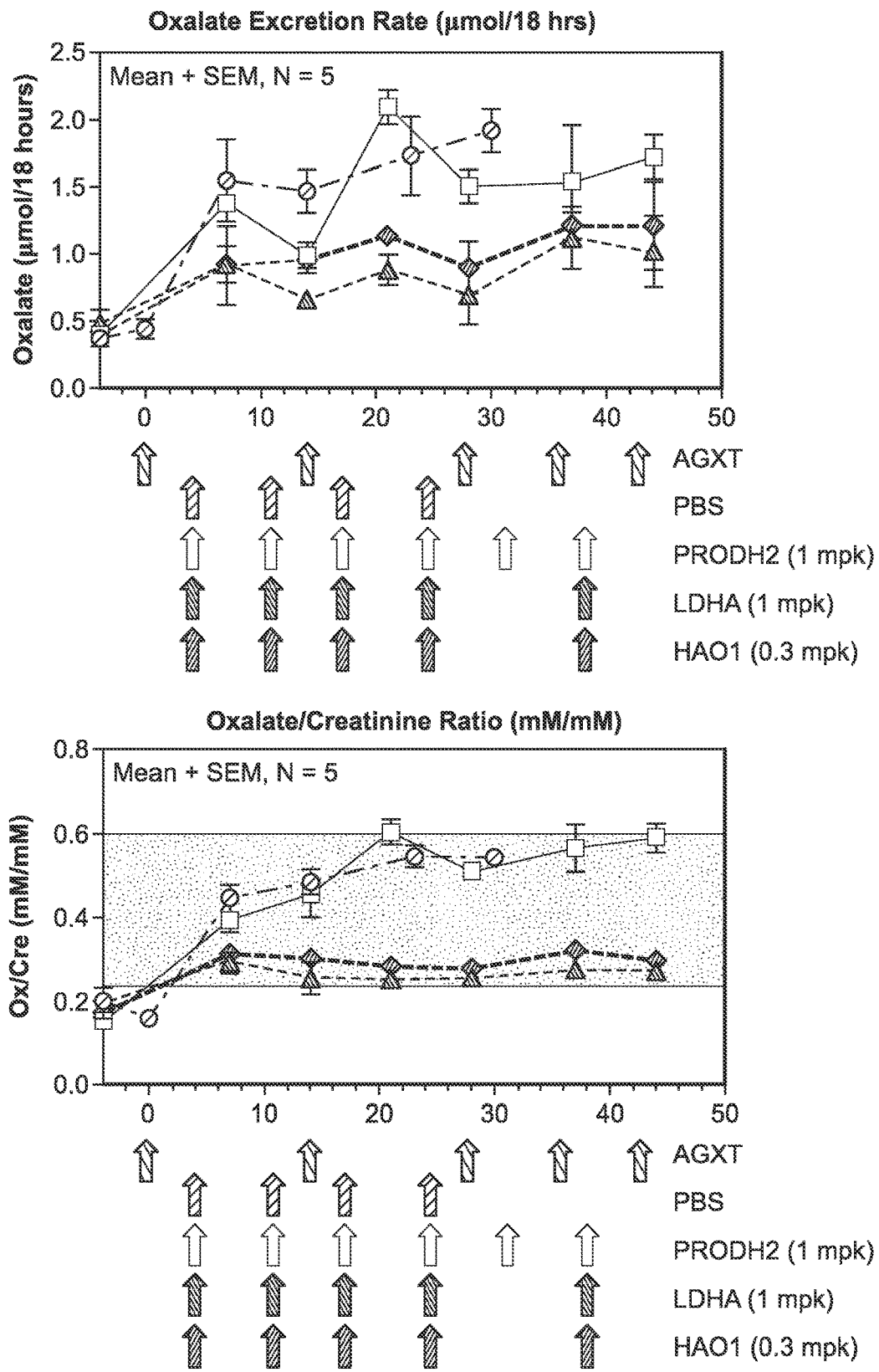
Figure 5C:
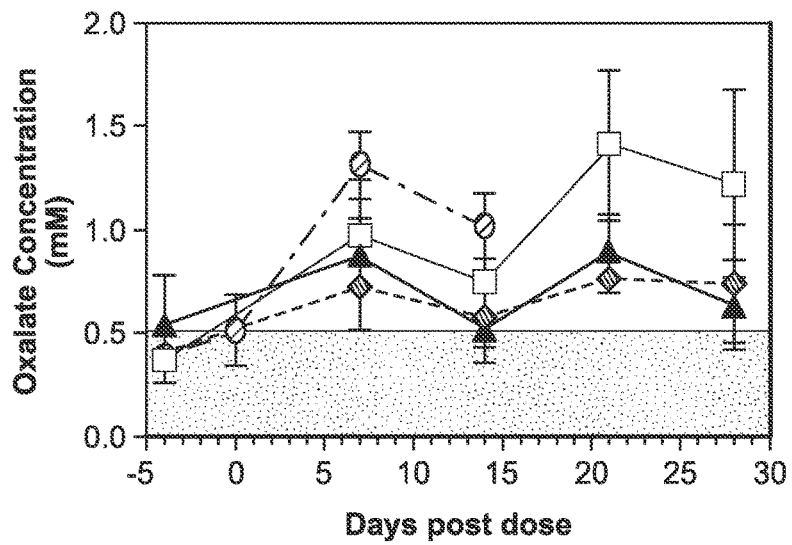
Figure 5C:
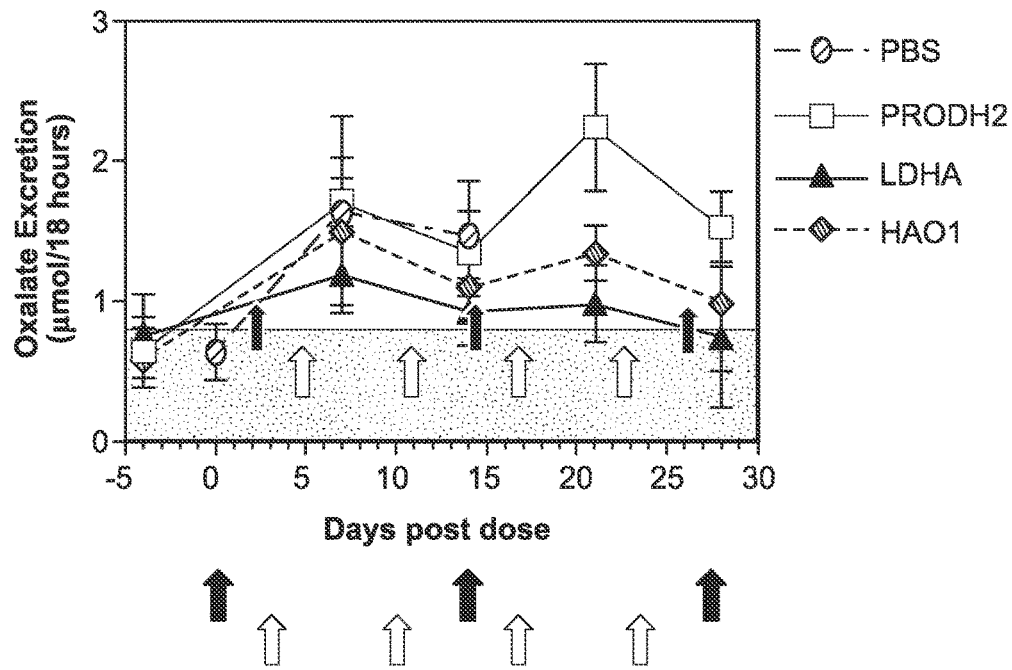
Figure 5D:
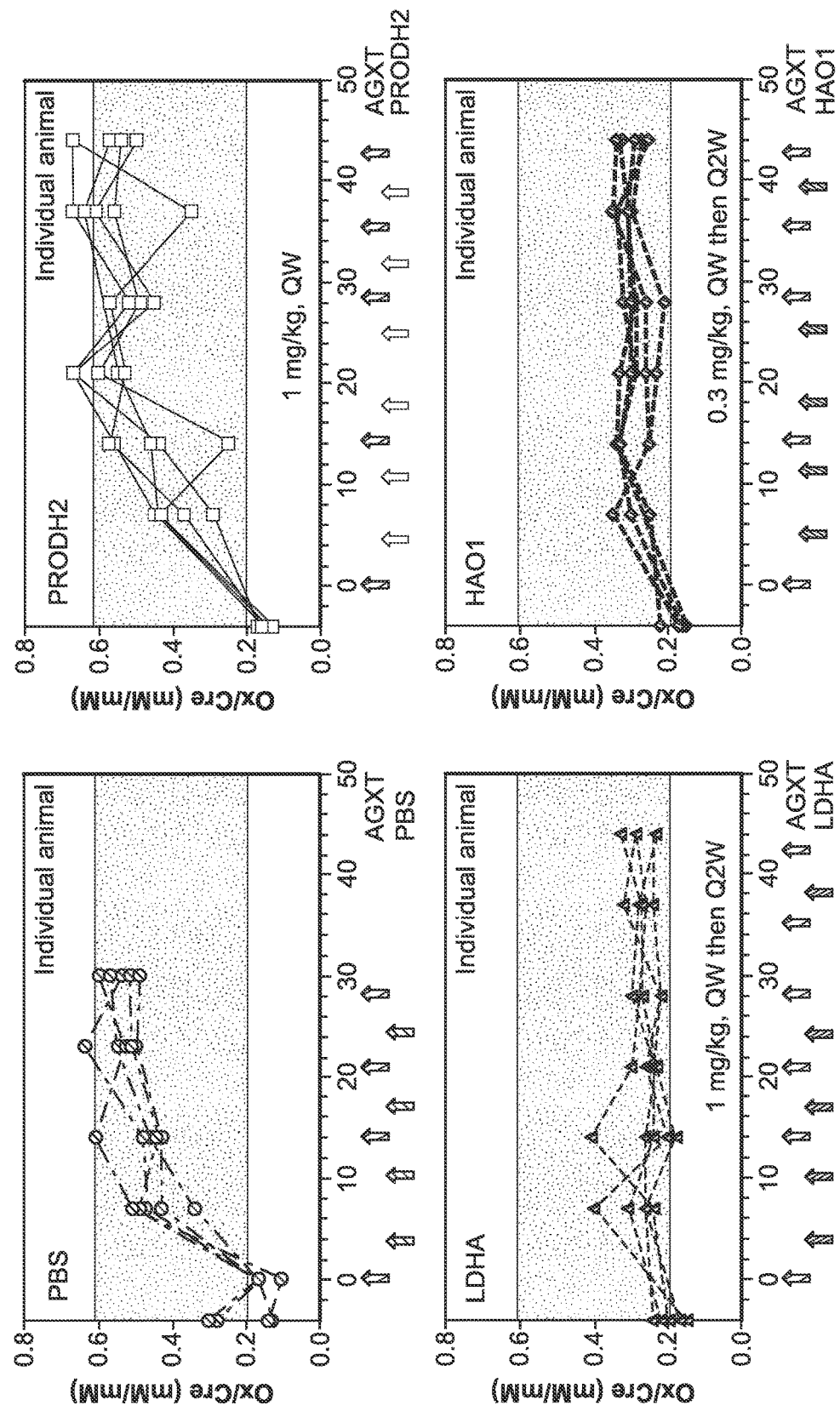
Figure 6:
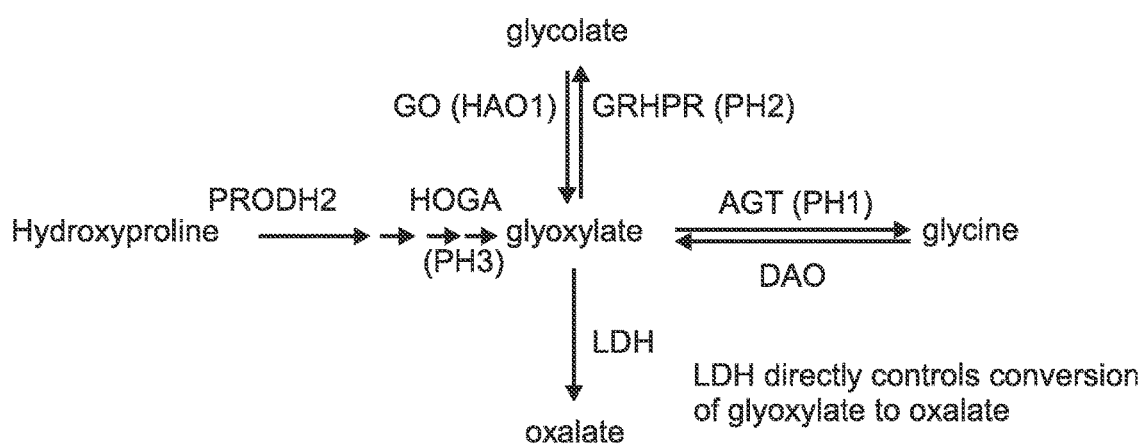
FIG. 6 depicts another schematic overview of the oxalate metabolism pathway. Primary hyperoxaluria (PH, including PH1) has been identified as an autosomal recessive disorder, and LDH (encoded by LDHA in the liver) is noted as controlling the final step of oxalate production. At least in view of its position within the oxalate metabolism pathway, LDHA is identified as a promising therapeutic target for all types of PH.

Animals were randomized and assigned to groups based on marker levels. Dosing of animals with lipid nanoparticles (LNPs) containing indicated DsiRNAs (an LNP formulation named EnCore-2072 was employed) was performed. Animals were dosed at 5 mg/kg iv, at indicated time points (upper arrows being AGXT DsiRNA injections or PBS, while lower arrows indicate LDHA DsiRNA injections, PBS injections, PRODH2 DsiRNA injections or HAO1 DsiRNA injections, as noted in each panel of FIG. 5A). Animals were assayed for oxalate excretion levels, where reduction of oxalate excretion was indicative of an amelioration/reduction of PH1 symptoms. As shown in FIGS. 5A through 5D, intravenous injection of LDHA-targeting DsiRNA reduced oxalate excretion in PH1 model mice (mice pre-treated with AGXT DsiRNA to simulate PH1), as compared to PBS-injected control PH1 model mice, and even as compared to PH1 model mice administered DsiRNAs targeting oxalate metabolism pathway components glycolate oxidase (HAO1) or PRODH2 (proline dehydrogenase (oxidase) 2; see FIG. 6). In each of FIGS. 5A through 5D, mice (n=5/group) were injected on day 0 and day 14 with AGXT-targeting DsiRNA (upper arrows of each series). For results presented in FIGS. 5B and 5D, administration of AGXT-targeting DsiRNA was additionally performed on days 28, 35 and 42. Mice treated with AGXT-targeting DsiRNA were then subjected to intravenous injection of PBS (filled circles of FIGS. 5A to 5D, upper left panels of FIGS. 5A and 5D), anti-PRODH2 DsiRNA (filled squares of FIGS. 5A to 5D, upper right panels of FIGS. 5A and 5D), anti-HAO1 DsiRNA (filled diamonds of FIGS. 5A to 5D, lower left panel of FIG. 5A; lower right panel of FIG. 5D) or anti-LDHA DsiRNA (filled triangles of FIGS. 5A to 5D, lower right panel of FIG. 5A; lower left panel of FIG. 5D), respectively, at days 3, 10, 17 and 24, with FIGS. 5B and 5D showing the impact of additional administrations of such DsiRNAs at days 31 and 38 (anti-PRODH2 DsiRNA) or at day 38 (anti-LDHA DsiRNA or anti-HAO1 DsiRNA). In FIGS. 5A and 5C, oxalate excretion was measured at days 0, 7 and 14 for PBS-treated PH1 model mice, while levels of oxalate excretion were assayed in DsiRNA-treated mice at days −4, 7, 14, 21 and 28. As shown in FIGS. 5B and 5D, extension of the studies respectively shown in FIGS. 5A and 5C was performed, with measurements of levels of oxalate excretion in DsiRNA-treated mice also performed at days 37 and 44. Both PBS- and PRODH2 DsiRNA-treated groups of mice were observed to exhibit dramatically elevated oxalate excretion levels when assayed at day 7 post-AGXT DsiRNA injection. PRODH2 DsiRNA-treated groups of mice were also observed to exhibit further elevated oxalate excretion levels when assayed at day 21 post-initial AGXT DsiRNA injection (while PBS-treated mice were only maintained until day 14; FIG. 5A). HAO1 DsiRNA-treated groups of mice were also observed to exhibit elevated oxalate excretion levels when assayed at day 7 or day 21 post-initial AGXT DsiRNA injection, though the levels of such elevations appeared to be reduced as compared to PBS-treated or PRODH2 DsiRNA-treated PH1 model mice (FIG. 5A). These results largely persisted through extended assessments; however, anti-HAO1 DsiRNA treatment more closely resembled anti-LDHA DsiRNA treatment at extended timepoints (FIG. 5B).

Remarkably, treatment of PH1 model mice with an LDHA-targeting DsiRNA under the same injection schedule described above (LDHA-402-M107/M48 DsiRNA in LNP 2185, administered by intravenous injection, where AGXT-m1533-M107/M48 in LNP 2185 was also administered by intravenous injection, at 1 mg/kg) revealed dramatic inhibitions of oxalate elevation at day 7, day 21 and later timepoints post-initial AGXT DsiRNA injection. Thus, reduced levels of LDHA mRNA and protein (as demonstrated in FIGS. 4A to 4C above) also translated into phenotypic effects in inhibiting elevation of oxalate excretion in PH1 model mice. FIGS. 5C and 5D show that all DsiRNAs tested in PH1 model mice (PRODH2-, HAO1- and LDHA-targeting DsiRNAs) showed at least some inhibitory impact upon oxalate concentration (e.g., left panel of FIG. 5C). However, LDHA-targeting DsiRNA demonstrated the greatest reduction of oxalate excretion, even as compared to HAO1-targeting DsiRNA. Such results indicated that reduction of oxalate concentration was necessary but not sufficient to observe downregulation of oxalate excretion.

Figure 5E:
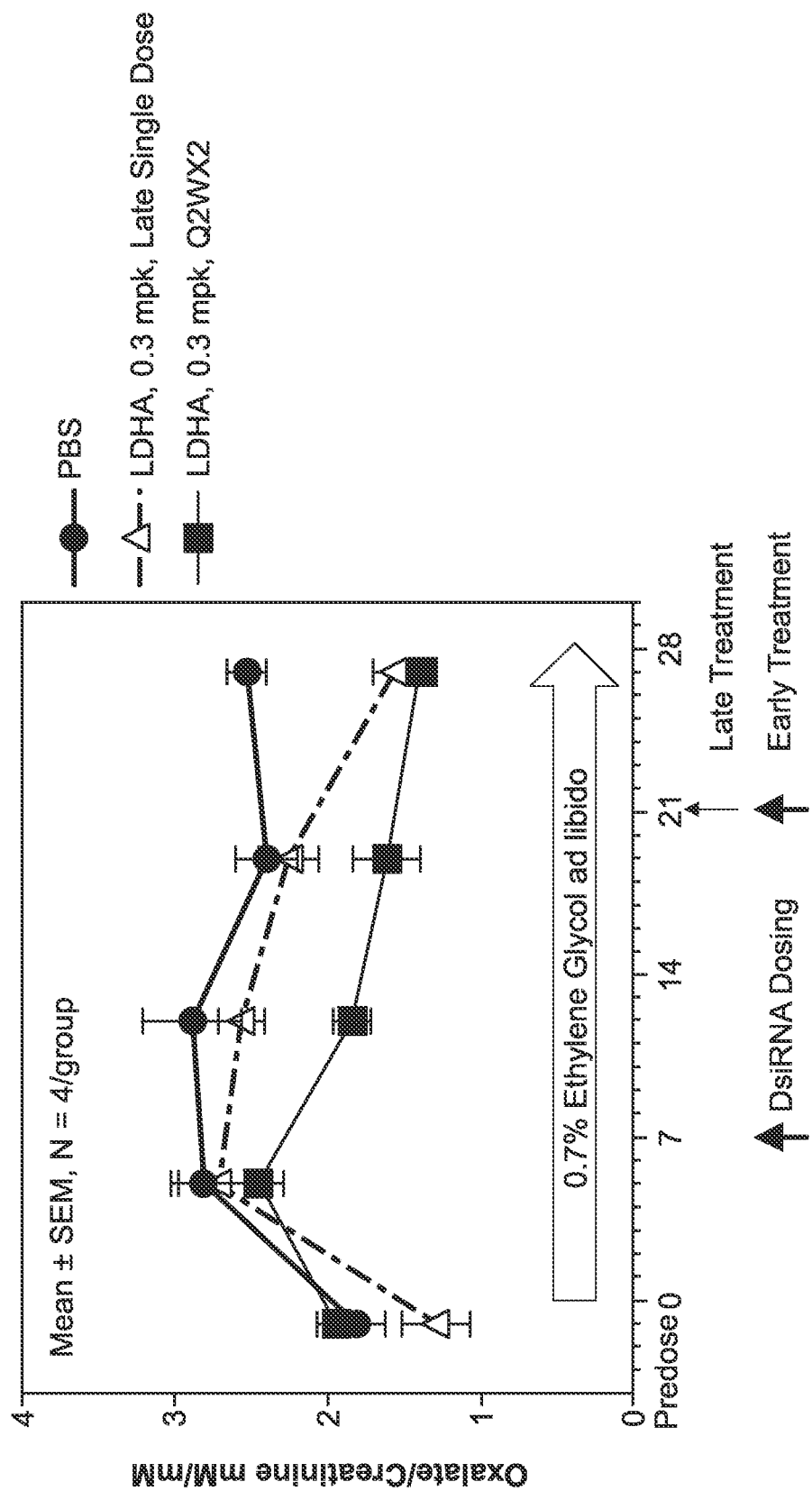
FIGS. 5E to 5G show that intravenous injection of LDHA-targeting DsiRNA also exerted a protective effect in Agxt$^{-/-}$ mice with respect to reducing urine oxalate levels, preventing ethylene glycol-induced kidney damage and preventing ethylene glycol-induced calcium oxalate crystals.
Figure 5F:
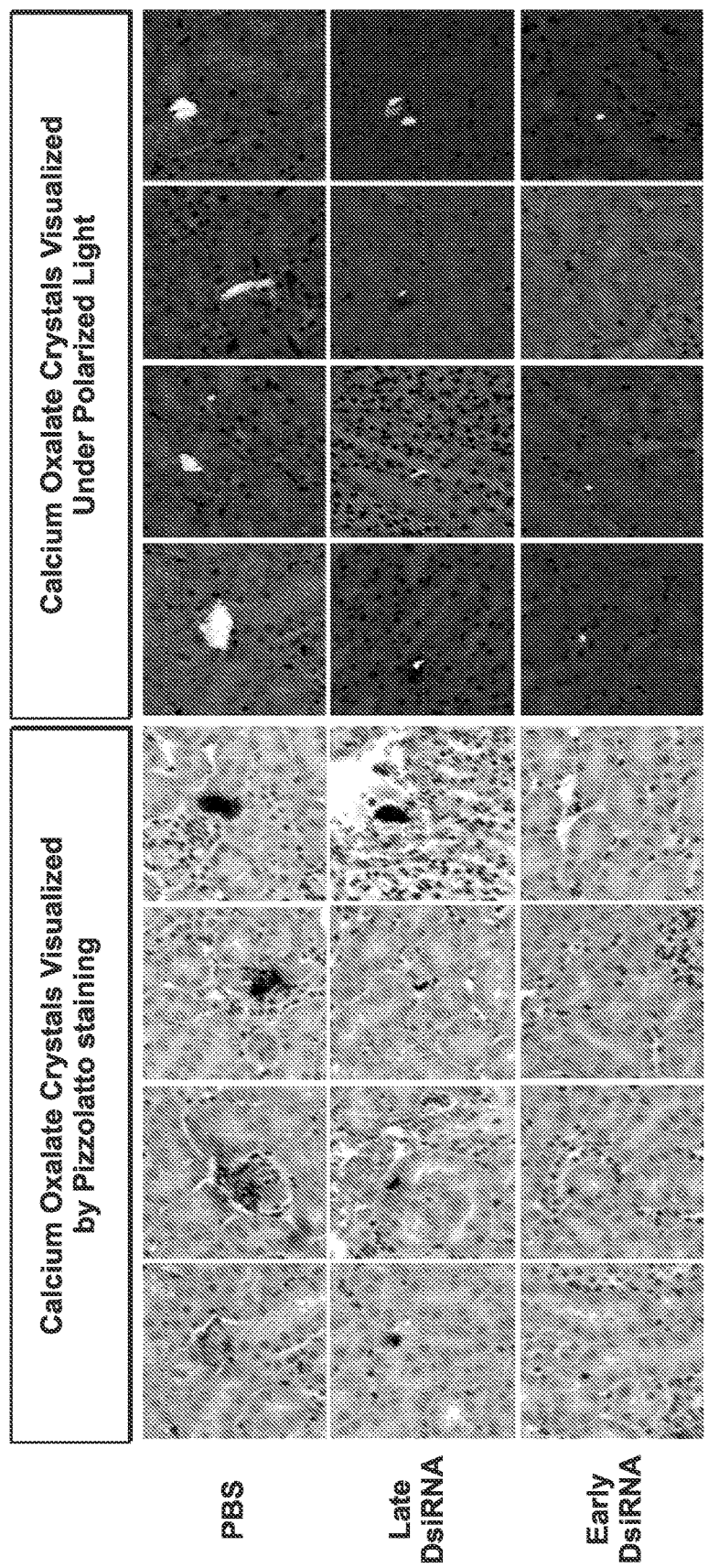
Figure 5G:
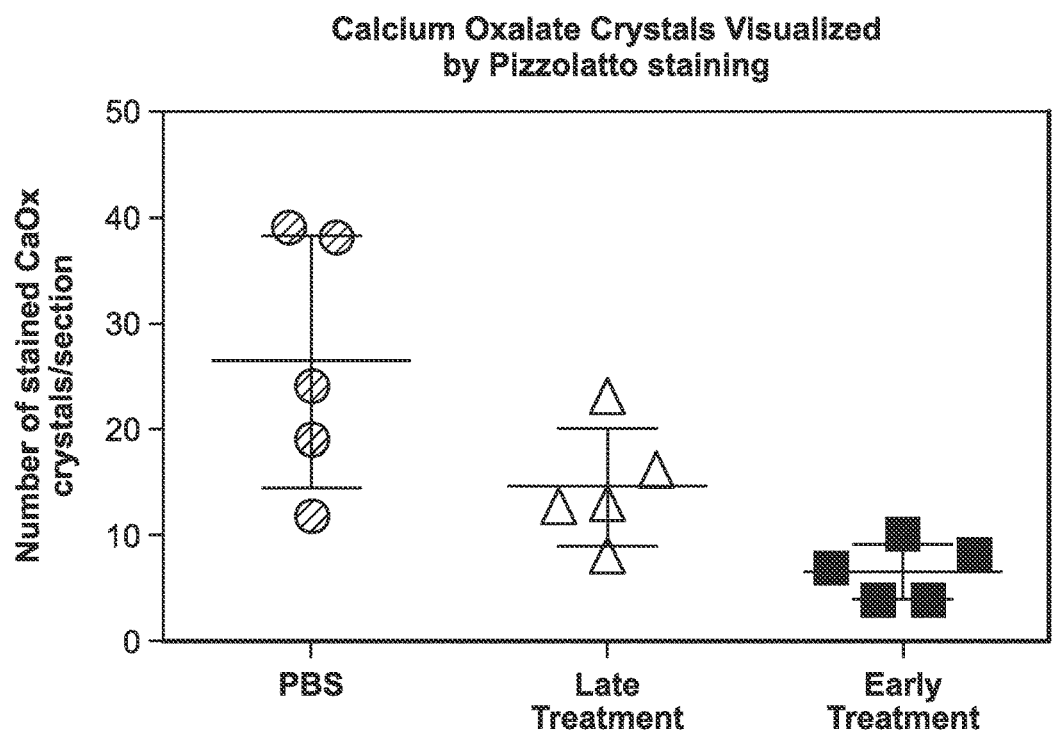
Figure 5G:
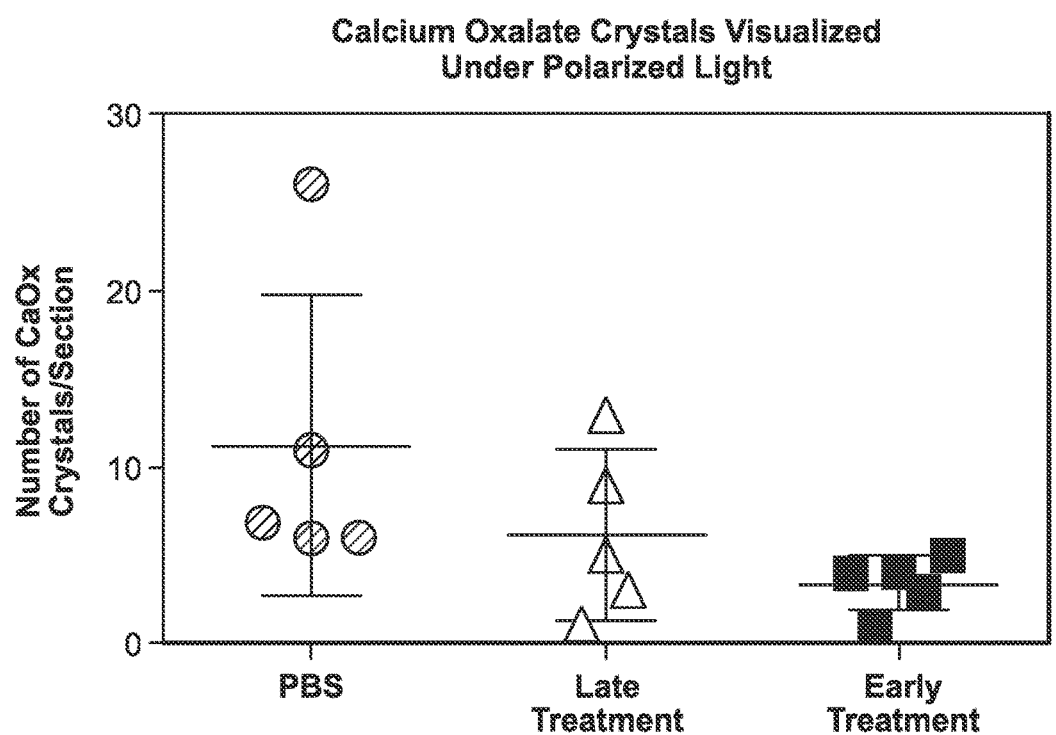

The impact of anti-LDHA DsiRNA treatment of $Agxt^{-/-}$ mice was assessed after challenge with ethylene glycol (a PH1 model). As shown in FIG. 5E, when $Agxt^{-/-}$ mice were challenged with ethylene glycol, LDHA DsiRNA administration (specifically, LDHA-718-M24/M527 (DP2685P: DP2692G) in 2185 LNP) was observed to reduce urine oxalate levels. As shown in FIGS. 5F and 5G, administration of LDHA DsiRNA (LDHA-718-M24/M527 (DP2685P: DP2692G) in 2185 LNP) was observed to prevent ethylene glycol-induced kidney damage and prevent ethylene glycol-induced calcium oxalate crystals in $Agxt^{-/-}$ mice.

Thus, in vivo results in PH1 model mice confirmed LDHA as a promising therapeutic target for gene silencing approaches (e.g., RNAi approaches), not only for PH1 but also for all types of PH.

Figure 5H:
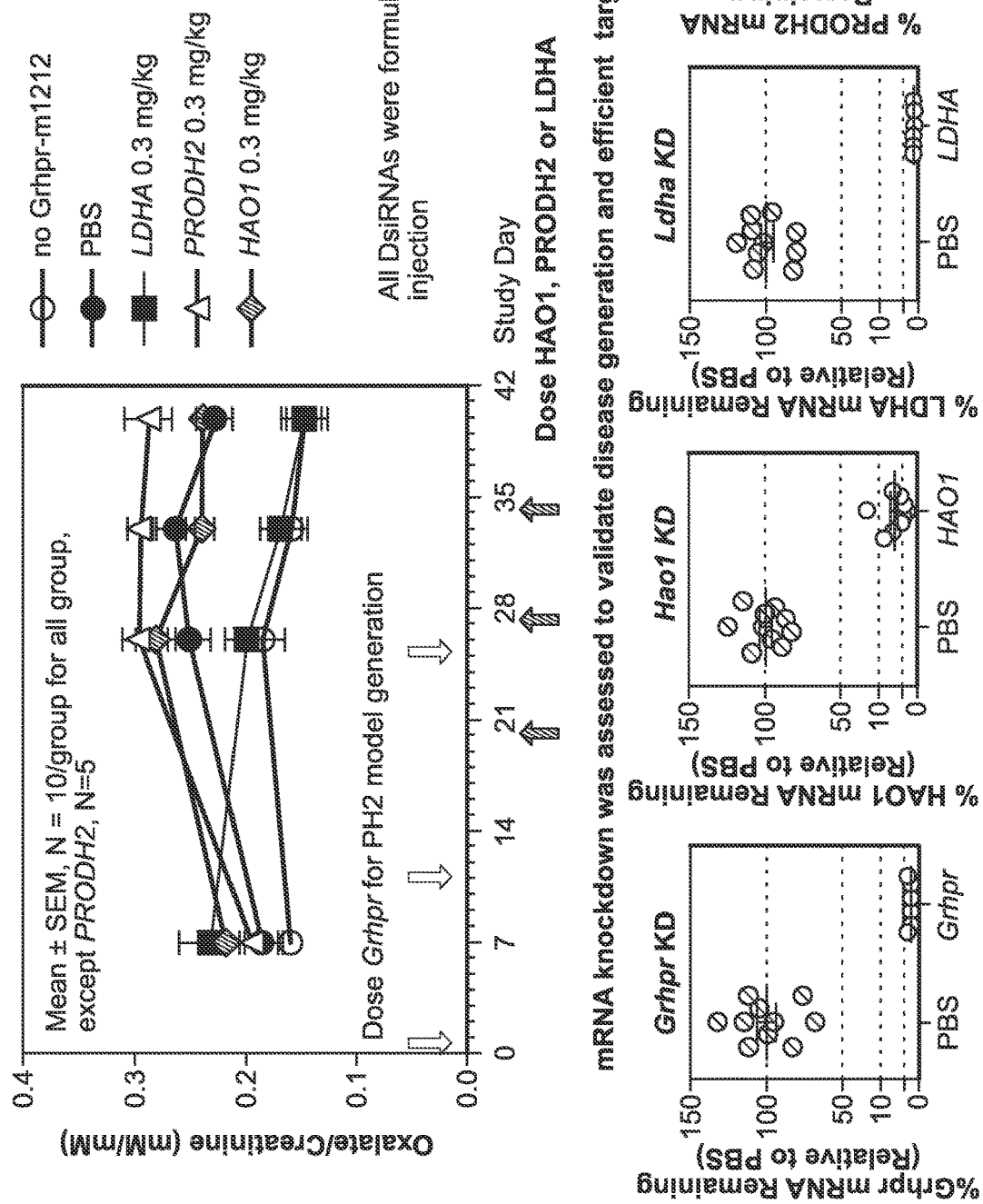
FIG. 5H shows that intravenous injection of LDHA-targeting DsiRNA reduced urine oxalate levels in PH2 model mice, in contrast to HAO1- and PRODH2-targeting DsiRNAs, which did not reduce urinary oxalate levels in the PH2 model mice.

Example 5: Lactate Dehydrogenase-Targeting DsiRNAs Also Effectively Reduced Urine Oxalate Levels in PH2 Model Mice A mouse model of PH2 was produced via DsiRNA-mediated knockdown of Grhpr (refer to FIG. 6 for role of Grhpr). To examine the efficacy of anti-LDHA DsiRNA treatment of PH2 in the PH2 model system, as well as to assess whether anti-LDHA DsiRNA treatment would exert a more pronounced impact upon PH2 than DsiRNAs targeting other components of the glyoxylate/oxalate pathway, anti-LDHA DsiRNA injection was compared with anti-PRODH2 DsiRNA injection and anti-HAO1 DsiRNA injection. As shown in FIG. 5H, intravenous injection of LDHA-targeting DsiRNA significantly reduced urine oxalate levels in PH2 model mice, in contrast to HAO1- and PRODH2-targeting DsiRNAs, which did not reduce urinary oxalate levels in the PH2 model mice. Thus, anti-LDHA DsiRNA treatment of PH2 was especially effective as compared to DsiRNAs targeting other components of the glyoxylate/oxalate pathway.

Figure 7A:
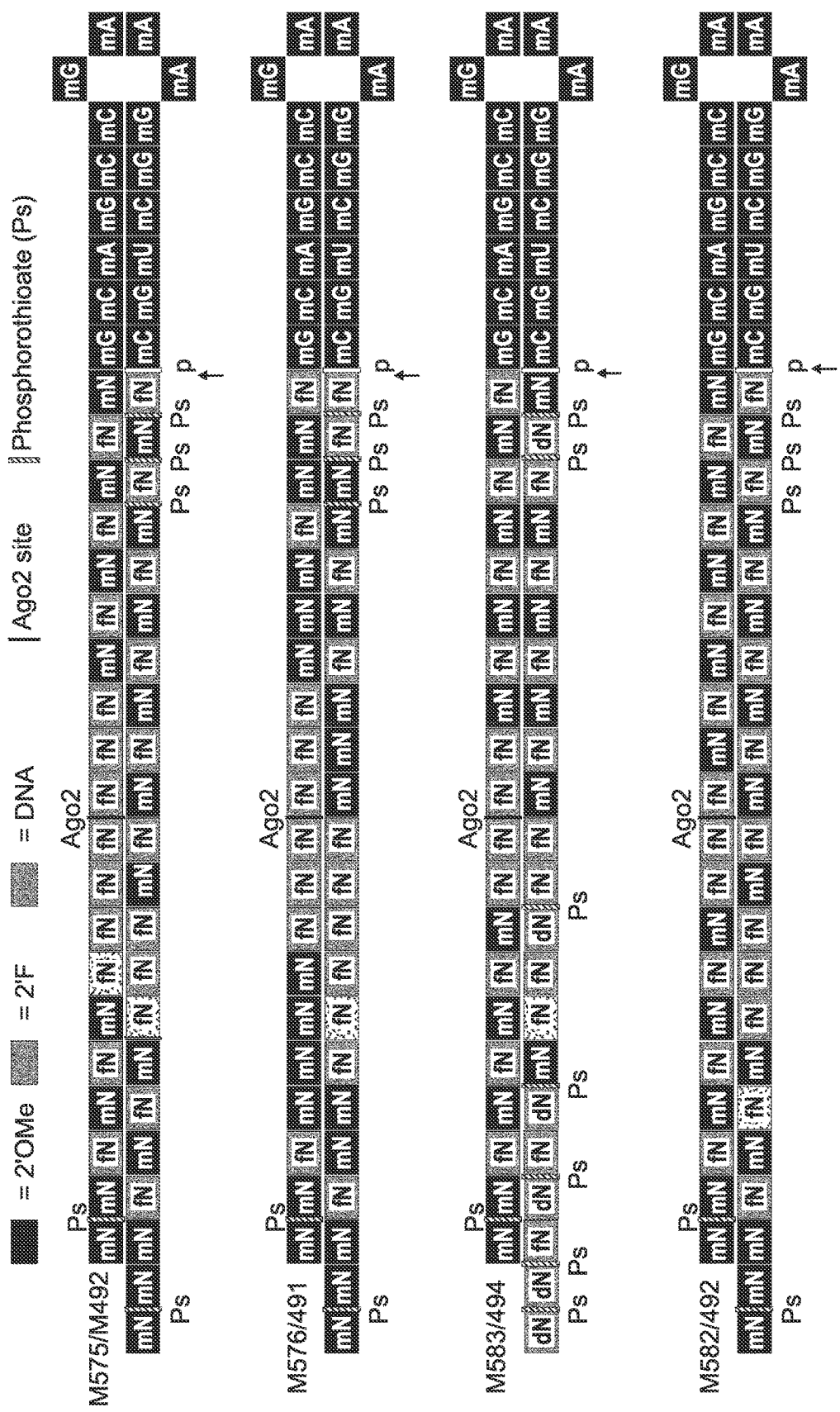
FIGS. 7A to 7C show modification patterns and tetraloop extensions used in synthesizing tetraloop-extended versions of LDHA-targeting DsiRNAs LDHA-718, LDHA-723 and LDHA-1360, as well as results obtained in testing such constructs for efficacy. "Ps" indicates a phosphorothioate linkage, while "p" indicates a terminal phosphate (with an arrow indicating the terminal residue of the second oligonucleotide strand (the non-tetraloop-possessing strand).

Example 6: Efficacy of Tetraloop-Extended Forms of LDHA-Targeting Dicer Substrates A selection of active DsiRNAs identified in the above Examples were used to synthesize corresponding tetraloop-possessing forms of such Dicer substrate molecules. FIG. 7A shows tetraloop sequences and modification patterns employed in such experiments. This mini-set of four modification and tetraloop-possessing construct structures had been validated for in vivo efficacy in HAO1-targeting constructs. The identified modification patterns and tetraloop-containing constructs were synthesized for DsiRNAs LDHA-718 (possessing a target sequence common to humans, rhesus and mouse, with respective tetraloop-containing passenger and guide strand sequences of SEQ ID NOs: 7214 and 7215), LDHA-723 (possessing a target sequence common to humans, rhesus and mouse) and LDHA-1360 (possessing a target sequence common to humans and rhesus).

Figure 7B:
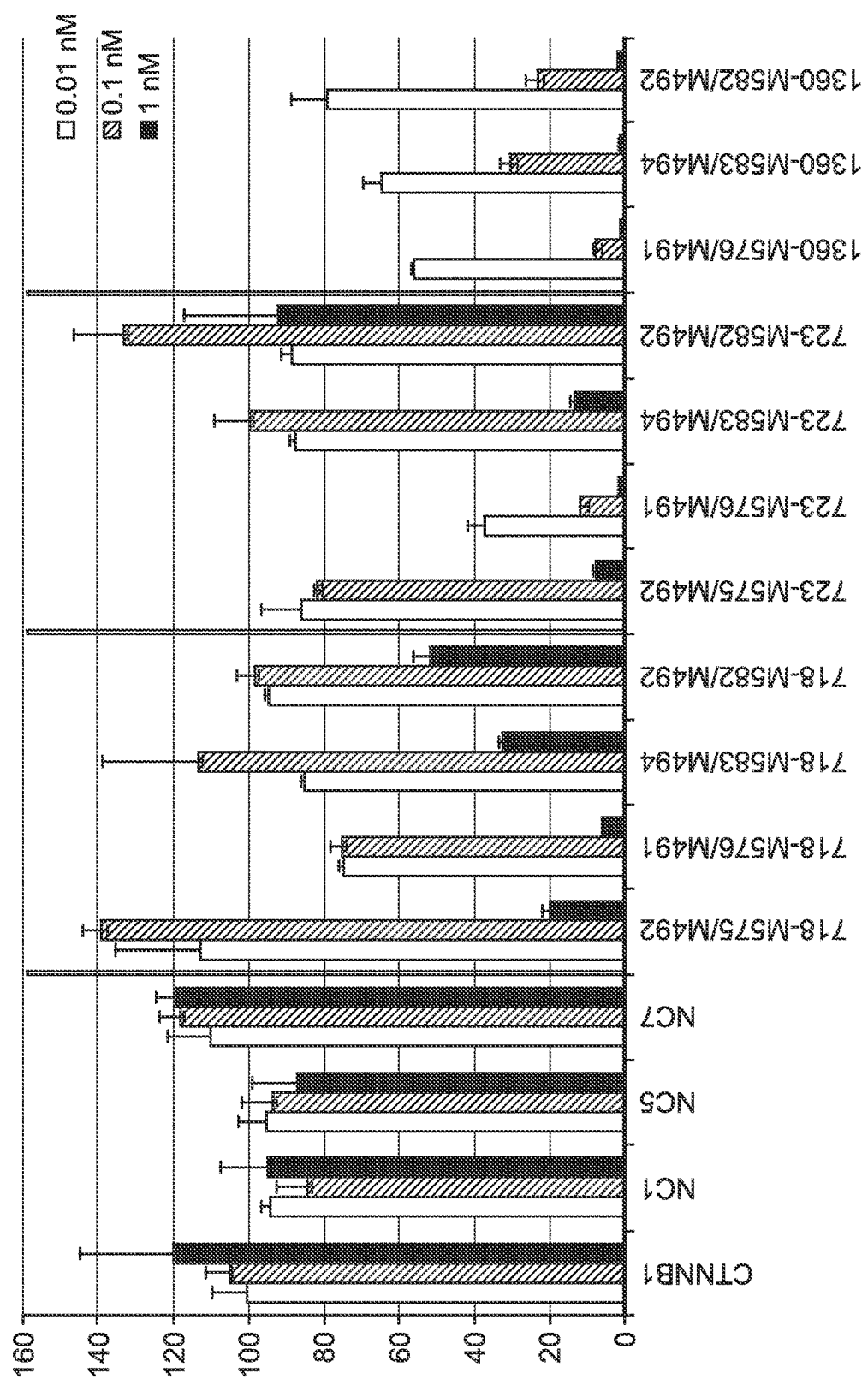
Figure 7C:
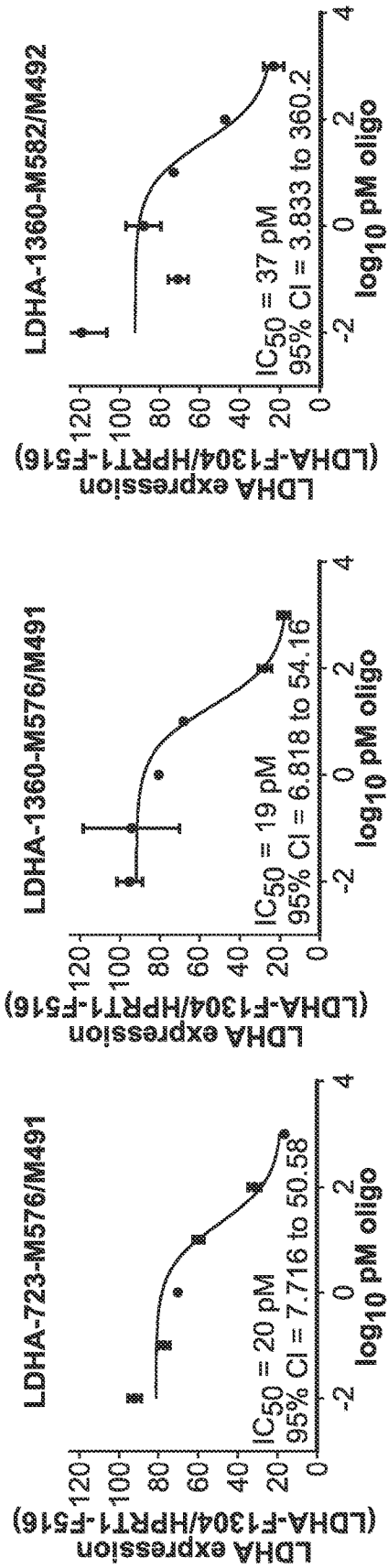
Figure 7C:
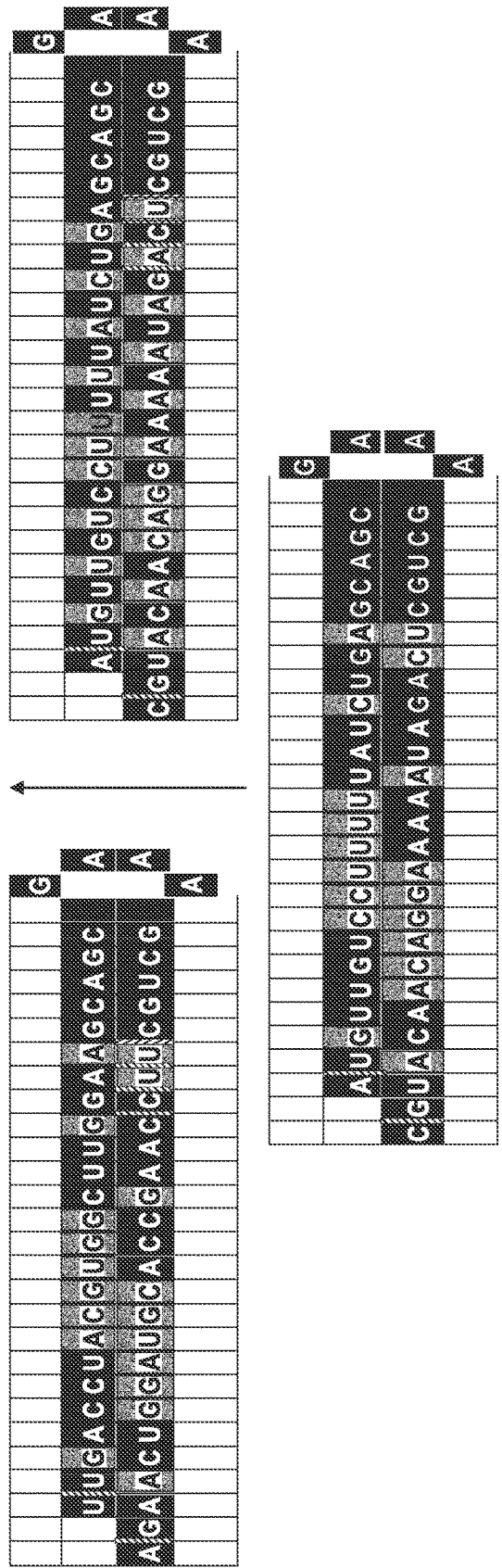

In vitro activities of the tetraloop constructs were examined in HeLa cells. As shown in FIG. 7B, the "M576/M491" modification pattern DsiRNAs possessing tetraloop sequences were identified as having robust LDHA knockdown properties in vitro across each of LDHA-718, LDHA-723 and LDHA-1360 targets, with approximately 50% or greater knockdown observed for LDHA-723 and LDHA-1360 constructs even at extremely low (0.01 nM) concentrations. As shown in FIG. 7C, dose-response curves were also obtained for tetraloop-possessing constructs derived from LDHA-723 and LDHA-1360 DsiRNAs. $IC_{50}$ values were calculated, and robust tetraloop-possessing LDHA-723 and LDHA-1360 structures were identified. The LDHA-723-M576/M491 modified tetraloop agent, identified to have an $IC_{50}$ of 20 pM, was selected for scale-up and conjugation (e.g., to GalNAc moieties), as it was potent and stable. It was also noted that the LDHA-1360 (possessing a target sequence common to humans and rhesus) tetraloop construct tolerated all modification patterns.

Figures 1, 8A:
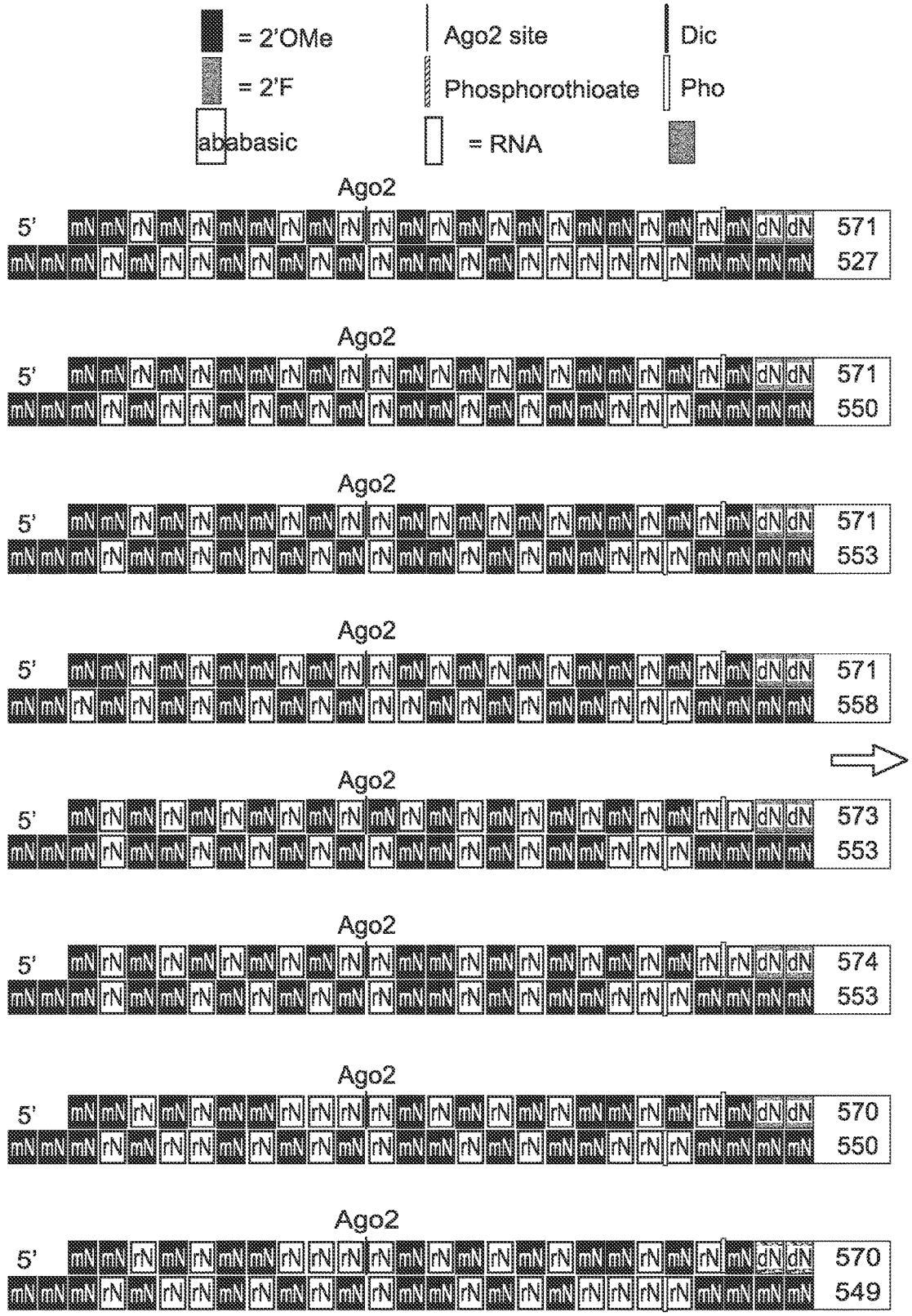
FIGS. 8A to 8C show a set of tetraloop-possessing structures/modification patterns that were applied to the LDHA-targeting DsiRNAs, and efficacy data for such constructs. Tested pairs of oligonucleotide sequences comprising tetraloop-containing agents LDHA-355, LDHA-360, LDHA-361, LDHA-367, LDHA-370, LDHA-399, LDHA-402, LDHA-719 and LDHA-892 are SEQ ID NOs: 7196 and 7197; SEQ ID NOs: 7198 and 7199; SEQ ID NOs: 7200 and 7201; SEQ ID NOs: 7202 and 7203; SEQ ID NOs: 7204 and 7205; SEQ ID NOs: 7206 and 7207; SEQ ID NOs: 7208 and 7209; SEQ ID NOs: 7210 and 7211; and SEQ ID NOs: 7212 and 7213, respectively.
Figures 2, 8A:
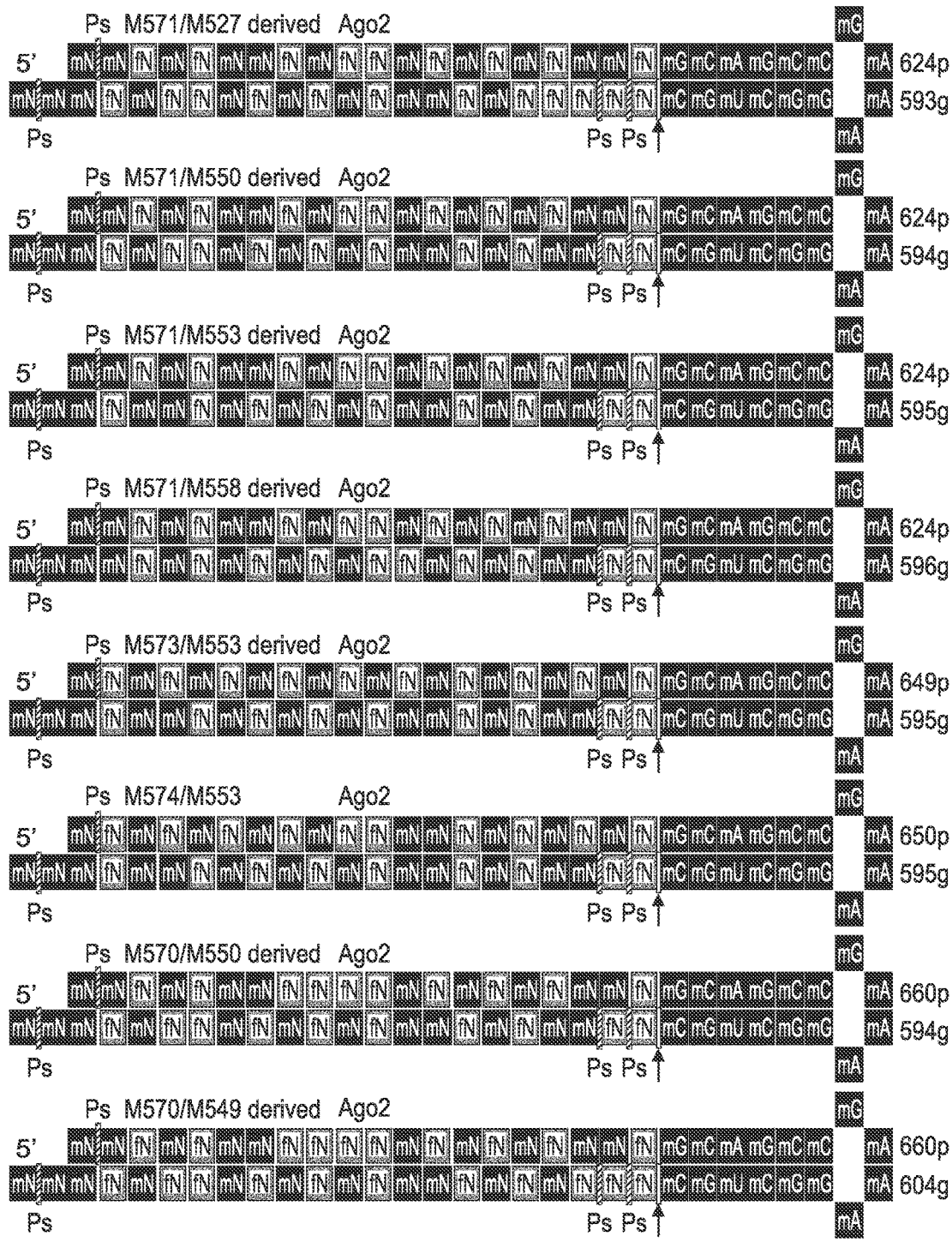
Figures 1, 8B:
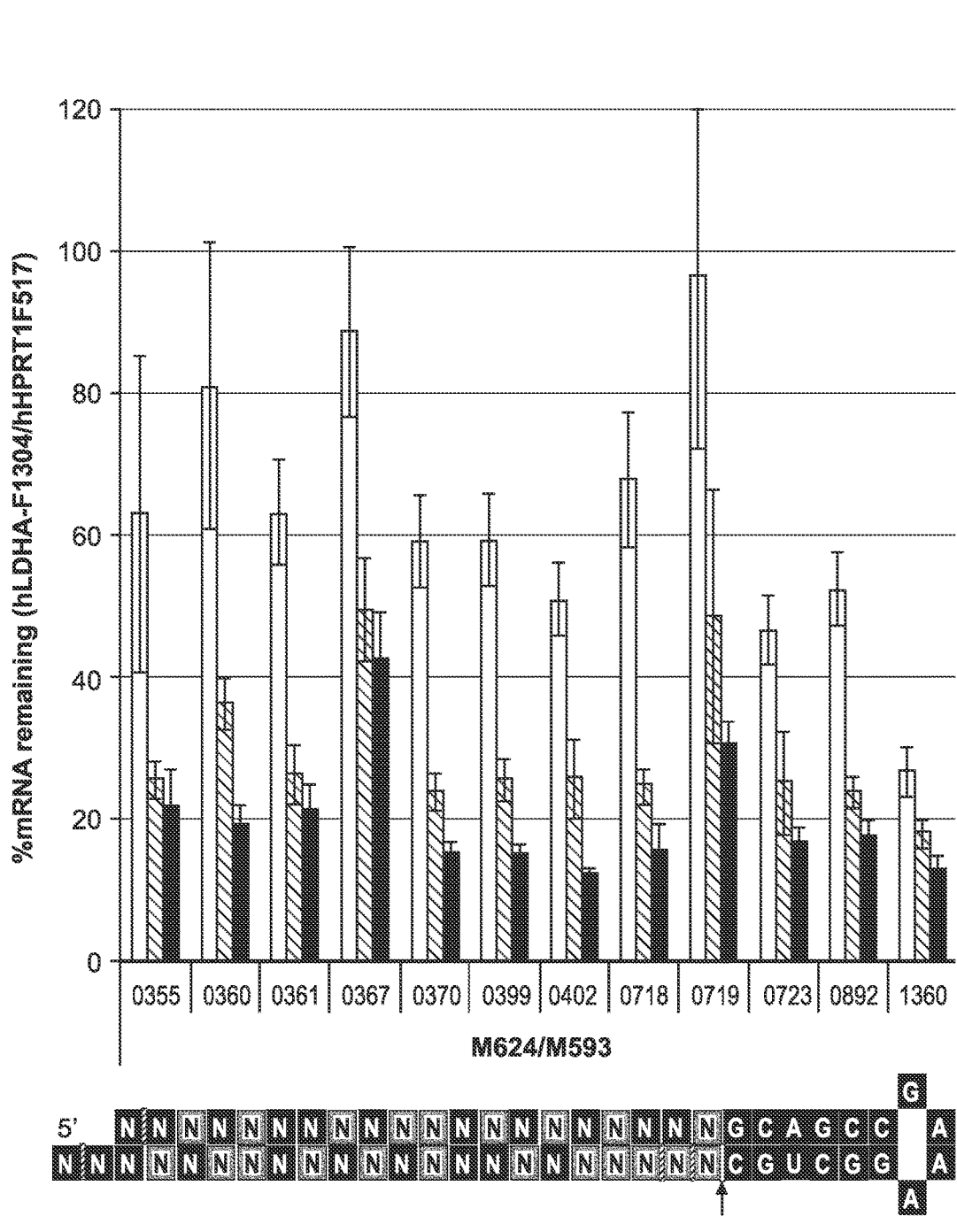
Figures 2, 8B:
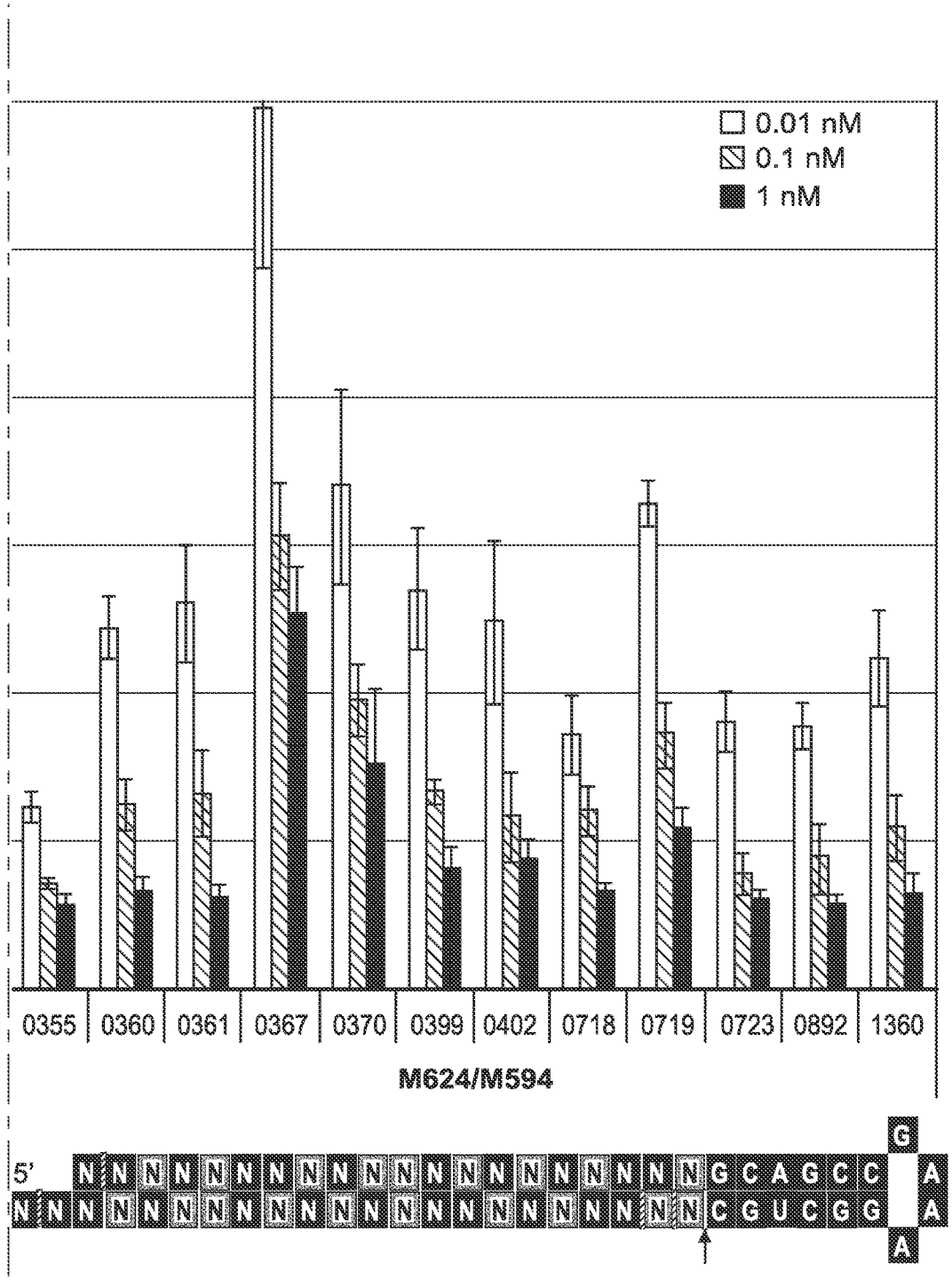
Figures 1, 8C:
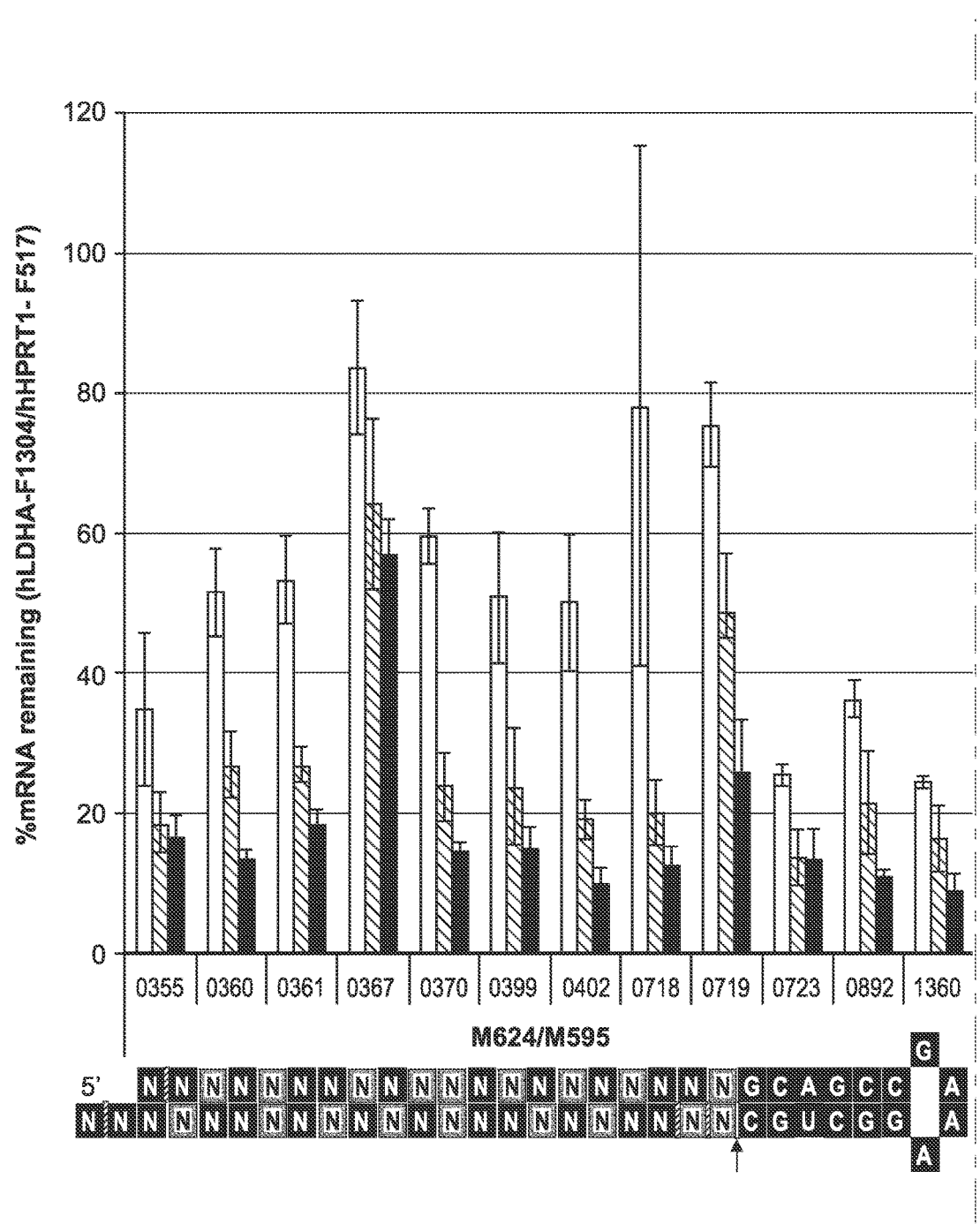
Figures 2, 8C:
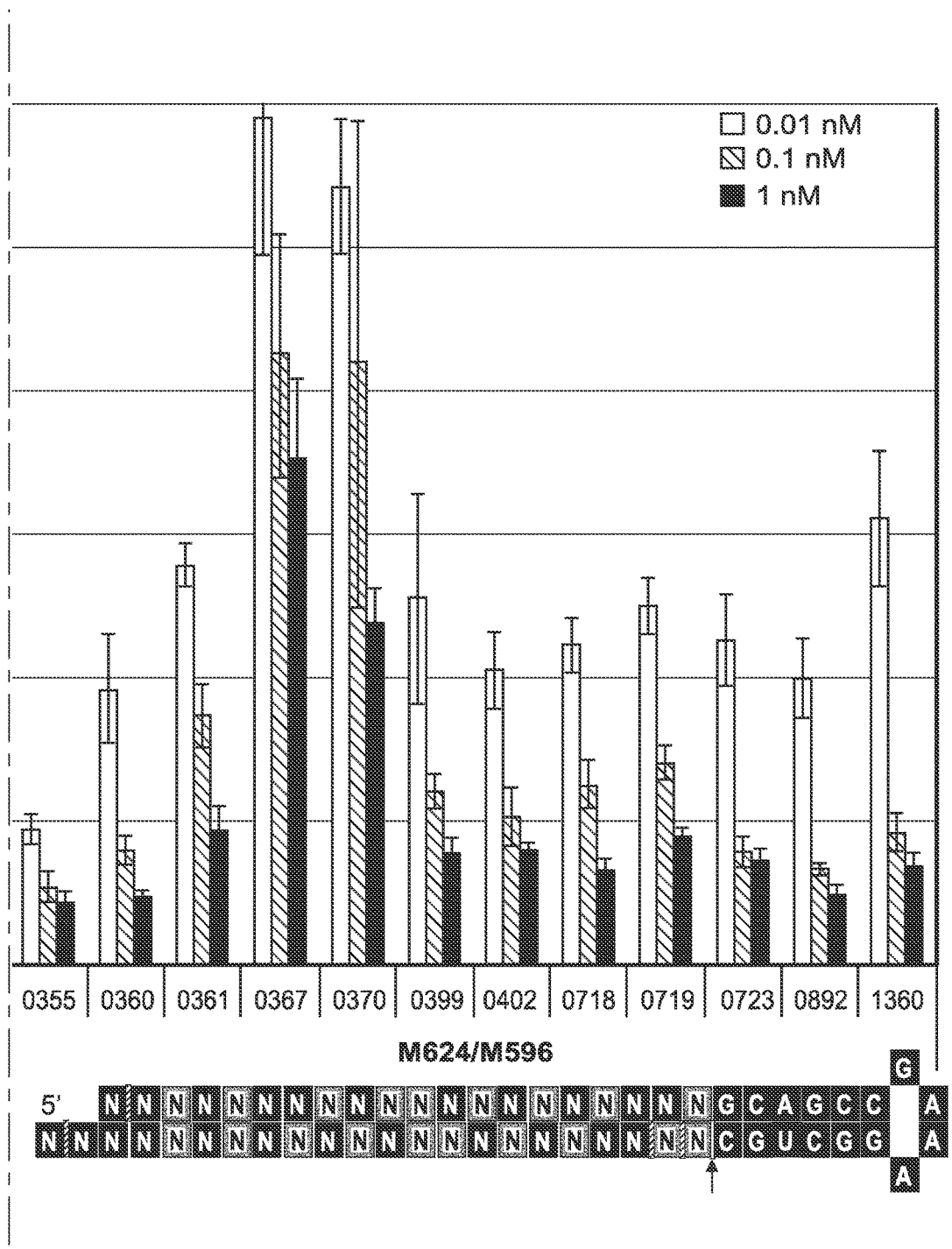
Figures 1, 8D:
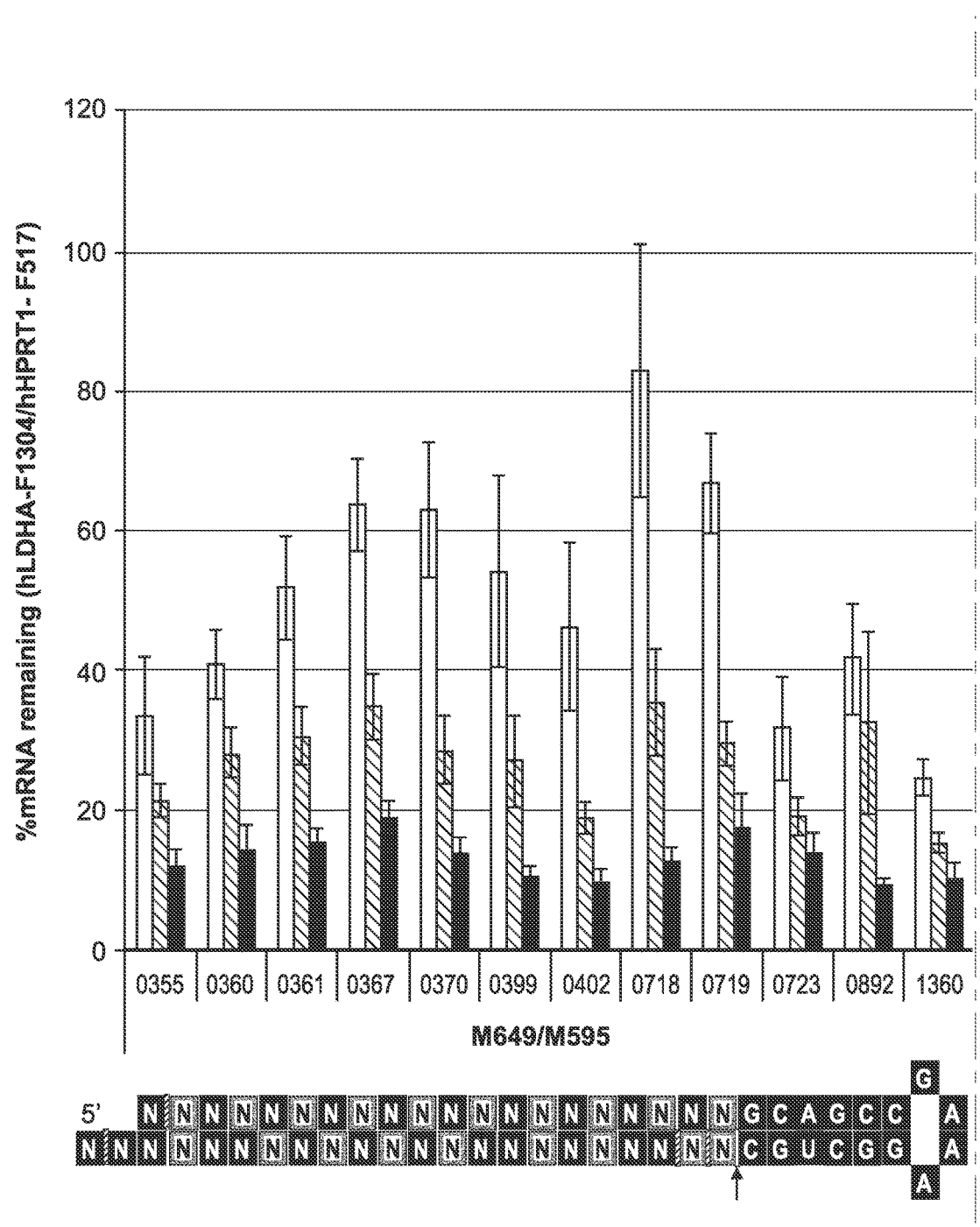
Figures 2, 8D:
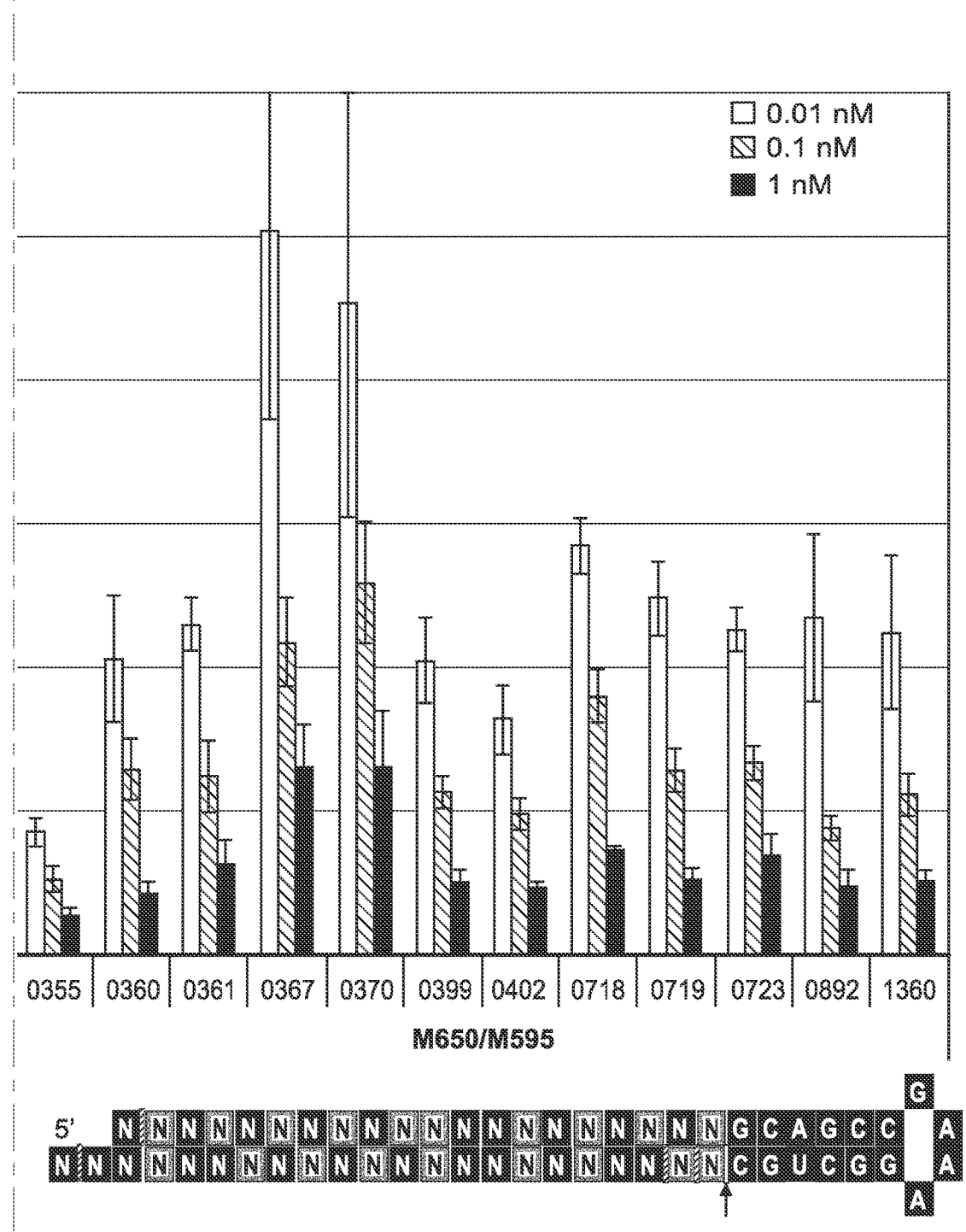
Figures 1, 8E:
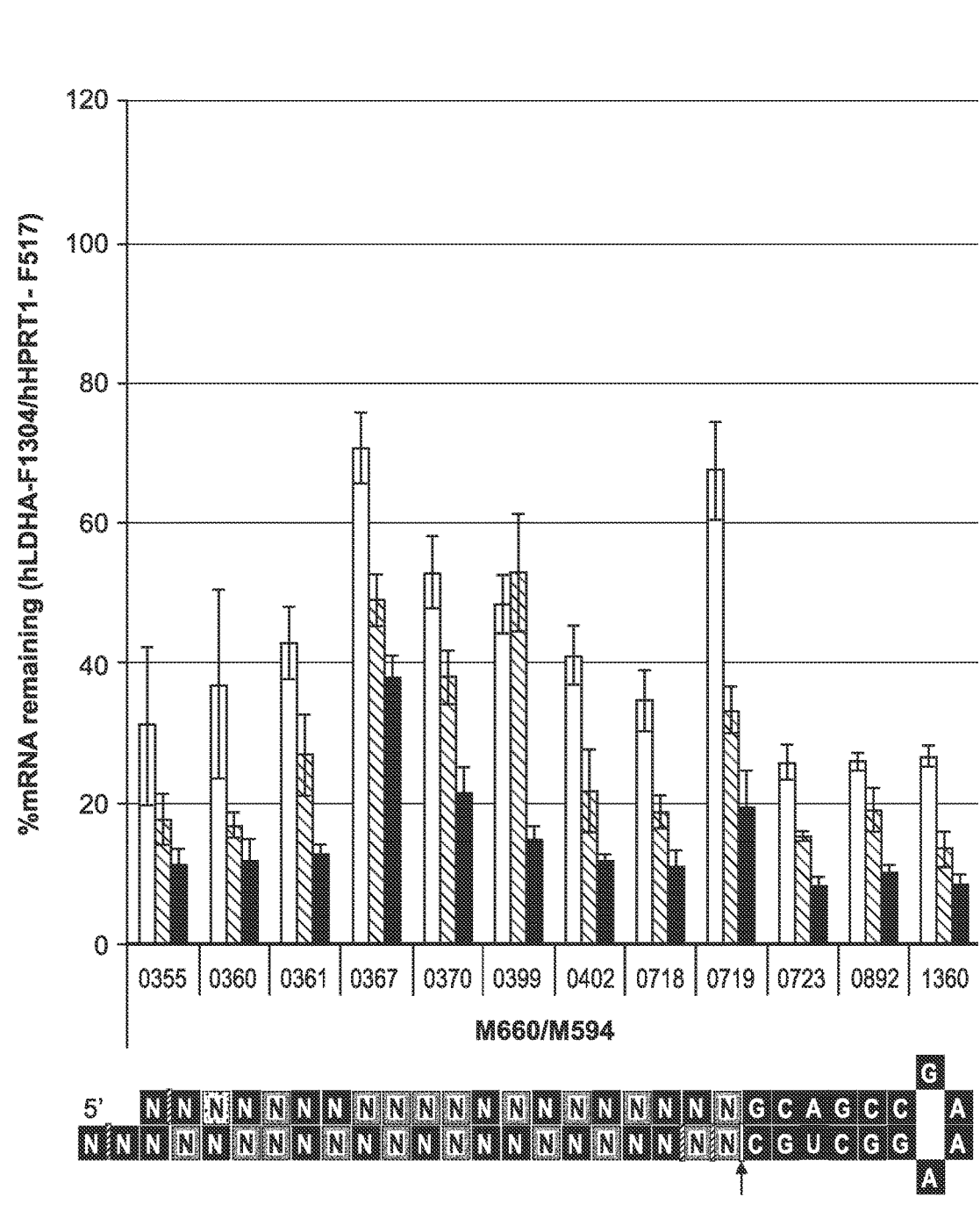
Figures 2, 8E:
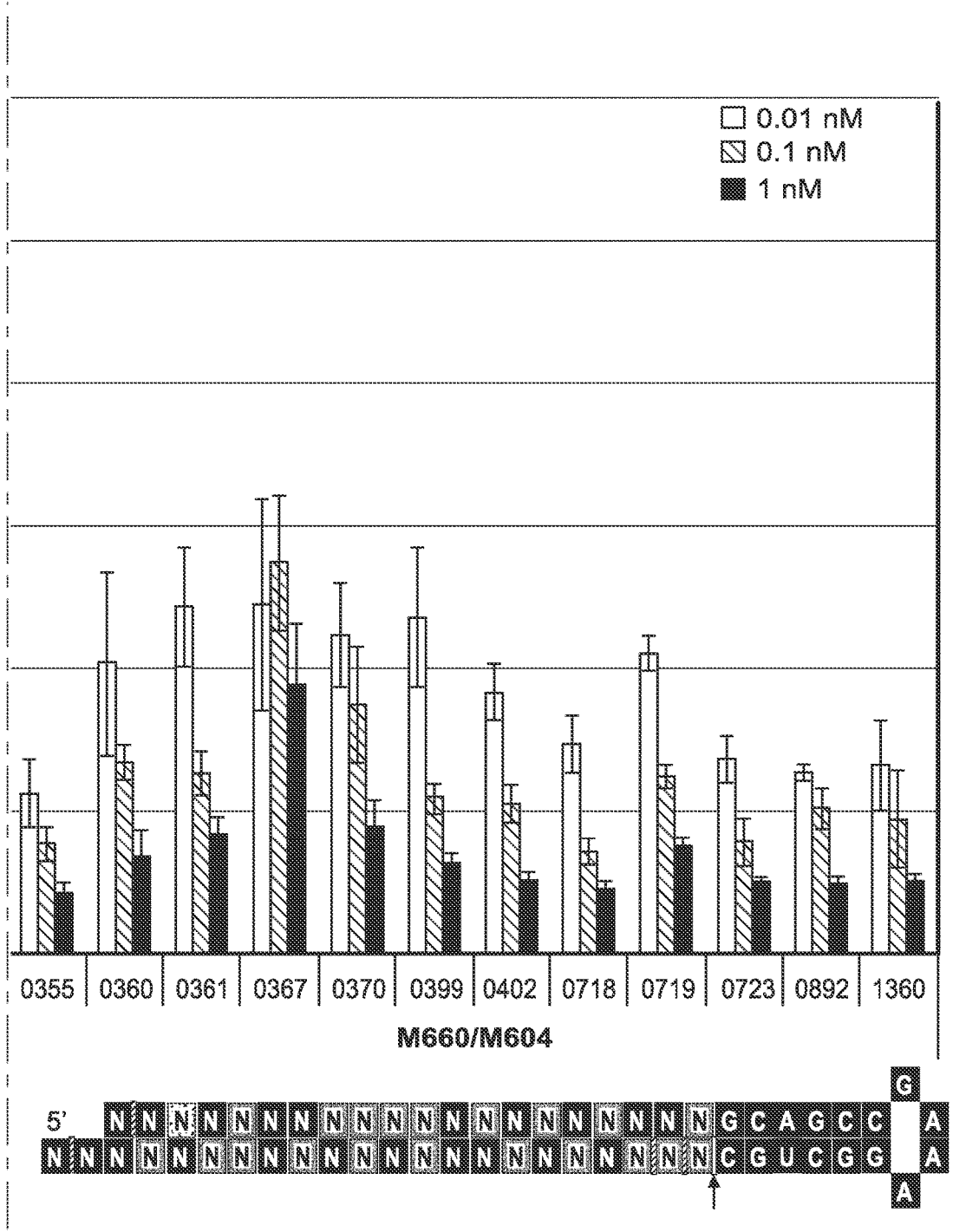

A broader screen for tetraloop-possessing agents that were both active and stable was also performed. In such experiments, previously unmodified residues within 25/27mer modification patterns were converted to 2'-F-modified residues, phosphorothioate linkages and tetraloop structures were added, in a "2'-F fill tetraloop screen". One goal of such a screen was to use 2'-O-Methyl modification pattern screening results to derive potent and stable LDHA tetraloop constructs. To this end, the most active 2'-O-methyl modification patterns for LDHA-718 were filled in with 2'-F modifications, as well as phosphorothioate linkages and tetraloop structures. A total of 96 different tetraloop constructs (eight modification patterns across twelve sequences) were tested in HeLa cells. Conversion of the 2'-O-methyl modification patterns of 25/27mer DsiRNAs to tetraloop-possessing agents was performed in the manner shown in FIG. 8A. As shown in FIGS. 8D to 8E, a number of highly modified tetraloop-possessing constructs were identified as potent in HeLa cell assays and were selected for scale-up synthesis. Thus, multiple sequences with multiple patterns were active as tetraloop constructs. It was noted that M660/M594 and M660/M604 modification patterns were tolerated by most tested sequences. The following constructs were selected for scale-up and in vivo testing: LDHA-355-M650/M595; LDHA-355-M624/M596; LDHA-402-M650/M595; LDHA-718-M660/M604; LDHA-723-M624/M595; LDHA-723-M649/M595; LDHA-892-M660/M594; and LDHA-1360-M624/M595. Dose curve and stability analyses are optionally performed upon such constructs.

Figure 9A:
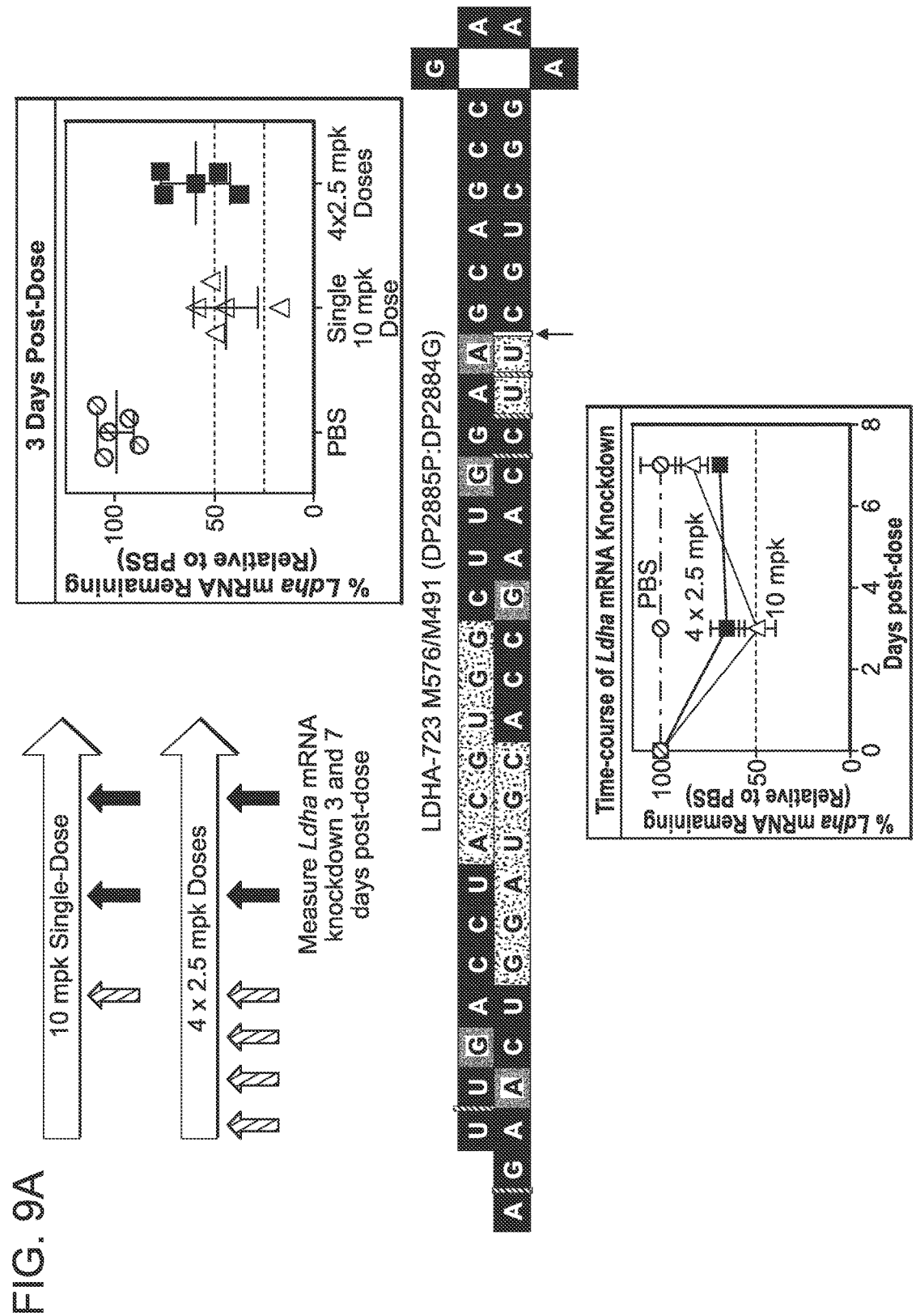
FIGS. 9A to 9C show that GalNAc-conjugated tetraloop-possessing agents of the invention showed dramatic knockdown efficacy in vivo, and that such knockdown efficacy produced reduced urine oxalate levels in treated PH1 model mice.

The LDHA-723 M576/M491 tetraloop construct was also conjugated to GalNAc moieties and tested for in vivo efficacy. As shown in FIG. 9A, this agent was highly effective at knocking down the mouse Ldha gene in liver, under either of the two dosing regimens examined (single dose at 10 mg/kg or 4×2.5 mg/kg dose). In particular, approximately 30% to 60% or greater knockdown of Ldha in liver was observed in all treated animals. Average levels of knockdown for single dose animals exceeded 50% at three days post-administration. Thus, the tetraloop and GalNAc-conjugated form of LDHA-723 M576/M491 was confirmed to be highly active in liver tissue.

Figure 9B:
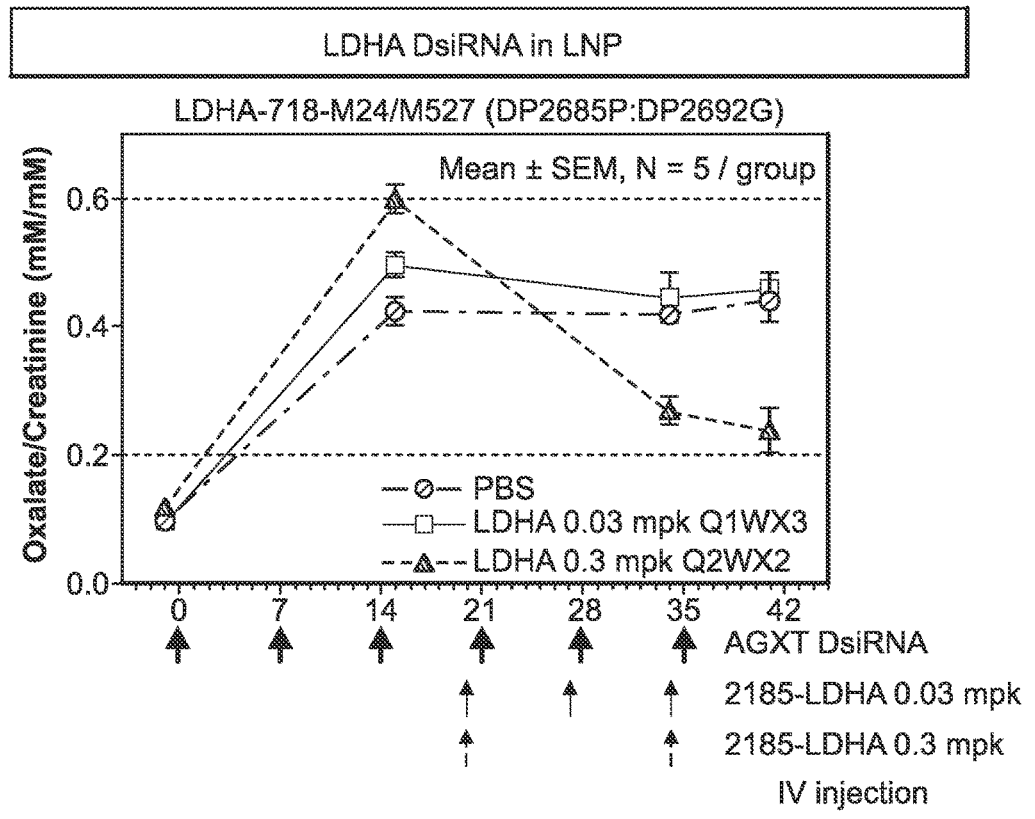
Figure 9B:
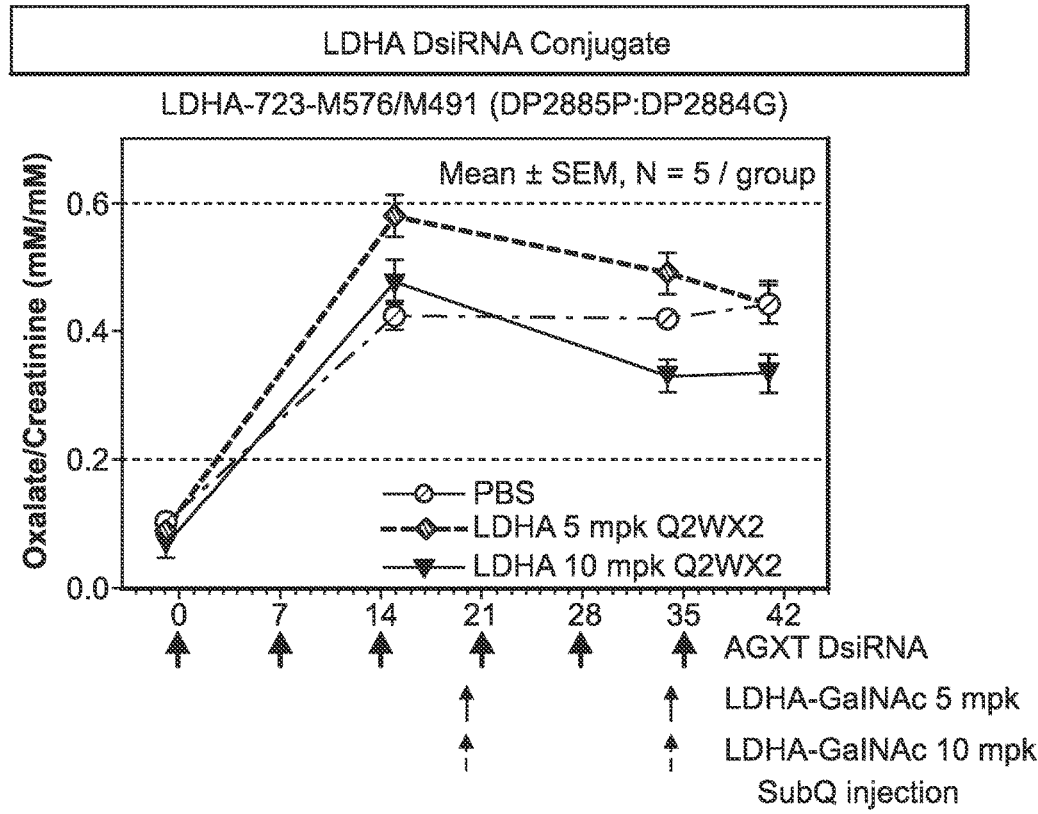

The tetraloop and GalNAc-conjugated form of LDHA-723 M576/M491 was also assessed for impact upon urine oxalate levels in PH1 model mice. In such experiments, C57BL/6 male mice were intravenously injected weekly with Agxt DsiRNA (in LNP 2185 formulation), to induce a PH1 model. Injection of LDHA-targeting DsiRNA constructs was then performed by dosing schedules indicated by arrows in FIG. 9B (with intravenous injection performed for LNP-formulated DsiRNA LDHA-718-M24/M527 (DP2685P:DP2692G), while subcutaneous injection was performed for the tetraloop and GalNAc-conjugated form of LDHA-723 M576/M491). Urine samples were collected manually at the indicated timepoints, and the tetraloop and GalNAc-conjugated form of LDHA-723 M576/M491 at 10 mg/kg was identified to have significantly reduced urine oxalate levels in the PH1 model system mice.

Figure 9C:
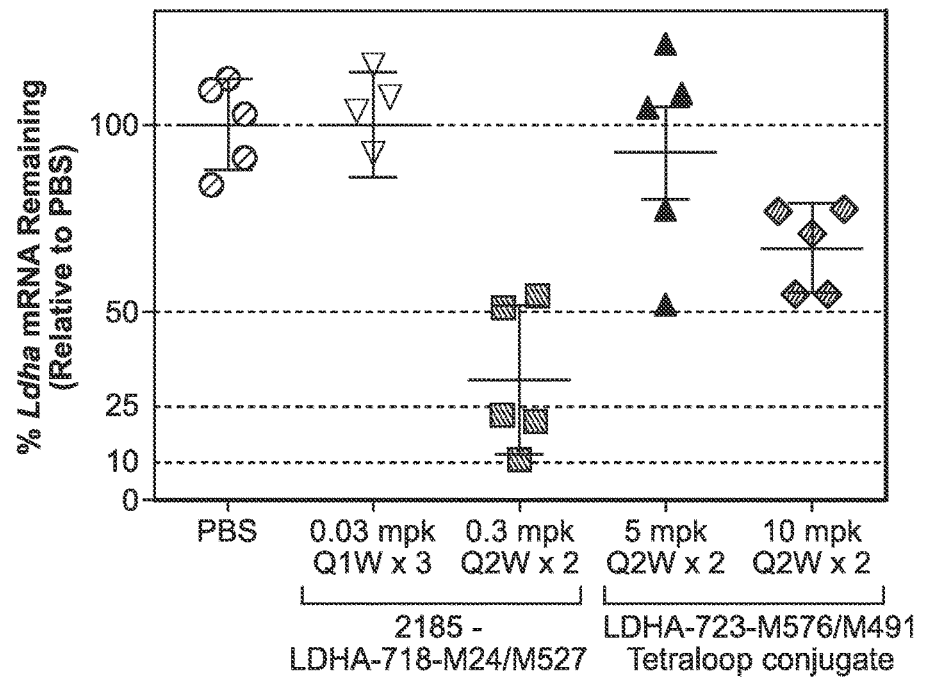
Figure 9C:
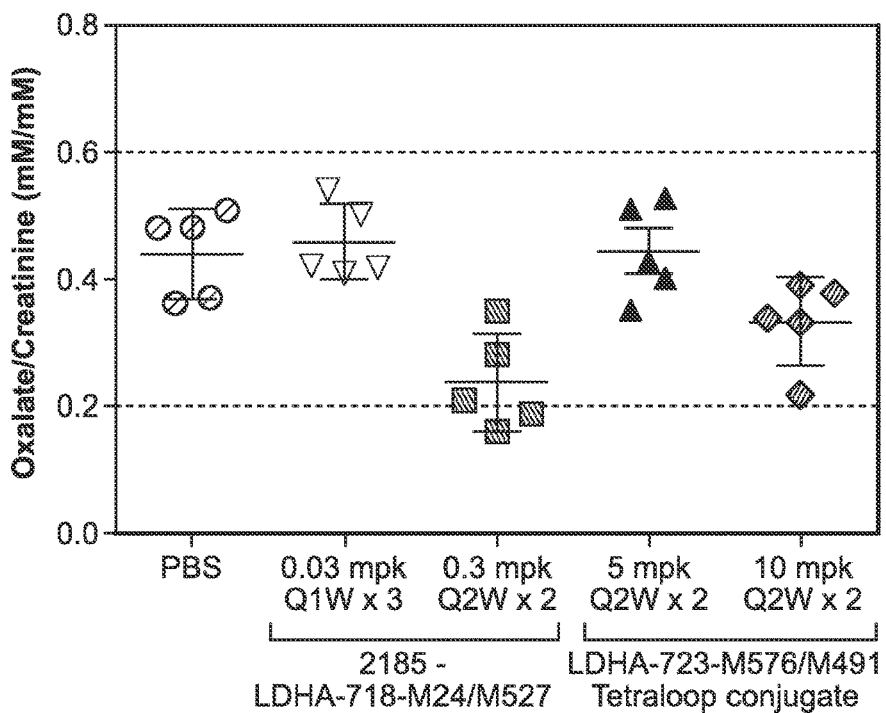

The urine oxalate-reducing efficacy of the tetraloop and GalNAc-conjugated form of LDHA-723 M576/M491 appeared to be dose-dependent, as was further demonstrated in FIG. 9C. Specifically, varying doses of either LNP-formulated LDHA-718 or tetraloop and GalNAc-conjugated form of LDHA-723 M576/M491 were injected intravenously weekly into C57BL/6 male mice that had been pre-treated (and continued to be treated) with Agxt DsiRNA (LNP 2185-formulated), and urine samples were obtained and assessed at seven days after the last dose. Both LNP-formulated LDHA-718 and the tetraloop and GalNAc-conjugated form of LDHA-723 M576/M491 were observed to exhibit a dose-dependent effect on both Ldha mRNA knockdown and reducing urine oxalate levels (FIG. 9C). Additional tetraloop and GalNAc-conjugated forms of LDHA-targeting DsiRNAs were also produced and tested, resulting in identification of certain tetraloop and GalNAc-conjugated forms of LDHA-targeting DsiRNAs possessing single dose $IC_{50}$ values of approximately 3.0 mg/kg (data not shown). Thus, highly active tetraloop and GalNAc-conjugated forms of LDHA-targeting DsiRNAs were identified.

Example 7: LNP-Formulated LDHA-Targeting DsiRNA Knocked Down LDHA Levels in Tumor Cells In Vivo The effect of an LNP-formulated LDHA RNAi agent (specifically, the LDHA-718-M571/M550 25/27mer DsiRNA) in a Hep3B tumor model in nude mice was examined.

LDHA-718-M571/M550 was formulated in EnCore lipid nanoparticles (LNP2540) and tested in Hep3B tumor bearing mice. To generate a tumor model, the nude mice were subcutaneously implanted with 5e6 Hep3B cells and matrigel. When tumors reached an average size of 200 $mm^3$, they were sorted into 3 groups (n=6), such that each group possessed similar average tumor size. These groups were then treated with either PBS, LNP2540/Control DsiRNA or with LNP2540/LDHA DsiRNA every day at 3 mpk for three days. After a four day break, the same treatment schedule was continued for another week. Tumor sizes were measured twice a week to monitor the tumor growth during LDHA treatment. In addition to monitoring tumor sizes, an additional set of mice (n=3) with tumors were also kept in this study to monitor the target knockdown. 24 h after the first round of dosing, the tumors from satellite mice were collected to determine LDHA mRNA knockdown (KD).

Figure 10A:
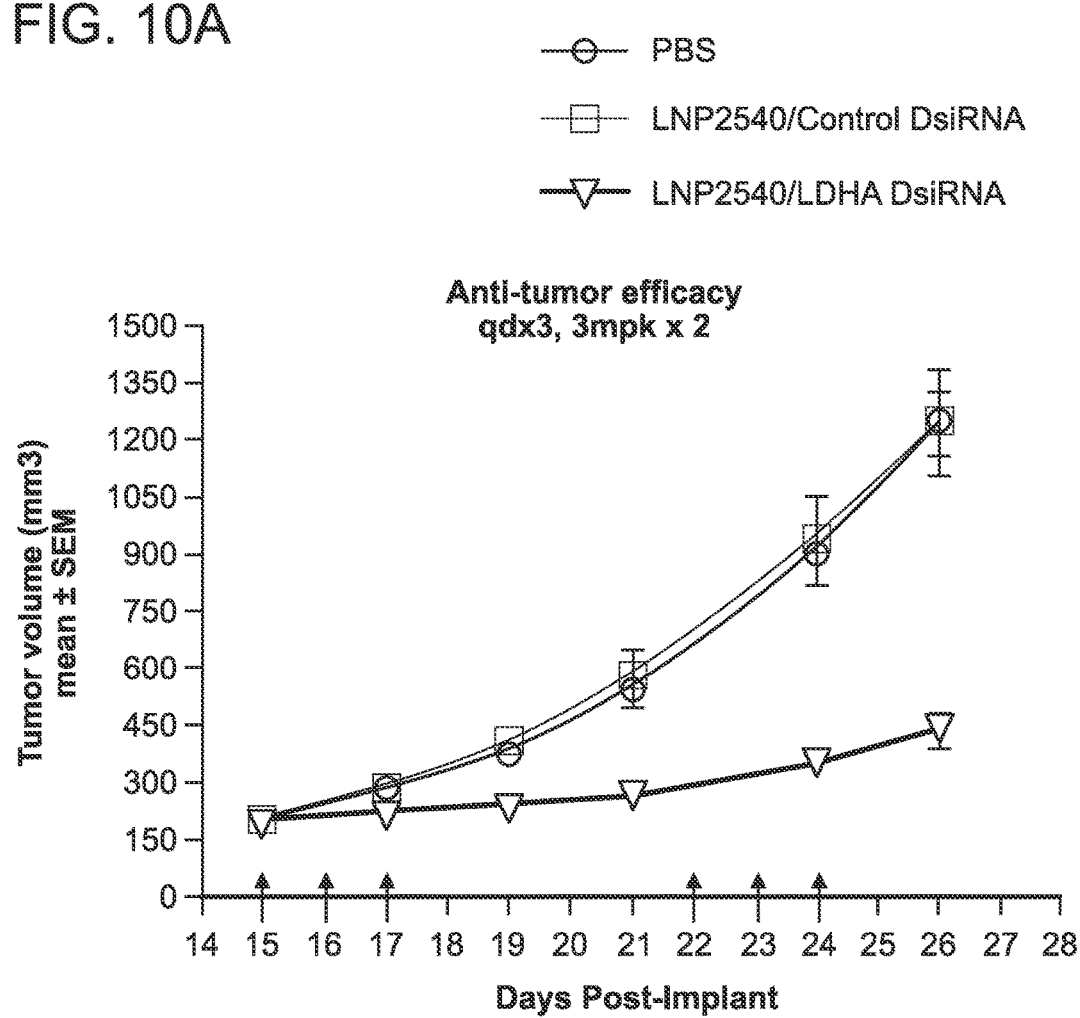

As shown in FIGS. 10A and 10B, LNP2540/LDHA-718-M571/M550 possessed high levels of anti-tumor efficacy (TGI of 78%; FIG. 10A) and also produced >75% knockdown of LDHA in Hep3B tumors of treated animals, on average (FIG. 10B), after a single round of dosing with the LNP/LDHA-718-M571/M550 DsiRNA.

Thus, an LNP-formulated LDHA DsiRNA was identified to be a robust inhibitor of liver tumor in vivo, and was also verified to have produced dramatic knockdown of LDHA in such liver tumor tissues.

Figure 11:
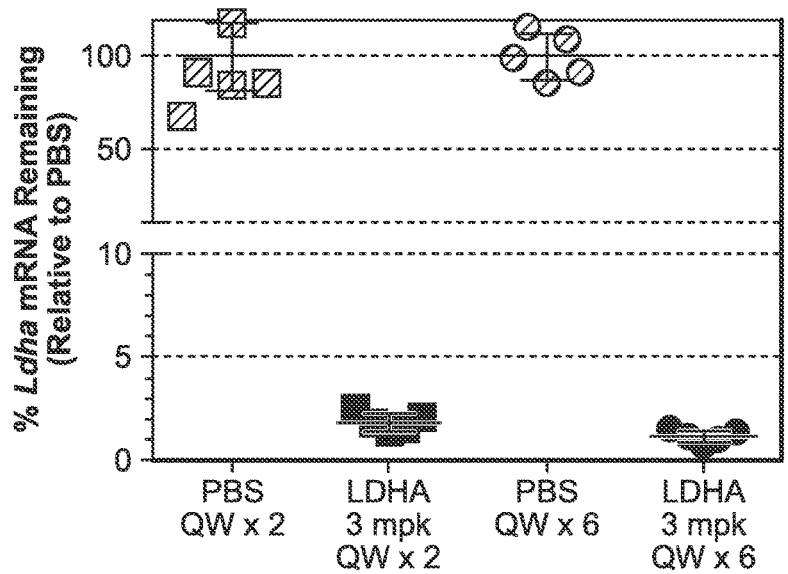
FIG. 11 shows that LNP-formulated LDHA-targeting DsiRNAs were well tolerated in vivo.
Figure 11:
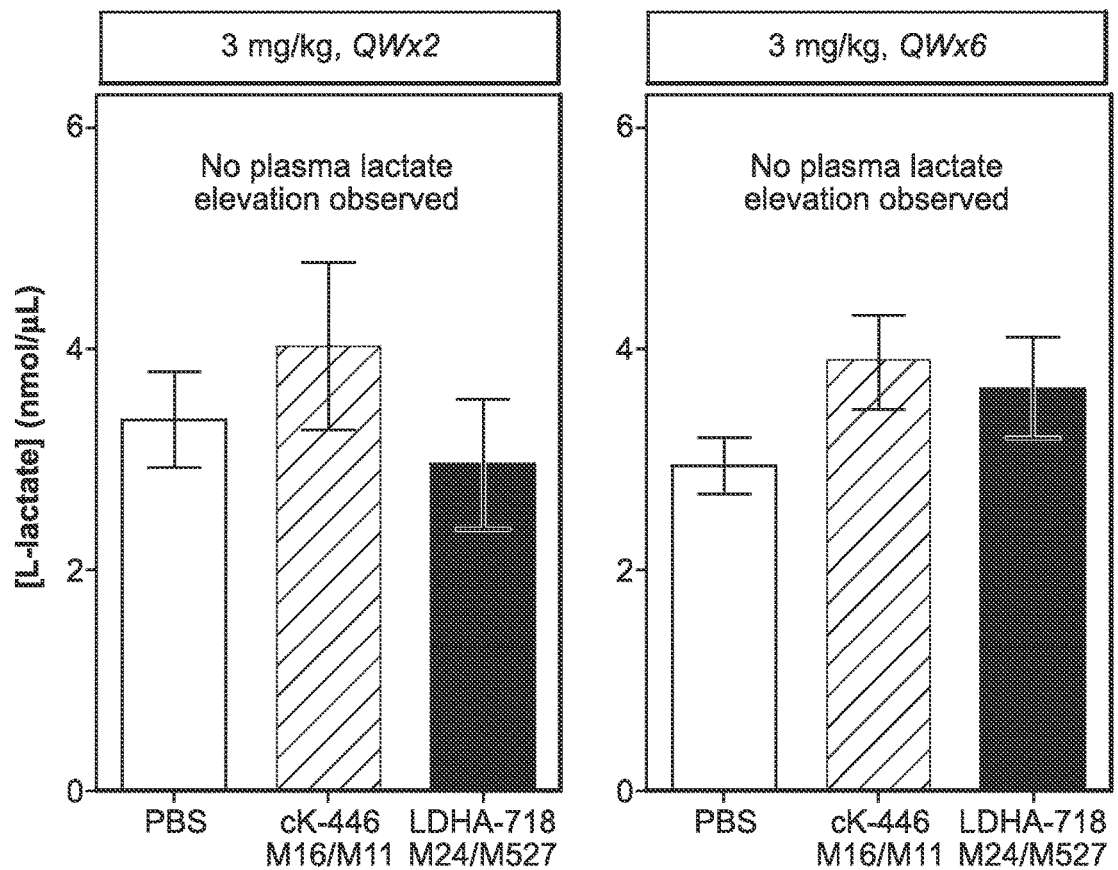

Example 8: Liver-Specific Ldha DsiRNA Knockdown in Wild-Type Mice was Well Tolerated In view of the role of liver LDHA in processing plasma lactate, it was possible that LDHA knockdown in liver would produce a deleterious buildup of plasma lactate levels. To examine whether LNP-formulated LDHA-targeting DsiRNAs exhibited toxicity (e.g., as might be expected if significant knockdown of LDHA in the liver caused plasma lactate to accumulate) wild-type mice were administered the LDHA-718-M24/M527 DsiRNA in LNP 2185, at a concentration of 3 mg/kg, weekly, via intravenous injection. As is shown in FIG. 11, LNP-formulated LDHA-targeting DsiRNAs were observed to have reduced the expression of mRNA in liver tissue to less than 2% of control levels at the end of the study (FIG. 11, at left). Meanwhile, no elevation of plasma lactate levels was observed in treated animals (FIG. 11, at center and right). Moreover, liver enzymes, blood chemistry, body weight and systemic lactic acid were all observed to be normal. Accordingly, LNP-formulated LDHA-targeting DsiRNAs were well tolerated in vivo.

Example 9: DsiRNA Inhibition of LDHA—Secondary Screen

A selection of asymmetric DsiRNAs (e.g., 24 targeting Hs LDHA, a selection of which also target Mm lactate dehydrogenase) of the above experiments (e.g., Examples 2-4) are also examined in a secondary assay ("Phase 2"). Specifically, the asymmetric DsiRNAs selected from those tested above are assessed for inhibition of human lactate dehydrogenase at 1 nM, 0.1 nM and 0.03 nM in the environment of human HeLa cells. These asymmetric DsiRNAs are then also assessed for inhibition of mouse LDHA at 1 nM, 0.1 nM and 0.03 nM in the environment of mouse B16-F10 cells. Most asymmetric DsiRNAs are expected to reproducibly exhibit significant LDHA inhibitory efficacies at sub-nanomolar concentrations when assayed in the environment of HeLa cells. In addition, a select number of asymmetric DsiRNAs are expected to be identified that possess significant mouse lactate dehydrogenase inhibitory efficacies at sub-nanomolar concentrations when assayed in the environment of mouse B16-F10 cells.

Example 10: Identification of Additional Modified Forms of LDHA-Targeting DsiRNAs that Reduce Lactate Dehydrogenase Levels In Vitro A selection (e.g., 12-24) of lactate dehydrogenase-targeting DsiRNAs of the above initial screen are prepared with 2'-O-methyl guide and passenger strand modification patterns as described above; exemplary modifications include "M107" modified passenger strands and above-described guide strand modification patterns "M8", "M17", "M35" and "M48"). For each of the DsiRNA sequences, DsiRNAs possessing each of the four guide strand modification patterns M8, M17, M35 and M48 are assayed for LDHA inhibition in human HeLa cells at 1.0 nM, 0.1 nM and 0.03 nM concentrations in the environment of the HeLa cells. Identification of a modification pattern that allows the DsiRNA to retain significant lactate dehydrogenase inhibitory efficacy in vitro is therefore achieved, with such highly active modified DsiRNA sequences possessing modification patterns believed to be capable of stabilizing such DsiRNAs and/or reducing immunogenicity of such DsiRNAs when therapeutically administered to a subject in vivo.

Example 11: Additional Forms of LDHA-Targeting DsiRNAs Possessing Modifications of Both Guide and Passenger Strands Additional LDHA-Targeting DsiRNAs of the above experiments are prepared with 2'-O-methyl passenger strand and guide strand modification patterns, e.g., as represented above (including, e.g., passenger strand modification patterns "SM14", "SM24", "SM107", "SM250", "SM251" and "SM252" and guide strand modification patterns "M48", "M8" and "M17"). For each of the DsiRNA sequences, DsiRNAs possessing each of the six passenger strand modification patterns M14, M24, M107, M250, M251 and M252 and one preferred guide strand modification pattern (selected from among guide strand modification patterns M48, M8 and M17) are assayed for lactate dehydrogenase inhibition in human HeLa cells at 1.0 nM, 0.1 nM and 0.03 nM (30 picomolar) concentrations in the environment of the HeLa cells. Duplexes possessing extensive modification of both guide and passenger strands are identified that still allow the DsiRNA to retain significant lactate dehydrogenase inhibitory efficacy in vitro. Highly active modified DsiRNA sequences so identified possess modification patterns believed to be capable of stabilizing such DsiRNAs and/or reducing immunogenicity of such DsiRNAs when therapeutically administered to a subject in vivo.

Example 12: Indications

The present body of knowledge in lactate dehydrogenase research indicates the need for methods to assay lactate dehydrogenase activity and for compounds that can regulate lactate dehydrogenase expression for research, diagnostic, and therapeutic use. As described herein, the nucleic acid molecules of the present invention can be used in assays to diagnose and/or monitor a disease state that has the potential to be treated by lactate dehydrogenase-targeting agents. In addition, the nucleic acid molecules can be used to treat such a disease state (e.g., PH1).

Other therapeutic agents can be combined with or used in conjunction with the nucleic acid molecules (e.g. DsiRNA molecules) of the instant invention. For example, for purpose of treating PH1, both anti-LDHA and anti-glycolate oxidase dsRNAs (e.g., DsiRNAs) can be combined to impede oxalate production. Those skilled in the art will recognize that other compounds and therapies used to treat the diseases and conditions described herein can be combined with the nucleic acid molecules of the instant invention (e.g. siNA molecules) and are hence within the scope of the instant invention. For example, for combination therapy, the nucleic acids of the invention can be prepared in one of at least two ways. First, the agents are physically combined in a preparation of nucleic acid and other agent, such as a mixture of a nucleic acid of the invention encapsulated in liposomes and other agent in a solution for intravenous administration, wherein both agents are present in a therapeutically effective concentration (e.g., the other agent in solution to deliver 1000-1250 mg/m2/day and liposome-associated nucleic acid of the invention in the same solution to deliver 0.1-100 mg/kg/day). Alternatively, the agents are administered separately but simultaneously or successively in their respective effective doses (e.g., 1000-1250 mg/m2/d other agent and 0.1 to 100 mg/kg/day nucleic acid of the invention).

Example 13: Serum Stability for DsiRNAs

Serum stability of DsiRNA agents is assessed via incubation of DsiRNA agents in 50% fetal bovine serum for various periods of time (up to 24 h) at 37° C. Serum is extracted and the nucleic acids are separated on a 20% non-denaturing PAGE and can be visualized with Gelstar stain. Relative levels of protection from nuclease degradation are assessed for DsiRNAs (optionally with and without modifications).

Example 14: Liver-Targeted LDHA Knockdown Effects in PH Model Mice

The etiology of chronic kidney stone formation and chronic kidney disease is tested using largely liver-specific LDHA-targeting agents and formulations of the invention. Combined PH1, PH2 and PH3 models (e.g., PH2/PH3, PH1/PH3, PH1/PH2 and/or PH1/PH2/PH3 models) are generated in large groups of mice, causing multiple simultaneous and interacting disruptions of mono- and dicarboxylic acid metabolism. LNP-formulated LDHA-targeting DsiRNAs and controls are tested in these animals, with the expectation that LDHA knockdown will prove beneficial/corrective to each model treated and examined.

Example 15: Diagnostic Uses

The DsiRNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of DsiRNA molecules involves utilizing reconstituted RNAi systems, for example, using cellular lysates or partially purified cellular lysates. DsiRNA molecules of this invention can be used as diagnostic tools to examine genetic drift and mutations within diseased cells. The close relationship between DsiRNA activity and the structure of the target lactate dehydrogenase RNA allows the detection of mutations in a region of the lactate dehydrogenase molecule, which alters the base-pairing and three-dimensional structure of the target lactate dehydrogenase RNA. By using multiple DsiRNA molecules described in this invention, one can map nucleotide changes, which are important to RNA structure and function in vitro, as well as in cells and tissues. Cleavage of target lactate dehydrogenase RNAs with DsiRNA molecules can be used to inhibit gene expression and define the role of specified gene products in the progression of PH1 or other lactate dehydrogenase-associated disease or disorder. In this manner, other genetic targets can be defined as important mediators of the disease. These experiments will lead to better treatment of the disease progression by affording the possibility of combination therapies (e.g., multiple DsiRNA molecules targeted to different genes, DsiRNA molecules coupled with known small molecule inhibitors, or intermittent treatment with combinations of DsiRNA molecules and/or other chemical or biological molecules). Other in vitro uses of DsiRNA molecules of this invention are well known in the art, and include detection of the presence of RNAs associated with a disease or related condition. Such RNA is detected by determining the presence of a cleavage product after treatment with a DsiRNA using standard methodologies, for example, fluorescence resonance emission transfer (FRET).

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying DsiRNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10351854B2). An electronic copy of the "Sequence Listing" will also be available from the USPTO upon request and payment of the fee set forth in 37 CFR 1.19(b)(3).

We claim:

1. A double stranded nucleic acid (dsNA) comprising a sense strand and an antisense strand, wherein the antisense strand is 19-35 nucleotides in length, wherein the antisense strand is complementary to a target lactate dehydrogenase mRNA sequence as set forth in SEQ ID NO: 401 along at least 19 nucleotides of said antisense strand length, and wherein the dsNA comprises one or more modified nucleotides.

2. The dsNA of claim 1, wherein the sense strand and antisense strand form a duplex such that the antisense strand comprises a two nucleotide overhang at its 3' end.

3. The dsNA of claim 1, wherein the dsNA comprises a duplex of 19 to 25 base pairs in length.

4. The dsNA of claim 2, wherein the sense strand is 25 to 53 nucleotides in length.

5. The dsNA of claim 2, wherein the sense strand is 36 nucleotides in length and/or wherein the antisense strand is 22 nucleotides in length.

6. The dsNA of claim 1, wherein the sense strand and the antisense strand are each in the range of 21 to 23 nucleotides in length.

7. The dsNA of claim 1, wherein the sense strand is 21 nucleotides in length and the antisense strand is 23 nucleotides in length.

8. The dsNA of claim 7, wherein the 3' terminus of the sense strand and the 5' terminus of the antisense strand form a blunt end.

9. The dsNA of claim 1, wherein the sense strand comprises a tetraloop at its 3' end.

10. The dsNA of claim 6, wherein the sense strand comprises a tetraloop at its 3' end.

11. The dsNA of claim 9, wherein the tetraloop comprises a single stranded loop having a sequence of GAAA.

12. The dsNA of claim 1, wherein the dsNA comprises at least one phosphorothioate linkage.

13. The dsNA of claim 11, wherein the dsNA comprises at least one phosphorothioate linkage.

14. The dsNA of claim 1, wherein the one or more modified nucleotides contains a 2' modification.

15. The dsNA of claim 14, wherein the one or more modified nucleotides are selected from a 2'-O-methyl nucleotide and a 2'-fluoro nucleotide.

16. The dsNA of claim 15, wherein the dsNA comprises at least one 2'-fluoro nucleotide and at least one 2'-O-methyl nucleotide.

17. The dsNA of claim 1, wherein the dsNA is attached to a moiety selected from the group consisting of a GalNAc moiety, a cholesterol moiety, and a cholesterol targeting ligand.

18. The dsNA of claim 15, wherein the dsNA is attached to a GalNAc moiety.

19. A pharmaceutical composition comprising the dsNA of claim 18 and a pharmaceutically acceptable carrier.

20. A nucleic acid comprising an oligonucleotide strand of 19-35 nucleotides in length, wherein said oligonucleotide strand is complementary to a target lactate dehydrogenase mRNA sequence as set forth in SEQ ID NO: 401 along at least 19 nucleotides of said oligonucleotide strand length, and wherein the nucleic acid comprises one or more modified nucleotides.

21. A mammalian cell containing the nucleic acid of claim 20.

22. A pharmaceutical composition comprising the nucleic acid of claim 20 and a pharmaceutically acceptable carrier.

23. A double stranded nucleic acid (dsNA) comprising a sense strand and an antisense strand, wherein the antisense strand is 19-35 nucleotides in length, wherein the antisense strand is complementary to a target lactate dehydrogenase mRNA sequence as set forth in SEQ ID NO: 401 along at least 19 nucleotides of said antisense strand length, wherein the complementary region of the antisense strand contains between one and four mismatched nucleotide residues relative to SEQ ID NO: 401, and wherein the dsNA comprises one or more modified nucleotides.

24. The dsNA of claim 23, wherein the complementary region of the antisense strand contains three, two, or one mismatched nucleotide residues relative to SEQ ID NO: 401.

25. The dsNA of claim 23, wherein the sense strand and antisense strand form a duplex such that the antisense strand comprises a two nucleotide overhang at its 3' end.

26. The dsNA of claim 23, wherein the dsNA comprises a duplex of 19 to 25 base pairs in length.

27. The dsNA of claim 25, wherein the sense strand is 25 to 53 nucleotides in length.

28. The dsNA of claim 25, wherein the sense strand is 36 nucleotides in length and/or wherein the antisense strand is 22 nucleotides in length.

29. The dsNA of claim 23, wherein the sense strand and the antisense strand are each in the range of 21 to 23 nucleotides in length.

30. The dsNA of claim 23, wherein the sense strand is 21 nucleotides in length and the antisense strand is 23 nucleotides in length.

31. The dsNA of claim 30, wherein the 3' terminus of the sense strand and the 5' terminus of the antisense strand form a blunt end.

32. The dsNA of claim 23, wherein the sense strand comprises a tetraloop at its 3' end.

33. The dsNA of claim 29, wherein the sense strand comprises a tetraloop at its 3' end.

34. The dsNA of claim 32, wherein the tetraloop comprises a single stranded loop having a sequence of GAAA.

* * * * *

UNITED STATES PATENT AND TRADEMARK OFFICE
CERTIFICATE OF CORRECTION

PATENT NO. : 10,351,854 B2  
APPLICATION NO. : 15/518009  
DATED : July 16, 2019  
INVENTOR(S) : Bob D. Brown et al.

Page 1 of 1

It is certified that error appears in the above-identified patent and that said Letters Patent is hereby corrected as shown below:

On the Title Page

Item (72) at Column 1, Line 9, please replace as follows "Chengjung Lai, Belmont, MA (US)".

Signed and Sealed this  
Fourteenth Day of January, 2025

Derrick Brent  
*Acting Director of the United States Patent and Trademark Office*